US012767638B2

(12) United States Patent
Trainor et al.

(10) Patent No.: US 12,767,638 B2
(45) Date of Patent: Oct. 20, 2026

(54) SUBSTITUTED CYCLIC MODULATORS OF PROTEIN PHOSPHATASE 2A (PP2A) AND METHODS USING SAME

(71) Applicant: Rappta Therapeutics Oy, Helsinki (FI)

(72) Inventors: George L. Trainor, Wilmington, DE (US); Maria Obdulia Rabal Gracia, Huesca (ES); Laura Fourmois, Montigny le Bretonneux (FR); Olga Gherbovet, Saint-Hilaire (FR); Frederic Cachoux, Caraman (FR)

(73) Assignee: RAPPTA THERAPEUTICS OY, Helsinki (FI)

(*) Notice: Subject to any disclaimer, the term of this patent is extended or adjusted under 35 U.S.C. 154(b) by 304 days.

(21) Appl. No.: 18/273,476

(22) PCT Filed: Feb. 7, 2022

(86) PCT No.: PCT/IB2022/000060

§ 371 (c)(1),
(2) Date: Jul. 20, 2023

(87) PCT Pub. No.: WO2022/167867

PCT Pub. Date: Aug. 11, 2022

(65) Prior Publication Data

US 2024/0174611 A1 May 30, 2024

Related U.S. Application Data

(60) Provisional application No. 63/273,405, filed on Oct. 29, 2021, provisional application No. 63/191,405, filed on May 21, 2021, provisional application No. 63/146,789, filed on Feb. 8, 2021.

(51) Int. Cl.

| | |
|---|---|
| ***C07D 211/96*** | (2006.01) |
| ***C07C 311/29*** | (2006.01) |
| ***C07D 205/04*** | (2006.01) |
| ***C07D 205/12*** | (2006.01) |
| ***C07D 207/09*** | (2006.01) |
| ***C07D 207/14*** | (2006.01) |
| ***C07D 207/48*** | (2006.01) |
| ***C07D 209/52*** | (2006.01) |
| ***C07D 211/28*** | (2006.01) |
| ***C07D 211/56*** | (2006.01) |
| ***C07D 211/58*** | (2006.01) |
| ***C07D 211/76*** | (2006.01) |
| ***C07D 231/56*** | (2006.01) |
| ***C07D 261/10*** | (2006.01) |
| ***C07D 309/14*** | (2006.01) |
| ***C07D 311/68*** | (2006.01) |
| ***C07D 311/96*** | (2006.01) |
| ***C07D 401/04*** | (2006.01) |
| ***C07D 401/12*** | (2006.01) |
| ***C07D 405/04*** | (2006.01) |
| ***C07D 409/04*** | (2006.01) |

(Continued)

(52) U.S. Cl.

CPC .......... *C07D 211/96* (2013.01); *C07C 311/29* (2013.01); *C07D 205/04* (2013.01); *C07D 205/12* (2013.01); *C07D 207/09* (2013.01); *C07D 207/14* (2013.01); *C07D 207/48* (2013.01); *C07D 209/52* (2013.01); *C07D 211/28* (2013.01); *C07D 211/56* (2013.01); *C07D 211/58* (2013.01); *C07D 211/76* (2013.01); *C07D 231/56* (2013.01); *C07D 261/10* (2013.01); *C07D 309/14* (2013.01); *C07D 311/68* (2013.01); *C07D 311/96* (2013.01); *C07D 401/04* (2013.01); *C07D 401/12* (2013.01); *C07D 405/04* (2013.01); *C07D 409/04* (2013.01); *C07D 417/04* (2013.01); *C07D 451/04* (2013.01); *C07C 2601/02* (2017.05); *C07C 2601/08* (2017.05); *C07C 2601/14* (2017.05); *C07C 2601/18* (2017.05); *C07C 2602/08* (2017.05); *C07C 2602/10* (2017.05); *C07C 2603/74* (2017.05)

(58) Field of Classification Search

CPC .................................................... C07D 211/96
See application file for complete search history.

(56) References Cited

U.S. PATENT DOCUMENTS

| | | | |
|---|---|---|---|
| 5,387,709 A | 2/1995 | Lardy et al. |
| 6,670,385 B1 | 12/2003 | Fischer et al. |
| 2002/0061480 A1 | 5/2002 | Gibson |

(Continued)

FOREIGN PATENT DOCUMENTS

| | | |
|---|---|---|
| CA | 2682849 A1 | 10/2008 |
| CN | 105481790 A | 4/2016 |

(Continued)

OTHER PUBLICATIONS

"STN International RN: 1834102-60-1", N-3-azetidinyl-2-bromo-4-(trifluoromethoxy)benzenesulfonamide hydrochloride, Dec. 22, 2015.

(Continued)

*Primary Examiner* — Golam M Shameem
(74) *Attorney, Agent, or Firm* — Blank Rome LLP

(57) ABSTRACT

The present disclosure relates in part to chemical modulators of protein phosphatase 2A (PP2A). The compounds of the present disclosure are useful in treating, preventing, and/or ameliorating cancer, diabetes, autoimmune disease, solid organ transplant rejection, graft vs host disease, chronic obstructive pulmonary disease (COPD), non-alcoholic fatty liver disease, abdominal aortic aneurysm, chronic liver disease, heart failure, neurodegenerative disease, and cardiac hypertrophy.

28 Claims, No Drawings

(51) Int. Cl.

| | |
|---|---|
| *C07D 417/04* | (2006.01) |
| *C07D 451/04* | (2006.01) |

(56) References Cited

U.S. PATENT DOCUMENTS

| | | | |
|---|---|---|---|
| 2004/0220216 | A1 | 11/2004 | Arrington et al. |
| 2004/0235832 | A1 | 11/2004 | Wu et al. |
| 2006/0019967 | A1 | 1/2006 | Wu et al. |
| 2007/0244328 | A1 | 10/2007 | Wang et al. |
| 2009/0036993 | A1 | 2/2009 | Nagano et al. |
| 2009/0042851 | A1 | 2/2009 | Despeyroux et al. |
| 2009/0170898 | A1 | 7/2009 | Bengtsson et al. |
| 2011/0230350 | A1 | 9/2011 | Frackenpohl et al. |
| 2012/0004363 | A1 | 1/2012 | Urushihara et al. |
| 2017/0001949 | A1 | 1/2017 | Xie et al. |
| 2017/0172951 | A1 | 6/2017 | Yang et al. |
| 2017/0197981 | A1 | 7/2017 | Shaw et al. |
| 2017/0226086 | A1 | 8/2017 | Li et al. |
| 2019/0201356 | A1 | 7/2019 | Yang et al. |
| 2020/0164047 | A1 | 5/2020 | Minucci et al. |
| 2020/0308122 | A1 | 10/2020 | Huang et al. |
| 2023/0210834 | A1 | 7/2023 | Fujimura et al. |

FOREIGN PATENT DOCUMENTS

| | | | |
|---|---|---|---|
| CN | 110835334 | A | 2/2020 |
| CN | 112409331 | A | 2/2021 |
| DE | 19717898 | A1 | 10/1998 |
| DE | 19924668 | A1 | 11/2000 |
| EP | 0472449 | A2 | 2/1992 |
| EP | 1524976 | A1 | 4/2005 |
| EP | 1979318 | A1 | 10/2008 |
| EP | 2681190 | A1 | 1/2014 |
| EP | 3538070 | A1 | 9/2019 |
| EP | 3731839 | A1 | 11/2020 |
| JP | 2001172257 | A | 6/2001 |
| KR | 20150060224 | A | 6/2015 |
| KR | 20210043801 | A | 4/2021 |
| WO | 9303013 | A1 | 2/1993 |
| WO | 9950205 | A2 | 10/1999 |
| WO | 02051831 | A1 | 7/2002 |
| WO | 2004085385 | A2 | 10/2004 |
| WO | 2004085420 | A1 | 10/2004 |
| WO | 2004096795 | A2 | 11/2004 |
| WO | 2005035551 | A2 | 4/2005 |
| WO | 2005044797 | A1 | 5/2005 |
| WO | 2005115374 | A1 | 12/2005 |
| WO | 2005115382 | A1 | 12/2005 |
| WO | 2005116001 | A1 | 12/2005 |
| WO | 2006024779 | A1 | 3/2006 |
| WO | 2006030211 | A2 | 3/2006 |
| WO | 2006047479 | A2 | 5/2006 |
| WO | 2006047503 | A2 | 5/2006 |
| WO | 2006048771 | A1 | 5/2006 |
| WO | 2006132348 | A1 | 12/2006 |
| WO | 2007002635 | A2 | 1/2007 |
| WO | 2007013974 | A2 | 2/2007 |
| WO | 2007084319 | A2 | 7/2007 |
| WO | 2007085718 | A1 | 8/2007 |
| WO | 2007129527 | A1 | 11/2007 |
| WO | 2007140317 | A2 | 12/2007 |
| WO | 2008022281 | A1 | 2/2008 |
| WO | 2008022286 | A2 | 2/2008 |
| WO | 2008061016 | A1 | 5/2008 |
| WO | 2009011850 | A2 | 1/2009 |
| WO | 2009124962 | A2 | 10/2009 |
| WO | 2009129267 | A2 | 10/2009 |
| WO | 2009143150 | A2 | 11/2009 |
| WO | 2010074776 | A2 | 7/2010 |
| WO | 2010104103 | A1 | 9/2010 |
| WO | 2010125831 | A1 | 11/2010 |
| WO | 2010133312 | A1 | 11/2010 |
| WO | 2011032169 | A2 | 3/2011 |
| WO | 2011060397 | A1 | 5/2011 |
| WO | 2011082400 | A2 | 7/2011 |
| WO | 2011103055 | A1 | 8/2011 |
| WO | 2011109059 | A1 | 9/2011 |
| WO | 2012016133 | A2 | 2/2012 |
| WO | 2012027481 | A1 | 3/2012 |
| WO | 2012080727 | A2 | 6/2012 |
| WO | 2012080729 | A2 | 6/2012 |
| WO | 2012129562 | A2 | 9/2012 |
| WO | 2013003586 | A1 | 1/2013 |
| WO | 2013066717 | A1 | 5/2013 |
| WO | 2013127268 | A1 | 9/2013 |
| WO | 2013130943 | A1 | 9/2013 |
| WO | 2014052622 | A1 | 4/2014 |
| WO | 2014078479 | A2 | 5/2014 |
| WO | 2014181287 | A1 | 11/2014 |
| WO | 2014194127 | A1 | 12/2014 |
| WO | 2015003816 | A2 | 1/2015 |
| WO | 2015051149 | A1 | 4/2015 |
| WO | 2015103527 | A1 | 7/2015 |
| WO | 2015130905 | A1 | 9/2015 |
| WO | 2015138496 | A1 | 9/2015 |
| WO | 2015138500 | A1 | 9/2015 |
| WO | 2015179414 | A1 | 11/2015 |
| WO | 2016128317 | A1 | 8/2016 |
| WO | 2016210134 | A1 | 12/2016 |
| WO | 2017044567 | A1 | 3/2017 |
| WO | 2017044569 | A1 | 3/2017 |
| WO | 2017044571 | A1 | 3/2017 |
| WO | 2017044572 | A1 | 3/2017 |
| WO | 2017044575 | A1 | 3/2017 |
| WO | 2017066705 | A1 | 4/2017 |
| WO | 2017176756 | A1 | 10/2017 |
| WO | 2018089358 | A1 | 5/2018 |
| WO | 2018211137 | A1 | 11/2018 |
| WO | 2018218087 | A1 | 11/2018 |
| WO | 2019025153 | A1 | 2/2019 |
| WO | 2019036562 | A1 | 2/2019 |
| WO | 2019056120 | A1 | 3/2019 |
| WO | 2019094732 | A1 | 5/2019 |
| WO | 2019137201 | A1 | 7/2019 |
| WO | 2019204505 | A2 | 10/2019 |
| WO | 2020123675 | A1 | 6/2020 |
| WO | 2020150439 | A1 | 7/2020 |
| WO | 2020172324 | A1 | 8/2020 |
| WO | 2021001825 | A1 | 1/2021 |
| WO | 2021007478 | A1 | 1/2021 |
| WO | 2021039824 | A1 | 3/2021 |
| WO | 2021076617 | A1 | 4/2021 |
| WO | 2021145729 | A1 | 7/2021 |
| WO | 2021150695 | A1 | 7/2021 |
| WO | 2021150697 | A1 | 7/2021 |
| WO | 2021150700 | A1 | 7/2021 |
| WO | 2021155253 | A1 | 8/2021 |
| WO | 2021170913 | A1 | 9/2021 |
| WO | 2021186023 | A1 | 9/2021 |
| WO | 2021188949 | A1 | 9/2021 |
| WO | 2022040604 | A1 | 2/2022 |
| WO | 2022086986 | A1 | 4/2022 |
| WO | 2022167866 | A1 | 8/2022 |

OTHER PUBLICATIONS

"STN International RN: 1835214-17-9", benzenesulfonamide, N-(1-(aminomethyl)-2-methylcyclohexyl)-4-(trifluoromethoxy), Dec. 23, 2015.

"STN International RN: 1835214-18-0", N-(1-(aminomethyl)-2-methylcyclohexyl)-4-(trifluoromethoxy)benzenesulfonamide hydrochloride, Dec. 23, 2015.

"STN International RN: 1835398-40-7", N-4-piperidinyl-4-(trifluoromethoxy)benzenesulfonamide hydrochloride, Dec. 24, 2015.

"STN International RN: 1836235-35-8", benzenesulfonamide, N-(3-methyl-4-piperidinyl)-4-(trifluoromethoxy), Dec. 26, 2015.

"STN International RN: 1836235-36-9", N-(3-methyl-4-piperidinyl)-4-(trifluoromethoxy)benzenesulfonamide hydrochloride, Dec. 26, 2015.

"STN International RN: 1836556-32-1", benzenesulfonamide, 2-bromo-N-3-piperidinyl-4-(trifluoromethoxy), Dec. 26, 2015.

(56) References Cited

OTHER PUBLICATIONS

"STN International RN: 1836556-33-2", 2-bromo-N-3-piperidinyl-4-(trifluoromethoxy)benzenesulfonamide hydrochloride, Dec. 26, 2015.
"STN International RN: 1836793-24-8", benzenesulfonamide, N-(4-methyl-3-piperidinyl)-4-(trifluoromethoxy), Dec. 27, 2015.
"STN International RN: 1836793-25-9", N-(4-methyl-3-piperidinyl)-4-(trifluoromethoxy)benzenesulfonamide hydrochloride, Dec. 27, 2015.
"STN International RN: 1836882-81-5", benzenesulfonamide, 3-chloro-4-(difluoromethoxy)-N-(3-methyl_4-piperidinyl), Dec. 27, 2015.
"STN International RN: 1836882-82-6", 3-chloro-4-(difluoromethoxy)-N-(3-methyl-4-piperidinyl)benzenesulfonamide hydrochloride, Dec. 27, 2015.
"STN International RN: 1839250-62-2", 2-bromo-N-(2-methyl-3-piperidinyl)-4-(trifluoromethoxy)benzenesulfonamide, Jan. 1, 2016.
"STN International RN: 1839250-63-3", 2-bromo-N-(2-methyl-3-piperidinyl)-4-(trifluoromethoxy)benzenesulfonamide hydrochloride, Jan. 1, 2016.
"STN International RN: 1840001-33-3", benzenesulfonamide, 2-bromo-N-4-piperidinyl-4-(trifluoromethoxy), Jan. 2, 2016.
"STN International RN: 1840001-34-4", 2-bromo-N-4-piperidinyl-4-(trifluoromethoxy)benzenesulfonamide hydrochloride, Jan. 2, 2016.
"STN International RN: 1917866-54-6", benzenesulfonamide, 3-chloro-4-(difluoromethoxy)-N-(3S)-3-piperidinyl, May 26, 2016.
"STN International RN: 1917989-79-7", benzenesulfonamide, 3-chloro-4-(difluoromethoxy)-N-(3R)-3-piperidinyl, May 26, 2016.
"STN International RN: 1918385-67-7", benzenesulfonamide, N-(3R)-3-piperidinyl-4-(trifluoromethoxy), May 27, 2016.
"STN International RN: 1921264-84-7", benzenesulfonamide, N-(3S)-3-piperidinyl-4-(trifluoromethoxy), May 31, 2016.
"STN International RN: 1927478-14-5", benzenesulfonamide, N-(3-methyl-3-pyrrolidinyl)-4-(trifluoromethoxy), Jun. 9, 2016.
"STN International RN: 1928876-19-0", benzenesulfonamide, 3-chloro-4-(difluoromethoxy)-N-(3-methyl-3-pyrrolidinyl), Jun. 11, 2016.
"STN International RN: 1938716-63-2", benzenesulfonamide, 4-(difluoromethoxy)-3-fluoro-N-(3R)-3-piperidinyl, Jun. 25, 2016.
"STN International RN: 1938716-64-3", 4-(difluoromethoxy)-3-fluoro-N-(3R)-3-piperidinylbenzenesulfonamide hydrochloride, Jun. 25, 2016.
"STN International RN: 1938782-30-9", 3-chloro-4-(difluoromethoxy)-N-(3R)-3-piperidinylbenzenesulfonamide hydrochloride, Jun. 25, 2016.
"STN International RN: 1939003-78-7", benzenesulfonamide, 4-(difluoromethoxy)-3-fluoro-N-(3S)-3-piperidinyl, Jun. 25, 2016.
"STN International RN: 1939003-79-8", 4-(difluoromethoxy)-3-fluoro-N-(3S)-3-piperidinylbenzenesulfonamide hydrochloride, Jun. 25, 2016.
"STN International RN: 1940717-99-6", benzenesulfonamide, 4-(difluoromethoxy)-3-fluoro-N-(2-methyl-3-piperidinyl), Jun. 29, 2016.
"STN International RN: 1940718-00-2", 4-(difluoromethoxy)-3-fluoro-N-(2-methyl-3-piperidinyl)benzenesulfonamide hydrochloride, Jun. 29, 2016.
"STN International RN: 1944826-72-5", benzenesulfonamide, 3-chloro-4-(difluoromethoxy)-N-6-oxaspiro[4.5]dec-9-yl, Jul. 5, 2016.
"STN International RN: 1945215-18-8", benzenesulfonamide, 4-(difluoromethoxy)-3-fluoro-N-1-oxaspiro[5.5]undec-4-yl, Jul. 5, 2016.
"STN International RN: 1953212-04-8", benzenesulfonamide, 3-chloro-4-(difluoromethoxy)-N-(6-oxo-5-azaspiro[3.5]non-9-yl), Jul. 17, 2016.
"STN International RN: 1955710-97-0", benzenesulfonamide, 3-chloro-N-(2-cyclopropyl-6-oxo-3-piperidinyl)-4-(difluoromethoxy), Jul. 21, 2016.
"STN International RN: 2005466-75-9", (2E)-2-propenamide, 3-(2-(4-(((4-difluoromethoxy)phenyl)sulfonylamino)-1-piperidinyl)phenyl)-N-hydroxy, Oct. 5, 2016.
"STN International RN: 2026955-36-0", N-(trans-3-aminocyclobutyl)-4-(difluoromethoxy)-3-fluorobenzenesulfonamide, Nov. 10, 2016.
"STN International RN: 2026955-37-1", N-(trans-3-aminocyclobutyl)-4-(difluoromethoxy)-3-fluorobenzenesulfonamide hydrochloride, Nov. 10, 2016.
"STN International RN: 2027001-79-0", 3-chloro-4-(difluoromethoxy)-N-(3S)-3-piperidinylbenzenesulfonamide hydrochloride, Nov. 10, 2016.
"STN International RN: 2032677-58-8", N-(2-(aminomethyl)cyclopentyl)-4-(difluoromethoxy)-3-fluorobenzenesulfonamide hydrochloride, Nov. 17, 2016.
"STN International RN: 2035358-54-2", benzenesulfonamide, N-(3-aminocyclohexyl)-4-(difluoromethoxy)-3-fluoro, Nov. 22, 2016.
"STN International RN: 2035358-55-3", N-(3-aminocyclohexyl)-4-(difluoromethoxy)-3-fluorobenzenesulfonamide hydrochloride, Nov. 22, 2016.
"STN International RN: 2035580-97-1", benzenesulfonamide, 4-(difluoromethoxy)-3-fluoro-N-3-pyrrolidinyl, Nov. 23, 2016.
"STN International RN: 2035580-98-2", 4-(difluoromethoxy)-3-fluoro-N-3-pyrrolidinylbenzenesulfonamide hydrochloride, Nov. 23, 2016.
"STN International RN: 2036278-41-6", benzenesulfonamide, N-(1-(aminomethyl)-2-methylcyclohexyl)-4-(difluoromethoxy)-3-fluoro, Nov. 24, 2016.
"STN International RN: 2036278-42-7", N-(1-(aminomethyl)-2-methylcyclohexyl)-4-(difluoromethoxy)-3-fluorobenzenesulfonamide hydrochloride, Nov. 24, 2016.
"STN International RN: 2036612-17-4", N-(6-amino-1,2,3,4-tetrahydro-1-naphthalenyl)-4-(difluoromethoxy)-3-fluorobenzenesulfonamide hydrochloride, Nov. 25, 2016.
"STN International RN: 2036689-83-3", benzenesulfonamide, 3-chloro-4-(difluoromethoxy)-N-(hexahydro-1H-azepin-3-yl), Nov. 25, 2016.
"STN International RN: 2036976-88-0", cyclohexanecarboxylic acid, 4-(((3-chloro-4-(difluoromethoxy)phenyl)sulfonyl) amino), Nov. 25, 2016.
"STN International RN: 2037362-85-7", N-(1-(aminomethyl)cyclopentyl)-4-(difluoromethoxy)-3-fluorobenzensulfonamide, Nov. 26, 2016.
"STN International RN: 2037362-86-8", N-(1-(aminomethyl)cyclopentyl)-4-(difluoromethoxy)-3-fluorobenzenesulfonamide hydrochloride, Nov. 26, 2016.
"STN International RN: 2037369-02-9", N-(4-aminocyclohexyl)-4-(difluoromethoxy)-3-fluorobenzenesulfonamide, Nov. 26, 2016.
"STN International CAS Registry No. 1210867-15-4", Benzenesulfonamide, N-[[1-(2-thienyl)cyclopentyl]methyl]-4-(trifluoromethoxy)-, Mar. 17, 2010.
"STN International CAS Registry No. 1223206-05-0", Benzenepropanoic acid, 3-bromo-β-[[[4-(trifluoromethoxy)phenyl]sulfonyl]amino]-, methyl ester, May 14, 2010.
"STN International CAS Registry No. 1384316-03-3", Cyclohexanepropanoic acid, β-[[[4-(trifluoromethoxy)phenyl]sulfonyl]amino]-, methyl ester, Jul. 25, 2012.
"STN International RN: 1008211-62-8", benzenesulfonamide, N-(hexahydro-2-oxo-1H-azepin-3-yl)-4-(trifluoromethoxy), Mar. 16, 2008.
"STN International RN: 1012985-67-9", benzenesulfonamide, N-(4-methylcyclohexyl)-4-(trifluoromethoxy), Apr. 9, 2008.
"STN International RN: 1013884-12-2", benzenesulfonamide, N-(tetrahydro-2-oxo-3-thienyl)-4-(trifluoromethoxy), Apr. 11, 2008.
"STN International RN: 1016468-44-2", benzenesulfonamide, 4-(trifluoromethoxy)-N-(4-(trifluoromethyl)cyclohexyl), Apr. 22, 2008.
"STN International RN: 1022840-07-8", benzenesulfonamide, N-(2,3-dihydro-1H-inden-2-yl)-4-(trifluoromethoxy), May 27, 2008.
"STN International RN: 1023174-16-4", benzenesulfonamide, N-(1-(phenylmethyl)-3-pyrrolidinyl)-4-(trifluoromethoxy), May 28, 2008.
"STN International RN: 1030749-77-9", cycloheptanecarboxylic acid, 1-(((4-(trifluoromethoxy)phenyl)sulfonyl)amino), methyl ester, Jun. 26, 2008.
"STN International RN: 1031495-12-1", benzenesulfonamide, N-(1-phenylcyclobutyl)-4-(trifluoromethoxy), Jun. 29, 2008.
"STN International RN: 1037233-50-3", N-(4-(aminomethyl)-4-(3-chlorophenyl)cyclohexyl)-4-(trifluoromethoxy)benzensulfonamide hydrochloride, Jul. 30, 2008.

(56) References Cited

OTHER PUBLICATIONS

"STN International RN: 1037363-47-5", benzenesulfonamide, N-(4-(aminomethyl)-4-(3-chlorophenyl)cyclohexyl)-4-(trifluoromethoxy), Jul. 31, 2008.
"STN International RN: 1057934-95-8", cyclohexanecarboxylic acid, 1-(((4-(trifluoromethoxy)phenyl)sulfonyl)amino), Oct. 7, 2008.
"STN International RN: 1147639-50-6", benzenesulfonamide, N-(1-acetyl-4-piperidinyl)-3-chloro-4-(difluoromethoxy), May 30, 2009.
"STN International RN: 1153138-83-0", benzenesulfonamide, N-(3-aminocyclobutyl)-3-chloro-4-(difluoromethoxy), Jun. 7, 2009.
"STN International RN: 1153766-50-7", benzenesulfonamide, N-4-piperidinyl-4-(trifluoromethoxy), Jun. 8, 2009.
"STN International RN: 1155139-89-1", benzenesulfonamide, 3-chloro-4-(difluoromethoxy)-N-4-piperidinyl, Jun. 10, 2009.
"STN International RN: 1156834-46-6", benzenesulfonamide, N-(2-aminocyclopropyl)-3-chloro-4-(difluoromethoxy), Jun. 14, 2009.
"STN International RN: 1157050-68-4", benzenesulfonamide, N-(2-aminocyclopropyl)-4-(trifluoromethoxy), Jun. 14, 2009.
"STN International RN: 1157097-34-1", benzenesulfonamide, N-(3-aminocyclobutyl)-4-(trifluoromethoxy), Jun. 14, 2009.
"STN International RN: 1197821-89-8", N-(1-(phenylmethyl)-4-piperidinyl)-4-(trifluoromethoxy)benzenesulfonamide hydrochloride, Dec. 16, 2009.
"STN International RN: 1198001-12-5", benzenesulfonamide, N-(1-(phenylmethyl)-4-piperidinyl)-4-(trifluoromethoxy), Dec. 17, 2009.
"STN International RN: 1240810-44-9", 1-piperidinecarboxylic acid, 4-(((4-(trifluoromethoxy)phenyl)sulfonyl)amino), ethyl ester, Sep. 14, 2010.
"STN International RN: 1259096-39-3", benzenesulfonamide, N-(1-ethyl-3-piperidinyl)-4-(trifluoromethoxy), Jan. 12, 2011.
"STN International RN: 1279004-30-6", benzenesulfonamide, 3-chloro-4-(difluoromethoxy)-N-(2,3-dihydro-1H-inden-1-yl), Apr. 12, 2011.
"STN International RN: 1279004-32-8", benzenesulfonamide, 3-chloro-N-(1-cyclopropyl-4-piperidinyl)-4-(difluoromethoxy), Apr. 12, 2011.
"STN International RN: 1279628-52-2", benzenesulfonamide, N-(1-benzoyl-3-piperidinyl)-3-chloro-4-(difluoromethoxy), Apr. 13, 2011.
"STN International RN: 1288719-53-8", benzenesulfonamide, N-(1-benzoyl-3-piperidinyl)-4-(trifluoromethoxy), May 1, 2011.
"STN International RN: 1294971-39-3", benzenesulfonamide, 3-chloro-4-(difluoromethoxy)-N-(3,4-dihydro-2H-1-benzothiopyran-4-yl), May 15, 2011.
"STN International RN: 1295538-12-3", benzenesulfonamide, 3-chloro-4-(difluoromethoxy)-N-(6-fluoro-3,4-dihydro-2H-1-benzothiopyran-4-yl), May 16, 2011.
"STN International RN: 1300350-10-0", benzenesulfonamide, 3-chloro-4-(difluoromethoxy)-N-(1-(2-fluorobenzoyl)-4-piperidinyl), Aug. 30, 2020.
"STN International RN: 1301100-80-0", benzenesulfonamide, N-(1-(3-methyl-1-oxobutyl)-4-piperidinyl)-4-(trifluoromethoxy), May 26, 2011.
"STN International RN: 1301752-30-6", benzenesulfonamide, 3-chloro-4-(difluoromethoxy)-N-(2-(trifluoromethyl)cyclohexyl), May 27, 2011.
"STN International RN: 1301752-68-0", cyclohexanecarboxylic acid, 1-(((3-chloro-4-(difluoromethoxy)phenyl)sulfonyl)amino), methyl ester, May 27, 2011.
"STN International RN: 1302196-50-4", cyclohexanecarboxamide, 1-(((3-chloro-4-(difluoromethoxy)phenyl)sulfonyl)amino)-N-ethyl, May 29, 2011.
"STN International RN: 1302760-43-5", benzenesulfonamide, N-(1-(2-pyrimidinyl)-3-piperidinyl)-4-(trifluoromethoxy), May 30, 2011.
"STN International RN: 1318033-07-6", benzenesulfonamide, 3-chloro-4-(difluoromethoxy)-N-(1-ethyl-3-piperidinyl), Aug. 15, 2011.
"STN International RN: 1324111-71-8", Benzenesulfonamide, N-(1-acetyl-4-piperidinyl)-4-(trifluoromethoxy), Aug. 28, 2011.
"STN International RN: 1331730-51-8", benzenesulfonamide, N-(1-(4-bromophenyl)cyclobutyl)-4-(difluoromethoxy), Sep. 12, 2011.
"STN International RN: 1359172-00-1", benzenesulfonamide, 4-(difluoromethoxy)-N-(4-hydroxy-1,3-dimethyl-2-cyclohexen-1-yl), Mar. 1, 2012.
"STN International RN: 1371052-76-4", benzenesulfonamide, 3-chloro-4-(difluoromethoxy)-N-(hexahydro-2-oxo-1H-azepin-3-yl), Apr. 29, 2012.
"STN International RN: 1374555-39-1", benzenesulfonamide, 4-(difluoromethoxy)-N-(1,3-dimethyl-4-oxo-2-cyclohexen-1-yl), May 25, 2012.
"STN International RN: 1379769-13-7", benzenesulfonamide, N-((1R,2S,3R,5R)-2,3-dihydroxy-5-phenylcyclopentyl)-4-(trifluoromethoxy), Jun. 22, 2012.
"STN International RN: 1384361-68-5", 1-piperidinecarboxylic acid, 4-cyano-4-(((4-(trifluoromethoxy)phenyl)sulfonyl)amino), ethyl ester, Jul. 25, 2012.
"STN International RN: 1384361-72-1", 3-oxetaneacetic acid, 3-(((4-(trifluoromethoxy)phenyl)sulfonyl)amino), ethyl, Jul. 25, 2012.
"STN International RN: 1384361-74-3", cyclopropanecarboxylic acid, 1-(((4-(trifluoromethoxy)phenyl)sulfonyl)amino), ethyl ester, Jul. 25, 2012.
"STN International RN: 1384361-76-5", cyclohexanecarboxylic acid, 4-methoxy-1-(((4-(trifluoromethoxy)phenyl)sulfonyl)amino), methyl ester, Jul. 25, 2012.
"STN International RN: 1384361-80-1", cyclohexanecarboxylic acid, 1-(((4-(trifluoromethoxy)phenyl)sulfonyl)amino), methyl ester, Jul. 25, 2012.
"STN International RN: 1384371-05-4", 1-piperidinecarboxylic acid, 4-cyano-4-(((4-(difluoromethoxy)phenyl)sulfonyl)amino), ethyl ester, Jul. 25, 2012.
"STN International RN: 2104048-13-5", Benzenesulfonamide, N-[(1S,2R,3S,5R)-2-(hydroxymethyl)-2'-oxo-3,5-diphenyl-1'-(phenylmethyl)spiro[cyclopentane-1,3'-[3H]indole]-3(1'H)-yl]-4-methyl, Jul. 29, 2017.
"STN International RN: 2227491-80-5", Benzenesulfonamide, 3-(cyclopentyloxy)-N-[1-[4-[(2,4-dioxo-1-imidazolidinyl)methyl]phenyl]cyclopentyl]-, Jun. 23, 2018.
"STN International RN: 2399101-06-3", benzenesulfonamide, N(1-(3-methylphenyl)cyclopentyl)-, Jan. 4, 2020.
"STN International RN: 2415532-08-8", benzenesulfonamide, N-(1-(tetrahydro-2H-pyran-4-yl)-3-pyrrolidinyl)-4-(trifluoromethoxy), May 3, 2020.
"STN International RN: 2421307-28-8", benzenesulfonamide, N-(2-oxo-1-phenyl-3-azetidinyl)-4-(trifluoromethoxy), Jun. 12, 2020.
"STN International RN: 2421517-19-1", benzenesulfonamide, 4-(difluoromethoxy)-3-fluoro-N-(2-oxo-1-phenyl-3-azetidinyl), Jun. 12, 2020.
"STN International RN: 2424873-51-6", benzenesulfonamide, 4-(difluoromethoxy)-3-fluoro-N-(3-methyl-3-oxetanyl), Jun. 16, 2020.
"STN International RN: 2425992-21-6", benzenesulfonamide, N-cyclopentyl-4-(difluoromethoxy)-3-fluoro, Jun. 17, 2020.
"STN International RN: 2427280-42-8", benzenesulfonamide, N-(3-methyl-3-oxetanyl)-4-(trifluoromethoxy), Jun. 19, 2020.
"STN International RN: 2428635-50-9", benzenesulfonamide, N-cyclohexyl-4-(difluoromethoxy)-3-fluoro, Jun. 19, 2020.
"STN International RN: 2430180-87-1", benzenesulfonamide, 4-(difluoromethoxy)-3-fluoro-N-(2-methylcyclopentyl), Jun. 21, 2020.
"STN International RN: 2431124-16-0", benzenesulfonamide, N-6-oxaspiro[2.5]oct-1-yl-4-(trifluoromethoxy), Jun. 23, 2020.
"STN International RN: 2432566-54-4", benzenesulfonamide, N-(1-methylcyclobutyl)-4-(trifluoromethoxy), Jun. 24, 2020.
"STN International RN: 2432683-19-5", benzenesulfonamide, N-(tetrahydro-2H-thiopyran-3-yl)-4-(trifluoromethoxy), Jun. 24, 2020.
"STN International RN: 2435428-57-0", benzenesulfonamide, N-(tetrahydro-4-methyl-3-thienyl)-4-(trifluoromethoxy), Jun. 27, 2020.
"STN International RN: 2451533-30-3", benzenesulfonamide, 4-(difluoromethoxy)-3-fluoro-N-(1-methylcyclobutyl), Jul. 31, 2020.
"STN International RN: 2454028-78-3", benzenesulfonamide, N-(3-methylcyclobutyl)-4-(trifluoromethoxy), Aug. 8, 2020.
"STN International RN: 2458083-78-6", N-(2-methyltetrahydrothiophen-3-yl)-4-(trifluoromethoxy)benzenesulfonamide, Aug. 15, 2020.
"STN International RN: 2462729-54-8", benzenesulfonamide, N-(tetrahydro-2,2-dimethyl-2H-pyran-4-yl)-4-(trifluoromethoxy), Aug. 28, 2020.
"STN International RN: 2463520-01-4", N-(tetrahydro-2H-thiopyran-4-yl)-4-(trifluoromethoxy)benzenesulfonamide, Aug. 28, 2020.

(56) References Cited

OTHER PUBLICATIONS

"STN International RN: 2463715-62-8", N-(2-methyltetrahydro-2H-pyran-4-yl)-4-(trifluoromethoxy)benzenesulfonamide, Aug. 28, 2020.
"STN International RN: 2464213-72-5", N-(tetrahydro-2,6-dimethyl-2H-pyran-4-yl)-4-(trifluoromethoxy)-benzenesulfonamide, Aug. 28, 2020.
"STN International RN: 2465783-39-3", N-(5-methyltetrahydrothiophen-3-yl)-4-(trifluoromethoxy)benzenesulfonamide, Aug. 30, 2020.
"STN International RN: 2465983-77-9", N-(4-methyltetrahydro-2H-pyran-4-yl)-4-(trifluoromethoxy)benzenesulfonamide, Aug. 30, 2020.
"STN International RN: 2467609-19-2", N-(tetrahydro-3-methyl-2H-pyran-3-yl)-4-(trifluoromethoxy)-benzenesulfonamide, Aug. 30, 2020.
"STN International RN: 2467659-90-9", Registry [Database online] ACS [retrieved Aug. 30, 2021], Benzenesulfonamide, N-(tetrahydro-2H-pyran-3-yl)-4-(trifluoromethoxy)-; and a list of relevant compounds, Aug. 30, 2020.
"STN International RN: 37459-37-3", Benzenesulfonamide, N-(2,3-dihydro-3-oxo-1-phenyl-1H-isoindol-1-yl)-4-methyl, Nov. 16, 1984.
"STN International RN: 524045-71-4", benzenesulfonamide, N-((3R)-1-hydroxy-2-oxo-3-pyrrolidinyl)-4-(trifluoromethoxy), Jun. 2, 2003.
"STN International RN: 78388-16-6", Benzenesulfonamide, 4-methyl-N-(9-phenyl-9H-fluoren-9-yl)-, Nov. 16, 1984.
"STN International RN: 855932-85-3", Acetamide, N-[4-[(2,5-dioxo-4-phenyl-4-imidazolidinyl)amino]sulfonyl]phenyl]-, Jul. 19, 2005.
"STN International RN: 857753-13-0", Benzenesulfonamide, 4-amino-N-(2,5-dioxo-4-phenyl-4-imidazolidinyl)-, Aug. 1, 2005.
"STN International RN: 858206-47-0", Hydantoin, 5-(p-nitrobenzenesulfonamido)-5-phenyl, Aug. 4, 2005.
"STN International RN: 879193-93-8", Benzenesulfonamide, N-[1-(2,3-dihydro-1,4-benzodioxin-6-yl)cyclopentyl]-4-(1-pyrrolidinylsulfonyl)-, Apr. 4, 2006.
"STN International RN: 92387-15-0", Benzenesulfonamide, 4-methyl-N-[9-(4-methylphenyl)-9H-fluoren-9-yl]-, Dec. 17, 1984.
"STN International RN: 924420-24-6", Benzenesulfonamide, N-[1-(2,3-dihydro-1,4-benzodioxin-6-yl)cyclopentyl]-4-ethoxy, Mar. 2, 2007.
"STN International RN: 950009-63-9", 2H-1,4-Benzoxazine-6-sulfonamide, N-[1-(2,3-dihydro-1,4-benzodioxin-6-yl)cyclopentyl]-3,4-dihydro-3-oxo, Oct. 10, 2007.
"STN International RN: 958589-30-5", 6-Quinolinesulfonamide, 1,2,3,4-tetrahydro-2-oxo-N-(1-phenylcyclopentyl)-, Dec. 18, 2007.
Chupak, et al., "Structure activity relationship studies on chemically non-reactive glycine sulfonamide inhibitors of diacylglycerol lipase", Bioorg Med Chem, 24(7), 2016, pp. 1455-1468.
Dang, et al., "Structure Optimization of Aloperine Derivatives as HIV-1 Entry Inhibitors", ACS Med Chem Lett, vol. 8, No. 11, 2017, pp. 1199-1203.
Farrington , et al., "Protein Phosphatase 2A Activation as a Therapeutic Strategy for Managing MYC-driven Cancers", J Biol Chem, vol. 295, No. 3, 2020, pp. 757-770.
Fedida-Metula, et al., "Lipid rafts couple store-operated Ca21 entry to constitutive activation of PKB/Akt in a Ca21/calmodulin-, Src- and PP2A-mediated pathway and promote melanoma tumor growth", Carcinogenesis, vol. 33, No. 4, 2012, pp. 740-750.
Garsi , et al., "Design, synthesis and anticancer activity of constrained sphingolipid-phenoxazine/phenothiazine hybrid constructs targetig protein phosphatase 2A", Bioorg Med Chem Lett, vol. 29, No. 18, 2019, pp. 2681-2685.
Kastrinsky , et al., "Reengineered tricyclic anti-cancer agents", Bioorg Med Chem, vol. 23, Sep. 11, 2015, pp. 6528-6534.
Kauko , et al., "Phosphoproteome and drug-response effects mediated by the three protein phosphatase 2A inhibitor proteins CIP2A, Set, and PME-1", J Biol Chem, vol. 295, No. 13, 2020, pp. 4194-4211.
Leonard , et al., "Selective PP2A Enhancement through Biased Heterotrimer Stabilization", Cell, vol. 181, No. 3, 2020, pp. 688-701.
International Search Report & Written Opinion dated Jun. 2, 2022 for corresponding PCT International Application No. PCT/IB2022/000060.
"STN International RN: 1384371-07-6", 3-oxetaneacetic acid, 3-(((4-(difluoromethoxy)phenyl)sulfonyl)amino), ethyl ester, Jul. 25, 2012.
"STN International RN: 1384371-08-7", cyclopropanecarboxylic acid, 1-(((4-(difluoromethoxy)phenyl)sulfonyl)amino), ethyl ester, Jul. 25, 2012.
"STN International RN: 1384371-09-8", cyclohexanecarboxylic acid, 1-(((4-(difluoromethoxy)phenyl)sulfonyl)amino)-4-methoxy, methyl ester, Jul. 25, 2012.
"STN International RN: 1384371-11-2", cyclohexanecarboxylic acid, 1-(((4-(difluoromethoxy)phenyl)sulfonyl)amino), methyl ester, Jul. 25, 2012.
"STN International RN: 1384522-26-2", cyclohexanecarboxylic acid, 2-(((4-(trifluoromethoxy)phenyl)sulfonyl)amino), ethyl ester, Jul. 27, 2012.
"STN International RN: 1384522-28-4", cyclopentanecarboxylic acid, 2-(((4-(trifluoromethoxy)phenyl)sulfonyl)amino), ethyl ester, Jul. 27, 2012.
"STN International RN: 1384522-29-5", 3-cyclohexene-1-carboxylic acid, 6-(((4-(trifluoromethoxy)phenyl)sulfonyl)amino), ethyl ester, Jul. 27, 2012.
"STN International RN: 1384522-30-8", 3-cyclohexene-1-carboxylic acid, 2-(((4-(trifluoromethoxy)phenyl)sulfonyl)amino), methyl ester, Jul. 27, 2012.
"STN International RN: 1384656-51-2", Cyclohexanecarboxylic acid, 2-(((4-(difluoromethoxy)phenyl)sulfonyl)amino), ethyl ester, Jul. 27, 2012.
"STN International RN: 1384656-54-5", cyclopentanecarboxylic acid, 2-(((4-(difluoromethoxy)phenyl)sulfonyl)amino), ethyl ester, Jul. 27, 2012.
"STN International RN: 1384656-55-6", 3-cyclohexene-1-carboxylic acid, 6-(((4-(difluoromethoxy)phenyl)sulfonyl)amino), ethyl ester, Jul. 27, 2012.
"STN International RN: 1384656-57-8", 3-cyclohexene-1-carboxylic acid, 2-(((4-(difluoromethoxy)phenyl)sulfonyl)amino), methyl ester, Jul. 27, 2012.
"STN International RN: 1396746-43-2", benzenesulfonamide, N-(3-hydroxycyclohexyl)-4-(trifluoromethoxy), Sep. 26, 2012.
"STN International RN: 1406739-41-0", benzenesulfonamide, 3-chloro-4-(difluoromethoxy)-N-3-piperidinyl, Nov. 26, 2012.
"STN International RN: 1422027-52-8", cyclobutanecarboxylic acid, 1-(((4-(difluoromethoxy)phenyl)sulfonyl)amino), Feb. 28, 2013.
"STN International RN: 1427896-73-8", benzenesulfonamide, N-(2-oxo-3-piperidinyl)-4-(trifluoromethoxy), Apr. 11, 2013.
"STN International RN: 1455155-87-9", benzenesulfonamide, 3-chloro-N-cyclopropyl-4-(difluoromethoxy), Oct. 5, 2013.
"STN International RN: 1455186-10-3", benzenesulfonamide, 3-chloro-4-(difluoromethoxy)-N-3-pyrrolidinyl, Oct. 5, 2013.
"STN International RN: 1455759-25-7", benzenesulfonamide, N-3-pyrrolidinyl-4-(trifluoromethoxy), Oct. 6, 2013.
"STN International RN: 1455987-34-4", benzenesulfonamide, N-cyclopropyl-4-(trifluoromethoxy), Oct. 6, 2013.
"STN International RN: 1457229-84-3", benzenesulfonamide, 3-chloro-N-cyclopentyl-4-(difluoromethoxy), Oct. 13, 2013.
"STN International RN: 1457886-95-1", benzenesulfonamide, 3-chloro-N-cyclohexyl-4-(difluoromethoxy), Oct. 14, 2013.
"STN International RN: 1466635-39-1", benzenesulfonamide, N-(2-aminocyclopentyl)-3-chloro-4-(difluoromethoxy), Nov. 1, 2013.
"STN International RN: 1468980-13-3", benzenesulfonamide, N-(3-hydroxycyclobutyl)-4-(trifluoromethoxy), Nov. 5, 2013.
"STN International RN: 1479603-33-2", benzenesulfonamide, N-3-piperidinyl-4-(trifluoromethoxy), Nov. 24, 2013.
"STN International RN: 1480450-62-1", benzenesulfonamide, 3-chloro-4-(difluoromethoxy)-N-(3-hydroxycyclobutyl), Nov. 26, 2013.
"STN International RN: 1482261-78-8", benzenesulfonamide, N-(2-aminocyclopentyl)-4-(trifluoromethoxy), Nov. 28, 2013.
"STN International RN: 1484552-50-2", benzenesulfonamide, N-3-azetidinyl-4-(trifluoromethoxy), Dec. 2, 2013.
"STN International RN: 1486228-13-0", benzenesulfonamide, N-3-azetidinyl-3-chloro-4-(difluoromethoxy), Dec. 4, 2013.

(56) References Cited

OTHER PUBLICATIONS

"STN International RN: 1567799-73-8", N-((4S)-4-methoxy-3-pyrrolidinyl)-4-(trifluoromethoxy)benzenesulfonamide hydrochloride, Mar. 14, 2014.
"STN International RN: 1569187-16-1", benzenesulfonamide, N-((4S)-4-methoxy-3-pyrrolidinyl)-4-(trifluoromethoxy), Mar. 16, 2014.
"STN International RN: 1572991-84-4", N-(4-aminocyclohexyl)-4-(trifluoromethoxy)benzenesulfonamide hydrochloride, Mar. 29, 2014.
"STN International RN: 1573439-22-1", benzenesulfonamide, N-(4-aminocyclohexyl)-4-(trifluoromethoxy), Mar. 29, 2014.
"STN International RN: 1580839-07-1", N-(2-(aminomethyl)cyclopentyl)-4-(trifluoromethoxy)benzenesulfonamide hydrochloride, Apr. 6, 2014.
"STN International RN: 1581032-23-6", benzenesulfonamide, N-(2-(aminomethyl)cyclopentyl)-4-(trifluoromethoxy), Apr. 8, 2014.
"STN International RN: 1583981-24-1", 3-chloro-4-(difluoromethoxy)-N-3-piperidinylbenzenesulfonamide hydrochloride, Apr. 15, 2014.
"STN International RN: 1584679-64-0", N-(1-(aminomethyl)cyclopentyl)-4-(trifluoromethoxy)benzenesulfonamide hydrochloride, Apr. 16, 2014.
"STN International RN: 1584973-61-4", benzenesulfonamide, N-(1-(aminomethyl)cyclopentyl)-4-(trifluoromethoxy), Apr. 17, 2014.
"STN International RN: 1585110-26-4", N-(2-(aminomethyl)cyclohexyl)-3-chloro-4-(difluoromethoxy)benzenesulfonamide hydrochloride, Apr. 17, 2014.
"STN International RN: 1585416-57-4", benzenesulfonamide, N-(2-(aminomethyl)cyclohexyl)-3-chloro-4-(difluoromethoxy), Apr. 18, 2014.
"STN International RN: 1586812-25-0", N-(4-aminocyclohexyl)-3-chloro-4-(difluoromethoxy)benzenesulfonamide hydrochloride, Apr. 19, 2014.
"STN International RN: 1586820-23-6", N-(2-(aminomethyl)cyclohexyl)-4-(trifluoromethoxy)benzenesulfonamide hydrochloride, Apr. 19, 2014.
"STN International RN: 1587054-82-7", Benzenesulfonamide, N-(4-aminocyclohexyl)-3-chloro-4-(difluoromethoxy), Apr. 20, 2014.
"STN International RN: 1587266-26-9", benzenesulfonamide, N-(2-(aminomethyl)cyclohexyl)-4-(trifluoromethoxy), Apr. 21, 2014.
"STN International RN: 1587538-02-0", N-3-azetidinyl-4-(trifluoromethoxy)benzenesulfonamide hydrochloride, Apr. 22, 2014.
"STN International RN: 1591504-37-8", N-3-piperidinyl-4-(trifluoromethoxy)benzenesulfonamide hydrochloride, Apr. 29, 2014.
"STN International RN: 1591599-44-8", N-(2-(aminomethyl)cyclopentyl)-3-chloro-4-(difluoromethoxy)benzenesulfonamide hydrochloride, Apr. 29, 2014.
"STN International RN: 1591631-03-6", N-3-azetidinyl-3-chloro-4-(difluoromethoxy)benzenesulfonamide hydrochloride, Apr. 29, 2014.
"STN International RN: 1592198-48-5", benzenesulfonamide, N-(2-(aminomethyl)cyclopentyl)-3-chloro-4-(difluoromethoxy), Apr. 30, 2014.
"STN International RN: 1598415-58-7", benzenesulfonamide, N-cycloheptyl-4-(difluoromethoxy), May 7, 2014.
"STN International RN: 2261422-12-0", benzenesulfonamide, N-(3-ethoxyspiro[3.3]hept-1-yl)-4-(trifluoromethoxy), Feb. 1, 2019.
"STN International RN: 2262394-69-2", 1-piperidineacetic acid, 4-(((4-(trifluoromethoxy)phenyl)sulfonyl)amino), Feb. 1, 2019.
"STN International RN: 2305202-95-1", benzenesulfonamide, N-((1R,2R)-2-aminocyclohexyl)-4-(trifluoromethoxy), Apr. 24, 2019.
"STN International RN: 2305202-96-2", N-((1R,2R)-2-aminocyclohexyl)-4-(trifluoromethoxy)benzenesulfonamide hydrochloride, Apr. 24, 2019.
"STN International RN: 2309701-42-4", benzenesulfonamide, N-(3,3-bis(hydroxymethyl)cyclobutyl)-4-(trifluoromethoxy), May 18, 2019.
"STN International RN: 2319047-73-7", benzenesulfonamide, N-(3-oxo-4-isoxazolidinyl)-4-(trifluoromethoxy), Jun. 1, 2019.
"STN International RN: 2323578-47-6", benzenesulfonamide, N-(2,2-dimethyl-3-pyrrolidinyl)-4-(trifluoromethoxy), Jun. 4, 2019.
"STN International RN: 2324042-90-0", benzenesulfonamide, 4-(difluoromethoxy)-N-(2,2-dimethyl-3-pyrrolidinyl)-3-fluoro, Jun. 6, 2019.
"STN International RN: 2324599-92-8", benzenesulfonamide, N-(tetrahydro-2H-pyran-4-yl)-4-(trifluoromethoxy), Jun. 6, 2019.
"STN International RN: 2326291-93-2", benzenesulfonamide, N-7-oxaspiro[3.5]non-1-yl-4-(trifluoromethoxy), Jun. 8, 2019.
"STN International RN: 2327725-40-4", benzenesulfonamide, N-(1,2,3,4-tetrahydro-1-naphthalenyl)-4-(trifluoromethoxy), Jun. 13, 2019.
"STN International RN: 2329297-97-2", benzenesulfonamide, N-(tetrahydro-3-furanyl)-4-(trifluoromethoxy), Jun. 13, 2019.
"STN International RN: 2329667-01-6", benzenesulfonamide, N-(2,3-dihydro-2-hydroxy-1H-inden-1-yl)-4-(trifluoromethoxy), Jun. 13, 2019.
"STN International RN: 2330578-67-9", benzenesulfonamide, N-(2-methylcyclohexyl)-4-(trifluoromethoxy), Jun. 15, 2019.
"STN International RN: 2371381-34-7", benzenesulfonamide, N-(cis-3-hydroxycyclobutyl)-4-(trifluoromethoxy), Sep. 2, 2019.
"STN International RN: 2398034-50-7", benzenesulfonamide, N-(cis-3-ethoxycyclobutyl)-4-(trifluoromethoxy), Jan. 3, 2020.
"STN International RN: 2415472-35-2", benzenesulfonamide, N-(1-(2-pyrazinyl)-3-azetidinyl)-4-(trifluoromethoxy), May 3, 2020.
"STN International RN: 524045-71-4", benzenesulfonamide, N-((3R)-1-hydroxy-2-oxo-3-pyrrolidinyl)-4-(trifluoromethoxy), Aug. 30, 2020.
"STN International RN: 909510-58-3", benzenesulfonamide, N-cyclooctyl-4-(trifluoromethoxy), Oct. 4, 2006.
"STN International RN: 909519-67-1", benzenesulfonamide, N-cyclopentyl-4-(trifluoromethoxy), Oct. 4, 2006.
"STN International RN: 909520-63-4", benzenesulfonamide, N-cycloheptyl-4-(trifluoromethoxy), Oct. 4, 2006.
"STN International RN: 909527-48-6", benzenesulfonamide, N-cyclohexyl-4-(trifluoromethoxy), Oct. 4, 2006.
"STN International RN: 920527-58-8", benzenesulfonamide, N-(2,3-dihydro-1H-inden-1-yl)-4-(trifluoromethoxy), Feb. 12, 2007.
"STN International RN: 931653-74-6", benzenesulfonamide, N-(3,4-dihydro-2H-1-benzopyran-4-yl)-4-(trifluoromethoxy), Apr. 22, 2007.
"STN International RN: 944748-77-0", rac N-((2R,4S)-2-(4-chlorophenyl)-1-(2,4-dichlorophenyl)-4-piperidinyl)-4-(trifluoromethoxy)benzenesulfonamide, Aug. 15, 2007.
"STN International RN: 944751-65-9", benzenesulfonamide, N-(2-(4-chlorophenyl)-1-(2,4-dichlorophenyl)-4-piperidinyl)-4-(trifluoromethoxy), Aug. 15, 2007.
"STN International RN: 949705-66-2", benzenesulfonamide, N-(1-cyclopropyl-4-piperidinyl)-4-(trifluoromethoxy), Oct. 9, 2007.
"STN International RN: 957062-79-2", benzenesulfonamide, 2-bromo-N-cyclopropyl-4-(trifluoromethoxy), Dec. 7, 2007.
"STN International RN: 1069987-77-4", 1H-Pyrrolo[1,2-a]azepine-5-carboxamide, octahydro-N-hydroxy-2-[4-[(2-methyl-4-quinolinyl)methoxy]phenyl]-3-oxo-2-[(phenylsulfonyl)amino]-, (2R,5R,9aR)-, Nov. 2, 2008.
"STN International RN: 1069997-55-2", (4R,7R,8aS)-N-hydroxy-7-(4-((2-methylquinolin-4-yl)methoxy)phenyl)-6-oxo-7-(phenylsulfonamido)octahydropyrrolo[1,2-a]pyrazine-4-carboxamide.
"STN International RN: 1070000-42-8", (3R,6R,7aR)-N-hydroxy-6-(4-((2-methylquinolin-4-yl)methoxy)phenyl)-5-oxo-6-(phenylsulfonamido)hexahydro-1H-pyrrolizine-3-carboxamide.
"STN International RN: 1070007-00-9", (4R,7R,8aS)-N-hydroxy-7-(4-((2-methylquinolin-4-yl)methoxy)phenyl)-6-oxo-7-(phenylsulfonamido)hexahydro-1H-pyrrolo[2,1-c][1,4]oxazine-4-carboxamide.
"STN International RN: 112080-80-5", Benzenesulfonamide, 4-methyl-N-[1-[(4-methylphenyl)sulfonyl]-2,5-dioxo-4-phenyl-3-(1-piperidinyl)-4-imidazolidinyl]-, Dec. 25, 1987.
"STN International RN: 112080-81-6", Benzenesulfonamide, 4-methyl-N-[1-[(4-methylphenyl)sulfonyl]-4-(4-nitrophenyl)-2,5-dioxo-3-(1-piperidinyl)-4-imidazolidinyl]-, Dec. 25, 1987.
"STN International RN: 1214493-67-0", 6-Quinazolinesulfonamide, 1,2,3,4-tetrahydro-2,4-dioxo-N-(1-phenylcyclopentyl)-, Mar. 25, 2010.
"STN International RN: 1241558-90-6", 1H-Indole-5-sulfonamide, 1-acetyl-N-[1-(4-fluorophenyl)cyclopentyl]-2,3-dihydro, Sep. 16, 2010.
"STN International RN: 1241559-76-1", Benzenesulfonamide, 2,4-difluoro-N-[1-(4-fluorophenyl)cyclopentyl]-, Sep. 16, 2010.
"STN International RN: 1246661-97-1", Benzenesulfonamide, N-[(1S)-2,3-dihydro-1-phenyl-1H-inden-1-yl]-4-methyl, Oct. 20, 2010.

(56) References Cited

OTHER PUBLICATIONS

"STN International RN: 1252544-86-7", Benzenesulfonamide, N-[1-(4-fluorophenyl)cyclopentyl]-2-nitro, Nov. 10, 2010.
"STN International RN: 1261241-00-2", rel-methyl (3aR,8aS)-3a-(phenylsulfonamido)-3,3a,8,8a-tetrahydropyrrolo[2,3-b]indole-1(2H)-carboxylate.
"STN International RN: 1261241-06-8", methyl (3aS,8aR)-3a-(phenylsulfonamido)-3,3a,8,8a-tetrahydropyrrolo[2,3-b]indole-1(2H)-carboxylate.
"STN International RN: 1278794-60-7", Acetamide, N-[5-[1-(4-fluorophenyl)cyclopentyl]amino]sulfonyl]-2-methoxyphenyl]-, Apr. 12, 2011.
"STN International RN: 1287681-13-3", Benzenesulfonamide, N-[1-(4-fluorophenyl)cyclopentyl]-2,5-dimethoxy, Apr. 29, 2011.
"STN International RN: 1288751-39-2", 2H-1,4-Benzoxazine-6-sulfonamide, N-[1-(4-fluorophenyl)cyclopentyl]-3,4-dihydro-3-oxo, May 1, 2011.
"STN International RN: 1288762-13-9", Propanoic acid, 3-[4-[[[1-(4-fluorophenyl)cyclopentyl]amino]sulfonyl]phenoxy]-, methyl ester, May 1, 2011.
"STN International RN: 1289898-31-2", Benzenesulfonamide, N-[1-(4-fluorophenyl)cyclopentyl]-4-methoxy-3-nitro, May 4, 2011.
"STN International RN: 1294093-27-8", 1H-Indole-5-sulfonamide, 1-acetyl-N-[1-(4-fluorophenyl)cyclopentyl]-2,3-dihydro-2-methyl, May 13, 2011.
"STN International RN: 1296251-34-7", Benzamide, N,N-diethyl-4-[[[1-(4-fluorophenyl)cyclopentyl]amino]sulfonyl]-, May 17, 2011.
"STN International RN: 1296814-40-8", Benzenesulfonamide, 2-(difluoromethoxy)-N-[1-(4-fluorophenyl)cyclopentyl]-, May 18, 2011.
"STN International RN: 1298749-76-4", Benzenesulfonamide, 4-(ethylsulfonyl)-N-[1-(4-fluorophenyl)cyclopentyl]-, May 22, 2011.
"STN International RN: 2037369-03-0", N-(4-aminocyclohexyl)-4-(difluoromethoxy)-3-fluorobenzenesulfonamide hydrochloride, Nov. 26, 2016.
"STN International RN: 2037541-50-5", benzenesulfonamide, 4-(difluoromethoxy)-3-fluoro-N-4-piperidinyl, Nov. 26, 2016.
"STN International RN: 2037541-51-6", 4-(difluoromethoxy)-3-fluoro-N-4-piperidinylbenzenesulfonamide hydrochloride, Nov. 26, 2016.
"STN International RN: 2037927-58-3", benzenesulfonamide, 4-(difluoromethoxy)-3-fluoro-N-(2-methyl-4-piperidinyl), Nov. 26, 2016.
"STN International RN: 2037927-59-4", 4-(difluoromethoxy)-3-fluoro-N-(2-methyl-4-piperidinyl)benzenesulfonamide hydrochloride, Nov. 26, 2016.
"STN International RN: 2038001-93-1", benzenesulfonamide, N-(3-aminobicyclo[3.3.1]non-9-yl)-4-(difluoromethoxy)-3-fluoro, Nov. 26, 2016.
"STN International RN: 2038001-94-2", N-(3-aminobicyclo[3.3.1]non-9-yl)-4-(difluoromethoxy)-3-fluorobenzenesulfonamide hydrochloride, Nov. 26, 2016.
"STN International RN: 2038219-83-7", benzenesulfonamide, 4-(difluoromethoxy)-3-fluoro-N-3-piperidinyl, Nov. 26, 2016.
"STN International RN: 2038219-84-8", 4-(difluoromethoxy)-3-fluoro-N-3-piperidinylbenzenesulfonamide hydrochloride, Nov. 26, 2016.
"STN International RN: 2038383-93-4", benzenesulfonamide, 3-chloro-4-(difluoromethoxy)-N-(4-methyl-4-piperidinyl), Nov. 27, 2016.
"STN International RN: 2038642-45-2", 4-(difluoromethoxy)-3-fluoro-N-(4-methyl-3-piperidinyl)benzenesulfonamide, Nov. 27, 2016.
"STN International RN: 2038642-46-3", 4-(difluoromethoxy)-3-fluoro-N-(4-methyl-3-piperidinyl)benzenesulfonamide hydrochloride, Nov. 27, 2016.
"STN International RN: 2039127-90-5", N-(2-(aminomethyl)cyclohexyl)-4-(difluoromethoxy)-3-fluorobenzenesulfonamide, Nov. 27, 2016.
"STN International RN: 2088843-75-6", benzenesulfonamide, N-((1R,2R,3S)-3-(diphenylamino)-2-hydroxycyclohexyl)-4-(trifluoromethoxy), Apr. 5, 2017.
"STN International RN: 2088843-77-8", benzenesulfonamide, N-((1S,2S,3R)-3-(diphenylamino)-2-hydroxycyclohexyl)-4-(trifluoromethoxy), Apr. 5, 2017.
"STN International RN: 2088843-87-0", rac N-((1R,2R,3S)-3-((4-bromophenyl)phenylamino)-2-hydroxycyclohexyl)-4-(trifluoromethoxy)benzenesulfonamide, Apr. 5, 2017.
"STN International RN: 2088843-89-2", rac N-((1R,2R,3S)-3-((4-cyanophenyl)phenylamino)-2-hydroxycyclohexyl)-4-(trifluoromethoxy)benzenesulfonamide, Apr. 5, 2017.
"STN International RN: 2088844-07-7", benzenesulfonamide, N-((1R,2R,3S)-2-hydroxy-3-(phenyl(phenylmethyl)amino)cyclohexyl)-4-(trifluoromethoxy), Apr. 5, 2017.
"STN International RN: 2088844-11-3", benzenesulfonamide, N-((1R,2R,3S)-3-(bis(phenylmethyl)amino)-2-hydroxycyclohexyl)-4-(trifluoromethoxy), Apr. 5, 2017.
"STN International RN: 2088844-49-7", rac N-((1R,2R,3S)-2-hydroxy-3-(phenylamino)cyclohexyl)-4-(trifluoromethoxy)benzenesulfonamide, Apr. 5, 2017.
"STN International RN: 2088844-69-1", rac N-((1R,2R,3S)-3-amino-2-hydroxycyclohexyl)-4-(trifluoromethoxy)benzenesulfonamide, Apr. 5, 2017.
"STN International RN: 2088844-70-4", rac N-((1R,2R,3S)-2-hydroxy-3-(phenyl(phenylmethyl)amino)cyclohexyl)-4-(trifluoromethoxy)benzensulfonamide, Apr. 5, 2017.
"STN International RN: 2088919-02-0", rac N-((1R,2R,3S)-3-((diphenylmethyl)amino)-2-hydroxycyclohexyl)-4-(trifluoromethoxy)benzenesulfonamide, Apr. 6, 2017.
"STN International RN: 2088919-09-7", benzenesulfonamide, N-((1S,2S,3R)-3-((diphenylmethyl)amino)-2-hydroxycyclohexyl)-4-(trifluoromethoxy), Apr. 6, 2017.
"STN International RN: 2088919-14-4", benzenesulfonamide, N-((3S)-1-(diphenylmethyl)-3-piperidinyl)-4-(trifluoromethoxy), Apr. 6, 2017.
"STN International RN: 2088919-15-5", benzenesulfonamide, N((3R)-1-(diphenylmethyl)-3-piperidinyl)-4-(trifluoromethoxy), Apr. 6, 2017.
"STN International RN: 2088919-18-8", N-((1S,2S,3R)-3-((bis(4-bromophenyl)methyl)amino)-2-hydroxycyclohexyl)-4-(trifluoromethoxy)benzenesulfonamide, Apr. 6, 2017.
"STN International RN: 2088919-20-2", N-((1S,2S,3R)-3-((bis(4-fluorophenyl)methyl)amino)-2-hydroxycyclohexyl)-4-(trifluoromethoxy)benzenesulfonamide, Apr. 6, 2017.
"STN International RN: 2088919-21-3", rac N-((1R,2R,3S)-3-(bis(phenylmethyl)amino)-2-hydroxycyclohexyl)-4-(trifluoromethoxy)benzenesulfonamide, Apr. 6, 2017.
"STN International RN: 2088919-25-7", arabinitol, 2-amino-1,5-anhydro-2,4-deoxy-4-(((4-(trifluoromethoxy)phenyl)sulfonyl)amino), Apr. 6, 2017.
"STN International RN: 2088919-27-9", D-xylitol, 4-amino-1,5-anhydro-2,4-dideoxy-2-(((4-(trifluoromethoxy)phenyl)sulfonyl)amino), Apr. 6, 2017.
"STN International RN: 2088919-41-7", benzenesulfonamide, N-((1S,2S,3R)-3-amino-2-hydroxycyclohexyl)-4-(trifluoromethoxy), Apr. 6, 2017.
"STN International RN: 2094435-38-6", benzenesulfonamide, 3-chloro-4-(difluoromethoxy)-N-(2,2-dimethyl-6-oxo-3-piperidinyl), May 4, 2017.
"STN International RN: 2174081-71-9", benzenesulfonamide, 4-(difluoromethoxy)-3-fluoro-N-(hexahydro-2-oxo-1H-azepin-3-yl), Feb. 16, 2018.
"STN International RN: 2176285-48-4", benzenesulfonamide, 3-chloro-N-(1-cyclopropyl-5-methyl-3-pyrrolidinyl)-4-(difluoromethoxy), Feb. 22, 2018.
"STN International RN: 2177127-77-2", benzenesulfonamide, N-(1-cyclopentyl-3-pyrrolidinyl)-4-(difluoromethoxy)-3-fluoro, Feb. 22, 2018.
"STN International RN: 2177127-87-4", benzenesulfonamide, 4-(difluoromethoxy)-N-(1-ethylcyclobutyl)-3-fluoro, Feb. 22, 2018.
"STN International RN: 2177127-92-1", benzenesulfonamide, N-(1-cyclopropyl-4-methyl-3-pyrrolidinyl)-4-(difluoromethoxy)-3-fluoro, Feb. 22, 2018.
"STN International RN: 2177127-99-8", benzenesulfonamide, 4-(difluoromethoxy)-3-fluoro-N-4-oxepanyl, Feb. 22, 2018.

(56) References Cited

OTHER PUBLICATIONS

"STN International RN: 2177962-12-6", rac 4-(difluoromethoxy)-N-((3R,4S)-tetrahydro-4-hydroxy-3-furanyl)benzenesulfonamide, Feb. 23, 2018.
"STN International RN: 2178102-48-0", benzenesulfonamide, 3-chloro-4-(difluoromethoxy)-N-(1-(2-methylcyclopropyl)-5-oxo-3-pyrrolidinyl), Feb. 23, 2018.
"STN International RN: 2186195-51-5", benzenesulfonamide, 3-chloro-4-(difluoromethoxy)-N-4-oxepanyl, Mar. 8, 2018.
"STN International RN: 2188510-62-3", benzenesulfonamide, 3-chloro-4-(difluoromethoxy)-N-(3-methylcyclobutyl), Mar. 11, 2018.
"STN International RN: 2190267-12-8", benzenesulfonamide, 3-chloro-N-(1-cyclopropyl-4-methyl-3-pyrrolidinyl)-4-(difluoromethoxy), Mar. 14, 2018.
"STN International RN: 2192447-65-5", benzenesulfonamide, 3-chloro-N-(1-cyclopentyl-3-pyrrolidinyl)-4-(difluoromethoxy), Mar. 17, 2018.
"STN International RN: 2194759-98-1", benzenesulfonamide, 4-(difluoromethoxy)-3-fluoro-N-(1-(2-methylcyclopropyl)-5-oxo-3-pyrrolidinyl), Mar. 21, 2018.
"STN International RN: 2208933-31-5", benzenesulfonamide, 4-(difluoromethoxy)-3-fluoro-N-(3-methylcyclobutyl), Apr. 10, 2018.
"STN International RN: 2208933-94-0", benzenesulfonamide, N-(1-cyclopropyl-5-methyl-3-pyrrolidinyl)-4-(difluoromethoxy)-3-fluoro, Apr. 10, 2018.
"STN International RN: 2249504-40-1", benzenesulfonamide, N-1,2-diazaspiro[2.5]oct-1-en-5-yl-4-(trifluoromethoxy), Nov. 21, 2018.
"STN International RN: 2249622-57-7", benzenesulfonamide, N-1,2-diazaspiro[2.5]oct-1-en-6-yl-4-(trifluoromethoxy), Nov. 21, 2018.
"STN International RN: 1299736-06-3", 5-Benzofuransulfonamide, N-[1-(4-fluorophenyl)cyclopentyl]-2,3-dihydro, May 24, 2011.
"STN International RN: 1301368-32-0", Benzenesulfonamide, 4-[(difluoromethyl)sulfonyl]-N-[1-(4-fluorophenyl)cyclopentyl]-, May 27, 2011.
"STN International RN: 1308305-02-3", Benzenesulfonamide, N-[(1S)-5-chloro-2,3-dihydro-1-phenyl-1H-inden-1-yl]-4-methyl, Jun. 9, 2011.
"STN International RN: 1327811-52-8", Benzenesulfonamide, N-[1-(2-fluorophenyl)cyclopentyl]-4-methoxy, Sep. 4, 2011.
"STN International RN: 1327844-73-4", Benzenesulfonamide, 2,5-dimethoxy-N-(1-phenylcyclopentyl)-, Sep. 4, 2011.
"STN International RN: 1327844-75-6", Benzenesulfonamide, N-[1-(2-fluorophenyl)cyclopentyl]-2,5-dimethoxy, Sep. 4, 2011.
"STN International RN: 1328051-98-4", 6-Benzoxazolesulfonamide, 2,3-dihydro-2-oxo-N-(1-phenylcyclopentyl)-, Sep. 4, 2011.
"STN International RN: 1328157-20-5", Acetamide, N-[4-[[[1-(2-fluorophenyl)cyclopentyl]amino]sulfonyl]phenyl]-, Sep. 4, 2011.
"STN International RN: 1328157-28-3", Acetamide, N-[3-[[[1-(2-fluorophenyl)cyclopentyl]amino]sulfonyl]phenyl]-, Sep. 4, 2011.
"STN International RN: 1328157-43-2", Benzenesulfonamide, 4-methoxy-N-(1-phenylcyclopentyl)-, Sep. 4, 2011.
"STN International RN: 1328158-29-7", 6-Benzoxazolesulfonamide, N-[1-(3-chlorophenyl)cyclopentyl]-2,3-dihydro-2-oxo, Sep. 4, 2011.
"STN International RN: 1328242-56-3", Acetamide, N-[3-[[(1-phenylcyclopentyl)amino]sulfonyl]phenyl]-, Sep. 5, 2011.
"STN International RN: 1328265-92-4", Benzenesulfonamide, N-[1-(2-fluorophenyl)cyclopentyl]-, Sep. 5, 2011.
"STN International RN: 1328295-30-2", Benzenesulfonamide, 4-fluoro-N-[1-(2-fluorophenyl)cyclopentyl]-, Sep. 5, 2011.
"STN International RN: 1328397-40-5", Acetamide, N-[2-[[[1-(2-fluorophenyl)cyclopentyl]amino]sulfonyl]phenyl]-, Sep. 5, 2011.
"STN International RN: 1328405-36-2", 6-Benzoxazolesulfonamide, N-[1-(2-fluorophenyl)cyclopentyl]-2,3-dihydro-2-oxo, Sep. 5, 2011.
"STN International RN: 1328458-60-1", 1H-Indole-5-sulfonamide, N-[1-(2-fluorophenyl)cyclopentyl]-2,3-dihydro-2-oxo, Sep. 5, 2011.
"STN International RN: 1328459-13-7", Acetamide, N-[4-[[(1-phenylcyclopentyl)amino]sulfonyl]phenyl]-, Sep. 5, 2011.
"STN International RN: 1328531-36-7", 1H-Indole-5-sulfonamide, 2,3-dihydro-2-oxo-N-(1-phenylcyclopentyl)-, Sep. 5, 2011.
"STN International RN: 1328578-03-5", Benzenesulfonamide, 4-ethoxy-N-(1-phenylcyclopentyl)-, Sep. 5, 2011.
"STN International RN: 1328813-76-8", Benzenesulfonamide, N-(1-phenylcyclopentyl)-, Sep. 6, 2011.
"STN International RN: 1328918-37-1", 1H-Indole-5-sulfonamide, N-[1-(3-chlorophenyl)cyclopentyl]-2,3-dihydro-2-oxo, Sep. 6, 2011.
"STN International RN: 1329301-59-8", Acetamide, N-[2-[[(1-phenylcyclopentyl)amino]sulfonyl]phenyl]-, Sep. 7, 2012.
"STN International RN: 1329302-90-0", Benzenesulfonamide, 4-fluoro-N-(1-phenylcyclopentyl)-, Sep. 7, 2012.
"STN International RN: 1329308-82-8", 1H-Indole-5-sulfonamide, 1-acetyl-2,3-dihydro-N-(1-phenylcyclopentyl)-, Sep. 7, 2012.
"STN International RN: 1331730-34-7", Glycine, N-[1-(3-bromophenyl)cyclopentyl]-N-[(3,4-dihydro-2,2-dimethyl-2H-1-benzopyran-6-yl)sulfonyl]-, Sep. 12, 2011.
"STN International RN: 1331730-35-8", Glycine, N-[1-(3',5'-dichloro[1,1'-biphenyl]-4-yl)cyclopentyl]-N-[(3,4-dihydro-2,2-dimethyl-2H-1-benzopyran-6-yl)sulfonyl]-, Sep. 12, 2011.
"STN International RN: 1331730-37-0", Glycine, N-[1-(4-bromophenyl)cyclopentyl]-N-(1-naphthalenylsulfonyl)-, Sep. 12, 2011.
"STN International RN: 1331730-38-1", Glycine, N-[1-(4-bromophenyl)cyclopentyl]-N-(2-naphthalenylsulfonyl)-, Sep. 12, 2011.
"STN International RN: 1331730-39-2", Glycine, N-[1-(4-bromophenyl)cyclopentyl]-N-[(4-methylphenyl)sulfonyl]-, Sep. 12, 2011.
"STN International RN: 1356832-79-5", 1'-methyl-2-tosylspiro[isoindoline-1,3'-pyrrolidine]-2', 3,5'-trione.
"STN International RN: 1363142-24-8", Benzenesulfonamide, N-(1-phenylcyclopentyl)-4-[[[(3-pyridinylmethyl)amino]carbonyl]amino]-, Mar. 28, 2012.
"STN International RN: 1364041-74-6", Pyrrolo[3,4-b ]pyrrole, octahydro-1-[(4-methylphenyl)sulfonyl]-5,6adiphenyl-, (3aS,6aR ).
"STN International RN: 1364041-76-8", Pyrrolo[3,4-b ]pyrrole, octahydro-1-[(4-methylphenyl)sulfonyl]-5,6adiphenyl-, (3aR , 6aS ).
"STN International RN: 136650-30-1", 6-(3-chlorophenyl)-5-(phenylsulfonyl)-3,4,5,6-tetrahydro-2H-1,6-methanobenzo[b][1,5]diazocin-11-one.
"STN International RN: 136650-31-2", 6-(3-chlorophenyl)-5-tosyl-3,4,5,6-tetrahydro-2H-1,6-methanobenzo[b][1,5]diazocin-11-one.
"STN International RN: 136650-32-3", 6-phenyl-5-tosyl-3,4,5,6-tetrahydro-2H-1,6-methanobenzo[b][1,5]diazocin-11-one.
"STN International RN: 136650-37-8", 7-phenyl-6-tosyl-2,3,4,5,6,7-hexahydro-1,7-methanobenzo[b][1,5]diazonin-12-one.
"STN International RN: 1368666-30-1", 2-Naphthalenesulfonamide, N-[1-(2-fluorophenyl)cyclopentyl]-, Apr. 15, 2012.
"STN International RN: 1370880-69-5", Benzenesulfonamide, 4-cyano-N-[1-(4-fluorophenyl)cyclopentyl]-, Apr. 29, 2012.
"STN International RN: 1370881-46-1", Benzenesulfonamide, 2-chloro-N-[1-(4-fluorophenyl)cyclopentyl]-5-(methylsulfonyl)-, Apr. 29, 2012.
"STN International RN: 1370881-65-4", Benzenesulfonamide, N-[1-(4-fluorophenyl)cyclopentyl]-3-(1H-tetrazol-1-yl)-, Apr. 29, 2012.
"STN International RN: 1370896-13-1", Benzenesulfonamide, N-[1-(4-fluorophenyl)cyclopentyl]-4,5-dimethoxy-2-methyl, Apr. 29, 2012.
"STN International RN: 1370928-44-1", Benzenesulfonamide, 2-bromo-N-[1-(4-fluorophenyl)cyclopentyl]-4,5-dimethoxy, Apr. 29, 2012.
"STN International RN: 1370949-37-3", Benzenesulfonamide, N-[1-(4-fluorophenyl)cyclopentyl]-4-(methylsulfonyl)-, Apr. 29, 2012.
"STN International RN: 1370952-06-9", Benzenesulfonamide, N-[1-(4-fluorophenyl)cyclopentyl]-3-(methylsulfonyl)-, Apr. 29, 2012.
"STN International RN: 1370980-03-2", Benzenesulfonamide, N-[1-(4-fluorophenyl)cyclopentyl]-4-methyl, Apr. 29, 2012.
"STN International RN: 1371006-23-3", Benzoic acid, 3-[[[1-(4-fluorophenyl)cyclopentyl]amino]sulfonyl]-, methyl ester, Apr. 29, 2012.
"STN International RN: 1371012-46-2", Benzenesulfonamide, N-[1-(4-fluorophenyl)cyclopentyl]-4-methoxy, Apr. 29, 2012.
"STN International RN: 1371048-99-5", 2H-1,4-Benzoxazine-7-sulfonamide, 6-chloro-N-[1-(4-fluorophenyl)cyclopentyl]-3,4-dihydro-3-oxo, Apr. 29, 2012.
"STN International RN: 1623806-77-8", benzenesulfonamide, N-(1-methyl-4-piperidinyl)-4-(trifluoromethoxy), Sep. 20, 2014.
"STN International RN: 1624110-87-7", benzenesulfonamide, 3-chloro-4-(difluoromethoxy)-N-(4-hydroxycyclohexyl), Sep. 23, 2014.

(56) References Cited

OTHER PUBLICATIONS

"STN International RN: 1624227-65-1", benzenesulfonamide, N-(4-hydroxycyclohexyl)-4-(trifluoromethoxy), Sep. 23, 2014.
"STN International RN: 1667727-74-3", benzenesulfonamide, N-(1-(4-((4-fluorophenyl)amino)phenyl)-3-pyrrolidinyl)-4-(trifluoromethoxy), Mar. 24, 2015.
"STN International RN: 1713958-80-5", benzenesulfonamide, N-(1-(hydroxymethyl)cyclobutyl)-4-(trifluoromethoxy), May 28, 2015.
"STN International RN: 1714340-58-5", benzenesulfonamide, N-(1-(hydroxymethyl)cyclopropyl)-4-(trifluoromethoxy), May 29, 2015.
"STN International RN: 1714661-46-7", benzenesulfonamide, 3-chloro-4-(difluoromethoxy)-N-(3-methylcyclopentyl), May 29, 2015.
"STN International RN: 1775183-16-8", benzenesulfonamide, 3-chloro-4-(difluoromethoxy)-N-(1-(hydroxymethyl)cyclopropyl), Jun. 7, 2015.
"STN International RN: 1775984-93-4", benzenesulfonamide, 3-chloro-4-(difluoromethoxy)-N-(1-(hydroxymethyl)cyclobutyl), Jun. 9, 2015.
"STN International RN: 1777435-24-1", benzenesulfonamide, N-(3-methylcyclopentyl)-4-(trifluoromethoxy), Jun. 11, 2015.
"STN International RN: 1786512-33-1", N-(3R)-3-pyrrolidinyl-4-(trifluoromethoxy)benzenesulfonamide, Jun. 24, 2015.
"STN International RN: 1786593-31-4", 3-chloro-4-(difluoromethoxy)-N-(3R)-3-pyrrolidinylbenzenesulfonamide, Jun. 24, 2015.
"STN International RN: 1786816-72-5", benzenesulfonamide, 3-chloro-4-(difluoromethoxy)-N-(3S)-3-pyrrolidinyl, Jun. 24, 2015.
"STN International RN: 1786906-93-1", benzenesulfonamide, N-(3S)-3-pyrrolidinyl-4-(trifluoromethoxy), Jun. 24, 2015.
"STN International RN: 1788783-67-4", N-(1-(2-pyridinyl)-3-pyrrolidinyl)-4-(trifluoromethoxy)benzenesulfonamide, Jun. 26, 2015.
"STN International RN: 1796975-75-1", N-(1-methyl-4-phenyl-3-pyrrolidinyl)-4-(trifluoromethoxy)benzenesulfonamide, Jul. 9, 2015.
"STN International RN: 1808673-47-3", cyclopentanecarboxamide, N-ethyl-1-(((4-(trifluoromethoxy)phenyl)sulfonyl)amino), Sep. 30, 2015.
"STN International RN: 1822103-26-3", N-((1R,2R)-2-aminocyclohexyl)-2-bromo-4-(trifluoromethoxy)benzenesulfonamide, Dec. 4, 2015.
"STN International RN: 1822103-27-4", N-((1R,2R)-2-aminocyclohexyl)-2-bromo-4-(trifluoromethoxy)benzenesulfonamide hydrochloride, Dec. 4, 2015.
"STN International RN: 1822200-45-2", benzenesulfonamide, N-((1R,2R)-2-aminocyclohexyl)-3-chloro-4-(difluoromethoxy), Dec. 4, 2015.
"STN International RN: 1822200-46-3", N-((1R,2R)-2-aminocyclohexyl)-3-chloro-4-(difluoromethoxy)benzenesulfonamide hydrochloride, Dec. 4, 2015.
"STN International RN: 1826286-77-4", benzenesulfonamide, 3-chloro-4-(difluoromethoxy)-N-(4-methyl-3-piperidinyl), Dec. 11, 2015.
"STN International RN: 1826286-78-5", 3-chloro-4-(difluoromethoxy)-N-(4-methyl-3-piperidinyl)-benzenesulfonamide hydrochloride, Dec. 11, 2015.
"STN International RN: 1826349-44-3", N-(2-(aminomethyl)cyclohexyl)-2-bromo-4-(trifluoromethoxy)benzenesulfonamide, Dec. 11, 2015.
"STN International RN: 1826349-45-4", N-(2-(aminomethyl)cyclohexyl)-2-bromo-4-(trifluoromethoxy)benzenesulfonamide hydrochloride, Dec. 11, 2015.
"STN International RN: 1826974-86-0", N-(2-methyl-4-piperidinyl)-4-(trifluoromethoxy)benzenesulfonamide, Dec. 12, 2015.
"STN International RN: 1826974-87-1", N-(2-methyl-4-piperidinyl)-4-(trifluoromethoxy)benzenesulfonamide hydrochloride, Dec. 12, 2015.
"STN International RN: 1827088-66-3", 3-chloro-4-(difluoromethoxy)-N-(2-methyl-4-piperidinyl)benzenesulfonamide, Dec. 12, 2015.
"STN International RN: 1827088-67-4", 3-chloro-4-(difluoromethoxy)-N-(2-methyl-4-piperidinyl)benzenesulfonamide hydrochloride, Dec. 12, 2015.
"STN International RN: 1827105-34-9", N-(1-(aminomethyl)cyclopentyl)-3-chloro-4-(difluoromethoxy)benzenesulfonamide, Dec. 12, 2015.
"STN International RN: 1827105-35-0", N-(1-(aminomethyl)cyclopentyl)-3-chloro-4-(difluoromethoxy)benzenesulfonamide hydrochloride, Dec. 12, 2015.
"STN International RN: 1827511-78-3", N-(1-(aminomethyl)cyclopentyl)-2-bromo-4-(trifluoromethoxy)benzenesulfonamide, Dec. 12, 2015.
"STN International RN: 1827511-79-4", N-(1-(aminomethyl)cyclopentyl)-2-bromo-4-(trifluoromethoxy)benzenesulfonamide hydrochloride, Dec. 12, 2015.
"STN International RN: 1827550-10-6", 2-bromo-N-(2-methyl-4-piperidinyl)-4-(trifluoromethoxy)benzenesulfonamide, Dec. 12, 2015.
"STN International RN: 1827550-11-7", 2-bromo-N-(2-methyl-4-piperidinyl)-4-(trifluoromethoxy)benzenesulfonamide hydrochloride, Dec. 12, 2015.
"STN International RN: 1828688-07-8", 2-bromo-N-(4-methyl-3-piperidinyl)-4-(trifluoromethoxy)benzenesulfonamide, Dec. 14, 2015.
"STN International RN: 1828688-08-9", 2-bromo-N-(4-methyl-3-piperidinyl)-4-(trifluoromethoxy)benzenesulfonamide hydrochloride, Dec. 13, 2015.
"STN International RN: 1828833-27-7", 3-chloro-4-(difluoromethoxy)-N-(2-methyl-3-piperidinyl)benzenesulfonamide, Dec. 14, 2015.
"STN International RN: 1828833-28-8", 3-chloro-4-(difluoromethoxy)-N-(2-methyl-3-piperidinyl)benzenesulfonamide hydrochloride, Dec. 13, 2015.
"STN International RN: 1828917-19-6", N-(4-aminocyclohexyl)-2-bromo-4-(trifluoromethoxy)benzenesulfonamide, Dec. 15, 2015.
"STN International RN: 1828917-20-9", N-(4-aminocyclohexyl)-2-bromo-4-(trifluoromethoxy)benzenesulfonamide hydrochloride, Dec. 15, 2015.
"STN International RN: 1829050-02-3", N-(2-methyl-3-piperidinyl)-4-(trifluoromethoxy)benzenesulfonamide, Dec. 15, 2015.
"STN International RN: 1829050-03-4", N-(2-methyl-3-piperidinyl)-4-(trifluoromethoxy)benzenesulfonamide hydrochloride, Dec. 15, 2015.
"STN International RN: 1830827-87-6", 3-chloro-4-(difluoromethoxy)-N-4-piperidinylbenzenesulfonamide hydrochloride, Dec. 17, 2015.
"STN International RN: 1831320-99-0", 2-bromo-N-(3-methyl-4-piperidinyl)-4-(trifluoromethoxy)benzenesulfonamide, Dec. 18, 2015.
"STN International RN: 1831321-00-6", 2-bromo-N-(3-methyl-4-piperidinyl)-4-(trifluoromethoxy)benzenesulfonamide hydrochloride, Dec. 18, 2015.
"STN International RN: 1831437-13-8", N-3-pyrrolidinyl-4-(trifluoromethoxy)benzenesulfonamide hydrochloride, Dec. 18, 2015.
"STN International RN: 1832124-90-9", N-(1-(aminomethyl)-2-methylcyclohexyl)-3-chloro-4-(difluoromethoxy)benzenesulfonamide, Dec. 19, 2015.
"STN International RN: 1832778-17-2", N-(2-(aminomethyl)cyclopentyl)-2-bromo-4-(trifluoromethoxy)benzenesulfonamide hydrochloride, Dec. 20, 2015.
"STN International RN: 1834102-59-8", N-3-azetidinyl-2-bromo-4-(trifluoromethoxy)benzenesulfonamide, Dec. 22, 2015.
"STN International RN: 1371118-74-9", Benzenesulfonamide, 3-cyano-N-[1-(4-fluorophenyl)cyclopentyl]-, Apr. 29, 2012.
"STN International RN: 1371126-10-1", Benzenesulfonamide, 4-(2-ethoxyethoxy)-N-[1-(4-fluorophenyl)cyclopentyl]-, Apr. 29, 2012.
"STN International RN: 1371378-59-4", 1,3-Benzenedicarboxylic acid, 5-[[[1-(4-fluorophenyl)cyclopentyl]amino]sulfonyl]-, 1,3-dimethyl ester, Apr. 30, 2012.
"STN International RN: 1371475-68-1", 6-Quinolinesulfonamide, N-[1-(4-fluorophenyl)cyclopentyl]-1,2,3,4-tetrahydro-2-oxo, Apr. 30, 2012.
"STN International RN: 1371485-16-3", Benzenesulfonamide, 2,5-difluoro-N-[1-(4-fluorophenyl)cyclopentyl]-, Apr. 30, 2012.
"STN International RN: 1371737-28-8", Benzenesulfonamide, N-[1-(4-fluorophenyl)cyclopentyl]-2-methoxy-5-nitro, May 1, 2012.
"STN International RN: 1371756-76-1", Benzenesulfonamide, 3,4-difluoro-N-[1-(4-fluorophenyl)cyclopentyl]-, May 1, 2012.
"STN International RN: 1371764-67-8", 6-Quinolinesulfonamide, 1-acetyl-N-[1-(4-fluorophenyl)cyclopentyl]-1,2,3,4-tetrahydro, May 1, 2012.
"STN International RN: 1371883-77-0", Benzenesulfonamide, 3,5-difluoro-N-[1-(4-fluorophenyl)cyclopentyl]-, May 1, 2012.

(56) References Cited

OTHER PUBLICATIONS

"STN International RN: 1371915-25-1", Benzoic acid, 4-[1-(4-fluorophenyl)cyclopentyl]amino]sulfonyl]-, methylester, May 1, 2012.
"STN International RN: 1371920-34-1", Benzenesulfonamide, 2-fluoro-N-[1-(4-fluorophenyl)cyclopentyl]-4,5-dimethoxy, May 1, 2012.
"STN International RN: 1372058-14-4", Benzenesulfonamide, N-[1-(4-fluorophenyl)cyclopentyl]-2-methyl-5-(methylsulfonyl)-, May 1, 2012.
"STN International RN: 1372093-64-5", Benzenesulfonamide, 2-bromo-N-[1-(4-fluorophenyl)cyclopentyl]-5-(methylsulfonyl)-, May 1, 2012.
"STN International RN: 1374031-65-8", Spiro[cyclopentane-1,3'-[3H]indole]-3-carboxylic acid, 1',2'-dihydro-1'-methyl-4-[[(4-methylphenyl)sulfonyl]amino]-2'-oxo-2,4-diphenyl-, methylester, (1R,2R,3S,4R)-rel, May 18, 2012.
"STN International RN: 1374031-67-0", Benzenesulfonamide, N-[(1R,3R,4S,5R)-1',2'-dihydro-4-(hydroxymethyl)-1'-methyl-2'-oxo-3,5-diphenylspiro[cyclopentane-1,3'-[3H]indol]-3-yl]-4-methyl-, rel, May 18, 2012.
"STN International RN: 1424457-03-3", Benzenesulfonamide, N-[1-(2,3-dihydro-1,4-benzodioxin-6-yl)cyclopentyl]-2,6-difluoro, Mar. 17, 2013.
"STN International RN: 1426332-65-1", Benzenesulfonamide, 4-fluoro-N-[2-(4-fluorophenyl)bicyclo[2.2.1]hept-2-yl]-, Mar. 26, 2013.
"STN International RN: 1426332-71-9", Benzenesulfonamide, 4-fluoro-N-(2-phenylbicyclo[2.2.1]hept-2-yl)-, Mar. 26, 2013.
"STN International RN: 1445320-08-0", Benzenesulfonamide, N-[1-(4-fluorophenyl)cyclopentyl]-4-nitro, Jul. 18, 2013.
"STN International RN: 1713230-03-5", rel-methyl (3aR,8aS)-3a-((4-nitrophenyl)sulfonamido)-3,3a,8,8atetrahydropyrrolo[2,3-b]indole-1(2H)-carboxylate.
"STN International RN: 1796836-46-8", Benzenesulfonamide, 4-methyl-N-(1-phenylcyclopentyl)-, Jul. 9, 2015.
"STN International RN: 1796841-72-9", Benzenesulfonamide, 4-chloro-N-(1-phenylcyclopentyl)-, Jul. 9, 2015.
"STN International RN: 1796847-81-8", Benzenesulfonamide, N-[1-(3-chlorophenyl)cyclopentyl]-4-methyl, Jul. 9, 2015.
"STN International RN: 1796849-53-0", Benzenesulfonamide, N-[1-(3-chlorophenyl)cyclopentyl]-, Jul. 9, 2015.
"STN International RN: 1796857-07-2", Benzenesulfonamide, 3,4-dimethyl-N-(1-phenylcyclopentyl)-, Jul. 9, 2015.
"STN International RN: 1796857-59-4", Benzenesulfonamide, N-[1-(2-fluorophenyl)cyclopentyl]-3,4-dimethyl, Jul. 9, 2015.
"STN International RN: 1796858-86-0", Benzenesulfonamide, 2-methoxy-5-methyl-N-(1-phenylcyclopentyl)-, Jul. 9, 2015.
"STN International RN: 1796871-75-4", Benzenesulfonamide, N-[1-(2-fluorophenyl)cyclopentyl]-4-methyl, Jul. 9, 2015.
"STN International RN: 1798784-95-8", Benzenesulfonamide, N-[(1R,3S)-2,3-dihydro-3-methyl-3-(1-methylethenyl)-1-phenyl-1H-inden-1-yl]-4-methyl-, rel-, Jul. 11, 2015.
"STN International RN: 1798784-96-9", Benzenesulfonamide, N-[(1R,3S)-2,3-dihydro-3,7-dimethyl-3-(1-methylethenyl)-1-phenyl-1H-inden-1-yl]-4-methyl-, rel-, Jul. 11, 2015.
"STN International RN: 1798784-97-0", Benzenesulfonamide, N-[(1R,3S)-2,3-dihydro-3-methyl-3-(1-methylethenyl)-1-(4-nitrophenyl)-1H-inden-1-yl]-4-methyl-, rel-, Jul. 11, 2015.
"STN International RN: 1798784-98-1", Benzenesulfonamide, N-[(1R,3S)-2,3-dihydro-3-methyl-3-(1-methylethenyl)-5-nitro-1-phenyl-1H-inden-1-yl]-4-methyl-, rel-, Jul. 11, 2015.
"STN International RN: 1832124-91-0", N-(1-(aminomethyl)-2-methylcyclohexyl)-3-chloro-4-(difluoromethoxy) benzenesulfonamide hydrochloride, Dec. 19, 2015.
"STN International RN: 1832475-75-8", 2-bromo-N-3-pyrrolidinyl-4-(trifluoromethoxy)benzenesulfonamide, Dec. 19, 2015.
"STN International RN: 1832475-76-9", 2-bromo-N-3-pyrrolidinyl-4-(trifluoromethoxy)benzenesulfonamide hydrochloride, Dec. 19, 2015.
"STN International RN: 1832666-70-2", 3-chloro-4-(difluoromethoxy)-N-3-pyrrolidinylbenzenesulfonamide hydrochloride, Dec. 20, 2015.
"STN International RN: 1832778-16-1", benzenesulfonamide, N-(2-(aminomethyl)cyclopentyl)-2-bromo-4-(trifluoromethoxy), Dec. 20, 2015.
"STN International RN: 1851321-36-2", Benzenesulfonamide, N-[(3R)-2,3-dihydro-2-oxo-3-phenyl-1-(phenylmethyl)-1H-indol-3-yl]-4-methyl-, Jan. 23, 2016.
"STN International RN: 1883697-11-7", Glycine, N-[1-(3',5'-dichloro[1,1'-biphenyl]-3-yl)cyclopentyl]-N-[(3,4-dihydro-2,2-dimethyl-2H-1-benzopyran-6-yl)sulfonyl]-, Mar. 19, 2016.
"STN International RN: 1926942-22-4", Benzenesulfonamide, 4-nitro-N-(9-phenyl-9H-fluoren-9-yl)-, Jun. 8, 2016.
"STN International RN: 1933488-68-6", tert-butyl (3aS,8aR)-4-((E)-3-hydroxy-3-methylbut-1-en-1-yl)-3a-((4-nitrophenyl)sulfonamido)-3,3a,8,8a-tetrahydropyrrolo[2,3-b]indole-1(2H)-carboxylate.
"STN International RN: 1997317-60-8", Rel-diethyl (1S,5'R)-5'-phenyl-1',2-ditosylspiro[isoindoline-1,3'-pyrrolidine]-2',2'-dicarboxylate.
"STN International RN: 1997317-61-9", Rel-diethyl (1S,5'S)-5'-phenyl-1',2-ditosylspiro[isoindoline-1,3'-pyrrolidine]-2',2'-dicarboxylate.
"STN International RN: 2031409-79-5", glycine, N-(3-(((4-(difluoromethoxy)-3-fluorophenyl)sulfonyl)amino)cyclobutyl)-N-ethyl, Nov. 16, 2016.
"STN International RN: 2032677-57-7", benzenesulfonamide, N-(2-(aminomethyl)cyclopentyl)-4-(difluoromethoxy)-3-fluoro, Nov. 17, 2016.
"STN International RN: 2039127-91-6", N-(2-(aminomethyl)cyclohexyl)-4-(difluoromethoxy)-3-fluorobenzenesulfonamide hydrochloride, Nov. 27, 2016.
"STN International RN: 2039403-30-8", cyclohexanecarboxylic acid, 4-(((4-(difluoromethoxy)-3-fluorophenyl)sulfonyl) amino), Nov. 29, 2016.
"STN International RN: 2039883-37-7", benzenesulfonamide, 4-(difluoromethoxy)-3-fluoro-N-(3-methyl-4-piperidinyl), Nov. 29, 2016.
"STN International RN: 2039883-38-8", 4-(difluoromethoxy)-3-fluoro-N-(3-methyl-4-piperidinyl)benzenesulfonamide hydrochloride, Nov. 29, 2016.
"STN International RN: 2088843-73-4", rac N-((1R,2R,3S)-3-(diphenylamino)-2-hydroxycyclohexyl)-4-(trifluoromethoxy)benzenesulfonamide, Apr. 5, 2017.
Internet literature; STN search results; CAS: Apr. 3, 2002-Aug. 28, 2020. Compound structures: RN 1667727-74-3, RN 1334066-54-4, and RN 2034235-57-7.
Database Registry, 2017, RN 2138563-35-4, RN 2138561-96-1, RN 2138082-91-2, RN 2138074-80-1, Retrieved from STN international [online]; [search date Nov. 21, 2025].
CAS Registry Nos. 2465445-05-8, 2402090-52-0, 2093734-49-5, 2034326-08-2, 2034235-57-7, 1990963-59-1, 1954114-05-6, 1333697-35-0, 1302688-95-4, 1295940-85-0, 1294794-24-3, 1100175-56-1, 2138563-35-4, 2138561-96-1, 2138082-91-2, and 2138074-80-1.

SUBSTITUTED CYCLIC MODULATORS OF PROTEIN PHOSPHATASE 2A (PP2A) AND METHODS USING SAME

This application is a 35 U.S.C. § 371 national phase application of, and claims priority to, International Application No. PCT/IB2022/000060, filed Feb. 7, 2022, which claims priority under 35 U.S.C. § 119 (e) to U.S. Provisional Patent Application No. 63/146,789, filed Feb. 8, 2021, U.S. Provisional Patent Application No. 63/191,405, filed May 21, 2021, and U.S. Provisional Patent Application No. 63/273,405, filed Oct. 29, 2021, all of which are incorporated herein by reference in their entireties.

BACKGROUND OF THE INVENTION

Protein phosphatase 2A (PP2A) is one of the four major serine threonine phosphatases and is implicated in the negative control of cell growth and division. PP2A holoenzymes are heterotrimeric proteins comprising a structural subunit (A), a catalytic subunit (C), and a regulatory subunit (B). The PP2A heterotrimeric protein phosphatase is a ubiquitous and conserved phosphatase with broad substrate specificity and diverse cellular functions.

PP2A function may be implicated in a variety of pathologies and indications including, but not limited to, cancer, diabetes, autoimmune disease, solid organ transplant rejection, graft vs host disease, chronic obstructive pulmonary disease (COPD), non-alcoholic fatty liver disease, abdominal aortic aneurysm, chronic liver disease, heart failure, neurodegenerative disease, and/or cardiac hypertrophy.

There is thus a need in the art for chemical modulators of PP2A for the treatment, prevention, and/or amelioration of PP2A associated pathologies and/or indications. The present disclosure addresses this need.

BRIEF SUMMARY OF THE INVENTION

The present disclosure provides certain compounds of formula (I), or a salt, solvate, enantiomer, diastereisomer, isotopologue, or tautomer thereof, or any mixtures thereof, selected from the group consisting of (Ia), (Ib), (Ic), (Id), (Ie), and (If), wherein the substituents in (Ia), (Ib), (Ic), (Id), (Ie), and (If) are defined elsewhere herein:

(Ia)

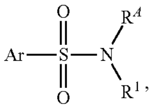

(Ib)

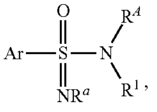

(Ic)

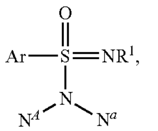

(Id)

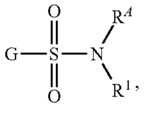

-continued (Ie)

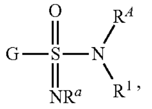

and (If)

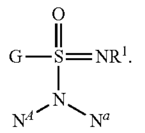

The present disclosure further provides a pharmaceutical composition comprising at least one compound of the present disclosure. In certain embodiments, the pharmaceutical composition further comprises at least one pharmaceutically acceptable carrier.

The present disclosure further provides a method of treating, preventing, and/or ameliorating a PP2A-related disease in a subject, the method comprising administering to a subject in need thereof a therapeutically effective amount of at least one compound of the present disclosure and/or at least one pharmaceutical composition of the present disclosure. In certain embodiments, the PP2A-related disease is selected from the group consisting of cancer, diabetes, autoimmune disease, solid organ transplant rejection, graft vs host disease, chronic obstructive pulmonary disease (COPD), non-alcoholic fatty liver disease, abdominal aortic aneurysm, chronic liver disease, heart failure, neurodegenerative disease, and cardiac hypertrophy.

DETAILED DESCRIPTION OF THE INVENTION

Reference will now be made in detail to certain embodiments of the disclosed subject matter. While the disclosed subject matter will be described in conjunction with the enumerated claims, it will be understood that the exemplified subject matter is not intended to limit the claims to the disclosed subject matter.

Throughout this document, values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include notjust about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. The statement "at least one of A and B" or "at least one of A or B" has the same meaning as "A, B, or A and B." In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section. All publications, patents, and patent documents referred to in this document are incorporated by reference herein in their entirety, as though individually incorporated by reference.

In the methods described herein, the acts can be carried out in any order, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation, and the resulting process will fall within the literal scope of the claimed process.

Definitions

The term "acyl" means a carbonyl attached to an alkenyl, alkyl, aryl, cycloalkyl, heteroaryl, heterocycle, or any other moiety were the atom attached to the carbonyl is carbon. Examples of acyl groups include formyl, alkanoyl and aroyl. An "acetyl" group refers to a —C(O)$CH_3$ group. One or more carbons in the acyl residue may be replaced by nitrogen, oxygen or sulfur as long as the point of attachment to the parent molecular moiety remains at the carbonyl. Examples include acetyl, benzoyl, propionyl, isobutyryl, t-butoxycarbonyl, benzyloxycarbonyl and the like.

The term "acylamino" as used herein, alone or in combination, embraces an acyl group attached to the parent moiety through an amino group. An example of an "acylamino" group is acetylamino ($CH_3C(O)NH$—).

The terms "administer," "administering", "administration," and the like, as used herein, refer to the methods that may be used to enable delivery of compounds or compositions to the desired site of biological action. These methods include, but are not limited to oral routes, intraduodenal routes, parenteral injection (including intravenous, subcutaneous, intraperitoneal, intramuscular, intravascular or infusion), topical and rectal administration. Those of skill in the art are familiar with administration techniques that can be employed with the compounds and methods described herein, e.g., as discussed in Goodman and Gilman, The Pharmacological Basis of Therapeutics, current ed.; Pergamon; and Remington's, Pharmaceutical Sciences (current edition), Mack Publishing Co., Easton, Pa. In certain embodiments, the compounds and compositions described herein are administered orally.

The terms "alkoxy" or "alkoxyl" as used herein refer to a group of from 1 to 6 carbon atoms of a straight, branched or cyclic configuration and combinations thereof attached to the parent structure through an oxygen. Examples of alkoxy include, but are not limited to, methoxy, ethoxy, propoxy, isopropoxy, cyclopropyloxy, sec-butoxy, isobutoxy, tert-butoxy, cyclohexyloxy and cycloheptyloxy.

In an embodiment, the term "alkenyl" means an alkyl group having one or more carbon-carbon double bonds. In an embodiment, the term "$C_2$-$C_6$ alkenyl" means an alkenyl moiety having from 2 to 6 carbon atoms.

Examples of unsaturated alkenyl groups include, but are not limited to, ethenyl (vinyl, —CH═$CH_2$), 1-propenyl (—CH═CH—$CH_3$), 2-propenyl (allyl, —CH—CH═$CH_2$), isopropenyl (1-methylvinyl, —C($CH_3$)═$CH_2$), butenyl, pentenyl, and hexenyl.

The term "alkenylene" as used herein refers to an alkene substituted at two or more positions, such as ethenyl (—CH═CH—). Unless otherwise specified, the term "alkenyl" may include "alkenylene" groups.

In an embodiment, the term "alkyl" means linear, branched, or cyclic hydrocarbon structures and combinations thereof, and which may be saturated or unsaturated (e.g. partially unsaturated, fully unsaturated). Thus, the term "alkyl" includes the sub-classes alkenyl, alkynyl, cycloalkyl, and the like. Alkyl groups may be optionally substituted as defined herein.

Examples of saturated straight-chain alkyl groups include methyl, ethyl, n-propyl, n-butyl, n-pentyl, n-hexyl, n-heptyl, n-octyl, n-nonyl, and n-decyl and branched-chain alkyl groups include isopropyl, tert-butyl, isobutyl, sec-butyl, and neopentyl. In an embodiment, alkyl is saturated alkyl having from 2 to 6 carbon atoms. In an embodiment, a straight chain or branched chain alkyl has 6 or fewer carbon atoms in its backbone (e.g., $C_1$-$C_6$ for straight chain, $C_3$-$C_6$ for branched chain). The term ($C_1$-$C_6$)alkyl may be understood as referring to alkyl groups containing 1 to 6 carbon atoms.

The term "alkylamino" means an alkyl group attached to the parent molecular moiety through an amino group. Alkylamino groups may be mono- or dialkylated, forming groups such as, for example, N-methylamino, N-ethylamino, N,N-dimethylamino, N,N-ethylmethylamino and the like.

The terms "alkylcarbonyl" and "alkoxycarbonyl" mean —C(═O)alkyl or —C(═O)alkoxy, respectively.

The term "alkylthio" means an alkyl thioether (alkyl-S—) group wherein the term alkyl is as defined for alkyl groups and wherein the sulfur may be singly or doubly oxidized. Examples of alkyl thioether groups include, but are not limited to, methylthio, ethylthio, n-propylthio, isopropylthio, n-butylthio, iso-butylthio, sec-butylthio, tert-butylthio, methanesulfonyl, ethanesulfinyl, and the like.

In an embodiment, the term "alkynyl" means an alkyl group having one or more carbon-carbon triple bonds. In an embodiment, the term "$C_2$-$C_6$ alkynyl" means an alkynyl moiety having from 2 to 6 carbon atoms.

Examples of unsaturated alkynyl groups include, but are not limited to, ethynyl (ethinyl, —C═CH) and 2-propynyl (propargyl, —$CH_2$—C═CH).

The term "alkylene" means a straight or branched chain saturated hydrocarbon attached at two or more positions, such as methylene (—$CH_2$—). Unless otherwise specified, the term "alkyl" may include "alkylene" groups.

Amido (carbamoyl, carbamyl, aminocarbonyl, carboxamide) means a group such as —C(═O)$NH_2$, —C(═O)NH (alkyl), or —C(═O)N$(alkyl)_2$, wherein alkyl groups are independently amino substituents, as defined for alkyl groups.

The term "amino" means —$NH_2$.

The terms "aryl" and "heteroaryl" as used herein refer to (i) a phenyl group (or benzene) or a monocyclic 5- or 6-membered heteroaromatic ring containing 1-4 heteroatoms selected from O, N, or S as defined for heterocycles; (ii) a bi cyclic 9- or 10-membered aromatic or heteroaromatic ring system containing 0-4 heteroatoms selected from O, N, or S as defined for carbocycles or heterocycles; or (iii) a tricyclic 13- or 14-membered aromatic or heteroaromatic ring system containing 0-5 heteroatoms selected from O, N, or S as defined for carbocycles or heterocycles. The aromatic 6- to 14-membered carbocyclic rings include, but are not limited to, benzene, naphthalene, anthracene, indane, tetralin, and fluorene and the 5- to 10-membered aromatic heterocyclic rings include, but are not limited to, imidazole, pyridine, indole, thiophene, benzopyranone, thiazole, furan, benzimidazole, quinoline, isoquinoline, quinoxaline, pyrimidine, pyrazine, tetrazole and pyrazole. As used herein aryl and heteroaryl refer to residues in which one or more rings are aromatic, but not all need be.

The term "arylalkyl" as used herein refers to a substituent in which an aryl residue is attached to the parent structure through alkyl. Examples of arylalkyl include, but are not limited to, benzyl, phenethyl and the like. Heteroarylalkyl refers to a substituent in which a heteroaryl residue is attached to the parent structure through alkyl. In certain embodiments, the alkyl group of an arylalkyl or a heteroarylalkyl is an alkyl group of from 1 to 6 carbons. Examples include, e.g., pyridinylmethyl, pyrimidinylethyl and the like.

The term "azido" as used herein means $—N_3$.

The term "carbamate" as used herein refers to an ester of carbamic acid (—NHC(═O)O—) which may be attached to the parent molecular moiety from either the nitrogen or acid end, and which may be optionally substituted as defined herein.

The term "carbonyl" as used herein refers to a —C(═O)— group and includes formyl (—C(═O)H).

The terms "carboxyl" or "carboxy" as used herein refer to —C(═O)OH or the corresponding "carboxylate" anion, such as is in a carboxylic acid salt.

The term "co-administered" refers to simultaneous administration in the same formulation or in two different formulations via the same or different routes or sequential administration by the same or different routes. By "sequential" administration is meant a time difference of from seconds, minutes, hours or days between the administration of the two or more separate compounds.

The term "combination therapy" means the administration of two or more therapeutic agents to treat a therapeutic condition or disorder described in the present disclosure. Such administration encompasses co-administration of these therapeutic agents in a substantially simultaneous manner, such as in a single formulation (e.g., a capsule or injection) having a fixed ratio of active ingredients or in multiple, separate dosage forms for each active ingredient. In addition, such administration also encompasses use of each type of therapeutic agent in a sequential manner. In either case, the treatment regimen will provide beneficial effects of the drug combination in treating the conditions or disorders described herein.

The term "comprising" is used in this specification to mean including the feature(s) or act(s) followed thereafter, without excluding the presence of one or more additional features or acts.

The term "cycloalkyl" or alternatively, "carbocycle", alone or in combination, means a saturated or partially saturated monocyclic, bicyclic or tricyclic alkyl group wherein each cyclic moiety may contain from 3 to 12 carbon atom ring members and which may optionally be a benzo fused ring system which is optionally substituted as defined herein. In an embodiment, cycloalkyl comprise from 3 to 7 carbon atoms or from 3 to 6 carbon atoms.

Examples of saturated monocyclic cycloalkyl groups include, but are not limited to, cyclopropyl, cyclobutyl, cyclopentyl, cyclohexyl, cycloheptyl, methylcyclopropyl, dimethylcyclopropyl, methylcyclobutyl, dimethylcyclobutyl), methylcyclopentyl, dimethylcyclopentyl and methylcyclohexyl.

Examples of saturated monocyclic cycloalkyl groups include, but are not limited to, cyclopropenyl, cyclobutenyl, cyclopentenyl, cyclohexenyl, methylcyclopropenyl, dimethylcyclopropenyl, methylcyclobutenyl, dimethylcyclobutenyl, methylcyclopentenyl, dimethylcyclopentenyl and methylcyclohexenyl.

Examples of bicyclic cycloalkyl groups include, but are not limited to, tetrahydronapthyl, indanyl, octahydronaphthyl, 2,3-dihydro-TH-indenyl, decalinyl and the like. "Bicyclic" and "tricyclic" as used together with "cycloalkyl" are intended to include both fused ring systems, such as decahydronaphthalene, octahydronaphthalene as well as the multicyclic (multicentered) saturated or partially unsaturated type, including spiro-ring fused systems. Examples of bicyclic and tricyclic types of isomer are bicyclo[1,1,1]pentane, norbornane, camphor, adamantane, bicyclo[3,2,1]octane, and [4,4.1]-bicyclononane.

The terms "cyano," "nitrile," or "carbonitrile" as used herein means —CN.

The term "diastereomers" as used herein refers to stereoisomers that have at least two asymmetric atoms, but which are not mirror-images of each other.

The term "disease" as used herein is intended to be generally synonymous, and is used interchangeably with, the terms "disorder" and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The terms "effective amount" or "therapeutically effective amount" as used herein, refer to a sufficient amount of at least one compound being administered which achieve a desired result, e.g., to relieve to some extent one or more symptoms of a disease or condition being treated. In certain instances, the result is a reduction and/or alleviation of the signs, symptoms, or causes of a disease, or any other desired alteration of a biological system. In specific instances, the result is a decrease in the growth of, the killing of, or the inducing of apoptosis in at least one abnormally proliferating cell, e.g., a cancer cell. In certain instances, an "effective amount" for therapeutic uses is the amount of the composition comprising a compound as set forth herein required to provide a clinically significant decrease in a disease. An appropriate "effective" amount in any individual case is determined using any suitable technique, such as a dose escalation study.

The terms "ester," "carboxylate," "carboxylic acid ester," or "oxycarbonyl" as used herein means —C(═O)Oalkyl, wherein alkyl is an ester substituent defined for alkyl above. Examples of ester groups include, but are not limited to, $—C(=O)OCH_3$, $—C(=O)OCH_2CH_3$, $—C(=O)OC(CH_3)_3$, and —C(═O)OPh.

The terms "halo" or "halogen" as used herein means, alone or in combination, fluorine, chlorine, bromine, or iodine. In an embodiment, halo may be fluorine or chlorine.

The term "haloalkoxy" means a haloalkyl group attached to the parent molecular moiety through an oxygen atom.

The term "haloalkyl" as used herein refers to an alkyl radical having the meaning as defined above wherein one or more hydrogens are replaced with a halogen. in an embodiment haloalkyl is monohaloalkyl, dihaloalkyl and polyhaloalkyl group. Examples of haloalkyl radicals include, but are not limited to, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" means a haloalkyl group attached at two or more positions. Examples include, but are not limited to, fluoromethylene (—CFH—), difluoromethylene ($—CF_2—$) and chloromethylene (—CHCl—).

The term "heterocycle" and, interchangeably, "heterocyclyl" means a cycloaliphatic or aryl carbocycle residue in which from one to four carbons is replaced by a heteroatom selected from the group consisting of N, O and S. The nitrogen and sulfur heteroatoms may optionally be oxidized, and the nitrogen heteroatom may optionally be quaternized. In an embodiment, the heterocycle is non-aromatic. In a further embodiment, the heterocycle is aromatic.

Examples of heterocycles include, but are not limited to, aziridine, azetidine pyrrolidine, pyrazole, pyrrole, indole, quinoline, isoquinoline, tetrahydroisoquinoline, benzofuran, benzodioxan, benzodioxole, tetrazole, morpholine, thiazole, pyridine, pyridazine, pyrimidine, thiophene, furan, oxazole, oxazoline, isoxazole, dioxane, tetrahydrofuran and the like. Examples of heterocyclyl residues include, but are not limited to, piperazinyl, piperidinyl, pyrazolidinyl, imidazolyl, imidazolinyl, imidazolidinyl, pyrazinyl, oxazolidinyl, isoxazolidinyl, thiazolidinyl, isothiazolyl, quinuclidinyl, isothiazolidinyl, benzimidazolyl, thiadiazolyl, benzopyranyl, benzothiazolyl, tetrahydrofuryl, tetrahydropyranyl, thienyl (also historically called thiophenyl), benzothienyl, thiamorpholinyl, oxadiazolyl, triazolyl and tetrahydroquinolinyl. It is to be noted that heteroaryl is a subset of heterocycle in which the heterocycle is aromatic. An oxygen heterocycle is a heterocycle containing at least one oxygen in the ring; it may contain additional oxygens, as well as other heteroatoms. A sulphur heterocycle is a heterocycle containing at least one sulphur in the ring; it may contain additional suphurs, as other heteroatoms. Oxygen heteroaryl is a subset of oxygen as other heteroatoms. Oxygen heteroaryl is a subset of oxygen heterocycle; examples include furan and oxazole. Sulphur heteroaryl is a subset of sulphur heterocycle; examples include, but are not limited to, thiophene and thiazine. A nitrogen heterocycle is a heterocycle containing at least one nitrogen in the ring; it may contain additional nitrogens, as well as other heteroatoms. Examples include, but are not limited to, piperidine, piperazine, morpholine, pyrrolidine and thiomorpholine. Nitrogen heteroaryl is a subset of nitrogen heterocycle; examples include, but are not limited to, pyridine, pyrrole and thiazole. The heterocycle groups may be optionally substituted unless specifically prohibited.

The term "hydroxy" means —OH.

As used herein, the term "increase" or the related terms "increased," "enhance" or "enhanced" may refer to a statistically significant increase, and the terms "decreased," "suppressed," or "inhibited" to a statistically significant decrease. For the avoidance of doubt, an increase generally refers to at least a 10% increase in a given parameter, and can encompass at least a 20% increase, 30% increase, 40% increase, 50% increase, 60% increase, 70% increase, 80% increase, 90% increase, 95% increase, 97% increase, 99% or even a 100% increase over the control, baseline, or prior-in-time value. Inhibition generally refers to at least a 10% decrease in a given parameter, and can encompass at least a 20% decrease, 30% decrease, 40% decrease, 50% decrease, 60% decrease, 70% decrease, 80% decrease, 90% decrease, 95% decrease, 97% decrease, 99% or even a 100% decrease over the control value.

The term "imino" as used herein means=N—.

As used herein, the term "modulate" means to increase or decrease the activity of PP2A. In an embodiment, compounds according to one or more embodiments disclosed in this specification may increase the activity of specific PP2A holoenzymes while decreasing the activity of other PP2A heterotrimers.

The term "nitro" as used herein means —$NO_2$.

The term "optionally substituted" may be used interchangeably with "unsubstituted or substituted". The term "substituted" means the replacement of one or more hydrogen atoms in a specified group with a specified radical. In an embodiment, 1, 2 or 3 hydrogen atoms are replaced with a specified radical. In the case of alkyl and cycloalkyl, more than three hydrogen atoms can be replaced by fluorine. In an embodiment, all available hydrogen atoms may be replaced by fluorine. Two substituents may be joined together to form a form a three to seven membered non-aromatic carbocycle or heterocycle consisting of zero to three heteroatoms, for example forming methylenedioxy or ethylenedioxy. In an embodiment, the formed carbocyclic or heterocyclic ring is fused ring or spiro ring.

The above groups, whether alone or part of another substituent, may themselves optionally be substituted with one or more groups selected from themselves and the additional substituents listed below. Further, the substituents listed below may themselves be substituents.

The term "oxo," when referred to as a substituent itself, refers to double bonded oxygen (═O).

The terms "oxy" or "oxa" as used herein means —O—.

As used herein, the term "patient" means all mammals including humans. Examples of patients include humans, cows, dogs, cats, goats, sheep, pigs, and rabbits. In some embodiments, the patient is a human.

The term "pharmaceutically acceptable salt" may refer to salts prepared from pharmaceutically acceptable non-toxic acids or bases including inorganic acids and bases and organic acids and bases. When the compounds disclosed in this specification are basic, salts may be prepared from pharmaceutically acceptable non-toxic acids including inorganic and organic acids. Suitable pharmaceutically acceptable acid addition salts for the compounds disclosed in this specificationinclude acetic, adipic, alginic, ascorbic, aspartic, benzenesulfonic (besylate), benzoic, boric, butyric, camphoric, camphorsulfonic, carbonic, citric, ethanedisulfonic, ethanesulfonic, ethylenediaminetetraacetic, formic, fumaric, glucoheptonic, gluconic, glutamic, hydrobromic, hydrochloric, hydroiodic, hydroxynaphthoic, isethionic, lactic, lactobionic, laurylsulfonic, maleic, malic, mandelic, methanesulfonic, mucic, naphthylenesulfonic, nitric, oleic, pamoic, pantothenic, phosphoric, pivalic, polygalacturonic, salicylic, stearic, succinic, sulfuric, tannic, tartaric acid, teoclatic, p-toluenesulfonic, and the like. When the compounds contain an acidic side chain, suitable pharmaceutically acceptable base addition salts for the compounds of the present invention include, but are not limited to, metallic salts made from aluminum, calcium, lithium, magnesium, potassium, sodium and zinc or organic salts made from lysine, arginine, N,N'dibenzylethylenediamine, chloroprocaine, choline, diethanolamine, ethylenediamine, meglumine (N-methylglucamine) and procaine. Further pharmaceutically acceptable salts include, when appropriate, nontoxic ammonium cations and carboxylate, sulfonate and phosphonate anions attached to alkyl having from 1 to 20 carbon atoms.

The terms "prevent," "preventing" or "prevention," and other grammatical equivalents as used herein, include preventing additional symptoms, preventing the underlying metabolic causes of symptoms, inhibiting the disease or condition, e.g., arresting the development of the disease or condition and are intended to include prophylaxis. The terms further include achieving a prophylactic benefit. For prophylactic benefit, the compositions are optionally administered to an individual at risk of developing a particular disease, to an individual reporting one or more of the physiological symptoms of a disease, or to an individual at risk of reoccurrence of the disease.

The term "stereoisomer" refers to a compound made up of the same atoms bonded by the same bonds but having different three-dimensional structures, which are not interchangeable. The present disclosure contemplates various stereoisomers and mixtures thereof and includes "enantiomers," which refers to two stereoisomers whose molecules are non-superimposable mirror images of one another.

The terms "sulfonate," "sulfonic acid," and "sulfonic," as used herein mean the —$SO_3H$ group and its anion as the sulfonic acid is used in salt formation.

The term "sulfanyl" as used herein means —S—.

The term "sulfinyl" as used herein means —S(═O)—.

The term "sulfonyl" as used herein means —$S(═O)_2$—.

The term "sulfonamido" (sulfinamoyl; sulfonic acid amide; sulfonamide) means —$S(═O)_2NH_2$, —$S(═O)_2NH$(alkyl), —$S(═O)_2N(alkyl)_2$, wherein alkyl are independently amino substituents, as defined for alkylamino groups. Examples of sulfonamido groups include, but are not limited to, —$S(═O)_2NH_2$, —$S(═O)_2NH(CH_3)$, —$S(═O)_2N(CH_3)_2$, —$S(═O)_2NH(CH_2CH_3)$, —$S(═O)_2N(CH_2CH_3)_2$, and —$S(═O)_2NHPh$.

The term "sulfonimidamide", may be understood as referring to a group —$NHS((═O)(NR^{18})$—.

The term "tautomer" or "tautomeric form" refers to structural isomers of different energies which are interconvertible via a low energy barrier. Some non-limiting examples of proton tautomers (also known as prototropic tautomers) include interconversions via migration of a proton, such as keto-enol and imine-enamine isomerizations. Valence tautomers include interconversions by reorganization of some of the bonding electrons.

Unless otherwise stated, all tautomeric forms of the compounds disclosed herein are within the scope of the invention.

The terms "thia" and "thio" as used herein refers to a —S— group or an ether wherein the oxygen is replaced with sulfur. The oxidized derivatives of the thio group, namely sulfinyl and sulfonyl, are included in the definition of thia and thio.

The terms "treat," "treating" or "treatment," and other grammatical equivalents as used herein, include alleviating, inhibiting or reducing symptoms, reducing or inhibiting severity of, delaying onset of, delaying recurrence of, abating or ameliorating a disease or condition symptoms, ameliorating the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition. The terms further include achieving a therapeutic benefit. By therapeutic benefit is meant eradication or amelioration of the underlying disorder being treated, and/or the eradication or amelioration of one or more of the physiological symptoms associated with the underlying disorder such that an improvement is observed in the individual.

Unless otherwise stated or depicted, structures of compounds according to one or more embodiments disclosed in this specification are also meant to include all stereoisomeric (e.g., enantiomeric, diastereomeric, and cis-trans isomeric) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and cis-trans isomeric (or conformational) mixtures of the present compounds are within the scope of the present disclosure. The configuration of any carbon-carbon double bond appearing herein is selected for convenience only and is not intended to designate a particular configuration; thus a carbon-carbon double bond depicted arbitrarily herein as trans may be cis, trans, or a mixture of the two in any proportion. Unless otherwise stated, all tautomeric forms of the compounds according to one or more embodiments disclosed in this specification are within the scope of the present disclosure. Additionally, the compounds of the present disclosure can exist in unsolvated as well as solvated forms with pharmaceutically acceptable solvents such as water, ethanol, and the like. In general, the solvated forms are considered equivalent to the unsolvated forms.

Compounds

In certain embodiments, the present disclosure relates to a compound of formula (I), or a salt, solvate, enantiomer, diastereoisomer, isotopologue, or tautomer thereof, selected from the group consisting of:

(Ia)

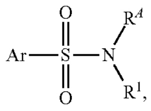

(Ib)

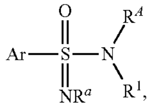

(Ic)

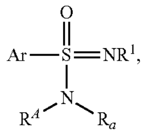

(Id)

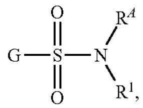

(Ie)

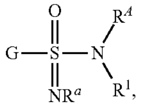

and (If)

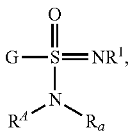

wherein:

Ar is $C_6$-$C_{10}$ aryl or $C_2$-$C_{10}$ heteroaryl, which is optionally substituted with at least one substituent selected from the group consisting of $C_1$-$C_6$ alkyl, $C_1$-$C_6$ haloalkyl, $C_1$-$C_6$ aminoalkyl, $C_1$-$C_6$ hydroxyalkyl, $C_2$-$C_6$ alkenyl, $C_2$-$C_6$ alkynyl, $C_1$-$C_6$ alkoxy, $C_1$-$C_6$ haloalkoxy, $C_2$-$C_{10}$ heteroaryl, $C_6$-$C_{10}$ aryl, $C_6$-$C_{10}$ aryloxy, halogen, OH, $NH_2$, CN, $NO_2$, —C(═O)$R^a$, —C(═O)O$R^a$, and —C(═O)N($R^a$)($R^a$), wherein each $C_6$-$C_{10}$ aryl, $C_2$-$C_{10}$ heteroaryl, or $C_6$-$C_{10}$ aryloxy substituent in Ar is independently optionally substituted with at least one substituent selected from the group consisting of $C_1$-$C_3$ alkyl, $C_1$-$C_3$ haloalkyl, $C_1$-$C_3$ alkoxy, $C_1$-$C_3$ haloalkoxy, F, Cl, Br, I, OH, CN, $NO_2$, —C(═O)O$R^a$, and —C(═O)N($R^a$)($R^a$), and wherein two vicinal substituents of Ar may combine to provide a 5- to 8-membered ring which is fused with Ar;

G is optionally substituted $C_3$-$C_8$ cycloalkyl, which is optionally substituted with at least one substituent selected from the group consisting of $C_1$-$C_6$ alkyl, $C_1$-$C_6$ haloalkyl, $C_1$-$C_6$ alkoxy, $C_1$-$C_6$ haloalkoxy, phenyl, halogen, OH, $NH_2$, CN, $NO_2$, —C(=O)$R^a$, —C(=O)O$R^a$, and —C(=O)N($R^a$)($R^a$), wherein the phenyl in G is optionally substituted with at least one substituent selected from the group consisting of $C_1$-$C_3$ alkyl, $C_1$-$C_3$ haloalkyl, $C_1$-$C_3$ alkoxy, $C_1$-$C_3$ haloalkoxy, F, Cl, Br, I, OH, CN, $NO_2$, —C(=O)O$R^a$, and —C(=O)N($R^a$)($R^a$), and wherein two substituents in G may combine to provide a $C_3$-$C_8$ cycloalkyl which is spiro, fused, or bridged with the $C_3$-$C_8$ cycloalkyl in G;

$R^1$ is selected from the group consisting of

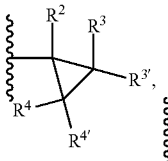

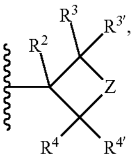

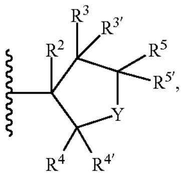

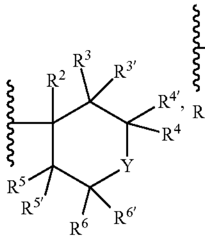

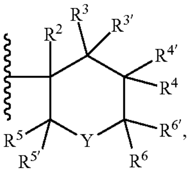

and

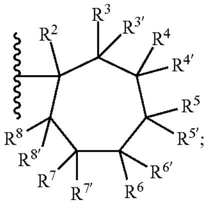

$R^2$ is selected from the group consisting of H, halogen, optionally substituted $C_1$-$C_6$ alkyl, optionally substituted phenyl, optionally substituted $C_3$-$C_6$ cycloalkyl, optionally substituted $C_2$-$C_{10}$ heterocyclyl, optionally substituted $C_1$-$C_6$ aminoalkyl, optionally substituted $C_1$-$C_6$ alkoxyalkyl, optionally substituted $C_1$-$C_6$ haloalkyl, optionally substituted $C_2$-$C_6$ alkynyl, —C(=O)O$R^a$, and —C(=O)N($R^a$)($R^a$), wherein each optional substituent in $R^2$ is at least one selected from the group consisting of halogen, $C_1$-$C_6$ alkyl, $C_1$-$C_3$ alkoxy, $C_1$-$C_3$ haloalkoxy, $C_1$-$C_3$ haloalkyl, —C(=O)O$R^a$, —S(=O)$_2$—$C_6$-$C_{10}$ aryl, and —S(=O)$_2$—$C_2$-$C_{10}$ heteroaryl;

$R^3$, $R^{3'}$, $R^4$, $R^{4'}$, $R^5$, $R^{5'}$, $R^6$, $R^{6'}$, $R^7$, $R^{7'}$, $R^8$, and $R^{8'}$ are each independently selected from the group consisting of H, $C_1$-$C_6$ alkyl, hydroxyl, $C_1$-$C_4$ haloalkyl, optionally substituted $C_3$-$C_8$ cycloalkyl, optionally substituted $C_2$-$C_6$ heterocyclyl, optionally substituted phenyl, and optionally substituted phenoxy, wherein each optional substituent in the heterocyclyl, phenyl, or phenoxy is at least one selected from the group consisting of $C_1$-$C_3$ alkyl, $C_1$-$C_3$ haloalkyl, $C_1$-$C_3$ alkoxy, $C_1$-$C_3$ haloalkoxy, halogen, OH, C(=O)O$R^a$, and C(=O)N($R^a$)($R^a$), wherein two geminal substituents selected from $R^3$, $R^{3'}$, $R^4$, $R^{4'}$, $R^5$, $R^{5'}$, $R^6$, $R^{6'}$, $R^7$, $R^{7'}$, $R^8$, and $R^{8'}$ may combine with the carbon atom to which they are bound to form a moiety selected from the group consisting of an optionally substituted $C_3$-$C_8$ cycloalkyl and an optionally substituted $C_2$-$C_{10}$ heterocyclyl, wherein two vicinal substituents selected from $R^3$, $R^{3'}$, $R^4$, $R^{4'}$, $R^5$, $R^{5'}$, $R^6$, $R^{6'}$, $R^7$, $R^{7'}$, $R^8$, and $R^{8'}$ may combine with the carbon atoms to which they are bound to form a moiety selected from the group consisting of an optionally substituted $C_3$-$C_8$ cycloalkyl, optionally substituted $C_2$-$C_{10}$ heterocyclyl, and optionally substituted phenyl;

wherein two substituents selected from $R^3$, $R^{3'}$, $R^4$, $R^{4'}$, R, $R^{5'}$, $R^6$, $R^{6'}$, $R^7$, $R^{7'}$, $R^8$, and $R^{8'}$, which are separated by two to five carbon atoms, may combine with the carbon atoms to which they are bound to form a moiety selected from the group consisting of optionally substituted $C_4$-$C_7$ cycloalkyl and optionally substituted $C_4$-$C_8$ heterocyclyl;

$R^{10}$ is selected from the group consisting of H, $C_1$-$C_6$ alkyl, $C_3$-$C_6$ cycloalkyl, optionally substituted phenyl, optionally substituted benzyl, —C(=O)OR, —C(=O)$R^b$, and —S(=O)$_2$-optionally substituted phenyl, wherein each optional substituent in the phenyl, benzyl, or —S(=O)$_2$-phenyl is independently at least one selected from the group consisting of F, Cl, Br, $C_1$-$C_3$ alkoxy, $C_1$-$C_3$ haloalkoxy, $C_1$-$C_3$ haloalkyl, hydroxyl, and —NH—C(=O)$R^a$;

$R^{10'}$ is selected from the group consisting of substituted phenyl, substituted benzyl, —C(=O)-optionally substituted $C_1$-$C_6$ alkyl, wherein the benzyl or phenyl in $R^{10'}$ is substituted with at least one substituent selected from the group consisting of halogen, $C_1$-$C_3$ haloalkyl, OH, and N($R^a$)($R^b$), and wherein the alkyl in $R^{10'}$ is substituted with at least one phenyl substituent;

Y is selected from the group consisting of C($R^a$)($R^a$), C=O, $NR^{10}$, $NR^{10'}$, and O, wherein if Y is C($R^a$)($R^a$) and $R^2$ is optionally substituted phenyl, then Ar comprises a $C_6$-$C_{10}$ aryl or $C_2$-$C_{10}$ heteroaryl substituted with at least one trifluoromethoxy substituent;

Z is selected from the group consisting of C=O, $NR^{10}$, $NR^{10'}$, O, and S;

$R^{A}$ is H or $C_1$-$C_6$ alkyl;

each occurrence of $R^a$ is independently selected from the group consisting of H, $C_1$-$C_6$ alkyl, benzyl, and $C_6$-$C_{10}$ aryl; and each occurrence of $R^b$ is independently selected from the group consisting of H, optionally substituted $C_1$-$C_6$ alkyl, optionally substituted benzyl, optionally substituted phenyl, and optionally substituted naphthyl, wherein the $C_1$-$C_6$ alkyl, benzyl, phenyl, or naphthyl in $R^b$ is independently optionally substituted with at least one selected from the group consisting of $C_1$-$C_3$ alkyl, $C_1$-$C_3$ haloalkyl, $C_1$-$C_3$ alkoxy, $C_1$-$C_3$ haloalkoxy, halogen, O$R^a$, CN, $NO_2$, C(=O)O$R^a$, and C(=O)N($R^a$)($R^a$);

wherein in (Ia), (Ib), and (Ic), at least one of the following applies:

a) $R^2$ is phenyl or $C_2$-$C_{10}$ heteroaryl, wherein the phenyl or heteroaryl is optionally substituted with at least one substituent selected from the group consisting of halogen, OH, $C_1$-$C_3$ haloalkoxy, $C_1$-$C_3$ haloalkyl, $C_1$-$C_3$ alkoxy, and $C_1$-$C_6$ alkyl;

b) at least one of $R^3$ and $R^{3'}$ is phenyl or $C_2$-$C_{10}$ heteroaryl, wherein the phenyl or heteroaryl is substituted with at least one substituent selected from the group consisting of halogen, OH, $C_1$-$C_3$ haloalkoxy, $C_1$-$C_3$ haloalkyl, $C_1$-$C_3$ alkoxy, and $C_1$-$C_6$ alkyl;

c) at least one of $R^3$, $R^{3'}$, $R^4$, and $R^{4'}$, is phenyl or $C_2$-$C_{10}$ heteroaryl, wherein the phenyl or heteroaryl is optionally substituted with at least one substituent selected from the group consisting of halogen, OH, $C_1$-$C_3$ haloalkoxy, $C_1$-$C_3$ haloalkyl, $C_1$-$C_3$ alkoxy, and $C_1$-$C_6$ alkyl, wherein one of Y and Z is present, and one of Y and Z is selected from the group consisting of C═O, $NR^{10}$, and O, wherein $R^{10}$ is selected from the group consisting of H, $C_3$-$C_6$ cycloalkyl, phenyl, optionally substituted benzyl, —C(═O)$OR^b$, —C(═O)$R^b$, —S(═O)$_2$-optionally substituted phenyl;

d) two geminal substituents selected from $R^3$, $R^{3'}$, $R^4$, $R^{4'}$, $R^5$, $R^{5'}$, $R^6$, $R^{6'}$, $R^7$, $R^{7'}$, $R^8$, and $R^{8'}$ combine with the carbon atom to which they are bound to form a $C_3$-$C_8$ cycloalkyl or $C_2$-$C_6$ heterocyclyl, wherein the cycloalkyl or heterocyclyl is substituted with at least one substituent selected from the group consisting of $C_1$-$C_3$ alkyl, $C_1$-$C_3$ haloalkyl, $C_1$-$C_3$ haloalkoxy, halogen, $N(R^a)(R^a)$, $OR^a$, C(═O)$R^a$, C(═O)$OR^a$, and C(═O)$N(R^a)(R^a)$, e) two vicinal substituents selected from $R^3$, $R^{3'}$, $R^4$, $R^{4'}$, $R^5$, $R^{5'}$, $R^6$, $R^{6'}$, $R^7$, $R^{7'}$, $R^8$, and $R^{8'}$ combine with the carbon atoms to which they are bound to form a $C_3$-$C_8$ cycloalkyl, $C_2$-$C_{10}$ heterocyclyl, or phenyl, wherein the cycloalkyl, heterocyclyl, or phenyl is substituted with at least one substituent selected from the group consisting of $C_1$-$C_3$ alkyl, $C_1$-$C_3$ haloalkyl, $C_1$-$C_3$ haloalkoxy, halogen, $OR^a$, C(═O)$R^a$, C(═O)$OR^a$, and C(═O)$N(R^a)(R^a)$;

f) two geminal substituents selected from $R^3$, $R^{3'}$, $R^4$, $R^{4'}$, $R^5$, $R^{5'}$, $R^6$, $R^{6'}$, $R^7$, $R^{7'}$, $R^8$, and $R^{8'}$ combine with the carbon atom to which they are bound to form a $C_3$-$C_8$ cycloalkyl or $C_2$-$C_6$ heterocyclyl, and two vicinal substituents selected from $R^3$, $R^{3'}$, $R^4$, $R^{4'}$, $R^5$, $R^{5'}$, $R^6$, $R^{6'}$, $R^7$, $R^{7'}$, $R^8$, and $R^{8'}$ combine with the carbon atoms to which they are bound to form a $C_3$-$C_8$ cycloalkyl, $C_2$-$C_{10}$ heterocyclyl, or phenyl, wherein each of the cycloalkyl, heterocyclyl, or phenyl is independently optionally substituted with at least one substituent selected from the group consisting of $C_1$-$C_3$ alkyl, $C_1$-$C_3$ haloalkyl, $C_1$-$C_3$ haloalkoxy, halogen, $N(R^a)(R^a)$, $OR^a$, C(═O)$R^a$, C(═O)$OR^a$, and C(═O)$N(R^a)(R^a)$;

g) Y is $N(R^{10'})$ and each of $R^4$, $R^{4'}$, $R^6$, and $R^{6'}$, if present, are independently selected from the group consisting of H, $C_1$-$C_6$ alkyl, hydroxyl, $C_1$-$C_4$ haloalkyl, phenyl, and phenoxy;

h) at least one of $R^2$, $R^3$, $R^{3'}$, $R^4$, and $R^{4'}$ is optionally substituted $C_3$-$C_8$ cycloalkyl or $C_2$-$C_{10}$ heterocyclyl, wherein each optional substituent in the cycloalkyl or heterocycloalkyl is independently selected from the group consisting of halogen, $C_1$-$C_6$ alkyl, $C_1$-$C_3$ haloalkyl, $C_1$-$C_3$ haloalkoxy, $OR^a$, $N(R^a)(R^b)$, C(═O)$R^a$, and C(═O)$OR^a$; and i) $R^2$ is selected from the group consisting of optionally substituted $C_1$-$C_6$ haloalkyl, optionally substituted $C_2$-$C_6$ aminoalkyl and optionally substituted $C_2$-$C_6$ alkynyl, wherein each optional substituent of the haloalkyl, aminoalkyl, and alkynyl in $R^2$ is at least one selected from the group consisting of $C_1$-$C_6$ alkyl, $C_1$-$C_3$ haloalkyl, $C_1$-$C_3$ haloalkoxy, halogen, C(═O)$R^a$, C(═O)$OR^a$, C(═O)$N(R^a)(R^a)$, S(═O)$_2$-optionally substituted phenyl and S(═O)$_2$-optionally substituted $C_2$-$C_{10}$ heteroaryl.

In certain embodiments, the $C_6$-$C_{10}$ aryl or $C_2$-$C_{10}$ heteroaryl substituted with at least one trifluoromethyl substituent is trifluoromethylphenyl. In certain embodiments, the trifluoromethyl phenyl is 4-trifluoromethylphenyl.

In certain embodiments, the compound of formula (I) is selected from the group consisting of:

(Ia-1)

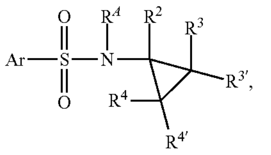

(Ia-2)

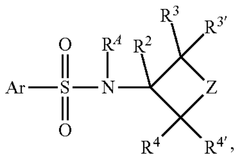

(Ia-3)

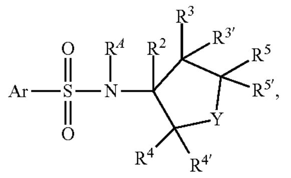

(Ia-4)

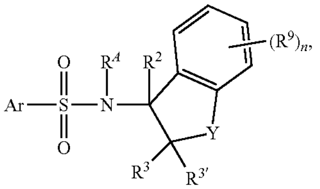

(Ia-5)

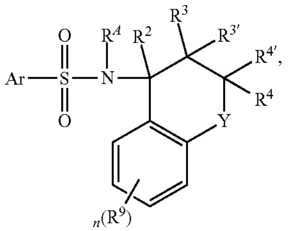

(Ia-6)

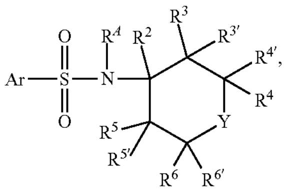

(Ia-7)

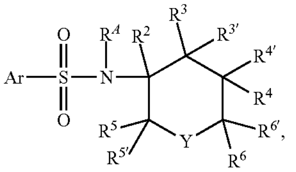

-continued
(Ia-8)
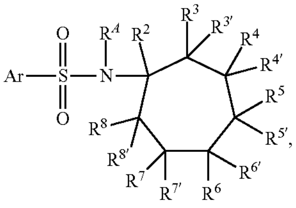
(Ib-1)
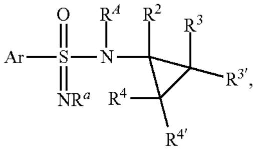
(Ib-2)
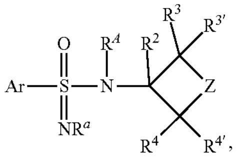
(Ib-3)
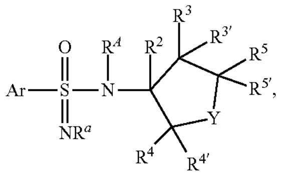
(Ib-4)
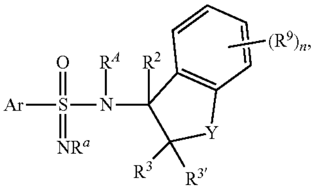
(Ib-5)
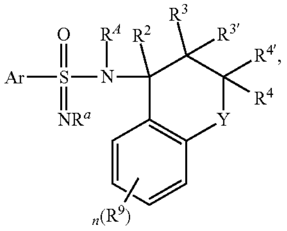
(Ib-6)
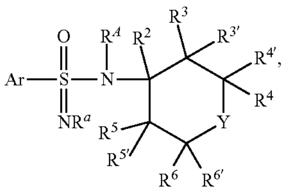
(Ib-7)
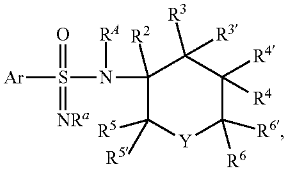
-continued
(Ib-8)
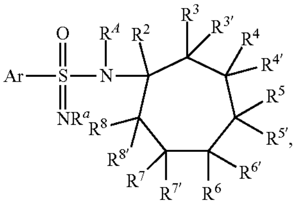
(Ic-1)
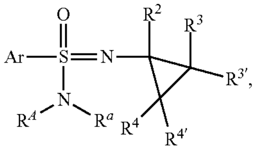
(Ic-2)
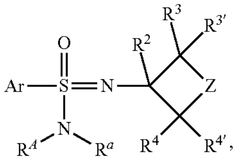
(Ic-3)
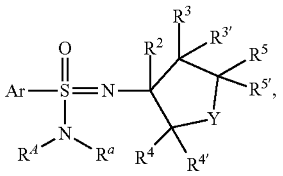
(Ic-4)
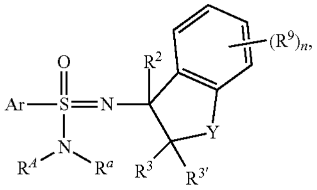
(Ic-5)
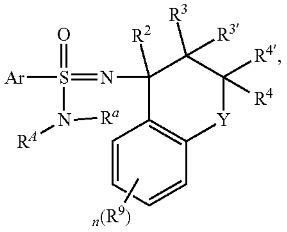
(Ic-6)
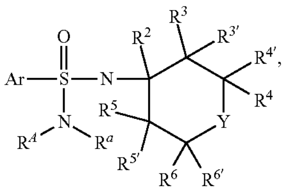
(Ic-7)
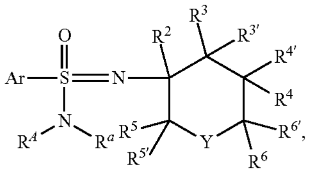

-continued (Ic-8)

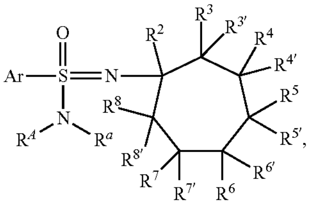

(Id-1)

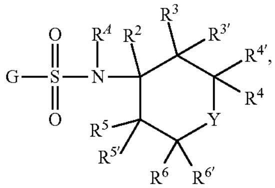

(Ie-1)

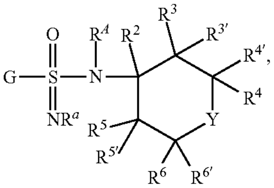

and (If-1)

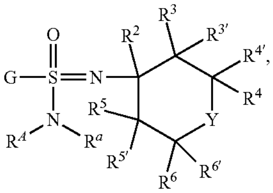

wherein:

each occurrence of $R^9$ is independently selected from the group consisting of F, Cl, Br, $C_1$-$C_3$ alkoxy, and $C_1$-$C_3$ haloalkoxy; and n is an integer selected from the group consisting of 0, 1, and 2.

In certain embodiments, $R^A$ is H. In certain embodiments, $R^A$ is methyl.

In certain embodiments, the compound of formula (I) is selected from the group consisting of:

(Ia')

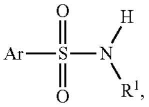

(Ib')

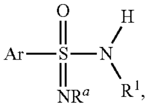

and (Ic')

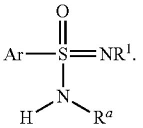

In certain embodiments, the compound of formula (I) is selected from the group consisting of:

(Ia'-1)

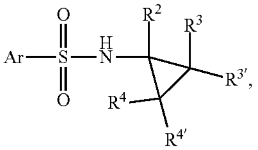

(Ia'-2)

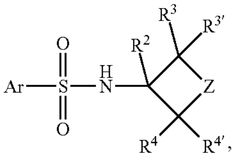

(Ia'-3)

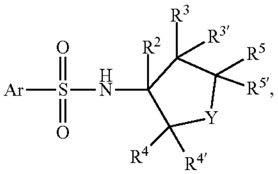

(Ia'-4)

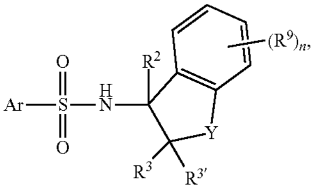

(Ia'-5)

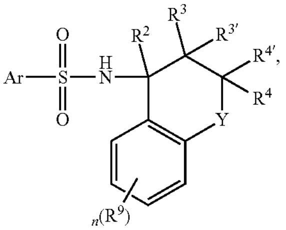

(Ia'-6)

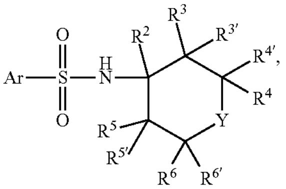

(Ia'-7)

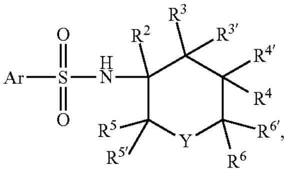

and (Ia'-8)

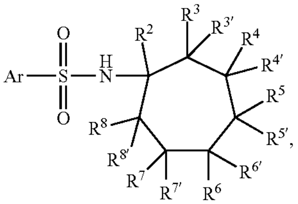

-continued
(Ib′-1)
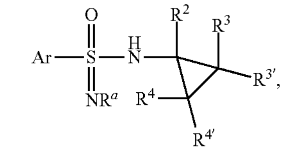
(Ib′-2)
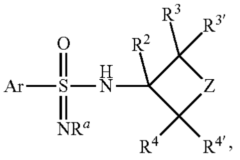
(Ib′-3)
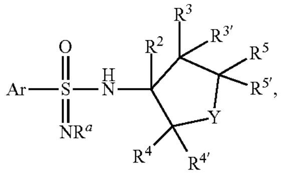
(Ib′-4)
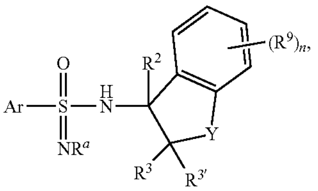
(Ib′-5)
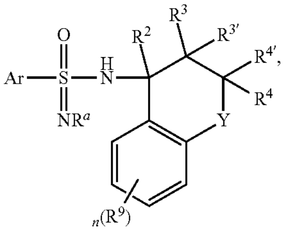
(Ib′-6)
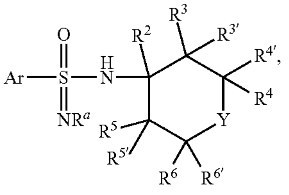
(Ib′-7)
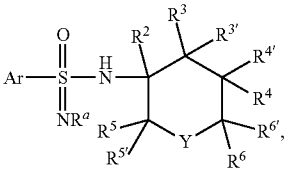
(Ib′-8)
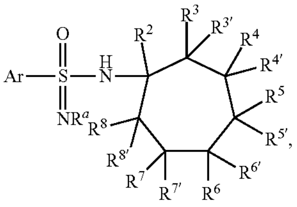
-continued
(Ic′-1)
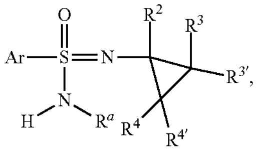
(Ic′-2)
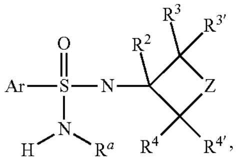
(Ic′-3)
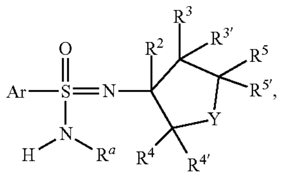
(Ic′-4)
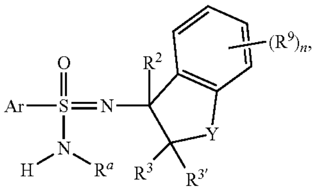
(Ic′-5)
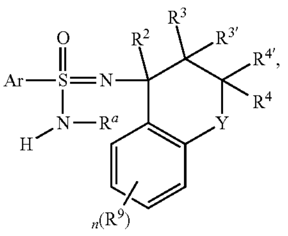
(Ic′-6)
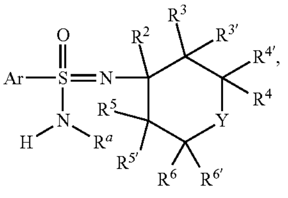
(Ic′-7)
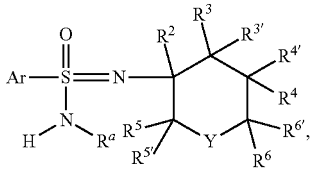
(Ic′-8)
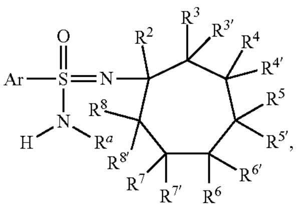

-continued
(Id'-1)
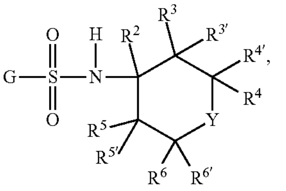
(Ie'-1)
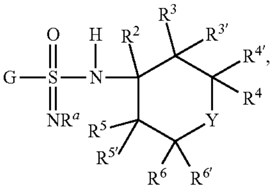
and
(If'-1)
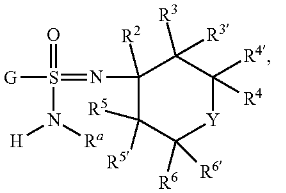
wherein:
each occurrence of $R^9$ is independently selected from the group consisting of F, Cl, Br, $C_1$-$C_3$ alkoxy, and $C_1$-$C_3$ haloalkoxy; and
n is an integer selected from the group consisting of 0, 1, and 2.
In certain embodiments, $R^1$ is selected from the group consisting of
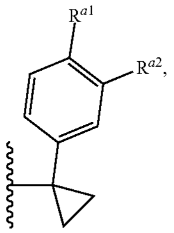
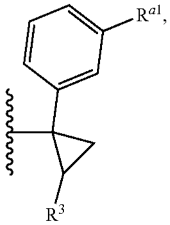
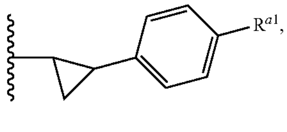
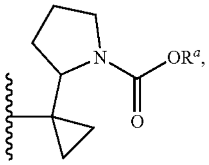
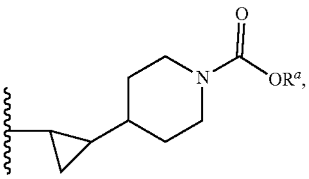
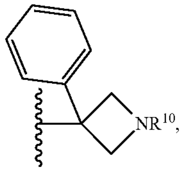
-continued
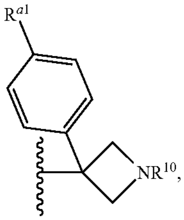
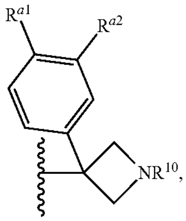
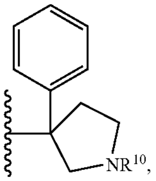
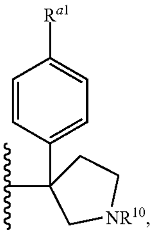
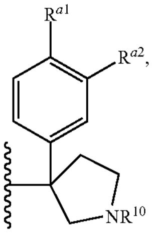
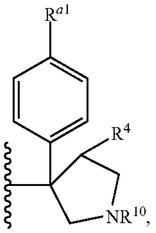
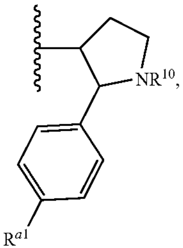
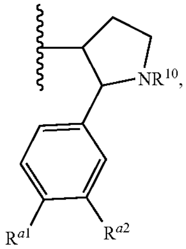
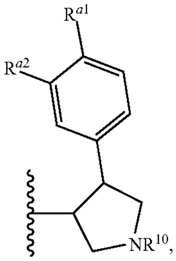
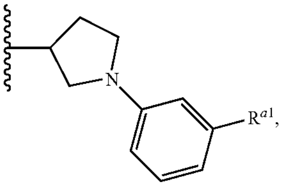
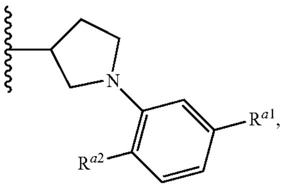
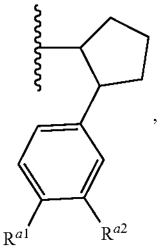
, -continued

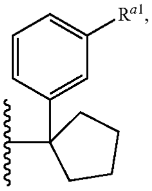
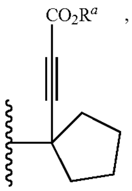
,
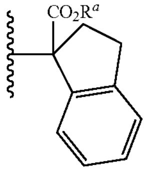
,
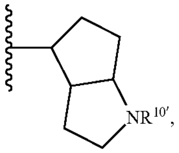
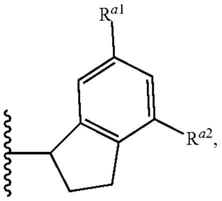
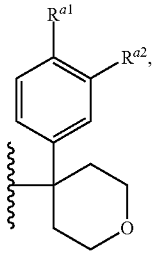
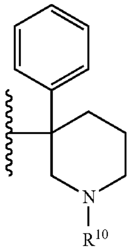
,
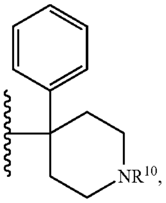
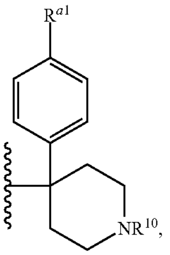
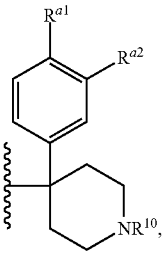
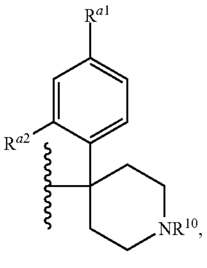
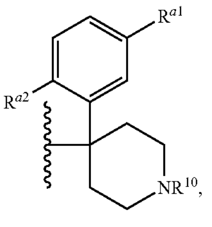
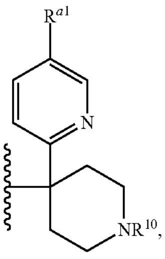
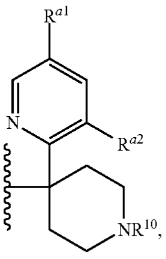
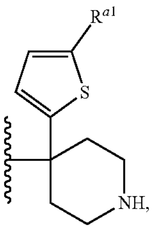

-continued

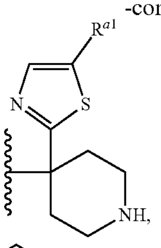
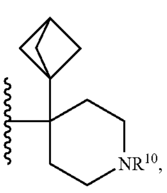
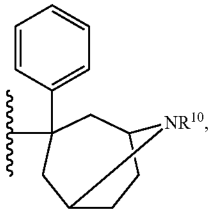
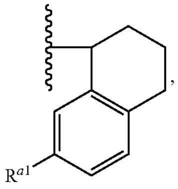
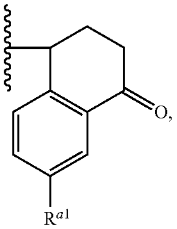
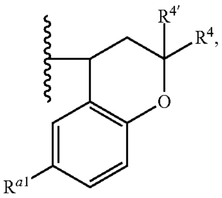
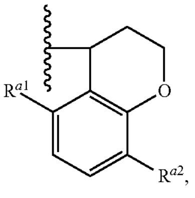
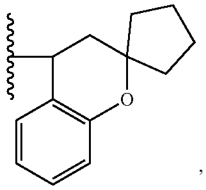
,
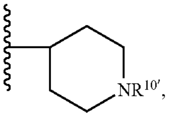
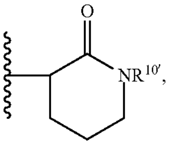
and
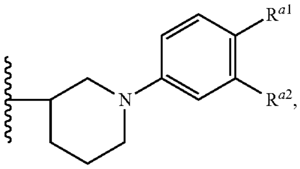

wherein $R^{a1}$ and $R^{a2}$ are each independently selected from the group consisting of F, Cl, Br, $C_1$-$C_3$ alkyl, $C_1$-$C_3$ haloalkyl, $C_1$-$C_3$ alkoxy, and $C_1$-$C_3$ haloalkoxy.

In certain embodiments, $R^{a1}$ is F. In certain embodiments, $R^{a1}$ is Cl. In certain embodiments, $R^{a1}$ is Br. In certain embodiments, $R^{a1}$ is Me. In certain embodiments, $R^{a1}$ is $CHF_2$. In certain embodiments, $R^{a1}$ is $CF_3$. In certain embodiments, $R^{a1}$ is OMe. In certain embodiments, $R^{a1}$ is OEt. In certain embodiments, $R^{a1}$ is $OCF_3$. In certain embodiments, $R^{a1}$ is $OCF_2H$.

In certain embodiments, $R^{a2}$ is F. In certain embodiments, $R^a2$ is $C_1$. In certain embodiments, $R^{a2}$ is Br. In certain embodiments, $R^{a2}$ is Me. In certain embodiments, $R^{a2}$ is $CHF_2$. In certain embodiments, $R^{a2}$ is $CF_3$. In certain embodiments, $R^{a2}$ is OMe. In certain embodiments, $R^{a2}$ is OEt. In certain embodiments, $R^{a2}$ is $OCF_3$. In certain embodiments, $R^{a2}$ is $OCF_2H$.

In certain embodiments, Ar is selected from the group consisting of

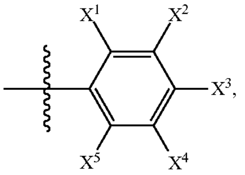

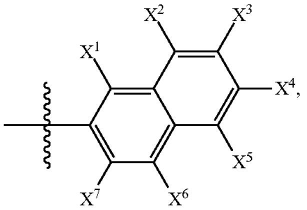

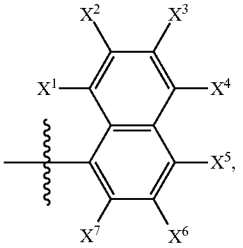

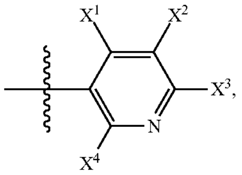

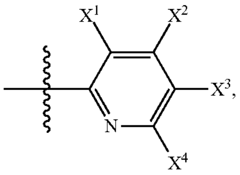

and

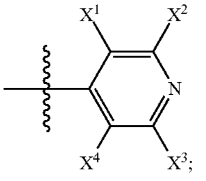

$X^1$, $X^2$, $X^3$, $X^4$, $X^5$, $X^6$, and $X^7$ are each independently selected from the group consisting of $C_1$-$C_6$ alkyl, F, Cl, $N(R^a)(R^b)$, $OR^b$, —C(═O)$OR^a$, —C(═O)$N(R^a)(R^a)$, $NH_2$, OH, $NO_2$, $C_1$-$C_3$ haloalkyl, $C_1$-$C_3$ haloalkoxy, and phenyl.

In certain embodiments, the compound of formula (I) is the compound of formula (Ia-1) or (Ia'-1), wherein at least two of $R^3$, $R^{3'}$, $R^4$, and $R^{4'}$ are H. In certain embodiments, the compound of formula (I) is the compound of formula (Ia-2) or (Ia'-2), wherein at least two of $R^3$, $R^{3'}$, $R^4$, and $R^{4'}$ are H. In certain embodiments, the compound of formula (I) is the compound of formula (Ia-3) or (Ia'-3), wherein at least four of $R^3$, $R^{3'}$, $R^4$, $R^{4'}$, $R^5$, and $R^5$ are H. In certain embodiments, the compound of formula (I) is the compound of formula (Ia-4) or (Ia'-4), wherein at least one of $R^3$ and $R^{3'}$ is H. In certain embodiments, the compound of formula (I) is the compound of formula (Ia-5) or (Ia'-5), wherein at least two of $R^3$, $R^{3'}$, $R^4$, and $R^{4'}$ are H. In certain embodiments, the compound of formula (I) is the compound of formula (Ia-6) or (Ia'-6), wherein at least six of $R^3$, $R^{3'}$, $R^4$, $R^{4'}$, $R^5$, $R^{5'}$, $R^6$, and $R^{6'}$ are H. In certain embodiments, the compound of formula (I) is the compound of formula (Ia-7) or (Ia'-7), wherein at least six of $R^3$, $R^{3'}$, $R^4$, $R^{4'}$, $R^5$, $R^5$, $R^6$, and $R^{6'}$ are H. In certain embodiments, the compound of formula (I) is the compound of formula (Ia-8) or (Ia'-8), wherein at least ten of $R^3$, $R^{3'}$, $R^4$, $R^{4'}$, $R^5$, $R^{5'}$, $R^6$, $R^{6'}$, $R^7$, $R^{7'}$, $R^8$, and $R^{8'}$ are H. In certain embodiments, the compound of formula (I) is the compound of formula (Ib-1) or (Ib'-1), wherein at least two of $R^3$, $R^{3'}$, $R^4$, and $R^{4'}$ are H. In certain embodiments, the compound of formula (I) is the compound of formula (Ib-2) or (Ib'-2), wherein at least two of $R^3$, $R^{3'}$, $R^4$, and $R^{4'}$ are H. In certain embodiments, the compound of formula (I) is the compound of formula (Ib-3) or (Ib'-3), wherein at least four of $R^3$, $R^{3'}$, $R^4$, $R^{4'}$, $R^5$, and $R^5$ are H. In certain embodiments, the compound of formula (I) is the compound of formula (Ib-4) or (Ib'-4), wherein at least one of $R^3$ and $R^{3'}$ is H. In certain embodiments, the compound of formula (I) is the compound of formula (Ib-5) or (Ib'-5), wherein at least two of $R^3$, $R^{3'}$, $R^4$, and $R^{4'}$ are H. In certain embodiments, the compound of formula (I) is the compound of formula (Ib-6) or (Ib'-6), wherein at least six of $R^3$, $R^{3'}$, $R^4$, $R^{4'}$, $R^5$, $R^5$, $R^6$, and $R^{6'}$ are H. In certain embodiments, the compound of formula (I) is the compound of formula (Ib-7) or (Ib'-7), wherein at least six of $R^3$, $R^{3'}$, $R^4$, $R^{4'}$, $R^5$, $R^5$, $R^6$, and $R^{6'}$ are H. In certain embodiments, the compound of formula (I) is the compound of formula (Ib-8) or (Ib'-8), wherein at least ten of $R^3$, $R^{3'}$, $R^4$, $R^{4'}$, $R^5$, $R^5$, $R^6$, $R^{6'}$, $R^7$, $R^{7'}$, R, and $R^{8'}$ are H. In certain embodiments, the compound of formula (I) is the compound of formula (Ic-1) or (Ic'-1), wherein at least two of $R^3$, $R^{3'}$, $R^4$, and $R^{4'}$ are H. In certain embodiments, the compound of formula (I) is the compound of formula (Ic-2) or (Ic'-2), wherein at least two of $R^3$, $R^{3'}$, $R^4$, and $R^{4'}$ are H. In certain embodiments, the compound of formula (I) is the compound of formula (Ic-3) or (Ic'-3), wherein at least four of $R^3$, $R^{3'}$, $R^4$, $R^{4'}$, $R^5$, and R are H. In certain embodiments, the compound of formula (I) is the compound of formula (Ic-4) or (Ic'-4), wherein at least one of $R^3$ and $R^{3'}$ is H. In certain embodiments, the compound of formula (I) is the compound of formula (Ic-5) or (Ic'-5), wherein at least two of $R^3$, $R^{3'}$, $R^4$, and $R^{4'}$ are H. In certain embodiments, the compound of formula (I) is the compound of formula (Ic-6) or (Ic'-6), wherein at least six of $R^3$, $R^{3'}$, $R^4$, $R^{4'}$, $R^5$, $R^5$, $R^6$, and $R^{6'}$ are H. In certain embodiments, the compound of formula (I) is the compound of formula (Ic-7) or (Ic'-7), wherein at least six of $R^3$, $R^{3'}$, $R^4$, $R^{4'}$, $R^5$, $R^{5'}$, $R^6$, and $R^{6'}$ are H. In certain embodiments, the compound of formula (I) is the compound of formula (Ic-8) or (Ic'-8), wherein at least ten of $R^3$, $R^{3'}$, $R^4$, $R^{4'}$, $R^5$, $R^5$, $R^6$, $R^{6'}$, $R^7$, $R^{7'}$, $R^8$, and $R^{8'}$ are H. In certain embodiments, the compound of formula (I) is the compound of formula (Id-1), wherein at least six of $R^3$, $R^{3'}$, $R^4$, $R^{4'}$, $R^5$, $R^{5'}$, $R^6$, and $R^{6'}$ are H. In certain embodiments, the compound of formula (I) is the compound of formula (Ie-1), wherein at least six of $R^3$, $R^{3'}$, $R^4$, $R^{4'}$, $R^5$, $R^{5'}$, $R^6$, and $R^{6'}$ are H. In certain embodiments, the compound of formula (I) is the compound of formula (If-1), wherein at least six of $R^3$, $R^{3'}$, $R^4$, $R^{4'}$, $R^5$, $R^1$, $R^6$, and $R^{6'}$ are H.

In certain embodiments, each of $X^1$, $X^2$, $X^3$, $X^4$, $X^5$, $X^6$, and $X^7$, if present, is H.

In certain embodiments, $X^1$, $X^2$, $X^3$, and $X^4$ are present and at least one of $X^1$, $X^2$, $X^3$, and $X^4$ is H. In certain embodiments, $X^1$, $X^2$, $X^3$, and $X^4$ are present and at least two of $X^1$, $X^2$, $X^3$, and $X^4$ are H. In certain embodiments, $X^1$, $X^2$, $X^3$, and $X^4$ are present and at least three of $X^1$, $X^2$, $X^3$, and $X^4$ are H.

In certain embodiments, $X^1$, $X^2$, $X^3$, $X^4$, and $X^5$ are present and at least one of $X^1$, $X^2$, $X^3$, $X^4$, and $X^5$ is H. In certain embodiments, $X^1$, $X^2$, $X^3$, $X^4$, and $X^5$ are present and at least two of $X^1$, $X^2$, $X^3$, $X^4$, and $X^5$ are H. In certain embodiments, $X^1$, $X^2$, $X^3$, $X^4$, and $X^5$ are present and at least three of $X^1$, $X^2$, $X^3$, $X^4$, and $X^5$ are H. In certain embodiments, $X^1$, $X^2$, $X^3$, $X^4$, and $X^5$ are present and at least four of $X^1$, $X^2$, $X^3$, $X^4$, and $X^5$ are H.

In certain embodiments, $X^1$, $X^2$, $X^3$, $X^4$, $X^5$, and $X^6$ are present and at least one of X, $X^2$, $X^3$, $X^4$, $X^5$, and $X^6$ is H. In certain embodiments, $X^1$, $X^2$, $X^3$, $X^4$, $X^5$, and $X^6$ are present and at least two of $X^1$, $X^2$, $X^3$, $X^4$, $X^5$, and $X^6$ are H. In certain embodiments, $X^1$, $X^2$, $X^3$, $X^4$, $X^5$, and $X^6$ are present and at least three of $X^1$, $X^2$, $X^3$, $X^4$, $X^5$, and $X^6$ are H. In certain embodiments, $X^1$, $X^2$, $X^3$, $X^4$, $X^5$, and $X^6$ are present and at least four of $X^1$, $X^2$, $X^3$, $X^4$, $X^5$, and $X^6$ are H. In certain embodiments, $X^1$, $X^2$, $X^3$, $X^4$, $X^5$, and $X^6$ are present and at least five of $X^1$, $X^2$, $X^3$, $X^4$, $X^5$, and $X^6$ are H.

In certain embodiments, $X^1$, $X^2$, $X^3$, $X^4$, $X^5$, $X^6$, and $X^7$ are present and at least one of $X^1$, $X^2$, $X^3$, $X^4$, $X^5$, $X^6$, and $X^7$ is H In certain embodiments, $X^1$, $X^2$, $X^3$, $X^4$, $X^5$, $X^6$, and $X^7$ are present and at least two of $X^1$, $X^2$, $X^3$, $X^4$, $X^5$, $X^6$, and $X^7$ are H. In certain embodiments, $X^1$, $X^2$, $X^3$, $X^4$, $X^5$, $X^6$, and $X^7$ are present and at least three of $X^1$, $X^2$, $X^3$, $X^4$, $X^5$, $X^6$, and $X^7$ are H. In certain embodiments, $X^1$, $X^2$, $X^3$, $X^4$, $X^5$, $X^6$, and $X^7$ are present and at least four of $X^1$, $X^2$, $X^3$, $X^4$, $X^5$, $X^6$, and $X^7$ are H. In certain embodiments, $X^1$, $X^2$, $X^3$, $X^4$, $X^5$, $X^6$, and $X^7$ are present and at least five of $X^1$, $X^2$, $X^3$, $X^4$, $X^5$, $X^6$, and $X^7$ are H. In certain embodiments, $X^1$, $X^2$, $X^3$, $X^4$, $X^5$, $X^6$, and $X^7$ are present and at least six of $X^1$, $X^2$, $X^3$, $X^4$, $X^5$, $X^6$, and $X^7$ are H.

In certain embodiments, $X^1$ is $OCF_3$. In certain embodiments, $X^1$ is

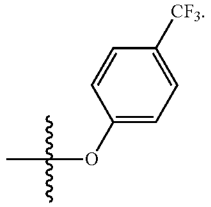 [SMILES: *Oc1ccc(C(F)(F)F)cc1]

In certain embodiments, $X^1$ is $CF_3$. In certain embodiments, $X^1$ is $NH_2$. In certain embodiments, $X^1$ is $O(CH(CH_3)_2)$. In certain embodiments, $X^2$ is $OCF_3$. In certain embodiments, $X^2$ is

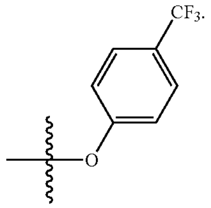 [SMILES: *Oc1ccc(C(F)(F)F)cc1]

In certain embodiments, $X^2$ is $CF_3$. In certain embodiments, $X^2$ is $NH_2$. In certain embodiments, $X^2$ is $O(CH(CH_3)_2)$. In certain embodiments, $X^3$ is $OCF_3$. In certain embodiments, $X^3$ is

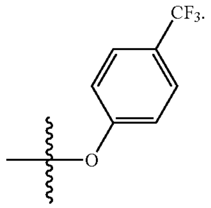 [SMILES: *Oc1ccc(C(F)(F)F)cc1]

In certain embodiments, $X^3$ is $CF_3$. In certain embodiments, $X^3$ is $NH_2$. In certain embodiments, $X^3$ is $O(CH(CH_3)_2)$. In certain embodiments, $X^4$ is $OCF_3$. In certain embodiments, $X^4$ is

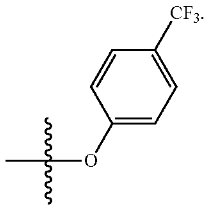 [SMILES: *Oc1ccc(C(F)(F)F)cc1]

In certain embodiments, $X^4$ is $CF_3$. In certain embodiments, $X^4$ is $NH_2$. In certain embodiments, $X^4$ is $O(CH(CH_3)_2)$. In certain embodiments, $X^5$ is $OCF_3$. In certain embodiments, $X^5$ is

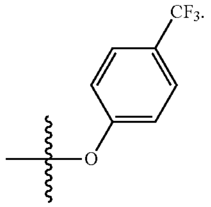 [SMILES: *Oc1ccc(C(F)(F)F)cc1]

certain embodiments, $X^5$ is $CF_3$. In certain embodiments, $X^5$ is $N_2$. In certain embodiments, $X^5$ is $O(CH(CH_3)_2)$. In certain embodiments, $X^6$ is $OCF_3$. In certain embodiments, $X^6$ is

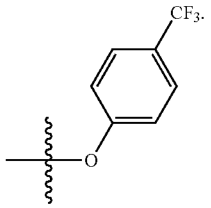 [SMILES: *Oc1ccc(C(F)(F)F)cc1]

In certain embodiments, $X^6$ is $CF_3$. In certain embodiments, $X^6$ is $NH_2$. In certain embodiments, $X^6$ is $O(CH(CH_3)_2)$. In certain embodiments, $X^7$ is $OCF_3$. In certain embodiments, $X^7$ is

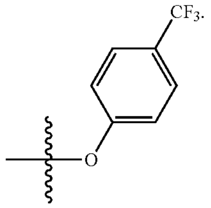 [SMILES: *Oc1ccc(C(F)(F)F)cc1]

In certain embodiments, $X^7$ is $CF_3$. In certain embodiments, $X^7$ is $NH_2$. In certain embodiments, $X^7$ is $O(CH(CH_3)_2)$.

In certain embodiments, Ar is

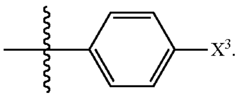

In certain embodiments, Ar is

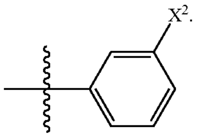

In certain embodiments, Ar is

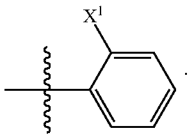

In certain embodiments, Ar is

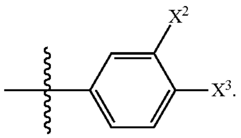

In certain embodiments, Ar is

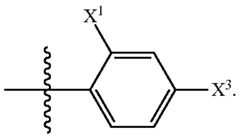

In certain embodiments, Ar is

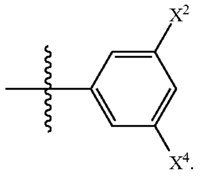

In certain embodiments, Ar is

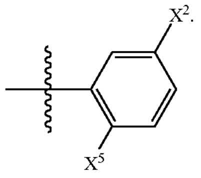

In certain embodiments, Ar is

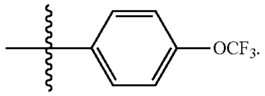 [SMILES: *c1ccc(OC(F)(F)F)cc1]

In certain embodiments, Ar is

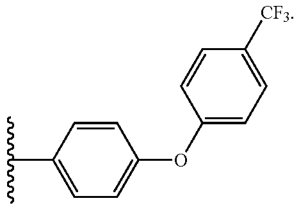 [SMILES: *c1ccc(Oc2ccc(C(F)(F)F)cc2)cc1]

In certain embodiments, Ar is

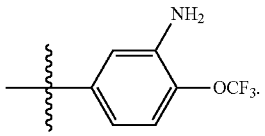 [SMILES: *c1ccc(OC(F)(F)F)c(N)c1]

In certain embodiments, Ar is

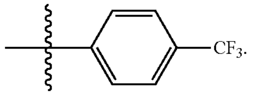

In certain embodiments, Ar is

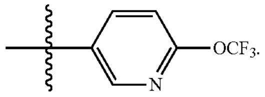 [SMILES: *c1ccc(OC(F)(F)F)nc1]

In certain embodiments, Ar is

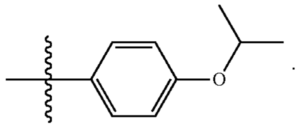 [SMILES: *c1ccc(OC(C)C)cc1]

In certain embodiments, Ar is

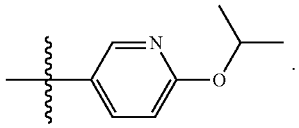

In certain embodiments, Ar is 1-naphthyl. In certain embodiments, Ar is 2-naphthyl. In certain embodiments, Ar is 2-pyridyl. In certain embodiments, Ar is 3-pyridyl. In certain embodiments, Ar is 4-pyridyl.

In certain embodiments, G is:

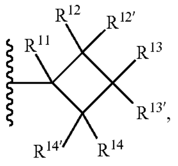

wherein:

$R^{11}$, $R^{12}$, $R^{12'}$, $R^{13}$, $R^{13'}$, $R^{14}$, and $R^{14'}$ are each independently selected from the group consisting of H, $C_1$-$C_6$ alkyl, $C_1$-$C_6$ haloalkyl, and optionally substituted phenyl, wherein each optional substituent in the phenyl is at least one selected from the group consisting of $C_1$-$C_3$ alkyl, $C_1$-$C_3$ haloalkyl, $C_1$-$C_3$ alkoxy, $C_1$-$C_3$ haloalkoxy, halogen, OH, C(=O)OR$^a$, and C(=O)N(R$^a$)(R$^a$), and wherein $R^{11}$ and $R^{13}$ or $R^{11}$ and $R^{13'}$ may optionally combine with the atoms to which they are bound to form a $C_3$-$C_8$ cycloalkyl.

In certain embodiments, at least one of $R^{11}$, $R^{12}$, $R^{12'}$, $R^{13}$, $R^{13'}$ $R^{14}$ and $R^{14'}$ is H; In certain embodiments, at least two of $R^{11}$, $R^{12}$, $R^{12'}$, $R^{13}$, $R^{13'}$, $R^{14}$, and $R^{14'}$ are H. In certain embodiments, at least three of $R^{11}$, $R^{12}$, $R^{12'}$, $R^{13}$, $R^{13'}$, $R^{14}$, and $R^{14'}$ are H. In certain embodiments, at least four of $R^{11}$, $R^{12}$, $R^{12'}$, $R^{13}$, $R^{13'}$, $R^{14}$, and $R^{14'}$ are H. In certain embodiments, at least five of $R^{11}$, $R^{12}$, $R^{12'}$, $R^{13}$, $R^{13'}$, $R^{14}$, and $R^{14'}$ are H. In certain embodiments, at least six of $R^{11}$, $R^{12}$, $R^{12'}$, $R^{13}$, $R^{13'}$, $R^{14}$, and $R^{14'}$ are H. In certain embodiments, each of $R^{11}$, $R^{12}$, $R^{12'}$, $R^{13}$, $R^{13'}$, $R^{14}$, and $R^{14'}$ are H.

In certain embodiments, at least one of $R^{11}$, $R^{12}$, $R^{12'}$, $R^{13}$, $R^{13'}$, $R^{14}$, and $R^{14'}$ is $CF_3$.

In certain embodiments, G is

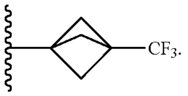 [SMILES: *C12CC(C(F)(F)F)(C1)C2]

In certain embodiments, $R^2$ is —$CH_2F$. In certain embodiments, $R^2$ is —C(=O)OEt. In certain embodiments, $R^2$ is Ph. In certain embodiments, $R^2$ is

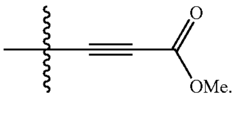

In certain embodiments, $R^2$ is

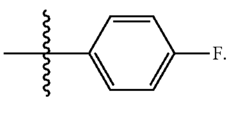 [SMILES: *c1ccc(F)cc1]

In certain embodiments, $R^2$ is

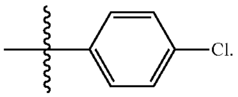 [SMILES: *c1ccc(Cl)cc1]

In certain embodiments, $R^2$ is

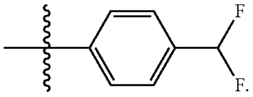 [SMILES: *c1ccc(C(F)F)cc1]

In certain embodiments, $R^2$ is

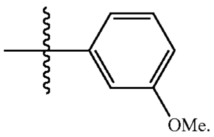 [SMILES: *c1cccc(OC)c1]

In certain embodiments, $R^2$ is

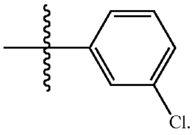 [SMILES: *c1cccc(Cl)c1]

In certain embodiments, $R^2$ is

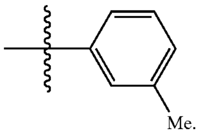 [SMILES: *c1cccc(C)c1]

In certain embodiments, $R^2$ is

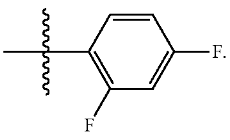 [SMILES: *c1ccc(F)cc1F]

In certain embodiments, $R^2$ is

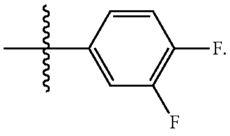 [SMILES: *c1ccc(F)c(F)c1]

In certain embodiments, $R^2$ is

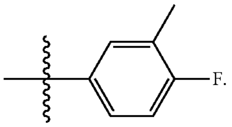 [SMILES: *c1ccc(F)c(C)c1]

In certain embodiments, $R^2$ is

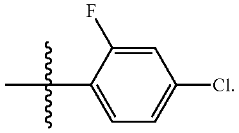

In certain embodiments, $R^2$ is

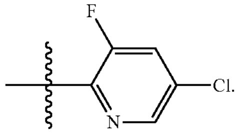 [SMILES: *c1ccc(Cl)cc1F]

In certain embodiments, $R^2$ is

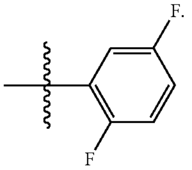 [SMILES: *c1cc(F)ccc1F]

In certain embodiments, $R^2$ is

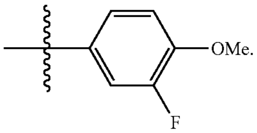 [SMILES: *c1ccc(OC)c(F)c1]

In certain embodiments, $R^2$ is

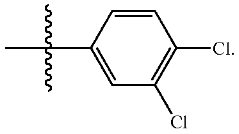 [SMILES: *c1ccc(Cl)c(Cl)c1]

In certain embodiments, $R^2$ is

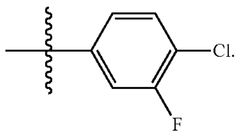 [SMILES: *c1ccc(Cl)c(F)c1]

In certain embodiments, $R^2$ is

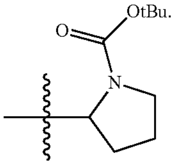 [SMILES: *C1CCCN1C(=O)OC(C)(C)C]

In certain embodiments, $R^2$ is

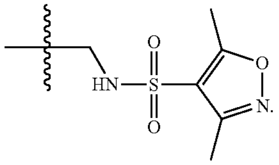 [SMILES: *CNS(=O)(=O)c1c(C)noc1C]

In certain embodiments, $R^2$ is

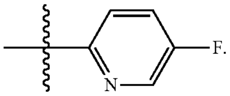 [SMILES: *c1ccc(F)cn1]

In certain embodiments, $R^2$ is

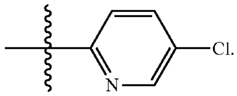 [SMILES: *c1ccc(Cl)cn1]

In certain embodiments, $R^2$ is

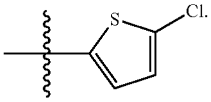 [SMILES: *c1ccc(Cl)s1]

In certain embodiments, $R^2$ is

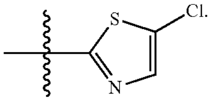 [SMILES: *c1ncc(Cl)s1]

In certain embodiments, $R^2$ is

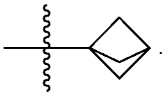

In certain embodiments, $R^3$ is methyl. In certain embodiments, $R^3$ is trifluoromethyl. In certain embodiments, $R^3$ is hydroxyl. In certain embodiments, $R^3$ is —C(═O)OMe. In certain embodiments, $R^3$ is Ph. In certain embodiments, $R^3$ is

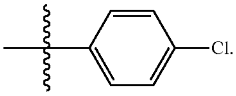 [SMILES: *c1ccc(Cl)cc1]

In certain embodiments, $R^3$ is

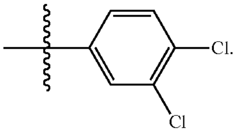 [SMILES: *c1ccc(Cl)c(Cl)c1]

In certain embodiments, $R^3$ is

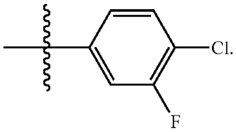 [SMILES: *c1ccc(Cl)c(F)c1]

In certain embodiments, $R^3$ is

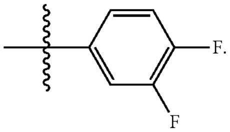 [SMILES: *c1ccc(F)c(F)c1]

In certain embodiments, $R^3$ is

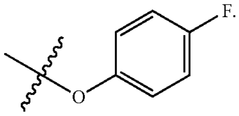 [SMILES: *Oc1ccc(F)cc1]

In certain embodiments, $R^3$ is F.

In certain embodiments, $R^{3'}$ is methyl. In certain embodiments, $R^{3'}$ is trifluoromethyl. In certain embodiments, $R^{3'}$ is hydroxyl. In certain embodiments, $R^{3'}$ is —C(═O)OMe. In certain embodiments, $R^{3'}$ is Ph. In certain embodiments, $R^{3'}$ is

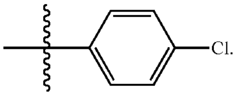 [SMILES: *c1ccc(Cl)cc1]

In certain embodiments, $R^{3'}$ is

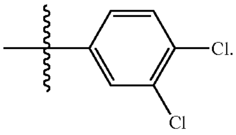 [SMILES: *c1ccc(Cl)c(Cl)c1]

In certain embodiments, $R^{3'}$ is

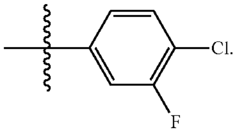 [SMILES: *c1ccc(Cl)c(F)c1]

In certain embodiments, $R^{3'}$ is

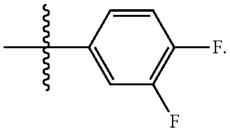 [SMILES: *c1ccc(F)c(F)c1]

In certain embodiments, $R^{3'}$ is

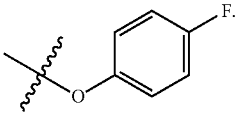 [SMILES: *Oc1ccc(F)cc1]

In certain embodiments, $R^{3'}$ is F.

In certain embodiments, $R^4$ is methyl. In certain embodiments, $R^4$ is trifluoromethyl. In certain embodiments, $R^4$ is hydroxyl. In certain embodiments, $R^4$ is —C(═O)OMe. In certain embodiments, R is Ph. In certain embodiments, R is

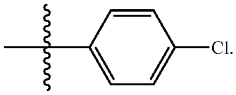

In certain embodiments, $R^4$ is

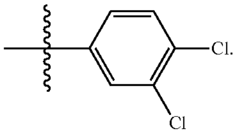 [SMILES: *c1ccc(Cl)c(Cl)c1]

In certain embodiments, $R^4$ is

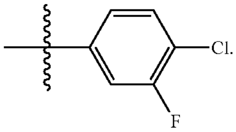 [SMILES: *c1ccc(Cl)c(F)c1]

In certain embodiments, $R^4$ is

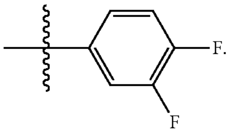 [SMILES: *c1ccc(F)c(F)c1]

In certain embodiments, $R^4$ is

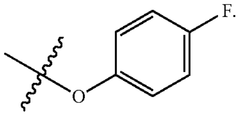 [SMILES: *Oc1ccc(F)cc1]

In certain embodiments, $R^4$ is F.

In certain embodiments, $R^{4'}$ is methyl. In certain embodiments, $R^{4'}$ is trifluoromethyl. In certain embodiments, $R^{4'}$ is hydroxyl. In certain embodiments, $R^{4'}$ is

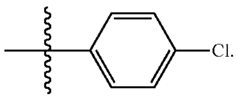 [SMILES: *c1ccc(Cl)cc1]

In certain embodiments, $R^{4'}$ is

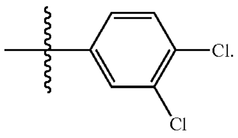 [SMILES: *c1ccc(Cl)c(Cl)c1]

In certain embodiments, $R^{4'}$ is

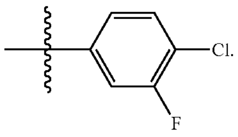 [SMILES: *c1ccc(Cl)c(F)c1]

In certain embodiments, $R^{4'}$ is

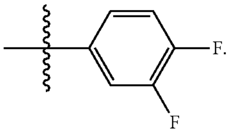 [SMILES: *c1ccc(F)c(F)c1]

In certain embodiments, $R^{4'}$ is

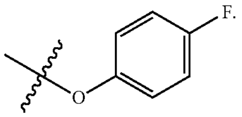 [SMILES: *Oc1ccc(F)cc1]

In certain embodiments, $R^{4'}$ is F.

In certain embodiments, $R^5$ is methyl. In certain embodiments, $R^5$ is trifluoromethyl. In certain embodiments, $R^5$ is hydroxyl. In certain embodiments, $R^5$ is —C(═O)OMe. In certain embodiments, $R^5$ is Ph. In certain embodiments, $R^5$ is

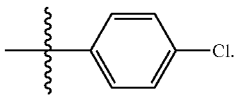

In certain embodiments, $R^5$ is

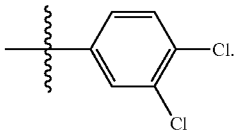

In certain embodiments, $R^5$ is

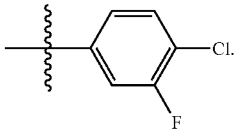

In certain embodiments, $R^5$ is

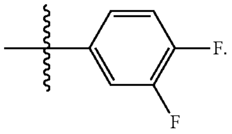 [SMILES: *c1ccc(F)c(F)c1]

In certain embodiments, $R^5$ is

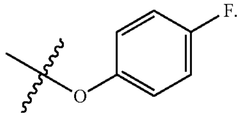 [SMILES: *Oc1ccc(F)cc1]

In certain embodiments, $R^5$ is F.

In certain embodiments, $R^{5'}$ is methyl. In certain embodiments, $R^{5'}$ is trifluoromethyl. In certain embodiments, $R^{5'}$ is hydroxyl. In certain embodiments, $R^{5'}$ is —C(═O)OMe. In certain embodiments, $R^{5'}$ is Ph. In certain embodiments, $R^{5'}$ is

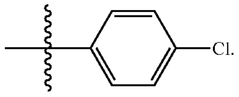 [SMILES: *c1ccc(Cl)cc1]

In certain embodiments, $R^{5'}$ is

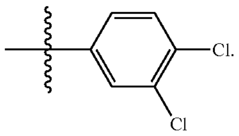

In certain embodiments, $R^{5'}$ is

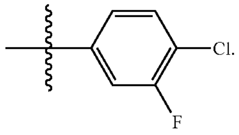 [SMILES: *c1ccc(Cl)c(F)c1]

In certain embodiments, $R^{5'}$ is

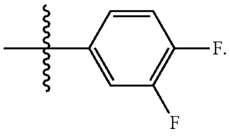 [SMILES: *c1ccc(F)c(F)c1]

In certain embodiments, $R^{5'}$ is

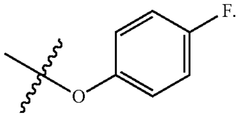 [SMILES: *Oc1ccc(F)cc1]

In certain embodiments, $R^{5'}$ is F.

In certain embodiments, $R^6$ is methyl. In certain embodiments, $R^6$ is trifluoromethyl. In certain embodiments, $R^6$ is hydroxyl. In certain embodiments, $R^6$ is —C(═O)OMe. In certain embodiments, $R^6$ is Ph. In certain embodiments, $R^6$ is

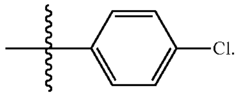 [SMILES: *c1ccc(Cl)cc1]

In certain embodiments, $R^6$ is

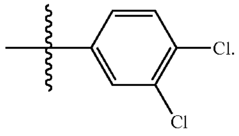

In certain embodiments, $R^6$ is

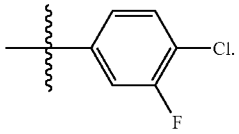

In certain embodiments, $R^6$ is

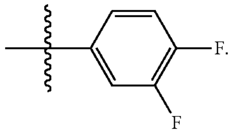 [SMILES: *c1ccc(F)c(F)c1]

In certain embodiments, $R^6$ is

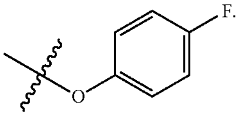 [SMILES: *Oc1ccc(F)cc1]

In certain embodiments, $R^6$ is F.

In certain embodiments, $R^{6'}$ is methyl. In certain embodiments, $R^{6'}$ is trifluoromethyl. In certain embodiments, $R^{6'}$ is hydroxyl. In certain embodiments, $R^{6'}$ is —C(═O)OMe. In certain embodiments, $R^6$ is Ph. In certain embodiments, $R^{6'}$ is

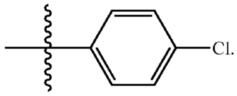 [SMILES: *c1ccc(Cl)cc1]

In certain embodiments, $R^{6'}$ is

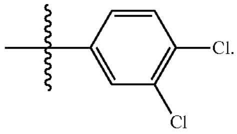 [SMILES: *c1ccc(Cl)c(Cl)c1]

In certain embodiments, $R^{6'}$ is

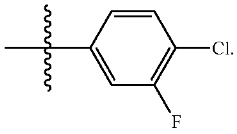 [SMILES: *c1ccc(Cl)c(F)c1]

In certain embodiments, $R^{6'}$ is

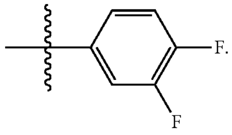 [SMILES: *c1ccc(F)c(F)c1]

In certain embodiments, $R^{6'}$ is

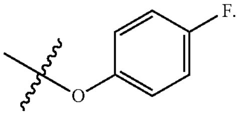 [SMILES: *Oc1ccc(F)cc1]

In certain embodiments, $R^{6'}$ is F.

In certain embodiments, $R^7$ is methyl. In certain embodiments, $R^7$ is trifluoromethyl. In certain embodiments, $R^7$ is hydroxyl. In certain embodiments, $R^7$ is —C(═O)OMe. In certain embodiments, $R^7$ is Ph. In certain embodiments, $R^7$ is

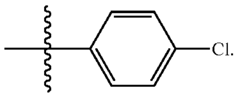 [SMILES: *c1ccc(Cl)cc1]

In certain embodiments, $R^7$ is

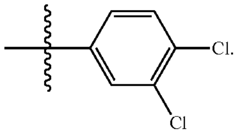 [SMILES: *c1ccc(Cl)c(Cl)c1]

In certain embodiments, $R^7$ is

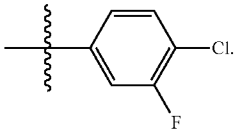 [SMILES: *c1ccc(Cl)c(F)c1]

In certain embodiments, $R^7$ is

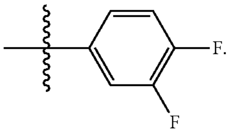 [SMILES: *c1ccc(F)c(F)c1]

In certain embodiments, $R^7$ is

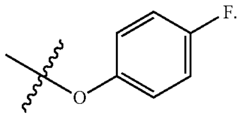 [SMILES: *Oc1ccc(F)cc1]

In certain embodiments, $R^7$ is F.

In certain embodiments, $R^{7'}$ is methyl. In certain embodiments, $R^{7'}$ is trifluoromethyl. In certain embodiments, $R^{7'}$ is hydroxyl. In certain embodiments $R^{7'}$ is —C(═O)OMe. In certain embodiments, $R^{7'}$ is Ph. In certain embodiments, $R^{7'}$ is

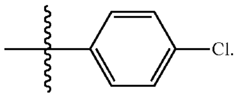 [SMILES: *c1ccc(Cl)cc1]

In certain embodiments, $R^{7'}$ is

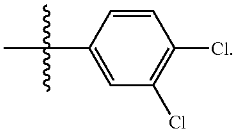 [SMILES: *c1ccc(Cl)c(Cl)c1]

In certain embodiments, $R^{7'}$ is

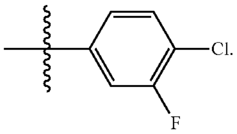 [SMILES: *c1ccc(Cl)c(F)c1]

In certain embodiments, $R^{7'}$ is

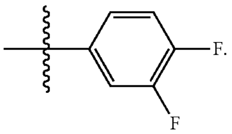 [SMILES: *c1ccc(F)c(F)c1]

In certain embodiments, $R^{7'}$ is

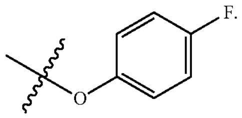 [SMILES: *Oc1ccc(F)cc1]

In certain embodiments, $R^{7'}$ is F.

In certain embodiments, $R^8$ is methyl. In certain embodiments, $R^8$ is trifluoromethyl. In certain embodiments, $R^8$ is hydroxyl. In certain embodiments, $R^8$ is —C(═O)OMe. In certain embodiments, $R^8$ is Ph. In certain embodiments, $R^8$ is

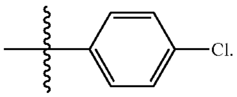 [SMILES: *c1ccc(Cl)cc1]

In certain embodiments, $R^8$ is

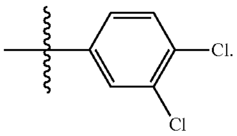 [SMILES: *c1ccc(Cl)c(Cl)c1]

In certain embodiments, $R^8$ is

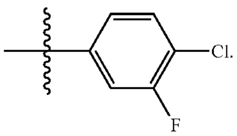 [SMILES: *c1ccc(Cl)c(F)c1]

In certain embodiments, $R^8$ is

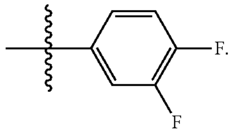 [SMILES: *c1ccc(F)c(F)c1]

In certain embodiments, $R^8$ is

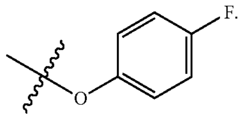

In certain embodiments, $R^8$ is F.

In certain embodiments, $R^{8'}$ is methyl. In certain embodiments, $R^{8'}$ is trifluoromethyl. In certain embodiments, $R^{8'}$ is hydroxyl. In certain embodiments, $R^{8'}$ is —C(═O)OMe. In certain embodiments, $R^{8'}$ is Ph. In certain embodiments, $R^8$ is

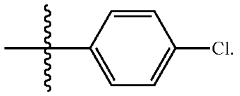 [SMILES: *c1ccc(Cl)cc1]

In certain embodiments, $R^{8'}$ is

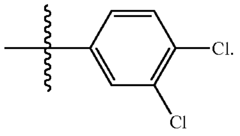

In certain embodiments, $R^{8'}$ is

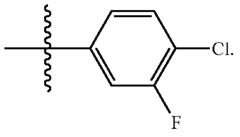 [SMILES: *c1ccc(Cl)c(F)c1]

In certain embodiments, $R^{8'}$ is

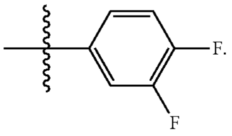 [SMILES: *c1ccc(F)c(F)c1]

In certain embodiments, $R^{8'}$ is

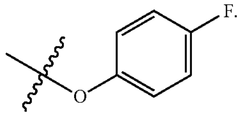

In certain embodiments, $R^{8'}$ is F.

In certain embodiments, Y is $NR^{10}$. In certain embodiments, Y is NH.

In certain embodiments, $R^{10}$ is H. In certain embodiments, $R^{10}$ is methyl. In certain 5 embodiments, $R^{10}$ is 3-methylbutyl. In certain embodiments, $R^{10}$ is tert-butyl. In certain embodiments, $R^{10}$ is cyclopropyl. In certain embodiments, $R^{10}$ is 3-oxetanyl. In certain embodiments, $R^{10}$ is —C(═O)$CH_2CH(CH_3)_2$. In certain embodiments, $R^{10}$ is —C(═O)Ot-Bu. In certain embodiments, $R^{10}$ is S(═O)$_2$ Me. In certain embodiments, $R^{10}$ is benzyl. In certain embodiments, $R^{10}$ is

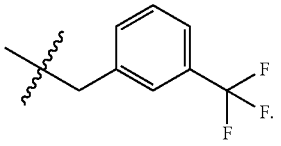 [SMILES: *Cc1cccc(C(F)(F)F)c1]

In certain embodiments, $R^{10}$ is

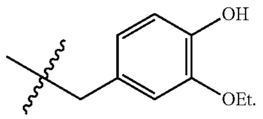

In certain embodiments, $R^{10}$ is

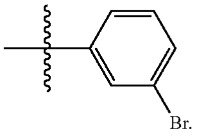 [SMILES: *c1cccc(Br)c1]

In certain embodiments, $R^{10}$ is

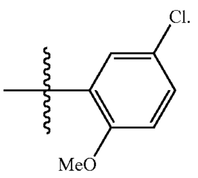 [SMILES: *c1cc(Cl)ccc1OC]

In certain embodiments, $R^{10}$ is

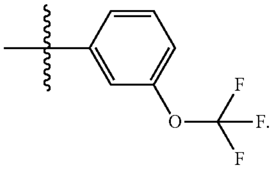 [SMILES: *c1cccc(OC(F)(F)F)c1]

In certain embodiments, $R^{10}$ is

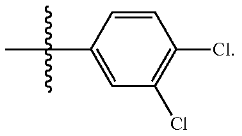 [SMILES: *c1ccc(Cl)c(Cl)c1]

In certain embodiments, $R^{10}$ is

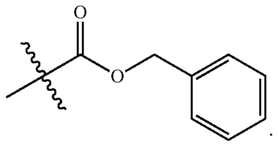 [SMILES: *C(=O)OCc1ccccc1]

In certain embodiments, $R^{10}$ is

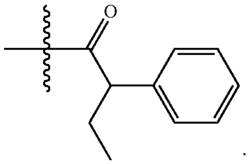 [SMILES: *C(=O)C(CC)c1ccccc1]

In certain embodiments, $R^{10}$ is

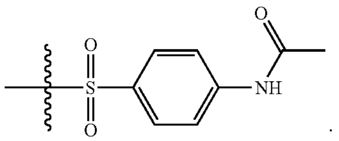

In certain embodiments, Y is $NR^{10'}$.

In certain embodiments, $R^{10'}$ is

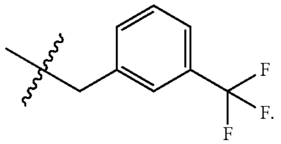 [SMILES: *Cc1cccc(C(F)(F)F)c1]

In certain embodiments, $R^{10'}$ is

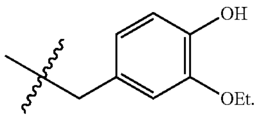 [SMILES: *Cc1ccc(O)c(OCC)c1]

In certain embodiments, $R^{10'}$ is

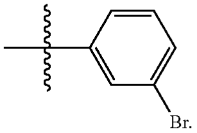 [SMILES: *c1cccc(Br)c1]

In certain embodiments, $R^{10'}$ is

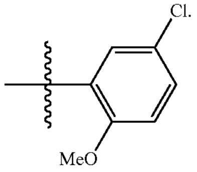 [SMILES: *c1cc(Cl)ccc1OC]

In certain embodiments, $R^{10'}$ is

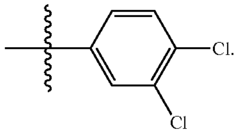

In certain embodiments, $R^{10'}$ is

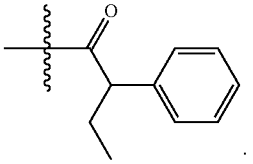 [SMILES: *C(=O)C(CC)c1ccccc1]

In certain embodiments, $R^1$ is

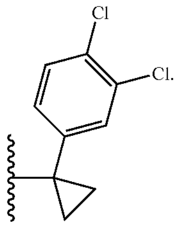 [SMILES: *C1(c2ccc(Cl)c(Cl)c2)CC1]

In certain embodiments, $R^1$ is

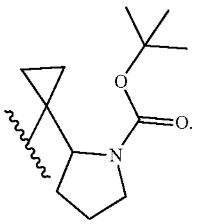 [SMILES: *C1(C2CCCN2C(=O)OC(C)(C)C)CC1]

In certain embodiments, $R^1$ is
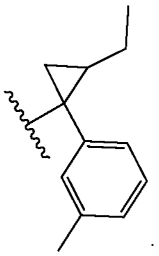 [SMILES: *C1(c2cccc(C)c2)CC1CC]
In certain embodiments, $R^1$ is
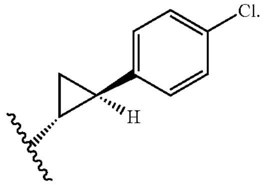 [SMILES: *[C@@H]1C[C@H]1c1ccc(Cl)cc1]
In certain embodiments, $R^1$ is
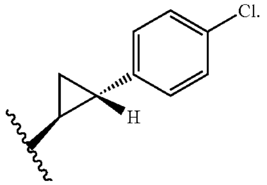 [SMILES: *[C@H]1C[C@@H]1c1ccc(Cl)cc1]
In certain embodiments $R^1$ is
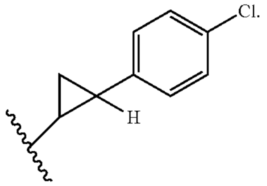 [SMILES: *C1CC1c1ccc(Cl)cc1]
In certain embodiments $R^1$ is
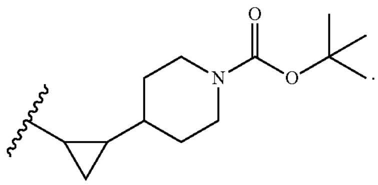 [SMILES: *C1CC1C1CCN(C(=O)OC(C)(C)C)CC1]
In certain embodiments, $R^1$ is
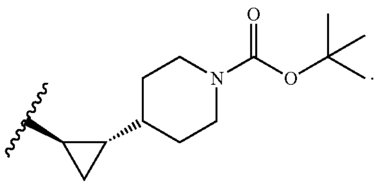 [SMILES: *[C@@H]1C[C@H]1C1CCN(C(=O)OC(C)(C)C)CC1]
In certain embodiments, $R^1$ is
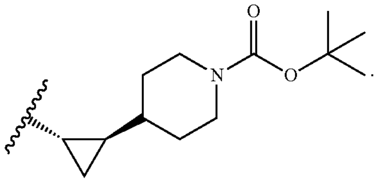 [SMILES: *[C@H]1C[C@@H]1C1CCN(C(=O)OC(C)(C)C)CC1]
In certain embodiments, $R^1$ is
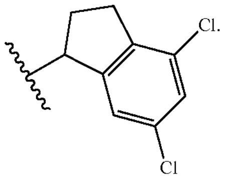 [SMILES: *C1CCc2c(Cl)cc(Cl)cc21]
In certain embodiments, $R^1$ is
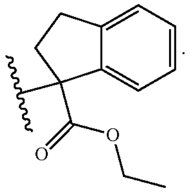 [SMILES: *C1(C(=O)OCC)CCc2ccccc21]
In certain embodiments, $R^1$ is
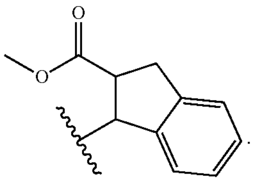 [SMILES: *C1c2ccccc2CC1C(=O)OC]
In certain embodiments, $R^1$ is
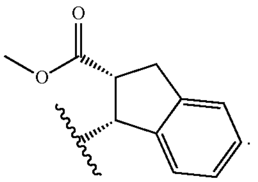 [SMILES: *[C@H]1c2ccccc2C[C@H]1C(=O)OC]

In certain embodiments, $R^1$ is
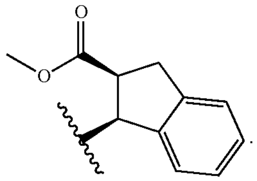 [SMILES: *[C@@H]1c2ccccc2C[C@@H]1C(=O)OC]
In certain embodiments, $R^1$ is
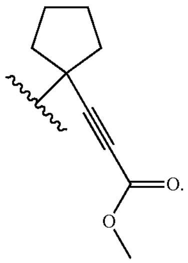 [SMILES: *C1(C#CC(=O)OC)CCCC1]
In certain embodiments, $R^1$ is
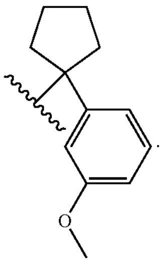 [SMILES: *C1(c2cccc(OC)c2)CCCC1]
In certain embodiments, $R^1$ is
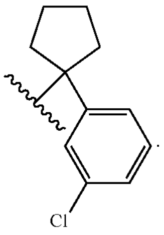 [SMILES: *C1(c2cccc(Cl)c2)CCCC1]
In certain embodiments, $R^1$ is
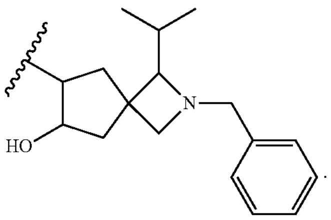 [SMILES: *C1CC2(CC1O)CN(Cc1ccccc1)C2C(C)C]
In certain embodiments, $R^1$ is
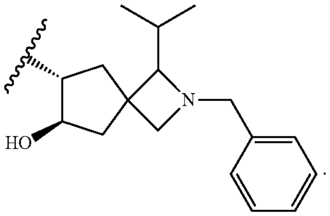 [SMILES: *[C@@H]1CC2(C[C@H]1O)CN(Cc1ccccc1)C2C(C)C]
In certain embodiments, $R^1$ is
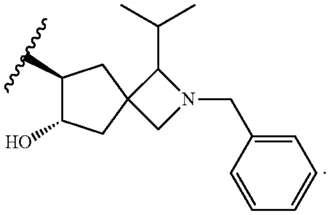 [SMILES: *[C@H]1CC2(C[C@@H]1O)CN(Cc1ccccc1)C2C(C)C]
In certain embodiments, $R^1$ is
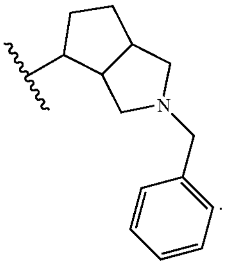 [SMILES: *C1CCC2CN(Cc3ccccc3)CC12]
In certain embodiments, $R^1$ is
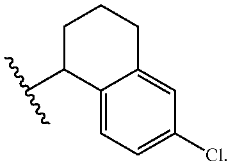 [SMILES: *C1CCCc2cc(Cl)ccc21]
In certain embodiments, $R^1$ is
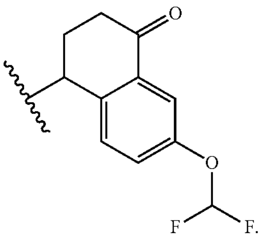 [SMILES: *C1CCC(=O)c2cc(OC(F)F)ccc21]

In certain embodiments, $R^1$ is
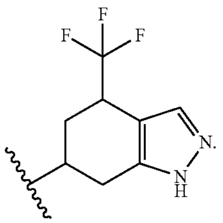 [SMILES: *C1Cc2[nH]ncc2C(C(F)(F)F)C1]
In certain embodiments, $R^1$ is
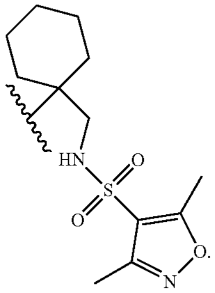 [SMILES: *C1(CNS(=O)(=O)c2c(C)noc2C)CCCCC1]
In certain embodiments, $R^1$ is
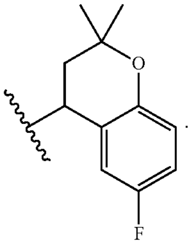 [SMILES: *C1CC(C)(C)Oc2ccc(F)cc21]
In certain embodiments, $R^1$ is
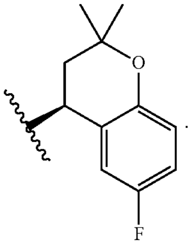 [SMILES: *[C@H]1CC(C)(C)Oc2ccc(F)cc21]
In certain embodiments, $R^1$ is
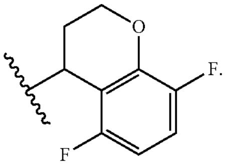 [SMILES: *C1CCOc2c(F)ccc(F)c21]
In certain embodiments, $R^1$ is
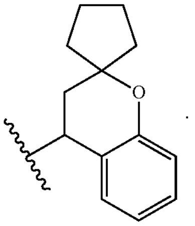 [SMILES: *C1CC2(CCCC2)Oc2ccccc21]
In certain embodiments, $R^1$ is
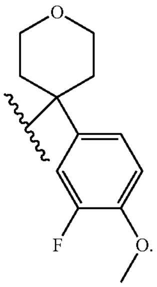 [SMILES: *C1(c2ccc(OC)c(F)c2)CCOCC1]
In certain embodiments, $R^1$ is
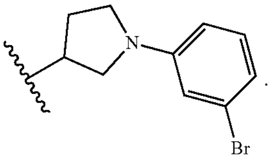 [SMILES: *C1CCN(c2cccc(Br)c2)C1]
In certain embodiments, $R^1$ is
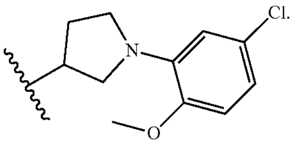 [SMILES: *C1CCN(c2cc(Cl)ccc2OC)C1]
In certain embodiments, $R^1$ is
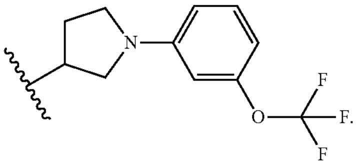 [SMILES: *C1CCN(c2cccc(OC(F)(F)F)c2)C1]

In certain embodiments, $R^1$ is
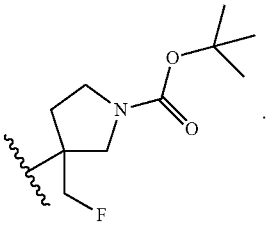 [SMILES: *C1(CF)CCN(C(=O)OC(C)(C)C)C1]
In certain embodiments, $R^1$ is
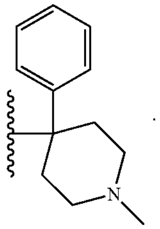 [SMILES: *C1(c2ccccc2)CCN(C)CC1]
In certain embodiments, $R^1$ is
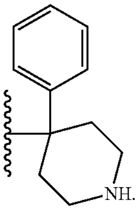 [SMILES: *C1(c2ccccc2)CCNCC1]
In certain embodiments, $R^1$ is
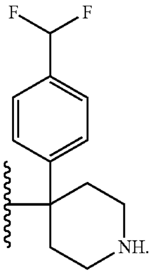 [SMILES: *C1(c2ccc(C(F)F)cc2)CCNCC1]
In certain embodiments, $R^1$ is
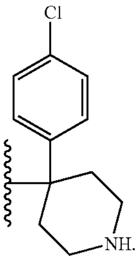 [SMILES: *C1(c2ccc(Cl)cc2)CCNCC1]
In certain embodiments, $R^1$ is
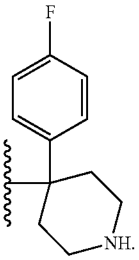 [SMILES: *C1(c2ccc(F)cc2)CCNCC1]
In certain embodiments, $R^1$ is
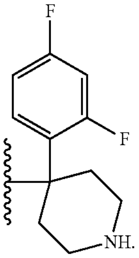 [SMILES: *C1(c2ccc(F)cc2F)CCNCC1]
In certain embodiments, $R^1$ is
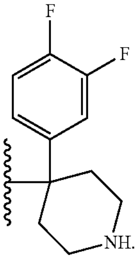 [SMILES: *C1(c2ccc(F)c(F)c2)CCNCC1]
In certain embodiments, $R^1$ is
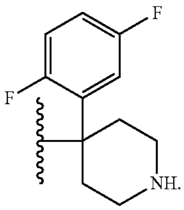 [SMILES: *C1(c2cc(F)ccc2F)CCNCC1]

In certain embodiments, $R^1$ is
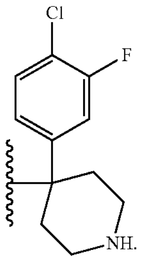 [SMILES: *C1(c2ccc(Cl)c(F)c2)CCNCC1]
In certain embodiments, $R^1$ is
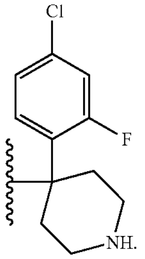 [SMILES: *C1(c2ccc(Cl)cc2F)CCNCC1]
In certain embodiments, $R^1$ is
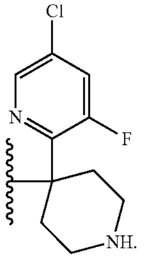 [SMILES: *C1(c2ncc(Cl)cc2F)CCNCC1]
In certain embodiments, $R^1$ is
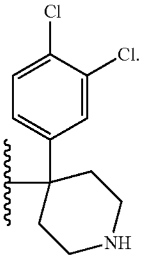 [SMILES: *C1(c2ccc(Cl)c(Cl)c2)CCNCC1]
In certain embodiments $R^1$ is
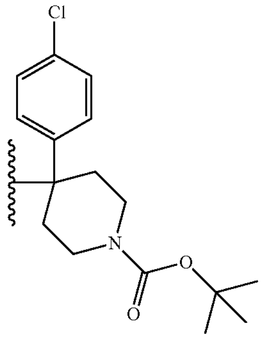
In certain embodiments, $R^1$ is
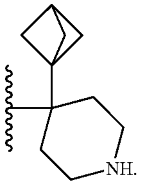 [SMILES: *C1(C23CC(C2)C3)CCNCC1]
In certain embodiments, $R^1$ is
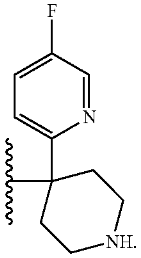 [SMILES: *C1(c2ccc(F)cn2)CCNCC1]
In certain embodiments, $R^1$ is
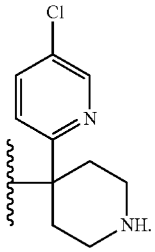 [SMILES: *C1(c2ccc(Cl)cn2)CCNCC1]

In certain embodiments, $R^1$ is
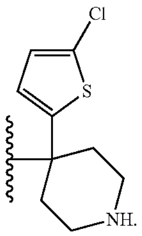 [SMILES: *C1(c2ccc(Cl)s2)CCNCC1]
In certain embodiments, $R^1$ is
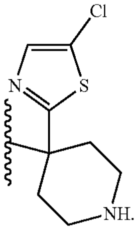 [SMILES: *C1(c2ncc(Cl)s2)CCNCC1]
In certain embodiments, $R^1$ is
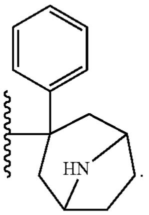 [SMILES: *C1(c2ccccc2)CC2CCC(C1)N2]
In certain embodiments, $R^1$ is
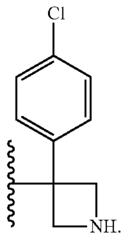
In certain embodiments, $R^1$ is
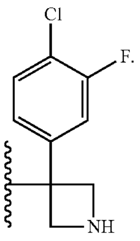 [SMILES: *C1(c2ccc(Cl)c(F)c2)CNC1]
In certain embodiments, $R^1$ is
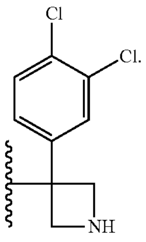 [SMILES: *C1(c2ccc(Cl)c(Cl)c2)CNC1]
In certain embodiments, $R^1$ is
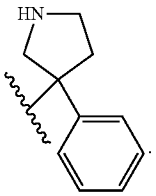 [SMILES: *C1(c2ccccc2)CCNC1]
In certain embodiments, $R^1$ is
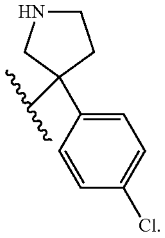 [SMILES: *C1(c2ccc(Cl)cc2)CCNC1]
In certain embodiments, $R^1$ is
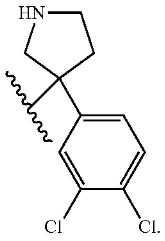 [SMILES: *C1(c2ccc(Cl)c(Cl)c2)CCNC1]
In certain embodiments, $R^1$ is
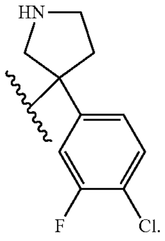 [SMILES: *C1(c2ccc(Cl)c(F)c2)CCNC1]

In certain embodiments, $R^1$ is
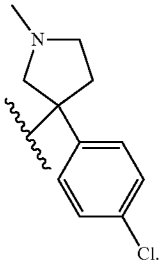 [SMILES: *C1(c2ccc(Cl)cc2)CCN(C)C1]
In certain embodiments, $R^1$ is
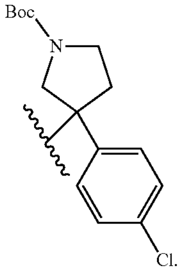 [SMILES: *C1(c2ccc(Cl)cc2)CCN(C(=O)OC(C)(C)C)C1]
In certain embodiments, $R^1$ is
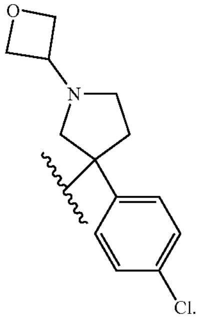 [SMILES: *C1(c2ccc(Cl)cc2)CCN(C2COC2)C1]
In certain embodiments, $R^1$ is
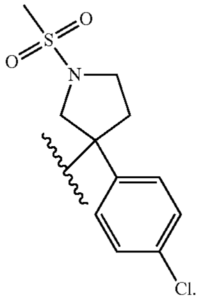 [SMILES: *C1(c2ccc(Cl)cc2)CCN(S(C)(=O)=O)C1]
In certain embodiments, $R^1$ is
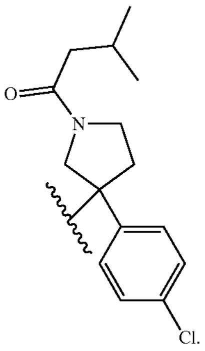 [SMILES: *C1(c2ccc(Cl)cc2)CCN(C(=O)CC(C)C)C1]
In certain embodiments, $R^1$ is
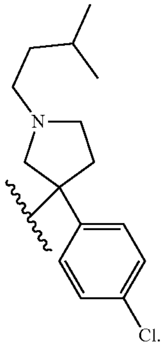 [SMILES: *C1(c2ccc(Cl)cc2)CCN(CCC(C)C)C1]
In certain embodiments, $R^1$ is
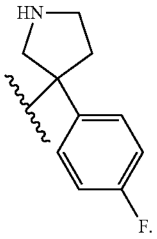 [SMILES: *C1(c2ccc(F)cc2)CCNC1]
In certain embodiments, $R^1$ is
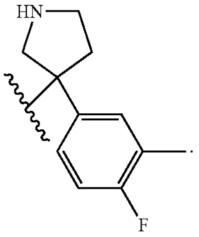 [SMILES: *C1(c2ccc(F)c(C)c2)CCNC1]

In certain embodiments, $R^1$ is
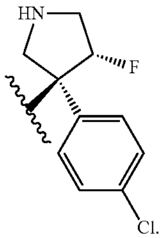 [SMILES: *[C@@]1(c2ccc(Cl)cc2)CNC[C@@H]1F]
Cl.
In certain embodiments, $R^1$ is
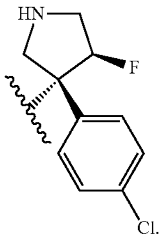 [SMILES: *[C@]1(c2ccc(Cl)cc2)CNC[C@H]1F]
Cl.
In certain embodiments, $R^1$ is
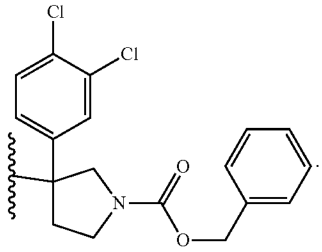 [SMILES: *C1(c2ccc(Cl)c(Cl)c2)CCN(C(=O)OCc2ccccc2)C1]
In certain embodiments, $R^1$ is
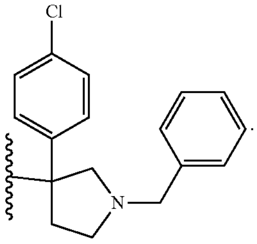 [SMILES: *C1(c2ccc(Cl)cc2)CCN(Cc2ccccc2)C1]
In certain embodiments, $R^1$ is
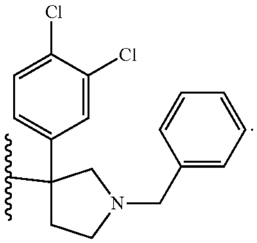 [SMILES: *C1(c2ccc(Cl)c(Cl)c2)CCN(Cc2ccccc2)C1]
In certain embodiments, $R^1$ is
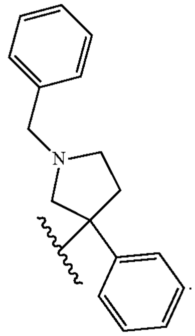 [SMILES: *C1(c2ccccc2)CCN(Cc2ccccc2)C1]
In certain embodiments, $R^1$ is
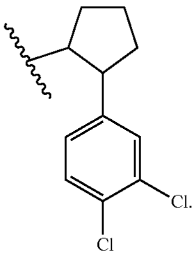 [SMILES: *C1CCCC1c1ccc(Cl)c(Cl)c1]
Cl.
In certain embodiments, $R^1$ is
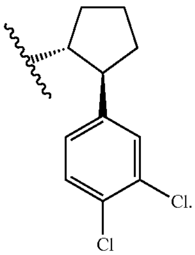 [SMILES: *[C@@H]1CCC[C@H]1c1ccc(Cl)c(Cl)c1]
Cl.

In certain embodiments, $R^1$ is
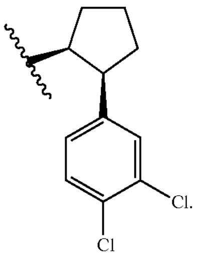 [SMILES: *[C@H]1CCC[C@H]1c1ccc(Cl)c(Cl)c1]
In certain embodiments, $R^1$ is
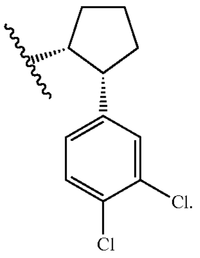 [SMILES: *[C@@H]1CCC[C@@H]1c1ccc(Cl)c(Cl)c1]
In certain embodiments, $R^1$ is
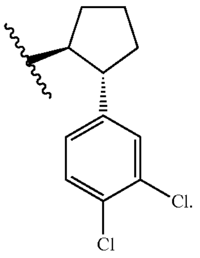 [SMILES: *[C@H]1CCC[C@@H]1c1ccc(Cl)c(Cl)c1]
In certain embodiments, $R^1$ is
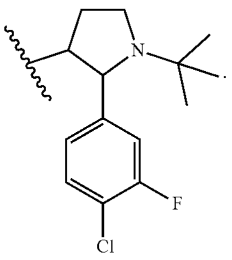 [SMILES: *C1CCN(C(C)(C)C)C1c1ccc(Cl)c(F)c1]
In certain embodiments, $R^1$ is
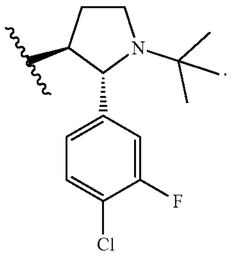 [SMILES: *[C@H]1CCN(C(C)(C)C)[C@@H]1c1ccc(Cl)c(F)c1]
In certain embodiments, $R^1$ is
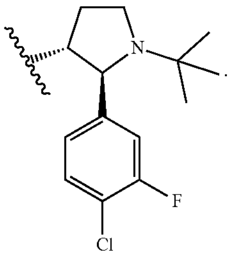 [SMILES: *[C@@H]1CCN(C(C)(C)C)[C@H]1c1ccc(Cl)c(F)c1]
In certain embodiments, $R^1$
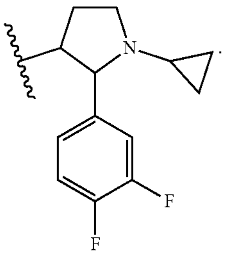 [SMILES: *C1CCN(C2CC2)C1c1ccc(F)c(F)c1]
In certain embodiments, $R^1$ is
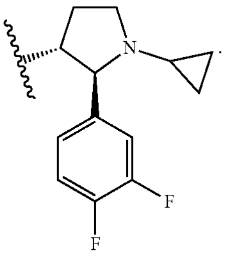 [SMILES: *[C@@H]1CCN(C2CC2)[C@H]1c1ccc(F)c(F)c1]

In certain embodiments, $R^1$ is
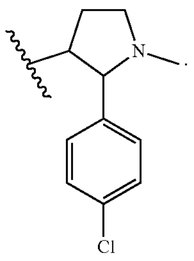 [SMILES: *C1CCN(C)C1c1ccc(Cl)cc1]
In certain embodiments, $R^1$ is
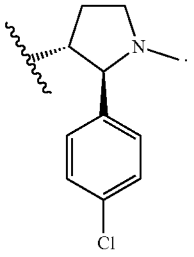 [SMILES: *[C@@H]1CCN(C)[C@H]1c1ccc(Cl)cc1]
In certain embodiments, $R^1$ is
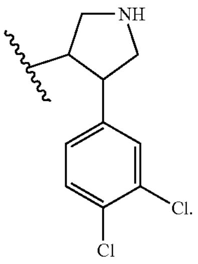 [SMILES: *C1CNCC1c1ccc(Cl)c(Cl)c1]
In certain embodiments, $R^1$ is
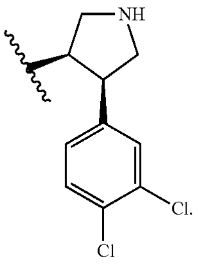 [SMILES: *[C@H]1CNC[C@H]1c1ccc(Cl)c(Cl)c1]
In certain embodiments, $R^1$ is
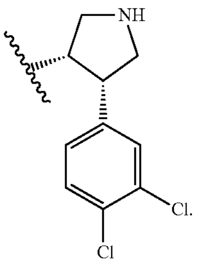 [SMILES: *[C@@H]1CNC[C@@H]1c1ccc(Cl)c(Cl)c1]
In certain embodiments, $R^1$ is
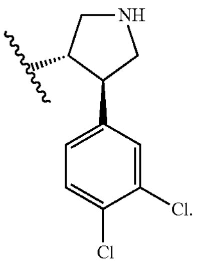 [SMILES: *[C@@H]1CNC[C@H]1c1ccc(Cl)c(Cl)c1]
In certain embodiments, $R^1$ is
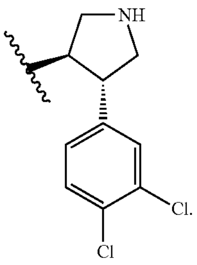 [SMILES: *[C@H]1CNC[C@@H]1c1ccc(Cl)c(Cl)c1]
In certain embodiments, $R^1$ is
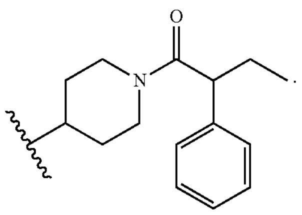 [SMILES: *C1CCN(C(=O)C(CC)c2ccccc2)CC1]
In certain embodiments, $R^1$ is
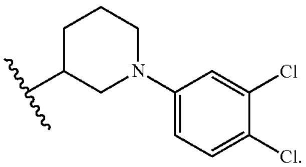 [SMILES: *C1CCCN(c2ccc(Cl)c(Cl)c2)C1]

In certain embodiments, $R^1$ is

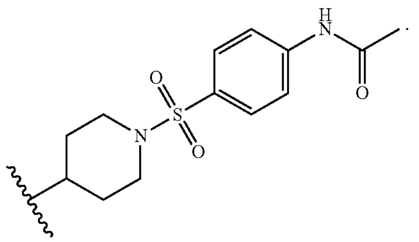 [SMILES: *C1CCN(S(=O)(=O)c2ccc(NC(C)=O)cc2)CC1]

In certain embodiments, $R^1$ is

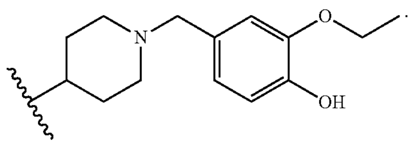 [SMILES: *C1CCN(Cc2ccc(O)c(OCC)c2)CC1]

In certain embodiments, $R^1$ is

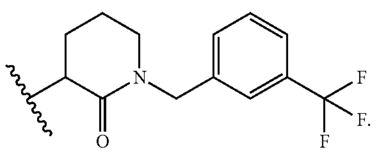 [SMILES: *C1CCCN(Cc2cccc(C(F)(F)F)c2)C1=O]

In certain embodiments, the present disclosure provides a compound of formula (II), or a salt, solvate, enantiomer, diastereoisomer, isotopologue, or tautomer thereof, selected from the group consisting of (IIa)

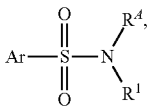

(IIb)

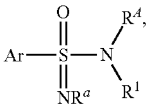

and (IIc)

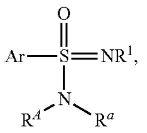

wherein:

Ar is $C_6$-$C_{10}$ aryl or $C_2$-$C_{10}$ heteroaryl, which is optionally substituted with at least one substituent selected from the group consisting of $C_1$-$C_6$ alkyl, $C_1$-$C_6$ haloalkyl, $C_1$-$C_6$ aminoalkyl, $C_1$-$C_6$ hydroxyalkyl, $C_2$-$C_6$ alkenyl, $C_2$-$C_6$ alkynyl, $C_1$-$C_6$ alkoxy, $C_1$-$C_6$ haloalkoxy, $C_2$-$C_{10}$ heteroaryl, $C_6$-$C_{10}$ aryl, $C_6$-$C_{10}$ aryloxy, halogen, OH, $NH_2$, CN, $NO_2$, —C(═O)OR$^a$, and —C(═O)N(R$^a$)(R$^a$), wherein each $C_6$-$C_{10}$ aryl, $C_2$-$C_{10}$ heteroaryl, or $C_6$-$C_{10}$ aryloxy substituent in Ar is independently optionally substituted with at least one substituent selected from the group consisting of $C_1$-$C_3$ alkyl, $C_1$-$C_3$ haloalkyl, $C_1$-$C_3$ alkoxy, $C_1$-$C_3$ haloalkoxy, F, Cl, Br, I, OH, CN, $N_{02}$, —C(═O)OR$^a$, and —C(═O)N(R$^a$)(R$^a$), and wherein two vicinal substituents of Ar may combine to provide a 5- to 8-membered ring which is fused with Ar;

$R^A$ is H or $C_1$-$C_6$ alkyl; and $R^1$ is selected from the group consisting of

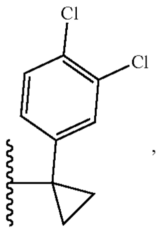

,

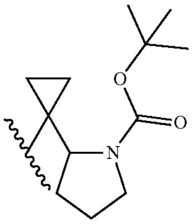

,

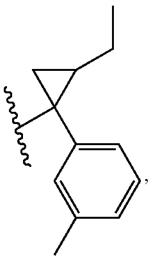

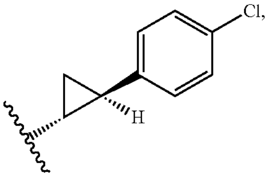

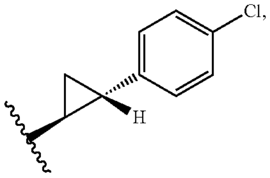

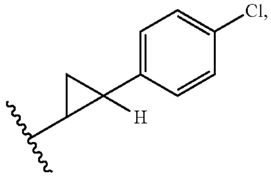

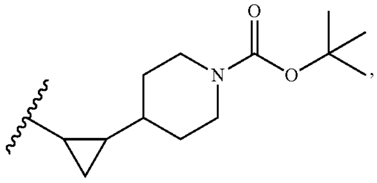

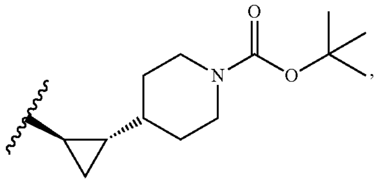

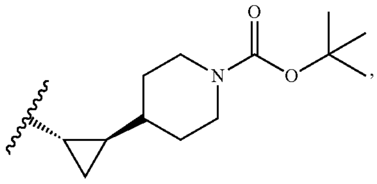

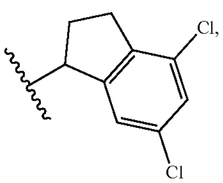

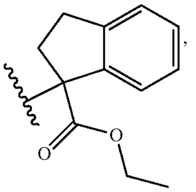

-continued
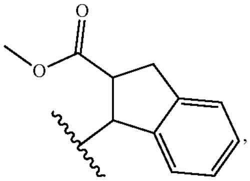,
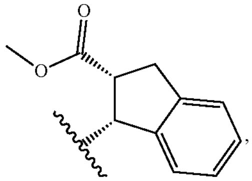,
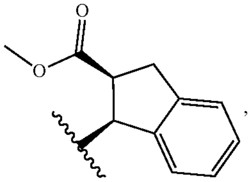,
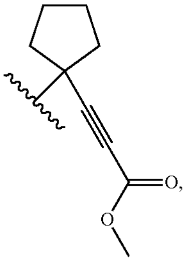,
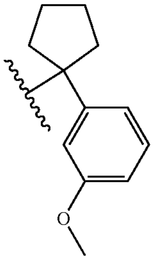,
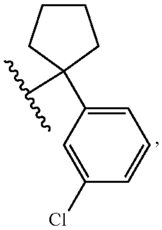,
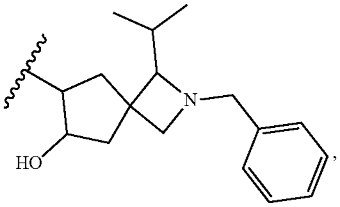,
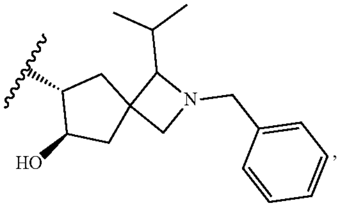,
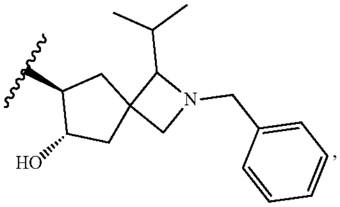,
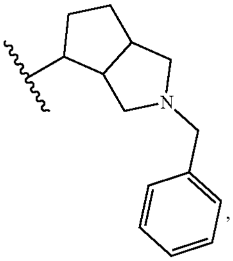,
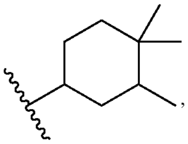,
-continued
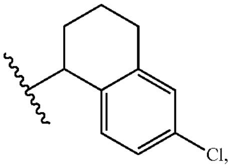,
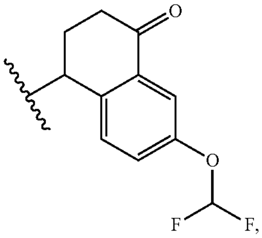,
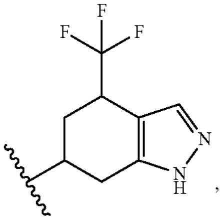,
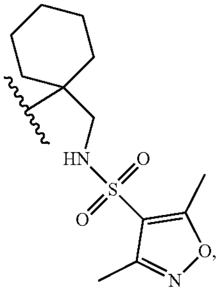,
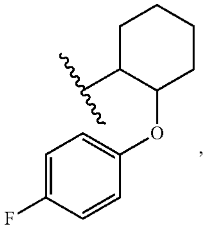,
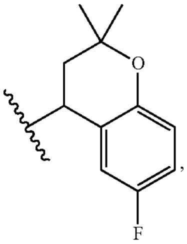,
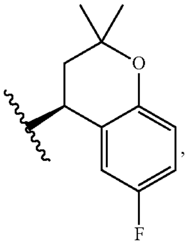,
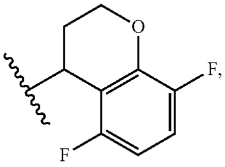,
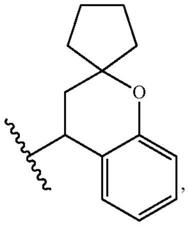,
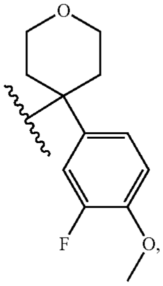,
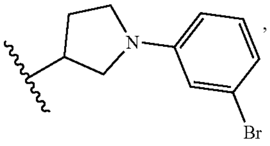,
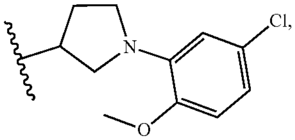,
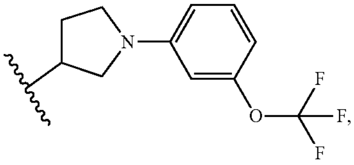, -continued
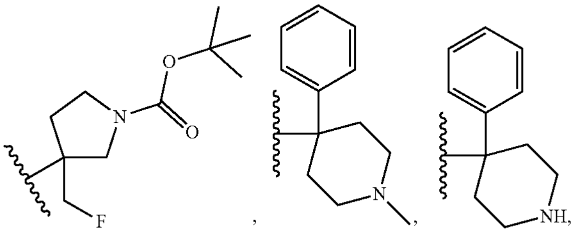
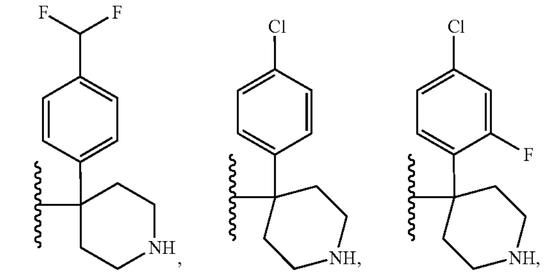
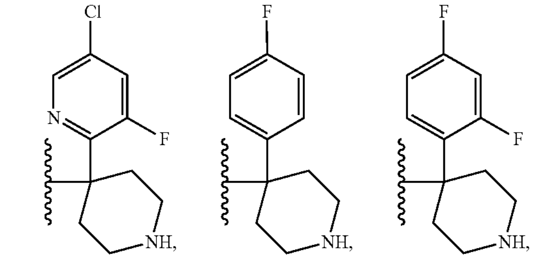
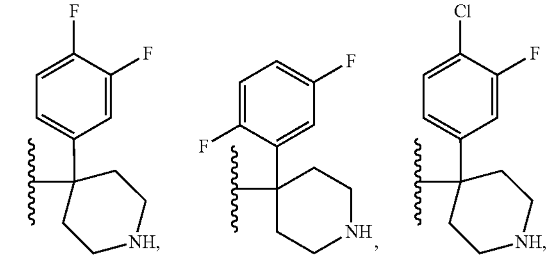
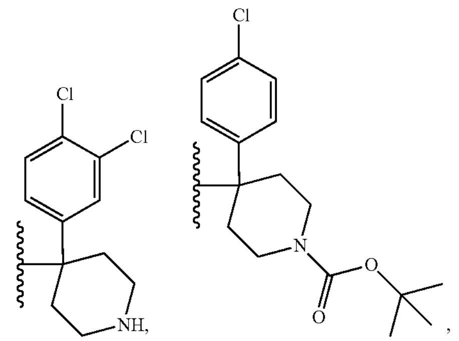
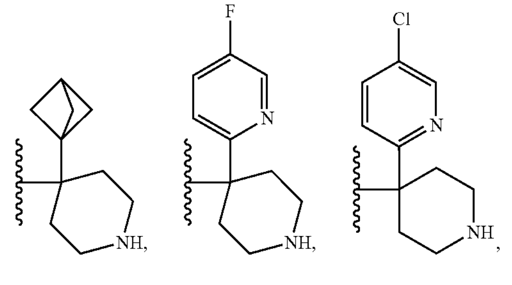
-continued
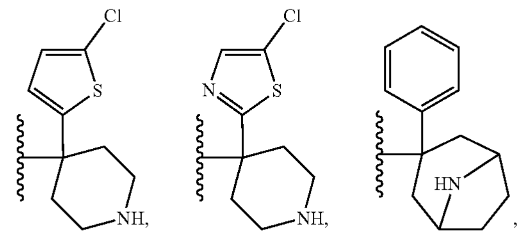
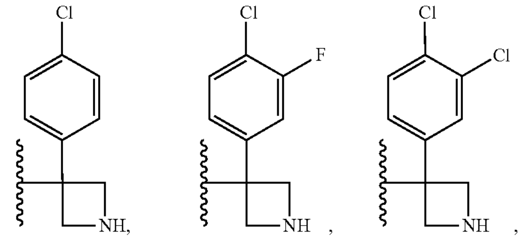
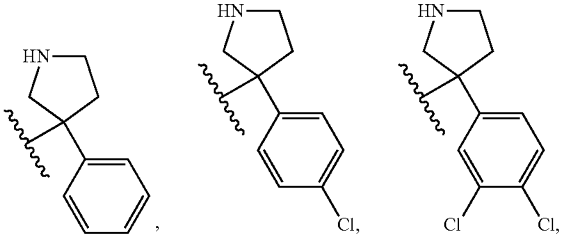
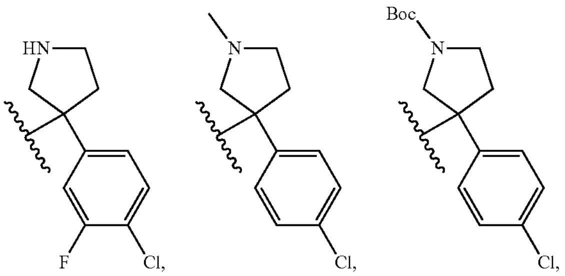
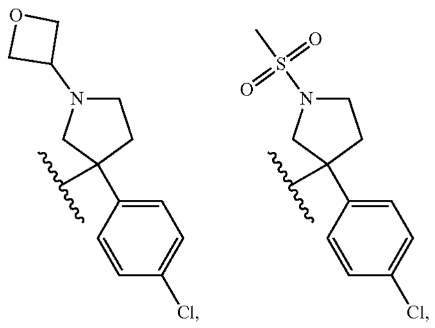
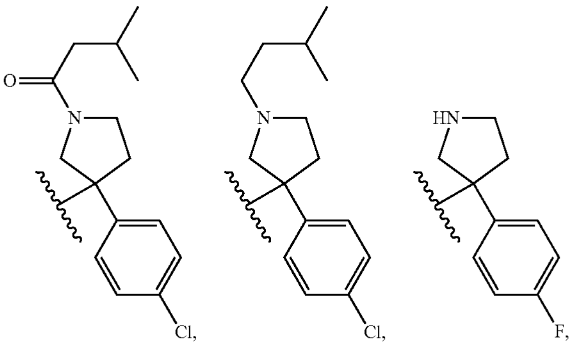

-continued
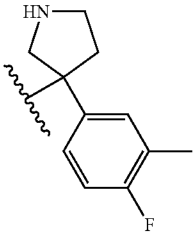
,
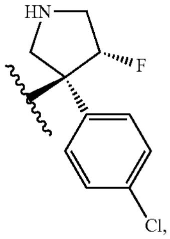
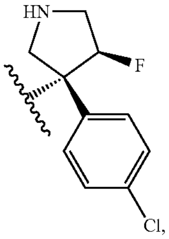
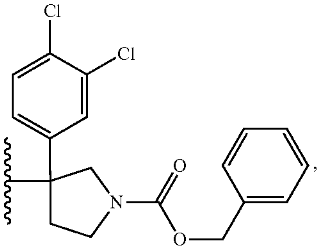
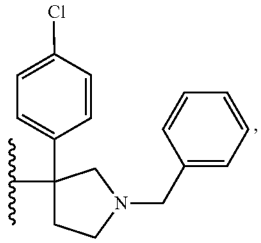
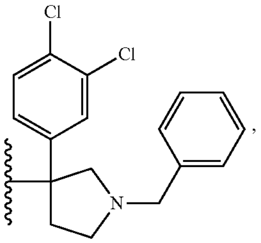
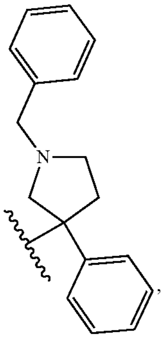
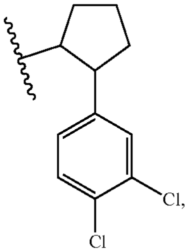
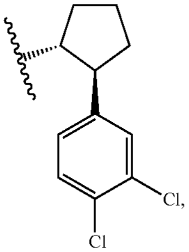
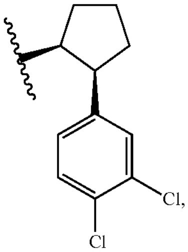
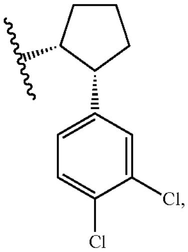
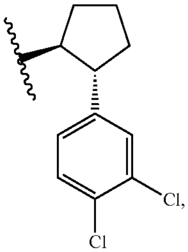
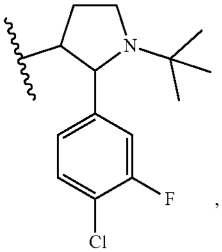
,
-continued
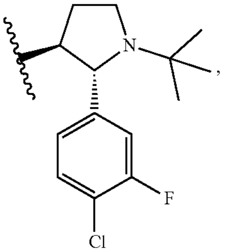
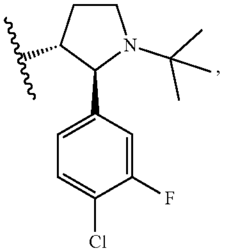
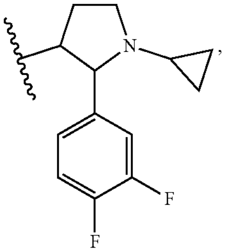
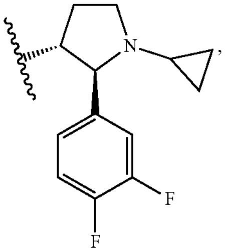
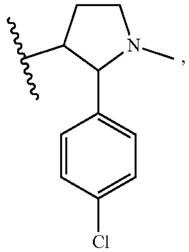
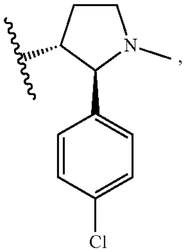
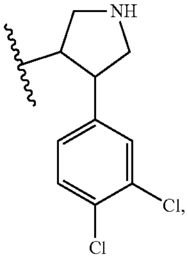
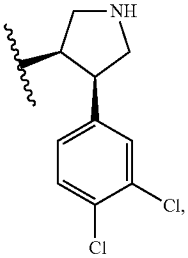
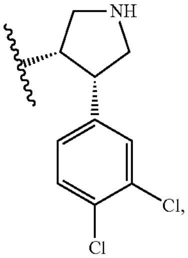
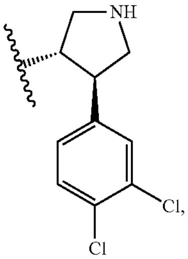
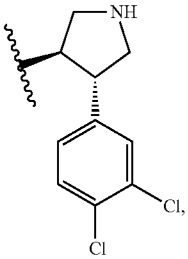
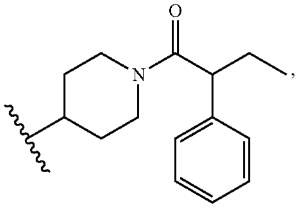
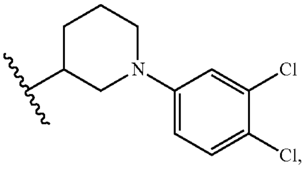

-continued

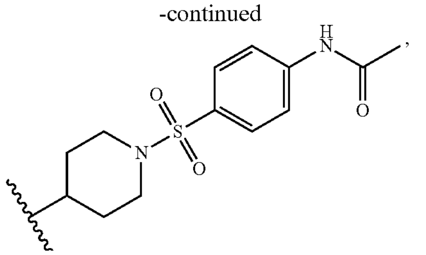

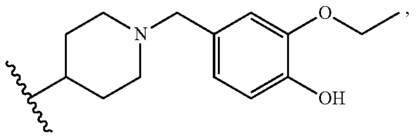

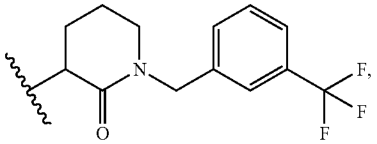

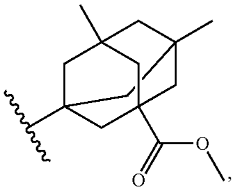

and

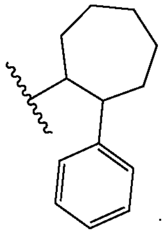

In certain embodiments, R is H. In certain embodiments, R is methyl.

In certain embodiments, the compound of formula (II) is selected from the group consisting of.

(IIa')

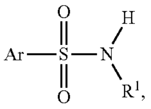

(IIb')

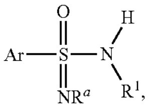

and (IIc')

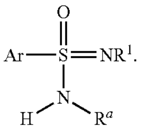

In certain embodiments, Ar is selected from the group consisting of

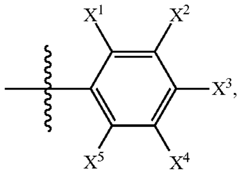

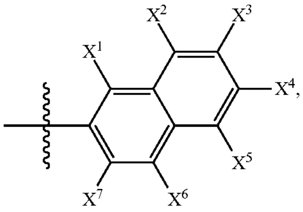

-continued

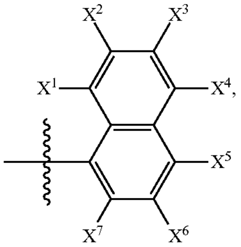

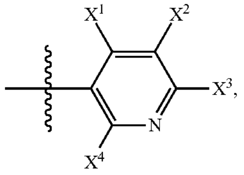

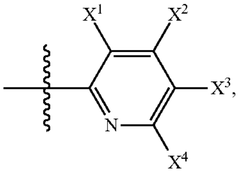

and

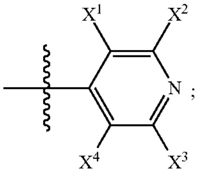

wherein $X^1$, $X^2$, $X^3$, $X^4$, $X^5$, $X^6$, and $X^7$ are each independently selected from the group consisting of $C_1$-$C_6$ alkyl, F, Cl, $N(R^a)(R^b)$, $OR^b$, $—C(=O)OR^a$, $—C(=O)N(R^a)(R^a)$, $NH_2$, OH, $NO_2$, $C_1$-$C_3$ haloalkyl, $C_1$-$C_3$ haloalkoxy, and phenyl.

In certain embodiments, at least one of $X^1$, $X^2$, $X^3$, $X^4$, $X^5$, $X^6$, and $X^7$, if present, is $O(CH(CH_3)_2)$. n certain embodiments, at least one of $X^1$, $X^2$, $X^3$, $X^4$, $X^5$, $X^6$, and $X^7$, if present, is $OCF_3$. n certain embodiments, at least one of $X^1$, $X^2$, $X^3$, $X^4$, $X^5$, $X^6$, and $X^7$, if present, is

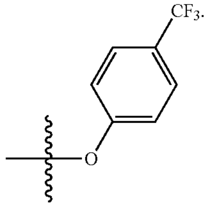 [SMILES: *Oc1ccc(C(F)(F)F)cc1]

In certain embodiments, Ar is

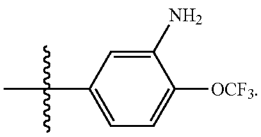 [SMILES: *c1ccc(OC(F)(F)F)c(N)c1]

In certain embodiments, Ar is

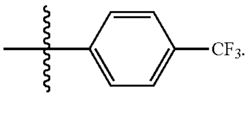 [SMILES: *c1ccc(C(F)(F)F)cc1]

In certain embodiments, Ar is

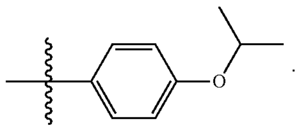 [SMILES: *c1ccc(OC(C)C)cc1]

In certain embodiments, Ar is

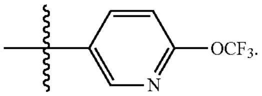 [SMILES: *c1ccc(OC(F)(F)F)nc1]

In certain embodiments, Ar is

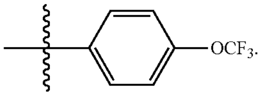

In certain embodiments, Ar is

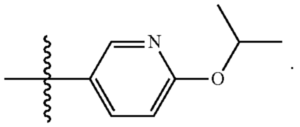 [SMILES: *c1ccc(OC(C)C)nc1]

In certain embodiments, Ar is

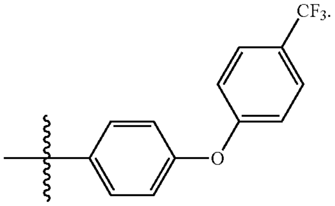 [SMILES: *c1ccc(Oc2ccc(C(F)(F)F)cc2)cc1]

In certain embodiments, the compound is selected from the group consisting of:
N-(6-fluoro-2,2-dimethylchroman-4-yl)-4-(trifluoromethoxy)benzenesulfonamide;
N-(1-(tert-butyl)-2-(4-chloro-3-fluorophenyl)pyrrolidin-3-yl)-4-(trifluoromethoxy)benzenesulfonamide;
tert-butyl 4-(2-((4-(trifluoromethoxy)phenyl)sulfonamido)cyclopropyl)piperidine-1-carboxylate;
tert-butyl 2-(1-((4-(trifluoromethoxy)phenyl)sulfonamido)cyclopropyl)pyrrolidine-1-carboxylate;
N-(6-(difluoromethoxy)-4-oxo-1,2,3,4-tetrahydronaphthalen-1-yl)-4-(trifluoromethoxy)benzenesulfonamide;
N-(1-(3-ethoxy-4-hydroxybenzyl)piperidin-4-yl)-4-(trifluoromethoxy)benzenesulfonamide; tert-butyl 3-(fluoromethyl)-3-((4-(trifluoromethoxy)phenyl)sulfonamido)pyrrolidine-1-carboxylate;
N-(1-cyclopropyl-2-(3,4-difluorophenyl)pyrrolidin-3-yl)-4-(trifluoromethoxy)benzenesulfonamide;
N-(2-oxo-1-(3-(trifluoromethyl)benzyl)piperidin-3-yl)-4-(trifluoromethoxy)benzenesulfonamide;
N-(spiro[chromane-2,1'-cyclopentan]-4-yl)-4-(trifluoromethoxy)benzenesulfonamide;
N-(1-benzyl-3-phenylpyrrolidin-3-yl)-4-(trifluoromethoxy)benzenesulfonamide;
N-(4-(3-fluoro-4-methoxyphenyl)tetrahydro-2H-pyran-4-yl)-4-(trifluoromethoxy)benzenesulfonamide;
N-(3-phenylpyrrolidin-3-yl)-4-(trifluoromethoxy)benzenesulfonamide;
N-(1-(3-chlorophenyl)cyclopentyl)-4-(trifluoromethoxy)benzenesulfonamide;
methyl 3-(1-((4-(trifluoromethoxy)phenyl)sulfonamido)cyclopentyl)propiolate;
N-(4,6-dichloro-2,3-dihydro-1H-inden-1-yl)-4-(trifluoromethoxy)benzenesulfonamide;
N-2-benzyl-7-hydroxy-1-isopropyl-2-azaspiro[3.4]octan-6-yl)-4-(trifluoromethoxy)benzenesulfonamide;
N-(6-chloro-1,2,3,4-tetrahydronaphthalen-1-yl)-4-(trifluoromethoxy)benzenesulfonamide;
N-(1-(3-methoxyphenyl)cyclopentyl)-4-(trifluoromethoxy)benzenesulfonamide;
N-(2-(4-chlorophenyl)-1-methylpyrrolidin-3-yl)-4-(trifluoromethoxy)benzenesulfonamide;
N-(1-(3,4-dichlorophenyl)piperidin-3-yl)-4-(trifluoromethoxy)benzenesulfonamide;
3,5-dimethyl-N-((1-((4-(trifluoromethoxy)phenyl)sulfonamido)cyclohexyl)methyl)isoxazole-4-sulfonamide;
N-(1-(2-phenylbutanoyl)piperidin-4-yl)-4-(trifluoromethoxy)benzenesulfonamide;
4-(trifluoromethoxy)-N-(1-(3-(trifluoromethoxy)phenyl)pyrrolidin-3-yl)benzenesulfonamide;
N-(2-ethyl-1-(m-tolyl)cyclopropyl)-4-(trifluoromethoxy)benzenesulfonamide;
N-(1-(5-chloro-2-methoxyphenyl)pyrrolidin-3-yl)-4-(trifluoromethoxy)benzenesulfonamide;
N-(5,8-difluorochroman-4-yl)-4-(trifluoromethoxy)benzenesulfonamide;
N-(2-(4-chlorophenyl)cyclopropyl)-4-(trifluoromethoxy)benzenesulfonamide;
N-(2-(3,4-dichlorophenyl)cyclopentyl)-4-(trifluoromethoxy)benzenesulfonamide;
N-(3-(4-chlorophenyl)pyrrolidin-3-yl)-4-(trifluoromethoxy)benzenesulfonamide;
N-(3-(3,4-dichlorophenyl)pyrrolidin-3-yl)-4-(trifluoromethoxy)benzenesulfonamide;
N-(4-(4-chlorophenyl)piperidin-4-yl)-4-(trifluoromethoxy)benzenesulfonamide;
N-(1-(3-bromophenyl)pyrrolidin-3-yl)-4-(trifluoromethoxy)benzenesulfonamide;
N-(3-(4-chlorophenyl)azetidin-3-yl)-4-(trifluoromethoxy)benzenesulfonamide;
N-(3-(3,4-dichlorophenyl)azetidin-3-yl)-4-(trifluoromethoxy)benzenesulfonamide;
N-(4-(3,4-dichlorophenyl)piperidin-4-yl)-4-(trifluoromethoxy)benzenesulfonamide;
N-(4-phenylpiperidin-4-yl)-4-(trifluoromethoxy)benzenesulfonamide;
benzyl 3-(3,4-dichlorophenyl)-3-((4-(trifluoromethoxy)phenyl)sulfonamido)pyrrolidine-1-carboxylate;
N-(3-(4-chloro-3-fluorophenyl)pyrrolidin-3-yl)-4-(trifluoromethoxy)benzenesulfonamide;
tert-butyl 4-(4-chlorophenyl)-4-((4-(trifluoromethoxy)phenyl)sulfonamido)piperidine-1-carboxylate;
N-(1-benzyl-3-(4-chlorophenyl)pyrrolidin-3-yl)-4-(4-(trifluoromethyl)phenoxy)benzenesulfonamide;
N-(1-benzyl-3-(3,4-dichlorophenyl)pyrrolidin-3-yl)-4-(4-(trifluoromethyl)phenoxy)benzenesulfonamide;
N-(4-(4-chloro-3-fluorophenyl)piperidin-4-yl)-4-(trifluoromethoxy)benzenesulfonamide;
N-(3-(4-chlorophenyl)pyrrolidin-3-yl)-4-(4-(trifluoromethyl)phenoxy)benzenesulfonamide;
N-(3-(4-chloro-3-fluorophenyl)azetidin-3-yl)-4-(trifluoromethoxy)benzenesulfonamide;
N-(4-(4-fluorophenyl)piperidin-4-yl)-4-(trifluoromethoxy)benzenesulfonamide;
N-(4-phenylpiperidin-4-yl)-6-(trifluoromethoxy)pyridine-3-sulfonamide;

N-(1-methyl-4-phenylpiperidin-4-yl)-4-(trifluoromethoxy) benzenesulfonamide;
N-(4-(4-chlorophenyl)piperidin-4-yl)-4-isopropoxybenzenesulfonamide;
N-(3-(4-chlorophenyl)pyrrolidin-3-yl)-4-(trifluoromethoxy) benzenesulfonimidamide;
N-(3-(4-chlorophenyl)pyrrolidin-3-yl)-6-(trifluoromethoxy) pyridine-3-sulfonamide;
N-(4-(5-fluoropyridin-2-yl)piperidin-4-yl)-4-(trifluoromethoxy)benzenesulfonamide;
N-(4-(bicyclo[1.1.1]pentan-1-yl)piperidin-4-yl)-4-(trifluoromethoxy)benzenesulfonamide;
N-(4-(4-chlorophenyl)piperidin-4-yl)-6-isopropoxypyridine-3-sulfonamide;
N-(3-(4-chlorophenyl)pyrrolidin-3-yl)-N'-methyl-4-(trifluoromethoxy)benzenesulfonimidamide;
N-(3-(4-chlorophenyl)-1-methylpyrrolidin-3-yl)-4-(trifluoromethoxy)benzenesulfonamide;
tert-butyl 3-(4-chlorophenyl)-3-((4-(trifluoromethoxy)phenyl)sulfonamido)pyrrolidine-1-carboxylate;
N-(3-(4-chlorophenyl)-1-(oxetan-3-yl)pyrrolidin-3-yl)-4-(trifluoromethoxy)benzenesulfonamide;
N-(3-(4-chlorophenyl)-1-(methylsulfonyl)pyrrolidin-3-yl)-4-(trifluoromethoxy)benzenesulfonamide;
N-(4-(5-chlorothiazol-2-yl)piperidin-4-yl)-4-(trifluoromethoxy)benzenesulfonamide;
N-(3-(4-fluorophenyl)pyrrolidin-3-yl)-4-(trifluoromethoxy) benzenesulfonamide;
N-(4-(4-fluorophenyl)piperidin-4-yl)-4-isopropoxybenzenesulfonamide;
N-(3-(4-chlorophenyl)-1-isopentylpyrrolidin-3-yl)-4-(trifluoromethoxy)benzenesulfonamide;
N-(4-(4-fluorophenyl)piperidin-4-yl)-6-isopropoxypyridine-3-sulfonamide;
N-(3-(4-fluorophenyl)pyrrolidin-3-yl)-4-isopropoxybenzenesulfonamide;
rac N-((3S,4S)-3-(4-chlorophenyl)-4-fluoropyrrolidin-3-yl)-4-(trifluoromethoxy)benzenesulfonamide;
N-(3-(4-chlorophenyl)pyrrolidin-3-yl)-6-isopropoxypyridine-3-sulfonamide;
N-(3-(4-chlorophenyl)-1-(3-methylbutanoyl)pyrrolidin-3-yl)-4-(trifluoromethoxy)benzenesulfonamide;
N-(4-(3,4-difluorophenyl)piperidin-4-yl)-4-(trifluoromethoxy)benzenesulfonamide;
N-(4-(2,4-difluorophenyl)piperidin-4-yl)-4-(trifluoromethoxy)benzenesulfonamide;
N-(3-(4-fluorophenyl)pyrrolidin-3-yl)-4-(trifluoromethoxy) benzenesulfonimidamide;
N-(3-(4-chlorophenyl)pyrrolidin-3-yl)-N-methyl-4-(trifluoromethoxy)benzenesulfonamide;
N-(3-phenyl-8-azabicyclo[3.2.1]octan-3-yl)-4-(trifluoromethoxy)benzenesulfonamide;
N-(4-(5-chloropyridin-2-yl)piperidin-4-yl)-4-(trifluoromethoxy)benzenesulfonamide;
N-(4-(2,5-difluorophenyl)piperidin-4-yl)-4-(trifluoromethoxy)benzenesulfonamide;
N-(1-(3,4-dichlorophenyl)cyclopropyl)-4-(trifluoromethoxy)benzenesulfonamide;
N-(3-phenylpiperidin-3-yl)-4-(trifluoromethoxy)benzenesulfonamide;
N-(4-(5-chlorothiophen-2-yl)piperidin-4-yl)-4-(trifluoromethoxy)benzenesulfonamide;
3-amino-N-(3-(4-fluorophenyl)pyrrolidin-3-yl)-4-(trifluoromethoxy)benzenesulfonamide;
3-amino-N-(3-(4-fluoro-3-methylphenyl)pyrrolidin-3-yl)-4-(trifluoromethoxy)benzenesulfonamide;
N-(4-(4-chloro-2-fluorophenyl)piperidin-4-yl)-4-(trifluoromethoxy)benzenesulfonamide;
N-(4-(5-chloro-3-fluoropyridin-2-yl)piperidin-4-yl)-4-(trifluoromethoxy)benzenesulfonamide;
N'-(4-(4-chlorophenyl)piperidin-4-yl)-4-(trifluoromethoxy) benzenesulfonimidamide;
N-(4-(4-chlorophenyl)piperidin-4-yl)-4-(trifluoromethyl) benzenesulfonamide;
N-(4-(4-chlorophenyl)piperidin-4-yl)-3-(trifluoromethyl)bicyclo[1.1.1]pentane-1-sulfonamide;
3-amino-N-(4-(4-chlorophenyl)piperidin-4-yl)-4-(trifluoromethoxy)benzenesulfonamide; and
N-(4-(4-(difluoromethyl)phenyl)piperidin-4-yl)-4-(trifluoromethoxy)benzenesulfonamide;
or a salt, solvate, isotopologue, or tautomer thereof.

In certain embodiments, the compound is selected from the group consisting of
(R)—N-(6-fluoro-2,2-dimethylchroman-4-yl)-4-(trifluoromethoxy)benzenesulfonamide;
N-((2R,3R)-1-(tert-butyl)-2-(4-chloro-3-fluorophenyl)pyrrolidin-3-yl)-4-(trifluoromethoxy)benzenesulfonamide;
N-((2R,3S)-1-(tert-butyl)-2-(4-chloro-3-fluorophenyl)pyrrolidin-3-yl)-4-(trifluoromethoxy)benzenesulfonamide;
tert-butyl 4-((1R,2R)-2-((4-(trifluoromethoxy)phenyl)sulfonamido)cyclopropyl)piperidine-1-carboxylate;
tert-butyl 4-((1R,2S)-2-((4-(trifluoromethoxy)phenyl)sulfonamido)cyclopropyl)piperidine-1-carboxylate;
(R)-tert-butyl 2-(1-((4-(trifluoromethoxy)phenyl)sulfonamido)cyclopropyl)pyrrolidine-1-carboxylate;
(R)—N-(6-(difluoromethoxy)-4-oxo-1,2,3,4-tetrahydronaphthalen-1-yl)-4-(trifluoromethoxy)benzenesulfonamide;
tert-butyl (R)-3-(fluoromethyl)-3-((4-(trifluoromethoxy) phenyl)sulfonamido)pyrrolidine-1-carboxylate;
N-((2R,3R)-1-cyclopropyl-2-(3,4-difluorophenyl)pyrrolidin-3-yl)-4-(trifluoromethoxy)benzenesulfonamide;
N-((2R,3S)-1-cyclopropyl-2-(3,4-difluorophenyl)pyrrolidin-3-yl)-4-(trifluoromethoxy)benzenesulfonamide;
(R)—N-(2-oxo-1-(3-(trifluoromethyl)benzyl)piperidin-3-yl)-4-(trifluoromethoxy)benzenesulfonamide;
(R)—N-(spiro[chromane-2,1'-cyclopentan]-4-yl)-4-(trifluoromethoxy)benzenesulfonamide;
(R)—N-(1-benzyl-3-phenylpyrrolidin-3-yl)-4-(trifluoromethoxy)benzenesulfonamide;
(R)—N-(3-phenylpyrrolidin-3-yl)-4-(trifluoromethoxy)benzenesulfonamide;
(R)—N-(4,6-dichloro-2,3-dihydro-1H-inden-1-yl)-4-(trifluoromethoxy)benzenesulfonamide;
N-((6R,7R)-2-benzyl-7-hydroxy-1-isopropyl-2-azaspiro [3.4]octan-6-yl)-4-(trifluoromethoxy)benzenesulfonamide;
N-((6R,7S)-2-benzyl-7-hydroxy-1-isopropyl-2-azaspiro [3.4]octan-6-yl)-4-(trifluoromethoxy)benzenesulfonamide;
(R)—N-(6-chloro-1,2,3,4-tetrahydronaphthalen-1-yl)-4-(trifluoromethoxy)benzenesulfonamide;
N-((2R,3R)-2-(4-chlorophenyl)-1-methylpyrrolidin-3-yl)-4-(trifluoromethoxy)benzenesulfonamide;
N-((2R,3S)-2-(4-chlorophenyl)-1-methylpyrrolidin-3-yl)-4-(trifluoromethoxy)benzenesulfonamide;
(R)—N-(1-(3,4-dichlorophenyl)piperidin-3-yl)-4-(trifluoromethoxy)benzenesulfonamide;
N-((1R,2R)-2-phenylcycloheptyl)-4-(trifluoromethoxy)benzenesulfonamide;
N-((1R,2S)-2-phenylcycloheptyl)-4-(trifluoromethoxy)benzenesulfonamide;

(R)—N-(1-(2-phenylbutanoyl)piperidin-4-yl)-4-(trifluoromethoxy)benzenesulfonamide;

(R)-4-(trifluoromethoxy)-N-(1-(3-(trifluoromethoxy)phenyl)pyrrolidin-3-yl)benzenesulfonamide;

N-((1R,2R)-2-ethyl-1-(m-tolyl)cyclopropyl)-4-(trifluoromethoxy)benzenesulfonamide;

N-((1R,2S)-2-ethyl-1-(m-tolyl)cyclopropyl)-4-(trifluoromethoxy)benzenesulfonamide;

(R)—N-(1-(5-chloro-2-methoxyphenyl)pyrrolidin-3-yl)-4-(trifluoromethoxy)benzenesulfonamide;

(R)—N-(5,8-difluorochroman-4-yl)-4-(trifluoromethoxy) benzenesulfonamide;

N-((1R,2R)-2-(4-chlorophenyl)cyclopropyl)-4-(trifluoromethoxy)benzenesulfonamide;

N-((1R,2S)-2-(4-chlorophenyl)cyclopropyl)-4-(trifluoromethoxy)benzenesulfonamide;

N-((1R,2R)-2-(3,4-dichlorophenyl)cyclopentyl)-4-(trifluoromethoxy)benzenesulfonamide;

N-((1R,2S)-2-(3,4-dichlorophenyl)cyclopentyl)-4-(trifluoromethoxy)benzenesulfonamide;

(R)—N-(3-(4-chlorophenyl)pyrrolidin-3-yl)-4-(trifluoromethoxy)benzenesulfonamide;

(R)—N-(3-(3,4-dichlorophenyl)pyrrolidin-3-yl)-4-(trifluoromethoxy)benzenesulfonamide;

(R)—N-(1-(3-bromophenyl)pyrrolidin-3-yl)-4-(trifluoromethoxy)benzenesulfonamide;

(R)-benzyl 3-(3,4-dichlorophenyl)-3-((4-(trifluoromethoxy) phenyl)sulfonamido)pyrrolidine-1-carboxylate;

N-((3R,4R)-4-(3,4-dichlorophenyl)pyrrolidin-3-yl)-4-(trifluoromethoxy)benzenesulfonamide;

N-((3R,4S)-4-(3,4-dichlorophenyl)pyrrolidin-3-yl)-4-(trifluoromethoxy)benzenesulfonamide;

(R)—N-(3-(4-chloro-3-fluorophenyl)pyrrolidin-3-yl)-4-(trifluoromethoxy)benzenesulfonamide;

(R)—N-(1-benzyl-3-(4-chlorophenyl)pyrrolidin-3-yl)-4-(4-(trifluoromethyl)phenoxy)benzenesulfonamide;

(R)—N-(1-benzyl-3-(3,4-dichlorophenyl)pyrrolidin-3-yl)-4-(4-(trifluoromethyl)phenoxy)benzenesulfonamide;

(R)—N-(3-(4-chlorophenyl)pyrrolidin-3-yl)-4-(4-(trifluoromethyl)phenoxy)benzenesulfonamide;

(R)—N—((R)-3-(4-chlorophenyl)yrrolidine-3-yl)-4-(trifluoromethoxy)benzenesulfonimidamide;

(R)—N—((S)-3-(4-chlorophenyl)yrrolidine-3-yl)-4-(trifluoromethoxy)benzenesulfonimidamide;

(R)—N-(3-(4-chlorophenyl)yrrolidine-3-yl)-6-(trifluoromethoxy)pyridine-3-sulfonamide;

(R)—N—((R)-3-(4-chlorophenyl)yrrolidine-3-yl)-N'-methyl-4-(trifluoromethoxy)benzenesulfonimidamide;

(R)—N—((S)-3-(4-chlorophenyl)yrrolidine-3-yl)-N'-methyl-4-(trifluoromethoxy)benzenesulfonimidamide;

(R)—N-(3-(4-chlorophenyl)-1-methylpyrrolidin-3-yl)-4-(trifluoromethoxy)benzenesulfonamide;

tert-butyl (R)-3-(4-chlorophenyl)-3-((4-(trifluoromethoxy) phenyl)yrrolidine)pyrrolidine-1-carboxylate;

(R)—N-(3-(4-chlorophenyl)-1-(oxetan-3-yl)yrrolidine-3-yl)-4-(trifluoromethoxy)benzenesulfonamide;

(R)—N-(3-(4-chlorophenyl)-1-(methylsulfonyl)yrrolidine-3-yl)-4-(trifluoromethoxy)benzenesulfonamide;

(R)—N-(3-(4-fluorophenyl)yrrolidine-3-yl)-4-(trifluoromethoxy)benzenesulfonamide;

(R)—N-(3-(4-chlorophenyl)-1-isopentylpyrrolidin-3-yl)-4-(trifluoromethoxy)benzenesulfonamide;

(R)—N-(3-(4-fluorophenyl)yrrolidine-3-yl)-4-isopropoxybenzenesulfonamide;

N-((3R,4R)-3-(4-chlorophenyl)-4-fluoropyrrolidin-3-yl)-4-(trifluoromethoxy)benzenesulfonamide;

N-((3R,4S)-3-(4-chlorophenyl)-4-fluoropyrrolidin-3-yl)-4-(trifluoromethoxy)benzenesulfonamide;

(R)—N-(3-(4-chlorophenyl)yrrolidine-3-yl)-6-isopropoxypyridine-3-sulfonamide;

(R)—N-(3-(4-chlorophenyl)-1-(3-methylbutanoyl)yrrolidine-3-yl)-4-(trifluoromethoxy)benzenesulfonamide;

(R)—N—((R)-3-(4-fluorophenyl)pyrrolidin-3-yl)-4-(trifluoromethoxy)benzenesulfonimidamide;

(R)—N—((S)-3-(4-fluorophenyl)pyrrolidin-3-yl)-4-(trifluoromethoxy)benzenesulfonimidamide;

(R)—N-(3-(4-chlorophenyl)pyrrolidin-3-yl)-N-methyl-4-(trifluoromethoxy)benzenesulfonamide;

(R)—N-(3-phenylpiperidin-3-yl)-4-(trifluoromethoxy)benzenesulfonamide;

(R)-3-amino-N-(3-(4-fluorophenyl)pyrrolidin-3-yl)-4-(trifluoromethoxy)benzenesulfonamide; and (R)-3-amino-N-(3-(4-fluoro-3-methylphenyl)pyrrolidin-3-yl)-4-(trifluoromethoxy)benzenesulfonamide;

or a salt, solvate, isotopologue, or tautomer thereof.

In certain embodiments, the compound is selected from the group consisting of (S)—N-(6-fluoro-2,2-dimethylchroman-4-yl)-4-(trifluoromethoxy)benzenesulfonamide;

N-((2S,3R)-1-(tert-butyl)-2-(4-chloro-3-fluorophenyl)pyrrolidin-3-yl)-4-(trifluoromethoxy)benzenesulfonamide;

N-((2S,3S)-1-(tert-butyl)-2-(4-chloro-3-fluorophenyl)pyrrolidin-3-yl)-4-(trifluoromethoxy)benzenesulfonamide;

tert-butyl 4-((1S,2S)-2-((4-(trifluoromethoxy)phenyl)sulfonamido)cyclopropyl)piperidine-1-carboxylate;

tert-butyl 4-((1S,2R)-2-((4-(trifluoromethoxy)phenyl)sulfonamido)cyclopropyl)piperidine-1-carboxylate;

(S)-tert-butyl 2-(1-((4-(trifluoromethoxy)phenyl)sulfonamido)cyclopropyl)pyrrolidine-1-carboxylate;

(S)—N-(6-(difluoromethoxy)-4-oxo-1,2,3,4-tetrahydronaphthalen-1-yl)-4-(trifluoromethoxy)benzenesulfonamide;

tert-butyl (S)-3-(fluoromethyl)-3-((4-(trifluoromethoxy) phenyl)sulfonamido)pyrrolidine-1-carboxylate;

N-((2S,3S)-1-cyclopropyl-2-(3,4-difluorophenyl)pyrrolidin-3-yl)-4-(trifluoromethoxy)benzenesulfonamide;

N-((2S,3R)-1-cyclopropyl-2-(3,4-difluorophenyl)pyrrolidin-3-yl)-4-(trifluoromethoxy)benzenesulfonamide;

(S)—N-(2-oxo-1-(3-(trifluoromethyl)benzyl)piperidin-3-yl)-4-(trifluoromethoxy)benzenesulfonamide;

(S)—N-(spiro[chromane-2,1'-cyclopentan]-4-yl)-4-(trifluoromethoxy)benzenesulfonamide;

(S)—N-(1-benzyl-3-phenylpyrrolidin-3-yl)-4-(trifluoromethoxy)benzenesulfonamide;

(S)—N-(3-phenylpyrrolidin-3-yl)-4-(trifluoromethoxy)benzenesulfonamide;

(S)—N-(4,6-dichloro-2,3-dihydro-TH-inden-1-yl)-4-(trifluoromethoxy)benzenesulfonamide;

N-((6S,7S)-2-benzyl-7-hydroxy-1-isopropyl-2-azaspiro [3.4]octan-6-yl)-4-(trifluoromethoxy)benzenesulfonamide;

N-((6S,7R)-2-benzyl-7-hydroxy-1-isopropyl-2-azaspiro [3.4]octan-6-yl)-4-(trifluoromethoxy)benzenesulfonamide;

(S)—N-(6-chloro-1,2,3,4-tetrahydronaphthalen-1-yl)-4-(trifluoromethoxy)benzenesulfonamide;

N-((2S,3S)-2-(4-chlorophenyl)-1-methylpyrrolidin-3-yl)-4-(trifluoromethoxy)benzenesulfonamide;

N-((2S,3R)-2-(4-chlorophenyl)-1-methylpyrrolidin-3-yl)-4-(trifluoromethoxy)benzenesulfonamide;

(S)—N-(1-(3,4-dichlorophenyl)piperidin-3-yl)-4-(trifluoromethoxy)benzenesulfonamide;

N-((1S,2S)-2-phenylcycloheptyl)-4-(trifluoromethoxy)benzenesulfonamide;
N-((1S,2R)-2-phenylcycloheptyl)-4-(trifluoromethoxy)benzenesulfonamide;
(S)—N-(1-(2-phenylbutanoyl)piperidin-4-yl)-4-(trifluoromethoxy)benzenesulfonamide;
(S)-4-(trifluoromethoxy)-N-(1-(3-(trifluoromethoxy)phenyl)pyrrolidin-3-yl)benzenesulfonamide;
N-((1S,2S)-2-ethyl-1-(m-tolyl)cyclopropyl)-4-(trifluoromethoxy)benzenesulfonamide;
N-((1S,2S)-2-ethyl-1-(m-tolyl)cyclopropyl)-4-(trifluoromethoxy)benzenesulfonamide;
(S)—N-(1-(5-chloro-2-methoxyphenyl)pyrrolidin-3-yl)-4-(trifluoromethoxy)benzenesulfonamide;
(S)—N-(5,8-difluorochroman-4-yl)-4-(trifluoromethoxy)benzenesulfonamide;
N-((1S,2S)-2-(4-chlorophenyl)cyclopropyl)-4-(trifluoromethoxy)benzenesulfonamide;
N-((1S,2R)-2-(4-chlorophenyl)cyclopropyl)-4-(trifluoromethoxy)benzenesulfonamide;
N-((1S,2S)-2-(3,4-dichlorophenyl)cyclopentyl)-4-(trifluoromethoxy)benzenesulfonamide;
N-((1S,2R)-2-(3,4-dichlorophenyl)cyclopentyl)-4-(trifluoromethoxy)benzenesulfonamide;
(S)—N-(3-(4-chlorophenyl)pyrrolidin-3-yl)-4-(trifluoromethoxy)benzenesulfonamide;
(S)—N-(3-(3,4-dichlorophenyl)pyrrolidin-3-yl)-4-(trifluoromethoxy)benzenesulfonamide;
(S)—N-(1-(3-bromophenyl)pyrrolidin-3-yl)-4-(trifluoromethoxy)benzenesulfonamide;
(S)-benzyl 3-(3,4-dichlorophenyl)-3-((4-(trifluoromethoxy)phenyl)sulfonamido)pyrrolidine-1-carboxylate;
N-((3S,4S)-4-(3,4-dichlorophenyl)pyrrolidin-3-yl)-4-(trifluoromethoxy)benzenesulfonamide;
N-((3S,4R)-4-(3,4-dichlorophenyl)pyrrolidin-3-yl)-4-(trifluoromethoxy)benzenesulfonamide;
(S)—N-(3-(4-chloro-3-fluorophenyl)pyrrolidin-3-yl)-4-(trifluoromethoxy)benzenesulfonamide;
(S)—N-(1-benzyl-3-(4-chlorophenyl)pyrrolidin-3-yl)-4-(4-(trifluoromethyl)phenoxy)benzenesulfonamide;
(S)—N-(1-benzyl-3-(3,4-dichlorophenyl)pyrrolidin-3-yl)-4-(4-(trifluoromethyl)phenoxy)benzenesulfonamide;
(S)—N-(3-(4-chlorophenyl)pyrrolidin-3-yl)-4-(4-(trifluoromethyl)phenoxy)benzenesulfonamide;
(S)—N—((S)-3-(4-chlorophenyl)pyrrolidin-3-yl)-4-(trifluoromethoxy)benzenesulfonimidamide;
(S)—N—((R)-3-(4-chlorophenyl)pyrrolidin-3-yl)-4-(trifluoromethoxy)benzenesulfonimidamide;
(S)—N-(3-(4-chlorophenyl)pyrrolidin-3-yl)-6-(trifluoromethoxy)pyridine-3-sulfonamide;
(S)—N—((S)-3-(4-chlorophenyl)pyrrolidin-3-yl)-N'-methyl-4-(trifluoromethoxy)benzenesulfonimidamide;
(S)—N—((R)-3-(4-chlorophenyl)pyrrolidin-3-yl)-N'-methyl-4-(trifluoromethoxy)benzenesulfonimidamide;
(S)—N-(3-(4-chlorophenyl)-1-methylpyrrolidin-3-yl)-4-(trifluoromethoxy)benzenesulfonamide;
tert-butyl (S)-3-(4-chlorophenyl)-3-((4-(trifluoromethoxy)phenyl)sulfonamido)pyrrolidine-1-carboxylate;
(S)—N-(3-(4-chlorophenyl)-1-(oxetan-3-yl)pyrrolidin-3-yl)-4-(trifluoromethoxy)benzenesulfonamide;
(S)—N-(3-(4-chlorophenyl)-1-(methylsulfonyl)pyrrolidin-3-yl)-4-(trifluoromethoxy)benzenesulfonamide;
(S)—N-(3-(4-fluorophenyl)pyrrolidin-3-yl)-4-(trifluoromethoxy)benzenesulfonamide;
(S)—N-(3-(4-chlorophenyl)-1-isopentylpyrrolidin-3-yl)-4-(trifluoromethoxy)benzenesulfonamide;
(S)—N-(3-(4-fluorophenyl)pyrrolidin-3-yl)-4-isopropoxybenzenesulfonamide;
N-((3S,4S)-3-(4-chlorophenyl)-4-fluoropyrrolidin-3-yl)-4-(trifluoromethoxy)benzenesulfonamide;
N-((3S,4R)-3-(4-chlorophenyl)-4-fluoropyrrolidin-3-yl)-4-(trifluoromethoxy)benzenesulfonamide;
(S)—N-(3-(4-chlorophenyl)pyrrolidin-3-yl)-6-isopropoxypyridine-3-sulfonamide;
(S)—N-(3-(4-chlorophenyl)-1-(3-methylbutanoyl)pyrrolidin-3-yl)-4-(trifluoromethoxy)benzenesulfonamide;
(S)—N—((S)-3-(4-fluorophenyl)pyrrolidin-3-yl)-4-(trifluoromethoxy)benzenesulfonimidamide;
(S)—N—((R)-3-(4-fluorophenyl)pyrrolidin-3-yl)-4-(trifluoromethoxy)benzenesulfonimidamide;
(S)—N-(3-(4-chlorophenyl)pyrrolidin-3-yl)-N-methyl-4-(trifluoromethoxy)benzenesulfonamide;
(S)—N-(3-phenylpiperidin-3-yl)-4-(trifluoromethoxy)benzenesulfonamide;
(S)-3-amino-N-(3-(4-fluorophenyl)pyrrolidin-3-yl)-4-(trifluoromethoxy)benzenesulfonamide;
and (S)-3-amino-N-(3-(4-fluoro-3-methylphenyl)pyrrolidin-3-yl)-4-(trifluoromethoxy)benzenesulfonamide;
or a salt, solvate, isotopologue, or tautomer thereof.

In certain embodiments, the compound is selected from the group consisting of N-(4-((4-((4-(trifluoromethoxy)phenyl)sulfonamido)piperidin-1-yl)sulfonyl)phenyl)acetamide;
methyl 1-((4-(trifluoromethoxy)phenyl)sulfonamido)-2,3-dihydro-1H-indene-2-carboxylate;
methyl (1R,2R)-1-((4-(trifluoromethoxy)phenyl)sulfonamido)-2,3-dihydro-1H-indene-2-carboxylate;
methyl (1R,2S)-1-((4-(trifluoromethoxy)phenyl)sulfonamido)-2,3-dihydro-1H-indene-2-carboxylate;
methyl (1S,2S)-1-((4-(trifluoromethoxy)phenyl)sulfonamido)-2,3-dihydro-1H-indene-2-carboxylate;
methyl (1S,2R)-1-((4-(trifluoromethoxy)phenyl)sulfonamido)-2,3-dihydro-1H-indene-2-carboxylate;
N-(2-(4-fluorophenoxy)cyclohexyl)-4-(trifluoromethoxy)benzenesulfonamide;
N-((1R,2R)-2-(4-fluorophenoxy)cyclohexyl)-4-(trifluoromethoxy)benzenesulfonamide;
N-((1R,2S)-2-(4-fluorophenoxy)cyclohexyl)-4-(trifluoromethoxy)benzenesulfonamide;
N-((1S,2S)-2-(4-fluorophenoxy)cyclohexyl)-4-(trifluoromethoxy)benzenesulfonamide;
N-((1S,2R)-2-(4-fluorophenoxy)cyclohexyl)-4-(trifluoromethoxy)benzenesulfonamide;
4-(trifluoromethoxy)-N-(3,4,4-trimethylcyclohexyl)benzenesulfonamide;
(R)-4-(trifluoromethoxy)-N-(3,4,4-trimethylcyclohexyl)benzenesulfonamide;
(S)-4-(trifluoromethoxy)-N-(3,4,4-trimethylcyclohexyl)benzenesulfonamide;
4-(trifluoromethoxy)-N-((1R,3R)-3,4,4-trimethylcyclohexyl)benzenesulfonamide;
4-(trifluoromethoxy)-N-((1R,3S)-3,4,4-trimethylcyclohexyl)benzenesulfonamide;
4-(trifluoromethoxy)-N-((1S,3S)-3,4,4-trimethylcyclohexyl)benzenesulfonamide;
4-(trifluoromethoxy)-N-((1S,3R)-3,4,4-trimethylcyclohexyl)benzenesulfonamide;
N-(2-phenylcycloheptyl)-4-(trifluoromethoxy)benzenesulfonamide;
N-((1R,2R)-2-phenylcycloheptyl)-4-(trifluoromethoxy)benzenesulfonamide;
N-((1R,2S)-2-phenylcycloheptyl)-4-(trifluoromethoxy)benzenesulfonamide;

N-((1S,2S)-2-phenylcycloheptyl)-4-(trifluoromethoxy)benzenesulfonamide;
N-((1S,2R)-2-phenylcycloheptyl)-4-(trifluoromethoxy)benzenesulfonamide;
ethyl 1-((4-(trifluoromethoxy)phenyl)sulfonamido)-2,3-dihydro-1H-indene-1-carboxylate;
ethyl (R)-1-((4-(trifluoromethoxy)phenyl)sulfonamido)-2,3-dihydro-1H-indene-1-carboxylate;
ethyl (S)-1-((4-(trifluoromethoxy)phenyl)sulfonamido)-2,3-dihydro-1H-indene-1-carboxylate;
methyl 3,5-dimethyl-7-((4-(trifluoromethoxy)phenyl)sulfonamido)adamantane-1-carboxylate;
N-(2-benzyloctahydrocyclopenta[c]pyrrol-4-yl)-4-(trifluoromethoxy)benzenesulfonamide;
(R)—N-(2-benzyloctahydrocyclopenta[c]pyrrol-4-yl)-4-(trifluoromethoxy)benzenesulfonamide;
(S)—N-(2-benzyloctahydrocyclopenta[c]pyrrol-4-yl)-4-(trifluoromethoxy)benzenesulfonamide;
4-(trifluoromethoxy)-N-(4-(trifluoromethyl)-4,5,6,7-tetrahydro-1H-indazol-6-yl)benzenesulfonamide;
4-(trifluoromethoxy)-N-((4R,6R)-4-(trifluoromethyl)-4,5,6,7-tetrahydro-1H-indazol-6-yl)benzenesulfonamide;
4-(trifluoromethoxy)-N-((4R,6S)-4-(trifluoromethyl)-4,5,6,7-tetrahydro-1H-indazol-6-yl)benzenesulfonamide;
4-(trifluoromethoxy)-N-((4S,6S)-4-(trifluoromethyl)-4,5,6,7-tetrahydro-1H-indazol-6-yl)benzenesulfonamide;
4-(trifluoromethoxy)-N-((4S,6R)-4-(trifluoromethyl)-4,5,6,7-tetrahydro-1H-indazol-6-yl)benzenesulfonamide;
or a salt, solvate, isotopologue, or tautomer thereof.

The compounds of the invention may possess one or more stereocenters, and each stereocenter may exist independently in either the (R) or (S) configuration. In certain embodiments, compounds described herein are present in optically active or racemic forms.

The compounds described herein encompass racemic, optically active, regioisomeric and stereoisomeric forms, or combinations thereof that possess the therapeutically useful properties described herein. Preparation of optically active forms is achieved in any suitable manner, including by way of non-limiting example, by resolution of the racemic form with recrystallization techniques, synthesis from optically active starting materials, chiral synthesis, or chromatographic separation using a chiral stationary phase. A compound illustrated herein by the racemic formula further represents either of the two enantiomers or mixtures thereof, or in the case where two or more chiral center are present, all diastereomers or mixtures thereof.

In certain embodiments, the compounds of the invention exist as tautomers. All tautomers are included within the scope of the compounds recited herein.

Compounds described herein also include isotopically labeled compounds wherein one or more atoms is replaced by an atom having the same atomic number, but an atomic mass or mass number different from the atomic mass or mass number usually found in nature (i.e. isotopologues). Examples of isotopes suitable for inclusion in the compounds described herein include and are not limited to $^{2}H$, $^{3}H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O^{18}O$, $^{32}P$, and $^{35}S$. In certain embodiments, substitution with heavier isotopes such as deuterium affords greater chemical stability. Isotopically labeled compounds are prepared by any suitable method or by processes using an appropriate isotopically labeled reagent in place of the non-labeled reagent otherwise employed.

In certain embodiments, the compounds described herein are labeled by other means, including, but not limited to, the use of chromophores or fluorescent moieties, bioluminescent labels, or chemiluminescent labels.

In all of the embodiments provided herein, examples of suitable optional substituents are not intended to limit the scope of the claimed invention. The compounds of the invention may contain any of the substituents, or combinations of substituents, provided herein.

Salts

The compounds described herein may form salts with acids or bases, and such salts are included in the present invention. The term “salts” embraces addition salts of free acids or bases that are useful within the methods of the invention. The term “pharmaceutically acceptable salt” refers to salts that possess toxicity profiles within a range that affords utility in pharmaceutical applications. In certain embodiments, the salts are pharmaceutically acceptable salts. Pharmaceutically unacceptable salts may nonetheless possess properties such as high crystallinity, which have utility in the practice of the present invention, such as for example utility in process of synthesis, purification or formulation of compounds useful within the methods of the invention.

Suitable pharmaceutically acceptable acid addition salts may be prepared from an inorganic acid or from an organic acid. Examples of inorganic acids include sulfate, hydrogen sulfate, hydrochloric, hydrobromic, hydriodic, nitric, carbonic, sulfuric, and phosphoric acids (including hydrogen phosphate and dihydrogen phosphate). Appropriate organic acids may be selected from aliphatic, cycloaliphatic, aromatic, aryl-aliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (or pamoic), methanesulfonic, ethanesulfonic, benzenesulfonic, pantothenic, sulfanilic, 2-hydroxyethanesulfonic, trifluoromethanesulfonic, p-toluenesulfonic, cyclohexylaminosulfonic, stearic, alginic, β-hydroxybutyric, salicylic, galactaric, galacturonic acid, glycerophosphonic acids and saccharin (e.g., saccharinate, saccharate). Salts may be comprised of a fraction of one, one or more than one molar equivalent of acid or base with respect to any compound of the invention.

Suitable pharmaceutically acceptable base addition salts of compounds of the invention include, for example, ammonium salts and metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylene-diamine, chloroprocaine, choline, diethanolamine, ethylenediamine, meglumine (or N-methylglucamine) and procaine. All of these salts may be prepared from the corresponding compound by reacting, for example, the appropriate acid or base with the compound.

Synthesis

The present invention further provides methods of preparing the compounds of the present invention. Compounds of the present teachings can be prepared in accordance with the procedures outlined here, from commercially available starting materials, compounds known in the literature, or readily prepared intermediates, by employing standard synthetic methods and procedures known to those skilled in the art. Standard synthetic methods and procedures for the preparation of organic molecules and functional group transformations and manipulations can be readily obtained from the relevant scientific literature or from standard textbooks in the field.

It is appreciated that where typical or preferred process conditions (i.e., reaction temperatures, times, mole ratios of reactants, solvents, pressures, and so forth) are given, other process conditions can also be used unless otherwise stated. Optimum reaction conditions can vary with the particular reactants or solvent used, but such conditions can be determined by one skilled in the art by routine optimization procedures. Those skilled in the art of organic synthesis will recognize that the nature and order of the synthetic steps presented can be varied for the purpose of optimizing the formation of the compounds described herein.

The processes described herein can be monitored according to any suitable method known in the art. For example, product formation can be monitored by spectroscopic means, such as nuclear magnetic resonance spectroscopy (e.g., $^{1}H$ or $^{13}C$), infrared spectroscopy, spectrophotometry (e.g., UV-visible), mass spectrometry, or by chromatography such as high pressure liquid chromatography (HPLC), gas chromatography (GC), gel-permeation chromatography (GPC), or thin layer chromatography (TLC).

Preparation of the compounds can involve protection and deprotection of various chemical groups. The need for protection and deprotection and the selection of appropriate protecting groups can be readily determined by one skilled in the art. The chemistry of protecting groups can be found, for example, in Greene, et al., Protective Groups in Organic Synthesis, 2d. Ed. (Wiley & Sons, 1991), the entire disclosure of which is incorporated by reference herein for all purposes.

The reactions or the processes described herein can be carried out in suitable solvents that can be readily selected by one skilled in the art of organic synthesis. Suitable solvents typically are substantially nonreactive with the reactants, intermediates, and/or products at the temperatures at which the reactions are carried out, i.e., temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected.

In certain embodiment, the compounds synthesized using the methods described herein may contain one or more chiral carbon atoms, giving rise to two or more isomers. The absolute stereochemistry may be depicted using wedge bonds (bold or parallel lines). In certain embodiments, the product formed in any of the reactions described may be a racemate. If a racemate is formed, the isomers making up the racemate may be separated using any suitable method for chiral resolution known to a person skilled in the art. Suitable methods for chiral resolution include, but are not limited to, supercritical fluid chromatography (SFC), chiral HPCL, crystallization, derivatization, or any combination thereof.

As described herein, "Enantiomer I" or "Diastereomer I" refers to the first enantiomer or diastereomer eluted from the chiral column under the specific chiral analytical conditions detailed for the specified compound(s); and "Enantiomer II" or "Diastereomer II" refers to the second enantiomer or diastereomer eluted from the chiral column under the specific chiral analytical conditions detailed for the specified compound(s). Such nomenclature does not imply or impart any particular relative and/or absolute configuration for these compounds.

In certain embodiments, separation of the isomers formed in one or more separate reactions may require forming a derivative prior to chiral resolution. A non-limiting example of derivatization is protecting one or more functional groups present in a compound using known protecting groups (such as esters, amides, carbamates, ethers, etc.), followed by separation of the isomers by a suitable method. The desired compound is finally obtained through removal of the protecting group.

The present disclosure provides compounds of formula (I) and formula (II). One skilled in the art would recognize that techniques and/or methods for the synthesis of a compound of formula (I) would, in many instances, be applicable to the synthesis of a compound of formula (II), and vice versa.

In certain embodiments, the compounds of the present disclosure having the structure of formula (I) comprise a sulfonamide of formula (Ia'), which can be prepared as described herein. A compound of formula (Ia'), wherein Ar, A, and $R^2$ are defined within the scope of the present disclosure, is prepared from the corresponding arylsulfonyl chloride 1-1 and amine 1-2 in the presence of a base and solvent (Scheme 1). A suitable base for the sulfonylation is $Et_3N$. A suitable solvent for the sulfonylation is $CH_2Cl_2$.

Scheme 1

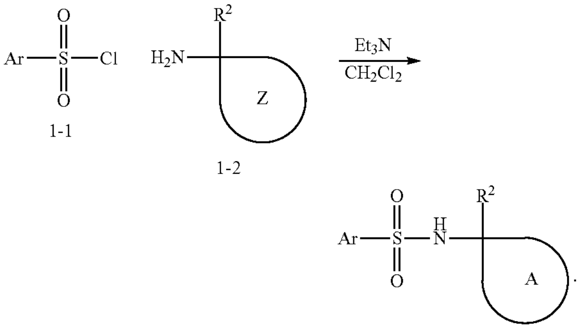

1-1

1-2

(Ia')

In certain embodiments each of the arylsulfonyl halide (1-1) and/or amine (1-2) compounds are commercially available. In other embodiments, at least one of the arylsulfonyl halide and the amine is synthesized using synthetic methods known to one of ordinary skill in the art.

In general, the compound of formula (Ia'), which is the compound of formula 2-6, wherein v is 1 or 2, w is 0 or 1, R is phenyl optionally substituted with at least one substituent selected from the group consisting of a halogen, $C_1$-$C_3$ alkoxy, and trifluoromethyl, X is a halogen selected from the group consisting of Cl and Br, and PG is a protecting group including, but not limited to, benzyl (Bn), tert-butyloxycarbonyl (Boc), and benzyloxycarbonyl (Cbz), may be prepared according to the synthesis provided in Scheme 2.

Scheme 2.

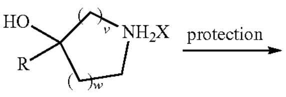

2-1

-continued

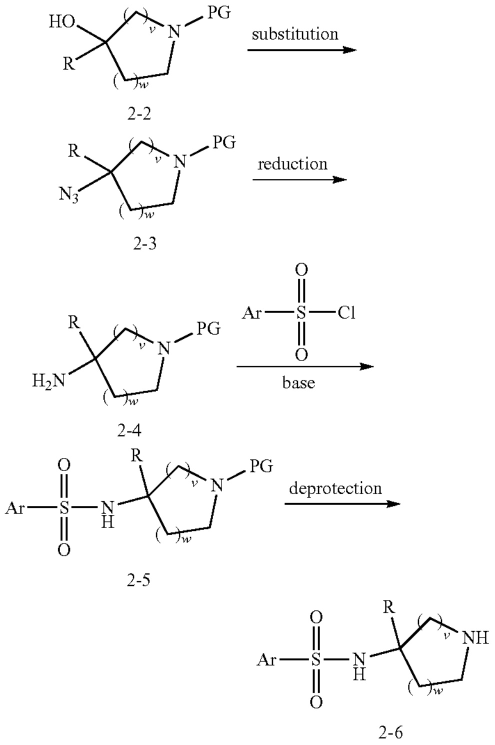

As illustrated in Scheme 2, cyclic ammonium halide 2-1 may be protected with a suitable protecting group, for example tert-butyloxycarbonyl (Boc), using a suitable protecting group precursor (e.g. di-tert-butylcarbonate), to afford protected amine 2-2. Displacement of the tertiary alcohol of 2-2 with an azide to afford tertiary azide 2-3 can be achieved with any of a number of conditions/reagents, including but not limited to: (a) TFA and $NaN_3$; (b) $BF_3{\cdot}Et_2O$ and TMS-$N_3$; (c) DBU and diphenylphosphoryl azide (DPPA); and (d) $SOCl_2$ or MsCl and $NaN_3$. Reduction of tertiary azide 2-3 to corresponding amine 2-4 can be achieved under suitable reaction conditions, including but not limited to treatment with $PPh_3$ and para-toluene sulfonic acid (PTSA). Amine 2-4 can be sulfonylated to corresponding sulfonamide 2-5 with an arylsulfonamide and any of a number of suitable basic reaction conditions, including but not limited to: (a) $Et_3N$ and DCM; (b) pyridine and THF; (c) neat pyridine; and (d) $Et_3N$, DMAP, and DCM. Removal of the protecting group (PG) to afford 2-6, can be achieved, depending on the identity of the specific protecting group employed, by treatment with: (a) HCl in dioxane; (b) TMS-I in ACN; and (c) $H_2$ and Pd/C in MeOH. In certain embodiments, the protecting group is Boc and is removed with HCl in dioxane. In certain embodiments, the protecting group is Cbz and is removed with TMS-I in ACN.

Alternatively, as illustrated in Scheme 3, the compound of formula 2-6 may be prepared from di-ammonium halide salt 3-1, which may be protected with a suitable protecting group, for example tert-butyloxycarbonyl (Boc), using a suitable protecting group precursor (e.g. di-tert-butylcarbonate), to afford mono-protected amine 2-4 directly. The compound of formula 2-6 may be prepared from mono-protected amine 2-4 following the sequence described elsewhere herein.

Scheme 3.

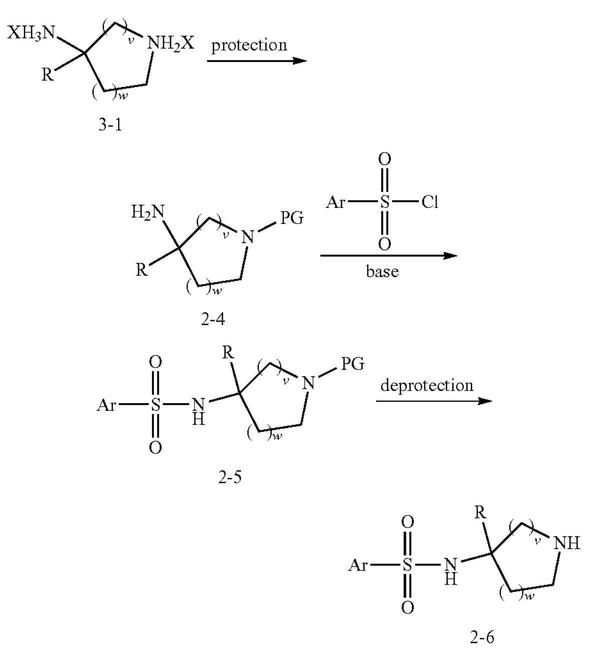

The compounds of the present disclosure having the structure of formula (I) comprise a sulfonimidamide of formula (Ib') or formula (Ic'), which can be prepared as described herein. A compound of formula (Ib') or formula (Ic'), wherein Ar, A, R, and $R^2$ are defined within the scope of the present disclosure, is prepared from the corresponding arylsulfonyl chloride 1-1 and amine 1-2 (Scheme 4). The arylsulfonyl chloride 1-1 may be reduced with a suitable reducing agent, for example $Na_2SO_3$, in the presence of a suitable base, for example $NaHCO_3$, to provide sulfinate 4-1. Sulfinate 4-1 may be chlorinated to the corresponding sulfinyl chloride 4-2 with a suitable chlorinating agent, for example oxalyl chloride. Sulfinyl chloride 4-2 may undergo condensation with a suitable amine (e.g., 4-3) in the presence of a suitable base, for example $Et_3N$, to afford sulfinamide 4-4. Sulfinamide 4-4 may be converted to the compound of formula (Ib') by oxidation with a suitable oxidant, for example t-BuOCl, with subsequent condensation of amine 1-2.

In certain embodiments, sulfinimidamide (Ib') may undergo tautomerization to afford sulfinimidamide (Ic'). In certain embodiments sulfinimidamide (Ic') may undergo tautomerization to afford sulfinimidamide (Ib'). In certain embodiments, the compounds of formula (Ib') and (Ic') may exist as a mixture.

Scheme 4.

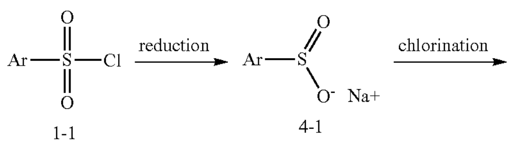

-continued

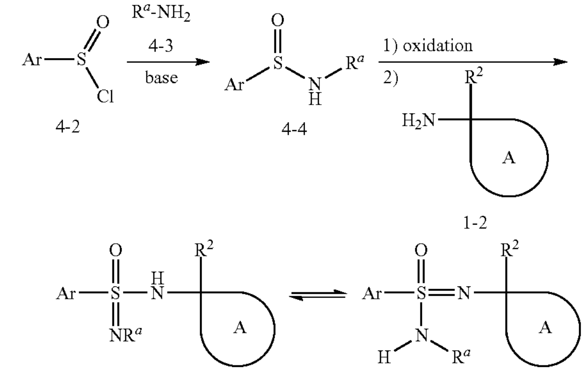

4-2 4-4 1-2

(Ib') (Ic')

In certain embodiments, N-alkyl-sulfonamides of formula (Ia"), wherein $R^B$ is $C_1$-$C_6$ alkyl, may be prepared from a sulfonamide of formula (Ia'). In certain embodiments, the compound of formula (Ia") is prepared from the compound of formula (Ia') by a modified Mitsunobu reaction (Scheme 5). In certain embodiments, sulfonamide (Ia') is treated with a dialkyl azodicarboxylate, non-limiting examples including diethyl azodicarboxylate (DEAD) and diisopropyl azodicarboxylate (DIAD), in the presence of a phosphine ligand, non-limiting examples including $PPh_3$, and a suitable primary or secondary alcohol.

Scheme 5

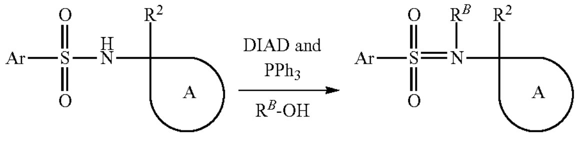

(Ia') (Ia")

As illustrated in Scheme 6, tertiary alcohol 2-2 may be converted to α-haloamide 6-1 with a suitable α-halonitrile, for example 2-chloroacetonitrile, using a suitable acid, for example trifluoroacetic acid. Removal of the α-haloacyl moiety of 6-1 may be achieved under suitable reaction conditions, including but not limited to treatment with thiourea in the presence of a suitable acid, for example acetic acid, at a suitable temperature, including but not limited to 80° C., to afford amine 2-4. Amine 2-4 can be sulfonylated to corresponding sulfonamide 2-5 with an arylsulfonamide and any of a number of suitable basic reaction conditions, including but not limited to: (a) $Et_3N$ and DCM; (b) pyridine and THF; (c) neat pyridine; and (d) $Et_3N$, DMAP, and DCM. Removal of the protecting group (PG), to afford 2-6, can be achieved, depending on the identity of the specific protecting group employed, as described elsewhere herein.

Scheme 6

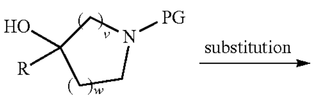

2-2

-continued

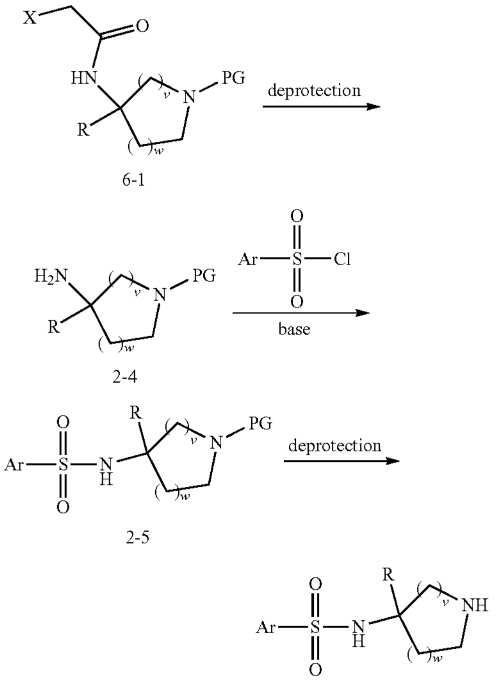

6-1 2-4 2-5 2-6

As illustrated in Scheme 7, secondary amine 7-1 may be protected with a suitable protecting group (PG'), for example benzyl, using suitable alkylating agent, for example benzyl bromide, in the presence of a suitable base, for example $Et_3N$, to afford 7-2. Nitrile 7-2 may be hydrolyzed to amide 7-3 in the presence of a suitable acid, including $H_2SO_4$, at a suitable temperature, for example 60° C. Hofmann rearrangement of amide 7-3 may be achieved under suitable reaction conditions, including but not limited to treatment with a suitable halogenating reagent, for example [bis(trifluoroacetoxy)iodo]benzene, to afford amine 7-4. Amine 7-4 can be sulfonylated to corresponding sulfonamide 7-5 with an arylsulfonamide and any of a number of suitable basic reaction conditions, including but not limited to: (a) $Et_3N$ and DCM; (b) pyridine and THF; (c) neat pyridine; and (d) $Et_3N$, DMAP, and DCM. Removal of the protecting group (PG'), to afford 2-6, can be achieved under suitable reaction conditions, including treatment with a suitable N-dealkylating reagent, including 1-chloroethyl carbonochloridate.

Scheme 7

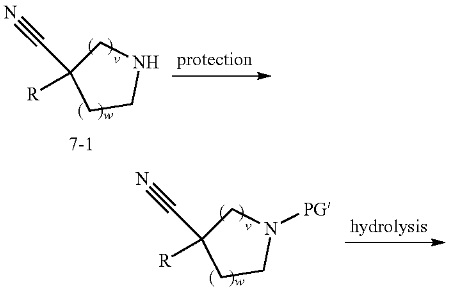

7-1 7-2

-continued

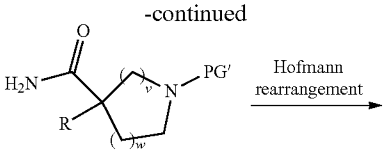

7-3

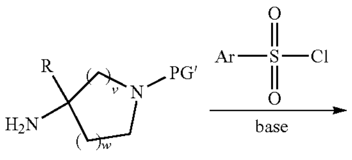

7-4

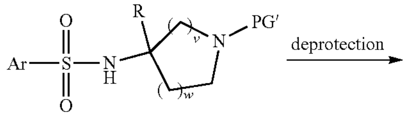

7-5

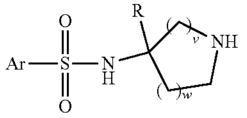

2-6

Methods

The present disclosure relates in part to a method of treating, preventing, and/or ameliorating a PP2A-related disease in a subject, the method comprising administering to a subject in need thereof a therapeutically effective amount of the compound of any one of the compounds of the present disclosure or a pharmaceutical composition of comprising any one of the compounds of the present disclosure and a pharmaceutically acceptable carrier.

In certain embodiments, the PP2A-related disease is at least one selected from the group consisting of cancer, diabetes, autoimmune disease, solid organ transplant rejection, graft vs host disease, chronic obstructive pulmonary disease (COPD), non-alcoholic fatty liver disease, abdominal aortic aneurysm, chronic liver disease, heart failure, neurodegenerative disease, and cardiac hypertrophy.

In certain embodiments, the subject is a mammal. In certain embodiments, the mammal is a human.

The present disclosure further relates in part to the use of a compound according to one or more embodiments disclosed herein, for example a compound of Formula (I) or (II), a salt, solvate, enantiomer, diastereomer, isotopologue, tautomer, or any mixture thereof, for use as a medicament for treating, preventing, and/or ameliorating a disease or condition in a patient.

The compounds according to one or more embodiments disclosed in this specification may be modulators of PP2A. The compounds described herein may exhibit anti-proliferative effects and may be useful as monotherapy in cancer treatment and/or in the treatment of other indications described in this specification. Additionally, they can be used in combination with other drugs to restore sensitivity to chemotherapy, targeted therapies, or immunotherapy where resistance has developed.

In certain embodiments, the disease or condition is ameliorated by modulation of PP2A. In certain embodiments, the disease or condition is at least one selected from the group consisting of cancer, diabetes, autoimmune disease, solid organ transplant rejection, graft vs host disease, chronic obstructive pulmonary disease (COPD), non-alcoholic fatty liver disease, abdominal aortic aneurysm, chronic liver disease, heart failure, neurodegenerative disease, and cardiac hypertrophy. In an embodiment, the disease is cancer.

In certain embodiments, a patient in need of treatment of a disease is administered a therapeutically effective amount of the compound according to one or more embodiments disclosed in this specification, for example a compound of Formula (I) or (II), a solvate, enantiomer, diastereomer, isotopologue, tautomer, or a pharmaceutically acceptable salt thereof.

In certain embodiments, a method of treating cancer in a patient having a tumor that expresses PP2A comprises administering to the patient a therapeutically effective amount of a compound of Formula (I) or (II), a solvate, enantiomer, diastereomer, isotopologue, tautomer, or a pharmaceutically acceptable salt thereof.

In certain embodiments, a method is provided for treating a malignant solid tumor in a patient in need thereof, comprising administering an effective amount of a compound or pharmaceutical composition provided herein to the patient. In certain embodiments, the malignant solid tumor is a carcinoma. In certain embodiments, the malignant tumor is a lymphoma. In certain embodiments, the malignant solid tumor is a sarcoma.

In certain embodiments, the cancer is of the bladder, blood, bone, bone marrow, brain, breast, colon, esophagus, gastrointestine, gum, head, kidney, liver, lung, nasopharynx, neck, ovary, prostate, skin, stomach, testis, tongue, and/or uterus. In addition, the cancer may specifically be at least one of the following histological types, though it is not limited to these: neoplasm, malignant; carcinoma; carcinoma, undifferentiated; giant or spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; non-encapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malig melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; Brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; Kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant-cell tumor of bone; Ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; Hodgkin's; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast-cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast-cell leukemia; megakaryoblastic leukemia; myeloid sarcoma; and hairy cell leukemia.

In certain embodiments, the autoimmune disease is at least one of colitis, multiple sclerosis, arthritis, rheumatoid arthritis, osteoarthritis, juvenile arthritis, psoriatic arthritis, acute pancreatitis, chronic pancreatitis, diabetes, insulin-dependent diabetes mellitus (IDDM or type I diabetes), insulitis, inflammatory bowel disease, Crohn's disease, ulcerative colitis, autoimmune hemolytic syndromes, autoimmune hepatitis, autoimmune neuropathy, autoimmune ovarian failure, autoimmune orchitis, autoimmune thrombocytopenia, reactive arthritis, ankylosing spondylitis, silicone implant associated autoimmune disease, Sjogren's syndrome, systemic lupus erythematosus (SLE), vasculitis syndromes (e.g., giant-cell arteritis, Behcet's disease & Wegener's granulomatosis), vitiligo, secondary hematologic manifestation of autoimmune diseases (e.g., anemias), drug-induced autoimmunity, Hashimoto's thyroiditis, hypophysitis, idiopathic thrombocytic pupura, metal-induced autoimmunity, myasthenia gravis, pemphigus, autoimmune deafness (e.g., Meniere's disease), Goodpasture's syndrome, Graves' disease, HIV-related autoimmune syndromes and Gullain-Barre disease.

In certain embodiments, the neurodegenerative disease is Alzheimer's disease. In certain embodiments, the neurodegenerative disease is Parkinson's disease.

PP2A enzymes may be involved in the regulation of cell transcription, cell cycle, and viral transformation. Many viruses, including cytomegalovirus, parainfluenza, DNA tumor viruses, and HIV-1, utilize different approaches to exploit PP2A in order to modify, control, or inactivate cellular activities of the host. Therefore, the compounds according to one or more embodiments disclosed in this specification may further be used in a method for treating a viral infection in a patient by administering to the patient a therapeutically effective amount of a compound according to one or more embodiments disclosed in this specification. Examples of viruses that may cause viral infections to be treated include, but are not limited to: a polyomavirus, such as John Cunningham Virus (JCV), Simian virus 40 (SV40), or BK Virus (BKV); influenza, Human Immunodeficiency Virus type 1 (HIV-1), Human Papilloma Virus (HPV), adenovirus, Epstein-Barr Virus (EBV), Hepatitis C Virus (HCV), Molluscum contagiosum virus (MCV); Human T-lymphotropic virus type 1 HTLV-1), Herpes Simplex Virus type 1 (HSV-1), cytomegalovirus (CMV), hepatitis B virus, Bovine papillomavirus (BPV-1), human T-cell lymphotropic virus type 1, Japanese encephalitis virus, respiratory syncytial virus (RSV), and West Nile virus.

The compounds or pharmaceutical compositions according to one or more embodiments disclosed in this specification may further be used in a method for treating a betacoronavirus infection in a patient by administering to the patient a therapeutically effective amount of a compound or pharmaceutical composition according to one or more embodiments disclosed in this specification.

The compounds according to one or more embodiments disclosed in this specification may further be used in the preventing of a betacoronavirus infection in a patient by administering to the patient a prophylactically effective amount of a compound or pharmaceutical composition according to one or more embodiments disclosed in this specification.

The compounds according to one or more embodiments disclosed in this specification may be used for the manufacture of a medicament for the treatment or prophylaxis of a betacoronavirus infection.

In certain embodiments betacoronavirus is selected from the group consisting of Severe Acute Respiratory Syndrome coronavirus SARS-CoV, Middle East Respiratory Syndrome MERS-CoV, and severe acute respiratory syndrome coronavirus 2 (SARS-CoV-2; originally known as nCoV-2019).

In certain embodiments the betacoronavirus is SARS-CoV.

In certain embodiments the betacoronavirus is SARS-CoV-2.

Serine/Threonine phosphatases, including PP2A may be involved in modulation of synaptic plasticity. Decreased PP2A activity is associated with maintenance of Long Term Potentiation (LTP) of synapses, thus treatment PP2A modulators such as those described here may reverse synaptic LTP. Psychostimulant drugs of abuse such as cocaine and methamphetamine are associated with deleterious synaptic LTP, which may underlie the pathology of addiction and relapse therefore PP2A modulators described here may be useful as treatments for psychostimulant abuse.

Pharmaceutical Compositions, Formulations, and Routes of Administration

The present disclosure relates also to a pharmaceutical composition comprising a compound according to one or more embodiments described in this specification, for example a compound of Formula I, an enantiomer, a diastereomer, a tautomer or a pharmaceutically acceptable salt thereof, and pharmaceutically acceptable carrier.

In certain embodiments, the pharmaceutical composition comprises a compound of Formula (I), (II), or a pharmaceutically acceptable salt thereof, together with one or more pharmaceutically carriers thereof and optionally one or more other therapeutic ingredients. The carrier(s) may be "acceptable" in the sense of being compatible with the other ingredients of the formulation and not deleterious to the recipient thereof.

The pharmaceutical compositions may be manufactured in any manner known in the art, e.g., by means of conventional mixing, dissolving, granulating, dragee-making, levigating, emulsifying, encapsulating, entrapping or compression processes. "pharmaceutically acceptable carrier" may refer to an excipient, carrier or adjuvant that can be administered to a patient, together with at least one therapeutic compound, and which does not destroy the pharmacological activity thereof and is generally safe, nontoxic and neither biologically nor otherwise undesirable when administered in doses sufficient to deliver a therapeutic amount of the compound.

The pharmaceutical formulations may include those suitable for oral, parenteral (including subcutaneous, intradermal, intramuscular, intravenous, intraarticular, and intramedullary), intraperitoneal, transmucosal, transdermal, intranasal, rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. Typically, these methods include the step of bringing into association a compound of Formula (I), (II), or a pharmaceutically acceptable salt, ester, amide, solvate, or enantiomer or diastereomer or tautomer thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the compounds of the present disclosure suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

The compounds of the present disclosure may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

In addition to the formulations described previously, a compound of the present disclosure may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

The compounds may also be formulated in rectal compositions such as suppositories or retention enemas, e.g., containing conventional suppository bases such as cocoa butter, polyethylene glycol, or other glycerides.

In an embodiment, compounds as disclosed herein may be administered topically, that is by non-systemic administration. This includes the application of a compound disclosed herein externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient for topical administration may comprise, for example, from 0.001% to 10% w/w (by weight) of the formulation. In certain embodiments, the active ingredient may comprise as much as 10% w/w. In other embodiments, it may comprise less than 5% w/w. In certain embodiments, the active ingredient may comprise from 2% w/w to 5% w/w. In other embodiments, it may comprise from 0.10% to 1T % w/w of the formulation.

For administration by inhalation, compounds of the present disclosure may be conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds disclosed herein may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

Intranasal delivery, in particular, may be useful for delivering compounds to the CNS. It had been shown that intranasal drug administration is a noninvasive method of bypassing the blood-brain barrier (BBB) to deliver neurotrophins and other therapeutic agents to the brain and spinal cord. Delivery from the nose to the CNS occurs within minutes along both the olfactory and trigeminal neural pathways. Intranasal delivery occurs by an extracellular route and does not require that drugs bind to any receptor or undergo axonal transport. Intranasal delivery also targets the nasal associated lymphatic tissues (NALT) and deep cervical lymph nodes. In addition, intranasally administered therapeutics are observed at high levels in the blood vessel walls and perivascular spaces of the cerebrovasculature. Using this intranasal method in animal models, researchers have successfully reduced stroke damage, reversed Alzheimer's neurodegeneration, reduced anxiety, improved memory, stimulated cerebral neurogenesis, and treated brain tumors.

In an embodiment, unit dosage formulations are those containing an effective dose or an appropriate fraction thereof, of the active ingredient.

It should be understood that in addition to the ingredients particularly mentioned above, the formulations described above may include other agents conventional in the art having regard to the type of formulation in question, for example those suitable for oral administration may include flavoring agents.

Combination Therapies

In certain instances, it may be appropriate to administer at least one of the compounds of Formula (I) or (II) (an enantiomer, a diastereomer, a tautomer or a pharmaceutically acceptable salt thereof) in combination with another therapeutic agent. By way of example only, if one of the side effects experienced by a patient upon receiving one of the compounds herein for the treatment of cancer is nausea, then it may be appropriate to administer an antiemetic agent in combination. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced). Or, by way of example only, the benefit of experienced by a patient may be increased by administering one of the compounds described herein with another therapeutic agent (which also includes a therapeutic regimen) that also has therapeutic benefit. By way of example only, in a treatment for cancer involving administration of one of the compounds described herein, increased therapeutic benefit may result by also providing the patient with another therapeutic agent for cancer. In any case, regardless of the disease, disorder or condition being treated, the overall benefit experienced by the patient may simply be additive of the two therapeutic agents or the patient may experience a synergistic benefit.

The instant compounds may be particularly useful in combination with therapeutic and/or anti-cancer agents. Thus, the present disclosure provides a combination of compounds of Formula (I) or (II) are used in a combination with therapeutic and/or anti-cancer agents for simultaneous, separate or sequential administration. The compounds of the present disclosure and the other anticancer agent can act additively or synergistically. A synergistic combination of the present compounds and another anticancer agent might allow the use of lower dosages of one or both of these agents and/or less frequent dosages of one or both of the instant compounds and other anticancer agents and/or to administer the agents less frequently can reduce any toxicity associated with the administration of the agents to a patient without reducing the efficacy of the agents in the treatment of cancer. In addition, a synergistic effect might result in the improved efficacy of these agents in the treatment of cancer and/or the reduction of any adverse or unwanted side effects associated with the use of either agent alone.

The therapeutic agent and/or anti-cancer agent can be administered according to therapeutic protocols well known in the art. It will be apparent to those skilled in the art that the administration of the therapeutic agent and/or anti-cancer agent can be varied depending on the disease being treated and the known effects of the anti-cancer agent on that disease. Also, in accordance with the knowledge of the skilled clinician, the therapeutic protocols (e.g., dosage amounts and times of administration) can be varied in view of the observed effects of the administered therapeutic agents (i.e., anti-neoplastic agent or radiation) on the patient, and in view of the observed responses of the disease to the administered therapeutic agents, and observed adverse effects.

In certain embodiments, the compounds according to one or more embodiments disclosed in this specification, for example compounds of Formula I, may be administered in combination with one or more agent selected from aromatase inhibitors, anti-estrogens, anti-progesterons, anti-androgens, or gonadorelin agonists, anti-inflammatory agents, antihistamines, anti-cancer agent, inhibitors of angiogenesis, topoisomerase 1 and 2 inhibitors, microtubule active agents, alkylating agents, antineoplastic, antimetabolite, dacarbazine (DTIC), platinum containing compound, lipid or protein kinase targeting agents, protein or lipid phosphatase targeting agents, anti-angiogenic agents, agents that induce cell differentiation, bradykinin 1 receptor and angiotensin II antagonists, cyclooxygenase inhibitors, heparanase inhibitors, lymphokines or cytokine inhibitors, bisphosphanates, rapamycin derivatives, anti-apoptotic pathway inhibitors, apoptotic pathway agonists, PPAR agonists, HSP90 inhibitor, smoothened antagonist, inhibitors of Ras isoforms, telomerase inhibitors, protease inhibitors, metalloproteinase inhibitors, aminopeptidase inhibitors, imununomodulators, therapeutic antibody and a protein kinase inhibitor, e.g., a tyrosine kinase or serine/threonine kinase inhibitor.

In certain embodiments, the combination of a compound of Formula I and an anti-cancer agent is provided for simultaneous, separate or sequential administration.

A person of ordinary skill in the art would be able to discern which combinations of agents would be useful based on the particular characteristics of the drugs and the cancer involved. Classes of such agents include the following: estrogen receptor modulators, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, HIV protease inhibitors, reverse transcriptase inhibitors, inhibitors of cell proliferation and survival signaling, bisphosphonates, aromatase inhibitors, siRNA therapeutics, γ-secretase inhibitors, agents that interfere with receptor tyrosine kinases (RTKs), agents that interfere with cell cycle checkpoints, PARP inhibitors, HDAC inhibitors, Smo antagonists (HH inhibitors), HSP90 inhibitors, CYP17 inhibitors, 3rd generation AR antagonists, JAK inhibitors e.g. Ruxolitinib (trade name Jakafi), and BTK kinase inhibitors.

Anticancer agents suitable for use in the combination therapy with compounds as disclosed herein include, but are not limited to:

1) alkaloids and natural product drugs, including, microtubule inhibitors (e.g., Vincristine, Vinblastine, and Vindesine, and vinorelbine etc.), microtubule stabilizers (e.g., Paclitaxel [Taxol], and Docetaxel, Taxotere, etc.), and chromatin function inhibitors, including, topoisomerase inhibitors, such as, epipodophyllotoxins (e.g., Etoposide [VP-161, and Teniposide [VM-261, etc.), and agents that target topoisomerase I (e.g., Camptothecin, topotecan (Hycamtin) and Irinotecan [CPT-11], rubitecan (Orathecin) etc.);
2) covalent DNA-binding agents [alkylating agents], including, nitrogen mustards (e.g., Mechloretharnine, chlormethine, Chlorambucil, Cyclophosphamide, estramustine (Emcyt, Estracit), ifosfamide, Ifosphamide, melphalan (Alkeran) etc.); alkyl sulfonates like Busulfan [Myleran], nitrosoureas (e.g., Carmustine or BCNU (bis-chloroethylnitrosourea), fotemustine Lomustine, and Semustine, streptozocin etc.), and other alkylating agents (e.g., Dacarbazine, procarbazine ethylenimine/methylmelamine, thriethylenemelamine (TEM), triethylene thiophosphoramide (thiotepa), hexamethylmelamine (HMM, altretamine), and Mitocycin, uramustine etc.) including Temozolomide (brand names Temodar and Temodal and Temcad), altretamine (also hexalen) and mitomycin; and
3) noncovalent DNA-binding agents [antitumor antibiotics], including nucleic acid inhibitors (e.g., Dactinomycin [Actinomycin Dl, etc.), anthracyclines (e.g., Daunorubicin [Daunomycin, and Cerubidine], Doxorubicin [Adrianycin], epirubicin (Ellence), and Idarubicin [Idamycin], valrubicin (Valstar) etc.), anthracenediones (e.g., anthracycline analogues, such as, [Mitoxantrone], etc.), bleomycins (Blenoxane), etc., amsacrine and plicamycin (Mithramycin), dactinomycin, mitomycin C.

In certain embodiments, a patient with cancer is treated with a combination of a compound of Formula (I) or (II) and radiation therapy. In certain embodiments, the method comprises administering to a patient with cancer a therapeutically effective amount of a compound of the disclosure, and adjunctively treating the patient with an effective amount of radiation therapy. In certain embodiments, the compound is administered to the patient in need thereof prior to, concurrently with, or subsequent to the treatment with radiation.

In an embodiment, the compounds or the pharmaceutical composition may further comprise or be administered in combination with one or more other antiviral agents including, but not limited to, oseltamivir phosphate, zanamivir or Virazole®, Remdesivir, Vidarabine, Acyclovir, Ganciclovir, Valganciclovir, Valacyclovir, Cidofovir, Famciclovir, Ribavirin, Amantadine, Rimantadine, Interferon, Oseltamivir, Palivizumab, Rimantadine, Zanamivir, nucleoside-analog reverse transcriptase inhibitors (NRTI) such as Zidovudine, Didanosine, Zalcitabine, Stavudine, Lamivudine and Abacavir, non-nucleoside reverse transcriptase inhibitors (NNRTI) such as Nevirapine, Delavirdine and Efavirenz, protease inhibitors such as Saquinavir, Ritonavir, Indinavir, Nelfinavir, Amprenavir, and other known antiviral compounds and preparations.

In an embodiment, the compounds or the pharmaceutical compositions may be co-administered with one or more antiviral agents. The compounds or the pharmaceutical compositions of the present invention may be administered in any order.

Controlled Release Formulations and Drug Delivery Systems

In certain embodiments, the compositions and/or formulations of the present invention may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release which is longer that the same amount of agent administered in bolus form.

For sustained release, the compounds may be formulated with a suitable polymer or hydrophobic material which provides sustained release properties to the compounds. As such, the compounds for use the method of the invention may be administered in the form of microparticles, for example, by injection or in the form of wafers or discs by implantation.

In certain embodiments of the invention, the compounds useful within the invention are administered to a subject, alone or in combination with another pharmaceutical agent, using a sustained release formulation.

The term delayed release is used herein in its conventional sense to refer to a drug formulation that provides for an initial release of the drug after some delay following drug administration and that may, although not necessarily, include a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

Administration/Dosing

The compound may be administered to an animal as frequently as several times daily, or it may be administered less frequently, such as once a day, once a week, once every two weeks, once a month, or even less frequently, such as once every several months or even once a year or less. It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on. The frequency of the dose is readily apparent to the skilled artisan and depends upon a number of factors, such as, but not limited to, type and severity of the disease being treated, and type and age of the animal.

In certain embodiments, the compositions of the invention are administered to the patient in dosages that range from one to five times per day or more. In other embodiments, the compositions of the invention are administered to the patient in range of dosages that include, but are not limited to, once every day, every two days, every three days to once a week, and once every two weeks. It will be readily apparent to one skilled in the art that the frequency of administration of the various combination compositions of the invention will vary from subject to subject depending on many factors including, but not limited to, age, disease or disorder to be treated, gender, overall health, and other factors. Thus, the invention should not be construed to be limited to any particular dosage regime and the precise dosage and composition to be administered to any patient will be determined by the attending physician taking all other factors about the patient into account.

Compounds according to one or more embodiments disclosed in this specification may be administered orally or via injection at a dose of from 0.1 to 500 mg/kg per day. The dose range for adult humans is generally from 5 mg to 2 g/day. Tablets or other forms of presentation provided in discrete units may conveniently contain an amount of one or more compound which is effective at such dosage or as a multiple of the same, for instance, units containing 5 mg to 500 mg, usually around 10 mg to 200 mg.

Compounds of the invention for administration may be in the range of from about 1 μg to about 7,500 mg, about 20 μg to about 7,000 mg, about 40 μg to about 6,500 mg, about 80 μg to about 6,000 mg, about 100 μg to about 5,500 mg, about 200 μg to about 5,000 mg, about 400 μg to about 4,000 mg, about 800 μg to about 3,000 mg, about 1 mg to about 2,500 mg, about 2 mg to about 2,000 mg, about 5 mg to about 1,000 mg, about 10 mg to about 750 mg, about 20 mg to about 600 mg, about 30 mg to about 500 mg, about 40 mg to about 400 mg, about 50 mg to about 300 mg, about 60 mg to about 250 mg, about 70 mg to about 200 mg, about 80 mg to about 150 mg, and any and all whole or partial increments there-in-between.

In some embodiments, the dose of a compound of the invention is from about 0.5 μg and about 5,000 mg. In some embodiments, a dose of a compound of the invention used in compositions described herein is less than about 5,000 mg, or less than about 4,000 mg, or less than about 3,000 mg, or less than about 2,000 mg, or less than about 1,000 mg, or less than about 800 mg, or less than about 600 mg, or less than about 500 mg, or less than about 200 mg, or less than about 50 mg. Similarly, in some embodiments, a dose of a second compound as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

The amount of active ingredient that may be combined with the carrier materials to produce a single dosage form will vary depending upon the host treated and the particular mode of administration.

Compounds of the present disclosure can be administered in various modes, e.g. orally, topically, or by injection. The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the indication or condition being treated. Also, the route of administration may vary depending on the condition and its severity.

LCMS Conditions

Method A: HPLC Alliance 2695 system employing Gemini NX—C18 Phenomenex (30×2 mm), 3 μm column, with eluents comprising eluent A=$H_2O$+0.05% TFA (v/v); and eluent B=$CH_3CN$+0.035% TFA. Oven temperature: 55° C.; Gradient: $t_{0\ min}$=2% B; $t_{2.5}$ min=98% B; $t_{3.5\ min}$=98% B; $t_{3.6\ min}$=2% B; $t_{5\ min}$=5% B (v/v). Flow rate: 0.9 mL/min. Positive electrospray ES+; Capillary: 3.5 kV; Cone voltage: 15 V.

Method B: Waters Acquity UPLC system employing Waters Acquity UPLC CSH C18 (50×2.1 mm), 1.7 μm column, with eluents comprising: eluent A=$H_2O$+0.02% HCOOH (v/v); and eluent B=$CH_3CN$+0.02% HCOOH (v/v). Oven temperature: 55° C.; Gradient: $t_{0\ min}$=0.2% B; $t_{4\ min}$=98% B; $t_{4.5\ min}$=98% B; $t_{4.6\ min}$=2% B; $t_{5\ min}$=2% B. Flow rate: 1 mL/min. Negative electrospray ES−; Capillary: 3 kV; Cone voltage: 15 V.

Method C: Waters Acquity UPLC system employing Waters Acquity UPLC CSH C18 (2.1×50 mm), 1.7 μm column, with eluents comprising: eluent A=$H_2O$+0.02% HCOOH; and eluent B=$CH_3CN$+0.02% HCOOH. Oven Temperature: 55° C.; Gradient: $t_{0\ min}$=2% B; $t_{4\ min}$=98% B; $t_{4.5\ min}$=98% B; $t_{4.6\ min}$=2% B; and $t_{5.0\ min}$=2% B (v/v). Flow rate: 1 mL/min. Electrospray Ionization Mode; Capillary: 3 kV; Sample cone: 15/30V.

Method D: Waters Acquity UPLC system employing Waters Acquity UPLC CSH C18 (2.1×50 mm), 1.7 μm column, A=$H_2O$+0.05% TFA (v/v); and eluent B=$CH_3CN$+ 0.035% TFA. Oven temperature: 55° C.; Gradient: $t_{0\ min}$=2% B; $t_{1\ min}$=98% B; $t_{1.5\ min}$=98% B; $t_{1.52\ min}$=2% B; $t_{1.7\ min}$=2% B (v/v). Flow rate: 0.8 mL/min. Positive electrospray ES+; Capillary: 0.8 kV; Cone voltage: 15 V.

Method E: Waters Acquity UPLC system employing Waters Acquity UPLC CSH C18 (2.1×50 mm), 1.7 μm column, A=$H_2O$+0.05% TFA (v/v); and eluent B=$CH_3CN$+0.035% TFA. Oven temperature: 55° C.; Gradient: $t_{0\ min}$=2% B; $t_{1\ min}$=98% B; $t_{1.5\ min}$=98% B; $t_{1.52\ min}$=2% B; $t_{1.7\ min}$=2% B (v/v). Flow rate: 0.8 mL/min. Positive electrospray ES+; Capillary: 0.8 kV; Cone voltage: 10 V.

Method F: Waters Acquity UPLC system employing Waters Acquity UPLC CSH C18 (2.1×100 mm), 1.7 μm column, A=$H_2O$+0.02% HCOOH (v/v); and B=$CH_3CN$+0.02% HCOOH. Oven temperature: 55° C.; Gradient: $t_{0\ min}$=2% B, $t_{15\ min}$=98% B, $t_{15.2\ min}$=2% B, $t_{18\ min}$=2% B (v/v). Flow rate: 0.7 mL/min. Electrospray ionization mode; Capillary: 3 kV; Sample Cone: 15/30 V.

Method G: Waters Acquity UPLC system employing Waters Acquity UPLC CSH C18 (2.1×50 mm), 1.7 μm column, A=$H_2O$+0.05% TFA (v/v); and eluent B=$CH_3CN$+0.035% TFA. Oven temperature: 55° C.; Gradient: $t_{0\ min}$=2% B; $t_{2.4\ min}$=98% B; $t_{3.0\ min}$=98% B; $t_{3.03\ min}$=2% B; $t_{3.5\ min}$=2% B (v/v). Flow rate: 0.8 mL/min. Positive electrospray ES+; Capillary: 0.8 kV; Cone voltage: 15 V.

Method H: Waters Acquity UPLC system employing Waters Acquity UPLC CSH C18 (50×2.1 mm), 1.7 μm column, with eluents comprising: eluent A=$H_2O$+0.02% HCOOH (v/v); and eluent B=$CH_3CN$+0.02% HCOOH (v/v). Oven temperature: 55° C.; Gradient: $t_{0\ min}$=0.2% B; $t_{4\ min}$=98% B; $t_{45\ min}$=98% B; $t_{46\ min}$=2% B; $t_{5\ min}$=2% B. Flow rate: 1 mL/min. Negative electrospray ES−; Capillary: 3 kV; Sample Cone: 15/30 V.

EXAMPLES

Various embodiments of the present application can be better understood by reference to the following Examples which are offered by way of illustration. The scope of the present application is not limited to the Examples given herein.

Example 1: Synthesis of Compounds 1-34

Procedure for Sulfonamide Synthesis—Sulfonyl Chloride and Amine Couplings

Each vial was charged with amine reagent (0.4221 mmol, 1.1 eq) and $Et_3N$ (1.5348 mmol, 4 eq, 214 μL). A solution of 4-(trifluoromethoxy)benzenesulfonyl chloride in DCM (0.384 mmol, 1.0 eq, 2 mL, 0.192 mmol/mL) was distributed in each vial. The reaction mixture was stirred at 25° C. overnight. The reaction mixture was filtered on a 3 mL ChemElut cartridge (pre-treated with HCl 1M (3 mL)) and eluted with 2 ml of DCM. The obtained fraction was concentrated under nitrogen flow at rt for 2 h, then dried under vacuum at 40° C. overnight. Purification was performed, when necessary, by SCX, PE-AX, or flash chromatography.

In certain embodiments, SCX: ISOLUTE—SCX (1 g, 6 mL) cartridges were used. The cartridges were eluted with 10 mL of DCM, then a solution of crude diluted in 1 mL was filtered by gravity. The cartridge was eluted twice with 4 mL of DCM and once with 2 mL of 2N $NH_3$ in MeOH. The desired fractions were concentrated under nitrogen flow at rt for 2 h, then dried under vacuum at 40° C. overnight.

In certain embodiments, PE-AX: ISOLUTE—PE-AX (1 g, 6 mL) cartridges were used. The cartridges were eluted with 10 mL DCM, then a solution of crude diluted in 1 mL was filtered by gravity. The cartridge was eluted twice with 4 mL of 1.25 N HCl in MeOH and once with 2 mL of 1.25 N HCl in MeOH. The desired fractions were concentrated under nitrogen flow at rt for 2 h, then dried under vacuum at 40° C. overnight.

In certain embodiments, flash chromatography was used, wherein the crude product was purified by flash chromatography on silica gel using a gradient of MeOH in DCM from 2% to 10%. The desired fractions were concentrated under nitrogen flow at rt for 2 h and then dried under vacuum at 40° C. overnight.

Unless otherwise indicated, LCMS analysis was performed using Method A.

The following compounds were prepared following the procedure and conditions provided herein:

N-(4-((4-((4-(trifluoromethoxy)phenyl)sulfonamido)piperidin-1-yl)sulfonyl)phenyl)acetamide (1)

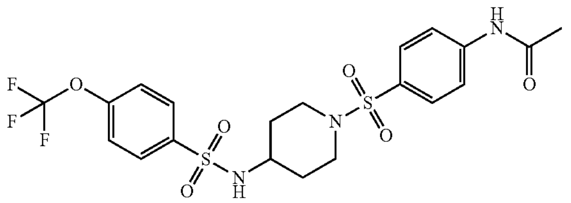 [SMILES: CC(=O)Nc1ccc(S(=O)(=O)N2CCC(NS(=O)(=O)c3ccc(OC(F)(F)F)cc3)CC2)cc1]

TABLE 1

| Analytical data for compound 1 | | | | | |
|---|---|---|---|---|---|
| Amount (mg) | Yield (%) | Purity (%) | MS (m/z) | Ion observed | $r_t$ (min) |
| 144.3 | 67.4 | 93.45 | 521.9 | [M + H]$^+$ | 2.3 |

Starting material (amine): N-(4-((4-aminopiperidin-1-yl)sulfonyl)phenyl)acetamide.

N-(1-(5-chloro-2-methoxyphenyl)pyrrolidin-3-yl)-4-(trifluoromethoxy)benzenesulfonamide (2)

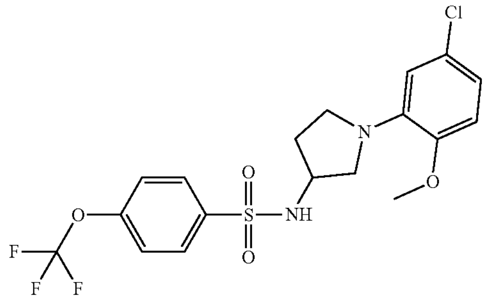 [SMILES: COc1ccc(Cl)cc1N1CCC(NS(=O)(=O)c2ccc(OC(F)(F)F)cc2)C1]

TABLE 2

| Analytical data for compound 2 | | | | | |
|---|---|---|---|---|---|
| Amount (mg) | Yield (%) | Purity (%) | MS (m/z) | Ion observed | $r_t$ (min) |
| 163.3 | 88.3 | 93.57 | 450.8 | [M + H]$^+$ | 2.72 |

Starting material (amine): 1-(5-chloro-2-methoxyphenyl) pyrrolidin-3-amine.

N-(1-(3-bromophenyl)pyrrolidin-3-yl)-4-(trifluoromethoxy)benzenesulfonamide (3)

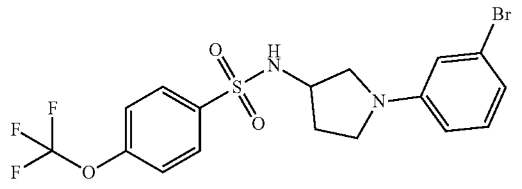 [SMILES: O=S(=O)(NC1CCN(c2cccc(Br)c2)C1)c1ccc(OC(F)(F)F)cc1]

TABLE 3

| Analytical data for compound 3 | | | | | |
|---|---|---|---|---|---|
| Amount (mg) | Yield (%) | Purity (%) | MS (m/z) | Ion observed | $r_t$ (min) |
| 170.2 | 95.3 | 100 | 466.8 | $[M+H]^+$ | 2.82 |

cis methyl 1-((4-(trifluoromethoxy)phenyl)sulfonamido)-2,3-dihydro-1H-indene-2-carboxylate (4)

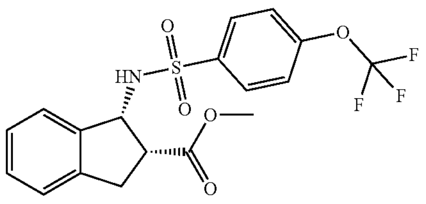 [SMILES: COC(=O)[C@@H]1Cc2ccccc2[C@@H]1NS(=O)(=O)c1ccc(OC(F)(F)F)cc1]

TABLE 4

| Analytical data for compound 4 | | | | | |
|---|---|---|---|---|---|
| Amount (mg) | Yield (%) | Purity (%) | MS (m/z) | Ion observed | $r_t$ (min) |
| 128.6 | 79 | 97.88 | 415.9 | $[M+H]^+$ | 2.55 |

Starting material (amine): cis methyl 1-amino-2,3-dihydro-1H-indene-2-carboxylate hydrochloride.

N-(1-(3,4-dichlorophenyl)piperidin-3-yl)-4-(trifluoromethoxy)benzenesulfonamide (5)

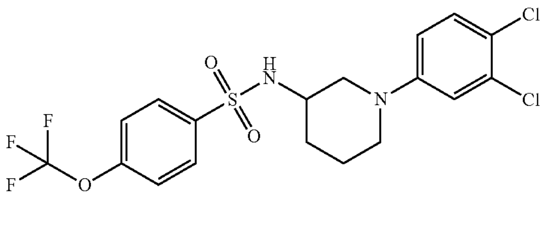 [SMILES: O=S(=O)(NC1CCCN(c2ccc(Cl)c(Cl)c2)C1)c1ccc(OC(F)(F)F)cc1]

TABLE 5

| Analytical data for compound 5 | | | | | |
|---|---|---|---|---|---|
| Amount (mg) | Yield (%) | Purity (%) | MS (m/z) | Ion observed | $r_t$ (min) |
| 153.9 | 84.5 | 98.83 | 468.8 | $[M+H]^+$ | 2.89 |

Starting material (amine): 1-(3,4-dichlorophenyl)piperidin-3-amine.

4-(trifluoromethoxy)-N-(1-(3-(trifluoromethoxy)phenyl)pyrrolidin-3-yl)benzenesulfonamide (6)

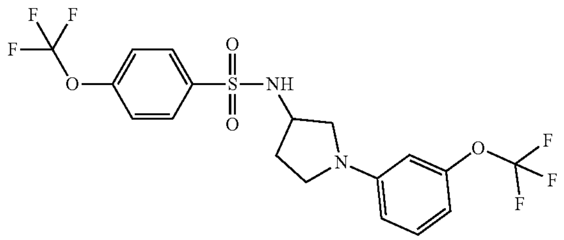 [SMILES: O=S(=O)(NC1CCN(c2cccc(OC(F)(F)F)c2)C1)c1ccc(OC(F)(F)F)cc1]

TABLE 6

| Analytical data for compound 6 | | | | | |
|---|---|---|---|---|---|
| Amount (mg) | Yield (%) | Purity (%) | MS (m/z) | Ion observed | $r_t$ (min) |
| 144 | 76.8 | 96.3 | 470.8 | $[M+H]^+$ | 2.85 |

Starting material (amine): 1-(3-(trifluoromethoxy)phenyl) pyrrolidin-3-amine.

N-(2-(4-fluorophenoxy)cyclohexyl)-4-(trifluoromethoxy)benzenesulfonamide (7)

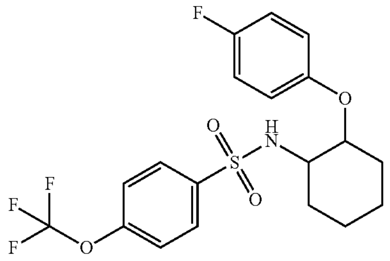 [SMILES: O=S(=O)(NC1CCCCC1Oc1ccc(F)cc1)c1ccc(OC(F)(F)F)cc1]

TABLE 7

| Analytical data for compound 7 | | | | | |
|---|---|---|---|---|---|
| Amount (mg) | Yield (%) | Purity (%) | MS (m/z) | Ion observed | $r_t$ (min) |
| 108 | 64.2 | 98.93 | 433.9 | $[M+H]^+$ | 2.83 |

Starting material (amine): 2-(4-fluorophenoxy)cyclohexan-1-amine.

4-(trifluoromethoxy)-N-(3,4,4-trimethylcyclohexyl) benzenesulfonamide (8)

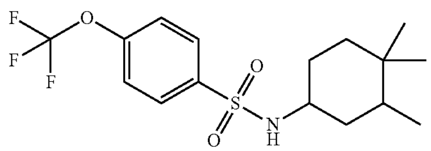 [SMILES: CC1CC(NS(=O)(=O)c2ccc(OC(F)(F)F)cc2)CCC1(C)C]

TABLE 8

| Analytical data for compound 8 | | | | | |
|---|---|---|---|---|---|
| Amount (mg) | Yield (%) | Purity (%) | MS (m/z) | Ion observed | $r_t$ (min) |
| 98.5 | 70.3 | 100 | 366 | $[M + H]^+$ | 2.84 |

Starting material (amine): 3,4,4-trimethylcyclohexan-1-amine.

trans N-(2-(4-chlorophenyl)-1-methylpyrrolidin-3-yl)-4-(trifluoromethoxy)benzenesulfonamide (9)

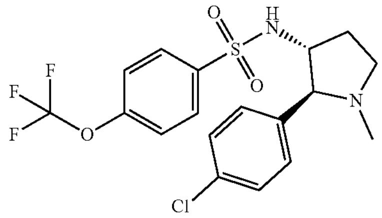 [SMILES: CN1CC[C@@H](NS(=O)(=O)c2ccc(OC(F)(F)F)cc2)[C@@H]1c1ccc(Cl)cc1]

TABLE 9

| Analytical data for compound 9 | | | | | |
|---|---|---|---|---|---|
| Amount (mg) | Yield (%) | Purity (%) | MS (m/z) | Ion observed | $r_t$ (min) |
| 112.2 | 65.4 | 97.21 | 434.8 | $[M + H]^+$ | 1.91 |

Starting material (amine): trans 2-(4-chlorophenyl)-1-methylpyrrolidin-3-amine.

N-(5,8-difluorochroman-4-yl)-4-(trifluoromethoxy) benzenesulfonamide (10)

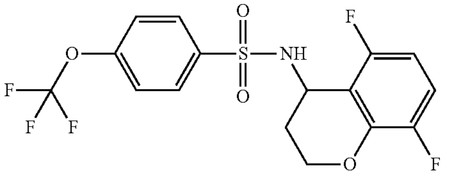 [SMILES: O=S(=O)(NC1CCOc2c(F)ccc(F)c21)c1ccc(OC(F)(F)F)cc1]

TABLE 10

| Analytical data for compound 10 | | | | | |
|---|---|---|---|---|---|
| Amount (mg) | Yield (%) | Purity (%) | MS (m/z) | Ion observed[a] | $r_t$ (min) |
| 127 | 79.9 | 98.81 | 407.9 | $[M - H]^-$ | 2.45 |

[a]LCMS Method B; Starting material (amine): 5,8-difluorochroman-4-amine.

N-(4,6-dichloro-2,3-dihydro-1H-inden-1-yl)-4-(trifluoromethoxy)benzenesulfonamide (11)

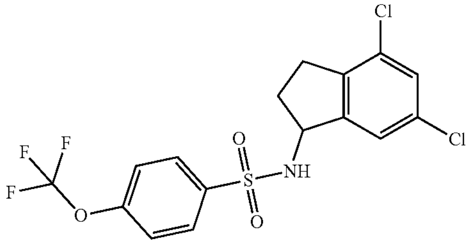 [SMILES: O=S(=O)(NC1CCc2c(Cl)cc(Cl)cc21)c1ccc(OC(F)(F)F)cc1]

TABLE 11

| Analytical data for compound 11 | | | | | |
|---|---|---|---|---|---|
| Amount (mg) | Yield (%) | Purity (%) | MS (m/z) | Ion observed[a] | $r_t$ (min) |
| 142 | 86.8 | 100 | 425.9 | $[M - H]^-$ | 2.92 |

[a]LCMS Method B; Starting material (amine): 4,6-dichloro-2,3-dihydro-1H-inden-1-amine.

N-(6-chloro-1,2,3,4-tetrahydronaphthalen-1-yl)-4-(trifluoromethoxy)benzenesulfonamide (12)

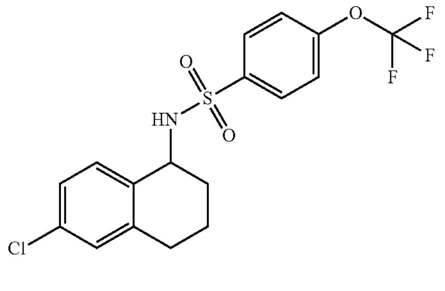 [SMILES: O=S(=O)(NC1CCCc2cc(Cl)ccc21)c1ccc(OC(F)(F)F)cc1]

TABLE 12

| Analytical data for compound 12 | | | | | |
|---|---|---|---|---|---|
| Amount (mg) | Yield (%) | Purity (%) | MS (m/z) | Ion observed[a] | $r_t$ (min) |
| 129 | 79.4 | 95.82 | 404 | $[M - H]^-$ | 2.84 |

[a]LCMS Method B; Starting material (amine): 6-chloro-1,2,3,4-tetrahydronaphthalen-1-amine.

N-(2-phenylcycloheptyl)-4-(trifluoromethoxy)benzenesulfonamide (13)

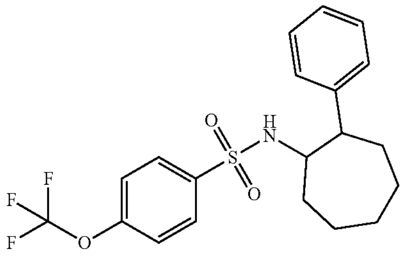 [SMILES: O=S(=O)(NC1CCCCCC1c1ccccc1)c1ccc(OC(F)(F)F)cc1]

TABLE 13

| Analytical data for compound 13 | | | | | |
|---|---|---|---|---|---|
| Amount (mg) | Yield (%) | Purity (%) | MS (m/z) | Ion observed | $r_t$ (min) |
| 131 | 80.9 | 98.01 | 413.9 | $[M + H]^+$ | 2.89 |

Starting material (amine): 2-phenylcycloheptan-1-amine.

N-(1-(3-chlorophenyl)cyclopentyl)-4-(trifluoromethoxy)benzenesulfonamide (14)

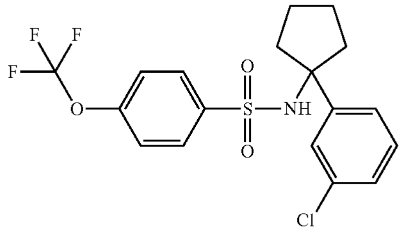 [SMILES: O=S(=O)(NC1(c2cccc(Cl)c2)CCCC1)c1ccc(OC(F)(F)F)cc1]

TABLE 14

| Analytical data for compound 14 | | | | | |
|---|---|---|---|---|---|
| Amount (mg) | Yield (%) | Purity (%) | MS (m/z) | Ion observed | $r_t$ (min) |
| 80.4 | 49.4 | 98.95 | 441.9 | $[M + Na]^+$ | 2.81 |

N-(1-(3-methoxyphenyl)cyclopentyl)-4-(trifluoromethoxy)benzenesulfonamide (15)

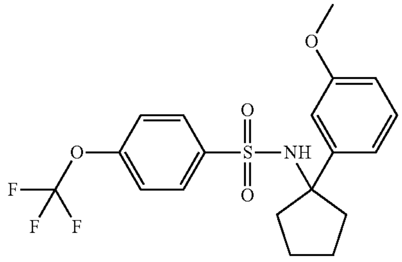 [SMILES: COc1cccc(C2(NS(=O)(=O)c3ccc(OC(F)(F)F)cc3)CCCC2)c1]

TABLE 15

| Analytical data for compound 15 | | | | | |
|---|---|---|---|---|---|
| Amount (mg) | Yield (%) | Purity (%) | MS (m/z) | Ion observed | $r_t$ (min) |
| 62.9 | 39 | 98.71 | 437.9 | $[M + Na]^+$ | 2.69 |

Starting material (amine): 1-(3-methoxyphenyl)cyclopentan-1-amine.

N-(2-oxo-1-(3-(trifluoromethyl)benzyl)piperidin-3-yl)-4-(trifluoromethoxy)benzenesulfonamide (16)

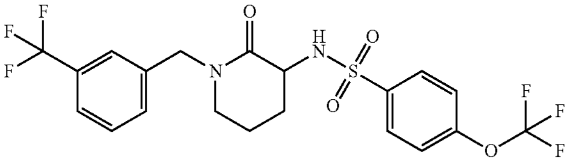 [SMILES: O=C1C(NS(=O)(=O)c2ccc(OC(F)(F)F)cc2)CCCN1Cc1cccc(C(F)(F)F)c1]

TABLE 16

| Analytical data for compound 16 | | | | | |
|---|---|---|---|---|---|
| Amount (mg) | Yield (%) | Purity (%) | MS (m/z) | Ion observed | $r_t$ (min) |
| 101.4 | 49.7 | 93.37 | 496.8 | $[M + H]^+$ | 2.65 |

Starting material (amine): 3-amino-1-(3-(trifluoromethyl)benzyl)piperidin-2-one.

N-(1-(2-phenylbutanoyl)piperidin-4-yl)-4-(trifluoromethoxy)benzenesulfonamide (17)

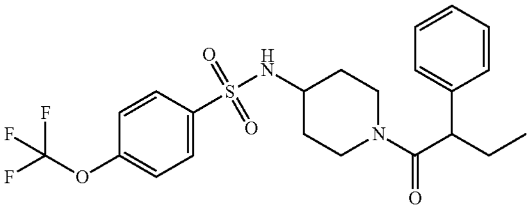 [SMILES: CCC(C(=O)N1CCC(NS(=O)(=O)c2ccc(OC(F)(F)F)cc2)CC1)c1ccccc1]

TABLE 17

| Analytical data for compound 17 | | | | | |
|---|---|---|---|---|---|
| Amount (mg) | Yield (%) | Purity (%) | MS (m/z) | Ion observed | $r_t$ (min) |
| 94 | 52.1 | 100 | 470.9 | $[M + H]^+$ | 2.58 |

Starting material (amine): 1-(4-aminopipeeridin-1-yl)-2-phenylbutan-1-one.

N-(spiro[chromane-2,1'-cyclopentan]-4-yl)-4-(trifluoromethoxy)benzenesulfonamide (18)

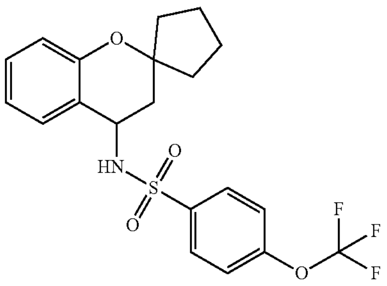 [SMILES: O=S(=O)(NC1CC2(CCCC2)Oc2ccccc21)c1ccc(OC(F)(F)F)cc1]

TABLE 18

| Analytical data for compound 18 | | | | | |
|---|---|---|---|---|---|
| Amount (mg) | Yield (%) | Purity (%) | MS (m/z) | Ion observed[a] | $r_t$ (min) |
| 82.6 | 49.6 | 98.56 | 426 | $[M-H]^-$ | 2.82 |

[a]LCMS Method B; Starting material (amine): spiro[chromane-2,1'-cyclopentan]-4-amine.

methyl 3-(1-((4-(trifluoromethoxy)phenyl)sulfonamido)cyclopentyl)propiolate (19)

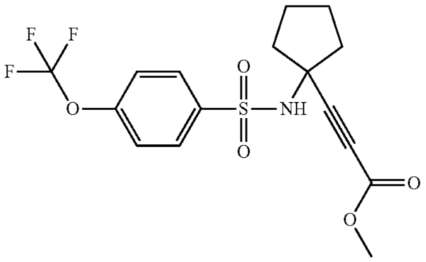 [SMILES: COC(=O)C#CC1(NS(=O)(=O)c2ccc(OC(F)(F)F)cc2)CCCC1]

TABLE 19

| Analytical data for compound 19 | | | | | |
|---|---|---|---|---|---|
| Amount (mg) | Yield (%) | Purity (%) | MS (m/z) | Ion observed | $r_t$ (min) |
| 52 | 34.6 | 100 | 391.9 | $[M+H]^+$ | 2.5 |

Starting material (amine): methyl 3-(1-aminocyclopentyl) propiolate.

ethyl 1-((4-(trifluoromethoxy)phenyl)sulfonamido)-2,3-dihydro-1H-indene-1-carboxylate (20)

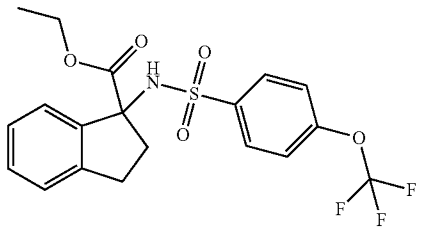 [SMILES: CCOC(=O)C1(NS(=O)(=O)c2ccc(OC(F)(F)F)cc2)CCc2ccccc21]

TABLE 20

| Analytical data for compound 20 | | | | | |
|---|---|---|---|---|---|
| Amount (mg) | Yield (%) | Purity (%) | MS (m/z) | Ion observed | $r_t$ (min) |
| 53 | 31.8 | 98.72 | 451.9 | $[M+Na]^+$ | 2.64 |

Starting material (amine): ethyl 1-amino-2,3-dihydro-1H-indene-1-carboxylate.

methyl 3,5-dimethyl-7-((4-(trifluoromethoxy)phenyl)sulfonamido)adamantane-1-carboxylate (21)

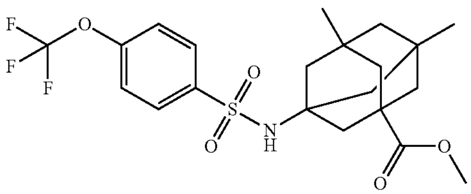 [SMILES: COC(=O)C12CC3(C)CC(C)(CC(NS(=O)(=O)c4ccc(OC(F)(F)F)cc4)(C3)C1)C2]

TABLE 21

| Analytical data for compound 21 | | | | | |
|---|---|---|---|---|---|
| Amount (mg) | Yield (%) | Purity (%) | MS (m/z) | Ion observed | $r_t$ (min) |
| 112.6 | 58.1 | 91.35 | 461.9 | $[M+H]^+$ | 2.8 |

Starting material (amine): methyl 3,5-dimethyl-7-(methylamino)adamantane-1-carboxylate.

N-(2-benzyloctahydrocyclopenta[c]pyrrol-4-yl)-4-(trifluoromethoxy)benzenesulfonamide (22)

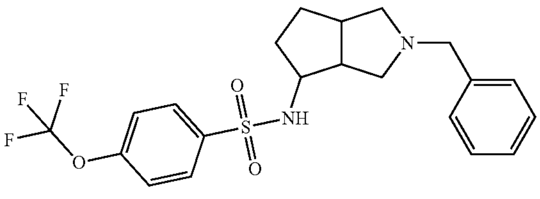 [SMILES: O=S(=O)(NC1CCC2CN(Cc3ccccc3)CC21)c1ccc(OC(F)(F)F)cc1]

TABLE 22

| Analytical data for compound 22 | | | | | |
|---|---|---|---|---|---|
| Amount (mg) | Yield (%) | Purity (%) | MS (m/z) | Ion observed | $r_t$ (min) |
| 175 | 99.4 | 96 | 440.9 | $[M + H]^+$ | 1.9 |

Starting material (amine): 2-benzyloctahydrocyclopenta[c]pyrrol-4-amine.

tert-butyl 2-(1-((4-(trifluoromethoxy)phenyl)sulfonamido)cyclopropyl)pyrrolidine-1-carboxylate (23)

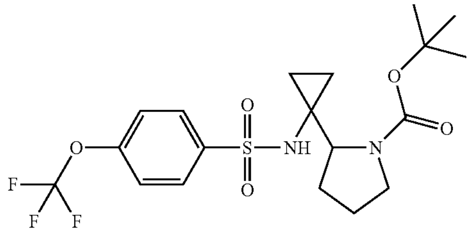 [SMILES: CC(C)(C)OC(=O)N1CCCC1C1(NS(=O)(=O)c2ccc(OC(F)(F)F)cc2)CC1]

TABLE 23

| Analytical data for compound 23 | | | | | |
|---|---|---|---|---|---|
| Amount (mg) | Yield (%) | Purity (%) | MS (m/z) | Ion observed | $r_t$ (min) |
| 159 | 83 | 90.26 | 450.9 | $[M + H]^+$ | 2.64 |

Starting material (amine): tert-butyl 2-(1-aminocyclopropyl)pyrrolidine-1-carboxylate.

trans tert-butyl 4-(2-((4-(trifluoromethoxy)phenyl)sulfonamido)cyclopropyl)piperidine-1-carboxylate (24)

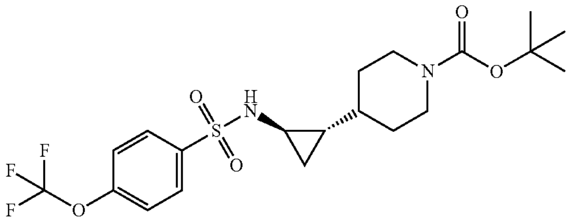 [SMILES: CC(C)(C)OC(=O)N1CCC([C@@H]2C[C@H]2NS(=O)(=O)c2ccc(OC(F)(F)F)cc2)CC1]

TABLE 24

| Analytical data for compound 24 | | | | | |
|---|---|---|---|---|---|
| Amount (mg) | Yield (%) | Purity (%) | MS (m/z) | Ion observed | $r_t$ (min) |
| 174 | 97.6 | 100 | 464.9 | $[M + H]^+$ | 2.69 |

Starting material (amine): trans tert-butyl 4-(2-aminocyclopropyl)piperidine-1-carboxylate.

N-(6-(difluoromethoxy)-4-oxo-1,2,3,4-tetrahydronaphthalen-1-yl)-4-(trifluoromethoxy)benzenesulfonamide (25)

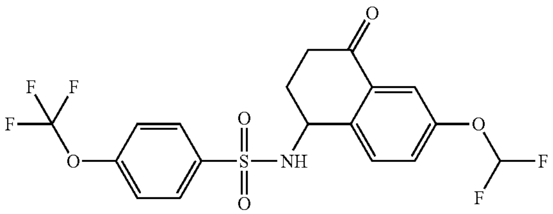 [SMILES: O=C1CCC(NS(=O)(=O)c2ccc(OC(F)(F)F)cc2)c2ccc(OC(F)F)cc21]

TABLE 25

| Analytical data for compound 25 | | | | | |
|---|---|---|---|---|---|
| Amount (mg) | Yield (%) | Purity (%) | MS (m/z) | Ion observed | $r_t$ (min) |
| 135.1 | 74.5 | 95.45 | 451.8 | $[M + H]^+$ | 2.53 |

Starting material (amine): 4-amino-7-(difluoromethoxy)-3,4-dihydronaphthalen-1(2H)-one.

4-(trifluoromethoxy)-N-(4-(trifluoromethyl)-4,5,6,7-tetrahydro-1H-indazol-6-yl)benzenesulfonamide (26)

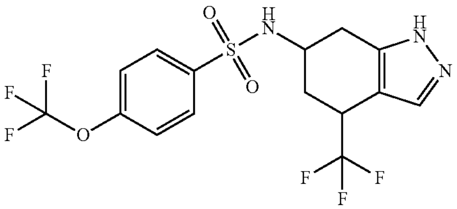 [SMILES: O=S(=O)(NC1Cc2[nH]ncc2C(C(F)(F)F)C1)c1ccc(OC(F)(F)F)cc1]

TABLE 26

| Analytical data for compound 26 | | | | | |
|---|---|---|---|---|---|
| Amount (mg) | Yield (%) | Purity (%) | MS (m/z) | Ion observed | $r_t$ (min) |
| 60 | 35.1 | 96.08 | 429.8 | $[M + H]^+$ | 2.29 |

Starting material (amine): 4-(trifluoromethyl)-4,5,6,7-tetrahydro-1H-indazol-6-amine.

(S)—N-(6-fluoro-2,2-dimethylchroman-4-yl)-4-(trifluoromethoxy)benzenesulfonamide (27)

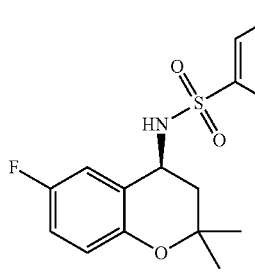

TABLE 27

| Analytical data for compound 27 | | | | | |
|---|---|---|---|---|---|
| Amount (mg) | Yield (%) | Purity (%) | MS (m/z) | Ion observed[a] | $r_t$ (min) |
| 120.1 | 68.7 | 92.11 | 418 | $[M-H]^-$ | 2.86 |

[a]LCMS Method B; Starting material (amine): (S)-6-fluoro-2,2-dimethylchroman-4-amine.

N-(2-ethyl-1-(m-tolyl)cyclopropyl)-4-(trifluoromethoxy)benzenesulfonamide (28)

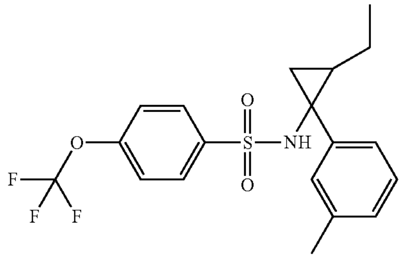 [SMILES: CCC1CC1(NS(=O)(=O)c1ccc(OC(F)(F)F)cc1)c1cccc(C)c1]

TABLE 28

| Analytical data for compound 28 | | | | | |
|---|---|---|---|---|---|
| Amount (mg) | Yield (%) | Purity (%) | MS (m/z) | Ion observed | $r_t$ (min) |
| 58.9 | 38.4 | 100 | 399.9 | $[M+H]^+$ | 2.85 |

Starting material (amine): 2-ethyl-1-(m-tolyl)cyclopropan-1-amine.

N-(4-(3-fluoro-4-methoxyphenyl)tetrahydro-2H-pyran-4-yl)-4-(trifluoromethoxy)benzenesulfonamide (29)

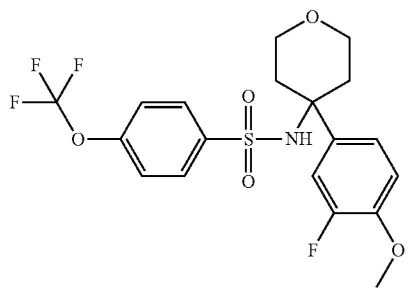 [SMILES: COc1ccc(C2(NS(=O)(=O)c3ccc(OC(F)(F)F)cc3)CCOCC2)cc1F]

TABLE 29

| Analytical data for compound 29 | | | | | |
|---|---|---|---|---|---|
| Amount (mg) | Yield (%) | Purity (%) | MS (m/z) | Ion observed[a] | $r_t$ (min) |
| 23.6 | 3.7 | 100 | 448 | $[M-H]^-$ | 2.2 |

[a]LCMS Method B; Starting material (amine): 4-(3-fluoro-4-methoxyphenyl)tetrahydro-2H-pyran-4-amine.

N-(1-(3-ethoxy-4-hydroxybenzyl)piperidin-4-yl)-4-(trifluoromethoxy)benzenesulfonamide (30)

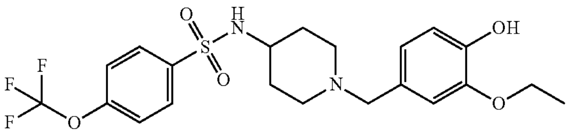 [SMILES: CCOc1cc(CN2CCC(NS(=O)(=O)c3ccc(OC(F)(F)F)cc3)CC2)ccc1O]

TABLE 30

| Analytical data for compound 30 | | | | | |
|---|---|---|---|---|---|
| Amount (mg) | Yield (%) | Purity (%) | MS (m/z) | Ion observed | $r_t$ (min) |
| 26 | 14 | 98.2 | 474.9 | $[M+H]^+$ | 1.77 |

Starting material (amine): 4-((4-aminopiperidin-1-yl)methyl)-2-ethoxyphenol.

rac N-((6R,7R)-2-benzyl-7-hydroxy-1-isopropyl-2-azaspiro[3.4]octan-6-yl)-4-(trifluoromethoxy)benzenesulfonamide (31)

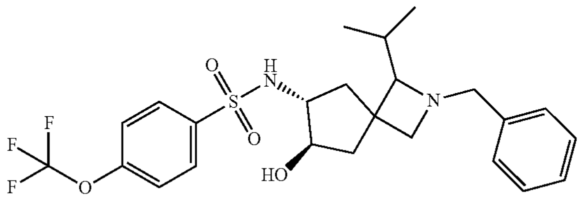 [SMILES: CC(C)C1N(Cc2ccccc2)CC12C[C@@H](O)[C@H](NS(=O)(=O)c1ccc(OC(F)(F)F)cc1)C2]

TABLE 31

| Analytical data for compound 31 | | | | | |
|---|---|---|---|---|---|
| Amount (mg) | Yield (%) | Purity (%) | MS (m/z) | Ion observed | $r_t$ (min) |
| 172.3 | 86.3 | 95.76 | 498.9 | $[M + H]^+$ | 1.90 (1.95) |
| $^1H$-NMR ($DMSO-d_6$, 500 MHz): δ (ppm) | 10.62 (br dd, J = 2.8, 1.3 Hz, 1H), 7.84-8.04 (m, 3H), 7.59 (dd, J = 15.2, 8.1 Hz, 2H), 7.51 (td, J = 6.4, 3.2 Hz, 2H), 7.39-7.47 (m, 3H), 4.75-5.14 (m, 1H), 4.32-4.47 (m, 1H), 4.14-4.31 (m, 1H), 3.62-4.04 (m, 3H), 3.43 (dd, J = 9.8, 6.4 Hz, 1H), 3.09-3.24 (m, 1H), 1.49-2.36 (m, 5H), 0.75-1.12 (m, 6H). | | | | |

Starting material (amine): rac (6R,7R)-7-amino-2-benzyl-1-isopropyl-2-azaspiro[3.4]octan-6-ol.

tert-butyl 3-(fluoromethyl)-3-((4-(trifluoromethoxy)phenyl)sulfonamido)pyrrolidine-1-carboxylate (32)

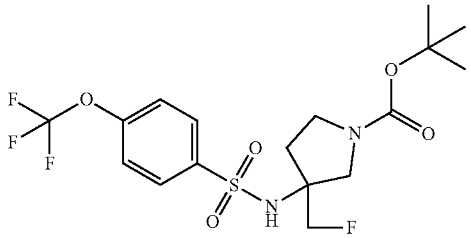 [SMILES: CC(C)(C)OC(=O)N1CCC(CF)(NS(=O)(=O)c2ccc(OC(F)(F)F)cc2)C1]

TABLE 32

| Analytical data for compound 32 | | | | | |
|---|---|---|---|---|---|
| Amount (mg) | Yield (%) | Purity (%) | MS (m/z) | Ion observed | $r_t$ (min) |
| 8.2 | 4.8 | 98.36 | 386.9 | $[M - tBu + H]^+$ | 2.51 |

Starting material (amine): tert-butyl 3-amino-3-(fluoromethyl)pyrrolidine-1-carboxylate.

3,5-dimethyl-N-((1-((4-(trifluoromethoxy)phenyl)sulfonamido)cyclohexyl)methyl)isoxazole-4-sulfonamide (33)

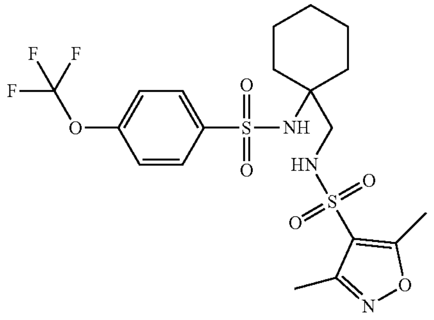 [SMILES: Cc1noc(C)c1S(=O)(=O)NCC1(NS(=O)(=O)c2ccc(OC(F)(F)F)cc2)CCCCC1]

TABLE 33

| Analytical data for compound 33 | | | | | |
|---|---|---|---|---|---|
| Amount (mg) | Yield (%) | Purity (%) | MS (m/z) | Ion observed | $r_t$ (min) |
| 50.3 | 22.7 | 88.61 | 511.8 | $[M + H]^+$ | 2.61 |

Starting material (amine): N-((1-aminocyclohexyl)methyl)-3,5-dimethylisoxazole-4-sulfonamide.

rac N-((2S,3R)-1-cyclopropyl-2-(3,4-difluorophenyl)pyrrolidin-3-yl)-4-(trifluoromethoxy)benzenesulfonamide (34)

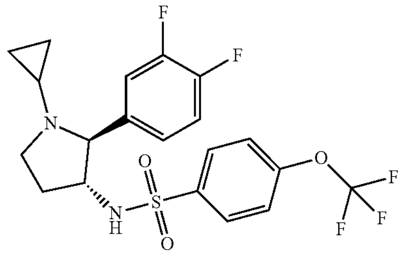 [SMILES: O=S(=O)(N[C@@H]1CCN(C2CC2)[C@H]1c1ccc(F)c(F)c1)c1ccc(OC(F)(F)F)cc1]

TABLE 34

| Analytical data for compound 34 | | | | | |
|---|---|---|---|---|---|
| Amount (mg) | Yield (%) | Purity (%) | MS (m/z) | Ion observed | $r_t$ (min) |
| 47.6 | 23.1 | 86.15 | 462.9 | $[M + H]^+$ | 1.96 |

Starting material (amine): rac (2S,3R)-1-cyclopropyl-2-(3,4-difluorophenyl)pyrrolidin-3-amine.

Example 2: N-(1-benzyl-3-phenylpyrrolidin-3-yl)-4-(trifluoromethoxy)benzenesulfonamide (35)

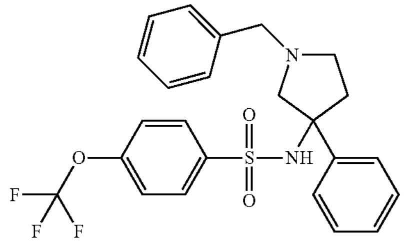 [SMILES: O=S(=O)(NC1(c2ccccc2)CCN(Cc2ccccc2)C1)c1ccc(OC(F)(F)F)cc1]

In a sealed tube, 4-(trifluoromethoxy)benzenesulfonyl chloride (35 μL, 0.198 mmol) was added to a stirred solution of 1-benzyl-3-phenyl-pyrrolidin-3-amine (50 mg, 0.198 mmol) and triethylamine (110 μL, 0.793 mmol) in anhydrous DCM (2.1611 mL). The solution was stirred at rt for 20 h. Water (10 mL) was added and the aqueous layer was extracted with dichloromethane (1x10 mL). The combined organic layers were washed with a saturated aqueous solution of sodium chloride, dried over sodium sulfate, filtered and concentrated under reduced pressure. The crude was purified by reverse-phase chromatography using a gradient of acetonitrile in water from 0% to 100% (0.1% AcOH in water). The crude was further purified by flash chromatography on silica gel using a gradient of methanol in dichloromethane from 0% to 5%. The residue was triturated in 2 M hydrogen chloride in diethyl ether (1.0 mL, 2.00 mmol), filtered, washed with diethyl ether and dried under vacuum at 60° C. for 20 h to afford the title compound as a yellow oil (39.9 mg, 39% yield, 98.9% purity, $t_r$=1.63 min). LCMS (Method C): m/z found 477 $[M+H]^+$; $^1$H-NMR (500 MHz, DMSO-$d_6$) δ (ppm) 10.55-11.48 (m, 1H), 8.45-9.18 (m, 1H), 7.44-7.70 (m, 5H), 7.25-7.40 (m, 2H), 7.10-7.20 (m, 2H), 6.94-7.05 (m, 5H), 4.38-4.60 (m, 2H), 3.41-4.22 (m, 4H), 2.93-3.06 (m, 1H), 2.18-2.28 (m, 1H).

Example 3: N-(3-phenylpyrrolidin-3-yl)-4-(trifluoromethoxy)benzenesulfonamide (36)

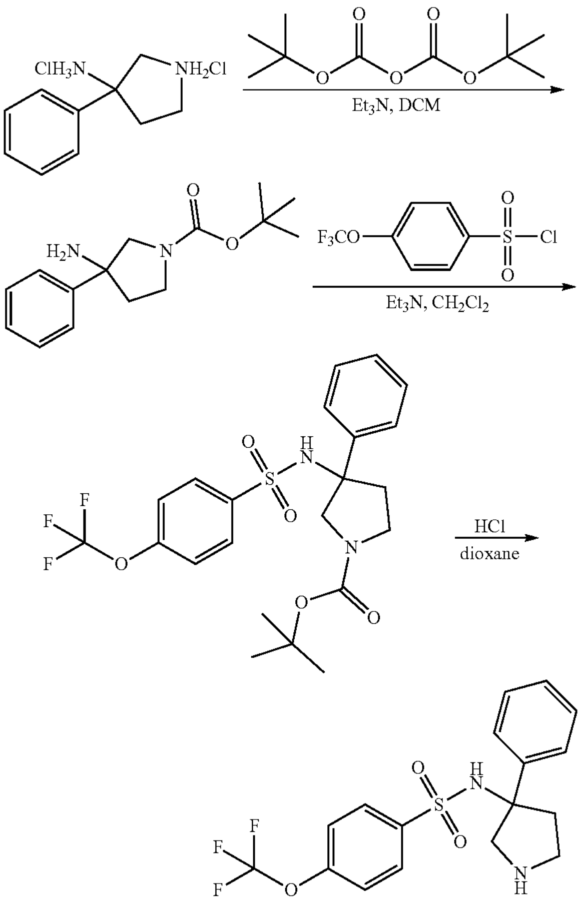

Step 1: Synthesis of tert-butyl 3-amino-3-phenylpyrrolidine-1-carboxylate

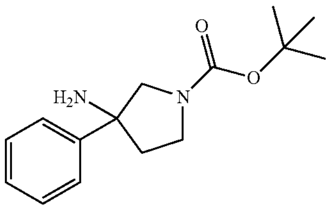 [SMILES: CC(C)(C)OC(=O)N1CCC(N)(c2ccccc2)C1]

In a sealed vial, to a stirred solution of 3-phenylpyrrolidin-3-amine·(2 HCl) (100 mg, 0.425 mmol) and triethylamine (0.24 mL, 1.70 mmol) in DCM (4.2526 mL) was added di-tert-butyl dicarbonate (93 mg, 0.425 mmol). The reaction mixture was stirred at rt overnight. Water and DCM were added, and the aqueous layer was extracted twice with DCM. Organic layers were washed with a saturated solution of $NH_4Cl$, then with a saturated solution of $NaHCO_3$, brine, then concentrated in vacuo to afford the title compound as a colorless oil (99.5 mg, 86% yield, $t_r$=0.55 min). LCMS (Method D): m/z found 263.2 $[M+H]^+$; $^1$H-NMR (DMSO-$d_6$, 400 MHz) δ (ppm) 7.47 (d, J=7.6 Hz, 2H), 7.33 (t, J=7.6 Hz, 2H), 7.22 (t, J=7.3 Hz, 1H), 3.58-3.35 (m, 4H), 2.23-1.85 (m, 4H), 1.42 (d, J=4.4 Hz, 10H).

Step 2: Synthesis of tert-butyl 3-phenyl-3-[[4-(trifluoromethoxy)phenyl]sulfonylamino]pyrrolidine-1-carboxylate

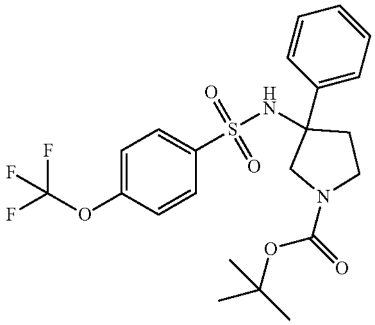 [SMILES: CC(C)(C)OC(=O)N1CCC(NS(=O)(=O)c2ccc(OC(F)(F)F)cc2)(c2ccccc2)C1]

In a sealed vial under nitrogen, 4-(trifluoromethoxy) benzenesulfonyl chloride (0.60 mL, 3.53 mmol) was added to a stirred solution of tert-butyl 3-amino-3-phenylpyrrolidine-1-carboxylate (925 mg, 3.53 mmol) and N,N-dimethylpyridin-4-amine (99%, 87 mg, 0.705 mmol) in DCM (35.258 mL). The solution was stirred at rt for 4 hours, diluted with an half saturated solution of $NaHCO_3$ and DCM, and the aqueous layer was extracted twice with DCM. The combined organic layers were filtered through phase separator then concentrated in vacuo and purified by flash chromatography on silica gel using a gradient of EtOAc in Heptane from 20% to 80% to afford the title compound as a white powder (1.371 g, 79% yield, $t_r$=1.00 min). LCMS (Method E): m/z 509 $[M+H]^+$; $^1$H-NMR (DMSO-$d_6$, 400 MHz) δ (ppm) 8.53 (d, J=7.9 Hz, 1H), 7.38 (dd, J=8.7, 1.6 Hz, 2H), 7.19 (d, J=7.4 Hz, 2H), 7.09-6.92 (m, 5H), 4.04 (d, J=11.4 Hz, 1H), 3.56-3.35 (m, 2H), 3.29 (s, 2H), 2.81-2.60 (m, 1H), 2.16 (ddt, J=21.2, 12.5, 8.4 Hz, 1H), 1.41 (d, J=4.6 Hz, 9H).

Step 3: Synthesis of N-(3-phenylpyrrolidin-3-yl)-4-(trifluoromethoxy)benzenesulfonamide (36)

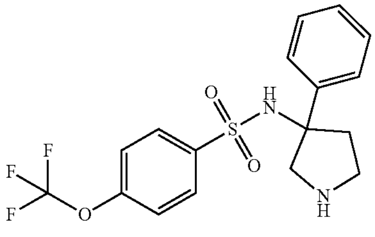 [SMILES: O=S(=O)(NC1(c2ccccc2)CCNC1)c1ccc(OC(F)(F)F)cc1]

In a round-bottomed flask, to a stirred solution of tert-butyl 3-phenyl-3-[[4-(trifluoromethoxy)phenyl]sulfonylamino]pyrrolidine-1-carboxylate (59 mg, 0.121 mmol) in diethyl ether (1.8375 mL) was added 2 M hydrogen chloride in diethyl ether (1.8 mL, 3.64 mmol). The mixture was stirred for 3 hours at rt, then 4 M hydrogen chloride in dioxane (1.8 mL, 7.28 mmol) was added and the mixture was stirred overnight at rt. The mixture was concentrated in vacuo, then sonicated in diethyl ether and filtered to afford the hydrogen chloride salt of the title compound as a white powder (46 mg, 89% yield, 99.3% purity, $t_r$=1.29 min). LCMS (Method C): m/z found 386.9 $[M+H]^+$; $^1$H-NMR (DMSO-$d_6$, 600 MHz): δ (ppm) 9.02-9.59 (m, 2H), 8.46-8.83 (m, 1H), 7.34 (d, J=9.0 Hz, 2H), 7.16 (d, J=8.1 Hz, 2H), 7.00-7.06 (m, 3H), 6.92-6.99 (m, 2H), 4.13 (d, J=11.9 Hz, 1H), 3.34-3.45 (m, 3H), 2.85 (ddd, J=9.3, 7.8, 4.0 Hz, 1H), 2.14 (dt, J=13.2, 9.8 Hz, 1H).

Example 4: rac N-((2S,3R)-1-(tert-butyl)-2-(4-chloro-3-fluorophenyl)pyrrolidin-3-yl)-4-(trifluoromethoxy)benzenesulfonamide (37 and 38)

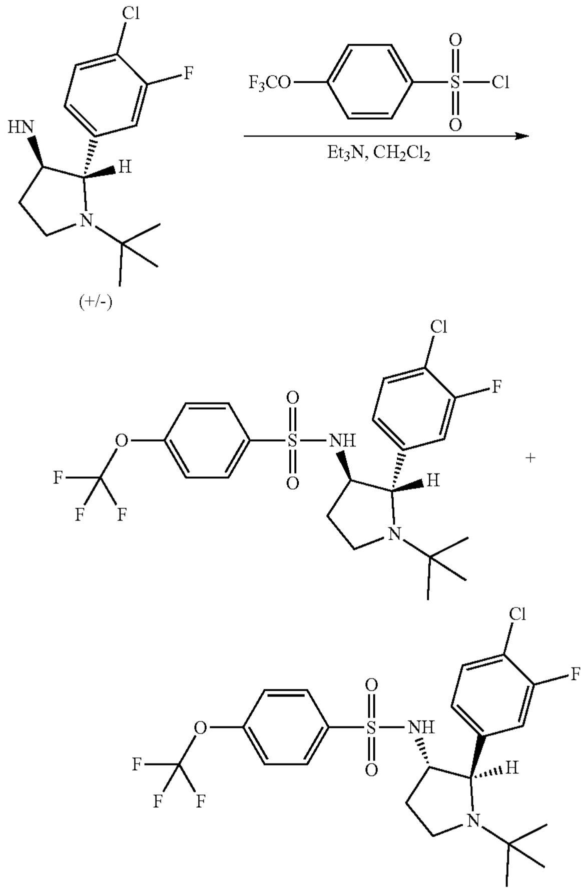

In a sealed tube, 4-(trifluoromethoxy)benzenesulfonyl chloride (542 μL, 3.20 mmol) was added to a stirred solution of racemic (2S,3R)-1-tert-butyl-2-(4-chloro-3-fluorophenyl) pyrrolidin-3-amine (95%, 1.004 g, 3.52 mmol) and triethylamine (1.8 mL, 12.8 mmol) in DCM (12.816 mL). The solution was stirred at rt for 20 h then was diluted with water and DCM. The aqueous layer was extracted twice with DCM, the combined organic layers were washed with brine, dried over sodium sulfate, filtered and concentrated. The crude was purified by flash chromatography on silica gel using a gradient of (MeOH+2% $NH_4OH$) in DCM from 0.2% to 5% to afford the racemic product as a white powder (1.14 g, 70.5% yield). Enantiomers were separated by chiral chromatography. A sample of the racemic mixture (125 mg)

was dissolved by sonication in a mixture of i-PrOH (1.5 mL), MeOH (1.5 mL), and ACN (2 mL), to provide a solution having a concentration of 25 mg/mL. The solution was filtered through a hydrophilic polypropylene filter (GHP, 0.45 μm). 20 injections of the sample solution were performed on a Chiralpak IB column (250×20 mm, 5 μm) using 10% i-PrOH in $CO_2$ as the mobile phase (Waters Prep SFC80, flow rate=50 mL/min, T=40° C., P=143 bar, UV detection at 210 nm) to afford the separated enantiomers.

Enantiomer I (37): (338.1 mg, 21% yield, 100% purity, $t_r$=1.82 min). LCMS (Method C): m/z found 494 $[M+H]^+$; $^1$H-NMR (500 MHz, DMSO-$d_6$) δ (ppm) 8.07 (s, 1H) 7.88 (d, J=8.80 Hz, 2H) 7.49-7.59 (m, 2H) 7.41 (t, J=8.07 Hz, 1H) 7.22-7.30 (m, 1H) 7.13-7.20 (m, 1H) 4.05 (m, J=2.40 Hz, 1H) 3.07-3.13 (m, 1H) 2.92-3.05 (m, 2H) 1.45-1.85 (m, 2H) 0.91 (s, 9H).

Enantiomer II (38): (287.0 mg, 18% yield, 100% purity, $t_r$=1.82 min). LCMS (Method C): m/z found 494 $[M+H]^+$; $^1$H-NMR (500 MHz, DMSO-$d_6$) δ (ppm) 8.04-8.15 (m, 1H) 7.80-7.95 (m, 2H) 7.50-7.64 (m, 2H) 7.36-7.46 (m, 1H) 7.22-7.31 (m, 1H) 7.13-7.20 (m, 1H) 4.05 (m, J=2.20 Hz, 1H) 3.07-3.15 (m, 1H) 2.89-3.06 (m, 2H) 1.48-1.86 (m, 2H) 0.91 (s, 9H).

Example 5: N-(3-(4-chlorophenyl)pyrrolidin-3-yl)-4-(trifluoromethoxy)benzenesulfonamide (39)

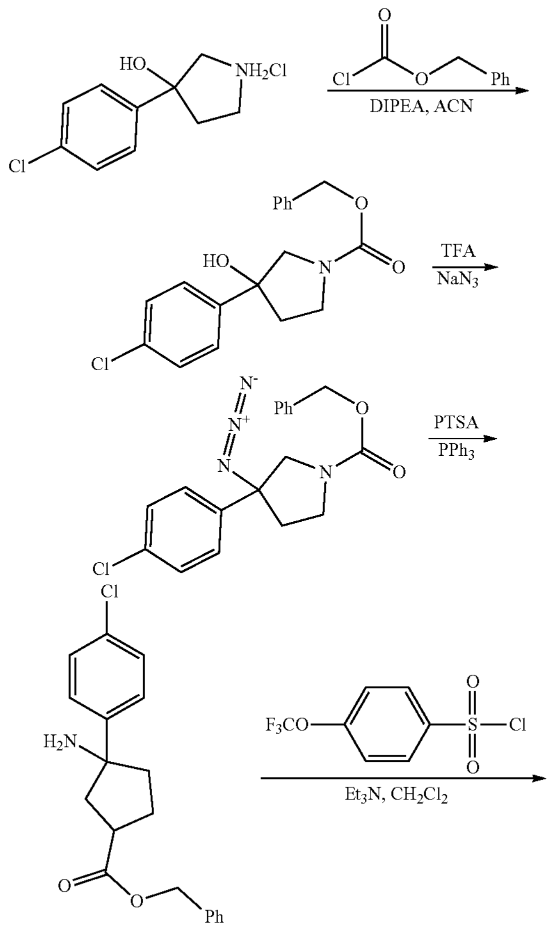

-continued

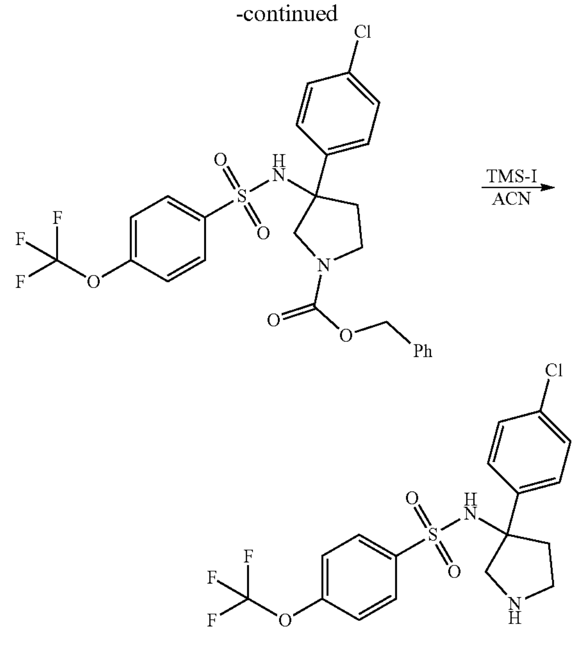

Step 1: Synthesis of benzyl 3-(4-chlorophenyl)-3-hydroxypyrrolidine-1-carboxylate

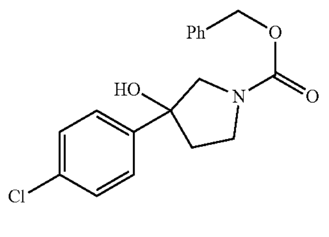 [SMILES: O=C(OCc1ccccc1)N1CCC(O)(c2ccc(Cl)cc2)C1]

A sealed vial was charged with 3-(4-chlorophenyl)pyrrolidin-3-ol hydrochloride (0.60 g, 2.56 mmol) and DIPEA (1.3 mL, 7.69 mmol) in anhydrous acetonitrile (9 mL). Benzyl chloroformate (97%, 413 μL, 2.82 mmol) was added dropwise at 0° C. and the reaction mixture was stirred at room temperature for 2 h. The reaction mixture was quenched with a saturated aqueous solution of sodium bicarbonate (50 mL). Then ethyl acetate (50 mL) and water (20 mL) were added. The aqueous layer was extracted with ethyl acetate (1×50 mL). The combined organic layers were washed with a saturated aqueous solution of sodium chloride, dried over sodium sulfate, filtered, and concentrated under reduced pressure. The crude was triturated in dichloromethane, filtered, and washed with dichloromethane to afford a white powder. The filtrate was purified by flash chromatography on silica gel using a gradient of methanol in dichloromethane from 1% to 5% to afford a beige powder, which was added to the white powder, and dried under vacuum at 50° C. for 20 h to afford the title compound (848 mg, 100% yield, $t_r$=0.89 min). LCMS (Method E); $^1$H-NMR (DMSO-$d_6$, 400 MHz) δ (ppm) 7.54 (d, J=8.6 Hz, 2H), 7.46-7.26 (m, 7H), 5.55 (s, 1H), 5.10 (d, J=9.8 Hz, 2H), 3.67-3.43 (m, 4H), 2.32-1.97 (m, 2H).

Step 2: Synthesis of benzyl 3-azido-3-(4-chlorophenyl)pyrrolidine-1-carboxylate

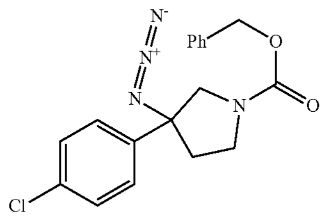 [SMILES: [N-]=[N+]=NC1(c2ccc(Cl)cc2)CCN(C(=O)OCc2ccccc2)C1]

A sealed vial was charged with benzyl 3-(4-chlorophenyl)-3-hydroxy-pyrrolidine-1-carboxylate (759 mg, 2.29 mmol) in a mixture of TFA (8.4 mL) and water (1.33 mL) at 0° C. Sodium azide (1.04 g, 16.0 mmol) was added at 0° C. and the reaction mixture was stirred at room temperature for 3 h. Dichloromethane (10 mL) and a saturated solution of sodium bicarbonate (15 mL) were added. The aqueous layer was extracted with dichloromethane (1×10 mL). The combined organic layers were washed with a saturated aqueous solution of sodium chloride, dried over sodium sulfate, filtered and concentrated under reduced pressure to afford the title compound as a yellow oil (815 mg, 100% yield, $t_r$=1.03 min). LCMS (Method E); $^1$H-NMR (DMSO-$d_6$, 400 MHz) δ (ppm) 7.60-7.48 (m, 4H), 7.47-7.28 (m, 6H), 5.12 (s, 2H), 4.07-3.88 (m, 1H), 3.75-3.38 (m, 3H), 2.58-2.52 (m, 1H), 2.41 (dt, J=22.4, 11.8 Hz, 1H).

Step 3: Synthesis of benzyl 3-amino-3-(4-chlorophenyl)pyrrolidine-1-carboxylate

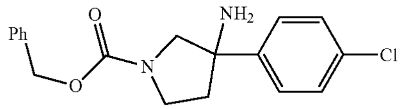 [SMILES: NC1(c2ccc(Cl)cc2)CCN(C(=O)OCc2ccccc2)C1]

In a round bottomed flask under nitrogen, triphenylphosphine (614 mg, 2.34 mmol) then 4-methylbenzenesulfonic acid hydrate (PTSA) (1.34 g, 7.02 mmol) were added to a stirred solution of benzyl 3-azido-3-(4-chlorophenyl)pyrrolidine-1-carboxylate (835 mg, 2.34 mmol) in THF (10 mL). The mixture was stirred at rt for 1.5 h. The suspension was filtered, washed with THF (5 mL) and dried under vacuum for 18 h to afford the title compound as a white powder (890 mg, 74% yield, $t_r$=1.04 min). LCMS (Method E): m/z found 331.3 $[M+H]^+$; $^1$H-NMR (DMSO-$d_6$, 400 MHz): δ (ppm) 8.51 (s, 3H), 7.59-7.51 (m, 4H), 7.50-7.46 (m, 2H), 7.43-7.31 (m, 5H), 7.11 (d, J=7.9 Hz, 2H), 5.13 (d, J=4.9 Hz, 2H), 4.07 (d, J=11.7 Hz, 1H), 3.82-3.53 (m, 3H), 2.53 (s, 1H), 2.47 (d, J=13.3 Hz, 1H), 2.29 (s, 3H).

Step 4: Synthesis of benzyl 3-(4-chlorophenyl)-3-((4-(trifluoromethoxy)phenyl)sulfonamido)pyrrolidine-1-carboxylate

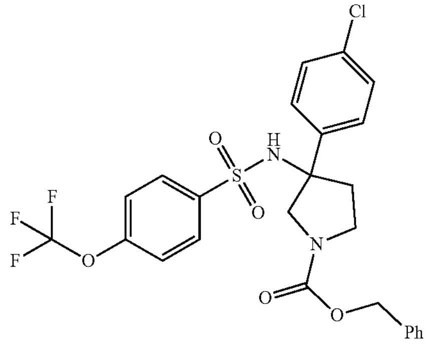 [SMILES: O=C(OCc1ccccc1)N1CCC(NS(=O)(=O)c2ccc(OC(F)(F)F)cc2)(c2ccc(Cl)cc2)C1]

In a sealed tube, 4-(trifluoromethoxy)benzenesulfonyl chloride (74 μL, 0.437 mmol) was added to a stirred solution of benzyl 3-amino-3-(4-chlorophenyl)pyrrolidine-1-carboxylate (200 mg, 0.398 mmol) and triethylamine (277 μL, 1.99 mmol) in DCM (6.1538 mL). The solution was stirred at room temperature for 3 h. Water (5 mL) was added and the aqueous layer was extracted with dichloromethane (1×10 mL). The combined organic layers were washed with a saturated aqueous solution of sodium chloride, dried over sodium sulfate, filtered and concentrated under reduced pressure. The crude was purified by flash chromatography on silica gel using a gradient of methanol in dichloromethane from 0% to 5% to afford the title compound as a yellow powder (64.4 mg, 27% yield, $t_r$=1.03 min). LCMS (Method E): m/z found 577.2 $[M+Na]^+$; $^1$H-NMR (DMSO-$d_6$, 400 MHz) δ (ppm) 8.64 (s, 1H), 7.46-7.30 (m, 7H), 7.25 (d, J=8.3 Hz, 2H), 7.10-7.00 (m, 4H), 5.16-5.00 (m, 2H), 4.14 (dd, J=19.3, 11.3 Hz, 1H), 3.66-3.32 (m, 3H), 2.69 (d, J=12.3 Hz, 1H), 2.37-2.07 (m, 1H).

Step 5: Synthesis of N-(3-(4-chlorophenyl)pyrrolidin-3-yl)-4-(trifluoromethoxy)benzenesulfonamide (39)

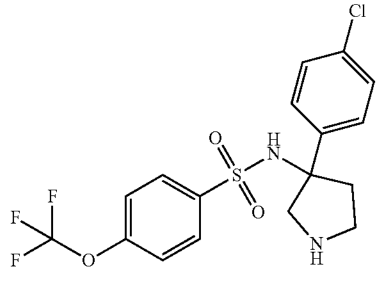 [SMILES: O=S(=O)(NC1(c2ccc(Cl)cc2)CCNC1)c1ccc(OC(F)(F)F)cc1]

In a round-bottomed flask, to a stirred suspension of N-[3-(4-chlorophenyl)-1-(2-phenoxyacetyl)pyrrolidin-3-yl]-4-(trifluoromethoxy)benzenesulfonamide (90%, 435 mg, 0.705 mmol) in acetonitrile (14 mL) at room temperature, was added iodo(trimethyl)silane (301 μL, 2.12 mmol). The reaction mixture was stirred at room temperature for 1 h. The reaction mixture was concentrated under reduced pressure and then partitioned between water (50 mL) and ethyl acetate (50 mL). The aqueous layer was extracted with ethyl acetate (2×25 mL). The combined organic layers were washed with a saturated aqueous solution of sodium chloride, dried over sodium sulfate, filtered and concentrated under reduced pressure. The crude was purified by flash chromatography on silica gel using a gradient of (MeOH+ 2% $NH_4OH$) in dichloromethane from 2% to 10%. The crude was further purified by reverse-phase flash chromatography using a gradient of acetonitrile in water (+0.1% AcOH) from 0% to 100%. The residue was triturated in 4 M hydrogen chloride in dioxane (1.8 mL, 7.05 mmol) and diethyl ether, filtered, washed with diethyl ether and dried under vacuum at 70° C. for 16 h to afford the hydrochloride salt of the title compound as an off-white powder (27.9 mg, 9% yield, 99.4% purity, $t_r$=1.38 min). LCMS (Method C): m/z found 421.2 $[M+H]^+$; $^1$H-NMR (DMSO-$d_6$, 500 MHz): δ (ppm) 9.47 (br s, 2H), 8.69-8.99 (m, 1H), 7.40 (d, J=7.8 Hz, 2H), 7.22 (d, J=8.1 Hz, 2H), 7.00-7.08 (m, 4H), 4.12 (br d, J=12.0 Hz, 1H), 3.34-3.43 (m, 3H), 2.82-2.89 (m, 1H), 2.10-2.18 (m, 1H).

Example 6: benzyl 3-(3,4-dichlorophenyl)-3-((4-(trifluoromethoxy)phenyl)sulfonamido)pyrrolidine-1-carboxylate (40) and N-(3-(3,4-dichlorophenyl) pyrrolidin-3-yl)-4-(trifluoromethoxy) benzenesulfonamide (41)

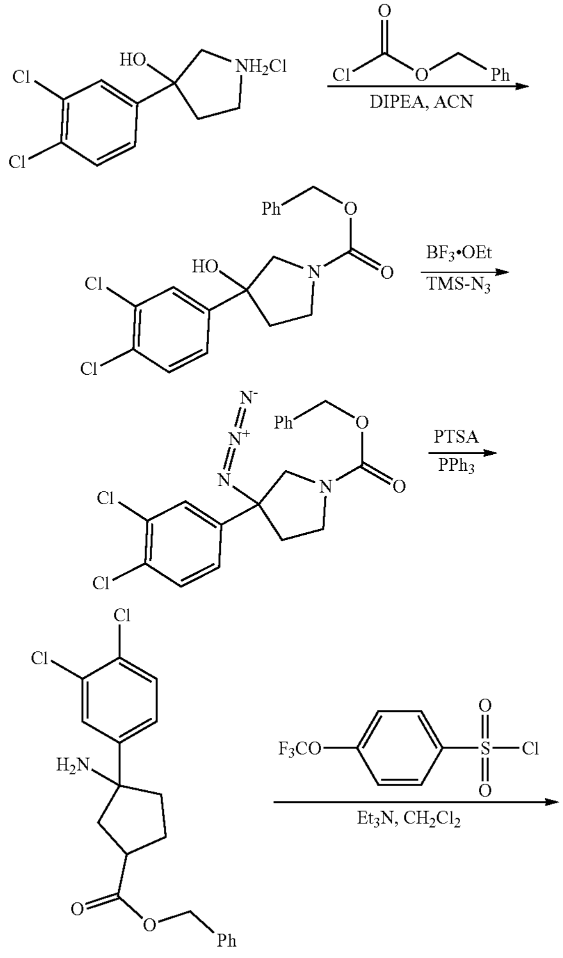

-continued

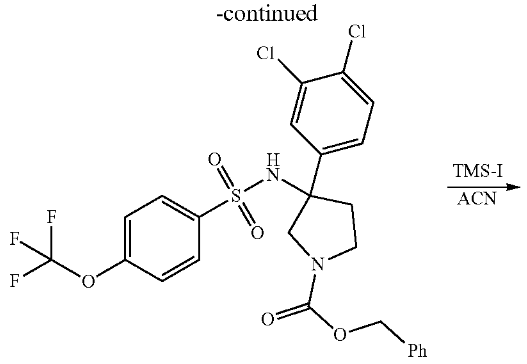

40

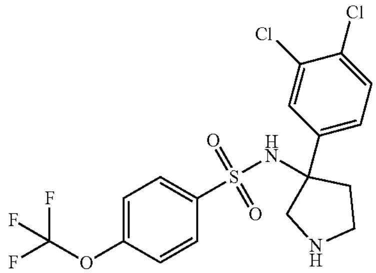

41

Step 1: Synthesis of benzyl 3-(3,4-dichlorophenyl)-3-hydroxypyrrolidine-1-carboxylate

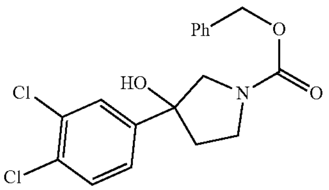 [SMILES: O=C(OCc1ccccc1)N1CCC(O)(c2ccc(Cl)c(Cl)c2)C1]

A sealed vial was charged with 3-(3,4-dichlorophenyl) pyrrolidin-3-ol hydrochloride (500 mg, 1.86 mmol) and DIPEA (1.0 mL, 5.73 mmol) in anhydrous acetonitrile (6.5 mL). Benzyl chloroformate (97%, 300 μL, 2.05 mmol) was added dropwise at 0° C. and the reaction mixture was stirred at room temperature for 4 h. The reaction mixture was quenched with a saturated aqueous solution of sodium bicarbonate and ethyl acetate and water were added. The layers were separated. The aqueous layer was extracted twice with ethyl acetate. The combined organic layers were washed with a saturated aqueous solution of sodium chloride, dried over sodium sulfate, filtered and concentrated under reduced pressure. The residue was purified by flash chromatography on silica gel using a gradient of EtOAc in DCM from 0% to 50% to afford the title compound as a beige gum (638 mg, 91% yield, $t_r$=0.94 min). LCMS (Method E); $^1$H-NMR (DMSO-$d_6$, 400 MHz) δ (ppm) 7.76 (d, J=2.1 Hz, 1H), 7.61 (dd, J=8.4, 3.7 Hz, 1H), 7.51 (dd, J=8.4, 2.2 Hz, 1H), 7.42-7.26 (m, 5H), 5.69 (s, 1H), 5.13-5.07 (m, 2H), 3.67-3.44 (m, 4H), 2.36-2.19 (m, 1H), 2.04 (dt, J=13.0, 6.6 Hz, 1H).

Step 2: benzyl 3-azido-3-(3,4-dichlorophenyl)pyrrolidine-1-carboxylate

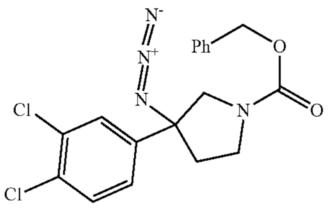 [SMILES: [N-]=[N+]=NC1(c2ccc(Cl)c(Cl)c2)CCN(C(=O)OCc2ccccc2)C1]

In a sealed vial, to a solution of benzyl 3-(3,4-dichlorophenyl)-3-hydroxy-pyrrolidine-1-carboxylate (358 mg, 0.978 mmol) in anhydrous DCM (5 mL) under nitrogen at 0° C. were added azido(trimethyl)silane (260 μL, 1.96 mmol) and boron trifluoride etherate (242 μL, 1.96 mmol). The reaction mixture was allowed to warm up to room temperature and was stirred at this temperature for 2 d. The reaction mixture was quenched with a saturated aqueous solution of $NaHCO_3$ dropwise. EtOAc was added and the layer were separated. The aqueous layer was extracted twice with EtOAc. The combined organic layers were washed with a saturated aqueous solution of sodium chloride, dried over sodium sulfate and concentrated under reduced pressure. The crude was purified by flash chromatography on silica gel using a gradient of EtOAc in heptane from 5% to 50%. The desired fractions were combined and concentrated to provide the title compound as a colorless oil (299.8 mg, 38% yield, $t_r$=1.11 min). LCMS (Method D); $^1$H-NMR (DMSO-$d_6$, 400 MHz) δ (ppm) 7.84 (t, J=2.5 Hz, 1H), 7.79 (t, J=2.3 Hz, 1H), 7.73 (dd, J=8.4, 4.9 Hz, 1H), 7.63 (dd, J=8.4, 5.6 Hz, 1H), 7.52 (ddd, J=12.6, 8.4, 2.2 Hz, 2H), 7.46-7.30 (m, 11H), 6.58 (dt, J=10.4, 2.0 Hz, 1H), 5.17-5.11 (m, 5H), 4.59-4.47 (m, 2H), 4.39-4.26 (m, 2H), 4.07-3.98 (m, 1H), 3.70-3.43 (m, 3H), 2.59-2.52 (m, 1H), 2.47-2.37 (m, 1H).

Step 3: Synthesis of benzyl 3-amino-3-(3,4-dichlorophenyl)pyrrolidine-1-carboxylate

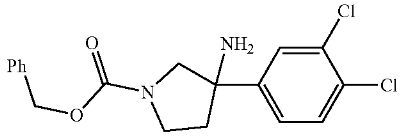 [SMILES: NC1(c2ccc(Cl)c(Cl)c2)CCN(C(=O)OCc2ccccc2)C1]

In a round bottomed flask under nitrogen, triphenylphosphine (121 mg, 0.463 mmol) then 4-methylbenzenesulfonic acid hydrate (PTSA) (262 mg, 1.38 mmol) were added to a stirred solution of benzyl 3-azido-3-(3,4-dichlorophenyl) pyrrolidine-1-carboxylate (50%, 360 mg, 0.460 mmol) in THF (2 mL). The mixture was stirred at room temperature overnight. The suspension was filtered, washed with THF, and dried under vacuum for 18 h to afford the title compound as a white powder (166.1 mg, 64% yield, $t_r$=0.67 min). LCMS (Method D): m/z found 348.2 $[M+H]^+$; $^1$H-NMR (DMSO-$d_6$, 400 MHz) δ (ppm) 8.46 (s, 2H), 7.86-7.73 (m, 2H), 7.54-7.45 (m, 3H), 7.43-7.31 (m, 5H), 7.11 (d, J=7.8 Hz, 2H), 5.21-5.07 (m, 2H), 4.07 (d, J=11.8 Hz, 1H), 3.82-3.52 (m, 3H), 2.60-2.45 (m, 2H), 2.29 (s, 3H).

Step 4: Synthesis of benzyl 3-(3,4-dichlorophenyl)-3-[[4-(trifluoromethoxy)phenyl]sulfonylamino]pyrrolidine-1-carboxylate (40)

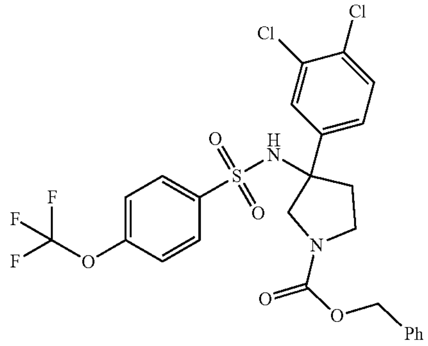 [SMILES: O=C(OCc1ccccc1)N1CCC(NS(=O)(=O)c2ccc(OC(F)(F)F)cc2)(c2ccc(Cl)c(Cl)c2)C1]

In a vial, to a stirred suspension of benzyl 3-amino-3-(3,4-dichlorophenyl)pyrrolidine-1-carboxylate (128 mg, 0.238 mmol) in DCM (2.4 mL) at room temperature were added successively triethylamine (166 μL, 1.19 mmol), 4-(trifluoromethoxy)benzenesulfonyl chloride (98%, 62 μL, 0.358 mmol) and N,N-dimethylpyridin-4-amine (5.8 mg, 0.0476 mmol). The reaction mixture was stirred at this temperature for 1 h and then it was heated at 40° C. for 4 h. The reaction mixture was diluted with DCM and a saturated aqueous solution of $NaHCO_3$. The layers were separated. The aqueous layer was extracted with DCM. The combined organic layers were washed with a saturated aqueous solution of NaCl, dried using a phase separator and concentrated under reduced pressure. The crude was purified by flash chromatography on silica gel using a gradient of EtOAc in heptane from 2% to 100%. The desired fractions were combined and concentrated to afford the title compound as a white foam (117.6 mg, 79% yield, $t_r$=1.06 min). LCMS (Method E): m/z found 611.2 $[M+Na]^+$; $^1$H-NMR (DMSO-$d_6$, 400 MHz) δ (ppm) 8.67 (s, 1H), 7.55-6.99 (m, 12H), 5.17-4.98 (m, 2H), 4.22-3.98 (m, 1H), 3.70-3.33 (m, 3H), 2.76-2.60 (m, 1H), 2.37-2.10 (m, 1H).

Step 5: N-(3-(3,4-dichlorophenyl)pyrrolidin-3-yl)-4-(trifluoromethoxy)benzenesulfonamide (41)

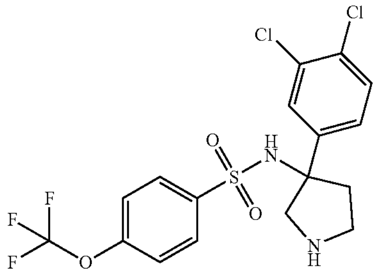 [SMILES: O=S(=O)(NC1(c2ccc(Cl)c(Cl)c2)CCNC1)c1ccc(OC(F)(F)F)cc1]

In a round-bottomed flask, to a stirred solution of benzyl 3-(3,4-dichlorophenyl)-3-[[4-(trifluoromethoxy)phenyl] sulfonylamino]pyrrolidine-1-carboxylate (89 mg, 0.150 mmol) in Acetonitrile (2.8 mL) at room temperature, was added iodo(trimethyl)silane (64 μL, 0.450 mmol). The reaction mixture was stirred at room temperature for 1.5 h. The reaction mixture was concentrated under reduced pressure and dried under vacuum. The crude was purified by flash chromatography on silica gel using a gradient of MeOH (0.7 N $NH_3$) in DCM from 2% to 20%. The desired fractions were combined and concentrated. The residue was triturated in MeOH, filtered, washed with MeOH and diethyl ether and dried under vacuum at 45° C. for 18 h to afford a first crop of the title compound as a white powder (23.4 mg, 34% yield). The filtrate and another fraction containing the title compound were combined. The resulting powder was solubilized in a mixture of MeOH/DCM and the homogenous solution was added to diethyl ether and stirred for 2 h. The formed precipitate was filtered, washed with diethyl ether and pentane, dried under vacuum at 45° C. for 18 h, and combined with the first crop to afford the title compound as a white powder (38.6 mg, 79% yield). The combined precipitate was further purified by reverse-phase preparative chromatography (C18 AQ 15.5 g) using a gradient of acetonitrile in water from 0% to 100% (0.1% AcOH in both). The desired fractions were combined and concentrated. Exchange salt (acetate to chloride) of the residue was performed in HCl 2 N in diethyl ether and was stirred at rt overnight. The suspension was filtered, washed with diethyl ether and pentane, and dried at 45° C. for 18 h to afford the hydrochloride salt of the title compound as a white powder (25.4 mg, 34% yield, 95.1% purity, $t_r$=1.47 min). LCMS (Method C): m/z found 455 $[M+H]^+$; $^1$H-NMR (500 MHz, DMSO-$d_6$) δ (ppm) 9.38-7.71 (m, 1H), 7.49 (d, J=8.8 Hz, 2H), 7.31-7.27 (m, 2H), 7.26 (s, 1H), 7.23 (d, J=2.2 Hz, 1H), 7.13 (dd, J=8.6, 2.2 Hz, 1H), 3.44-3.37 (m, J=11.6, 0.9 Hz, 1H), 3.29-3.21 (m, 1H), 3.03-2.93 (m, 1H), 2.90 (d, J=11.7 Hz, 1H), 2.86-2.79 (m, 1H), 2.49-2.44 (m, 1H), 2.07-1.97 (m, 1H).

Example 7: rac N-((1R,2S)-2-(4-chlorophenyl)cyclopropyl)-4-(trifluoromethoxy)benzenesulfonamide (42)

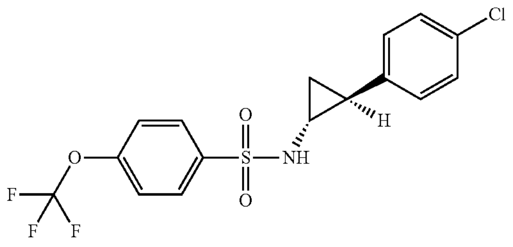 [SMILES: O=S(=O)(N[C@@H]1C[C@H]1c1ccc(Cl)cc1)c1ccc(OC(F)(F)F)cc1]

In a round bottomed flask under $N_2$, 4-(trifluoromethoxy) benzenesulfonyl chloride (0.059 mL, 0.349 mmol) was added to a stirred solution of racemic (1R,2S)-2-(4-chlorophenyl)cyclopropan-1-amine hydrochloride (95%, 75 mg, 0.349 mmol) and triethylamine (0.19 mL, 1.40 mmol) in anhydrous DCM (2.3273 mL). The solution was stirred at rt overnight then DCM and a half saturated solution of $NaHCO_3$ were added, and the aqueous layer was extracted twice with DCM. The combined organic layers were filtered through phase separator, then concentrated in vacuo and purified by flash chromatography on silica gel using an isocratic eluent comprising 100% DCM to afford the title compound as a white powder (111.1 mg, yield=81% yield, 100% purity, $t_r$=2.71 min). LCMS (Method C): m/z found 392 $[M+H]^+$; $^1$H-NMR (500 MHz, DMSO-$d_6$) δ (ppm) 8.32 (d, J=3.4 Hz, 1H), 7.87 (d, J=8.8 Hz, 2H), 7.59 (d, J=8.1 Hz, 2H), 7.25 (d, J=8.6 Hz, 2H), 6.92 (d, J=8.6 Hz, 2H), 2.39-2.23 (m, 1H), 1.95-1.74 (m, 1H), 1.23-1.03 (m, 2H).

Example 8: N-(2-(3,4-dichlorophenyl)cyclopentyl)-4-(trifluoromethoxy)benzenesulfonamide (43 and 44)

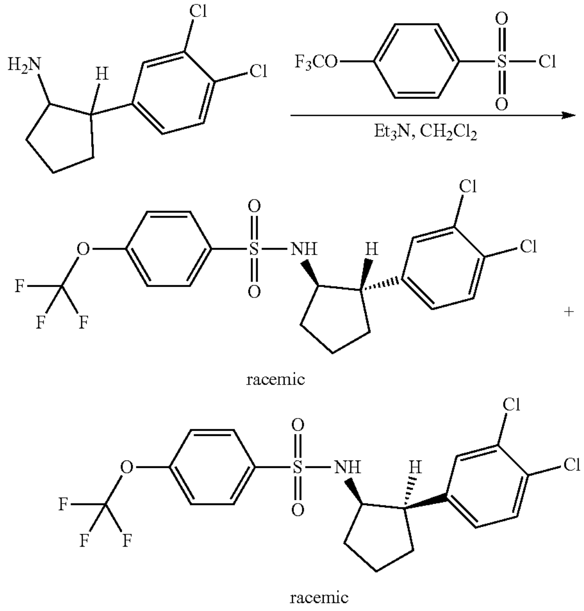

In a sealed tube under nitrogen, triethylamine (242 μL, 1.74 mmol) was added to a stirred solution of 4-(trifluoromethoxy)benzenesulfonyl chloride (113 mg, 0.435 mmol) and 2-(3,4-dichlorophenyl)cyclopentan-1-amine (100 mg, 0.435 mmol) in DCM (2 mL). The solution was stirred at rt for 16 h and was poured into half saturated aqueous $NaHCO_3$. The aqueous layer was extracted twice with DCM. The combined organic layers were washed with brine, dried over sodium sulfate, filtered and concentrated. The crude product was purified by flash chromatography on silica gel using a gradient of (MeOH+2% $NH_4OH$) in DCM from 1% to 5% to afford two fractions. The first fraction was concentrated and the residue was triturated in pentane. The obtained suspension was filtered and dried under reduced pressure at 45° C. for 16 h to afford diastereomer I (racemic) of the title compound (43) as a white powder (42 mg, 21% yield, 98.9% purity, $t_r$=3 min). LCMS (Method C): m/z found 452.1 $[M-H]^-$; $^1$H-NMR (500 MHz, DMSO-$d_6$) δ (ppm) 7.71-7.62 (m, 3H), 7.47-7.42 (m, 2H), 7.40 (d, J=8.3 Hz, 1H), 7.35 (d, J=2.0 Hz, 1H), 7.11 (dd, J=8.3, 2.0 Hz, 1H), 3.92-3.79 (m, 1H), 3.16-3.04 (m, 1H), 1.94-1.71 (m, 4H), 1.62-1.49 (m, 1H), 1.46-1.32 (m, 1H). The second fraction was concentrated and purified by reverse phase chromatography using a gradient of (MeCN+0.1% AcOH) in ($H_2O$+0.1% AcOH) from 0% to 100%. The desired fraction was concentrated and the residue was diluted in DCM and half saturated aqueous $NaHCO_3$. The aqueous layer was extracted with DCM. The combined organic layers were washed with brine, dried over sodium sulfate, filtered and concentrated. The residue was triturated in pentane, then a few drops $Et_2O$ were added. The obtained suspension was filtered, the residue was washed with pentane, and dried under reduced pressure at 45° C. for 64 h to afford diastereomer II (racemic) of the title compound (42) as a white powder (31 mg, 15% yield, 99.3% purity, $t_r$=2.98 min). LCMS (Method C): m/z found 452.2 $[M-H]^-$; $^1$H-NMR (500 MHz, DMSO-$d_6$) δ (ppm) 8.07 (s, 1H), 7.66 (d, J=8.8 Hz, 2H), 7.39-7.31 (m, 4H), 7.10 (dd, J=8.3, 2.0 Hz, 1H), 3.54 (q, J=8.5 Hz, 1H), 2.89-2.67 (m, 1H), 2.03-1.80 (m, 2H), 1.75-1.50 (m, 3H), 1.48-1.33 (m, 1H).

Example 9: N-(4-(4-chlorophenyl)piperidin-4-yl)-4-(trifluoromethoxy)benzenesulfonamide (45)

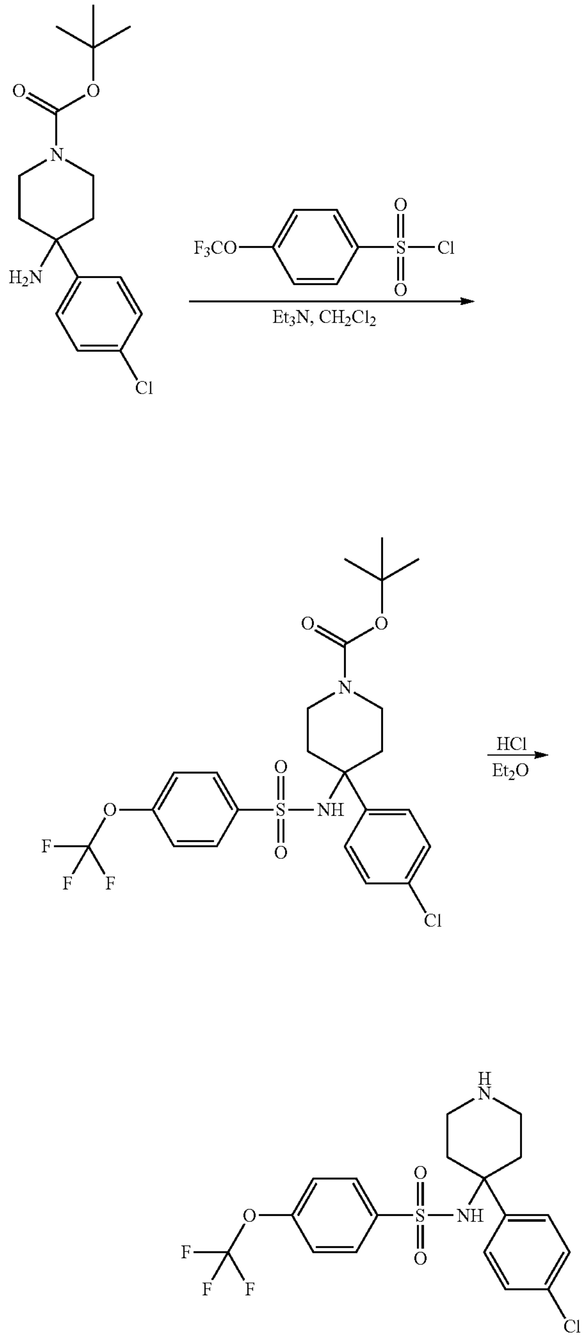

Step 1: Synthesis of tert-butyl 4-(4-chlorophenyl)-4-((4-(trifluoromethoxy)phenyl)sulfonamido)piperidine-1-carboxylate

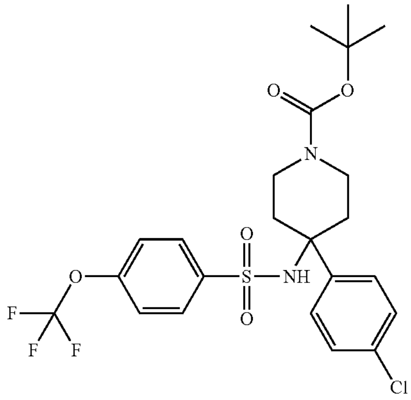 [SMILES: CC(C)(C)OC(=O)N1CCC(NS(=O)(=O)c2ccc(OC(F)(F)F)cc2)(c2ccc(Cl)cc2)CC1]

In a vial, to a stirred suspension of tert-butyl 4-amino-4-(4-chlorophenyl)piperidine-1-carboxylate (200 mg, 0.643 mmol) in DCM (6.4844 mL) at room temperature were added successively triethylamine (0.45 mL, 3.22 mmol), 4-(trifluoromethoxy)benzenesulfonyl chloride (98%, 168 μL, 0.968 mmol) and N,N-dimethylpyridin-4-amine (16 mg, 0.129 mmol). The reaction mixture was stirred at this temperature for 1 h and then it was heated at 40° C. overnight. The reaction mixture was diluted with DCM and a saturated aqueous solution of $NaHCO_3$. The layers were separated. The aqueous layer was extracted with DCM. The combined organic layers were washed with a saturated aqueous solution of NaCl, dried using a phase separator and concentrated under reduced pressure. The crude was purified by flash chromatography on silica gel using a gradient of EtOAc in heptane from 0% to 100%. The desired fractions were combined and concentrated to afford the title compound as a white foam (327.3 mg, 95.08% yield, 98.74% purity, $t_r$=1.06 min). LCMS (Method E): m/z found 435.2 $[M-Boc+H]^+$; $^1$H-NMR (400 MHz, DMSO-$d_6$) δ (ppm) 8.22 (s, 1H), 7.43-7.35 (m, 2H), 7.23 (d, J=8.1 Hz, 2H), 7.10 (d, J=8.7 Hz, 2H), 6.99 (d, J=8.6 Hz, 2H), 3.69 (d, J=13.4 Hz, 2H), 3.23 (s, 2H), 2.35 (d, J=13.5 Hz, 2H), 1.72 (t, J=10.4 Hz, 2H), 1.40 (s, 9H).

Step 2: Synthesis of N-(4-(4-chlorophenyl)piperidin-4-yl)-4-(trifluoromethoxy)benzenesulfonamide (45)

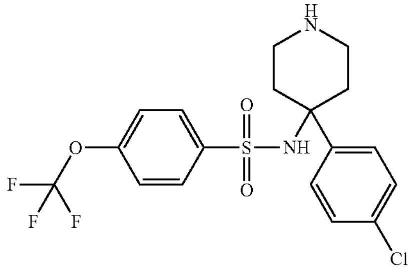 [SMILES: O=S(=O)(NC1(c2ccc(Cl)cc2)CCNCC1)c1ccc(OC(F)(F)F)cc1]

In a round-bottomed flask, to a stirred solution of 4 M hydrogen chloride in dioxane (9.0 mL, 36.0 mmol) in diethyl ether (20 mL) was added tert-butyl 4-(4-chlorophenyl)-4-[[4-(trifluoromethoxy)phenyl]sulfonylamino]piperidine-1-carboxylate (293 mg, 0.548 mmol). The mixture was stirred overnight at rt then filtered and washed with diethyl ether to afford the hydrochloride salt of the title compound as a white powder (190.5 mg, 73.799% yield, 100% purity, $t_r$=1.62 min). LCMS (Method C): m/z found 434.8 $[M+H]^+$; $^1$H-NMR (DMSO-$d_6$, 500 MHz) δ (ppm) 8.87-8.64 (m, 2H), 8.51 (br s, 1H), 7.37 (d, J=9.0 Hz, 2H), 7.22 (d, J=8.3 Hz, 2H), 7.12-7.06 (m, 2H), 7.04-6.97 (m, 2H), 3.27-3.14 (m, 4H), 2.57 (br d, J=13.7 Hz, 2H), 2.08-1.98 (m, 2H).

Example 10: N-(3-phenylazetidin-3-yl)-4-(trifluoromethoxy)benzenesulfonamide (46)

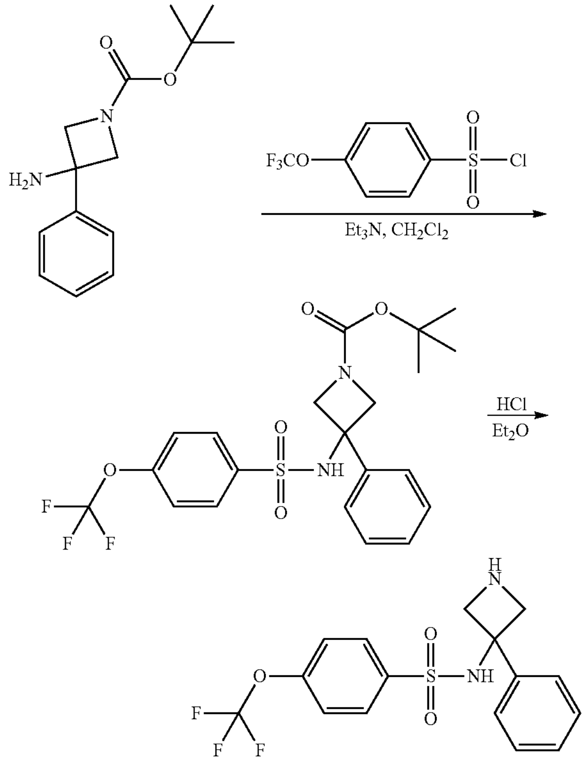

Step 1: Synthesis of tert-butyl 3-phenyl-3-((4-(trifluoromethoxy)phenyl)sulfonamido)azetidine-1-carboxylate

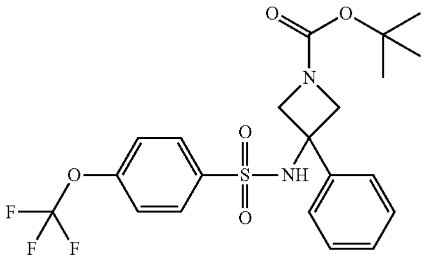 [SMILES: CC(C)(C)OC(=O)N1CC(NS(=O)(=O)c2ccc(OC(F)(F)F)cc2)(c2ccccc2)C1]

In a sealed tube under nitrogen, a solution of 4-(trifluoromethoxy)benzenesulfonyl chloride (105 mg, 0.403 mmol) in dry THF (500 μL) was added to a stirred solution of tert-butyl 3-amino-3-phenylazetidine-1-carboxylate (100 mg, 0.403 mmol) and pyridine (65 μL, 0.805 mmol) in THF (1 mL). The mixture was stirred at rt for 16 h, then diluted with half saturated aqueous $NaHCO_3$ and EtOAc. The aqueous layer was extracted with EtOAc. The combined organic layers were washed with brine, dried over sodium sulfate, filtered and concentrated. The crude was purified by flash chromatography on silica gel using a gradient of (MeOH+2% $NH_4OH$) in DCM from 0.2% to 5% to afford the title compound as a white solid (92 mg, 48% yield, $t_r$=0.99 min). LCMS (Method E): m/z found 417.3 $[M-Boc+H]^+$; $^1$H-NMR (DMSO-$d_6$, 400 MHz) δ (ppm) 9.07 (s, 1H), 7.43-7.36 (m, 2H), 7.23 (d, J=8.0 Hz, 2H), 7.16-7.09 (m, 2H), 7.09-7.03 (m, 3H), 4.32-4.11 (m, 4H), 1.37 (s, 9H).

Step 2: Synthesis of N-(3-phenylazetidin-3-yl)-4-(trifluoromethoxy)benzenesulfonamide (46)

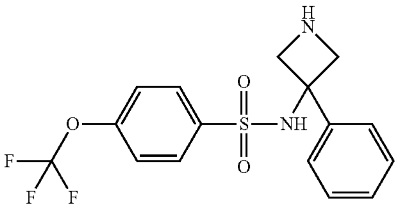 [SMILES: O=S(=O)(NC1(c2ccccc2)CNC1)c1ccc(OC(F)(F)F)cc1]

In a sealed tube under nitrogen, 4 M hydrogen chloride in dioxane (79 μL, 0.317 mmol) was added to a stirred solution of tert-butyl 3-phenyl-3-[[4-(trifluoromethoxy)phenyl]sulfonylamino]azetidine-1-carboxylate (100%, 30 mg, 0.0635 mmol) in 1,4-dioxane (500 μL). The mixture was stirred at rt for 16 h and additional 4 M hydrogen chloride in dioxane (159 μL, 0.635 mmol) was added. The mixture was stirred at rt for 24 h. The suspension was diluted with $Et_2O$ (2 mL), stirred at rt 2 h then filtered. The residue was washed with $Et_2O$ and dried under reduced pressure at 60° C. for 64 h to afford the hydrochloride salt of the title compound as a white powder (23 mg, 88% yield, 99.8% purity, $t_r$=1.17 min). LCMS (Method C): m/z found 373 $[M+H]^+$; $^1$H-NMR (DMSO-$d_6$, 500 MHz) δ (ppm) 8.5-10.3 (m, 3H), 7.32 (d, 2H, J=8.8 Hz), 7.17 (d, 2H, J=8.1 Hz), 7.0-7.1 (m, 5H), 4.41 (s, 4H).

Example 11: N-(3-(4-chlorophenyl)azetidin-3-yl)-4-(trifluoromethoxy)benzenesulfonamide (47)

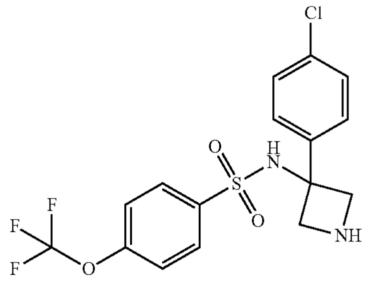 [SMILES: O=S(=O)(NC1(c2ccc(Cl)cc2)CNC1)c1ccc(OC(F)(F)F)cc1]

Step 1: Synthesis of benzyl 3-(4-chlorophenyl)-3-hydroxy-azetidine-1-carboxylate

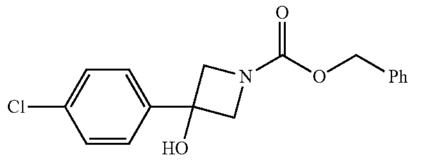 [SMILES: O=C(OCc1ccccc1)N1CC(O)(c2ccc(Cl)cc2)C1]

A sealed vial was charged with 3-(4-chlorophenyl)azetidinium-3-ol 2,2,2 trifluoroacetate (500 mg, 1.68 mmol) and DIPEA (1.2 mL, 6.72 mmol) in anhydrous ACN (6 mL). Benzyl chloromformate (263 µL, 1.85 mmol) was added dropwise at 0° C. and the reaction mixture was stirred at room temperature for 2 h. The reaction mixture was quenched with a saturated aqueous solution of ammonium chloride (15 mL) and ethyl acetate (15 mL) and water (10 mL) were added. The aqueous layer was extracted with ethyl acetate (1×15 mL). The combined organic layers were washed with a saturated aqueous solution of sodium chloride, dried over sodium sulfate, filtered and concentrated under reduced pressure. The residue was purified by flash chromatography on silica gel using a gradient of methanol in dichloromethane from 1% to 5% to afford the title compound as a beige powder (530 mg, 100% purity, 99% yield, $t_r$=0.90 min). LCMS (Method E): m/z found 318.1 $[M+H]^+$; 1H-NMR (DMSO-$d_6$, 400 MHz): δ (ppm) 7.56-7.50 (m, 2H), 7.47-7.42 (m, 2H), 7.40-7.29 (m, 5H), 6.50 (s, 1H), 5.10 (s, 2H), 4.13 (s, 4H).

Step 2: Synthesis of benzyl 3-(4-chlorophenyl)-3-methylsulfonyloxy-azetidine-1-carboxylate

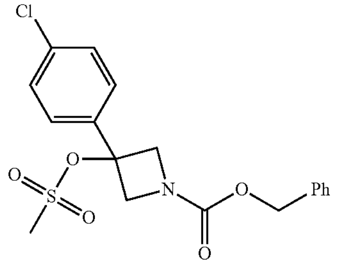 [SMILES: CS(=O)(=O)OC1(c2ccc(Cl)cc2)CN(C(=O)OCc2ccccc2)C1]

In a sealed vial, to a stirred solution of benzyl 3-(4-chlorophenyl)-3-hydroxy-azetidine-1-carboxylate (100%, 460 mg, 1.45 mmol) in anhydrous DCM (8 mL) at room temperature under nitrogen were added successively triethylamine (404 µL, 2.90 mmol) and methanesulfonyl chloride (100%, 225 µL, 2.90 mmol). The reaction mixture was stirred at room temperature for 2 h. The reaction mixture was concentrated under reduced pressure and dried under vacuum to afford the title compound as a brown oil (585 mg, 92% purity, 94% yield, $t_r$=1.01 min). LCMS (Method D); $^1$H-NMR (Chloroform-d, 400 MHz): δ (ppm) 7.44 (s, 4H), 7.39-7.28 (m, 5H), 5.10 (s, 2H), 4.72-4.47 (m, 4H), 2.55 (s, 3H).

Step 3: Synthesis of benzyl 3-azido-3-(4-chlorophenyl)azetidine-1-carboxylate

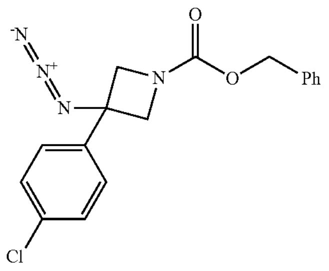

A sealed vial was charged with benzyl 3-(4-chlorophenyl)-3-methylsulfonyloxy-azetidine-1-carboxylate (570 mg, 1.44 mmol) in a mixture of anhydrous DCM (1.5 mL) and anhydrous DMF (8 mL). $NaN_3$ (281 mg, 4.32 mmol) was added at room temperature and the reaction mixture was stirred at 50° C. for 18 h. The reaction mixture was quenched with a saturated aqueous solution of ammonium chloride (2 mL) and water (2 mL) and dichloromethane (5 mL) were added. The aqueous layer was extracted with dichloromethane (1×3 mL). The combined organic layers were dried over sodium sulfate, filtered and concentrated under reduced pressure. The crude was purified by flash chromatography on silica gel using a gradient of ethyl acetate in cyclohexane from 10% to 40% to afford the title compound as a yellow oil (279 mg, 100% purity, 57% yield, $t_r$=1.02 min). LCMS (Method E): m/z found 343.3 $[M+H]^+$; $^1$H-NMR (DMSO-$d_6$, 400 MHz): δ (ppm) 7.63-7.45 (m, 4H), 7.42-7.23 (m, 5H), 5.08 (d, J=2.2 Hz, 2H), 4.79-4.17 (m, 4H).

Step 4: Synthesis of benzyl 3-amino-3-(4-chlorophenyl)azetidine-1-carboxylate

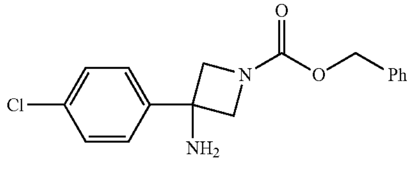 [SMILES: NC1(c2ccc(Cl)cc2)CN(C(=O)OCc2ccccc2)C1]

In a round bottomed flask under nitrogen, triphenylphosphine (211 mg, 0.805 mmol) then 4-methylbenzenesulfonic acid (459 mg, 2.42 mmol) were added to a stirred solution of benzyl 3-azido-3-(4-chlorophenyl)azetidine-1-carboxylate (276 mg, 0.805 mmol) in THF (3.4 mL). The mixture was stirred at rt for 1.5 h. The suspension was filtered, washed with THF (5 mL) and dried under vacuum for 18 h to afford the title compound as a white powder (263 mg, 100% purity, 67% yield, $t_r$=0.61 min). LCMS (Method E): m/z found 317.2 $[M+H]^+$; $^1$H-NMR (DMSO-$d_6$, 400 MHz): δ (ppm) 8.88 (s, 3H), 7.61-7.52 (m, 4H), 7.51-7.45 (m, 2H), 7.42-7.30 (m, 5H), 7.11 (d, J=7.8 Hz, 2H), 5.10 (s, 2H), 4.36 (t, J=11.5 Hz, 4H), 2.29 (s, 3H).

Step 5: Synthesis of benzyl 3-(4-chlorophenyl)-3-[[4-(trifluoromethoxy)phenyl]sulfonylamino]azetidine-1-carboxylate

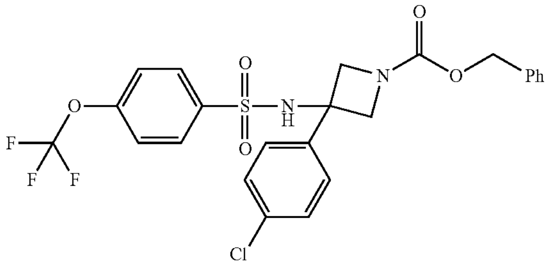 [SMILES: O=C(OCc1ccccc1)N1CC(NS(=O)(=O)c2ccc(OC(F)(F)F)cc2)(c2ccc(Cl)cc2)C1]

A sealed vial under nitrogen was charged with benzyl 3-amino-3-(4-chlorophenyl)azetidine-1-carboxylate 4-methylbenzenesulfonic acid (100 mg, 0.205 mmol) and triethylamine (143 µL, 1.02 mmol) in anhydrous DCM (4 mL). 4-(trifluoromethoxy)benzenesulfonyl chloride (38 µL, 0.225 mmol) was added and the reaction mixture was stirred at room temperature for 22 h and at 40° C. for 3 h. The reaction mixture was quenched with a saturated aqueous solution of ammonium chloride (10 mL) and dichloromethane (5 mL) was added. The aqueous layer was extracted with dichloromethane (1×5 mL). The combined organic layers were dried over sodium sulfate, filtered and concentrated under reduced pressure. The crude was purified by flash chromatography on silica gel using a gradient of methanol in dichloromethane from 0% to 5% to afford the title compound as a beige powder (86 mg, 92% purity, 72% yield, $t_r$=1.03 min). LCMS (Method E): m/z found 541.2 $[M+H]^+$; $^1$H-NMR (DMSO-$d_6$, 400 MHz): δ (ppm) 9.17 (s, 1H), 7.44-7.30 (m, 7H), 7.26 (d, J=8.1 Hz, 2H), 7.18-7.06 (m, 4H), 5.05 (s, 2H), 4.34 (s, 4H).

Step 6: Synthesis of N-[3-(4-chlorophenyl)azetidin-3-yl]-4-(trifluoromethoxy)benzenesulfonamide (47)

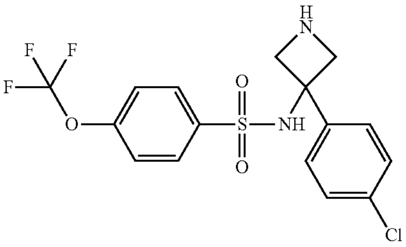 [SMILES: O=S(=O)(NC1(c2ccc(Cl)cc2)CNC1)c1ccc(OC(F)(F)F)cc1]

In a round-bottomed flask, to a stirred suspension of benzyl 3-(4-chlorophenyl)-3-[[4-(trifluoromethoxy)phenyl]sulfonylamino]azetidine-1-carboxylate (80 mg, 0.148 mmol) in acetonitrile (3 mL) at room temperature, was added iodo(trimethyl)silane (63 µL, 0.444 mmol). The reaction mixture was stirred at room temperature for 1 h. The reaction mixture was concentrated under reduced pressure. The crude was purified by flash chromatography on silica gel using a gradient of ammoniacal methanol in dichloromethane from 4% to 15%. The residue was purified by reverse-phase flash chromatography using a gradient of acetonitrile in water from 0% to 100% (+0.1% AcOH in water). The residue was triturated in 4 M HCl in diethyl ether (370 µL, 1.48 mmol) for 3 h, filtered, washed with diethyl ether and dried under vacuum at 70° C. for 16 h to afford the hydrochloride salt of the title compound as a white powder (28.5 mg, 100% purity, 44% yield, $t_r$=1.31 min). LCMS (Method C): m/z found 407 $[M+H]^+$; $^1$H-NMR (DMSO-$d_6$, 400 MHz): δ (ppm) 9.17 (s, 1H), 7.44-7.30 (m, 7H), 7.26 (d, J=8.1 Hz, 2H), 7.18-7.06 (m, 4H), 5.05 (s, 2H), 4.34 (s, 4H).

Example 12: N-(3-(3,4-dichlorophenyl)azetidin-3-yl)-4-(trifluoromethoxy)benzenesulfonamide (48)

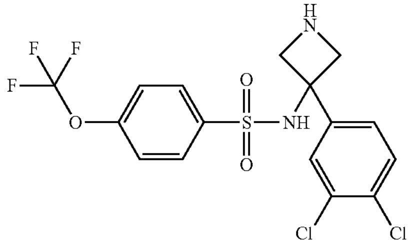 [SMILES: O=S(=O)(NC1(c2ccc(Cl)c(Cl)c2)CNC1)c1ccc(OC(F)(F)F)cc1]

Step 1: Synthesis of benzyl 3-(3,4-dichlorophenyl)-3-hydroxy-azetidine-1-carboxylate

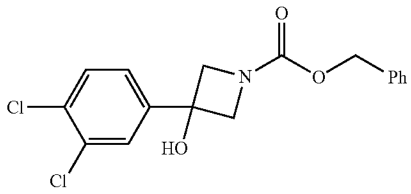 [SMILES: O=C(OCc1ccccc1)N1CC(O)(c2ccc(Cl)c(Cl)c2)C1]

In a three-neck round-bottomed flask, to a stirred suspension of magnesium (113 mg, 4.63 mmol) and iodine crystal (catalytic) in anhydrous THF (2 mL) at rt under nitrogen was added few drops of a solution of 1-bromo-3,4-dichlorobenzene (97%, 0.46 mL, 3.48 mmol) in anhydrous THF (1.5 mL). The reaction was heated at 50° C. until a color change (orange to yellow) was observed. Then, the rest of the solution was added dropwise and was stirred at this temperature for 1 h (until magnesium was consumed). Then the reaction mixture was cooled to 0° C. and a solution of benzyl 3-oxoazetidine-1-carboxylate (95%, 500 mg, 2.31 mmol) in anhydrous THF (1.3 mL) was added dropwise. The reaction mixture was allowed to warm up to rt and was stirred at this temperature overnight. The reaction mixture was poured into a saturated aqueous solution of $NH_4Cl$ and EtOAc was added. The layers were separated. The aqueous layer was extracted twice with EtOAc. The combined organic layers were washed with a saturated aqueous solution of NaCl, dried over sodium sulfate, filtered and concentrated under reduced pressure. The crude was purified by flash chromatography on silica gel using a gradient of EtOAc in heptane from 0% to 75%. The desired fractions were combined and concentrated to afford the title compound as a colorless oil (776.2 mg, 100% purity, 95% yield, $t_r$=0.95 min). LCMS (Method E); $^1$H-NMR (400 MHz, DMSO-$d_6$) δ 7.72 (d, J=2.2 Hz, 1H), 7.65 (d, J=8.4 Hz, 1H), 7.51 (dd, J=8.4, 2.2 Hz, 1H), 7.42-7.36 (m, 4H), 7.36-7.31 (m, 1H), 6.63 (s, 1H), 5.10 (s, 2H), 4.22-4.08 (m, 4H).

Step 2: Synthesis of benzyl 3-(3,4-dichlorophenyl)-3-methylsulfonyloxy-azetidine-1-carboxylate

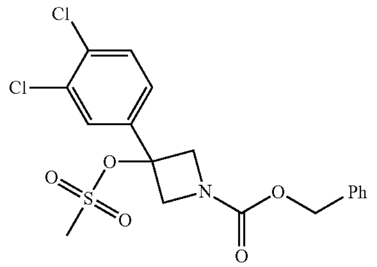 [SMILES: CS(=O)(=O)OC1(c2ccc(Cl)c(Cl)c2)CN(C(=O)OCc2ccccc2)C1]

In a round-bottomed flask, to a stirred solution of benzyl 3-(3,4-dichlorophenyl)-3-hydroxy-azetidine-1-carboxylate (660 mg, 1.87 mmol) in anhydrous DCM (9 mL) at 0° C. under nitrogen were added triethylamine (1.0 mL, 7.17 mmol) and methanesulfonyl chloride (100%, 290 μL, 3.73 mmol). The reaction mixture was stirred at room temperature for 2 h. The reaction mixture was concentrated under reduced pressure to afford the title compound as a yellow gum (137.5 mg). The crude was used directly in the next step without any purification. $^1$H-NMR (400 MHz, DMSO-$d_6$) δ 7.88 (d, J=2.2 Hz, 1H), 7.74 (d, J=8.4 Hz, 1H), 7.59 (dd, J=8.4, 2.2 Hz, 1H), 7.40-7.29 (m, 5H), 5.08 (s, 2H), 4.59-4.49 (m, 4H).

Step 3: Synthesis of benzyl 3-azido-3-(3,4-dichlorophenyl)azetidine-1-carboxylate

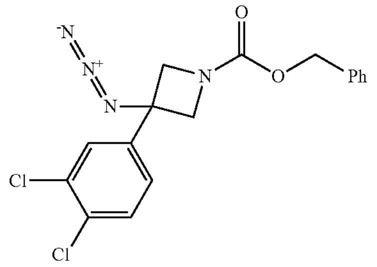

A sealed vial was charged with benzyl 3-(3,4-dichlorophenyl)-3-methylsulfonyloxy-azetidine-1-carboxylate (806 mg, 1.87 mmol) in a mixture of anhydrous DMF (9.2492 mL) and sodium azide (365 mg, 5.62 mmol) was added at 0° C. The reaction mixture was stirred at 50° C. for 18 h. The reaction mixture was quenched with a saturated aqueous solution of ammonium chloride (25 mL) and water (25 mL) and dichloromethane (50 mL) were added. The aqueous layer was extracted with dichloromethane (1×50 mL). The combined organic layers were dried using a phase separator and concentrated under reduced pressure. The crude was purified by flash chromatography on silica gel using a gradient of ethyl acetate in heptane from 0% to 50% to afford the title compound as a colorless oil (577.8 mg, 98% purity, 80.139% yield, $t_r$=1.06 min). LCMS (Method E); $^1$H-NMR (400 MHz, Chloroform-d) δ 7.53-7.48 (m, 2H), 7.40-7.31 (m, 5H), 7.23 (dd, J=8.4, 2.3 Hz, 1H), 5.14 (s, 2H), 4.35 (d, J=1.7 Hz, 4H).

Step 4: Synthesis of benzyl 3-amino-3-(3,4-dichlorophenyl)azetidine-1-carboxylate

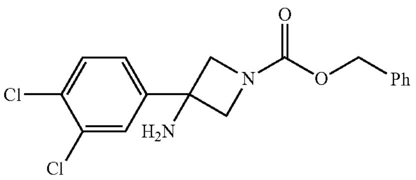 [SMILES: NC1(c2ccc(Cl)c(Cl)c2)CN(C(=O)OCc2ccccc2)C1]

In a round bottomed flask under nitrogen, triphenylphosphine (426 mg, 1.62 mmol), then 4-methylbenzenesulfonic acid (920 mg, 4.84 mmol) were added to a stirred solution of benzyl 3-azido-3-(3,4-dichlorophenyl)azetidine-1-carboxylate (98%, 621 mg, 1.61 mmol) in THF (9 mL). The mixture was stirred at room temperature 2 h. The suspension was filtered, washed with few THF and dried under vacuum for 18 h to afford the title compound as a white powder (596.2 mg, 100% purity, 70.624% yield, $t_r$=0.65 min). LCMS (Method E): m/z found 351.2 [M+H-pTSA]$^+$; $^1$H-NMR (400 MHz, DMSO-$d_6$) δ 8.83 (s, 3H), 7.86-7.74 (m, 2H), 7.53 (dd, J=8.5, 2.3 Hz, 1H), 7.50-7.44 (m, 2H), 7.44-7.29 (m, 5H), 7.11 (d, J=7.8 Hz, 2H), 5.10 (s, 2H), 4.44 (s, 2H), 4.32 (d, J=9.7 Hz, 2H), 2.29 (s, 3H).

Step 5: Synthesis of benzyl 3-(3,4-dichlorophenyl)-3-[[4-(trifluoromethoxy)phenyl]sulfonylamino]azetidine-1-carboxylate

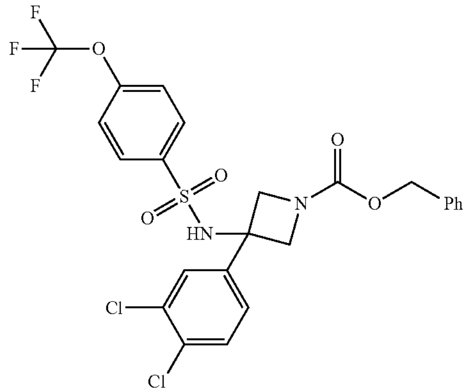 [SMILES: O=C(OCc1ccccc1)N1CC(NS(=O)(=O)c2ccc(OC(F)(F)F)cc2)(c2ccc(Cl)c(Cl)c2)C1]

In a vial, to a stirred suspension of 1-((benzyloxy)carbonyl)-3-(3,4-dichlorophenyl)azetidin-3-aminium 4-methylbenzenesulfonate (202 mg, 0.386 mmol) in DCM (2.5 mL) at room temperature were added successively triethylamine (269 μL, 1.93 mmol), 4-(trifluoromethoxy)benzenesulfonyl chloride (98%, 101 μL, 0.581 mmol) and N,N-dimethylpyridin-4-amine (4.8 mg, 0.0397 mmol). The reaction mixture was heated at 40° C. and was stirred at this temperature for 4 h. The reaction mixture was cooled to room temperature and diluted with a saturated aqueous solution of $NaHCO_3$. The layers were separated. The aqueous layer was extracted twice with DCM. The combined organic layers were washed with a saturated aqueous solution of NaCl, dried using a phase separator and concentrated under reduced pressure. The crude was purified by flash chromatography on silica gel using a gradient of ethyl acetate in heptane from 10% to 100%. The desired fractions were combined and concentrated to afford the title compound as a white solid (79 mg, 98% purity, 36% yield, $t_r$=1.05 min). LCMS (Method E); $^1$H-NMR (400 MHz, DMSO-$d_6$) δ 9.19 (s, 1H), 7.46-7.41 (m, 2H), 7.41-7.25 (m, 9H), 7.19 (dd, J=8.4, 2.2 Hz, 1H), 5.06 (s, 2H), 4.40-4.29 (m, 4H).

Step 6: Synthesis of N-[3-(3,4-dichlorophenyl)azetidin-3-yl]-4-(trifluoromethoxy)benzenesulfonamide (48)

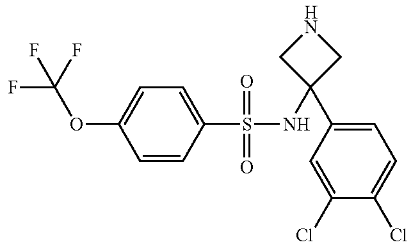 [SMILES: O=S(=O)(NC1(c2ccc(Cl)c(Cl)c2)CNC1)c1ccc(OC(F)(F)F)cc1]

In a round-bottomed flask, to a stirred solution of benzyl 3-(3,4-dichlorophenyl)-3-[[4-(trifluoromethoxy)phenyl]sulfonylamino]azetidine-1-carboxylate (79 mg, 0.137 mmol) in anhydrous ACN (2 mL) at room temperature, was added iodo(trimethyl)silane (58 μL, 0.408 mmol). The reaction mixture was stirred at room temperature for 1.5 h. The reaction mixture was concentrated under reduced pressure and dried under vacuum. The residue was triturated in acetonitrile, filtered, washed with acetonitrile and dried under vacuum at rt overnight. To the residue was added water, triethylamine (96 μL, 0.689 mmol) and methyl tetrahydrofuran. The layers were separated. The organic layer was washed one more time with water and triethylamine (96 μL, 0.689 mmol). The combined aqueous layers were washed once with methyl tetrahydrofuran. The combined organic layers were dried over $Na_2SO_4$, filtered and concentrated under reduced pressure. To the residue was added diethyl ether and 2 M hydrogen chloride in $Et_2O$ (0.69 mL, 1.37 mmol). The resulting suspension was stirred at room temperature overnight, filtered, washed with diethyl ether and dried under vacuum at 45° C. for 18 h to afford the hydrochloride salt of the title compound as a white powder (34.4 mg, 96.57% purity, 51% yield, $t_r$=1.64 min). LCMS (Method C): m/z found 441 $[M+H]^+$; $^1$H-NMR (500 MHz, DMSO-$d_6$) δ 10.12-8.76 (m, 3H), 7.40 (s, 2H), 7.36-7.32 (m, 1H), 7.31-7.28 (m, 1H), 7.27-7.23 (m, 2H), 7.19-7.12 (m, 1H), 4.55-4.29 (m, 4H).

Example 13: N-(4-(3,4-dichlorophenyl)piperidin-4-yl)-4-(trifluoromethoxy)benzenesulfonamide (49)

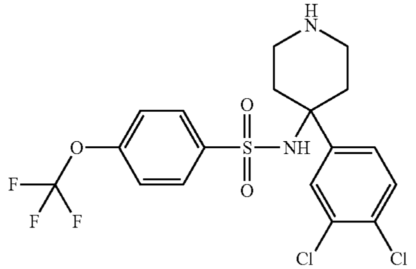 [SMILES: O=S(=O)(NC1(c2ccc(Cl)c(Cl)c2)CCNCC1)c1ccc(OC(F)(F)F)cc1]

Step 1: Synthesis of benzyl 4-oxopiperidine-1-carboxylate

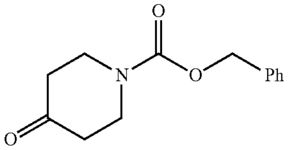 [SMILES: O=C1CCN(C(=O)OCc2ccccc2)CC1]

In a round-bottomed flask, to a stirred solution of piperidin-4-one hydrochloride (1:1) (98%, 3.00 g, 21.7 mmol) and DIPEA (23 mL, 0.132 mol) in DCM (70 mL) at room temperature under nitrogen were added benzyl chloroformate (6.2 mL, 43.6 mmol) and DMAP (265 mg, 2.17 mmol). The reaction mixture was stirred at room temperature for 5 h. The reaction mixture was quenched with a saturated aqueous solution of ammonium chloride. Then dichloromethane and water were added. The layers were separated. The aqueous layer was extracted twice with dichloromethane. The combined organic layers were washed once with a saturated aqueous solution of NaCl, dried using a phase separator and concentrated under reduced pressure. The crude was purified by flash chromatography on silica gel using a gradient of ethyl acetate in cyclohexane from 10% to 75% to afford the title compound as a yellow oil (3.89 g, 100% purity, 77% yield, $t_r$=0.71 min). LCMS (Method D); $^1$H-NMR (400 MHz, DMSO-$d_6$) δ 7.43-7.35 (m, 4H), 7.37-7.30 (m, 1H), 5.13 (s, 2H), 3.70 (t, J=6.1 Hz, 4H), 2.40 (t, J=6.3 Hz, 4H).

Step 2: Synthesis of benzyl 4-(3,4-dichlorophenyl)-4-hydroxy-piperidine-1-carboxylate

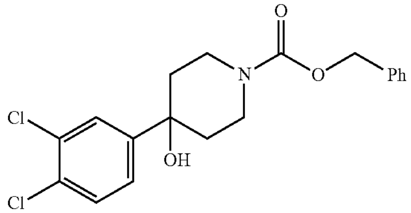

In a three-neck round-bottomed flask, to a stirred suspension of magnesium (198 mg, 8.15 mmol) and iodine crystal in anhydrous THF (6.8 mL) at room temperature under nitrogen was added few drops of a solution of 1-bromo-3,4-dichlorobenzene (97%, 823 μL, 6.23 mmol) in anhydrous THF (3 mL). The reaction was heated at 50° C. until decoloration (orange to colorless) was observed. Then, the rest of the solution was added dropwise and was stirred at 50° C. for 1 h (until magnesium was consumed). Then the reaction mixture was cooled to 0° C. and a solution of benzyl 4-oxopiperidine-1-carboxylate (1.00 g, 4.29 mmol) in anhydrous THF (3 mL) was added dropwise at 0° C. The reaction mixture was allowed to warm up to room temperature and stirred at room temperature overnight. The reaction mixture was poured into a saturated aqueous solution of ammonium chloride. The aqueous layer was extracted three times with ethyl acetate. The combined organic layers were washed with a saturated aqueous solution of sodium chloride, dried over sodium sulfate, filtered and concentrated under reduced pressure. The crude was purified by flash chromatography on silica gel using a gradient of ethyl acetate in heptane from 10% to 100% to afford the title compound as white solid (1.04 g, 98% purity, 63% yield, $t_r$=1.00 min). LCMS (Method D); $^1$H-NMR (400 MHz, DMSO-$d_6$) δ 7.71 (d, J=2.1 Hz, 1H), 7.58 (d, J=8.5 Hz, 1H), 7.46 (dd, J=8.5, 2.1 Hz, 1H), 7.40-7.36 (m, 4H), 7.36-7.30 (m, 1H), 5.36 (s, 1H), 5.10 (s, 2H), 3.95 (dd, J=13.4, 3.3 Hz, 2H), 3.28-3.09 (m, 2H), 1.86 (td, J=13.1, 4.8 Hz, 2H), 1.57 (d, J=13.2 Hz, 2H).

Step 3: Synthesis of benzyl 4-azido-4-(3,4-dichlorophenyl)piperidine-1-carboxylate

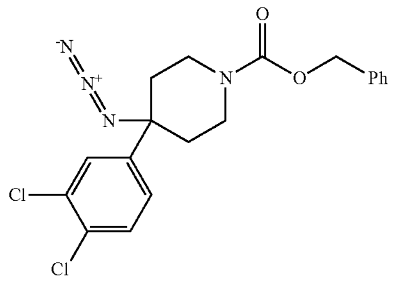

In a three neck round-bottom flask, a solution of benzyl 4-(3,4-dichlorophenyl)-4-hydroxy-piperidine-1-carboxylate (300 mg, 0.789 mmol) in anhydrous DCM (3.6 mL) was added dropwise at 0° C. to a solution of azido(trimethyl) silane (126 μL, 0.949 mmol) and $BF_3$ etherate (585 μL, 4.74 mmol) in anhydrous DCM (2 mL). The reaction mixture was allowed to warm up to room temperature and stirred at this temperature overnight. The reaction mixture was poured in a saturated aqueous solution of $NaHCO_3$ (50 mL). The aqueous layer was extracted three times with dichloromethane. The combined organic layers were washed with a saturated aqueous solution of NaCl, dried using a phase separator and concentrated under reduced pressure to afford the title compound as a colorless oil (301.9 mg, 60% purity, 57% yield, $t_r$=1.12 min). LCMS (Method E); $^1$H-NMR (400 MHz, DMSO-$d_6$) δ 7.78 (d, J=2.3 Hz, 1H), 7.72 (d, J=8.5 Hz, 1H), 7.54 (dd, J=8.5, 2.3 Hz, 1H), 7.41-7.30 (m, 5H), 5.10 (s, 2H), 3.95 (d, J=13.3 Hz, 2H), 3.30-3.07 (m, 2H), 2.06-1.94 (m, 4H). The product was obtained as an inseparable mixture with benzyl 4-(3,4-dichlorophenyl)-3,6-dihydro-2H-pyridine-1-carboxylate.

Step 4: Synthesis of benzyl 4-amino-4-(3,4-dichlorophenyl)piperidine-1-carboxylate

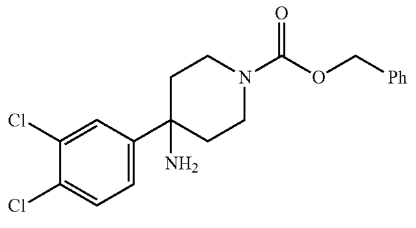 [SMILES: NC1(c2ccc(Cl)c(Cl)c2)CCN(C(=O)OCc2ccccc2)CC1]

In a round bottomed flask under nitrogen, triphenylphosphine (134 mg, 0.512 mmol) then p-toluenesulfonic acid (255 mg, 1.34 mmol) were added to a stirred solution of a inseparable mixture of benzyl 4-azido-4-(3,4-dichlorophenyl)piperidine-1-carboxylate (60%, 302 mg, 0.447 mmol) and benzyl 4-(3,4-dichlorophenyl)-3,6-dihydro-2H-pyridine-1-carboxylate (40%, 302 mg, 0.333 mmol) in THF (2.1 mL). The mixture was stirred at room temperature overnight. The suspension was filtered, washed with few THF. The filtrate was concentrated and purified by reverse-phase chromatography (C18Aq-100 g) using a gradient of acetonitrile in water from 0% to 100% (0.1% AcOH in water and acetonitrile). The desired fractions were combined and concentrated to afford the title compound as a colorless oil (84.9 mg, 84% purity, 42% yield, $t_r$=0.67 min). LCMS (Method E); $^1$H-NMR (400 MHz, DMSO-$d_6$) δ 7.86 (d, J=2.3 Hz, 1H), 7.72 (d, J=8.6 Hz, 1H), 7.57 (dd, J=8.6, 2.3 Hz, 1H), 7.40-7.30 (m, 5H), 7.11 (d, J=7.8 Hz, 2H), 5.09 (s, 2H), 3.70-3.57 (m, 2H), 3.39-3.33 (m, 2H), 2.35-2.20 (m, 2H), 1.90-1.77 (m, 2H).

Step 5: Synthesis of benzyl 4-(3,4-dichlorophenyl)-4-[[4-(trifluoromethoxy)phenyl]sulfonylamino]piperidine-1-carboxylate

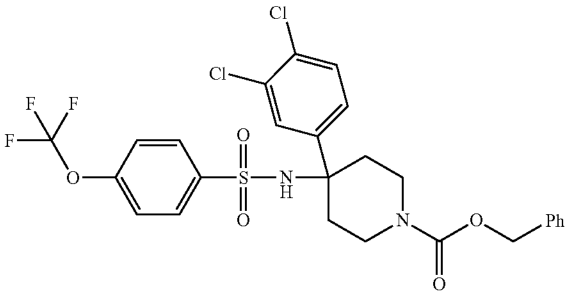 [SMILES: O=C(OCc1ccccc1)N1CCC(NS(=O)(=O)c2ccc(OC(F)(F)F)cc2)(c2ccc(Cl)c(Cl)c2)CC1]

In a vial, to a stirred suspension of benzyl 4-amino-4-(3,4-dichlorophenyl)piperidine-1-carboxylate (84%, 87 mg, 0.192 mmol) in DCM (1.9 mL) at room temperature were added successively triethylamine (134 μL, 0.961 mmol), 4-(trifluoromethoxy)benzenesulfonyl chloride (98%, 50 μL, 0.290 mmol) and N,N-dimethylpyridin-4-amine (2.4 mg, 0.0198 mmol). The reaction mixture was stirred at this temperature for 1 h and then it was heated at 40° C. overnight. The reaction mixture was cooled to room temperature and diluted with a saturated aqueous solution of $NaHCO_3$. The layers were separated. The aqueous layer was extracted twice with DCM. The combined organic layers were washed with a saturated aqueous solution of NaCl, dried using a phase separator and concentrated under reduced pressure. The crude was purified by flash chromatography on silica gel using a gradient of methanol in dichloromethane from 0.5% to 10%. The desired fractions were combined and concentrated to afford the title compound as a colorless gum (51 mg, 93% purity, 41% yield, $t_r$=1.08 min). LCMS (Method E); $^1$H-NMR (400 MHz, DMSO-$d_6$) δ 8.28 (s, 1H), 7.46-7.41 (m, 2H), 7.40-7.29 (m, 5H), 7.28-7.22 (m, 4H), 7.13 (dd, J=8.5, 2.2 Hz, 1H), 5.08 (s, 2H), 3.87-3.76 (m, 2H), 3.31-3.24 (m, 2H), 2.41-2.32 (m, 2H), 1.86-1.72 (m, 2H).

Step 6: Synthesis of N-[4-(3,4-dichlorophenyl)-4-piperidyl]-4-(trifluoromethoxy)benzenesulfonamide (49)

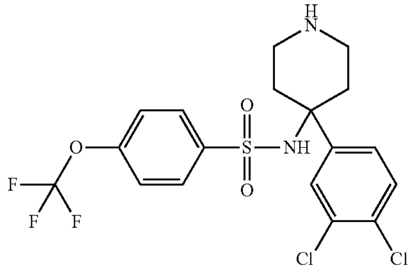 [SMILES: O=S(=O)(NC1(c2ccc(Cl)c(Cl)c2)CCNCC1)c1ccc(OC(F)(F)F)cc1]

In a round-bottomed flask, to a stirred solution of benzyl 4-(3,4-dichlorophenyl)-4-[[4-(trifluoromethoxy)phenyl]sulfonylamino]piperidine-1-carboxylate (51 mg, 0.0845 mmol) in Acetonitrile (1.3 mL) at room temperature, was added iodo(trimethyl)silane (36 μL, 0.254 mmol). The reaction mixture was stirred at room temperature for 1.5 h. The reaction mixture was concentrated under reduced pressure and dried under vacuum The crude was dry loaded onto decalite and purified by flash chromatography on silica gel using a gradient of methanol (0.7 N $NH_3$) in dichloromethane from 1% to 20%. The desired fractions were combined and washed with water and triethylamine (59 μL, 0.423 mmol). The aqueous layer was extracted once with dichloromethane. The combined organic layers were dried over sodium sulfate, filtered and concentrated under reduced pressure. The residue was purified by reverse-phase preparative chromatography (C18Aq 30 g) using a gradient of acetonitrile in water from 0% to 100% (0.1% AcOH in both). The desired fractions were combined and concentrated. Exchange salt (acetate to chlorhydrate) of the residue was performed in diethyl ether, then a solution of 2 M hydrogen chloride in $Et_2O$ (0.43 mL, 0.850 mmol) and was stirred at rt overnight. The suspension was filtered, washed with diethyl ether and dried at 45° C. over the weekend to afford the hydrochloride salt of the title compound as a white powder (20.4 mg, 99.75% purity, 48% yield, $t_r$=1.49 min). LCMS (Method C): m/z found 469 $[M+H]^+$; $^1$H-NMR (500 MHz, DMSO-$d_6$) δ 8.70 (br d, J=0.7 Hz, 2H), 8.51 (s, 1H), 7.43 (d, J=8.8 Hz, 2H), 7.32-7.27 (m, 1H), 7.27-7.22 (m, 3H), 7.17-7.09 (m, 1H), 3.23 (br d, J=6.4 Hz, 4H), 2.54 (br s, 2H), 2.13-1.95 (m, 2H).

Example 14: N-(4-phenylpiperidin-4-yl)-4-(trifluoromethoxy)benzenesulfonamide (50)

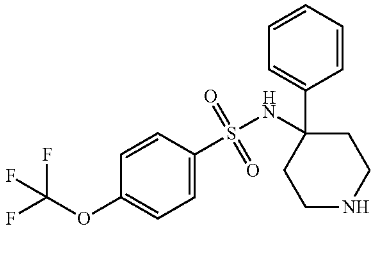 [SMILES: O=S(=O)(NC1(c2ccccc2)CCNCC1)c1ccc(OC(F)(F)F)cc1]

Step 1: Synthesis of tert-butyl 4-phenyl-4-[[4-(trifluoromethoxy)phenyl]sulfonylamino]piperidine-1-carboxylate

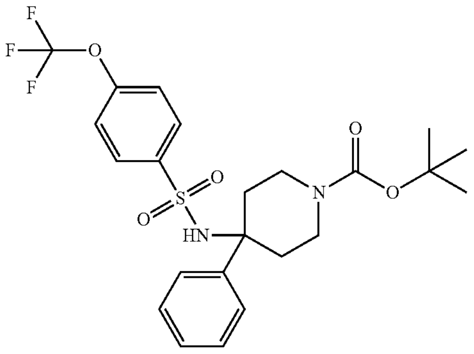 [SMILES: CC(C)(C)OC(=O)N1CCC(NS(=O)(=O)c2ccc(OC(F)(F)F)cc2)(c2ccccc2)CC1]

A sealed vial was charged with tert-butyl 4-amino-4-phenylpiperidine-1-carboxylate (150 mg, 0.543 mmol), DMAP (13 mg, 0.109 mmol) and triethylamine (303 μL, 2.17 mmol) in DCM (9 mL). 4-(trifluoromethoxy)benzenesulfonyl chloride (101 μL, 0.597 mmol) was added and the reaction mixture was stirred at 40° C. for 18 h. The reaction mixture was quenched with a saturated aqueous solution of ammonium chloride (5 mL) and water (15 mL) and dichloromethane (10 mL) were added. The aqueous layer was extracted with dichloromethane (1×15 mL). The combined organic layers were dried over sodium sulfate, filtered and concentrated under reduced pressure. The crude was purified by flash chromatography on silica gel using a gradient of methanol in dichloromethane from 0% to 5% to afford the title compound as a white powder (266 mg, 98% purity, 96% yield, $t_r$=1.03 min). LCMS (Method E): m/z found 523.3 $[M+Na]^+$; $^1$H-NMR (DMSO-$d_6$, 400 MHz): δ (ppm) 8.16 (s, 1H), 7.40-7.30 (m, 2H), 7.17 (d, J=8.1 Hz, 2H), 7.08 (dd, J=7.7, 1.8 Hz, 2H), 7.00-6.89 (m, 3H), 3.70 (d, J=13.4 Hz, 2H), 3.24 (s, 2H), 2.38 (d, J=13.6 Hz, 2H), 1.73 (t, J=10.5 Hz, 2H), 1.40 (s, 9H).

Step 2: Synthesis of N-(4-phenyl-4-piperidyl)-4-(trifluoromethoxy)benzenesulfonamide

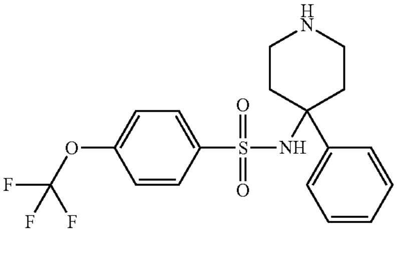 [SMILES: O=S(=O)(NC1(c2ccccc2)CCNCC1)c1ccc(OC(F)(F)F)cc1]

In a round-bottomed flask, to a stirred solution of 2 M hydrogen chloride in diethyl ether (15 mL, 30.0 mmol) was added tert-butyl 4-phenyl-4-[[4-(trifluoromethoxy)phenyl]sulfonylamino]piperidine-1-carboxylate (265 mg, 0.529 mmol). The mixture was stirred for 18 h at room temperature then filtered and washed with diethyl ether to afford the hydrochloride salt of the title compound as a white powder (175.8 mg, 99.9% purity, 77% yield, $t_r$=1.71 min). LCMS (Method C): m/z found 401.0 $[M+H]^+$; $^1$H-NMR (500 MHz, DMSO-$d_6$, 300K) 6 ppm 8.79 (br s, 2H), 8.43 (br s, 1H), 7.28-7.36 (m, 2H), 7.12-7.19 (m, 2H), 7.04-7.10 (m, 2H), 6.91-7.03 (m, 3H), 3.12-3.29 (m, 4H), 2.59 (br d, J=13.7 Hz, 2H), 1.98-2.10 (m, 2H).

Example 15: rac N-((3R,4R)-4-(3,4-dichlorophenyl) pyrrolidin-3-yl)-4-(trifluoromethoxy)benzenesulfonamide (51)

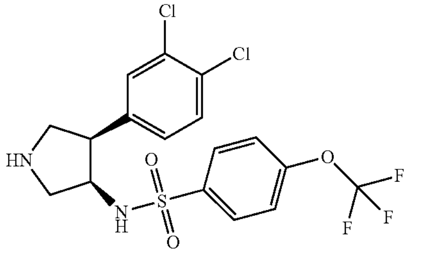 [SMILES: O=S(=O)(N[C@H]1CNC[C@H]1c1ccc(Cl)c(Cl)c1)c1ccc(OC(F)(F)F)cc1]

Step 1: Synthesis of tert-butyl rac-(3R,4S)-3-(3,4-dichlorophenyl)-4-hydroxy-pyrrolidine-1-carboxylate

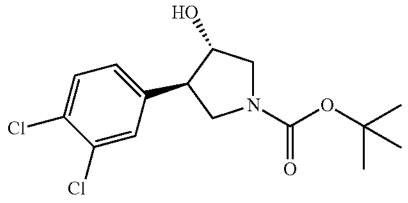 [SMILES: CC(C)(C)OC(=O)N1C[C@@H](O)[C@H](c2ccc(Cl)c(Cl)c2)C1]

In a three necked round bottomed flask equipped with a thermometer and a reflux condenser, under nitrogen, a suspension of copper(I) iodide (93 mg, 0.486 mmol) and iodine (25 mg, 0.0972 mmol) in dry THF (18 mL) was stirred at rt. A few drops of a solution of 1-bromo-3,4-dichlorobenzene (2493 μL, 19.4 mmol) in dry THF (18 mL) were added and the mixture was stirred with progressive heating until discoloration of the mixture (60° C.). The rest of the solution was added dropwise over 20 sec and the mixture was stirred at 60° C. until magnesium was consumed (30 min). The mixture was stirred at 0° C., magnesium (520 mg, 21.4 mmol) was added then a solution of tert-butyl 6-oxa-3-azabicyclo[3.1.0]hexane-3-carboxylate (1.80 g, 9.72 mmol) in dry THF (9 mL) was added dropwise over 20 seconds. The mixture was stirred at rt for 2 h and was cooled to 0° C. The mixture was quenched with saturated aqueous $NH_4Cl$ and extracted twice with EtOAc. The combined organic layers were washed with brine, dried over sodium sulfate, filtered and concentrated. The crude was purified by flash chromatography on silica gel using a gradient of EtOAc in heptane from 5% to 30%. The desired fractions were concentrated and purified by reverse phase chromatography on silica gel using a gradient of (MeCN+0.2% AcOH) in ($H_2O$+0.2% AcOH) from 0% to 100%. The desired fractions were combined and ACN was evaporated. The mixture was basified with aqueous saturated $NaHCO_3$ and extracted three times with DCM. The combined organic layers were washed with brine, dried over sodium sulfate, filtered and concentrated to afford the title compound as a white foam (1.32 g, >95% purity, 24% yield, $t_r$=0.93 min). LCMS (Method E): m/z found 276.1 $[M-tBu+H]^+$; $^1$H-NMR (DMSO-$d_6$, 400 MHz): δ (ppm) 7.64-7.52 (m, 2H), 7.30 (dd, J=8.4, 2.1 Hz, 1H), 5.34 (d, J=5.3 Hz, 1H), 4.22 (p, J=6.7 Hz, 1H), 3.71 (dd, J=10.6, 7.8 Hz, 1H), 3.57 (dd, J=10.8, 6.6 Hz, 1H), 3.31-3.24 (m, 1H), 3.24-3.11 (m, 1H), 3.11-2.96 (m, 1H), 1.41 (d, J=3.9 Hz, 9H).

Step 2: Synthesis of tert-butyl rac-(3R,4S)-3-(3,4-dichlorophenyl)-4-methylsulfonyloxy-pyrrolidine-1-carboxylate

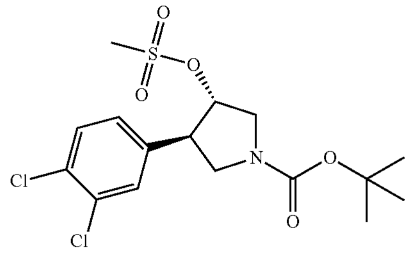 [SMILES: CC(C)(C)OC(=O)N1C[C@@H](OS(C)(=O)=O)[C@H](c2ccc(Cl)c(Cl)c2)C1]

In a round bottomed flask under nitrogen, a solution of tert-butyl rac-(3R,4S)-3-(3,4-dichlorophenyl)-4-hydroxy-pyrrolidine-1-carboxylate (100%, 470 mg, 1.41 mmol) and triethylamine (394 μL, 2.83 mmol) in dry DCM (10 mL) was stirred at 0° C. Methanesulfonyl chloride (164 μL, 2.12 mmol) was added dropwise and the mixture was stirred at 0° C. for 10 min and at rt for 3 h. The mixture was washed twice with saturated aqueous $NaHCO_3$, the combined aqueous layers were extracted with DCM, the combined organic layers were dried over sodium sulfate, filtered and concentrated to afford the title compound as a colorless oil (520 mg, 100% purity, 89% yield, $t_r$=0.98 min). LCMS (Method E): m/z found 310.1 $[M\text{-}Boc+H]^+$; $^1$H-NMR (DMSO-$d_6$, 400 MHz): δ (ppm) 7.70-7.57 (m, 2H), 7.34 (dd, J=8.4, 2.0 Hz, 1H), 5.28 (q, J=5.6 Hz, 1H), 3.88-3.58 (m, 3H), 3.48-3.37 (m, 2H), 3.16 (s, 3H), 1.43 (s, 9H).

Step 3: Synthesis of tert-butyl rac-(3R,4R)-3-azido-4-(3,4-dichlorophenyl)pyrrolidine-1-carboxylate

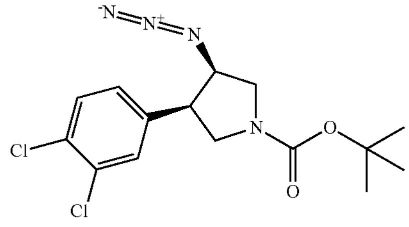

In a sealed tube under nitrogen, sodium azide (330 mg, 5.07 mmol) was added to a stirred solution of tert-butyl rac-(3R,4S)-3-(3,4-dichlorophenyl)-4-methylsulfonyloxy-pyrrolidine-1-carboxylate (520 mg, 1.27 mmol) in dry DMF (5 mL). The mixture was stirred at 75° C. for 23 h. The mixture was allowed to cool to rt and was diluted with EtOAc and saturated aqueous $NaHCO_3$. The organic layer was washed with saturated aqueous $NaHCO_3$, dried over sodium sulfate, filtered and concentrated. The crude was purified by flash chromatography on silica gel using a gradient of EtOAc in heptane from 5% to 30% to afford the title compound as a colorless oil (335 mg, 100% purity, 74% yield, $t_r$=1.09 min). LCMS (Method E): m/z found 300.9 $[M-tBu+H]^+$; $^1H$-NMR (DMSO-$d_6$, 400 MHz): δ (ppm) 7.67-7.56 (m, 2H), 7.35 (dd, J=8.4, 2.0 Hz, 1H), 4.63 (t, J=3.9 Hz, 1H), 3.79-3.66 (m, 2H), 3.65-3.53 (m, 1H), 3.53-3.41 (m, 2H), 1.43 (s, 9H).

Step 4: Synthesis of tert-butyl rac-(3R,4R)-3-amino-4-(3,4-dichlorophenyl)pyrrolidine-1-carboxylate

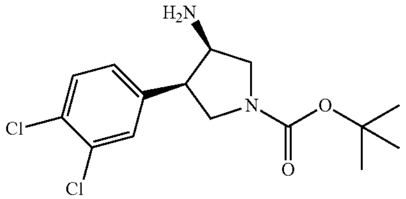 [SMILES: CC(C)(C)OC(=O)N1C[C@H](N)[C@H](c2ccc(Cl)c(Cl)c2)C1]

In a sealed tube under nitrogen, polymer bound triphenylphosphine (344 mg, 1.03 mmol) was added to a stirred solution of tert-butyl rac-(3R,4R)-3-azido-4-(3,4-dichlorophenyl)pyrrolidine-1-carboxylate (335 mg, 0.938 mmol) in THF (5 mL) and water (2 mL). The solution was stirred at 45° C. for 16 h and was filtered. The residue was washed with DCM and the filtrate was dried over sodium sulfate, filtered and concentrated to afford the title compound as a colorless oil (203 mg, 100% purity, 65% yield, $t_r$=0.63 min). LCMS (Method E): m/z found 275.1 $[M-tBu+H]^+$; $^1H$-NMR (DMSO-$d_6$, 400 MHz): δ (ppm) 7.58 (d, J=8.3 Hz, 1H), 7.49 (d, J=3.4 Hz, 1H), 7.23 (d, J=8.0 Hz, 1H), 3.65-3.52 (m, 3H), 3.51-3.33 (m, 2H), 3.17-3.02 (m, 1H), 1.43 (s, 9H).

Step 5: Synthesis of tert-butyl rac-(3R,4R)-3-(3,4-dichlorophenyl)-4-[[4-(trifluoromethoxy)phenyl]sulfonylamino]pyrrolidine-1-carboxylate

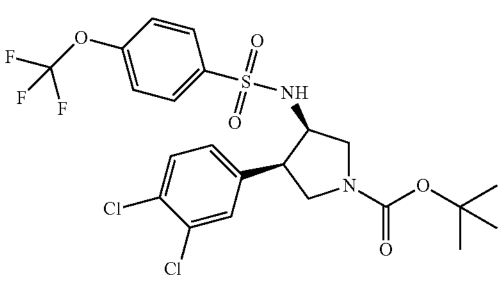 [SMILES: CC(C)(C)OC(=O)N1C[C@H](NS(=O)(=O)c2ccc(OC(F)(F)F)cc2)[C@H](c2ccc(Cl)c(Cl)c2)C1]

In a sealed tube under nitrogen, 4-(trifluoromethoxy)benzenesulfonyl chloride (46 μL, 0.272 mmol) was added to a stirred solution of tert-butyl rac-(3R,4R)-3-amino-4-(3,4-dichlorophenyl)pyrrolidine-1-carboxylate (90 mg, 0.272 mmol), triethylamine (151 μL, 1.09 mmol) and N,N-dimethylpyridin-4-amine (99%, 3.4 mg, 0.0272 mmol) in dry DCM (300 μL). The mixture was stirred at rt for 16 h and was poured into half saturated $NaHCO_3$. The aqueous layer was extracted with DCM, the combined organic layers were washed with brine, dried over sodium sulfate, filtered and concentrated. The crude was purified by flash chromatography on silica gel using a gradient of (MeOH+2% $NH_4OH$) in DCM from 0.5% to 5% to afford the title compound as a white solid (98 mg, 99% purity, 64% yield, $t_r$=1.08 min). LCMS (Method D): m/z found 499.1 $[M-tBu+H]^+$; $^1H$-NMR (DMSO-$d_6$, 400 MHz): δ (ppm) 8.21-7.95 (m, 1H), 7.72 (t, J=8.4 Hz, 2H), 7.47 (t, J=7.6 Hz, 3H), 7.36-7.25 (m, 1H), 7.16-7.00 (m, 1H), 4.28-4.02 (m, 1H), 3.70-3.44 (m, 3H), 3.43-3.32 (m, 1H), 3.14-2.90 (m, 1H), 1.39 (d, J=18.2 Hz, 9H).

Step 6: Synthesis of N-[rac-(3R,4R)-4-(3,4-dichlorophenyl)pyrrolidin-3-yl]-4-(trifluoromethoxy)benzenesulfonamide

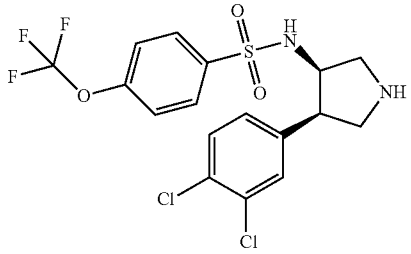 [SMILES: O=S(=O)(N[C@H]1CNC[C@H]1c1ccc(Cl)c(Cl)c1)c1ccc(OC(F)(F)F)cc1]

In a sealed tube under nitrogen, 4 M hydrogen chloride in dioxane (1.7 mL, 6.84 mmol) was added to a stirred suspension of tert-butyl rac-(3R,4R)-3-(3,4-dichlorophenyl)-4-[[4-(trifluoromethoxy)phenyl]sulfonylamino]pyrrolidine-1-carboxylate (95 mg, 0.171 mmol) in Diethyl ether (2 mL). The mixture was stirred at rt for 16 h and Methanol (1 mL) was added. The mixture was stirred at rt for 4 h and was concentrated. The residue was triturated in $Et_2O$ and the suspension was filtered. The residue was washed with $Et_2O$ and dried under reduced pressure at 60° C. for 16 h to afford the hydrochloride salt of the title compound as a white powder. (76 mg, 100% purity, 90% yield, $t_r$=1.5 min). LCMS (Method C): m/z found 455.0 $[M+H]^+$; $^1H$-NMR (DMSO-$d_6$, 600 MHz) δ 9.43 (br s, 2H), 8.1-8.7 (m, 1H), 7.7-7.7 (m, 2H), 7.4-7.5 (m, 3H), 7.39 (d, 1H, J=2.1 Hz), 7.12 (dd, 1H, J=2.2, 8.4 Hz), 4.33 (br s, 1H), 3.5-3.7 (m, 3H), 3.42 (dd, 1H, J=6.2, 12.5 Hz), 3.02 (dd, 1H, J=3.0, 12.4 Hz).

Example 16: N-(3-(4-chloro-3-fluorophenyl)pyrrolidin-3-yl)-4-(trifluoromethoxy)benzenesulfonamide (52)

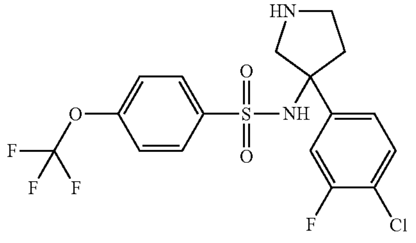 [SMILES: O=S(=O)(NC1(c2ccc(Cl)c(F)c2)CCNC1)c1ccc(OC(F)(F)F)cc1]

Step 1: Synthesis of benzyl 3-oxopyrrolidine-1-carboxylate

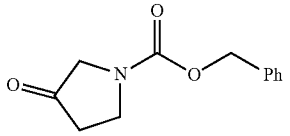 [SMILES: O=C1CCN(C(=O)OCc2ccccc2)C1]

In a round-bottomed flask, to a stirred solution of pyrrolidin-3-one hydrochloride (1:1) (97%, 5.00 g, 39.9 mmol) and DIPEA (42 mL, 0.239 mol) in DCM (200 mL) at room temperature under nitrogen were added benzyl chloroformate (12 mL, 83.8 mmol) and DMAP (487 mg, 3.99 mmol). The reaction mixture was stirred at room temperature for 18 h. The reaction mixture was quenched with a saturated aqueous solution of ammonium chloride (50 mL) and dichloromethane (100 mL) and water (50 mL) were added. The aqueous layer was extracted with dichloromethane (2×25 mL). The combined organic layers were dried over sodium sulfate, filtered and concentrated under reduced pressure. The crude was purified by flash chromatography on silica gel using a gradient of ethyl acetate in cyclohexane from 20% to 100% to afford the title compound as a yellow oil (4.59 g, 100% purity, 53% yield, $t_r$=0.68 min). LCMS (Method E); $^1$H-NMR (DMSO-$d_6$, 400 MHz): δ (ppm) 7.45-7.25 (m, 5H), 5.13 (s, 2H), 3.73 (d, J=24.2 Hz, 4H), 2.58 (t, J=7.2 Hz, 2H).

Step 2: Synthesis of benzyl 3-(4-chloro-3-fluoro-phenyl)-3-hydroxy-pyrrolidine-1-carboxylate

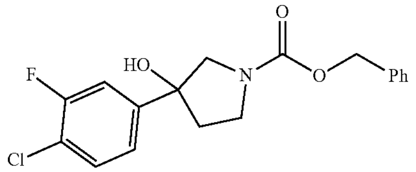 [SMILES: O=C(OCc1ccccc1)N1CCC(O)(c2ccc(Cl)c(F)c2)C1]

In a three-neck round-bottomed flask, to a stirred solution of 0.5 M bromo(4-chloro-3-fluorophenyl)magnesium (5.3 mL, 2.65 mmol) at 0° C. under nitrogen was added dropwise a solution of benzyl 3-oxopyrrolidine-1-carboxylate (97%, 500 mg, 2.21 mmol) in anhydrous THF (4.5 mL). The reaction mixture was allowed to warm up to room temperature and was stirred at this temperature overnight. The reaction mixture was poured into a saturated aqueous solution of $NH_4Cl$ and EtOAc was added. The layers were separated. The aqueous layer was extracted twice with EtOAc. The combined organic layers were washed with a saturated aqueous solution of NaCl, dried over sodium sulfate, filtered and concentrated under reduced pressure. The crude was purified by flash chromatography on silica gel using a gradient of EtOAc in heptane from 0% to 50%. The desired fractions were combined and concentrated to afford the title compound as a pale yellow oil (355.7 mg, 100% purity, 46% yield, $t_r$=0.90 min). LCMS (Method E); $^1$H-NMR (400 MHz, DMSO-$d_6$) δ 7.60-7.52 (m, 2H), 7.42-7.29 (m, 6H), 5.68 (s, 1H), 5.12-5.07 (m, 2H), 3.65-3.45 (m, 4H), 2.34-2.21 (m, 1H), 2.04 (dt, J=12.7, 6.7 Hz, 1H).

Step 3: Synthesis of benzyl 3-azido-3-(4-chloro-3-fluoro-phenyl)pyrrolidine-1-carboxylate

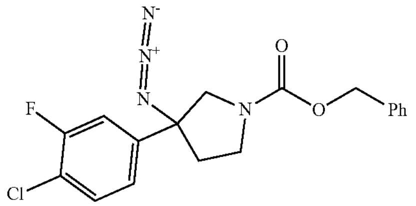 [SMILES: [N-]=[N+]=NC1(c2ccc(Cl)c(F)c2)CCN(C(=O)OCc2ccccc2)C1]

In a round-bottomed flask, to a stirred solution of benzyl 3-(4-chloro-3-fluoro-phenyl)-3-hydroxy-pyrrolidine-1-carboxylate (286 mg, 0.818 mmol) in a mixture of TFA (2.8 mL) and water (0.45 mL) at 0° C. was added $NaN_3$ (372 mg, 5.72 mmol). The reaction mixture was stirred at room temperature overnight. After this time, the reaction mixture was heated at 50° C. for 8 h. The reaction mixture was cooled to room temperature and was poured slowly in a saturated aqueous solution of $NaHCO_3$ and ice. The aqueous layer was extracted three times with DCM. The combined organic layers were washed with a saturated aqueous solution of NaCl, dried using a phase separator and concentrated under reduced pressure. The crude was purified by flash chromatography on silica gel using a gradient of EtOAc in Heptane from 5% to 50%. The desired fractions were combined and concentrated to afford the title compound as a pale yellow oil (212.2 mg, 88% purity, 61% yield, $t_r$=1.04 min). LCMS (Method E); $^1$H-NMR (400 MHz, DMSO-$d_6$) δ 7.73-7.64 (m, 2H), 7.44-7.30 (m, 6H), 5.12 (s, 2H), 4.01 (ddd, J=10.0, 7.5, 3.1 Hz, 1H), 3.69-3.43 (m, 3H), 2.58-2.51 (m, 1H), 2.48-2.32 (m, 1H).

Step 4: Synthesis of benzyl 3-amino-3-(4-chloro-3-fluoro-phenyl)pyrrolidine-1-carboxylate

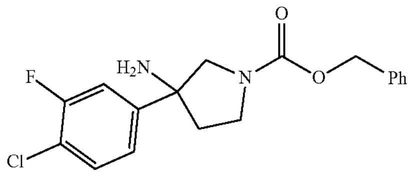 [SMILES: NC1(c2ccc(Cl)c(F)c2)CCN(C(=O)OCc2ccccc2)C1]

In a round-bottomed flask under nitrogen, triphenylphosphine (150 mg, 0.572 mmol) and 4-methylbenzenesulfonic acid (300 mg, 1.58 mmol) were added to a stirred solution of benzyl 3-azido-3-(4-chloro-3-fluoro-phenyl)pyrrolidine-1-carboxylate (88%, 212 mg, 0.498 mmol) in THF (2.5 mL). The mixture was stirred at room temperature overnight. The suspension was filtered, washed with few THF, then diethyl ether and dried under vacuum for 72 h to afford the title compound as a white powder (210 mg, 98% purity, 79% yield, $t_r$=0.62 min). LCMS (Method E): m/z found 349.3 [M+H-pTSA]; $^1$H-NMR (400 MHz, DMSO-$d_6$) δ 8.52 (s, 3H), 7.73 (q, J=7.9 Hz, 1H), 7.64 (dd, J=10.8, 2.2 Hz, 1H), 7.50-7.45 (m, 2H), 7.43-7.31 (m, 6H), 7.11 (d, J=7.9 Hz, 2H), 5.18-5.08 (m, 2H), 4.06 (d, J=11.7 Hz, 1H), 3.81-3.52 (m, 3H), 2.57-2.45 (m, 2H), 2.29 (s, 3H).

Step 5: Synthesis of benzyl 3-(4-chloro-3-fluoro-phenyl)-3-[[4-(trifluoromethoxy)phenyl]sulfonylamino]pyrrolidine-1-carboxylate

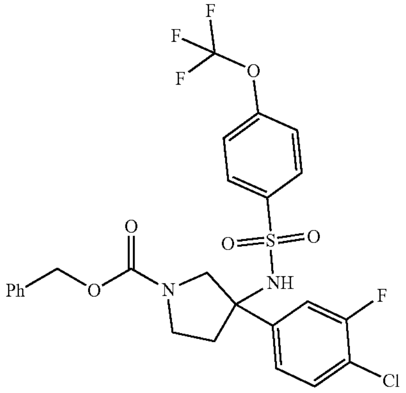 [SMILES: O=C(OCc1ccccc1)N1CCC(NS(=O)(=O)c2ccc(OC(F)(F)F)cc2)(c2ccc(Cl)c(F)c2)C1]

In a sealed vial, to a stirred suspension of benzyl 3-amino-3-(4-chloro-3-fluoro-phenyl)pyrrolidine-1-carboxylate 4-methylbenzenesulfonic acid (80 mg, 0.154 mmol) in DCM (1.5 mL) at room temperature were added successively triethylamine (104 μL, 0.746 mmol), 4-(trifluoromethoxy) benzenesulfonyl chloride (98%, 40 μL, 0.231 mmol) and finally N,N-dimethylpyridin-4-amine (3.7 mg, 0.0306 mmol). The reaction mixture was stirred at this temperature for 1 h and then it was heated at 40° C. for 3 h. The reaction mixture was cooled to room temperature and diluted with a saturated aqueous solution of $NaHCO_3$. The layers were separated. The aqueous layer was extracted twice with DCM. The combined organic layers were washed with a saturated aqueous solution of NaCl, dried using a phase separator and concentrated under reduced pressure. The residue was triturated in DCM. To the suspension was added diethyl ether and the suspension was stirred for 1 h. The resulting suspension was filtered, washed with diethyl ether (+ few drops of DCM) and dried under vacuum at 40° C. for 16 h to afford the title compound as a white powder (75.5 mg, 96% purity, 82% yield, $t_r$=1.03 min). LCMS (Method E): m/z found 595.2 $[M+Na]^+$; $^1$H-NMR (400 MHz, DMSO-$d_6$) δ 8.68 (d, J=5.6 Hz, 1H), 7.49 (dd, J=8.7, 1.4 Hz, 2H), 7.41-7.20 (m, 8H), 7.06-6.99 (m, 1H), 6.97 (dd, J=8.4, 1.7 Hz, 1H), 5.15-5.01 (m, 2H), 4.12 (dd, J=20.4, 11.5 Hz, 1H), 3.60 (dd, J=15.0, 11.4 Hz, 1H), 3.54-3.33 (m, 2H), 2.77-2.62 (m, 1H), 2.35-2.13 (m, 1H).

Step 6: Synthesis of N-(3-(4-chloro-3-fluorophenyl) pyrrolidin-3-yl)-4-(trifluoromethoxy)benzenesulfonamide

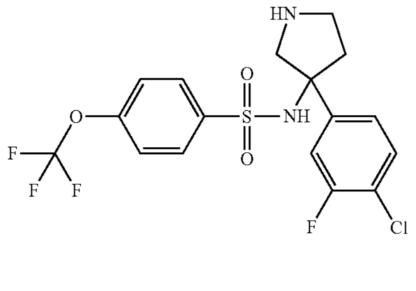 [SMILES: O=S(=O)(NC1(c2ccc(Cl)c(F)c2)CCNC1)c1ccc(OC(F)(F)F)cc1]

In a round-bottomed flask under nitrogen, to a stirred solution of benzyl 3-(4-chloro-3-fluoro-phenyl)-3-[[4-(trifluoromethoxy)phenyl]sulfonylamino]pyrrolidine-1-carboxylate (75 mg, 0.130 mmol) in anhydrous acetonitrile (1.9 mL) at room temperature, was added iodo(trimethyl)silane (55 μL, 0.386 mmol). The reaction mixture was stirred at room temperature for 1.5 h. The reaction mixture was concentrated under reduced pressure and dried under vacuum. The crude was purified by flash chromatography on silica gel using a gradient of MeOH (0.7 N $NH_3$) in DCM from 2% to 20%. The desired fractions were combined and concentrated. The residue was purified by reverse-phase preparative chromatography (C18Aq 100 g) using a gradient of acetonitrile in water from 0% to 100% (0.1% AcOH in water and acetonitrile). The desired fractions were combined and concentrated. Exchange salt of the residue was performed in diethyl ether, then a solution of 2 M hydrogen chloride in $Et_2O$ (0.65 mL, 1.30 mmol) was added and was stirred at rt for 2 h. The suspension was filtered, washed with diethyl ether and dried at 45° C. for 18 h to afford the hydrochloride salt of the title compound as an off-white powder (32.3 mg, 98.43% purity, 51% yield, $t_r$=1.38 min). LCMS (Method C): m/z found 439 $[M+H]^+$; $^1$H-NMR (500 MHz, DMSO-$d_6$) δ 9.68-9.17 (m, 2H), 8.81 (br s, 1H), 7.46 (d, J=8.8 Hz, 2H), 7.27 (d, J=8.3 Hz, 2H), 7.22 (t, J=8.1 Hz, 1H), 7.06 (dd, J=10.5, 2.0 Hz, 1H), 6.97 (dd, J=8.4, 1.8 Hz, 1H), 4.16-4.00 (m, 1H), 3.46-3.34 (m, 3H), 2.88-2.79 (m, 1H), 2.25-2.08 (m, 1H).

Example 17: tert-butyl 4-(4-chlorophenyl)-4-((4-(trifluoromethoxy)phenyl)sulfonamido)piperidine-1-carboxylate (53)

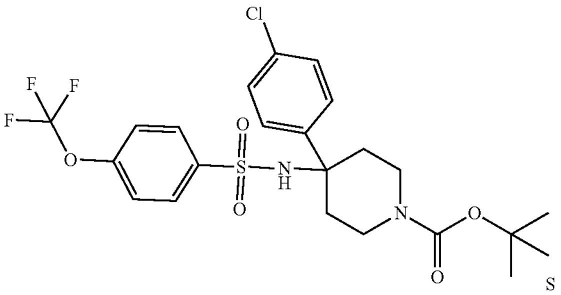

In a vial, to a stirred suspension of tert-butyl 4-amino-4-(4-chlorophenyl)piperidine-1-carboxylate (200 mg, 0.643 mmol) in DCM (6.4844 mL) at room temperature were added successively triethylamine (0.45 mL, 3.22 mmol), 4-(trifluoromethoxy)benzenesulfonyl chloride (98%, 168 μL, 0.968 mmol) and DMAP (16 mg, 0.129 mmol). The reaction mixture was stirred at this temperature for 1 h and then it was heated at 40° C. overnight. The reaction mixture was diluted with DCM and a saturated aqueous solution of $NaHCO_3$. The layers were separated. The aqueous layer was extracted with DCM. The combined organic layers were washed with a saturated aqueous solution of NaCl, dried using a phase separator and concentrated under reduced pressure. The crude was purified by flash chromatography on silica gel using a gradient of EtOAc in Heptane from 0% to 100%. The desired fractions were combined and concentrated to afford the title compound as a white foam (327.3 mg, 98.74% purity, 95.08% yield, $t_r$=3.0 min). The product may be further dried under reduced pressure at 45° C. LCMS (Method C): m/z found 534 $[M+H]^+$; $^1$H-NMR (DMSO-$d_6$, 600 MHz) δ 8.21 (s, 1H), 7.38 (d, 2H, J=8.9 Hz), 7.22 (d, 2H, J=8.1 Hz), 7.09 (d, 2H, J=8.8 Hz), 6.98 (d, 2H, J=8.8 Hz), 3.68 (br d, 2H, J=13.2 Hz), 3.22 (br d, 2H, J=2.3 Hz), 2.34 (br d, 2H, J=13.2 Hz), 1.71 (br t, 2H, J=10.6 Hz), 1.39 (s, 9H).

Example 18: N-(1-benzyl-3-(4-chlorophenyl)pyrrolidin-3-yl)-4-(4-(trifluoromethyl)phenoxy)benzenesulfonamide (54)

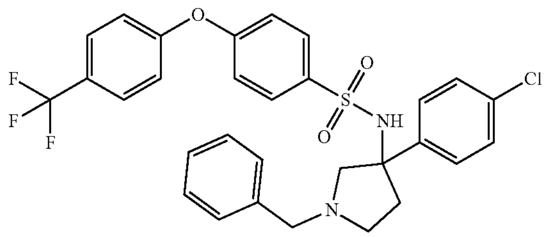 [SMILES: O=S(=O)(NC1(c2ccc(Cl)cc2)CCN(Cc2ccccc2)C1)c1ccc(Oc2ccc(C(F)(F)F)cc2)cc1]

Step 1: Synthesis of 1-benzylpyrrolidin-3-one

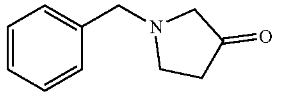

In a sealed vial, to a stirred suspension of pyrrolidin-3-one hydrochloride (1:1) (97%, 5.00 g, 39.9 mmol) in a mixture of (bromomethyl)benzene (5.5 mL, 46.3 mmol) in ethyl acetate (8.75 mL) and DCE (95 mL) at room temperature was added triethylamine (14 mL, 0.100 mol) and the reaction mixture was stirred at 70° C. overnight. The reaction mixture was poured into water. The layers were separated. The aqueous layer was extracted twice with DCM. The combined organic layers were washed with a saturated aqueous solution of sodium chloride, dried over sodium sulfate, filtered and concentrated under reduced pressure. The crude was purified by flash chromatography on silica gel using a gradient of EtOAc in Heptane from 2% to 100%. The desired fractions were combined and concentrated to afford the title compound as a yellow oil (2.43 g, 100% purity, 34.759% yield). $^1$H-NMR (400 MHz, DMSO-$d_6$) δ 7.38-7.23 (m, 5H), 3.69 (s, 2H), 2.89-2.83 (m, 4H), 2.35 (t, J=6.9 Hz, 2H).

Step 2: Synthesis of 1-benzyl-3-(4-chlorophenyl)pyrrolidin-3-ol

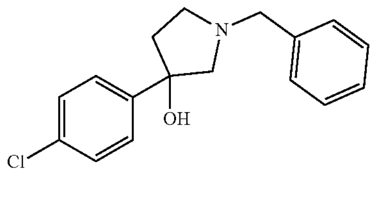 [SMILES: OC1(c2ccc(Cl)cc2)CCN(Cc2ccccc2)C1]

In a three-neck round-bottomed flask, to a stirred solution of 1 M bromo(4-chlorophenyl)magnesium (3.1 mL, 3.15 mmol) in anhydrous THF (11 mL) at 0° C. under nitrogen was added a solution of 1-benzylpyrrolidin-3-one (500 mg, 2.85 mmol). The reaction mixture was allowed to warm up to room temperature and stirred at this temperature overnight. The reaction mixture was quenched with a saturated aqueous solution of $NH_4Cl$ and EtOAc was added. The layers were separated. The aqueous layer was extracted twice with EtOAc. The combined organic layers were washed with a saturated aqueous solution of NaCl, dried over sodium sulfate, filtered and concentrated under reduced pressure. The crude was purified by flash chromatography on silica gel using a gradient of EtOAc in heptane from 2% to 100%. The desired fractions were combined and concentrated to afford the title compound as a brown oil (382.9 mg, 95% purity, 44.298% yield, $t_r$=0.58 min). LCMS (Method D): m/z found 288.1 $[M+H]^+$; $^1$H-NMR (400 MHz, DMSO-$d_6$) δ 7.54-7.49 (m, 2H), 7.38-7.29 (m, 6H), 7.24 (ddd, J=9.3, 4.1, 1.9 Hz, 1H), 5.34 (s, 1H), 3.67 (s, 2H), 2.85-2.72 (m, 3H), 2.67 (d, J=9.7 Hz, 1H), 2.15-1.99 (m, 2H).

Step 3: Synthesis of 3-azido-1-benzyl-3-(4-chlorophenyl)pyrrolidine

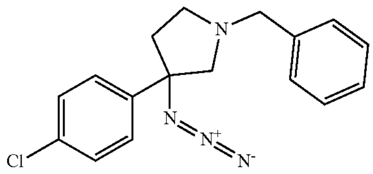 [SMILES: [N-]=[N+]=NC1(c2ccc(Cl)cc2)CCN(Cc2ccccc2)C1]

In a sealed vial, to a solution of 1-benzyl-3-(4-chlorophenyl)pyrrolidin-3-ol (935 mg, 3.25 mmol) in anhydrous DCM (16.414 mL) under nitrogen at 0° C. were added azido (trimethyl)silane (0.86 mL, 6.51 mmol) and $BF_3$ etherate (0.80 mL, 6.51 mmol). The reaction mixture was allowed to warm up to room temperature and was stirred at this temperature overnight. Then, the reaction mixture was stirred at 40° C. overnight once more. Additional azido (trimethyl)silane (0.86 mL, 6.51 mmol) and $BF_3$ etherate (0.80 mL, 6.51 mmol) were added at 0° C. and the reaction mixture was stirred at r.t for 4 h. Additional $BF_3$ etherate (0.80 mL, 6.50 mmol) was added at 0° C. and the reaction mixture was stirred at rt overnight. The reaction mixture was quenched with a saturated aqueous solution of $NaHCO_3$ dropwise (bubbled). DCM was added and the layer were separated. The aqueous layer was extracted twice with DCM. The combined organic layers were washed with a saturated aqueous solution of sodium chloride, dried using a phase separator and concentrated under reduced pressure. The crude was purified by flash chromatography on silica gel using a gradient of EtOAc in Heptane from 1% to 100%. The desired fractions were combined and concentrated to afford the title product (535 mg, 100% purity, 52.116% yield, $t_r$=0.63 min). LCMS (Method E): m/z found 313.2 $[M+H]^+$; $^1$H-NMR (500 MHz, DMSO-$d_6$) δ 7.45 (d, J=3.7 Hz, 4H), 7.39-7.29 (m, 4H), 7.25 (dt, J=5.5, 2.8 Hz, 1H), 3.71 (d, J=3.3 Hz, 2H), 3.18 (d, J=10.2 Hz, 1H), 2.99 (q, J=7.7, 7.0 Hz, 1H), 2.80 (d, J=10.2 Hz, 1H), 2.61 (q, J=7.9, 7.4 Hz, 1H), 2.43-2.35 (m, 2H).

Step 4: Synthesis of 1-benzyl-3-(4-chlorophenyl)pyrrolidin-3-amine

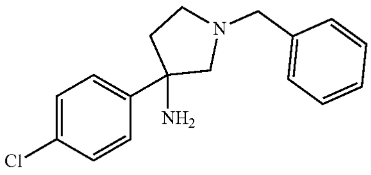 [SMILES: NC1(c2ccc(Cl)cc2)CCN(Cc2ccccc2)C1]

In a round bottomed flask under nitrogen, triphenylphosphine (452 mg, 1.72 mmol) then 4-methylbenzenesulfonic acid (976 mg, 5.13 mmol) were added to a stirred solution of 3-azido-1-benzyl-3-(4-chlorophenyl)pyrrolidine (535 mg, 1.71 mmol) in THF (10 mL). The mixture was stirred at room temperature 2.5 h. The suspension was filtered, washed with few THF and $Et_2O$ and dried under vacuum for 18 h to afford the title compound as a white powder (919 mg, 100% purity, 85.126% yield, $t_r$=0.48 min). LCMS (Method E): m/z found 287.2 $[M+H]^+$; $^1$H-NMR (400 MHz, DMSO-$d_6$) δ 8.79 (s, 1H), 8.54 (s, 1H), 7.74-7.18 (m, 13H), 7.12 (d, J=7.8 Hz, 4H), 4.48 (s, 2H), 4.14 (s, 1H), 2.62 (d, J=41.2 Hz, 2H), 2.39 (d, J=47.9 Hz, 1H), 2.30 (s, 6H).

Step 5: Synthesis of N-(1-benzyl-3-(4-chlorophenyl)pyrrolidin-3-yl)-4-(4-(trifluoromethyl)phenoxy) benzenesulfonamide (54)

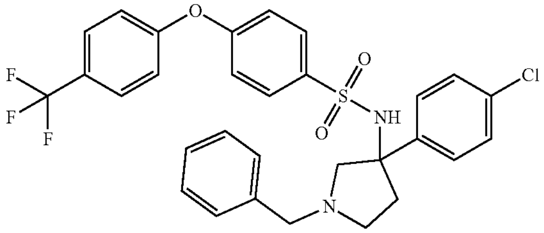 [SMILES: O=S(=O)(NC1(c2ccc(Cl)cc2)CCN(Cc2ccccc2)C1)c1ccc(Oc2ccc(C(F)(F)F)cc2)cc1]

In a vial, to a stirred suspension of 4-[4-(trifluoromethyl) phenoxy]benzenesulfonyl chloride (107 µL, 0.487 mmol) in DCM (15 mL) at room temperature were added successively 1-benzyl-3-(4-chlorophenyl)pyrrolidin-3-amine; 4-methylbenzenesulfonic acid (300 mg, 0.475 mmol) and triethylamine (0.50 mL, 3.59 mmol). The reaction mixture was stirred at this temperature overnight. The reaction mixture was diluted with DCM and a saturated aqueous solution of $NaHCO_3$. The layers were separated. The aqueous layer was extracted with DCM. The combined organic layers were washed with a saturated aqueous solution of NaCl, dried using a phase separator and concentrated under reduced pressure. The crude was purified by flash chromatography on silica gel using a gradient of EtOAc in Heptane from 0% to 50%. The desired fractions were combined and concentrated to afford the title compound as a white foam (132.8 mg, 96.02% purity, 47.596% yield, $t_r$=2.01 min). The product may be dried at reduced pressure at 45° C. LCMS (Method C): m/z found 587 $[M+H]^+$; $^1$H-NMR (400 MHz, DMSO-$d_6$) δ 8.40 (s, 1H), 7.82 (d, J=8.7 Hz, 2H), 7.47-7.38 (m, 2H), 7.33-7.13 (m, 12H), 7.00-6.93 (m, 2H), 3.65 (s, 2H), 3.16-3.03 (m, 2H), 2.64 (t, J=7.1 Hz, 2H), 2.18-2.08 (m, 1H).

Example 19: N-(1-benzyl-3-(3,4-dichlorophenyl) pyrrolidin-3-yl)-4-(4-(trifluoromethyl)phenoxy)benzenesulfonamide (55)

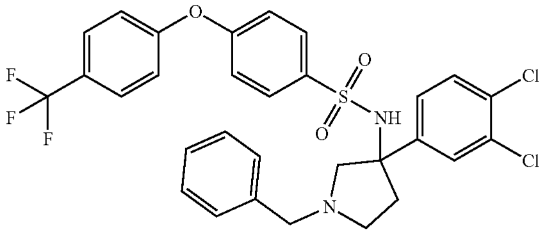 [SMILES: O=S(=O)(NC1(c2ccc(Cl)c(Cl)c2)CCN(Cc2ccccc2)C1)c1ccc(Oc2ccc(C(F)(F)F)cc2)cc1]

Step 1: Synthesis of 1-benzylpyrrolidin-3-one

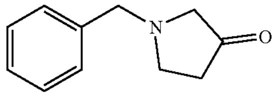 [SMILES: O=C1CCN(Cc2ccccc2)C1]

In a sealed vial, to a stirred suspension of pyrrolidin-3-one hydrochloride (1:1) (97%, 5.00 g, 39.9 mmol) in a mixture of ethyl acetate (8.75 mL) and DCE (95 mL) at room temperature were added (bromomethyl)benzene (5.5 mL, 46.3 mmol) and triethylamine (14 mL, 0.100 mol). The reaction mixture was stirred at 70° C. overnight. The reaction mixture was poured into water. The layers were separated. The aqueous layer was extracted twice with DCM. The combined organic layers were washed with a saturated aqueous solution of sodium chloride, dried over sodium sulfate, filtered and concentrated under reduced pressure. The crude was purified by flash chromatography on silica gel using a gradient of EtOAc in Heptane from 2% to 100%. The desired fractions were combined and concentrated to afford the title compound as a yellow oil (2.43 g, 100% purity, 34% yield). $^1$H-NMR (400 MHz, DMSO-$d_6$) δ 7.38-7.23 (m, 5H), 3.69 (s, 2H), 2.89-2.83 (m, 4H), 2.35 (t, J=6.9 Hz, 2H).

Step 2: Synthesis of 1-benzyl-3-(3,4-dichlorophenyl)pyrrolidin-3-ol

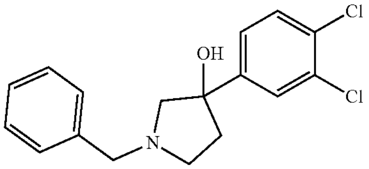 [SMILES: OC1(c2ccc(Cl)c(Cl)c2)CCN(Cc2ccccc2)C1]

In a three-neck round-bottomed flask, to a stirred suspension of magnesium (97 mg, 3.99 mmol) and iodine crystal in dry THF (2.2 mL) at rt under nitrogen was added few drops 5 of a solution of 1-bromo-3,4-dichlorobenzene (97%, 0.45 mL, 3.42 mmol) in dry THF. The reaction was heated at 50° C. until decoloration (orange to yellow). Then, the rest of the solution was added dropwise and was stirred at this temperature for 1 h (until magnesium was consumed). Then the reaction mixture was cooled to rt and a solution of 1-benzylpyrrolidin-3-one (500 mg, 2.85 mmol) in dry THF (1.5 mL) was added dropwise. The reaction mixture was stirred at this temperature overnight. The reaction mixture was poured into a saturated aqueous solution of $NH_4Cl$ and EtOAc was added. The layers were separated. The aqueous layer was extracted twice with EtOAc. The combined organic layers were washed with a saturated aqueous solution of NaCl, dried over sodium sulfate, filtered and concentrated under reduced pressure. The crude was purified by flash chromatography on silica gel using a gradient of EtOAc in heptane from 0% to 50%. The desired fractions were combined and concentrated to afford the title compound as an orange oil (335.5 mg, 100% purity, 37% yield, $t_r$=0.62 min). LCMS (Method E): m/z found 322.2 $[M+H]^+$; $^1$H-NMR (400 MHz, DMSO-$d_6$) δ 7.71 (d, J=2.1 Hz, 1H), 7.57 (d, J=8.4 Hz, 1H), 7.48 (dd, J=8.4, 2.1 Hz, 1H), 7.37-7.30 (m, 4H), 7.27-7.20 (m, 1H), 5.52 (s, 1H), 3.67 (d, J=1.8 Hz, 2H), 2.87-2.80 (m, 2H), 2.73 (q, J=8.0 Hz, 1H), 2.64 (d, J=9.7 Hz, 1H), 2.15-1.99 (m, 2H).

Step 3: Synthesis of 3-azido-1-benzyl-3-(3,4-dichlorophenyl)pyrrolidine

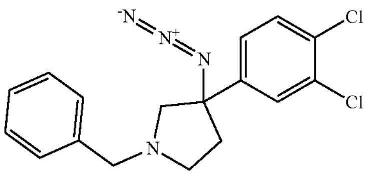

In a sealed vial, to a solution of 1-benzyl-3-(3,4-dichlorophenyl)pyrrolidin-3-ol (436 mg, 1.35 mmol) in dry DCM (6.8 mL) under nitrogen at 0° C. were added azido(trimethyl)silane (360 μL, 2.71 mmol) and $BF_3$ etherate (335 μL, 2.71 mmol). The reaction mixture was allowed to warm up to 40° C. and was stirred at this temperature overnight. Additional azido(trimethyl)silane (180 μL, 1.36 mmol) and $BF_3$ etherate (167 μL, 1.35 mmol) were added at rt and the reaction mixture was stirred at 40° C. one more night. Additional $BF_3$ etherate (500 μL, 4.05 mmol) was added at rt and the reaction mixture was stirred at 40° C. one more night. The reaction mixture was quenched with a saturated aqueous solution of $NaHCO_3$ dropwise (bubbled). EtOAc was added and the layer were separated. The aqueous layer was extracted twice with EtOAc. The combined organic layers were washed with a saturated aqueous solution of sodium chloride, dried over sodium sulfate and concentrated under reduced pressure. The crude was purified by flash chromatography on silica gel using a gradient of EtOAc in Heptane from 2% to 75%. The desired fractions were combined and concentrated to afford the title compound as a colorless oil (276.9 mg, 100% purity, 59% yield, $t_r$=0.68 min). LCMS (Method E): m/z found 347.2 $[M+H]^+$; $^1$H-NMR (400 MHz, DMSO-$d_6$) δ 7.71 (d, J=2.2 Hz, 1H), 7.65 (d, J=8.5 Hz, 1H), 7.46 (dd, J=8.5, 2.3 Hz, 1H), 7.37-7.31 (m, 4H), 7.26 (ddd, J=8.6, 5.4, 3.4 Hz, 1H), 3.72 (d, J=3.2 Hz, 2H), 3.19 (d, J=10.2 Hz, 1H), 3.03-2.94 (m, 1H), 2.83 (d, J=10.2 Hz, 1H), 2.68-2.59 (m, 1H), 2.41 (t, J=7.2 Hz, 2H).

Step 4: Synthesis of 1-benzyl-3-(3,4-dichlorophenyl)pyrrolidin-3-amine

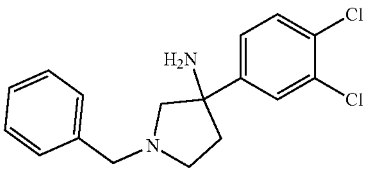 [SMILES: NC1(c2ccc(Cl)c(Cl)c2)CCN(Cc2ccccc2)C1]

In a round bottomed flask under nitrogen, triphenylphosphine (264 mg, 1.01 mmol) then 4-methylbenzenesulfonic acid hydrate (569 mg, 2.99 mmol) were added to a stirred solution of 3-azido-1-benzyl-3-(3,4-dichlorophenyl)pyrrolidine (347 mg, 1.00 mmol) in THF (4.4 mL). The mixture was stirred at room temperature overnight. The suspension was filtered, washed with minimum of THF and dried under vacuum for 18 h to afford the 4-methylbenzenesulfonic acid salt of the title compound as a white powder (601.1 mg, 98% purity, 89% yield, $t_r$=1.04 min). LCMS (Method E): m/z found 321.2 $[M+H]^+$; $^1$H-NMR (400 MHz, Methanol-$d_4$) δ 7.77 (d, J=2.4 Hz, 1H), 7.74-7.65 (m, 5H), 7.58-7.42 (m, 6H), 7.26 (d, J=8.0 Hz, 4H), 4.63-4.38 (m, 2H), 4.15-3.91 (m, 1H), 3.87-3.71 (m, 1H), 3.68-3.46 (m, 1H), 3.02-2.73 (m, 2H), 2.40 (s, 6H).

Step 5: Synthesis of N-(1-benzyl-3-(3,4-dichlorophenyl)pyrrolidin-3-yl)-4-(4-(trifluoromethyl)phenoxy)benzenesulfonamide (55)

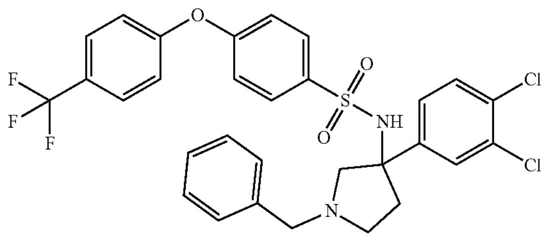 [SMILES: O=S(=O)(NC1(c2ccc(Cl)c(Cl)c2)CCN(Cc2ccccc2)C1)c1ccc(Oc2ccc(C(F)(F)F)cc2)cc1]

In a vial, to a stirred suspension of triethylamine (209 μL, 1.50 mmol) and 1-benzyl-3-(3,4-dichlorophenyl)pyrrolidin-3-aminium 4-methylbenzenesulfonate (200 mg, 0.300 mmol) in DCM (3,0046 mL) at room temperature was added triethylamine (209 μL, 1.50 mmol). The reaction mixture was stirred at room temperature overnight, diluted with an half saturated solution of $NaHCO_3$ and DCM, and the aqueous layer was extracted twice with DCM. The combined organic layers were filtered through phase separator then concentrated in vacuo and purified by flash chromatography on silica gel using a gradient of MeOH (0.7 N $NH_3$) in DCM from 0% to 4% to afford the title compound as a white powder (172 mg, 93.69% purity, 82% yield, $t_r$=2.10 min). LCMS (Method C): m/z found 621 [M+H]; $^1$H-NMR (500 MHz, DMSO-$d_6$) δ 8.47 (s, 1H), 7.81 (d, J=8.8 Hz, 2H), 0.00 (d, J=9.0 Hz, 2H), 7.37 (d, J=8.3 Hz, 1H), 7.34-7.21 (m, 8H), 0.00 (dd, J=8.6, 2.2 Hz, 1H), 6.95 (d, J=8.8 Hz, 2H), 3.64 (s, 2H), 3.18-2.97 (m, 2H), 2.71-2.55 (m, 2H), 2.47-2.42 (m, 1H), 2.18-2.09 (m, 1H).

Example 20: N-(4-(4-chloro-3-fluorophenyl)piperidin-4-yl)-4-(trifluoromethoxy)benzenesulfonamide (56)

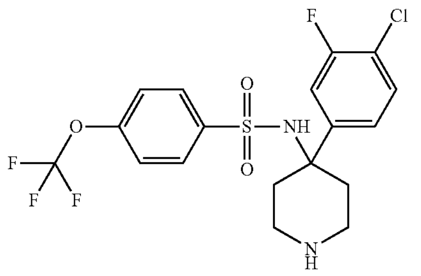 [SMILES: O=S(=O)(NC1(c2ccc(Cl)c(F)c2)CCNCC1)c1ccc(OC(F)(F)F)cc1]

Step 1: Synthesis of benzyl 4-oxopiperidine-1-carboxylate

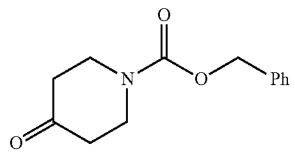 [SMILES: O=C1CCN(C(=O)OCc2ccccc2)CC1]

In a round-bottomed flask, to a stirred solution of piperidin-4-one hydrochloride (1:1) (98%, 3.00 g, 21.7 mmol) and DIPEA (23 mL, 0.132 mol) in DCM (70 mL) at room temperature under nitrogen were added benzyl chloroformate (6.2 mL, 43.6 mmol) and DMAP (265 mg, 2.17 mmol). The reaction mixture was stirred at room temperature for 5 h. The reaction mixture was quenched with a saturated aqueous solution of ammonium chloride. Then dichloromethane and water were added. The layers were separated. The aqueous layer was extracted twice with dichloromethane. The combined organic layers were washed once with a saturated aqueous solution of NaCl, dried using a phase separator and concentrated under reduced pressure. The crude was purified by flash chromatography on silica gel using a gradient of ethyl acetate in cyclohexane from 10% to 75% to afford the title compound as a yellow oil (3.89 g, 100% purity, 77% yield, $t_r$=0.71 min). LCMS (Method D); $^1$H-NMR (400 MHz, DMSO-$d_6$) δ 7.43-7.35 (m, 4H), 7.37-7.30 (m, 1H), 5.13 (s, 2H), 3.70 (t, J=6.1 Hz, 4H), 2.40 (t, J=6.3 Hz, 4H).

Step 2: Synthesis of benzyl 4-(4-chloro-3-fluoro-phenyl)-4-hydroxy-piperidine-1-carboxylate

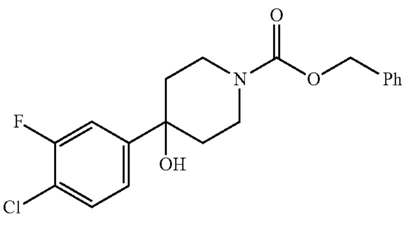

In a three neck round-bottom flask, to a stirred solution of benzyl 4-oxopiperidine-1-carboxylate (500 mg, 2.14 mmol) in anhydrous THF (4.3 mL) at 0° C. under nitrogen was added dropwise a solution of 0.5 M bromo(4-chloro-3-fluorophenyl)magnesium (5.2 mL, 2.60 mmol). The reaction mixture was allowed to warm up to room temperature and was stirred at this temperature overnight. The reaction mixture was poured into a saturated aqueous solution of $NH_4Cl$ and ethyl acetate was added. The layers were separated. The aqueous layer was extracted twice with ethyl acetate. The combined organic layers were washed with a saturated aqueous solution of NaCl, dried over sodium sulfate, filtered and concentrated under reduced pressure. The crude was purified by flash chromatography on silica gel using a gradient of ethyl acetate in heptane from 10% to 100%. The desired fractions were combined and concentrated to afford the title compound as a colorless oil (239.4 mg, 100% purity, 31% yield, $t_r$=0.94). LCMS (Method E); $^1$H-NMR (400 MHz, DMSO-$d_6$) δ 7.55-7.46 (m, 2H), 7.39 (d, J=4.3 Hz, 4H), 7.34 (ddd, J=8.6, 6.4, 2.4 Hz, 2H), 5.35 (s, 1H), 5.10 (s, 2H), 3.94 (d, J=10.7 Hz, 2H), 3.30-3.11 (m, 2H), 1.86 (td, J=13.1, 4.7 Hz, 3H), 1.58 (d, J=13.1 Hz, 2H).

Step 3: Synthesis of benzyl 4-azido-4-(4-chloro-3-fluoro-phenyl)piperidine-1-carboxylate

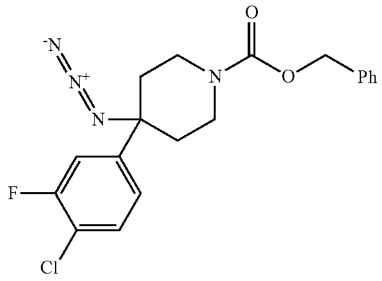

In a three round-bottom flask, a solution of benzyl 4-(4-chloro-3-fluoro-phenyl)-4-hydroxy-piperidine-1-carboxylate (185 mg, 0.509 mmol) in DCM-Anhydrous (2.8 mL) was added dropwise at 0° C. to a solution of azido(trimethyl) silane (81 μL, 0.613 mmol) and $BF_3$ etherate (377 μL, 3.06 mmol) in anhydrous DCM (0.74 mL). The reaction mixture was allowed to warm up to room temperature and stirred at this temperature overnight. The reaction mixture was poured in a saturated aqueous solution of $NaHCO_3$ (30 mL). The aqueous layer was extracted three times with DCM. The combined organic layers were washed with a saturated aqueous solution of NaCl, dried using a phase separator and concentrated under reduced pressure to afford the title compound as a colorless oil (188.2 mg, 69% purity, 66% yield, $t_r$=1.08 min). LCMS (Method E); $^1$H-NMR (400 MHz, DMSO-$d_6$) δ 7.68 (t, J=8.2 Hz, 1H), 7.62 (dd, J=11.1, 2.2 Hz, 1H), 7.45-7.28 (m, 6H), 5.10 (s, 2H), 4.00-3.88 (m, 2H), 3.29-3.08 (m, 2H), 2.08-1.93 (m, 4H).

Step 4: Synthesis of benzyl 4-amino-4-(4-chloro-3-fluoro-phenyl)piperidine-1-carboxylate

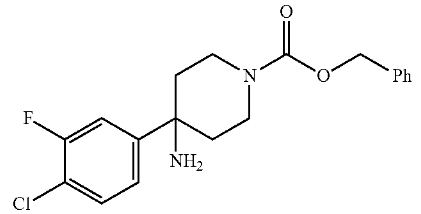

In a round bottomed flask under nitrogen, triphenylphosphine (150 mg, 0.572 mmol) then 4-methylbenzenesulfonic acid hydrate (300 mg, 1.58 mmol) were added to a stirred solution of an inseparable mixture of benzyl 4-azido-4-(4-chloro-3-fluoro-phenyl)piperidine-1-carboxylate (69%, 188 mg, 0.334 mmol) and benzyl 4-(4-chloro-3-fluoro-phenyl)-3,6-dihydro-2H-pyridine-1-carboxylate (31%, 188 mg, 0.169 mmol) in THF (2.5 mL). The mixture was stirred at room temperature overnight. The suspension was filtered, washed with few THF. The filtrate was concentrated. The crude was purified by reverse-phase chromatography (Redisep C18Aq-30g) using a gradient of acetonitrile in water from 0% to 100% (0.1% AcOH in water and acetonitrile). The desired fractions were combined and concentrated to afford the title compound as a colorless oil (66.4 mg, 86% purity, 47% yield, $t_r$=0.65 min). LCMS (Method E); $^1$H-NMR (400 MHz, DMSO-$d_6$) δ 7.73-7.65 (m, 2H), 7.50-7.43 (m, 1H), 7.42-7.30 (m, 5H), 7.11 (d, J=7.8 Hz, 2H), 5.09 (s, 2H), 3.77-3.59 (m, 2H), 3.30-3.19 (m, 2H), 2.40-2.24 (m, 2H), 1.90-1.79 (m, 2H).

Step 5: Synthesis of benzyl 4-(4-chloro-3-fluoro-phenyl)-4-[[4-(trifluoromethoxy)phenyl]sulfonylamino]piperidine-1-carboxylate

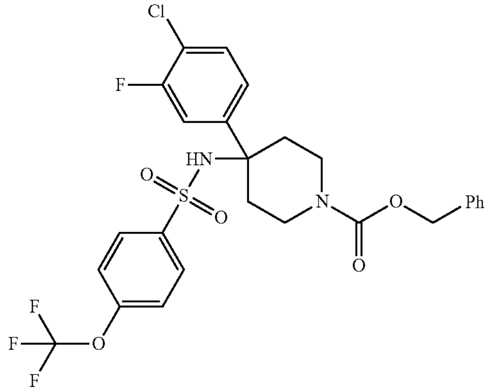 [SMILES: O=C(OCc1ccccc1)N1CCC(NS(=O)(=O)c2ccc(OC(F)(F)F)cc2)(c2ccc(Cl)c(F)c2)CC1]

In a vial, to a stirred solution of benzyl 4-amino-4-(4-chloro-3-fluoro-phenyl)piperidine-1-carboxylate (74%, 66 mg, 0.135 mmol) in DCM (1.3 mL) at room temperature were added successively triethylamine (94 μL, 0.674 mmol), 4-(trifluoromethoxy)benzenesulfonyl chloride (98%, 35 μL, 0.204 mmol) and N,N-dimethylpyridin-4-amine (1.7 mg, 0.0139 mmol). The reaction mixture was heated at 40° C. and stirred at this temperature overnight. The reaction mixture was cooled to room temperature. The organic layer was washed with a saturated aqueous solution of $NH_4Cl$, then a saturated aqueous solution of $NaHCO_3$ and finally with a saturated aqueous solution of NaCl. The organic layer was dried using a phase separator and concentrated under reduced pressure. The crude was purified by flash chromatography on silica gel using a gradient of ethyl acetate in heptane from 10% to 100%. The desired fractions were combined and concentrated to afford the title compound as a colorless gum (34.9 mg, 94% purity, 41% yield, $t_r$=1.05 min). LCMS (Method E); $^1$H-NMR (400 MHz, DMSO-$d_6$) δ 8.29 (s, 1H), 7.47-7.42 (m, 2H), 7.41-7.34 (m, 4H), 7.34-7.29 (m, 1H), 7.26 (d, J=8.2 Hz, 2H), 7.23-7.16 (m, 1H), 7.06-6.95 (m, 2H), 5.08 (s, 2H), 3.81 (d, J=13.5 Hz, 2H), 3.32-3.21 (m, 2H), 2.36 (d, J=13.8 Hz, 2H), 1.84-1.71 (m, 2H).

Step 6: N-(4-(4-chloro-3-fluorophenyl)piperidin-4-yl)-4-(trifluoromethoxy)benzenesulfonamide

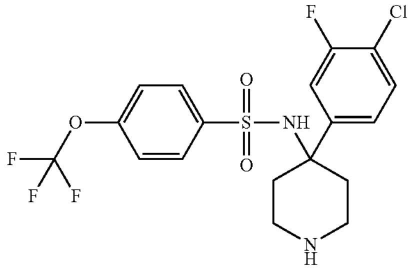 [SMILES: O=S(=O)(NC1(c2ccc(Cl)c(F)c2)CCNCC1)c1ccc(OC(F)(F)F)cc1]

In a round-bottomed flask, to a stirred solution of benzyl 4-(4-chloro-3-fluoro-phenyl)-4-[[4-(trifluoromethoxy)phenyl]sulfonylamino]piperidine-1-carboxylate (35 mg, 0.0595 mmol) in acetonitrile (0.86 mL) at room temperature, was added iodo(trimethyl)silane (25 μL, 0.178 mmol). The reaction mixture was stirred at room temperature for 1.5 h. The reaction mixture was concentrated under reduced pressure and dried under vacuum. The crude was dry loaded onto decalite and purified by flash chromatography on silica gel using a gradient of MeOH (0.7N $NH_3$) in DCM from 1% to 20%. The desired fractions were combined and washed with water and triethylamine (41 μL, 0.297 mmol). The aqueous layer was extracted once with dichloromethane and methyl tetrahydrofuran. The combined organic layers were dried over sodium sulfate, filtered and concentrated under reduced pressure. The residue was purified by reverse-phase preparative chromatography (C18Aq 15.5 g) using a gradient of acetonitrile in water from 0% to 100% (0.1% AcOH in both). The desired fractions were combined and concentrated. Exchange salt of the residue was performed in diethyl ether, then a solution of 2 M hydrogen chloride in $Et_2O$ (0.30 mL, 0.595 mmol) was added and stirred at rt overnight. The suspension was filtered, washed with diethyl ether and dried at 45° C. for 24 h to afford the hydrochloride salt of the title compound as a white powder (16.5 mg, 99.56% purity, 57% yield, $t_r$=1.42 min). LCMS (Method C): m/z found 453 $[M+H]^+$; $^1$H-NMR (600 MHz, DMSO-$d_6$) δ 8.83-8.59 (m, 2H), 8.51 (s, 1H), 7.47-7.39 (m, 2H), 7.28-7.25 (m, 2H), 7.23 (s, 1H), 7.06-7.02 (m, 1H), 7.01-6.95 (m, 1H), 3.27-3.17 (m, 4H), 2.60-2.52 (m, 2H), 2.08-1.97 (m, 2H).

Example 21: N-(3-(4-chlorophenyl)pyrrolidin-3-yl)-4-(4-(trifluoromethyl)phenoxy)benzenesulfonamide (57)

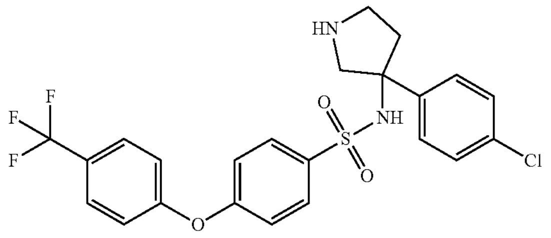 [SMILES: O=S(=O)(NC1(c2ccc(Cl)cc2)CCNC1)c1ccc(Oc2ccc(C(F)(F)F)cc2)cc1]

Step 1: Synthesis of benzyl 3-(4-chlorophenyl)-3-[[4-[4-(trifluoromethyl)phenoxy]phenyl]sulfonylamino]pyrrolidine-1-carboxylate

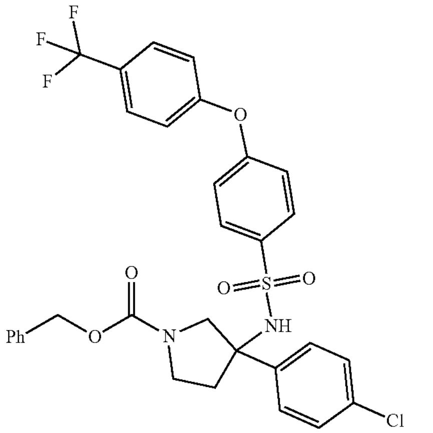 [SMILES: O=C(OCc1ccccc1)N1CCC(NS(=O)(=O)c2ccc(Oc3ccc(C(F)(F)F)cc3)cc2)(c2ccc(Cl)cc2)C1]

A sealed vial was charged with 1-((benzyloxy)carbonyl)-3-(4-chlorophenyl)pyrrolidin-3-aminium-4-methylbenzenesulfonate (250 mg, 0.497 mmol), 4-dimethylaminopyridine (12 mg, 0.0994 mmol) and triethylamine (0.35 mL, 2.49 mmol) in DCM (4.5968 mL). 4-[4-(trifluoromethyl)phenoxy]benzenesulfonyl chloride (0.13 mL, 0.596 mmol) was added and the reaction mixture was stirred at 40° C. for 24 h. The reaction mixture was quenched with a saturated aqueous solution of ammonium chloride and dichloromethane was added. The aqueous layer was extracted with dichloromethane. The combined organic layers were washed with a saturated aqueous solution of sodium carbonate, then with a saturated aqueous solution of sodium chloride, dried using a phase separator and concentrated under reduced pressure. The residue was triturated in MeOH, filtered, washed with MeOH and dried under vacuum for 18 h. The filtrate was concentrated under reduced pressure. A solution of this mixture in methanol (20 mL) was stirred with a pTsOH functionalized microporous polystyrene resin (MP-TsOH) (746 mg, 1.49 mmol) at rt overnight. Additional MP-TsOH (497 mg, 0.994 mmol) was added and the mixture was stirred at rt for 1 h. The resin was filtered and washed with MeOH and DCM. The filtrate was concentrated under reduced pressure to afford the title product as a colorless solid (250 mg, 98% purity, 78.12% yield, $t_r$=1.11 min). LCMS (Method D): m/z found 653.3 $[M+Na]^+$; $^1$H-NMR (DMSO-$d_6$, 400 MHz) δ (ppm) 8.50 (d, J=7.5 Hz, 1H), 7.83 (d, J=7.0 Hz, 2H), 7.76-7.65 (m, 2H), 7.36 (ddd, J=14.2, 9.0, 4.6 Hz, 6H), 7.28-7.04 (m, 8H), 6.93 (d, J=8.8 Hz, 2H), 5.07 (d, J=9.6 Hz, 2H), 4.14 (dd, J=29.2, 11.1 Hz, 1H), 3.64-3.32 (m, 3H), 2.67 (s, 1H), 2.27-2.10 (m, 1H)

Step 2: Synthesis of N-(3-(4-chlorophenyl)pyrrolidin-3-yl)-4-(4-(trifluoromethyl)phenoxy)benzenesulfonamide (57)

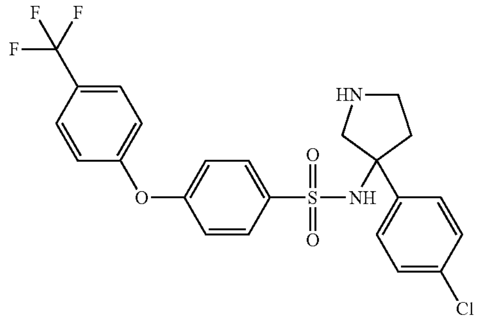 [SMILES: O=S(=O)(NC1(c2ccc(Cl)cc2)CCNC1)c1ccc(Oc2ccc(C(F)(F)F)cc2)cc1]

In a round-bottomed flask, to a stirred suspension of benzyl 3-(4-chlorophenyl)-3-[[4-[4-(trifluoromethyl)phenoxy]phenyl]sulfonylamino]pyrrolidine-1-carboxylate (98%, 245 mg, 0.380 mmol) in anhydrous acetonitrile (10 mL) at room temperature, was added iodo(trimethyl)silane (0.16 mL, 1.14 mmol). The reaction mixture was stirred at room temperature for 1.5 h, then the reaction mixture was concentrated under reduced pressure.

The crude was purified by flash chromatography on silica gel using a gradient of ammoniacal methanol in dichloromethane from 5% to 18%. The desired fractions were combined and washed with water (30 mL) and triethylamine (0.53 mL, 3.80 mmol). The organic layer was dried over sodium sulfate, filtered and concentrated under reduced pressure. The residue was triturated in methanol, filtered, washed with methanol and dried under vacuum for 18 h. The solid obtained was triturated in 2 M hydrogen chloride in diethyl ether (0.57 mL, 1.14 mmol) for 2 h, filtered, rinsed with diethyl ether, pentane and dried under vacuum at 45° C. for 4 h to afford the HCl salt of the title compound as a white powder (79.1 mg, 99.72% purity, 38.87% yield, $t_r$=1.97 min). LCMS (Method C): m/z observed 497.1 $[M+H]^+$; $^1$H-NMR (500 MHz, DMSO-$d_6$) δ 9.42 (br d, J=2.0 Hz, 2H), 8.89-8.25 (m, 1H), 7.85 (d, J=8.6 Hz, 2H), 7.32 (d, J=8.8 Hz, 2H), 7.24 (d, J=8.6 Hz, 2H), 7.19-7.14 (m, 2H), 7.13-7.02 (m, 2H), 6.89 (d, J=8.8 Hz, 2H), 4.18-4.06 (m, 1H), 3.44-3.34 (m, 3H), 2.93-2.77 (m, 1H), 2.23-2.04 (m, 1H).

Example 22: N-(3-(4-chloro-3-fluorophenyl)azetidin-3-yl)-4-(trifluoromethoxy)benzenesulfonamide (58)

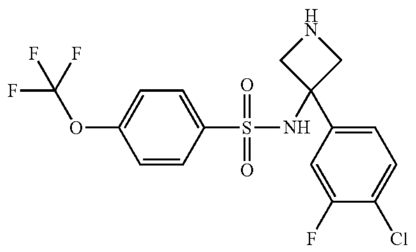 [SMILES: O=S(=O)(NC1(c2ccc(Cl)c(F)c2)CNC1)c1ccc(OC(F)(F)F)cc1]

Step 1: Synthesis of benzyl 3-(4-chloro-3-fluorophenyl)-3-hydroxyazetidine-1-carboxylate

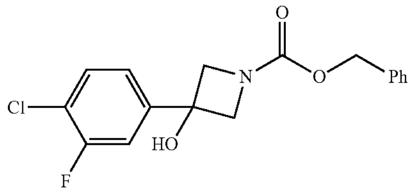 [SMILES: O=C(OCc1ccccc1)N1CC(O)(c2ccc(Cl)c(F)c2)C1]

In a three-neck round-bottomed flask, to a stirred suspension of magnesium (113 mg, 4.63 mmol) and a catalytic amount of iodine in anhydrous THF (2 mL) at rt under nitrogen was added few drops of a solution of 4-bromo-1-chloro-2-fluorobenzene (98%, 430 μL, 3.48 mmol) in anhydrous THF (1.5 mL). The reaction mixture was heated at 50° C. until decoloration (orange to yellow) was observed. Next, the rest of the solution was added dropwise and was stirred at this temperature for 1 h (until magnesium was consumed). The reaction mixture was then cooled to 0° C. and a solution of benzyl 3-oxoazetidine-1-carboxylate (95%, 500 mg, 2.31 mmol) in anhydrous THF (1.6 mL) was added dropwise. The reaction mixture was stirred at rt for 3 h, then the reaction mixture was poured into a saturated aqueous solution of $NH_4Cl$, and EtOAc was added. The layers were separated, then the aqueous layer was extracted twice with EtOAc. The combined organic layers were washed with a saturated aqueous solution of NaCl, dried over sodium sulfate, filtered and concentrated under reduced pressure. The crude was purified by flash chromatography on silica gel using a gradient of EtOAc in heptane from 10% to 100%. The desired fractions were combined and concentrated to afford the title compound as a colorless oil (590.4 mg, 100% purity, 76% yield, $t_r$=0.90 min). LCMS (Method E); $^1$H-NMR (400 MHz, DMSO-$d_6$) δ 7.64-7.55 (m, 1H), 7.51 (dd, J=10.8, 2.1 Hz, 1H), 7.42-7.36 (m, 5H), 7.36-7.30 (m, 1H), 6.63 (s, 1H), 5.10 (s, 2H), 4.26-4.05 (m, 4H).

Step 2: Synthesis of benzyl 3-(4-chloro-3-fluoro-phenyl)-3-methylsulfonyloxy-azetidine-1-carboxylate

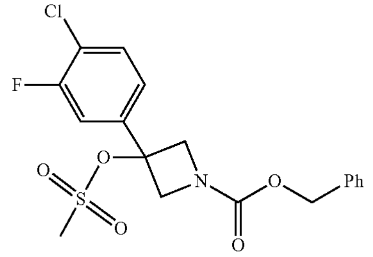 [SMILES: CS(=O)(=O)OC1(c2ccc(Cl)c(F)c2)CN(C(=O)OCc2ccccc2)C1]

In a round-bottomed flask, to a stirred solution of benzyl 3-(4-chloro-3-fluoro-phenyl)-3-hydroxy-azetidine-1-carboxylate (250 mg, 0.745 mmol) in anhydrous DCM (3.5 mL) at room temperature under nitrogen were added triethylamine (414 μL, 2.97 mmol) and methanesulfonyl chloride (115 μL, 1.49 mmol). The reaction mixture was stirred for 2 h, then the reaction mixture was concentrated under reduced pressure. The crude was diluted in dichloromethane and was washed twice with water. The organic layer was washed once with a saturated aqueous solution of NaCl, dried using a phase separator and concentrated under reduced pressure to afford the title compound as a yellow oil (324 mg, 95% purity, 100% yield). The crude was used directly in the next step without any purification. $^1$H-NMR (400 MHz, Chloroform-d) δ 7.52-7.47 (m, 1H), 7.40-7.32 (m, 5H), 7.32-7.28 (m, 1H), 7.27-7.23 (m, 1H), 5.12 (s, 2H), 4.68 (d, J=11.2 Hz, 2H), 4.52-4.44 (m, 2H), 2.73 (s, 3H).

Step 3: Synthesis of benzyl 3-azido-3-(4-chloro-3-fluoro-phenyl)azetidine-1-carboxylate

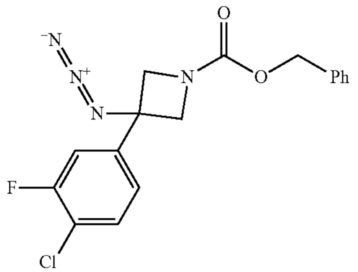

A sealed vial was charged with benzyl 3-(4-chloro-3-fluoro-phenyl)-3-methylsulfonyloxy-azetidine-1-carboxylate (95%, 155 mg, 0.356 mmol) in anhydrous DMF (1.78 mL), then $NaN_3$ (28 mg, 0.428 mmol) was added at room temperature and the reaction mixture was stirred at 40° C. overnight. The reaction mixture was cooled to room temperature, then water (20 mL) and EtOAc were added. The layers were separated. The aqueous layer was extracted twice with EtOAc. The combined organic layers were washed once with water and once with a saturated aqueous solution of NaCl, dried over sodium sulfate, filtered and concentrated under reduced pressure. The crude was purified by flash chromatography on silica gel using a gradient of EtOAc in Heptane from 5% to 50%. The desired fractions were combined and concentrated to afford the title compound as a colorless oil (91.7 mg, 100% purity, 77% yield, $t_r$=1.02 min). LCMS (Method E): m/z found 317.2 $[M-N_3+H]^+$; $^1$H-NMR (400 MHz, DMSO-$d_6$) δ 7.70 (t, J=8.1 Hz, 1H), 7.66 (dd, J=10.5, 2.1 Hz, 1H), 7.42-7.30 (m, 6H), 5.07 (s, 2H), 4.46 (d, J=9.3 Hz, 2H), 4.27 (d, J=9.5 Hz, 2H).

Step 4: Synthesis of benzyl 3-amino-3-(4-chloro-3-fluorophenyl)azetidine-1-carboxylate

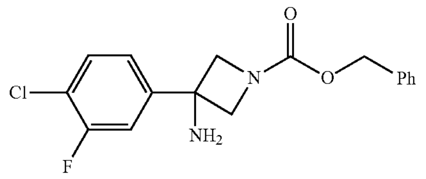 [SMILES: NC1(c2ccc(Cl)c(F)c2)CN(C(=O)OCc2ccccc2)C1]

In a round bottomed flask under nitrogen, triphenylphosphine (67 mg, 0.256 mmol) and 4-methylbenzenesulfonic acid hydrate (145 mg, 0.763 mmol) were added successively to a stirred solution of benzyl 3-azido-3-(4-chloro-3-fluorophenyl)azetidine-1-carboxylate (92 mg, 0.254 mmol) in THF (1.4 mL). The mixture was stirred at room temperature overnight and the resulting suspension was filtered, washed with THF and dried under vacuum for 18 h to afford the p-toluenesulfonic acid salt of the title compound as a white powder (99 mg, 100% purity, 77% yield, $t_r$=0.63 min). LCMS (Method E): m/z found 335.2 $[M+H-APTS]^+$; $^1$H-NMR (400 MHz, DMSO-$d_6$) δ 8.77 (s, 3H), 7.75 (t, J=8.1 Hz, 1H), 7.64 (dd, J=10.6, 2.2 Hz, 1H), 7.50-7.44 (m, 2H), 7.43-7.31 (m, 6H), 7.11 (d, J=7.8 Hz, 2H), 5.10 (s, 2H), 4.53-4.37 (m, 2H), 4.32 (d, J=9.6 Hz, 2H), 2.29 (s, 3H).

Step 5: Synthesis of benzyl 3-(4-chloro-3-fluorophenyl)-3-((4-(trifluoromethoxy)phenyl)sulfonamido)azetidine-1-carboxylate

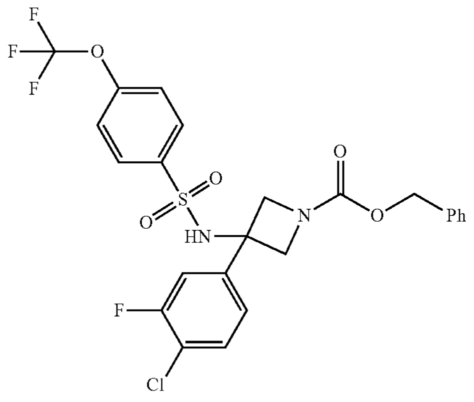 [SMILES: O=C(OCc1ccccc1)N1CC(NS(=O)(=O)c2ccc(OC(F)(F)F)cc2)(c2ccc(Cl)c(F)c2)C1]

In a vial, to a stirred suspension of benzyl 3-amino-3-(4-chloro-3-fluoro-phenyl)azetidine-1-carboxylate; 4-methylbenzenesulfonic acid (99 mg, 0.195 mmol) in DCM (1.3 mL) at room temperature were added successively triethylamine (136 µL, 0.976 mmol), 4-(trifluoromethoxy)benzenesulfonyl chloride (98%, 51 µL, 0.295 mmol) and N,N-dimethylpyridin-4-amine (2.5 mg, 0.0201 mmol). The reaction mixture was stirred at 40° C. for 4 h. The reaction mixture was cooled to room temperature and diluted with dichloromethane. The organic layer was washed once with a saturated aqueous solution of $NH_4Cl$, once with a saturated aqueous solution of $NaHCO_3$, and once with a saturated aqueous solution of NaCl. The organic layer was dried using a phase separator and concentrated under reduced pressure. The crude was purified by flash chromatography on silica gel using a gradient of ethyl acetate in heptane from 10% to 50%. The desired fractions were combined and concentrated to afford the title compound as a white solid (65.3 mg, 100% purity, 60% yield, $t_r$=1.02 min). LCMS (Method E); $^1$H-NMR (400 MHz, DMSO-$d_6$) δ 9.20 (s, 1H), 7.48-7.42 (m, 2H), 7.41-7.32 (m, 5H), 7.32-7.25 (m, 3H), 7.09 (dd, J=10.5, 2.1 Hz, 1H), 7.05 (dd, J=8.4, 2.1 Hz, 1H), 5.05 (s, 2H), 4.34 (s, 4H).

Step 6: Synthesis of N-(3-(4-chloro-3-fluorophenyl)azetidin-3-yl)-4-(trifluoromethoxy)benzenesulfonamide (58)

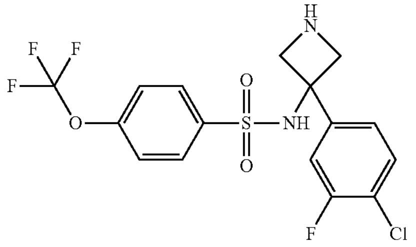 [SMILES: O=S(=O)(NC1(c2ccc(Cl)c(F)c2)CNC1)c1ccc(OC(F)(F)F)cc1]

In a round-bottomed flask, to a stirred solution of benzyl 3-(4-chloro-3-fluoro-phenyl)-3-[[4-(trifluoromethoxy)phenyl]sulfonylamino]azetidine-1-carboxylate (65 mg, 0.116 mmol) in acetonitrile (1.7 mL) at room temperature, was added iodo(trimethyl)silane (49 µL, 0.346 mmol). The reaction mixture was stirred at room temperature for 1.5 h. The reaction mixture was concentrated under reduced pressure. The crude was purified by flash chromatography on silica gel using a gradient of methanol (+0.7 N ammonia) in dichloromethane from 2% to 20%. The desired fractions were combined and water and triethylamine (81 µL, 0.583 mmol) were added. The layers were separated, then the aqueous layers were extracted once with dichloromethane. The combined organic layers were dried over $Na_2SO_4$, filtered, and concentrated under reduced pressure. To the residue was added diethyl ether and 2 M hydrogen chloride in $Et_2O$ (0.60 mL, 1.20 mmol). The suspension was stirred at room temperature overnight, filtered, washed with diethyl ether, and dried under vacuum at 45° C. for 2 days to afford the HCl salt of the title compound as a white powder (28.4 mg, 97.99% purity, 52% yield, $t_r$=1.57 min). LCMS (Method C): m/z found 425 $[M+H-HCl]^+$; $^1$H-NMR (DMSO-$d_6$, 500 MHz): δ (ppm) 8.98-9.94 (m, 3H), 7.42 (d, J=7.9 Hz, 2H), 7.25-7.31 (m, 3H), 7.12 (br d, J=9.9 Hz, 1H), 7.02 (d, J=8.2 Hz, 1H), 4.36-4.44 (m, 4H).

Example 23: N-(4-(4-fluorophenyl)piperidin-4-yl)-4-(trifluoromethoxy)benzenesulfonamide (59)

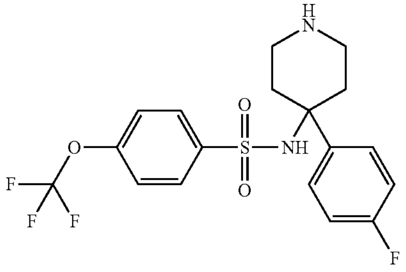 [SMILES: O=S(=O)(NC1(c2ccc(F)cc2)CCNCC1)c1ccc(OC(F)(F)F)cc1]

Step 1: Synthesis of tert-butyl 4-((tert-butoxycarbonyl)amino)-4-(4-fluorophenyl)piperidine-1-carboxylate

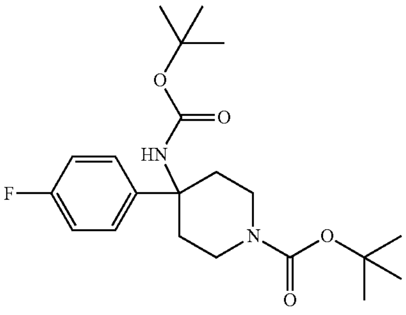 [SMILES: CC(C)(C)OC(=O)NC1(c2ccc(F)cc2)CCN(C(=O)OC(C)(C)C)CC1]

In a sealed vial, to a stirred solution of 4-(4-fluorophenyl)piperidin-4-amine dihydrochloride (150 mg, 0.561 mmol) and triethylamine (313 μL, 2.25 mmol) in DCM (2 mL) was added tert-butoxycarbonyl tert-butyl carbonate (123 mg, 0.561 mmol). The reaction mixture was stirred at rt overnight. Water (1 mL) and DCM (1 mL) were added, and the aqueous layer was extracted twice with DCM. Organic layers were washed with a saturated solution of $NH_4Cl$, then with a saturated solution of $NaHCO_3$, filtered through phase separator, and concentrated in vacuo to afford the title compound as a colorless oil (142 mg, 81% purity, 70% yield, $t_r$=0.58 min). LCMS (Method E): m/z found 295.3 $[M+H]^+$; $^1$H-NMR (DMSO-$d_6$, 400 MHz) δ (ppm) 7.61-7.51 (m, 2H), 7.17-7.07 (m, 2H), 3.71 (d, J=12.4 Hz, 2H), 3.27 (s, 2H), 1.90 (s, 2H), 1.77 (td, J=12.7, 12.1, 4.6 Hz, 2H), 1.54 (t, J=9.9 Hz, 2H), 1.41 (s, 9H).

Step 2: Synthesis of tert-butyl 4-(4-fluorophenyl)-4-((4-(trifluoromethoxy)phenyl)sulfonamido)piperidine-1-carboxylate

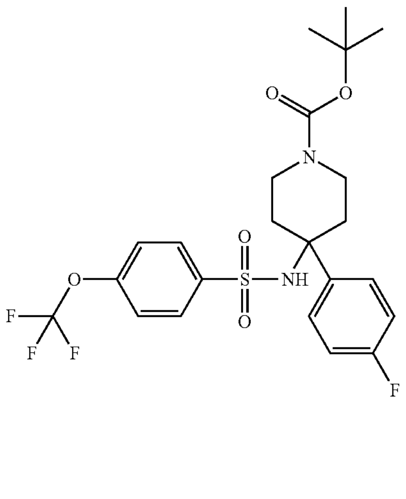 [SMILES: CC(C)(C)OC(=O)N1CCC(NS(=O)(=O)c2ccc(OC(F)(F)F)cc2)(c2ccc(F)cc2)CC1]

A sealed vial was charged with tert-butyl 4-amino-4-(4-fluorophenyl)piperidine-1-carboxylate (70%, 146 mg, 0.347 mmol), N,N-dimethylpyridin-4-amine (8.5 mg, 0.0694 mmol) and triethylamine (145 μL, 1.04 mmol) in DCM (3 mL). 4-(trifluoromethoxy)benzenesulfonyl chloride (65 μL, 0.382 mmol) was then added to the reaction mixture and it was stirred at 40° C. overnight. The reaction mixture was diluted with DCM and a saturated aqueous solution of $NaHCO_3$, then the layers were separated. The aqueous layer was extracted twice with DCM. The combined organic layers were washed with a saturated aqueous solution of NaCl, dried using a phase separator and concentrated under reduced pressure. The crude was purified by flash chromatography on silica gel using a gradient of MeOH in DCM from 0% to 5%. The desired fractions were combined and concentrated. The resulting white residue was purified by reverse-phase preparative chromatography using a gradient of acetonitrile in water from 0% to 100% (0.10% TFA in water and acetonitrile). The desired fractions were combined and concentrated to afford the title compound as a white solid (114 mg, 96% purity, 61% yield, $t_r$=1.02 min). LCMS (Method E): m/z found 419.3 $[M-Boc+H]^+$; $^1$H-NMR (DMSO-$d_6$, 400 MHz) δ (ppm) 8.19 (s, 1H), 7.38 (d, J=8.8 Hz, 2H), 7.22 (d, J=8.2 Hz, 2H), 7.10 (dd, J=8.8, 5.4 Hz, 2H), 6.73 (t, J=8.8 Hz, 2H), 3.70 (d, J=13.3 Hz, 2H), 3.24 (s, 2H), 2.37 (d, J=13.3 Hz, 2H), 1.71 (t, J=10.2 Hz, 2H), 1.40 (s, 9H).

Step 3: Synthesis of N-(4-(4-fluorophenyl)piperidin-4-yl)-4-(trifluoromethoxy)benzenesulfonamide (59)

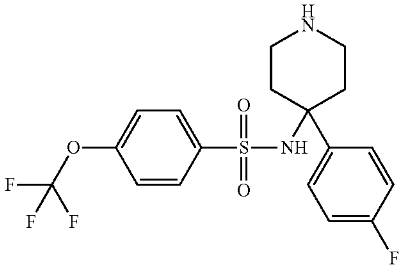 [SMILES: O=S(=O)(NC1(c2ccc(F)cc2)CCNCC1)c1ccc(OC(F)(F)F)cc1]

In a round-bottomed flask, to a stirred suspension of tert-butyl 4-(4-fluorophenyl)-4-[[4-(trifluoromethoxy)phenyl]sulfonylamino]piperidine-1-carboxylate (96%, 114 mg, 0.211 mmol) in diethyl ether (2 mL) at rt was added 2 M hydrogen chloride in $Et_2O$ (1.1 mL, 2.20 mmol). The reaction mixture was stirred at rt overnight. The suspension was filtered, washed with $Et_2O$, and dried under vacuum to afford the HCl salt of the title compound as a white solid (89 mg, 98.32% purity, 93% yield, $t_r$=1.27 min). LCMS (Method B): m/z found 419.1 $[M+H]^+$; $^1$H-NMR (DMSO-$d_6$, 500 MHz) δ 8.5-8.9 (m, 2H), 8.45 (s, 1H), 7.3-7.4 (m, 2H), 7.22 (dd, 2H, J=0.9, 8.9 Hz), 7.10 (dd, 2H, J=5.3, 8.9 Hz), 6.76 (t, 2H, J=8.9 Hz), 3.2-3.3 (m, 4H), 2.58 (br d, 2H, J=13.4 Hz), 1.9-2.1 (m, 2H).

Example 24: N-(4-phenylpiperidin-4-yl)-6-(trifluoromethoxy)pyridine-3-sulfonamide (60)

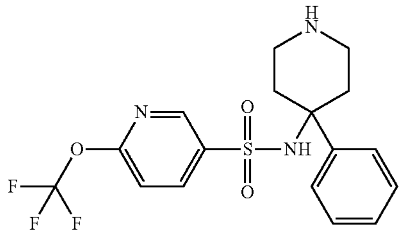 [SMILES: O=S(=O)(NC1(c2ccccc2)CCNCC1)c1ccc(OC(F)(F)F)nc1]

Step 1: Synthesis of 5-(benzylthio)-2-(trifluoromethoxy)pyridine

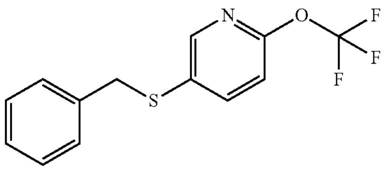 [SMILES: FC(F)(F)Oc1ccc(SCc2ccccc2)cn1]

A sealed vial was charged with 5-bromo-2-(trifluoromethoxy)pyridine (95%, 1.00 g, 3.93 mmol) and DIPEA (1.4 mL, 7.85 mmol) in anhydrous 1,4-dioxane (13.086 mL). The reaction mixture was degassed with argon for 5 min. Next, Xantphos (227 mg, 0.393 mmol), tris(dibenzylideneacetone)dipalladium(0) (180 mg, 0.196 mmol) and benzyl mercaptan (922 μL, 7.85 mmol) were added and the reaction mixture was stirred at 105° C. for 3 hours The mixture was cooled to rt, filtered on a pad of decalite, washed with dioxane and DCM, concentrated and purified by flash chromatography on silica gel using a gradient of EtOAc in Heptane from 0 to 10% to afford the title compound as a pale yellow oil (1072 mg, 96% purity, 92% yield, $t_r$=1.03 min). LCMS (Method D): m/z found 286.1 $[M+H]^+$; $^1$H-NMR (DMSO-$d_6$, 400 MHz) δ (ppm) 8.30-8.25 (m, 1H), 7.99 (dd, J=8.6, 2.6 Hz, 1H), 7.36-7.21 (m, 6H), 4.31 (s, 2H).

Step 2: Synthesis of tert-butyl 4-phenyl-4-((6-(trifluoromethoxy)pyridine)-3-sulfonamido)piperidine-1-carboxylate

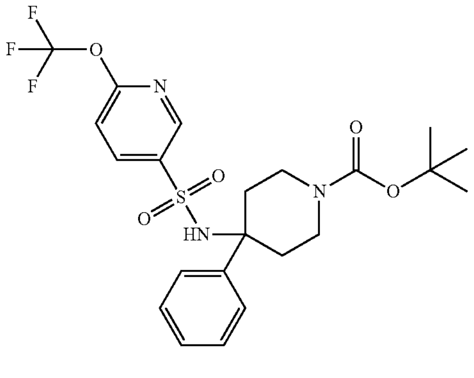 [SMILES: CC(C)(C)OC(=O)N1CCC(NS(=O)(=O)c2ccc(OC(F)(F)F)nc2)(c2ccccc2)CC1]

In a sealed vial, to a stirred solution of 5-benzylsulfanyl-2-(trifluoromethoxy)pyridine (150 mg, 0.526 mmol) in acetonitrile (4.41 mL) at 0° C. under nitrogen were added successively water (0.1119 mL), acetic acid (0.1692 mL), and 1,3-dichloro-5,5-dimethyl-imidazolidine-2,4-dione (207 mg, 1.05 mmol). The reaction mixture was stirred at 0° C. for 2 h, then concentrated in vacuo, dissolved in DCM (5 mL) and quenched with 10 mL of 5% $NaHCO_3$ at 0° C. The organic layer was dried through phase separator and added dropwise to a solution of tert-butyl 4-amino-4-phenylpiperidine-1-carboxylate (174 mg, 0.631 mmol) and triethylamine (0.37 mL, 2.63 mmol) in DCM (3 mL), and stirred overnight at 40° C. A half saturated solution of $NaHCO_3$ was added, and the mixture was extracted twice with DCM. The combined organic layers were dried over phase separator, concentrated in vacuo and purified by flash chromatography on silica gel using a gradient of methanol in DCM from 0% to 5%. The product obtained was re-purified by flash chromatography on silica gel using a gradient of EtOAc in Heptane from 0% to 50% to afford the title compound as a beige solid (16.2 mg, 91% purity, 5.59% yield, $t_r$=1.0 min) LCMS (Method E): m/z found 402.3 $[M-H+Boc]^+$; $^1$H-NMR (DMSO-$d_6$, 400 MHz) δ (ppm) 8.35 (s, 1H), 8.05 (d, J=2.4 Hz, 1H), 7.73 (dd, J=8.6, 2.5 Hz, 1H), 7.13-7.04 (m, 3H), 6.97 (dd, J=5.3, 1.7 Hz, 3H), 3.72 (d, J=13.5 Hz, 2H), 2.42 (d, J=13.3 Hz, 2H), 1.76 (t, J=10.6 Hz, 2H), 1.40 (s, 9H).

Step 3: Synthesis of N-(4-phenylpiperidin-4-yl)-6-(trifluoromethoxy)pyridine-3-sulfonamide (60)

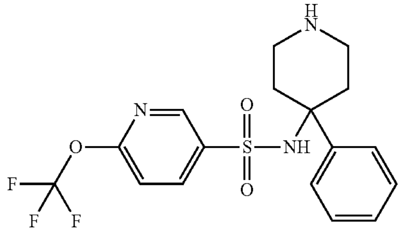 [SMILES: O=S(=O)(NC1(c2ccccc2)CCNCC1)c1ccc(OC(F)(F)F)nc1]

In a round bottomed flask, to a stirred solution of 4 M hydrogen chloride in dioxane (0.20 mL, 0.798 mmol) in diethyl ether (0.1996 mL) was added tert-butyl 4-phenyl-4-[[6-(trifluoromethoxy)-3-pyridyl]sulfonylamino]piperidine-1-carboxylate (91%, 11 mg, 0.0200 mmol). The mixture was stirred overnight at rt, filtered washed with $Et_2O$ and dried overnight under vacuum at 45° C. to afford the HCl salt of the expected compound as a white powder (6.9 mg, 97.23% purity, 76.77% yield, $t_r$=1.30 min). LCMS (Method C): m/z found 402.0 $[M+H]^+$; $^1$H-NMR (DMSO-$d_6$, 500 MHz) δ (ppm) 8.63 (br s, 3H), 8.05 (d, J=2.2 Hz, 1H), 7.73 (dd, J=8.7, 2.6 Hz, 1H), 6.98-7.11 (m, 6H), 3.26 (br d, J=13.4 Hz, 4H), 2.62 (br d, J=13.9 Hz, 2H), 2.04 (br s, 2H).

Example 25: N-(1-methyl-4-phenylpiperidin-4-yl)-4-(trifluoromethoxy)benzenesulfonamide (61)

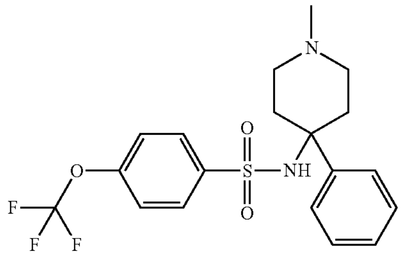 [SMILES: CN1CCC(NS(=O)(=O)c2ccc(OC(F)(F)F)cc2)(c2ccccc2)CC1]

Step 1: Synthesis of tert-butyl 4-phenyl-4-((4-(trifluoromethoxy)phenyl)sulfonamido)piperidine-1-carboxylate

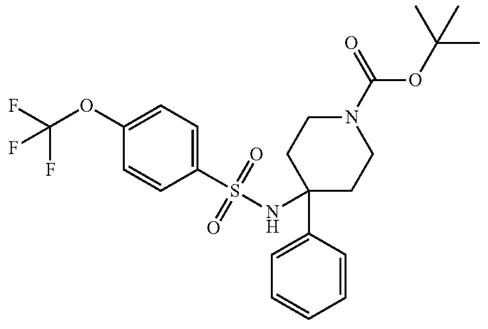 [SMILES: CC(C)(C)OC(=O)N1CCC(NS(=O)(=O)c2ccc(OC(F)(F)F)cc2)(c2ccccc2)CC1]

A sealed vial was charged with tert-butyl 4-amino-4-phenylpiperidine-1-carboxylate (265 mg, 0.959 mmol), DMAP (23 mg, 0.192 mmol) and triethylamine (535 μL, 3.84 mmol) in DCM (15 mL). 4-(trifluoromethoxy)benzenesulfonyl chloride (179 μL, 1.05 mmol) was added and the reaction mixture was stirred at 40° C. for 18 h, then the reaction mixture was quenched by the addition of a saturated aqueous solution of ammonium chloride (5 mL), water (10 mL), and dichloromethane (10 mL). The aqueous layer was extracted with dichloromethane (1×15 mL). The combined organic layers were dried over sodium sulfate, filtered, and concentrated under reduced pressure. The crude was purified by flash chromatography on silica gel using a gradient of methanol in dichloromethane from 0% to 5% to afford the title compound as a white powder (438 mg, 100% purity, 91% yield, $t_r$=1.03 min). LCMS (Method E): m/z found 523.3 $[M+Na]^+$; $^1$H-NMR (DMSO-$d_6$, 400 MHz): δ (ppm) 8.16 (s, 1H), 7.37-7.32 (m, 2H), 7.17 (d, J=8.0 Hz, 2H), 7.08 (dd, J=7.7, 1.9 Hz, 2H), 7.00-6.89 (m, 3H), 3.70 (d, J=13.6 Hz, 2H), 3.24 (s, 2H), 2.38 (d, J=13.3 Hz, 2H), 1.73 (t, J=10.6 Hz, 2H), 1.40 (s, 9H).

Step 2: Synthesis of N-(4-phenyl-4-piperidyl)-4-(trifluoromethoxy)benzenesulfonamide

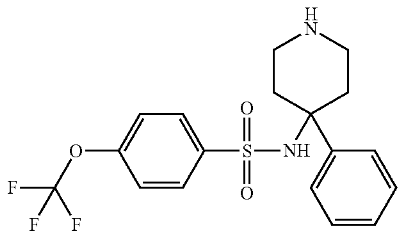 [SMILES: O=S(=O)(NC1(c2ccccc2)CCNCC1)c1ccc(OC(F)(F)F)cc1]

In a round-bottomed flask, to a stirred solution of 2 M hydrogen chloride in diethyl ether (25 mL, 49.2 mmol) was added tert-butyl 4-phenyl-4-[[4-(trifluoromethoxy)phenyl]sulfonylamino]piperidine-1-carboxylate (435 mg, 0.869 mmol). The mixture was stirred for 36 h at room temperature then filtered, washed with diethyl ether, and dried under vacuum at 50° C. for 3 days to afford the HCl salt of the title compound as a white powder (345 mg, 100% purity, 91% yield, $t_r$=0.64 min). LCMS (Method E): m/z found (DMSO-$d_6$, 400 MHz) δ (ppm) 8.81 (s, 2H), 8.45 (s, 1H), 7.38-7.27 (m, 2H), 7.16 (d, J=8.1 Hz, 2H), 7.07 (dd, J=8.0, 1.6 Hz, 2H), 6.97 (qd, J=8.6, 7.6, 2.7 Hz, 3H), 3.24 (d, J=8.2 Hz, 4H), 2.60 (d, J=13.6 Hz, 2H), 2.16-1.95 (m, 2H).

Step 3: Synthesis of N-(1-methyl-4-phenylpiperidin-4-yl)-4-(trifluoromethoxy)benzenesulfonamide (61)

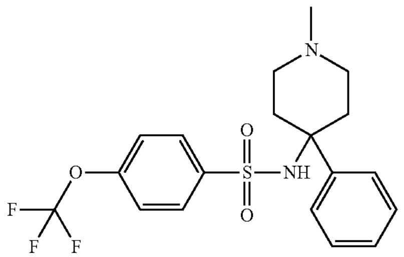 [SMILES: CN1CCC(NS(=O)(=O)c2ccc(OC(F)(F)F)cc2)(c2ccccc2)CC1]

In a sealed vial under nitrogen, a solution of N-(4-phenyl-4-piperidyl)-4-(trifluoromethoxy)benzenesulfonamide hydrochloride (100 mg, 0.229 mmol) and formaldehyde (8.2 mg, 0.275 mmol) in DCM (2.289 mL) and methanol (1 mL) was stirred at rt for 10 min. triethylamine (0.035 mL, 0.252 mmol) and acetic acid (0.026 mL, 0.458 mmol) were added and the mixture was stirred at rt for 30 min. Polymer bound $NaBH_3CN$ (229 mg, 0.458 mmol) was added and the mixture was stirred at rt for 16 h, then the mixture was filtered, the residue was washed with MeOH, the filtrate was concentrated and subsequently purified by flash chromatography on silica gel using a gradient of (MeOH+2% $NH_4OH$) in DCM from 5% to 10%. Desired fractions were gathered, $Et_2O$ (5 mL) and HCl 2 N in $Et_2O$ (5 mL) were added. The mixture was stirred overnight at rt, filtered, washed with $Et_2O$, then dried overnight under vacuum at 45° C. to afford the title compound as a white powder (77.2 mg, 100% purity, 75% yield, $t_r$=1.25 min). LCMS (Method B): m/z found 415 $[M+H]^+$; $^1$H-NMR (DMSO-$d_6$, 500 MHz): δ (ppm) 10.54 (br s, 1H), 8.41 (s, 1H), 7.32 (br d, J=8.6 Hz, 2H), 7.13 (br d, J=8.3 Hz, 2H), 7.06 (br d, J=7.3 Hz, 2H), 6.91-7.01 (m, 3H), 3.45 (br d, J=11.7 Hz, 2H), 3.32-3.39 (m, 2H), 2.60-2.98 (m, 5H), 2.08 (br t, J=12.3 Hz, 2H).

Example 26: N-(4-(4-chlorophenyl)piperidin-4-yl)-4-isopropoxybenzenesulfonamide (62)

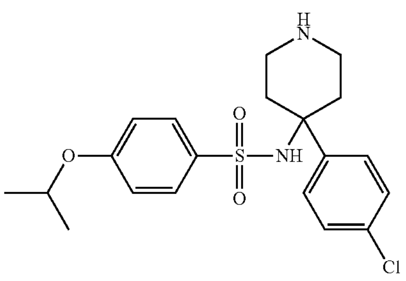 [SMILES: CC(C)Oc1ccc(S(=O)(=O)NC2(c3ccc(Cl)cc3)CCNCC2)cc1]

Step 1: Synthesis of tert-butyl 4-(4-chlorophenyl)-4-((4-isopropoxyphenyl)sulfonamido)piperidine-1-carboxylate

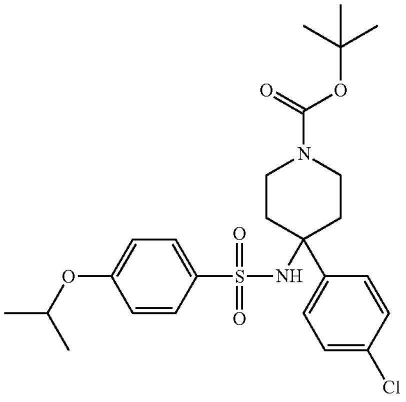 [SMILES: CC(C)Oc1ccc(S(=O)(=O)NC2(c3ccc(Cl)cc3)CCN(C(=O)OC(C)(C)C)CC2)cc1]

A sealed vial was charged with tert-butyl 4-amino-4-(4-chlorophenyl)piperidine-1-carboxylate (75 mg, 0.241 mmol) and triethylamine (101 μL, 0.724 mmol) in DCM (2 mL). 4-(propan-2-yloxy)benzenesulfonyl chloride (98%, 64 mg, 0.265 mmol) was then added and the reaction mixture was stirred at rt for 24 h. The reaction mixture was then heated at 40° C. for 2 h and N,N-dimethylpyridin-4-amine (5.9 mg, 0.0483 mmol) was added. The reaction mixture was stirred at 40° C. overnight. The reaction mixture was diluted with DCM and a saturated aqueous solution of $NaHCO_3$, and the layers were separated. The aqueous layer was extracted twice with DCM. The combined organic layers were washed with a saturated aqueous solution of NaCl, dried using a phase separator, and concentrated under reduced pressure. The crude was purified by flash chromatography on silica gel using a gradient of MeOH in DCM from 0% to 5%. The desired fractions were combined and concentrated to afford the title compound as an off white solid (82 mg, 98% purity, 65% yield, $t_r$=1.05 min). LCMS (Method E): m/z found 409.4 $[M\text{-}Boc+H]^+$; $^1$H-NMR (DMSO-$d_6$, 400 MHz): δ (ppm) 7.89 (s, 1H), 7.24-7.15 (m, 2H), 7.11 (d, J=8.7 Hz, 2H), 7.02 (d, J=8.7 Hz, 2H), 6.72 (d, J=8.9 Hz, 2H), 4.63 (p, J=6.0 Hz, 1H), 3.68 (d, J=13.2 Hz, 2H), 3.28-3.07 (m, 2H), 2.31 (d, J=13.9 Hz, 2H), 1.67 (t, J=10.4 Hz, 2H), 1.39 (s, 9H), 1.29 (d, J=6.0 Hz, 6H).

Step 2: Synthesis of N-(4-(4-chlorophenyl)piperidin-4-yl)-4-isopropoxybenzenesulfonamide (62)

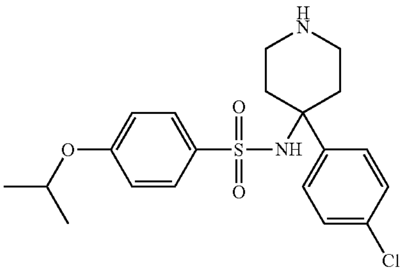 [SMILES: CC(C)Oc1ccc(S(=O)(=O)NC2(c3ccc(Cl)cc3)CCNCC2)cc1]

In a round-bottomed flask, to a stirred suspension of tert-butyl 4-(4-chlorophenyl)-4-[(4-isopropoxyphenyl)sulfonylamino]piperidine-1-carboxylate (80 mg, 0.157 mmol) in diethyl ether (1.5 mL) at rt under nitrogen was added 2 M hydrogen chloride in $Et_2O$ (786 μL, 1.57 mmol). The reaction mixture was stirred at rt overnight. Next, 4 M hydrogen chloride in 1,4-dioxane (0.20 mL, 0.786 mmol) was added at rt and the reaction mixture was stirred at rt for 4 h. The suspension was filtered, washed with $Et_2O$ and dried overnight at 40° C. to afford the HCl salt of the title compound as a white solid (47 mg, 99.73% purity, 67% yield, $t_r$=1.56 min). LCMS (Method C) m/z found 409 $[M+H]^+$; $^1$H-NMR (DMSO-$d_6$, 500 MHz) δ 8.63 (br s, 2H), 8.10 (s, 1H), 7.16 (d, 2H, J=8.8 Hz), 7.1-7.1 (m, 2H), 7.0-7.1 (m, 2H), 6.70 (d, 2H, J=9.0 Hz), 4.62 (quin, 1H, J=6.0 Hz), 3.1-3.3 (m, 4H), 2.4-2.6 (m, 2H), 1.8-2.1 (m, 2H), 1.28 (d, 6H, J=6.1 Hz).

Example 27: N-(3-(4-chlorophenyl)pyrrolidin-3-yl)-4-(trifluoromethoxy)benzenesulfonimidamide (63)

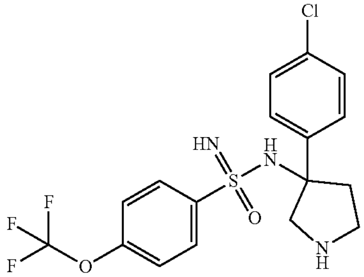 [SMILES: N=S(=O)(NC1(c2ccc(Cl)cc2)CCNC1)c1ccc(OC(F)(F)F)cc1]

Step 1: Synthesis of sodium 4-(trifluoromethoxy)benzenesulfinate

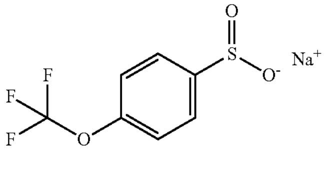 [SMILES: O=S([O-])c1ccc(OC(F)(F)F)cc1 ; [Na+]]

In a round-bottom flask equipped with a condenser, a solution of 4-(trifluoromethoxy)benzenesulfonyl chloride (0.65 mL, 3.84 mmol), sodium sulfite (1081 mg, 8.44 mmol) and $NaHCO_3$ (0.71 g, 8.44 mmol) in water (10 mL) was stirred at 65° C. for 20 h. The mixture was allowed to cool to rt, then concentrated. Methanol (10 mL) was added to the residue, the suspension was stirred at rt for 2 h, then filtered. The residue was washed with MeOH and the filtrate was concentrated to afford the title compound as a white powder (430 mg, 45% yield, $t_r$=0.91 min). LCMS (Method E); $^1$H-NMR (DMSO-$d_6$, 400 MHz): δ (ppm) 7.56 (d, J=8.5 Hz, 2H), 7.28 (d, J=8.4 Hz, 2H).

Step 2: Synthesis of 4-(trifluoromethoxy)benzenesulfinyl chloride

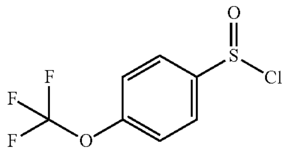 [SMILES: O=S(Cl)c1ccc(OC(F)(F)F)cc1]

In a round-bottom flask, to a stirred suspension of sodium 4-(trifluoromethoxy)benzenesulfinate (430 mg, 1.73 mmol) in anhydrous DCM (4.3173 mL) at room temperature under nitrogen were added successively oxalyl dichloride (0.23 mL, 2.60 mmol) and anhydrous DMF (0.0173 mL). The reaction mixture was stirred at room temperature for 1 h. The reaction mixture was concentrated under reduced pressure and dried under vacuum to afford the title compound as a white powder (1.23 g, 25% purity, 72% yield). The compound was used in the next step without further purification.

Step 3: Synthesis of N-[(3,4-dimethoxyphenyl) methyl]-4-(trifluoromethoxy)benzenesulfinamide

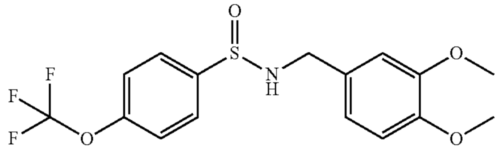 [SMILES: COc1ccc(CNS(=O)c2ccc(OC(F)(F)F)cc2)cc1OC]

In a round-bottom flask, to a stirred suspension of 4-(trifluoromethoxy)benzenesulfinyl chloride (25%, 1.10 g, 1.12 mmol) in anhydrous DCM (3.7473 mL) at room temperature under nitrogen were added successively 1-(3,4-dimethoxyphenyl)methanamine (98%, 0.26 mL, 1.69 mmol) and triethylamine (0.47 mL, 3.37 mmol). The reaction mixture was stirred at room temperature for 20 h. Water was added, and the aqueous layer was extracted twice with dichloromethane. The combined organic layers were dried through phase separator and concentrated under reduced pressure. The crude was purified by flash chromatography on silica gel using a gradient of methanol in dichloromethane from 0% to 5%, and once again using a gradient of MeOH (0.7 N $NH_3$) in DCM from 0% to 5%. Desired fractions were combined and concentrated in vacuo to afford the title compound as a pale yellow oil (142 mg, 97% purity, 33% yield, $t_r$=0.86 min). LCMS (Method E): m/z found 376.2 $[M+H]^+$; $^1$H-NMR (DMSO-$d_6$, 400 MHz): δ (ppm) 7.90-7.70 (m, 2H), 7.70-7.43 (m, 2H), 7.19-7.09 (m, 1H), 6.84 (d, J=8.2 Hz, 1H), 6.80 (d, J=1.9 Hz, 1H), 6.73 (dd, J=8.2, 2.0 Hz, 1H), 3.95 (dd, J=14.1, 5.2 Hz, 1H), 3.71 (d, J=0.9 Hz, 7H).

Step 4: Synthesis of benzyl 3-(4-chlorophenyl)-3-[[N-[(3,4-dimethoxyphenyl)methyl]-S-[4-(trifluoromethoxy)phenyl]sulfonimidoyl]amino]pyrrolidine-1-carboxylate

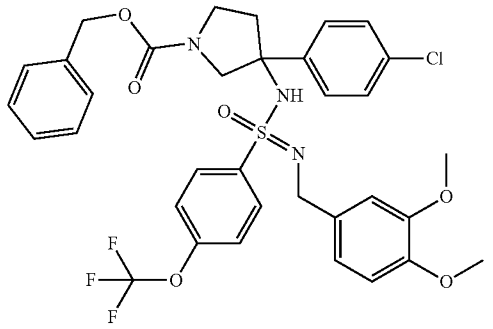 [SMILES: COc1ccc(CN=S(=O)(NC2(c3ccc(Cl)cc3)CCN(C(=O)OCc3ccccc3)C2)c2ccc(OC(F)(F)F)cc2)cc1OC]

In a round-bottom flask, to a stirred solution of N-[(3,4-dimethoxyphenyl)methyl]-4-(trifluoromethoxy)benzenesulfinamide (112 mg, 0.297 mmol) in tetrachloromethane (1.2 mL, 12.8 mmol) at 0° C. under nitrogen was added tert-butyl hypochlorite (0.040 mL, 0.356 mmol). The reaction mixture was stirred at 0° C. for 1 h in the dark. The reaction mixture was concentrated under reduced pressure at 2° C. The residue was dissolved in anhydrous THF (0.9292 mL), benzyl 3-amino-3-(4-chlorophenyl)pyrrolidine-1-carboxylate (108 mg, 0.327 mmol), DIPEA (156 μL, 0.891 mmol) and N,N-dimethylpyridin-4-amine (99%, 3.7 mg, 0.0297 mmol) were added successively, and the reaction mixture was stirred at 40° C. for 18 h. The reaction mixture was cooled to rt, quenched with water (20 mL) and ethyl acetate (20 mL) was added. The aqueous layer was extracted with ethyl acetate (20 mL). The combined organic layers were washed with a saturated aqueous solution of sodium chloride, dried over sodium sulfate, filtered and concentrated under reduced pressure. The crude was purified by flash chromatography on silica gel using a gradient of MeOH (0.7 N $NH_3$) in DCM from 0% to 6% to afford the title compound a colorless oil (145 mg, 90% purity, 62% yield, $t_r$=1.11 min). LCMS (Method E): m/z found 704.1 $[M+H]^+$; $^1$H-NMR (DMSO-$d_6$, 400 MHz): δ (ppm) 7.79 (d, J=8.8 Hz, 2H), 7.34 (dd, J=9.0, 4.5 Hz, 12H), 6.96-6.31 (m, 3H), 5.07 (d, J=4.3 Hz, 2H), 4.17-3.98 (m, 1H), 3.94-3.48 (m, 10H), 3.39 (s, 1H), 2.70-2.53 (m, 1H), 2.35-2.15 (m, 1H).

Step 5: Synthesis of benzyl 3-(4-chlorophenyl)-3-[[[4-(trifluoromethoxy)phenyl]sulfonimidoyl]amino]pyrrolidine-1-carboxylate

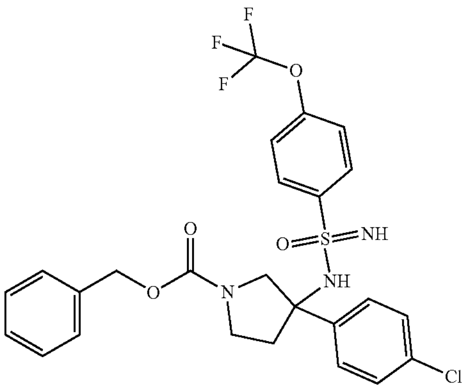 [SMILES: N=S(=O)(NC1(c2ccc(Cl)cc2)CCN(C(=O)OCc2ccccc2)C1)c1ccc(OC(F)(F)F)cc1]

In a round-bottom flask, to a stirred solution of benzyl 3-4-chloropentyl)-3-[[N-[(3,4-dimethoxyphenyl)methyl]-S-[4-(trifluoromethoxy)phenyl]sulfonimidoyl]amino]pyrrolidine-1-carboxylate (145 mg, 0.206 mmol) in a mixture of acetonitrile (2.75 mL) and water (1.38 mL) at 0° C. under nitrogen was added ceric ammonium nitrate (282 mg, 0.515 mmol). The reaction mixture was stirred at 0° C. for 2 h. The reaction mixture was diluted with water. The aqueous layer was extracted three times with ethyl acetate. The combined organic layers were washed with a saturated aqueous solution of NaCl, dried over $Na_2SO_4$, filtered, concentrated under reduced pressure and purified by flash chromatography on silica gel using a gradient of MeOH in DCM from 2% to 10%. The desired fractions were combined and concentrated to afford the title compound as an off-white solid (77 mg, 91% purity, 61% yield, $t_r$=0.97 min). LCMS (Method E): m/z found 576.2; $^1$H-NMR (DMSO-$d_6$, 400 MHz): δ (ppm) 8.10-6.47 (m, 14H), 5.15-4.95 (m, 2H), 4.84-3.36 (m, 5H), 2.94-2.54 (m, 1H), 2.30-1.86 (m, 1H).

Step 6: Synthesis of N-(3-(4-chlorophenyl)pyrrolidin-3-yl)-4-(trifluoromethoxy)benzenesulfonimidamide (63)

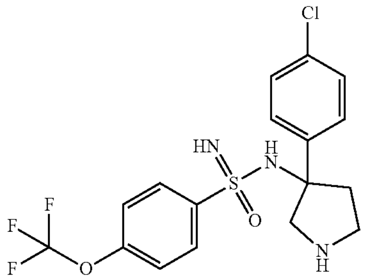 [SMILES: N=S(=O)(NC1(c2ccc(Cl)cc2)CCNC1)c1ccc(OC(F)(F)F)cc1]

In a sealed vial, a suspension of benzyl 3-(4-chlorophenyl)-3-[[[4-(trifluoromethoxy)phenyl]sulfonimidoyl]amino]pyrrolidine-1-carboxylate (77 mg, 0.139 mmol) in anhydrous ACN (3.4749 mL) was stirred at rt under nitrogen. Iodo(trimethyl)silane (83 mg, 0.417 mmol) was added dropwise, the mixture was stirred at rt for 1.5 h, concentrated in vacuo and purified by flash chromatography on silica gel using a gradient of MeOH (0.7 N $NH_3$) in DCM from 2% to 15%. Desired fractions were combined, water, and triethylamine (0.19 mL, 1.39 mmol) were added, the aqueous layer was extracted twice with DCM, and the combined organic layers were concentrated in vacuo. The resulting oil was dissolved in diethyl ether, pentane was added and the resulting solid was filtered to afford the expected compound as an off-white powder (24 mg, 92.9% purity, 38% yield, $t_r$=4.48 min). LCMS (Method F): m/z found 420; $^1$H-NMR (DMSO-$d_6$, 600 MHz)+TFA: δ (ppm) 7.69-7.77 (m, 2H), 7.35 (dd, J=15.2, 8.1 Hz, 2H), 7.13-7.26 (m, 4H), 3.81-4.04 (m, 1H), 3.12-3.66 (m, 3H), 2.69-2.89 (m, 1H), 2.13-2.32 (m, 1H).

Example 28: N-(3-(4-chlorophenyl)pyrrolidin-3-yl)-6-(trifluoromethoxy)pyridine-3-sulfonamide (64)

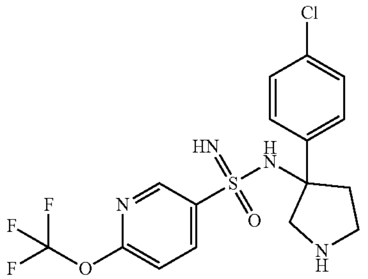 [SMILES: N=S(=O)(NC1(c2ccc(Cl)cc2)CCNC1)c1ccc(OC(F)(F)F)nc1]

Step 1: Synthesis of benzyl 3-(4-chlorophenyl)-3-hydroxypyrrolidine-1-carboxylate

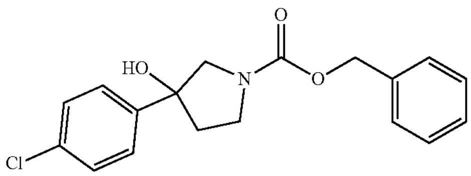 [SMILES: O=C(OCc1ccccc1)N1CCC(O)(c2ccc(Cl)cc2)C1]

In a three-neck round-bottomed flask, to a stirred suspension of magnesium (2.04 g, 84.1 mmol) and iodine crystal in anhydrous THF (90 mL) at room temperature under nitrogen was added few drops of a solution of 1-bromo-4-chlorobenzene (12.28 g, 64.2 mmol) in anhydrous THF (50 mL). The Grignard reaction was heated at 50° C. until decoloration (orange to colorless) was observed. Then, the rest of the solution was added dropwise and was stirred at 50° C. for 1 h (until magnesium was consumed). Then the reaction mixture was cooled to 0° C. and a solution of benzyl 3-oxopyrrolidine-1-carboxylate (97%, 10.00 g, 44.2 mmol) in anhydrous THF (50 mL) was added dropwise at 0° C. The reaction mixture was allowed to warm up to room temperature and stirred at room temperature for 18 h. The reaction mixture was quenched with a saturated aqueous solution of ammonium chloride (50 mL), then ethyl acetate (100 mL) and water (50 mL) were added. The aqueous layer was extracted with ethyl acetate (100 mL). The combined organic layers were washed with a saturated aqueous solution of sodium chloride, dried over sodium sulfate, filtered and concentrated under reduced pressure. The residue was triturated in DCM, filtered, washed with few DCM and dried under vacuum. The filtrate was concentrated and purified by flash chromatography on silica gel using a gradient of methanol in dichloromethane from 0% to 4%. The desired fractions were concentrated and combined with the first residue isolated to afford the title compound as a beige solid (8.939 g, 100% purity, 60.9% yield, $t_r$=0.89 min). LCMS (Method E): m/z found 332.3 $[M+H]^+$; $^1$H-NMR (DMSO-$d_6$, 400 MHz): δ (ppm) 7.59-7.49 (m, 2H), 7.45-7.25 (m, 7H), 5.56 (s, 1H), 5.09 (d, J=9.8 Hz, 2H), 3.67-3.39 (m, 4H), 2.30-2.16 (m, 1H), 2.04 (dt, J=12.7, 6.4 Hz, 1H).

Step 2: Synthesis of benzyl 3-azido-3-(4-chlorophenyl)pyrrolidine-1-carboxylate

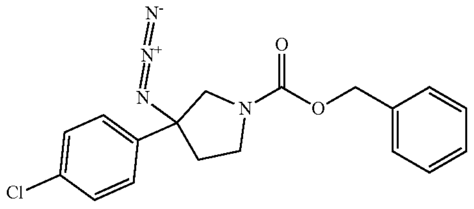 [SMILES: [N-]=[N+]=NC1(c2ccc(Cl)cc2)CCN(C(=O)OCc2ccccc2)C1]

In a round-bottomed flask, to a solution of benzyl 3-(4-chlorophenyl)-3-hydroxy-pyrrolidine-1-carboxylate (8.88 g, 26.8 mmol) in anhydrous DCM (100 mL) under nitrogen at 0° C. were added azido(trimethyl)silane (4.3 mL, 32.1 mmol) and $BF_3$ etherate (20 mL, 0.161 mol). The reaction mixture was allowed to warm up to room temperature and was stirred at this temperature overnight. The reaction mixture was quenched at 0° C. with a saturated aqueous solution of sodium bicarbonate (50 mL), then water (30 mL) and dichloromethane (50 mL) were added. The aqueous layer was extracted with DCM (2×50 mL). The combined organic layers were washed with a saturated aqueous solution of sodium chloride, dried using a phase separator and concentrated under reduced pressure to afford the title product as a brown oil (8.838 g, 70% purity, 64.8% yield, $t_r$=1.03 min). LCMS (Method E): m/z found 357.4 $[M+H]^+$; $^1$H-NMR (DMSO-$d_6$, 400 MHz): δ (ppm) 7.61-7.48 (m, 5H), 7.47-7.28 (m, 9H), 6.45 (d, J=12.4 Hz, OH), 5.15 (d, J=3.9 Hz, 1H), 5.12 (s, 2H), 4.58-4.43 (m, 1H), 4.38-4.23 (m, 1H), 4.02-3.95 (m, 1H), 3.70-3.42 (m, 3H), 2.59-2.51 (m, 1H), 2.40 (dt, J=22.5, 11.8 Hz, 1H).

Step 3: Synthesis of benzyl 3-amino-3-(4-chlorophenyl)pyrrolidine-1-carboxylate

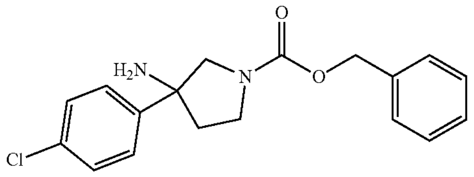 [SMILES: NC1(c2ccc(Cl)cc2)CCN(C(=O)OCc2ccccc2)C1]

In a round bottomed flask under nitrogen, triphenylphosphine (4.22 g, 16.1 mmol) then 4-methylbenzenesulfonic acid hydrate (9.18 g, 48.2 mmol) were added at room temperature to a stirred solution of benzyl 3-azido-3-(4-chlorophenyl)pyrrolidine-1-carboxylate (70%, 8.83 g, 17.3 mmol) in THF (76.5 mL). The mixture was stirred at room temperature overnight. The suspension was filtered, washed with diethyl ether and dried under vacuum at 45° C. for 48 h to afford the 4-methylbenzenesulfonic acid salt of the title compound as a white solid (6.68 g, 100% purity, 76.7% yield, $t_r$=0.62 min). LCMS (Method E): m/z found 331.3 $[M+H]^+$; $^1$H-NMR (DMSO-$d_6$, 400 MHz): δ (ppm) 8.49 (s, 3H), 7.56 (d, J=7.0 Hz, 4H), 7.47 (d, J=8.1 Hz, 2H), 7.43-7.30 (m, 5H), 7.22-6.94 (m, 3H), 5.19-5.08 (m, 2H), 4.06 (d, J=12.1 Hz, 1H), 3.80-3.52 (m, 3H), 2.46 (s, 1H), 2.29 (s, 3H).

Step 4: Synthesis of benzyl 3-(4-chlorophenyl)-3-[[4-(trifluoromethoxy)phenyl]sulfonylamino]pyrrolidine-1-carboxylate

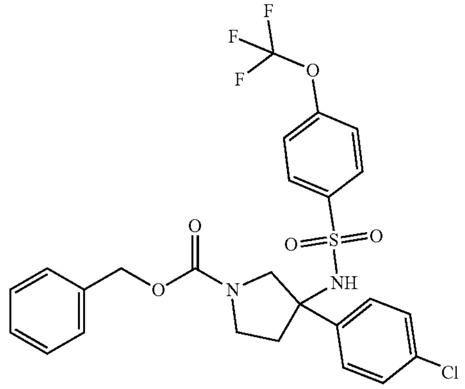 [SMILES: O=C(OCc1ccccc1)N1CCC(NS(=O)(=O)c2ccc(OC(F)(F)F)cc2)(c2ccc(Cl)cc2)C1]

A round-bottomed flask was charged with benzyl 3-amino-3-(4-chlorophenyl)pyrrolidine-1-carboxylate; 4-methylbenzenesulfonic acid (6.41 g, 12.7 mmol), triethylamine (14 mL, 0.102 mol) and 4-(trifluoromethoxy)benzenesulfonyl chloride (2.6 mL, 15.3 mmol) in DCM (117.86 mL). 4-Dimethylaminopyridine (311 mg, 2.55 mmol) was added and the reaction mixture was stirred at 40° C. (hotplate regulated at 45° C.) for 20 h. To the reaction mixture was added a saturated aqueous solution of ammonium chloride and dichloromethane. The layers were separated. The organic layer was washed with a saturated aqueous solution of $NaHCO_3$ and then a saturated aqueous solution of sodium chloride, dried using a phase separator and concentrated under reduced pressure. The residue was triturated in MeOH, filtered, washed with MeOH and dried under vacuum for 18 h to afford the title compound as a white powder (3.3 g, 97% purity, 45.3% yield, $t_r$=0.62 min). LCMS (Method E); $^1$H-NMR (DMSO-$d_6$, 400 MHz): δ (ppm) 7.79-7.67 (m, OH), 7.52 (dd, J=8.5, 1.5 Hz, OH), 7.44-7.24 (m, 1H), 5.20-4.97 (m, OH), 3.71-3.43 (m, 1H).

Step 5: Synthesis of 5-benzylsulfanyl-2-(trifluoromethoxy)pyridine

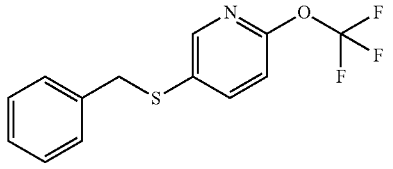 [SMILES: FC(F)(F)Oc1ccc(SCc2ccccc2)cn1]

A sealed vial was charged with 5-bromo-2-(trifluoromethoxy)pyridine (0.58 mL, 4.13 mmol), $Pd_2(dba)_3$ (95%, 199 mg, 0.207 mmol), (5-diphenylphosphanyl-9,9-dimethyl-xanthen-4-yl)-diphenyl-phosphane (98%, 244 mg, 0.413 mmol) in degassed anhydrous 1,4-dioxane-anhydrous (21 mL). Benzyl mercaptan (0.73 mL, 6.20 mmol) was added and the reaction mixture was stirred at 105° C. for 3 hours The mixture was cooled to rt, filtered on a pad of decalite, washed with dioxane, and DCM and concentrated. The crude was purified by flash silica gel chromatography using a gradient of 100% heptanes to 10% EtOAc in heptanes over 10 column volumes to afford the title compound as a beige solid (0.95 g, 95% purity, 76.6% yield, $t_r$=1.08 min). LCMS (Method E): m/z found 286 $[M+H]^+$; $^1$H-NMR (DMSO-$d_6$, 400 MHz): δ (ppm) 8.30-8.25 (m, 1H), 7.99 (dd, J=8.6, 2.6 Hz, 1H), 7.36-7.21 (m, 6H), 4.31 (s, 2H).

Step 6: Synthesis of 6-(trifluoromethoxy)pyridine-3-sulfonyl chloride

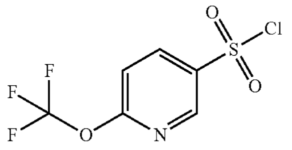 [SMILES: O=S(=O)(Cl)c1ccc(OC(F)(F)F)nc1]

In a three neck round bottom flask equipped with a thermometer, to a stirred solution of 5-benzylsulfanyl-2-(trifluoromethoxy)pyridine (0.95 g, 3.33 mmol) in acetonitrile (20 mL) at 0° C. under nitrogen were added successively water (1 mL) and acetic acid (1.5 mL), followed by the portion-wise addition of 1,3-dichloro-5,5-dimethyl-imidazolidine-2,4-dione (722 mg, 3.66 mmol). The reaction mixture was stirred at 0° C. for 2 h, then concentrated in vacuo, dissolved in DCM and quenched with 10 mL $NaHCO_3$ 5% at 0° C. The organic layer was separated and dried through phase separator and concentrated in vacuo. The crude was purified by flash chromatography on silica gel using a gradient of Heptane/DCM (100/0 to 1/1). Fractions were collected and solvent removed under vacuum to afford the title compound as a colorless oil (450 mg, 60% purity, 30.993% yield). $^1$H-NMR (400 MHz, DMSO-$d_6$) δ 8.50 (dd, J=2.4, 0.5 Hz, 1H), 8.13 (dd, J=8.4, 2.4 Hz, 1H), 7.25 (dd, J=8.4, 0.6 Hz, 1H).

Step 7: Synthesis of benzyl 3-(4-chlorophenyl)-3-[[6-(trifluoromethoxy)-3-pyridyl]sulfonylamino] pyrrolidine-1-carboxylate

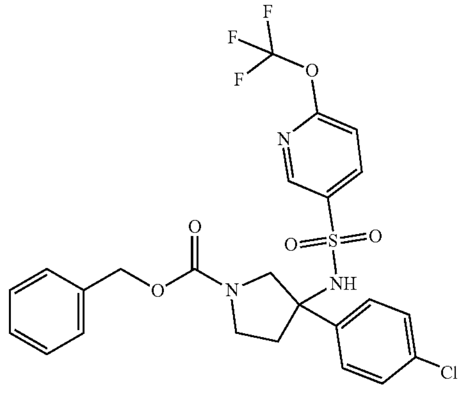 [SMILES: O=C(OCc1ccccc1)N1CCC(NS(=O)(=O)c2ccc(OC(F)(F)F)nc2)(c2ccc(Cl)cc2)C1]

In a round-bottomed flask, equipped with a condenser, to a stirred suspension of 6-(trifluoromethoxy)pyridine-3-sulfonyl chloride (60%, 450 mg, 1.03 mmol) in anhydrous DCM (9 mL), were successively added N,N-dimethylpyridin-4-amine (99%, 21 mg, 0.172 mmol) and N,N-diethylethanamine (0.30 mL, 2.15 mmol), followed by benzyl 3-amino-3-(4-chlorophenyl)pyrrolidine-1-carboxylate (95%, 300 mg, 0.862 mmol). The reaction mixture was stirred 5 h at reflux. The reaction was cooled at 25° C. and the mixture was quenched with a saturated solution of $NH_4Cl$. The phases were separated and the aqueous layer was extracted twice with DCM. Combined organic layers were washed once with water, dried over $Na_2SO_4$, filtered and concentrated under reduced pressure. The crude was purified by flash silica gel chromatography using a gradient of DCM/MeOH from 99/1 to 9/1 over 20 column volumes to afford the title compound as a beige solid (212 mg, 70% purity, 31% yield, $t_r$=1.96 min). LCMS (Method G): m/z found 556 $[M+H]^+$; $^1$H-NMR (400 MHz, DMSO-$d_6$) δ 7.61 (d, J=8.6 Hz, 1H), 7.56-7.25 (m, 11H), 6.49-6.42 (m, 1H), 5.16-5.12 (m, 2H), 4.60-4.43 (m, 2H), 4.40-4.26 (m, 2H), 3.89-3.60 (m, 1H).

Step 8: Synthesis of N-(3-(4-chlorophenyl)pyrrolidin-3-yl)-6-(trifluoromethoxy)pyridine-3-sulfonamide (64)

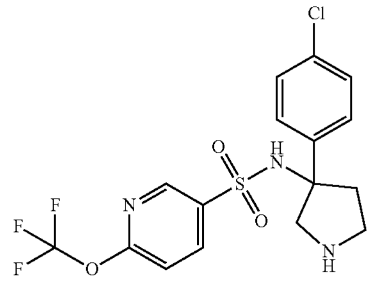 [SMILES: O=S(=O)(NC1(c2ccc(Cl)cc2)CCNC1)c1ccc(OC(F)(F)F)nc1]

Under nitrogen, to a stirred solution of benzyl 3-(4-chlorophenyl)-3-[[6-(trifluoromethoxy)-3-pyridyl]sulfonylamino]pyrrolidine-1-carboxylate (70%, 80 mg, 0.101 mmol) in acetonitrile (1.0 mL) was added iodo(trimethyl) silane (0.043 mL, 0.302 mmol) at 0° C. The reaction mixture was stirred at 0° C. for 2 h and the solvent was removed under vacuum. 1 M hydrogen chloride in $Et_2O$ (0.30 mL, 0.302 mmol) was added and the mixture was stirred at 25° C. for 30 min and the solvent was removed in vacuo. The crude was purified by reverse-phase preparative chromatography (C18aq, 25 g) using a gradient of acetonitrile+0.10% AcOH/water+0.10% AcOH from 0% to 100%. Fractions were collected and the solvent was removed in vacuo. The residue was taken up with DCM and was washed with a 1 M solution of $NaHCO_3$. Phases were separated and the aqueous layer was extracted twice with DCM. Combined organic layers were washed once with water, dried over $Na_2SO_4$, filtered and concentrated under reduced pressure. The residue was dissolved in dioxane (1 mL) and 1 M hydrogen chloride in $Et_2O$ (0.30 mL, 0.302 mmol) was added. The mixture was stirred at 25° C. for 1 h. The dioxane and $Et_2O$ was removed under vacuum. The residue was triturated in anhydrous $Et_2O$, filtered, washed with anhydrous $Et_2O$ and dried under vacuum at 25° C. for 16 h to afford the hydrochloride salt of title compound as a white solid (11 mg, 94.81% purity, 23% yield, $t_r$=1.2 min). LCMS (Method H): m/z found 422 $[M+H]^+$; $^1$H-NMR (DMSO-$d_6$, 600 MHz) δ 9.47 (br s, 2H), 9.07 (s, 1H), 8.14 (d, 1H, J=2.5

Hz), 7.87 (dd, 1H, J=2.6, 8.6 Hz), 7.15 (dd, 1H, J=0.6, 8.7 Hz), 7.0-7.1 (m, 4H), 4.15 (br d, 1H, J=11.7 Hz), 3.41 (br d, 3H, J=8.5 Hz), 2.8-3.0 (m, 1H), 2.16 (td, 1H, J=9.8, 13.3 Hz).

Example 29: N-(4-(5-fluoropyridin-2-yl)piperidin-4-yl)-4-(trifluoromethoxy)benzenesulfonamide (65)

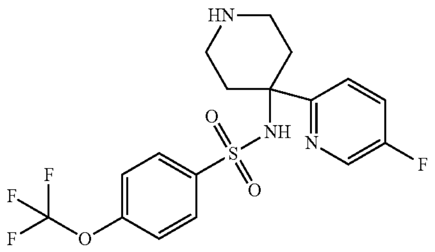 [SMILES: O=S(=O)(NC1(c2ccc(F)cn2)CCNCC1)c1ccc(OC(F)(F)F)cc1]

Step 1: Synthesis of 1-benzylpiperidin-4-one

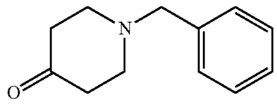 [SMILES: O=C1CCN(Cc2ccccc2)CC1]

In a sealed round-bottom flask, to a stirred suspension of piperidin-4-one hydrochloride (98%, 3.00 g, 21.7 mmol) in acetonitrile (50 mL) at room temperature was added $K_2CO_3$ (7.49 g, 54.2 mmol) and bromomethylbenzene (3.1 mL, 26.0 mmol). The reaction mixture was stirred at 60° C. overnight. The reaction mixture was poured into water. The layers were separated. The aqueous layer was extracted twice with DCM. The combined organic layers were washed with a saturated aqueous solution of sodium chloride, dried over sodium sulfate, filtered and concentrated under reduced pressure. The crude was purified by flash chromatography on silica gel using a gradient of EtOAc in Heptane from 10% to 100%. The desired fractions were combined and concentrated to afford the title compound as a yellow liquid (2.49 g, 87% purity, 53% yield, $t_r$=0.58 min). LCMS (Method E); $^1$H-NMR (DMSO-$d_6$, 400 MHz): δ (ppm) 7.38-7.25 (m, 5H), 3.61 (s, 2H), 2.68 (t, J=6.1 Hz, 4H), 2.35 (t, J=6.1 Hz, 4H).

Step 2: Synthesis of 1-benzylpiperidine-4-carbonitrile

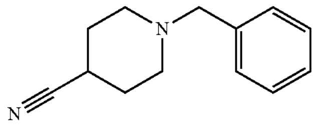 [SMILES: N#CC1CCN(Cc2ccccc2)CC1]

In a round-bottom flask, to a stirred solution of 1-benzylpiperidin-4-one (87%, 1.00 g, 4.60 mmol) and 1-(isocyanomethylsulfonyl)-4-methyl-benzene (98%, 916 mg, 4.60 mmol) in DME (36.459 mL) at 0° C. was added dropwise a solution of KOt-Bu (1.03 g, 9.19 mmol) dissolved in 16 mL of a 1:1 mixture of DME and tert-butyl alcohol. The reaction mixture was stirred at 0° C. for 1 h. The reaction mixture was allowed to warm up to room temperature and stirred at this temperature overnight. Water (50 mL) was added and the mixture was extracted three times with EtOAc (30 mL). The combined organic layers were washed with brine, dried over sodium sulfate, filtered and concentrated under reduced pressure. The crude was purified by flash chromatography using a gradient of MeOH in DCM from 1% to 8%. The desired fractions were combined and concentrated under reduced pressure to afford the title compound as a yellow oil (811.1 mg, 91% purity, 80% yield, $t_r$=0.41 min). LCMS (Method E): m/z found 201.3 $[M+H]^+$; $^1$H-NMR (DMSO-$d_6$, 400 MHz): δ (ppm) 7.37-7.20 (m, 5H), 3.46 (s, 2H), 2.86 (tt, J=8.4, 4.3 Hz, 1H), 2.52 (d, J=13.9 Hz, 2H), 2.25 (t, J=10.1 Hz, 2H), 1.85 (ddt, J=13.9, 7.3, 3.8 Hz, 2H), 1.75-1.63 (m, 2H).

Step 3: Synthesis of 1-benzyl-4-(5-fluoro-2-pyridyl) piperidine-4-carbonitrile

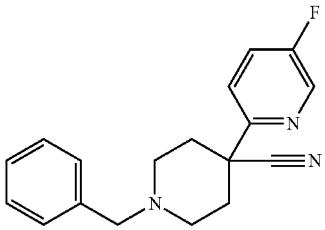 [SMILES: N#CC1(c2ccc(F)cn2)CCN(Cc2ccccc2)CC1]

In a sealed tube, to a stirred solution of 1-benzylpiperidine-4-carbonitrile (91%, 810 mg, 3.68 mmol) in anhydrous toluene (36.80 mL) at rt under nitrogen was added 2-bromo-5-fluoropyridine (98%, 661 mg, 3.68 mmol). The reaction mixture was cooled to 0° C. and 1 M NaHMDS (7.4 mL, 7.36 mmol) was added dropwise. The solution was stirred at 0° C. for 1 h, then at rt overnight. The reaction mixture was quenched with a saturated aqueous solution of ammonium chloride to reach pH 7, then EtOAc was added. The layers were separated and the aqueous layer was extracted with EtOAc. The combined organic layers were washed with brine, dried over sodium sulfate, filtered and concentrated under reduced pressure. The crude was purified by flash chromatography on silica gel using a gradient of EtOAc in cyclohexane from 10% to 80%. The desired fractions were combined and concentrated under reduced pressure to afford the expected product as an off-white solid (923.3 mg, 99% purity, 84% yield, $t_r$=0.53 min). LCMS (Method E): m/z found 296.4 $[M+H]^+$; $^1$H-NMR (DMSO-$d_6$, 400 MHz): δ (ppm) 8.63 (d, J=3.0 Hz, 1H), 7.84 (td, J=8.7, 3.0 Hz, 1H), 7.71 (dd, J=8.8, 4.2 Hz, 1H), 7.37-7.22 (m, 5H), 3.57 (s, 2H), 2.94 (dt, J=12.5, 3.4 Hz, 2H), 2.33 (td, J=11.8, 3.1 Hz, 2H), 2.18-2.07 (m, 4H).

Step 4: Synthesis of 1-benzyl-4-(5-fluoro-2-pyridyl)piperidine-4-carboxamide

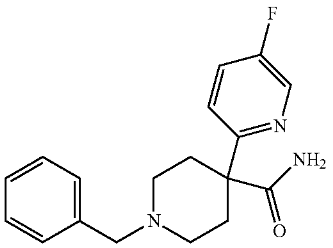 [SMILES: NC(=O)C1(c2ccc(F)cn2)CCN(Cc2ccccc2)CC1]

In a sealed tube, a mixture of 1-benzyl-4-(5-fluoro-2-pyridyl)piperidine-4-carbonitrile (99%, 200 mg, 0.670 mmol) in $H_2SO_4$ (2.6853 mL) and water (0.6713 mL) was stirred at 65° C. for 1.5 h. The mixture was poured in iced water and basified with aqueous 30% NaOH to reach pH 10-11. Water and DCM were added to obtain two homogeneous layers, and the aqueous layer was extracted twice with DCM. The combined organic layers were dried over sodium sulfate, filtered and concentrated under reduced pressure to afford the title compound as a white solid (198.9 mg, 99% purity, 94% yield, $t_r$=0.47 min). LCMS (Method D): m/z found 314.2 $[M+H]^+$; $^1$H-NMR (DMSO, 400 MHz): δ (ppm) 8.52 (d, J=3.0 Hz, 1H), 7.69 (td, J=8.8, 3.1 Hz, 1H), 7.47 (dd, J=8.9, 4.4 Hz, 1H), 7.37-7.19 (m, 5H), 7.03 (d, J=34.4 Hz, 2H), 3.39 (s, 2H), 2.44 (s, 1H), 2.39-2.20 (m, 2H), 2.06 (d, J=11.7 Hz, 2H).

Step 5: Synthesis of 1-benzyl-4-(5-fluoro-2-pyridyl)piperidin-4-amine

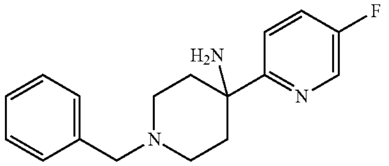 [SMILES: NC1(c2ccc(F)cn2)CCN(Cc2ccccc2)CC1]

In a sealed tube, 1-benzyl-4-(5-fluoro-2-pyridyl)piperidine-4-carboxamide (99%, 335 mg, 1.06 mmol) was charged and dissolved in acetonitrile (3.00 mL) and water (3.00 mL). [Bis(trifluoroacetoxy)iodo]benzene (96%, 484 mg, 1.08 mmol) was then charged, and the reaction was stirred at rt overnight and at 80° C. for 4 h. The reaction mixture was concentrated under reduced pressure and dried under vacuum overnight. The residue was dissolved in $Et_2O$ and 2 M hydrogen chloride in $Et_2O$ (11 mL, 21.2 mmol) was added. The suspension was stirred at rt 2 h, filtered and washed with $Et_2O$. The resulting gum was dissolved in MeOH and concentrated under reduced pressure. The residue was poured in a saturated aqueous solution of $Na_2CO_3$ to reach pH 10 and the aqueous layer was extracted twice with DCM. The combined organic layers were washed with brine, dried over sodium sulfate, filtered and concentrated under reduced pressure to afford the title compound as a brown oil (270 mg, 65% purity, 58% yield, $t_r$=0.45 min). LCMS (Method D): m/z found 286.2 $[M+H]^+$; $^1$H-NMR (DMSO-$d_6$, 400 MHz): δ (ppm) 8.48 (d, J=2.9 Hz, 1H), 7.74-7.61 (m, 2H), 7.36-7.28 (m, 5H), 6.41 (s, OH), 5.76 (s, OH), 3.48 (s, 2H), 2.48 (s, 1H), 2.19-1.94 (m, 3H), 1.88 (s, 2H), 1.51 (dq, J=11.4, 2.2 Hz, 2H).

Step 6: Synthesis of N-[1-benzyl-4-(5-fluoro-2-pyridyl)-4-piperidyl]-4-(trifluoromethoxy)benzenesulfonamide

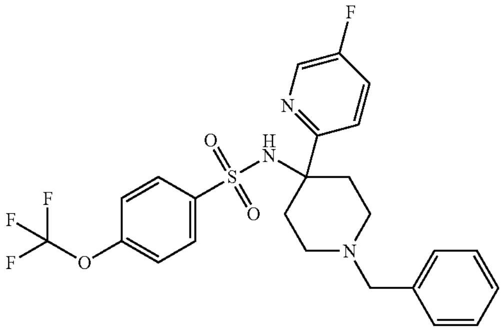 [SMILES: O=S(=O)(NC1(c2ccc(F)cn2)CCN(Cc2ccccc2)CC1)c1ccc(OC(F)(F)F)cc1]

A sealed vial was charged with 1-benzyl-4-(5-fluoro-2-pyridyl)piperidin-4-amine (59%, 270 mg, 0.558 mmol) and triethylamine (0.39 mL, 2.79 mmol) in DCM (5.1633 mL). 4-(trifluoromethoxy)benzenesulfonyl chloride (98%, 116 μL, 0.670 mmol) and 4-dimethylaminopyridine (14 mg, 0.112 mmol) were added and the reaction mixture was stirred at 40° C. overnight. The reaction mixture was quenched with a saturated aqueous solution of ammonium chloride and dichloromethane was added. The aqueous layer was extracted with dichloromethane. The combined organic layers were washed with a saturated aqueous solution of sodium chloride, dried using a phase separator and concentrated under reduced pressure. The crude was purified by flash chromatography on silica gel using a gradient of MeOH in DCM from 2% to 10%. The desired fractions were combined and concentrated to afford the title compound as an off-white foam (262.7 mg, 100% purity, 92% yield, $t_r$=0.68 min). LCMS (Method D): m/z found 510.2 $[M+H]^+$; $^1$H-NMR (DMSO-$d_6$, 400 MHz): δ (ppm) 8.12 (s, 1H), 8.09 (d, J=2.8 Hz, 1H), 7.50-7.41 (m, 2H), 7.36-7.20 (m, 9H), 3.42 (s, 2H), 2.42 (s, 3H), 2.32 (d, J=13.7 Hz, 2H), 2.04 (s, 2H).

Step 7: Synthesis of N-[4-(5-fluoro-2-pyridyl)-4-piperidyl]-4-(trifluoromethoxy)benzenesulfonamide

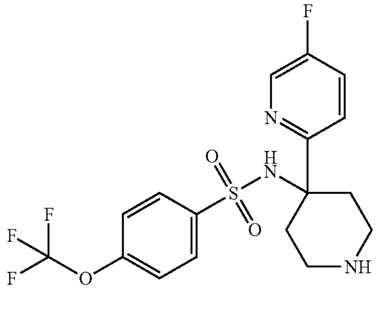 [SMILES: O=S(=O)(NC1(c2ccc(F)cn2)CCNCC1)c1ccc(OC(F)(F)F)cc1]

To a stirred solution of 1-chloroethyl carbonochloridate (99%, 0.10 mL, 0.954 mmol) 20 in DCE (12 mL) under nitrogen was added N-[1-benzyl-4-(5-fluoro-2-pyridyl)-4-piperidyl]-4-(trifluoromethoxy)benzenesulfonamide (100%, 243 mg, 0.477 mmol). The reaction mixture was stirred at room temperature for 2 days, then concentrated under reduced pressure. The residue was dissolved in MeOH (12 mL) and the reaction mixture was stirred at 65° C. overnight. The reaction mixture was cooled to room temperature and concentrated under 25 reduced pressure. The resulting white solid was triturated in a mixture of dichloromethane and methanol (95:5, 15 mL), and the resulting white powder was filtered, and washed twice with a mixture of dichloromethane and methanol (95:5, 2×5 mL). The resulting solid was once again triturated in a mixture of dichloromethane and methanol (95:5, 10 mL), the resulting powder was filtered, washed with a mixture of dichloromethane and methanol (95:5, 2×5 mL), dried under vacuum at 45° C. to afford the title compound as a white powder (132.8 mg, 99% purity, 66% yield, $t_r$=0.62 min). LCMS (Method E): m/z found 420.4 $[M+H]^+$; $^1$H-NMR (400 MHz, DMSO-$d_6$) δ 8.52 (s, 2H), 8.14 (d, J=2.9 Hz, 1H), 7.45-7.40 (m, 2H), 7.36 (dd, J=8.6, 2.9 Hz, 1H), 7.33-7.27 (m, 3H), 3.25-3.13 (m, 4H), 2.58-2.52 (m, 2H), 2.21-2.10 (m, 2H).

Step 8: Synthesis of N-(4-(5-fluoropyridin-2-yl)piperidin-4-yl)-4-(trifluoromethoxy)benzenesulfonamide (65)

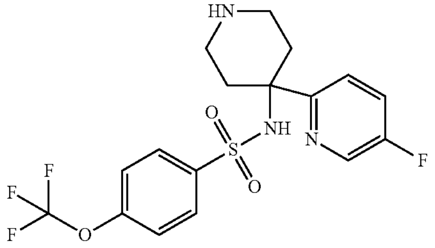 [SMILES: O=S(=O)(NC1(c2ccc(F)cn2)CCNCC1)c1ccc(OC(F)(F)F)cc1]

In a round-bottomed flask, to a stirred suspension of N-[4-(5-fluoro-2-pyridyl)-4-piperidyl]-4-(trifluoromethoxy)benzenesulfonamide (133 mg, 0.317 mmol) in $Et_2O$ (3.4 mL) at room temperature under nitrogen was added a solution of 2 M HCl in $Et_2O$ (2.4 mL, 4.80 mmol). After 10 minutes, MeOH (3.4 mL) was added and the mixture was stirred at room temperature for 4 h. The resulting suspension was filtered, washed three times with $Et_2O$ (3×5 mL) and dried at 45° C. for 18 h to afford the hydrochloride salt of title compound as a white powder (112.3 mg, 99.02% purity, 78% yield, $t_r$=0.62 min). LCMS (Method H): m/z found 420 $[M+H]^+$; $^1$H-NMR (DMSO-$d_6$, 500 MHz) δ 8.77 (br d, 2H, J=18.1 Hz), 8.56 (s, 1H), 8.13 (d, 1H, J=2.9 Hz), 7.4-7.5 (m, 2H), 7.3-7.4 (m, 1H), 7.2-7.3 (m, 3H), 3.1-3.3 (m, 4H), 2.56 (br d, 2H, J=14.2 Hz), 2.1-2.2 (m, 2H).

Example 30: N-(4-(bicyclo[1.1.1]pentan-1-yl)piperidin-4-yl)-4-(trifluoromethoxy)benzenesulfonamide (66)

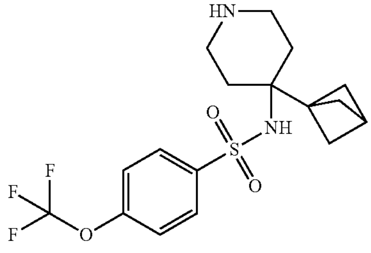 [SMILES: O=S(=O)(NC1(C23CC(C2)C3)CCNCC1)c1ccc(OC(F)(F)F)cc1]

Step 1: Synthesis of tert-butyl 4-(1-bicyclo[1.1.1]pentanyl)-4-nitro-piperidine-1-carboxylate

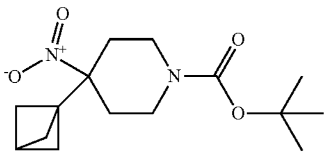

In a three-neck flask under nitrogen at −78° C., to a stirred solution of 2 M lithium diisopropyl amide (LDA) in THF/heptane (1.3 mL, 2.52 mmol) was added dropwise tert-butyl 4-nitropiperidine-1-carboxylate (553 mg, 2.40 mmol) in anhydrous THF (6 mL). The reaction mixture was stirred at −78° C. for 30 min. Next, a solution of 0.5 M $ZnCl_2$ in THF (6.0 mL, 3.00 mmol) was added at −78° C. The reaction mixture was allowed to warm up to 0° C. and stirred at 0° C. for 5 min, before the drop-wise addition of 0.15 M tricyclo[1.1.1.0$^{1,3}$]pentane (8.0 mL, 1.20 mmol). The reaction mixture was stirred at 0° C. for 2 h and was allowed to warm up slowly to room temperature. The reaction mixture was stirred at this temperature overnight. A saturated aqueous solution of $NH_4Cl$ (12 mL) was added at 0° C. and was stirred at this temperature for 1 h. Next, EtOAc (20 mL) was added and the layers were separated. The aqueous layer was extracted twice with EtOAc (15 mL). The combined organic layers were washed once with a saturated aqueous solution of $NH_4Cl$ (15 mL) and once with a saturated aqueous solution of sodium chloride (15 mL), dried over $Na_2SO_4$, filtered and concentrated under reduced pressure. The crude was purified by flash silica gel chromatography using a gradient of EtOAc in cyclohexane from 2% to 100% to afford the title compound as a white solid (80.9 mg, 98% purity, 22% yield, $t_r$=1.03 min). LCMS (Method E); $^1$H-NMR (400 MHz, CDCl3) δ 4.11-4.01 (m, 2H), 2.70 (t, J=13.1 Hz, 2H), 2.53 (s, 1H), 2.45 (dq, J=14.9, 2.7 Hz, 2H), 1.72 (s, 6H), 1.62 (td, J=13.5, 4.9 Hz, 2H), 1.45 (s, 9H).

Step 2: Synthesis of tert-butyl 4-amino-4-(1-bicyclo [1.1.1]pentanyl)piperidine-1-carboxylate

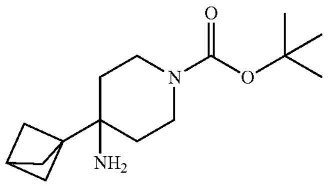 [SMILES: CC(C)(C)OC(=O)N1CCC(N)(C23CC(C2)C3)CC1]

A sealed vial was charged with tert-butyl 4-(1-bicyclo [1.1.1]pentanyl)-4-nitro-piperidine-1-carboxylate (79 mg, 0.267 mmol), $NH_4Cl$ (57 mg, 1.07 mmol) and iron (60 mg, 1.07 mmol) in a mixture of water (0.5 mL) and MeOH (2 mL). The reaction mixture was allowed to warm up to 70° C. and was stirred at this temperature for 3.5 h. The reaction mixture was cooled to room temperature, filtered through a pad of celite, washed twice with MeOH and the filtrate was concentrated under reduced pressure. The residue was dissolved in a mixture of dichloromethane (10 mL) and a half saturated aqueous solution of sodium bicarbonate (10 mL) was added. The layers were separated and the aqueous layer was extracted with dichloromethane (2×10 mL). The combined organic layers were washed once with a saturated aqueous solution of sodium bicarbonate and once with a saturated aqueous solution of sodium chloride, dried using a phase separator, and concentrated under reduced pressure to afford the title compound as an off-white solid (69.5 mg, 95% purity, 93% yield, $t_r$=0.58 min). LCMS (Method E): m/z found 267.4 $[M+H]^+$; $^1$H-NMR (400 MHz, DMSO-$d_6$) δ 3.69 (d, J=12.8 Hz, 2H), 3.11-2.91 (m, 3H), 2.45 (s, 1H), 1.58 (s, 6H), 1.39 (s, 9H), 1.32-1.21 (m, 2H), 1.17-1.07 (m, 2H).

Step 3: Synthesis of tert-butyl 4-(1-bicyclo[1.1.1] pentanyl)-4-[[4-(trifluoromethoxy)phenyl]sulfonylamino]piperidine-1-carboxylate

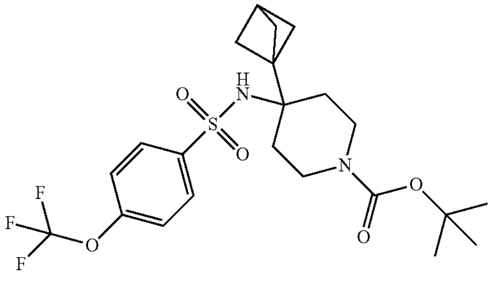 [SMILES: CC(C)(C)OC(=O)N1CCC(NS(=O)(=O)c2ccc(OC(F)(F)F)cc2)(C23CC(C2)C3)CC1]

In a round-bottomed flask, to a stirred suspension of tert-butyl 4-amino-4-(1-bicyclo[1.1.1]pentanyl)piperidine-1-carboxylate (67 mg, 0.252 mmol) and pyridine (41 μL, 0.503 mmol) in acetonitrile (2.5 mL) at room temperature was added 4-(trifluoromethoxy)benzenesulfonyl chloride (98%, 52 μL, 0.302 mmol). The reaction mixture was stirred at room temperature overnight. The reaction mixture was quenched with a half saturated aqueous solution of ammonium chloride (10 mL), then dichloromethane (15 mL) was added. The layers were separated. The aqueous layer was extracted twice with dichloromethane (10 mL). The combined organic layer were washed once with saturated aqueous solution of ammonium chloride (10 mL), once with a saturated aqueous layer of sodium bicarbonate, once with a saturated aqueous solution of sodium chloride, dried using a phase separator, and concentrated under reduced pressure. The crude was purified by flash silica gel chromatography using a gradient of ammoniacal methanol (0.7 N) in dichloromethane from 0% to 10%. The desired fractions were combined and concentrated under reduced pressure to afford the title compound as an off-white solid (75.1 mg, 98% purity, 60% yield, $t_r$=1.09 min). LCMS (Method E): m/z found 513.4 $[M+Na]^+$; $^1$H-NMR (400 MHz, DMSO-$d_6$) δ 8.01-7.90 (m, 2H), 7.64-7.53 (m, 2H), 7.51 (s, 1H), 3.58 (d, J=13.5 Hz, 2H), 2.55-2.52 (m, 2H), 2.39 (s, 1H), 1.85 (d, J=13.8 Hz, 2H), 1.33 (s, 9H), 1.28 (ddd, J=16.2, 12.2, 4.3 Hz, 2H).

Step 4: Synthesis of N-(4-(bicyclo[1.1.1]pentan-1-yl)piperidin-4-yl)-4-(trifluoromethoxy)benzenesulfonamide (66)

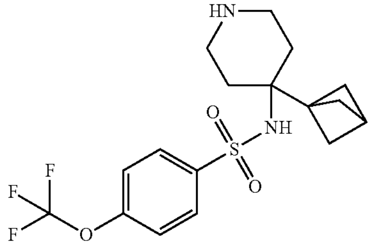 [SMILES: O=S(=O)(NC1(C23CC(C2)C3)CCNCC1)c1ccc(OC(F)(F)F)cc1]

In a round-bottomed flask, to a stirred solution of tert-butyl 4-(1-bicyclo[1.1.1]pentanyl)-4-[[4-(trifluoromethoxy) phenyl]sulfonylamino]piperidine-1-carboxylate (75 mg, 0.153 mmol) in $Et_2O$ (1.5 mL) at room temperature under nitrogen was added a solution of 4 M hydrogen chloride in dioxane (380 μL, 1.52 mmol). The reaction mixture was stirred at this temperature. After 4 h, a solution of 2 M hydrogen chloride in $Et_2O$ (800 μL, 1.60 mmol) was added. The reaction mixture was stirred at room temperature for 40 h. The resulting suspension was filtered, washed twice with diethyl ether (2×2 mL) and dried under vacuum at 45° C. for 18 h to afford the hydrochloride salt of the title compound as a white powder (56.8 mg, 100% purity, 87% yield, $t_r$=1.23 min). LCMS (Method H): m/z found 391 $[M+H]^+$; $^1$H-NMR (DMSO-$d_6$, 500 MHz): δ (ppm) 8.36-8.52 (m, 2H), 7.98 (d, J=7.9 Hz, 2H), 7.71 (s, 1H), 7.62 (d, J=8.1 Hz, 2H), 3.10 (br d, J=12.5 Hz, 2H), 2.53-2.64 (m, 2H), 2.38 (s, 1H), 2.01 (br d, J=13.7 Hz, 2H), 1.61-1.70 (m, 2H), 1.57 (s, 6H).

Example 31: N-(4-(4-chlorophenyl)piperidin-4-yl)-6-isopropoxypyridine-3-sulfonamide (67)

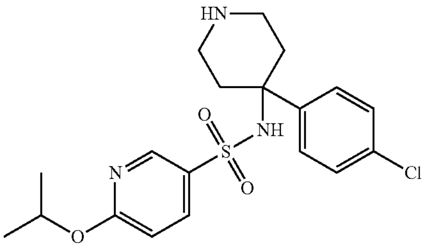 [SMILES: CC(C)Oc1ccc(S(=O)(=O)NC2(c3ccc(Cl)cc3)CCNCC2)cn1]

Step 1: Synthesis of tert-butyl 4-(4-chlorophenyl)-4-[(6-isopropoxy-3-pyridyl)sulfonylamino]piperidine-1-carboxylate

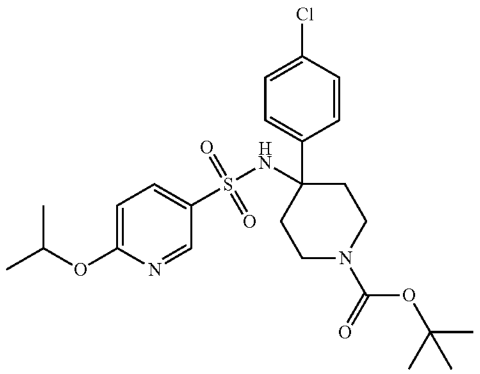 [SMILES: CC(C)Oc1ccc(S(=O)(=O)NC2(c3ccc(Cl)cc3)CCN(C(=O)OC(C)(C)C)CC2)cn1]

A sealed vial was charged with tert-butyl 4-amino-4-(4-chlorophenyl)piperidine-1-carboxylate (95%, 75 mg, 0.229 mmol), N,N-dimethylpyridin-4-amine (5.6 mg, 0.0458 mmol) and triethylamine (96 μL, 0.688 mmol) in DCM (2.2807 mL). 6-(propan-2-yloxy)pyridine-3-sulfonyl chloride (95%, 47 μL, 0.252 mmol) was added to the reaction mixture and it was stirred at 40° C. overnight. Additional N,N-dimethylpyridin-4-amine (5.6 mg, 0.0458 mmol), 6-(propan-2-yloxy)pyridine-3-sulfonyl chloride (95%, 28 mg, 0.115 mmol) and triethylamine (48 μL, 0.344 mmol) were added at rt and the reaction mixture was stirred at rt overnight. The reaction mixture was diluted with DCM and a saturated aqueous solution of $NaHCO_3$ was added. The layers were separated. The aqueous layer was extracted twice with DCM. The combined organic layers were washed with a saturated aqueous solution of NaCl, dried using a phase separator and concentrated under reduced pressure. The crude was purified by flash chromatography on silica gel using a gradient of MeOH in DCM from 0% to 5%. The desired fractions were combined and concentrated to afford the title compound as an off white solid (75 mg, 96% purity, 62% yield, $t_r$=1.09 min). LCMS (Method E): m/z found 532.3 $[M+Na]^+$; $^1$H-NMR (DMSO-$d_6$, 400 MHz): δ (ppm) 8.09 (s, 1H), 7.85 (d, J=2.6 Hz, 1H), 7.50 (dd, J=8.8, 2.6 Hz, 1H), 7.11 (d, J=8.7 Hz, 2H), 7.03 (d, J=8.7 Hz, 2H), 6.55 (d, J=8.8 Hz, 1H), 5.23 (hept, J=6.2 Hz, 1H), 3.71 (d, J=13.3 Hz, 2H), 3.26 (s, 2H), 2.36 (d, J=13.5 Hz, 2H), 1.70 (t, J=10.6 Hz, 2H), 1.40 (s, 9H), 1.30 (d, J=6.2 Hz, 6H).

Step 2: Synthesis of N-(4-(4-chlorophenyl)piperidin-4-yl)-6-isopropoxypyridine-3-sulfonamide (67)

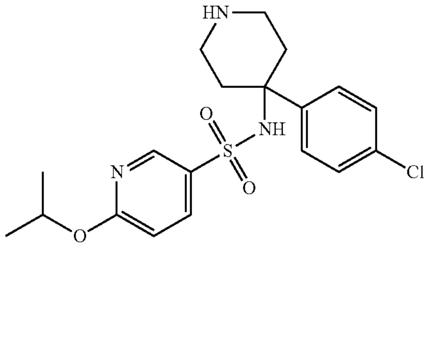 [SMILES: CC(C)Oc1ccc(S(=O)(=O)NC2(c3ccc(Cl)cc3)CCNCC2)cn1]

In a round-bottomed flask, to a stirred solution of tert-butyl 4-(4-chlorophenyl)-4-[(6-isopropoxy-3-pyridyl)sulfonylamino]piperidine-1-carboxylate (73 mg, 0.143 mmol) in $Et_{20}$ (2.269 mL) at rt was added 2 M HCl in $Et_2O$ (0.72 mL, 1.43 mmol). The reaction mixture was stirred at rt for 8 h. Additional 2 M HCl in $Et_2O$ (1.0 mL, 2.00 mmol) was added and the reaction mixture was stirred at rt for 20 h. Next, 4 M HCl in 1,4-dioxane (0.80 mL, 3.20 mmol) was added and the reaction mixture was stirred at rt for 24 h. The suspension was filtered, washed with $Et_2O$ (5 mL) and dried under vacuum at 50° C. for 18 h. The resulting powder was purified by reverse-phase flash chromatography using a gradient of acetonitrile in water from 0% to 100% (0.1% AcOH in water and acetonitrile). The residue was stirred in 2 M HCl in $Et_2O$ (0.72 mL, 1.43 mmol) for 2 h, The resulting suspension was filtered, washed with $Et_2O$ and dried under vacuum at 40° C. for 3 days to afford the title compound as a white powder (34 mg, 98.99% purity, 54% yield, $t_r$=1.25 min). LCMS (Method H): m/z found 410 $[M+H]^+$; $^1$H-NMR (DMSO-$d_6$, 500 MHz): δ (ppm) 8.70 (br s, 2H), 8.35 (s, 1H), 7.85 (d, J=2.4 Hz, 1H), 7.49 (dd, J=8.8, 2.4 Hz, 1H), 7.05-7.15 (m, 4H), 6.55 (d, J=8.8 Hz, 1H), 5.22 (spt, J=6.2 Hz, 1H), 3.17-3.29 (m, 4H), 2.54-2.60 (m, 2H), 1.95-2.05 (m, 2H), 1.30 (d, J=6.4 Hz, 6H).

Example 32: N-(3-(4-chlorophenyl)pyrrolidin-3-yl)-N'-methyl-4-(trifluoromethoxy)benzenesulfonimidamide (68)

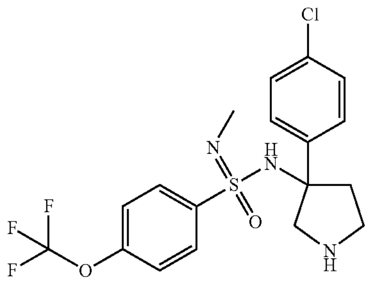 [SMILES: CN=S(=O)(NC1(c2ccc(Cl)cc2)CCNC1)c1ccc(OC(F)(F)F)cc1]

Step 1: Synthesis of N-methyl-4-(trifluoromethoxy)benzenesulfinamide

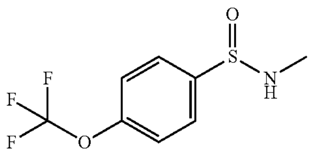

In a round-bottomed flask, to a stirred suspension of 4-(trifluoromethoxy)benzenesulfinyl chloride (95%, 300 mg, 1.17 mmol) in anhydrous DCM (3.8836 mL) at room temperature under nitrogen were added successively 2 M methylamine in THF (0.87 mL, 1.75 mmol) and triethylamine (0.49 mL, 3.50 mmol). The reaction mixture was stirred at room temperature for 20 h. Water was added, and the aqueous layer was extracted twice with dichloromethane. The combined organic layers were filtered dried through phase separator and concentrated under reduced pressure. The crude was purified by flash chromatography on silica gel using a gradient of methanol in dichloromethane from 0% to 6% to afford the title compound as a pale yellow oil (151 mg, 92% purity, 50% yield, $t_r$=0.75 min). LCMS (Method E): m/z found 240.1 $[M+H]^+$; $^1$H-NMR (DMSO-$d_6$, 400 MHz): δ (ppm) 7.76-7.69 (m, 2H), 7.59-7.53 (m, 2H), 6.63 (q, J=5.1 Hz, 1H), 2.26 (d, J=5.1 Hz, 3H).

Step 2: Synthesis of benzyl 3-(4-chlorophenyl)-3-[[N-methyl-S-[4-(trifluoromethoxy)phenyl]sulfonimidoyl]amino]pyrrolidine-1-carboxylate

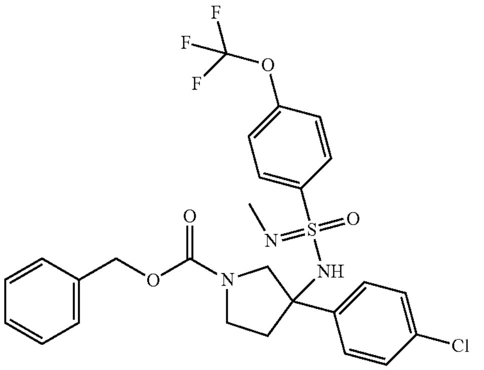 [SMILES: CN=S(=O)(NC1(c2ccc(Cl)cc2)CCN(C(=O)OCc2ccccc2)C1)c1ccc(OC(F)(F)F)cc1]

In a sealed vial, to a stirred solution of N-methyl-4-(trifluoromethoxy)benzenesulfinamide (100 mg, 0.418 mmol) in tetrachloromethane (1.7 mL, 18.1 mmol) at 0° C. under nitrogen was added tert-butyl hypochlorite (0.057 mL, 0.502 mmol). The reaction mixture was stirred at 0° C. for 1 h in the dark. The reaction mixture was concentrated under reduced pressure at 2° C. The residue was dissolved in anhydrous THF (1.3076 mL), then benzyl 3-amino-3-(4-chlorophenyl)pyrrolidine-1-carboxylate (152 mg, 0.460 mmol), DIPEA (219 μL, 1.25 mmol) and N,N-dimethylpyridin-4-amine (99%, 5.2 mg, 0.0418 mmol) were added successively, and the reaction mixture was stirred at 40° C. for 18 h. The reaction mixture was cooled to rt, quenched with water (20 mL) and EtOAc (20 mL) was added. The aqueous layer was extracted with EtOAc (20 mL). The combined organic layers were washed with a saturated aqueous solution of sodium chloride, dried over sodium sulfate, filtered and concentrated under reduced pressure. The crude was purified by flash chromatography on silica gel using a gradient of MeOH (0.7 N $NH_3$) in DCM from 2% to 10%, and once again using a gradient of MeOH (0.7 N $NH_3$) in DCM from 0% to 4% to afford the title compound as a pale yellow foam (112 mg, 96% purity, 45% yield, $t_r$=1.05 min). LCMS (Method E): m/z found 568.4 $[M+H]^+$; $^1$H-NMR (DMSO-$d_6$, 400 MHz): δ (ppm) 7.93-7.61 (m, 2H), 7.54-7.02 (m, 11H), 7.00-6.56 (m, 1H), 5.18-4.98 (m, 2H), 4.04 (dd, J=19.0, 10.5 Hz, 1H), 3.79-3.49 (m, 2H), 3.49-3.37 (m, 1H), 2.65-2.53 (m, 1H), 2.32-1.85 (m, 4H).

Step 3: Synthesis of N-(3-(4-chlorophenyl)pyrrolidin-3-yl)-N'-methyl-4-(trifluoromethoxy)benzenesulfonimidamide (68)

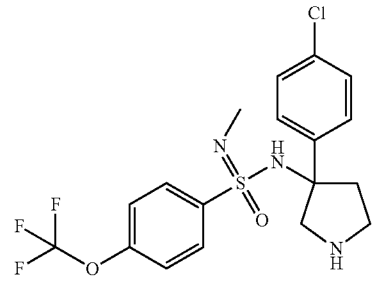 [SMILES: CN=S(=O)(NC1(c2ccc(Cl)cc2)CCNC1)c1ccc(OC(F)(F)F)cc1]

In a sealed vial under nitrogen, a solution of benzyl 3-(4-chlorophenyl)-3-[[N-methyl-S-[4-(trifluoromethoxy)phenyl]sulfonimidoyl]amino]pyrrolidine-1-carboxylate (96%, 112 mg, 0.189 mmol) in Acetonitrile (1.8929 mL) was stirred at rt. Next, iodo(trimethyl)silane (0.081 mL, 0.568 mmol) was added and the mixture was stirred at rt for 1 h. MeOH (0.092 mL, 2.27 mmol) was added at 0° C., the mixture was stirred at rt for 1 h, concentrated in vacuo, and purified by flash chromatography on silica gel using a gradient of MeOH (0.7 N $NH_3$) in DCM from 0% to 8%. The desired fractions were gathered, washed with a saturated $Na_2CO_3$ solution, filtered through phase separator and concentrated in vacuo. 2 M HCl (0.95 mL, 1.89 mmol) in $Et_2O$ was added and the mixture was stirred overnight at rt, filtered, washed with $Et_2O$ and dried under vacuum at 45° C. overnight to afford the bis(HCl) salt of the title compound as an off-white powder (23.3 mg, 98.86% purity, 26% yield, $t_r$=1.41 min). LCMS (Method H): m/z $[M+H]^+$; (DMSO-$d_6$, 500 MHz) δ 9.1-9.7 (m, 2H), 7.8-8.0 (m, 2H), 7.2-7.6 (m, 6H), 6.6-7.2 (m, 1H), 3.7-4.3 (m, 1H), 3.4-3.7 (m, 2H), 3.1-3.3 (m, 1H), 2.7-2.8 (m, 1H), 2.0-2.3 (m, 4H).

Example 33: N-(3-(4-chlorophenyl)-1-methylpyrrolidin-3-yl)-4-(trifluoromethoxy)benzenesulfonamide (69)

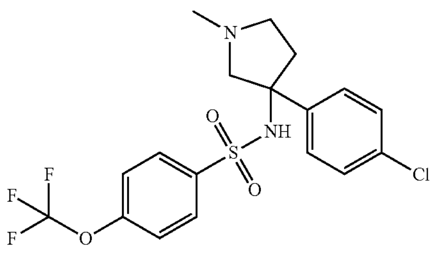 [SMILES: CN1CCC(NS(=O)(=O)c2ccc(OC(F)(F)F)cc2)(c2ccc(Cl)cc2)C1]

In a sealed vial under nitrogen, a solution of N-[3-(4-chlorophenyl)pyrrolidin-3-yl]-4-(trifluoromethoxy)benzenesulfonamide hydrochloride (60 mg, 0.131 mmol) and formaldehyde (4.7 mg, 0.157 mmol) in DCM (1.3 mL) and MeOH (0.6 mL) was stirred at room temperature for 10 min. Next, $Et_3N$ (20 μL, 0.144 mmol) and AcOH (19 μL, 0.328 mmol) were added and the mixture was stirred at room temperature for 30 min. Polymer bound $NaBH_3CN$ (131 mg, 0.262 mmol) was added and the mixture was stirred at room temperature for 18 h. The mixture was filtered, the residue was washed with dichloromethane and methanol, the filtrate was concentrated and purified by flash chromatography on silica gel using a gradient of ammoniacal methanol in dichloromethane from 2% to 10%. The residue was triturated in 2 M HCl in $Et_2O$ (656 μL, 1.31 mmol), filtered, washed with $Et_{20}$ and dried under vacuum at 50° C. for 18 h to afford the of the title compound as a white powder (47.4 mg, 99.86% purity, 77% yield, $t_r$=1.36 min). LCMS (Method H): m/z found 435.1 $[M+H]^+$; $^1$H-NMR (DMSO-$d_6$, 500 MHz): δ (ppm) 10.32-11.03 (m, 1H), 8.74-9.21 (m, 1H), 7.40 (d, J=8.8 Hz, 2H), 7.23 (d, J=8.3 Hz, 2H), 7.03 (s, 4H), 3.33-4.71 (m, 3H), 3.14-3.28 (m, 1H), 2.77-3.07 (m, 4H), 2.21-2.42 (m, 1H).

Example 34: N-(3-(4-chlorophenyl)-1-methylpyrrolidin-3-yl)-4-(trifluoromethoxy)benzenesulfonamide (70)

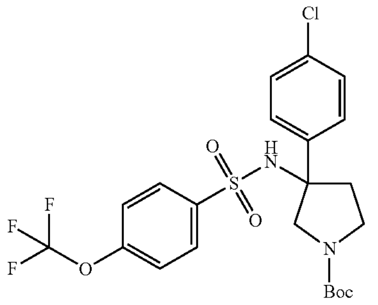 [SMILES: CC(C)(C)OC(=O)N1CCC(NS(=O)(=O)c2ccc(OC(F)(F)F)cc2)(c2ccc(Cl)cc2)C1]

In a sealed vial, to a stirred solution of N-[3-(4-chlorophenyl)pyrrolidin-3-yl]-4-(trifluoromethoxy)benzenesulfonamide hydrochloride (50 mg, 0.109 mmol) and triethylamine (76 μL, 0.547 mmol) in DCM (1 mL) was added di-tert-butyl dicarbonate (25 mg, 0.115 mmol). The reaction mixture was stirred at room temperature for 18 h. Water and dichloromethane were added. The aqueous layer was extracted with dichloromethane (2×5 mL). The combined organic layers were dried over sodium sulfate, filtered and concentrated under vacuum pressure. The crude was purified by flash chromatography on silica gel using a gradient of methanol in dichloromethane from 0% to 3%. The residue was triturated in pentane, filtered, washed with pentane and dried under vacuum at 50° C. for 4 days to afford the title compound as a colorless oil (45.3 mg, 98.4% purity, 78.3% yield, $t_r$=2.87 min). LCMS (Method H): m/z found 519 $[M-H]^-$; $^1$H-NMR (DMSO-$d_6$, 500 MHz) δ 8.59 (br s, 1H), 7.42 (d, 2H, J=8.6 Hz), 7.24 (br d, 2H, J=7.1 Hz), 7.04 (d, 4H, J=1.2 Hz), 4.01 (dd, 1H, J=7.8, 11.0 Hz), 3.3-3.5 (m, 2H), 3.2-3.3 (m, 1H), 2.6-2.8 (m, 1H), 2.0-2.3 (m, 1H), 1.40 (d, 9H, J=5.1 Hz).

Example 35: N-(3-(4-chlorophenyl)-1-(oxetan-3-yl)pyrrolidin-3-yl)-4-(trifluoromethoxy)benzenesulfonamide (71)

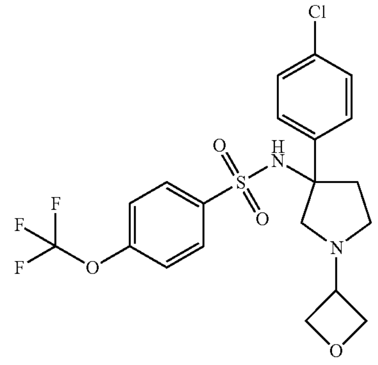 [SMILES: O=S(=O)(NC1(c2ccc(Cl)cc2)CCN(C2COC2)C1)c1ccc(OC(F)(F)F)cc1]

In a sealed vial under nitrogen, to a stirred solution of N-[3-(4-chlorophenyl)pyrrolidin-3-yl]-4-(trifluoromethoxy)benzenesulfonamide (100 mg, 0.238 mmol) in MeOH (2.3763 mL) were added oxetan-3-one (0.030 mL, 0.475 mmol) and acetic acid (0.027 mL, 0.475 mmol) and the mixture was stirred at rt for 30 min. Polymer bound $NaBH_3CN$ (238 mg, 0.475 mmol) was added and the mixture was stirred at rt overnight. The mixture was filtered, the residue was washed with MeOH and EtOAc, the filtrate was concentrated, then the crude product was purified by flash chromatography on silica gel using a gradient of MeOH in DCM from 0% to 10%. The desired fractions were gathered, concentrated in vacuo. The resulting solid was triturated with $Et_2O$, filtered, and dried under vacuum for 72 h at 45° C. to afford the title product as a white powder (70.7 mg, 98.9% purity, 62% yield, $t_r$=1.49 min). LCMS (Method H): m/z found 477 $[M+H]^+$; $^1$H-NMR (500 MHz, DMSO-$d_6$) δ 8.57-8.19 (m, 1H), 7.49-7.44 (m, 2H), 7.27 (d, J=8.1 Hz, 2H), 7.15-7.11 (m, 2H), 7.03 (d, J=8.6 Hz, 2H), 4.62-4.26 (m, 5H), 3.81-3.66 (m, 1H), 3.20-2.90 (m, 2H), 2.77-2.60 (m, 2H), 2.17-2.08 (m, 1H).

Example 36: N-(3-(4-chlorophenyl)-1-(methylsulfonyl)pyrrolidin-3-yl)-4-(trifluoromethoxy)benzenesulfonamide (72)

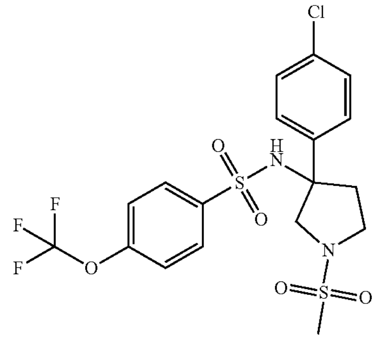 [SMILES: CS(=O)(=O)N1CCC(NS(=O)(=O)c2ccc(OC(F)(F)F)cc2)(c2ccc(Cl)cc2)C1]

In a vial, to a stirred solution of N-[3-(4-chlorophenyl)pyrrolidin-3-yl]-4-(trifluoromethoxy)benzenesulfonamide (98%, 70 mg, 0.163 mmol) in DCM (1.6466 mL) at room temperature were added successively triethylamine (114 μL, 0.815 mmol) and methanesulfonyl chloride (15 μL, 0.196 mmol). The reaction mixture was stirred at rt overnight. Additional N,N-dimethylpyridin-4-amine (99%, 4.0 mg, 0.0326 mmol) was added and the reaction mixture was stirred at rt for 4.5 h. Then, the reaction mixture was heated at 40° C. overnight. The reaction mixture was diluted with DCM and a saturated aqueous solution of $NaHCO_3$ was added. The layers were separated. The aqueous layer was extracted 10 with DCM. The combined organic layers were washed with a saturated aqueous solution of NaCl, dried using a phase separator and concentrated under reduced pressure. The crude was purified by flash chromatography on silica gel using a gradient of MeOH in DCM from 0% to 5%. The desired fractions were combined and concentrated to afford the expected product as a colorless oil. $Et_2O$ was added and the precipitate formed was filtered and washed with $Et_2O$. The precipitate was combined and dried under vacuum for 18 h at 45° C. to afford the expected compound as a white powder (41.8 mg, 97.77% purity, 50.25% yield, $t_r$=2.37 min). LCMS (Method H): m/z found 499.1 $[M+H]^+$; $^1$H-NMR (500 MHz, DMSO-$d_6$) δ 8.61 (s, 1H), 7.43-7.36 (m, 2H), 7.23 (d, J=8.1 Hz, 2H), 7.07-6.96 (m, 4H), 4.08 (dd, J=10.6, 1.3 Hz, 1H), 3.52 (d, J=10.6 Hz, 1H), 3.46 (td, J=9.5, 6.8 Hz, 1H), 3.39 (td, J=8.9, 2.7 Hz, 1H), 2.97 (s, 3H), 2.77 (dd, J=12.9, 6.2 Hz, 1H), 2.21 (dt, J=12.8, 8.9 Hz, 1H).

Example 37: N-(4-(5-chlorothiazol-2-yl)piperidin-4-yl)-4-(trifluoromethoxy)benzenesulfonamide (73)

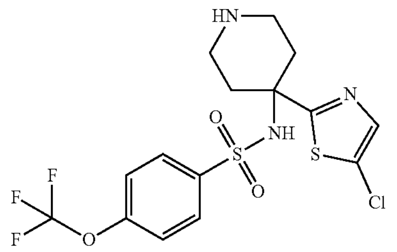 [SMILES: O=S(=O)(NC1(c2ncc(Cl)s2)CCNCC1)c1ccc(OC(F)(F)F)cc1]

Step 1: Synthesis of tert-butyl 4-carbamoyl-4-[[4-(trifluoromethoxy)phenyl]sulfonylamino]piperidine-1-carboxylate

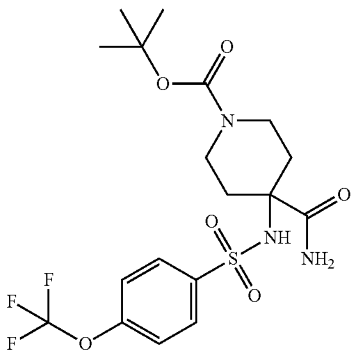 [SMILES: CC(C)(C)OC(=O)N1CCC(NS(=O)(=O)c2ccc(OC(F)(F)F)cc2)(C(N)=O)CC1]

In a screwed vial, to a stirred solution of tert-butyl 4-amino-4-carbamoylpiperidine-1-carboxylate (95%, 1.50 g, 5.86 mmol) in DCM (51 mL) at room temperature were added successively triethylamine (3.3 mL, 23.4 mmol), DMAP (99%, 145 mg, 1.17 mmol) and 4-(trifluoromethoxy)benzenesulfonyl chloride (98%, 1.2 mL, 7.03 mmol). The reaction mixture was stirred at room temperature for 18 h. The reaction mixture was quenched with a saturated aqueous solution of ammonium chloride (20 mL), then water (20 mL) and DCM were added. The aqueous layer was extracted with DCM (20 mL). The combined organic layers were washed with a saturated aqueous solution of sodium chloride and concentrated under reduced pressure. The crude was purified by flash chromatography on silica gel using a gradient of ammoniacal MeOH in DCM from 1% to 5% to afford the title compound as a beige powder (2.46 g, 100% purity, 90% yield, $t_r$=0.83 min). LCMS (Method E): m/z found 368.3 $[M-C(=O)OtBu+H]^+$; $^1$H-NMR (DMSO-$d_6$, 400 MHz): δ (ppm) 7.96 (s, 1H), 7.95-7.90 (m, 2H), 7.60-7.52 (m, 2H), 7.02 (d, J=38.9 Hz, 2H), 3.49-3.35 (m, 2H), 2.87 (ddd, J=13.4, 9.2, 3.8 Hz, 2H), 1.86-1.65 (m, 4H), 1.35 (s, 9H).

Step 2: Synthesis of tert-butyl 4-carbamothioyl-4-[[4-(trifluoromethoxy)phenyl]sulfonylamino]piperidine-1-carboxylate

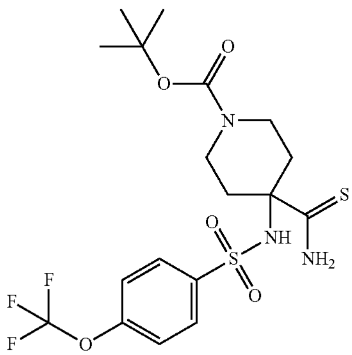 [SMILES: CC(C)(C)OC(=O)N1CCC(NS(=O)(=O)c2ccc(OC(F)(F)F)cc2)(C(N)=S)CC1]

A sealed vial was successively charged with tert-butyl 4-carbamoyl-4-[[4-(trifluoromethoxy)phenyl]sulfonylamino]piperidine-1-carboxylate (0.80 g, 1.71 mmol) and Lawesson's reagent (97%, 357 mg, 0.856 mmol) in anhydrous THF (12 mL). The reaction mixture was stirred at 60° C. for 20 h. The reaction mixture was quenched with a saturated aqueous solution of sodium bicarbonate (5 mL) and water (15 mL) and dichloromethane (15 mL) were added. The aqueous layer was extracted with dichloromethane (15 mL). The combined organic layers were washed with a saturated aqueous solution of sodium chloride, dried over sodium sulfate, filtered and concentrated under reduced pressure. The crude was purified by flash chromatography on silica gel using a gradient of methanol in dichloromethane from 0% to 5% to afford the title compound as a white powder (548 mg, 100% purity, 66% yield, $t_r$=0.91 min). LCMS (Method E): m/z found 384.3 $[M-C(=O)OtBu+H]^+$; $^1$H-NMR (DMSO-$d_6$, 500 MHz): δ (ppm) 9.72 (s, 1H), 8.60 (s, 1H), 8.06 (s, 1H), 7.96-7.89 (m, 2H), 7.58-7.51 (m, 2H), 3.57 (d, J=13.3 Hz, 2H), 2.71 (t, J=12.5 Hz, 2H), 2.00 (d, J=13.8 Hz, 2H), 1.93 (d, J=12.7 Hz, 3H), 1.35 (s, 9H).

Step 3: Synthesis of tert-butyl 4-thiazol-2-yl-4-[[4-(trifluoromethoxy)phenyl]sulfonylamino]piperidine-1-carboxylate

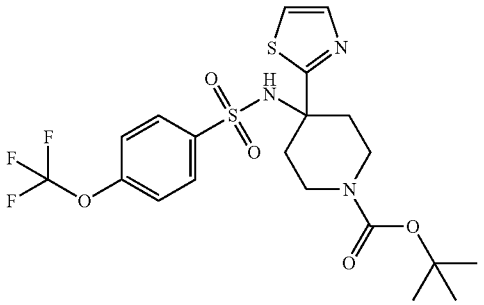 [SMILES: CC(C)(C)OC(=O)N1CCC(NS(=O)(=O)c2ccc(OC(F)(F)F)cc2)(c2nccs2)CC1]

A sealed vial was charged with tert-butyl 4-carbamothioyl-4-[[4-(trifluoromethoxy)phenyl]sulfonylamino]piperidine-1-carboxylate (98%, 515 mg, 1.04 mmol) and chloroacetaldehyde (50% aqueous solution) (269 μL, 2.09 mmol) in Acetone (20 mL). The reaction mixture was stirred at 60° C. for 18 h. The reaction mixture was cooled to room temperature and water (10 mL) and EtOAc (10 mL) were added. The aqueous layer was extracted with EtOAc (10 mL). The combined organic layers were washed with a saturated aqueous solution of sodium chloride, dried over sodium sulfate, filtered and concentrated under reduced pressure. The crude was purified by flash chromatography on silica gel using a gradient of methanol in dichloromethane from 1% to 4% to afford the title compound as a white powder (128 mg, 97% purity, 23% yield, $t_r$=0.98 min). LCMS (Method E): m/z found 508.3 $[M+H]^+$; $^1$H-NMR (DMSO-$d_6$, 400 MHz): δ (ppm) 8.60 (s, 1H), 7.68-7.56 (m, 2H), 7.47 (d, J=3.2 Hz, 1H), 7.42-7.40 (m, 2H), 7.38 (t, J=1.1 Hz, 1H), 3.49 (dt, J=13.6, 4.5 Hz, 2H), 3.17 (t, J=11.4 Hz, 2H), 2.28 (d, J=14.1 Hz, 2H), 2.05-1.95 (m, 2H), 1.38 (s, 9H).

Step 4: Synthesis of tert-butyl 4-(5-chlorothiazol-2-yl)-4-[[4-(trifluoromethoxy)phenyl]sulfonylamino]piperidine-1-carboxylate

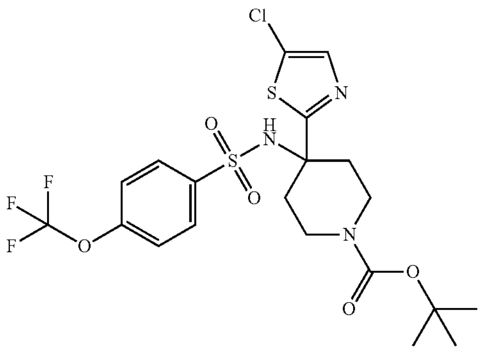 [SMILES: CC(C)(C)OC(=O)N1CCC(NS(=O)(=O)c2ccc(OC(F)(F)F)cc2)(c2ncc(Cl)s2)CC1]

A sealed vial was charged with tert-butyl 4-thiazol-2-yl-4-[[4-(trifluoromethoxy)phenyl]sulfonylamino]piperidine-1-carboxylate (97%, 275 mg, 0.526 mmol) and N-chlorosuccinimide (77 mg, 0.578 mmol) in anhydrous DMF (13.75 mL). The reaction mixture was stirred at room temperature for 18 h. Additional N-chlorosuccinimide (70 mg, 0.526 mmol) was added and the reaction mixture was stirred at room temperature for 4 h. The reaction mixture was quenched with a saturated aqueous solution of sodium bicarbonate (5 mL), and water (10 mL) and ethyl acetate (10 mL) were added. The aqueous layer was extracted with ethyl acetate (10 mL). The combined organic layers were washed with a saturated aqueous solution of sodium chloride, dried over sodium sulfate, filtered and concentrated under reduced pressure. The crude was purified by flash chromatography on silica gel using a gradient of ethyl acetate in cyclohexane from 10% to 40% to afford the title compound as a white powder (93.1 mg, 97% purity, 32% yield, $t_r$=1.06 min). LCMS (Method E): m/z found $[M-tBu+H]^+$; $^1$H-NMR (DMSO-$d_6$, 400 MHz): δ (ppm) 8.69 (s, 1H), 7.74-7.66 (m, 2H), 7.48-7.43 (m, 2H), 7.41 (s, 1H), 3.50 (dt, J=13.8, 4.6 Hz, 2H), 3.13 (t, J=11.7 Hz, 2H), 2.22 (d, J=13.7 Hz, 2H), 2.04-1.90 (m, 2H), 1.38 (s, 9H).

Step 5: Synthesis of N-(4-(5-chlorothiazol-2-yl)piperidin-4-yl)-4-(trifluoromethoxy)benzenesulfonamide (73)

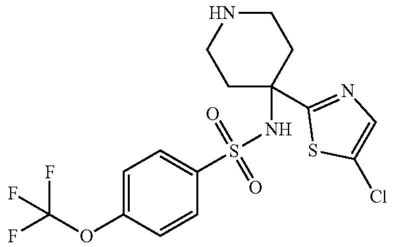 [SMILES: O=S(=O)(NC1(c2ncc(Cl)s2)CCNCC1)c1ccc(OC(F)(F)F)cc1]

In a sealed tube under nitrogen, 4 M hydrogen chloride in dioxane (803 μL, 3.21 mmol) was added to a stirred solution of tert-butyl 4-(5-chlorothiazol-2-yl)-4-[[4-(trifluoromethoxy)phenyl]sulfonylamino]piperidine-1-carboxylate (87 mg, 0.161 mmol) in dry 1,4-4ioxane (870 μL). The solution was stirred at room temperature for 2 h. MeOH was added to dissolve the obtained suspension, then the mixture was concentrated. The residue was sonicated in MeOH (3 mL) and the suspension was added dropwise to stirred $Et_2O$ (30 mL). The suspension was stirred at room temperature for 30 min, then filtered. The residue was washed with $Et_2O$ and dried under reduced pressure at 45° C. to afford the hydrochloride salt of the title compound as a white powder (70 mg, 96.1% purity, 87% yield, $t_r$=1.21 min). LCMS (Method H): m/z found 442 $[M+H]^+$; $^1$H-NMR (DMSO-$d_6$, 500 MHz) δ 8.92 (s, 3H), 7.6-7.8 (m, 2H), 7.4-7.5 (m, 3H), 3.14 (br s, 4H), 2.4-2.5 (m, 2H), 2.28 (ddd, 2H, J=4.3, 9.7, 14.4 Hz).

Example 38: N-(3-(4-fluorophenyl)pyrrolidin-3-yl)-4-(trifluoromethoxy)benzenesulfonamide (74)

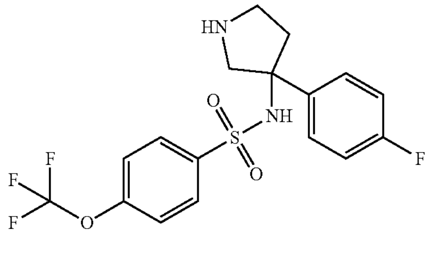 [SMILES: O=S(=O)(NC1(c2ccc(F)cc2)CCNC1)c1ccc(OC(F)(F)F)cc1]

Step 1: Synthesis of benzyl 3-(4-fluorophenyl)-3-hydroxy-pyrrolidine-1-carboxylate

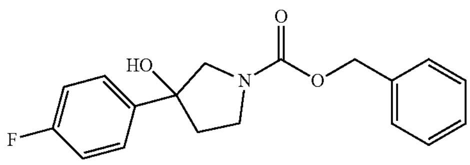 [SMILES: O=C(OCc1ccccc1)N1CCC(O)(c2ccc(F)cc2)C1]

In a three-neck-round-bottom flask, to a stirred suspension of magnesium (106 mg, 4.36 mmol) and iodine (one crystal) in anhydrous THF (3.41 mL) at room temperature under nitrogen was added few drops of a solution of 1-bromo-4-fluorobenzene (95%, 576 mg, 3.13 mmol) in anhydrous THF (1.47 mL). The reaction mixture was then heated at 60° C. by adding a few drops of the previous solution until the decoloration (orange to colorless) of the reaction mixture was observed. Then, the rest of the solution was added dropwise at 60° C. and the reaction was stirred at 60° C. for 1 h. After this time, the reaction mixture was cooled to 0° C. and a solution of benzyl 3-oxopyrrolidine-1-carboxylate (98%, 500 mg, 2.23 mmol) in anhydrous THF (1.47 mL) was added dropwise. Then, the reaction mixture was stirred at room temperature 2 h. The reaction mixture was cooled to 0° C. and was quenched with a saturated aqueous solution of ammonium chloride dropwise (10 mL). EtOAc was added (5 mL) and the two layers were stirred at room temperature overnight. The aqueous layer was extracted three times with ethyl acetate. The combined organic layers were washed with a saturated aqueous solution of sodium chloride, dried over sodium sulfate, filtered, and concentrated under reduced pressure. The crude was purified by flash chromatography with solid deposit using a gradient of EtOAc in heptane from 20% to 100%. Fractions containing product were combined and concentrated under reduced pressure to afford the title compound as a beige solid (381.5 mg, 91% purity, 49% yield, $t_r$=0.86 min). LCMS (Method E): m/z found 316.3 $[M+H]^+$; $^1$H-NMR (DMSO-$d_6$, 400 MHz): δ (ppm) 7.60-7.50 (m, 2H), 7.44-7.27 (m, 5H), 7.17 (ddd, J=12.7, 7.5, 3.8 Hz, 2H), 5.52 (d, J=1.9 Hz, 1H), 5.10 (d, J=9.5 Hz, 2H), 3.64-3.45 (m, 4H), 2.25 (dq, J=12.0, 9.1 Hz, 1H), 2.05 (dtd, J=12.7, 6.2, 3.1 Hz, 1H).

Step 2: Synthesis of benzyl 3-[(2-chloroacetyl)amino]-3-(4-fluorophenyl)pyrrolidine-1-carboxylate

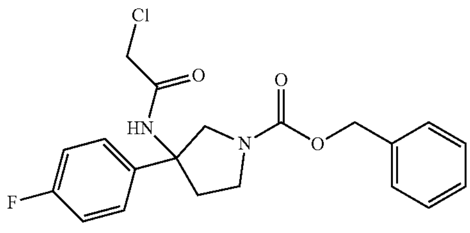 [SMILES: O=C(CCl)NC1(c2ccc(F)cc2)CCN(C(=O)OCc2ccccc2)C1]

A sealed vial was successively charged with benzyl 3-(4-fluorophenyl)-3-hydroxy-pyrrolidine-1-carboxylate (91%, 380 mg, 1.10 mmol), chloroacetonitrile (7.0 mL, 0.111 mol) and trifluoroacetic acid (2.1 mL, 27.4 mmol). The reaction mixture was stirred at room temperature for 1 h. The reaction mixture was poured into water at 0° C. and quenched with a saturated aqueous solution of sodium bicarbonate until pH 9. The aqueous layer was extracted with dichloromethane. The combined organic layers were dried over sodium sulfate, filtered, and concentrated under reduced pressure. The crude was purified by flash chromatography on silica gel using a gradient of methanol in dichloromethane from 0% to 5% to afford the title compound as a pale yellow solid (205.7 mg, 96% purity, 46% yield, $t_r$=0.87 min). LCMS (Method E): m/z found 391.3 $[M+H]^+$; $^1$H-NMR (DMSO-$d_6$, 400 MHz): δ (ppm) 8.80 (d, J=3.6 Hz, 1H), 7.44-7.29 (m, 7H), 7.15 (dtt, J=8.9, 6.3, 3.0 Hz, 2H), 5.15-5.04 (m, 2H), 4.13-3.91 (m, 3H), 3.67 (dd, J=27.7, 11.3 Hz, 1H), 3.46 (ddd, J=19.3, 8.7, 5.2 Hz, 2H), 2.67-2.53 (m, 1H), 2.34-2.17 (m, 1H).

Step 3: Synthesis of benzyl 3-amino-3-(4-fluorophenyl)pyrrolidine-1-carboxylate

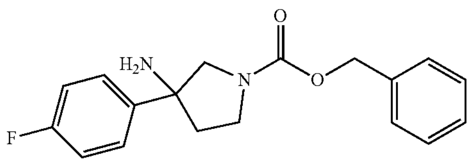 [SMILES: NC1(c2ccc(F)cc2)CCN(C(=O)OCc2ccccc2)C1]

A sealed vial was charged with benzyl 3-[(2-chloroacetyl)amino]-3-(4-fluorophenyl)pyrrolidine-1-carboxylate (96%, 205 mg, 0.504 mmol) and thiourea (50 mg, 0.655 mmol) in a mixture of EtOH (4.19 mL) and Acetic acid (0.84 mL). The reaction mixture was stirred at 80° C. overnight. Reaction mixture was diluted in DCM and saturated aqueous solution of $NaHCO_3$ was added (until pH 9 aqueous phase). The aqueous layer was extracted twice with DCM and the combined organic layers were washed with brine, dried using phase separator and concentrated under reduced pressure. The crude was purified by flash chromatography on silica gel using a gradient of MeOH in DCM from 0% to 8%. The desired fractions were combined and concentrated to afford the title compound as a yellow oil (151.9 mg, 90% purity, 86% yield, $t_r$=0.60 min). LCMS (Method E): m/z found 315.3 $[M+H]^+$; $^1$H-NMR (DMSO-$d_6$, 400 MHz): δ (ppm) 7.56-7.48 (m, 2H), 7.41-7.27 (m, 5H), 7.13 (ddd, J=9.0, 7.9, 4.9 Hz, 2H), 5.09 (d, J=5.5 Hz, 2H), 3.67-3.40 (m, 4H), 2.22-1.93 (m, 4H).

Step 4: Synthesis of benzyl 3-(4-fluorophenyl)-3-[[4-(trifluoromethoxy)phenyl]sulfonylamino]pyrrolidine-1-carboxylate

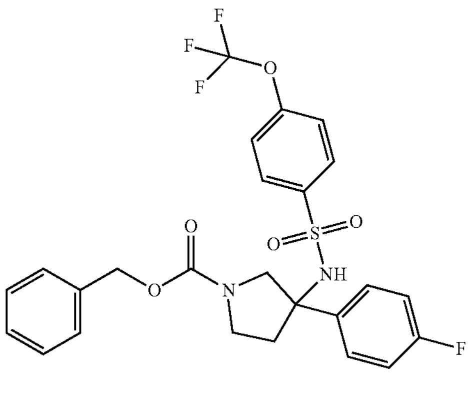 [SMILES: O=C(OCc1ccccc1)N1CCC(NS(=O)(=O)c2ccc(OC(F)(F)F)cc2)(c2ccc(F)cc2)C1]

A sealed vial was charged with benzyl 3-amino-3-(4-fluorophenyl)pyrrolidine-1-carboxylate (75 mg, 0.239 mmol), 4-dimethylaminopyridine (5.8 mg, 0.0477 mmol) and triethylamine (0.17 mL, 1.19 mmol) in DCM (2.2067 mL). 4-(trifluoromethoxy)benzenesulfonyl chloride (49 µL, 0.286 mmol) was added and the reaction mixture was stirred at 40° C. for 20 h. The reaction mixture was quenched with a saturated aqueous solution of ammonium chloride and dichloromethane was added. The layers were separated and the aqueous layer was extracted with dichloromethane. The combined organic layers were washed with a saturated aqueous solution of sodium chloride, dried using a phase separator, and concentrated under reduced pressure. The crude product was purified by flash chromatography on silica gel using a gradient of MeOH in DCM from 0% to 5%. The desired fractions were combined and concentrated to afford the title compound as a yellow solid (113.9 mg, 97% purity, 86% yield, $t_r$=1.00 min). LCMS (Method D): m/z found 561.3 $[M+Na]^+$; $^1$H-NMR (DMSO-$d_6$, 400 MHz): δ (ppm) 8.60 (s, 1H), 7.46-7.30 (m, 7H), 7.28-7.21 (m, 2H), 7.08 (ddd, J=8.8, 5.3, 1.1 Hz, 2H), 6.79 (td, J=8.8, 5.0 Hz, 2H), 5.14-5.02 (m, 2H), 4.16 (dd, J=17.3, 11.3 Hz, 1H), 3.63-3.32 (m, 3H), 2.81-2.65 (m, 1H), 2.28-2.11 (m, 1H).

Step 5: Synthesis of N-(3-(4-fluorophenyl)pyrrolidin-3-yl)-4-(trifluoromethoxy)benzenesulfonamide (74)

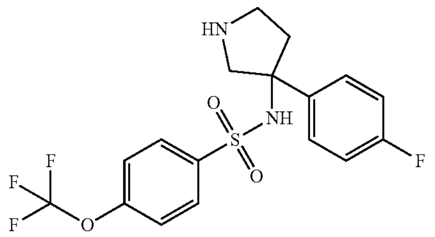 [SMILES: O=S(=O)(NC1(c2ccc(F)cc2)CCNC1)c1ccc(OC(F)(F)F)cc1]

In a round-bottomed flask, to a stirred suspension of benzyl 3-(4-fluorophenyl)-3-[[4-(trifluoromethoxy)phenyl]sulfonylamino]pyrrolidine-1-carboxylate (97%, 114 mg, 0.205 mmol) in anhydrous ACN (5.2877 mL) at room temperature, was added iodo(trimethyl)silane (88 µL, 0.615 mmol). The reaction mixture was stirred at room temperature for 30 min. Next, the reaction mixture was concentrated under reduced pressure. The residue was stirred in 2 M HCl in $Et_2O$ (2.5 mL, 5.00 mmol) and $Et_2O$ (5 mL) for 30 min, then MeOH (0.2 mL) was added. The mixture was stirred at room temperature for 2 h, filtered, washed with $Et_2O$ and pentane, and dried under vacuum at 45° C. for 2 h. The residue was suspended in MeOH (5 mL) and 7 M ammoniacal MeOH (0.20 mL, 1.40 mmol) was added. The reaction mixture was stirred at room temperature overnight and concentrated under reduced pressure. The residue was triturated in a mixture of water (8 mL), DCM (8 mL) and MeOH (0.8 mL), and stirred at room temperature for 30 min. A saturated aqueous solution of sodium carbonate was added to reach pH 9. The layers were separated and the aqueous layer was extracted twice with DCM. The combined organic layers were dried using a phase separator and concentrated under reduced pressure. The residue was triturated again in 2 M HCl in $Et_2O$ (2.1 mL, 4.10 mmol) and $Et_2O$ (2 mL) for 2 h and concentrated under reduced pressure. The beige solid was dissolved in a minimum of MeOH, and poured in $Et_2O$. The precipitated product was filtered, rinsed with $Et_2O$, and dried under vacuum for 24 h at 45° C. to afford the hydrochloride salt of the title product as an off-white solid (49.3 mg, 99.62% purity, 54% yield, $t_r$=1.22 min). LCMS (Method H): m/z found 405.2 $[M+H]^+$; $^1$H-NMR (600 MHz, DMSO-$d_6$) δ ppm 9.80 (m, 2H), 9.00 (m, 1H), 7.42 (m, 2H), 7.21 (d, J=8.1 Hz, 2H), 7.11 (m, 2H), 6.75 (t, J=8.8 Hz, 2H), 4.13 (dd, J=12.0, 1.2 Hz, 1H), 3.39 (m, 3H), 2.94 (m, 1H), 2.11 (dt, J=13.1, 9.7 Hz, 1H).

Example 39: N-(4-(4-fluorophenyl)piperidin-4-yl)-4-isopropoxybenzenesulfonamide (75)

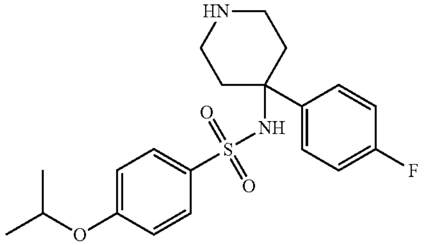 [SMILES: CC(C)Oc1ccc(S(=O)(=O)NC2(c3ccc(F)cc3)CCNCC2)cc1]

Step 1: Synthesis of tert-butyl 4-amino-4-(4-fluorophenyl)piperidine-1-carboxylate

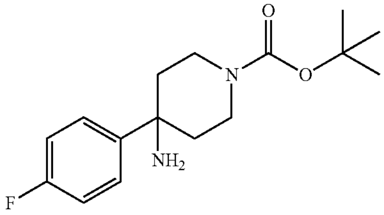 [SMILES: CC(C)(C)OC(=O)N1CCC(N)(c2ccc(F)cc2)CC1]

In a sealed vial, to a stirred solution of 4-(4-fluorophenyl)piperidin-4-amine dihydrochloride (150 mg, 0.561 mmol) and triethylamine (313 µL, 2.25 mmol) in DCM (2.7 mL) was added tert-butoxycarbonyl tert-butyl carbonate (110 mg, 0.505 mmol). The reaction mixture was stirred at rt overnight. Water and DCM were added, and the aqueous layer was extracted twice with DCM. Organic layers were washed with a saturated solution of $NH_4Cl$, then with a saturated solution of $NaHCO_3$, filtered through phase separator, then concentrated under reduced pressure. The crude was purified by flash chromatography on silica gel using a gradient of ammoniacal methanol in DCM from 5% to 15%. The desired fractions were combined and concentrated to afford the title compound as a colorless oil (112 mg, 82% purity, 55.6% yield, $t_r$=0.60 min). LCMS (Method E): m/z found 295.3 $[M+H]^+$; $^1$H-NMR (DMSO-$d_6$, 400 MHz): δ (ppm) 7.61-7.49 (m, 2H), 7.17-7.06 (m, 2H), 3.71 (d, J=12.5 Hz, 2H), 3.27 (s, 2H), 1.86 (s, 2H), 1.77 (td, J=12.9, 4.6 Hz, 2H), 1.53 (d, J=11.8 Hz, 2H), 1.41 (s, 9H).

Step 2: Synthesis of tert-butyl 4-(4-fluorophenyl)-4-[(4-isopropoxyphenyl)sulfonylamino]piperidine-1-carboxylate

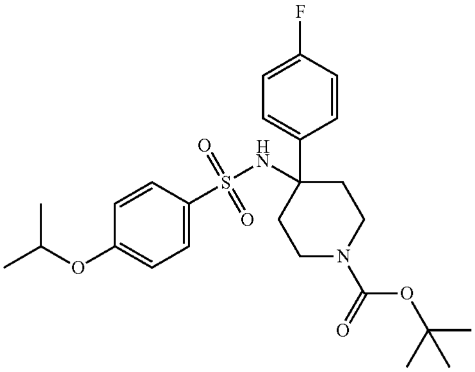 [SMILES: CC(C)Oc1ccc(S(=O)(=O)NC2(c3ccc(F)cc3)CCN(C(=O)OC(C)(C)C)CC2)cc1]

In a sealed vial, to a stirred solution of tert-butyl 4-amino-4-(4-fluorophenyl)piperidine-1-carboxylate (82%, 112 mg, 0.312 mmol) in DCM (2.7 mL) at room temperature were added successively triethylamine (130 μL, 0.936 mmol), 4-(propan-2-yloxy)benzenesulfonyl chloride (98%, 54 μL, 0.343 mmol) and N,N-dimethylpyridin-4-amine (7.6 mg, 0.0624 mmol). The reaction mixture was stirred at 40° C. overnight. The reaction mixture was diluted with DCM and a saturated aqueous solution of $NaHCO_3$. The layers were separated. The aqueous layer was extracted twice with DCM. The combined organic layers were washed with a saturated aqueous solution of NaCl, dried using a phase separator and concentrated under reduced pressure. The crude product was purified by flash chromatography on silica gel using a gradient of MeOH in DCM from 0% to 5%. The desired fractions were combined and concentrated. The resulting white residue was repurified by reverse-phase preparative chromatography using a gradient of acetonitrile in water from 0% to 100% (0.1% TFA in water and acetonitrile). The desired fractions were combined and concentrated to afford the title compound as a white solid (97.8 mg, 100% purity, 63.6% yield, $t_r$=1.02 min). LCMS (Method E): m/z found 515.4 $[M+Na]^+$; $^1$H-NMR (DMSO-$d_6$, 400 MHz): δ (ppm) 7.85 (s, 1H), 7.23-7.07 (m, 4H), 6.83-6.65 (m, 4H), 4.66-4.56 (m, 1H), 3.68 (d, J=13.0 Hz, 2H), 3.20 (s, 2H), 2.32 (d, J=13.0 Hz, 2H), 1.68 (t, J=10.6 Hz, 2H), 1.39 (s, 9H), 1.27 (d, J=6.0 Hz, 6H).

Step 3: Synthesis of N-(4-(4-fluorophenyl)piperidin-4-yl)-4-isopropoxybenzenesulfonamide (75)

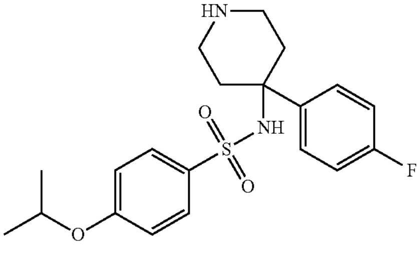 [SMILES: CC(C)Oc1ccc(S(=O)(=O)NC2(c3ccc(F)cc3)CCNCC2)cc1]

In a round-bottomed flask, to a stirred suspension of tert-butyl 4-(4-fluorophenyl)-4-[(4-isopropoxyphenyl)sulfonylamino]piperidine-1-carboxylate (98 mg, 0.199 mmol) in $Et_2O$ (1.88 mL) at rt was added 2 M HCl in $Et_2O$ (1.0 mL, 2.07 mmol). The reaction mixture was stirred at rt overnight. Additional 4 M HCl in 1,4-dioxane (0.50 mL, 1.99 mmol) was added and the reaction mixture was stirred at rt for 4 h. Additional 4 M HCl in 1,4-dioxane (0.99 mL, 3.97 mmol) was added and the reaction mixture was stirred at rt overnight. The suspension was filtered, washed with $Et_2O$ and dried under vacuum at 45° C. to afford the title compound as a white solid (75.6 mg, 100% purity, 88.8% yield, $t_r$=1.19 min). LCMS (Method H): m/z found 393.2 $[M+H]^+$; $^1$H-NMR (500 MHz, DMSO-$d_6$) δ ppm 1.27 (d, J=6.11 Hz, 6H) 1.95-2.04 (m, 2H) 2.51-2.56 (m, 2H) 3.17-3.24 (m, 4H) 4.60 (spt, J=6.03 Hz, 1H) 6.70 (d, J=7.93 Hz, 2H) 6.80 (t, J=8.33 Hz, 2H) 7.09-7.14 (m, 1H) 7.14-7.18 (m, 1H) 8.09 (s, 1H) 8.80 (br s, 2H).

Example 40: N-(3-(4-chlorophenyl)-1-isopentylpyrrolidin-3-yl)-4-(trifluoromethoxy)benzenesulfonamide (76)

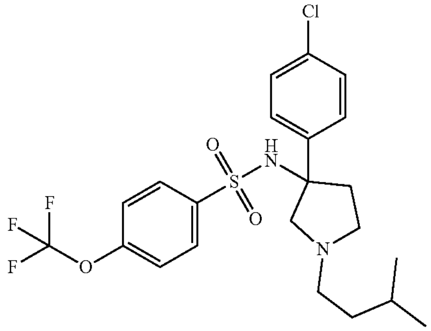 [SMILES: CC(C)CCN1CCC(NS(=O)(=O)c2ccc(OC(F)(F)F)cc2)(c2ccc(Cl)cc2)C1]

Step 1: Synthesis of N-[3-(4-chlorophenyl)-1-(3-methylbutanoyl)pyrrolidin-3-yl]-4-(trifluoromethoxy)benzenesulfonamide

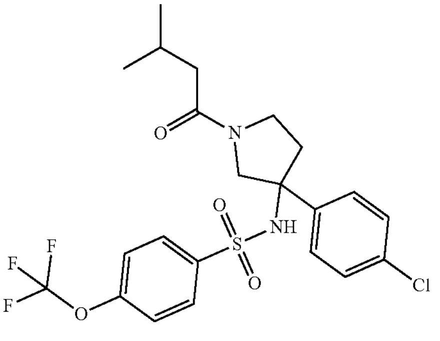 [SMILES: CC(C)CC(=O)N1CCC(NS(=O)(=O)c2ccc(OC(F)(F)F)cc2)(c2ccc(Cl)cc2)C1]

To a stirred solution of N-[3-(4-chlorophenyl)pyrrolidin-3-yl]-4-(trifluoromethoxy)benzenesulfonamide (150 mg, 0.356 mmol) and DIPEA (249 μL, 1.43 mmol) in DCM (3.2 mL) was added 3-methylbutanoyl chloride (48 μL, 0.392 mmol) dropwise at 0° C. The reaction mixture was stirred at room temperature for 18 h. The reaction mixture was quenched with a saturated aqueous solution of ammonium chloride (10 mL). Then water (5 mL) and dichloromethane (10 mL) were added. The layers were separated. The aqueous layer was extracted twice with dichloromethane (2×10 mL). The combined organic layers were washed once with a saturated aqueous solution of sodium bicarbonate and once with a saturated aqueous solution of sodium chloride, dried using a phase separator and concentrated under reduced pressure. The crude was purified by flash chromatography on silica gel using a gradient of methanol in dichloromethane from 0% to 10%. The residue was dissolved in 2 mL of dichloromethane, then diethyl ether (4 mL) and pentane (4 mL). The resulting suspension was filtered, washed with pentane and dried under vacuum at 45° C. for 18 h to afford the title compound as a white powder (147.9 mg, 98.77% purity, 82% yield, $t_r$=2.62 min). LCMS (Method H): m/z found 505 $[M+H]^+$; $^1$H-NMR (500 MHz, DMSO-$d_6$) δ ppm 0.87-0.93 (m, 6H) 1.95-2.04 (m, 1H) 2.04-2.28 (m, 3H) 2.61-2.81 (m, 1H) 3.48 (s, 3H) 4.13-4.23 (m, 1H) 7.04-7.11 (m, 4H) 7.25 (ddd, J=8.86, 4.10, 0.73 Hz, 2H) 7.40-7.45 (m, 2H) 8.59 (s, 1H).

Step 2: Synthesis of N-(3-(4-chlorophenyl)-1-isopentylpyrrolidin-3-yl)-4-(trifluoromethoxy)benzenesulfonamide (76)

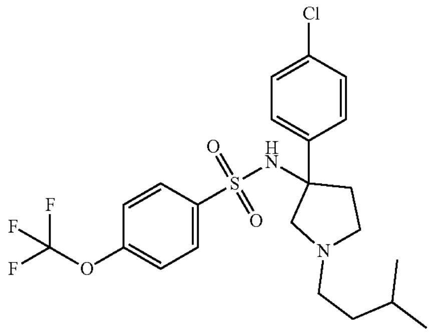 [SMILES: CC(C)CCN1CCC(NS(=O)(=O)c2ccc(OC(F)(F)F)cc2)(c2ccc(Cl)cc2)C1]

In a sealed tube under nitrogen, a solution of N-[3-(4-chlorophenyl)-1-(3-methylbutanoyl)pyrrolidin-3-yl]-4-(trifluoromethoxy)benzenesulfonamide (97 mg, 0.193 mmol) in anhydrous THF (1.8 mL) was stirred at 0° C. 2 M $BH_3{\cdot}SMe_2$ (289 μL, 0.578 mmol) was added dropwise and the mixture was stirred at rt for 1 h and at 60° C. for 4 h. The mixture was stirred at 0° C. and MeOH (1.5 mL) was added dropwise. The mixture was stirred at 0° C. for 15 min, then aqueous 4N HCl (1.5 mL) was added. The mixture was stirred at 60° C. for 1 h, then cooled to 0° C. The mixture was basified with aqueous 4 N NaOH (2 mL, pH 12.5) 25 and extracted three times with DCM. The combined organic layers were washed once a saturated aqueous solution of sodium chloride, dried using a phase separator and concentrated under reduced pressure. The crude product was purified by flash chromatography on silica gel using a gradient of methanol in dichloromethane from 1% to 10%. The desired fractions were combined and concentrated under reduced pressure. The resulting white solid was diluted in $Et_2O$ and 2 M HCl in $Et_2O$ (0.96 mL, 1.93 mmol) was added. The mixture was stirred at room temperature for 3 h and the resulting suspension was filtered, washed twice with diethyl ether and dried under vacuum at 45° C. for 18 h to afford the hydrochloride salt title compound as a white powder (68.9 mg, 100% purity, 68% yield, $t_r$=1.69 min). LCMS (Method H): m/z found 491.2 $[M+H]^+$; $^1$H-NMR (600 MHz, DMSO-$d_6$) δ ppm 0.87-0.95 (m, 6H) 1.53-1.69 (m, 3H) 2.16-2.37 (m, 1H) 2.78-3.03 (m, 1H) 3.20-3.28 (m, 2H) 3.33-3.39 (m, 1H) 3.41-3.83 (m, 2H) 4.00-4.52 (m, 1H) 7.01-7.10 (m, 4H) 7.19-7.26 (m, 2H) 7.40 (d, J=8.66 Hz, 2H) 8.82-9.08 (m, 1H) 10.31-11.05 (m, 1H).

Example 41: N-(4-(4-fluorophenyl)piperidin-4-yl)-6-isopropoxypyridine-3-sulfonamide (77)

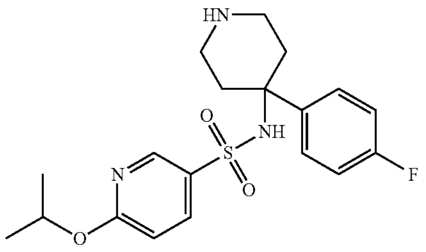 [SMILES: CC(C)Oc1ccc(S(=O)(=O)NC2(c3ccc(F)cc3)CCNCC2)cn1]

Step 1: Synthesis of tert-butyl 4-amino-4-(4-fluorophenyl)piperidine-1-carboxylate

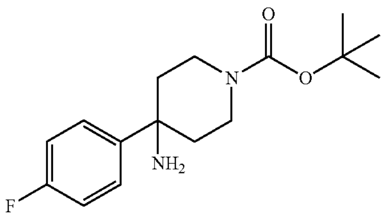 [SMILES: CC(C)(C)OC(=O)N1CCC(N)(c2ccc(F)cc2)CC1]

In a sealed vial, to a stirred solution of 4-(4-fluorophenyl)piperidin-4-amine dihydrochloride (150 mg, 0.561 mmol) and triethylamine (313 μL, 2.25 mmol) in DCM (2 mL) was added tert-butoxycarbonyl tert-butyl carbonate (123 mg, 0.561 mmol). The reaction mixture was stirred at room temperature overnight. Water (5 mL) and DCM (5 mL) were added and the layers were separated. The aqueous layer was extracted twice with DCM (2×10 mL). The combined organic layers were washed with a saturated solution of $NH_4Cl$ (10 mL), then with a saturated solution of $NaHCO_3$ (10 mL) and finally with a saturated aqueous solution of sodium chloride. The organic layer was filtered using a phase separator, then concentrated under reduced pressure to afford the title compound as a colorless oil (163 mg, 82% purity, 81% yield, $t_r$=0.60 min). LCMS (Method E): m/z found 295.3 $[M+H]^+$; $^1$H-NMR (400 MHz, DMSO) δ 7.59-7.51 (m, 2H), 7.16-7.07 (m, 2H), 3.70 (d, J=13.0 Hz, 2H), 3.30-3.09 (m, 2H), 2.09-2.04 (m, 2H), 1.78 (ddd, J=13.3, 11.8, 4.6 Hz, 2H), 1.58-1.50 (m, 2H), 1.41 (s, 9H).

Step 2: Synthesis of tert-butyl 4-(4-fluorophenyl)-4-[(6-isopropoxy-3-pyridyl)sulfonylamino]piperidine-1-carboxylate

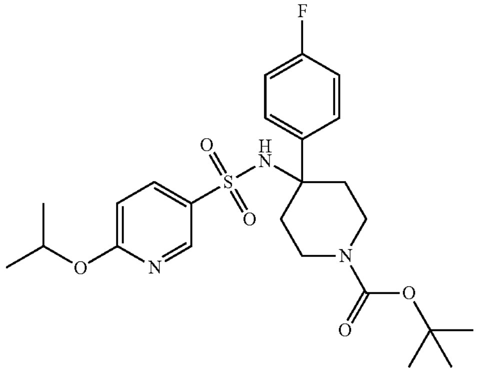 [SMILES: CC(C)Oc1ccc(S(=O)(=O)NC2(c3ccc(F)cc3)CCN(C(=O)OC(C)(C)C)CC2)cn1]

To a stirred solution of tert-butyl 4-amino-4-(4-fluorophenyl)piperidine-1-carboxylate (82%, 80 mg, 0.223 mmol), triethylamine (93 μL, 0.669 mmol) and N,N-dimethylpyridin-4-amine (5.4 mg, 0.0446 mmol) in DCM (1.5 mL) was added 6-(propan-2-yloxy)pyridine-3-sulfonyl chloride (95%, 61 mg, 0.245 mmol). The reaction mixture was stirred at 40° C. overnight. Additional 6-(propan-2-yloxy)pyridine-3-sulfonyl chloride (95%, 28 mg, 0.112 mmol), triethylamine (47 μL, 0.334 mmol) and N,N-dimethylpyridin-4-amine (2.7 mg, 0.0223 mmol) were added at room temperature and the reaction mixture was stirred at 40° C. for 6 additional hours. The reaction mixture was cooled to room temperature, diluted with DCM (10 mL) and a saturated aqueous solution of ammonium chloride (10 mL) was added. The layers were separated. The organic layer was washed once with a saturated aqueous solution of sodium bicarbonate (10 mL) and once with a saturated aqueous solution of sodium chloride (10 mL), dried using a phase separator and concentrated under reduced pressure. The crude was purified by flash chromatography on silica gel using a gradient of methanol in dichloromethane from 0.5% to 10%. The desired fractions were combined and concentrated under reduced pressure to afford the title compound as a colorless oil (112.4 mg, 96% purity, 98% yield, $t_r$=1.04 min). LCMS (Method E): m/z found 516.3 $[M+Na]^+$; $^1$H-NMR (400 MHz, DMSO-$d_6$) δ 8.05 (s, 1H), 7.82 (d, J=2.5 Hz, 1H), 7.51 (dd, J=8.7, 2.7 Hz, 1H), 7.17-7.09 (m, 2H), 6.85-6.74 (m, 2H), 6.56 (d, J=9.0 Hz, 1H), 5.20 (hept, J=6.1 Hz, 1H), 3.71 (d, J=13.3 Hz, 2H), 3.27 (m, 2H), 2.38 (d, J=13.5 Hz, 2H), 1.71 (s, 2H), 1.40 (s, 9H), 1.29 (d, J=6.1 Hz, 6H).

Step 3: Synthesis of N-(4-(4-fluorophenyl)piperidin-4-yl)-6-isopropoxypyridine-3-sulfonamide (77)

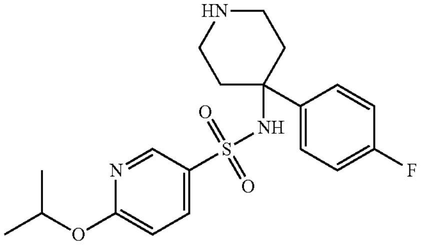 [SMILES: CC(C)Oc1ccc(S(=O)(=O)NC2(c3ccc(F)cc3)CCNCC2)cn1]

In a round-bottom flask, to a stirred solution of tert-butyl 4-(4-fluorophenyl)-4-[(6-isopropoxy-3-pyridyl)sulfonylamino]piperidine-1-carboxylate (112 mg, 0.226 mmol) in $Et_2O$ (0.55 mL) was added 4 M HCl in $Et_2O$ (0.65 mL, 2.60 mmol). The mixture was stirred overnight at room temperature, then filtered and washed twice with $Et_2O$ (2×2 mL). The resulting white powder was dissolved in a minimum of MeOH and was poured slowly into $Et_2O$ (20 mL). The suspension was stirred at room temperature for 2 h, then filtered, washed twice with $Et_2O$ (2×2 mL) and dried under vacuum at 45° C. for 18 h to afford the hydrochloride salt of the title compound as a white powder (78.1 mg, 97.7% purity, 79% yield, $t_r$=1.15 min). LCMS (Method H): m/z found 394 $[M+H]^+$; $^1$H-NMR (DMSO-$d_6$, 500 MHz) δ 8.75 (br s, 2H), 8.33 (br s, 1H), 7.82 (d, 1H, J=2.4 Hz), 7.51 (dd, 1H, J=2.4, 8.8 Hz), 7.14 (dd, 2H, J=5.4, 8.8 Hz), 6.83 (t, 2H, J=8.8 Hz), 6.56 (d, 1H, J=8.8 Hz), 5.19 (spt, 1H, J=6.2 Hz), 3.1-3.3 (m, 4H), 2.58 (br d, 2H, J=13.7 Hz), 1.8-2.2 (m, 2H), 1.28 (d, 6H, J=6.4 Hz).

Example 42: N-(3-(4-fluorophenyl)pyrrolidin-3-yl)-4-isopropoxybenzenesulfonamide (78)

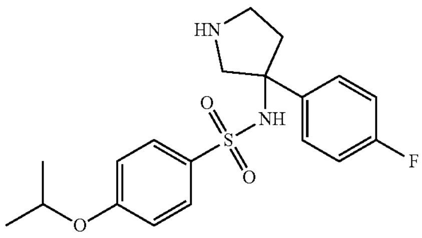 [SMILES: CC(C)Oc1ccc(S(=O)(=O)NC2(c3ccc(F)cc3)CCNC2)cc1]

Step 1: Synthesis of benzyl 3-(4-fluorophenyl)-3-[[4-(trifluoromethoxy)phenyl]sulfonylamino]pyrrolidine-1-carboxylate

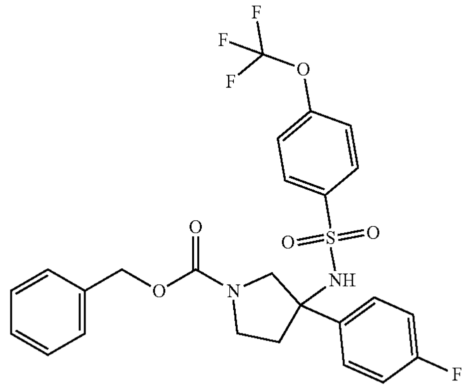 [SMILES: O=C(OCc1ccccc1)N1CCC(NS(=O)(=O)c2ccc(OC(F)(F)F)cc2)(c2ccc(F)cc2)C1]

A sealed vial was charged with benzyl 3-amino-3-(4-fluorophenyl)pyrrolidine-1-carboxylate (75 mg, 0.239 mmol), 4-dimethylaminopyridine (5.8 mg, 0.0477 mmol) and triethylamine (0.17 mL, 1.19 mmol) in DCM (2.2067 mL). 4-(trifluoromethoxy)benzenesulfonyl chloride (49 μL, 0.286 mmol) was added and the reaction mixture was stirred at 40° C. for 20 h. The reaction mixture was quenched with a saturated aqueous solution of ammonium chloride and dichloromethane was added. The aqueous layer was extracted with dichloromethane. The combined organic layers were washed with a saturated aqueous solution of sodium chloride, dried using a phase separator and concentrated under reduced pressure. The crude was purified by flash chromatography on silica gel using a gradient of MeOH in DCM from 0% to 5%. The desired fractions were combined and concentrated to afford the title compound as a yellow solid (113.9 mg, 97% purity, 86% yield, $t_r$=1.00 min). LCMS (Method D): m/z found 561.3 $[M+Na]^+$; $^1$H-NMR (DMSO-$d_6$, 400 MHz): δ (ppm) 8.60 (s, 1H), 7.46-7.30 (m, 7H), 7.28-7.21 (m, 2H), 7.08 (ddd, J=8.8, 5.3, 1.1 Hz, 2H), 6.79 (td, J=8.8, 5.0 Hz, 2H), 5.14-5.02 (m, 2H), 4.16 (dd, J=17.3, 11.3 Hz, 1H), 3.63-3.32 (m, 3H), 2.81-2.65 (m, 1H), 2.28-2.11 (m, 1H).

Step 2: Synthesis of N-(3-(4-fluorophenyl)pyrrolidin-3-yl)-4-isopropoxybenzenesulfonamide (78)

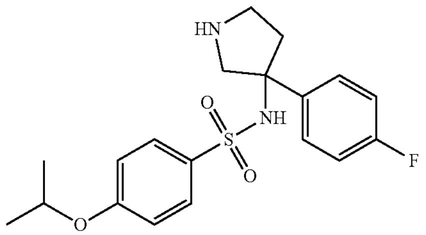 [SMILES: CC(C)Oc1ccc(S(=O)(=O)NC2(c3ccc(F)cc3)CCNC2)cc1]

In a round-bottomed flask, to a stirred suspension of benzyl 3-(4-fluorophenyl)-3-[(4-isopropoxyphenyl)sulfonylamino]pyrrolidine-1-carboxylate (97%, 85 mg, 0.162 mmol) in anhydrous ACN (4.1651 mL) at room temperature, was added iodo(trimethyl)silane (69 μL, 0.485 mmol). The reaction mixture was stirred at room temperature for 30 min. The reaction mixture was concentrated under reduced pressure. The residue was triturated in 2 M HCl in $Et_2O$ (2.5 mL, 5.00 mmol) and $Et_2O$ (5 mL) for 30 min, then MeOH (0.2 mL) was added and the mixture was stirred at room temperature for 2 h, filtered, washed with $Et_2O$ and pentane and dried under vacuum at 45° C. for 2 h. The residue was suspended in MeOH (5 mL) and 7 M ammonia in MeOH (0.20 mL, 1.40 mmol) was added. The reaction mixture was stirred at room temperature overnight and concentrated under reduced pressure. The residue was triturated between water (8 mL), DCM (8 mL), and MeOH (0.8 mL), and stirred at room temperature for 30 min. A saturated aqueous solution of sodium carbonate was added to reach pH 9. The layers were separated and the aqueous layer was extracted twice with 10 DCM. The combined organic layers were dried using a phase separator and concentrated under reduced pressure. The residue was triturated again in 2 M hydrogen chloride in diethyl ether (2.0 mL, 4.00 mmol) and $Et_2O$ (2 mL) for 2 h and concentrated under reduced pressure. The pink gum was dissolved in a minimal amount of MeOH, and poured in $Et_2O$. The precipitated product was filtered, rinsed with few ether, and dried under vacuum for 24 h at 45° C. to afford the hydrochloride salt of the title compound as a pale pink solid (16.8 mg, 94.49% purity, 24% yield, $t_r$=1.14 min). LCMS (Method H): m/z found 379.2 $[M+H]^+$; $^1$H-NMR (DMSO-$d_6$, 600 MHz): δ (ppm) 8.65-9.69 (m, 2H), 8.19-8.49 (m, 1H), 7.14-7.22 (m, 2H), 7.09 (dd, J=8.8, 5.4 Hz, 2H), 6.81 (t, J=8.8 Hz, 2H), 6.70 (d, J=8.9 Hz, 2H), 4.61 (dt, J=12.0, 6.0 Hz, 1H), 4.05 (br d, J=11.4 Hz, 1H), 3.35-3.42 (m, 2H), 3.28-3.31 (m, 1H), 2.78-2.86 (m, 1H), 2.04-2.15 (m, 1H), 1.26 (dd, J=6.0, 0.7 Hz, 6H).

Example 43: N-((3S,4S)-3-(4-chlorophenyl)-4-fluoropyrrolidin-3-yl)-4-(trifluoromethoxy)benzenesulfonamide (79)

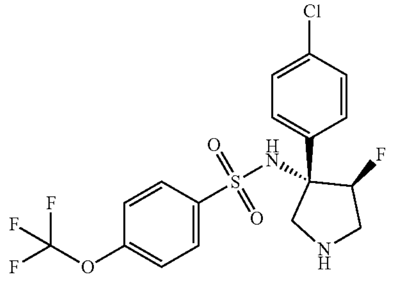 [SMILES: O=S(=O)(N[C@@]1(c2ccc(Cl)cc2)CNC[C@@H]1F)c1ccc(OC(F)(F)F)cc1]

Step 1: Synthesis of benzyl 3-(4-chlorophenyl)-2,5-dihydropyrrole-1-carboxylate

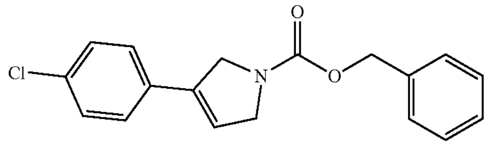 [SMILES: O=C(OCc1ccccc1)N1CC=C(c2ccc(Cl)cc2)C1]

In round-bottom flask, to a solution of benzyl 3-(4-chlorophenyl)-3-hydroxy-pyrrolidine-1-carboxylate (9.64 g, 29.1 mmol) in anhydrous DCM (150 mL) under nitrogen at 0° C. were added azido(trimethyl)silane (4.6 mL, 34.9 mmol) and $BF_3 \cdot Et_2O$ (22 mL, 0.174 mol). The reaction mixture was allowed to warm up to room temperature and was stirred at this temperature for 20 h. The reaction mixture was quenched at 0° C. with a saturated aqueous solution of sodium bicarbonate (50 mL), then water (30 mL) and DCM (20 mL) were added. The aqueous layer was extracted once with DCM (50 mL). The combined organic layers were dried over sodium sulfate, filtered and concentrated under reduced pressure to afford a mixture of benzyl 3-azido-3-(4-chlorophenyl)pyrrolidine-1-carboxylate and benzyl 3-(4-chlorophenyl)-2,5-dihydropyrrole-1-carboxylate, which was used in the next step without further purification (9.99 g, 62% purity, $t_r$=1.03 min). LCMS (Method E): m/z found 314.2 $[M+H]^+$.

In a round bottomed flask under nitrogen, triphenylphosphine (4.55 g, 17.4 mmol) then p-toluenesulfonic acid hydrate (9.91 g, 52.1 mmol) were added to a stirred solution of a mixture of benzyl 3-azido-3-(4-chlorophenyl)pyrrolidine-1-carboxylate and benzyl 3-(4-chlorophenyl)-2,5-dihydropyrrole-1-carboxylate (62%, 9.99 g, 17.4 mmol) in THF (75 mL) at room temperature. The mixture was stirred at room temperature for 16 h. The suspension was filtered, washed with THF (25 mL) and dried under vacuum at 40° C. for 3 days to afford the pTsOH salt of benzyl 3-amino-3-(4-chlorophenyl)pyrrolidine-1-carboxylate as a white powder (7.09 g, 80% yield). The filtrate was then concentrated under reduced pressure. The crude was purified by flash chromatography on silica gel using a isocratic mode of 100% of dichloromethane to afford the title compound as a white powder (1.1 g, 99% purity, 20% yield, $t_r$=1.03 min). LCMS (Method E): m/z found 314.2 $[M+H]^+$; $^1$H-NMR (DMSO-$d_6$, 400 MHz): δ (ppm) 7.57-7.48 (m, 2H), 7.47-

7.28 (m, 7H), 6.46 (d, J=12.3 Hz, 1H), 5.15 (d, J=3.6 Hz, 2H), 4.41 (dd, J=77.5, 22.6 Hz, 4H).

Step 3: Synthesis of benzyl rac-(3R,4R)-3-amino-3-(4-chlorophenyl)-4-fluoro-pyrrolidine-1-carboxylate

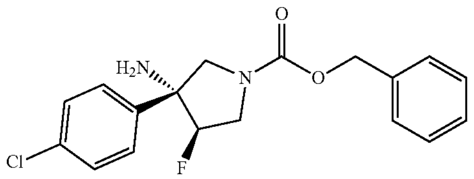 [SMILES: N[C@]1(c2ccc(Cl)cc2)CN(C(=O)OCc2ccccc2)C[C@H]1F]

To a stirred solution of benzyl 3-(4-chlorophenyl)-2,5-dihydropyrrole-1-carboxylate (1.0 g, 3.19 mmol) in anhydrous ACN (40 mL) at 0° C. was added 1-(chloromethyl)-4-fluoro-1,4-diazoniabicyclo[2.2.2]octane ditetrafluoroborate (98%, 3.0 g, 8.30 mmol). The reaction mixture was stirred at 0° C. for 15 minutes and warmed at 25° C. for 16 h. The residue was taken up with a saturated solution of $NaHCO_3$ and DCM. Phases were separated and the aqueous layer was extracted twice with DCM. Combined organic layers were washed once with water, dried over $Na_2SO_4$, filtered and concentrated under reduced pressure. The crude was purified by reverse-phase preparative chromatography (C18aq 50 g) using a gradient of acetonitrile in water (both solvent contains 0.1% AcOH) from 0% to 100%. Solvent was removed and the residue was taken up with a saturated solution of $NaHCO_3$ and DCM. Phases were separated and the aqueous layer was extracted twice with DCM. Combined organic layers were dried over $Na_2SO_4$, filtered and concentrated under reduced pressure to afford the title compound (220 mg, 62% purity, 12% yield, $t_r$=0.65 min). LCMS (Method D): m/z found 349.3 $[M+H]^+$.

Step 4: Synthesis of rac-benzyl (3R,4R)-3-(4-chlorophenyl)-4-fluoro-3-((4-(trifluoromethoxy)phenyl)sulfonamido)pyrrolidine-1-carboxylate

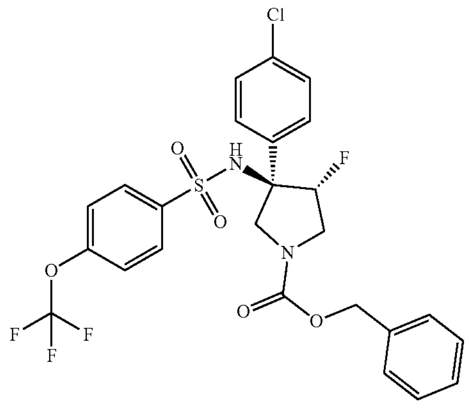 [SMILES: O=C(OCc1ccccc1)N1C[C@@H](F)[C@@](NS(=O)(=O)c2ccc(OC(F)(F)F)cc2)(c2ccc(Cl)cc2)C1]

In a round-bottomed flask equipped with condenser, to a stirred suspension of benzyl rac-(3R,4R)-3-amino-3-(4-chlorophenyl)-4-fluoro-pyrrolidine-1-carboxylate (136 mg, 0.391 mmol) in anhydrous DCM (4.0 mL), were successively added N,N-diethylethanamine (0.11 mL, 0.782 mmol) and N,N-dimethylpyridin-4-amine (24 mg, 0.196 mmol), followed by 4-(trifluoromethoxy)benzenesulfonyl chloride (98%, 0.10 mL, 0.587 mmol). The reaction mixture was stirred 5 h at reflux. The reaction was cooled to 25° C. and the mixture was quenched with a saturated solution of $NH_4Cl$. Phases were separated and the aqueous layer was extracted twice with DCM. Combined organic layers were washed once with water, dried over $Na_2SO_4$, filtered and concentrated under reduced pressure. The crude was purified by flash silica gel chromatography a gradient of MeOH in DCM from 1% to 10% to afford the title compound as a mixture of enantiomers (120 mg, 90% purity, 48% yield, $t_r$=1.05 min). LCMS (Method D): m/z found 573.4 $[M+H]^+$; $^1$H-NMR (DMSO-$d_6$, 500 MHz): δ (ppm) 8.85 (d, J=5.6 Hz, 1H), 7.23-7.43 (m, 9H), 7.02-7.12 (m, 4H), 5.62-5.81 (m, 1H), 5.04-5.16 (m, 2H), 4.44-4.55 (m, 1H), 3.86-4.06 (m, 1H), 3.50-3.81 (m, 2H).

Step 5: Synthesis of rac-N-((3S,4S)-3-(4-chlorophenyl)-4-fluoropyrrolidin-3-yl)-4-(trifluoromethoxy)benzenesulfonamide (79)

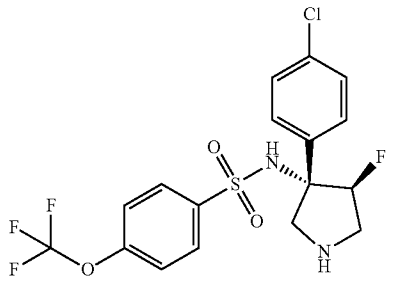 [SMILES: O=S(=O)(N[C@@]1(c2ccc(Cl)cc2)CNC[C@@H]1F)c1ccc(OC(F)(F)F)cc1]

In a round-bottomed flask, to a stirred solution of benzyl rac-(3R,4R)-3-(4-chlorophenyl)-4-fluoro-3-[[4-(trifluoromethoxy)phenyl]sulfonylamino]pyrrolidine-1-carboxylate (130 mg, 0.227 mmol) in ACN (3.036 mL) at room temperature, was added iodo(trimethyl)silane (97 μL, 0.681 mmol). The reaction mixture was stirred at room temperature for 2 h. The reaction mixture was concentrated under reduced pressure and dried under vacuum. The crude was purified by flash chromatography on silica gel using a gradient of MeOH with 2% of $NH_4OH$ in DCM from 0% to 7%. The desired fractions were combined, then water, triethylamine (158 μL, 1.13 mmol) and a solution of $Na_2CO_3$ (2 N, pH 10-12) were added. Phases were separated and the aqueous layer was extracted twice with dichloromethane. The combined organic layers were dried over $Na_2SO_4$, filtered and concentrated under reduced pressure. The resulting off-white solid was re-suspended in $Et_{20}$ and a solution of 1 M HCl in $Et_2O$ (2.3 mL, 2.27 mmol) was added. The suspension was stirred at rt overnight, filtered, washed with $Et_2O$, and dried at 45° C. for 24 h to afford the hydrochloride salt of the title compound as a white powder (49 mg, 97.4% purity, 45% yield, $t_r$=1.41 min). LCMS (Method H): m/z 439 $[M+H]^+$; $^1$H-NMR (DMSO-$d_6$, 600 MHz): δ (ppm) 9.51-10.55 (m, 2H), 9.20 (br s, 1H), 7.39-7.45 (m, 2H), 7.23 (d, J=8.2 Hz, 2H), 7.07-7.10 (m, 2H), 6.99-7.07 (m, 2H), 5.78-5.92 (m, 1H), 4.49 (d, J=12.3 Hz, 1H), 3.79-3.91 (m, 1H), 3.65-3.75 (m, 1H), 3.55 (dd, J=12.3, 2.3 Hz, 1H).

Example 44: N-(3-(4-chlorophenyl)pyrrolidin-3-yl)-6-isopropoxypyridine-3-sulfonamide (80)

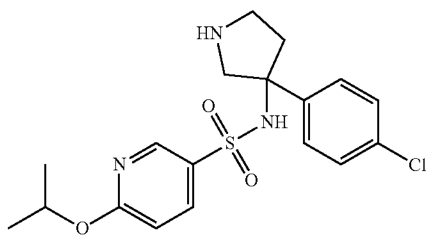 [SMILES: CC(C)Oc1ccc(S(=O)(=O)NC2(c3ccc(Cl)cc3)CCNC2)cn1]

Step 1: Synthesis of benzyl 3-(4-chlorophenyl)-3-[(6-isopropoxy-3-pyridyl)sulfonylamino]pyrrolidine-1-carboxylate

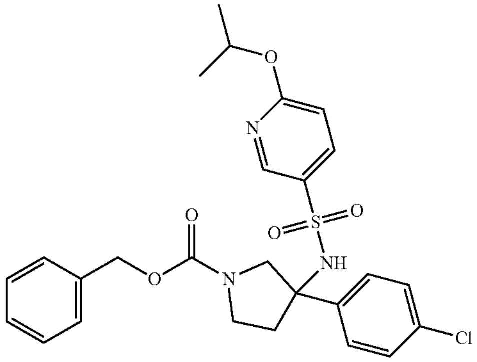 [SMILES: CC(C)Oc1ccc(S(=O)(=O)NC2(c3ccc(Cl)cc3)CCN(C(=O)OCc3ccccc3)C2)cn1]

To a stirred solution of benzyl 3-amino-3-(4-chlorophenyl)pyrrolidine-1-carboxylate (100 mg, 0.303 mmol) in DCM (2.0 mL) were added 6-(propan-2-yloxy)pyridine-3-sulfonyl chloride (95%, 90 mg, 0.364 mmol) and N,N-dimethylpyridin-4-amine (7.4 mg, 0.0607 mmol) and triethylamine (92.147 mg, 0.9106 mmol). The reaction mixture was stirred at 40° C. overnight. The reaction mixture was cooled to room temperature, diluted with DCM (13 mL) and a saturated aqueous solution of ammonium chloride (13 mL) was added. The layers were separated. The organic layer was washed once with a saturated aqueous solution of sodium bicarbonate (13 mL) and once with a saturated aqueous solution of sodium chloride (13 mL), dried over $Na_2SO_4$, filtered and concentrated under reduced pressure. The crude was purified by flash chromatography on silica gel using a gradient of methanol in dichloromethane from 0% to 1.5%. The desired fractions were combined and concentrated under reduced pressure to afford the title compound as a white powder (139 mg, 98% purity, 85% yield, $t_r$=1.03 min). LCMS (Method D): m/z found 530.04 $[M+H]^+$; $^1$H-NMR (400 MHz, DMSO-$d_6$) δ 8.49 (s, 1H), 7.90 (t, J=2.9 Hz, 1H), 7.56 (ddd, J=8.8, 2.7, 1.3 Hz, 1H), 7.44-7.29 (m, 5H), 7.10 (d, J=4.2 Hz, 4H), 6.59 (dd, J=8.8, 2.3 Hz, 1H), 5.29-5.17 (m, 1H), 5.14-5.01 (m, 2H), 4.20-4.08 (m, 1H), 3.63-3.33 (m, 3H), 2.74-2.69 (m, 1H), 2.24-2.11 (m, 1H), 1.30 (d, J=6.2 Hz, 6H).

Step 2: Synthesis of N-(3-(4-chlorophenyl)pyrrolidin-3-yl)-6-isopropoxypyridine-3-sulfonamide (80)

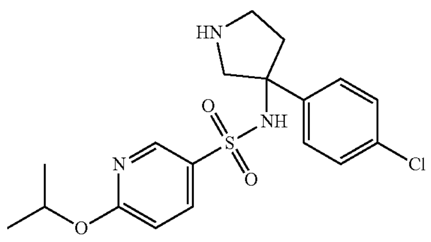 [SMILES: CC(C)Oc1ccc(S(=O)(=O)NC2(c3ccc(Cl)cc3)CCNC2)cn1]

In a round-bottom flask, to a stirred solution of benzyl 3-(4-chlorophenyl)-3-[(6-isopropoxy-3-pyridyl)sulfonylamino]pyrrolidine-1-carboxylate (131 mg, 0.247 mmol) in anhydrous ACN (4.9 mL) at room temperature under nitrogen was added iodo(trimethyl)silane (106 μL, 0.741 mmol). The reaction mixture was stirred at this temperature for 1.5 h and was concentrated under reduced pressure. The residue was dissolved in a minimal amount of ACN and poured into $Et_2O$. The resulting suspension was stirred for 1 h, filtered washed with $Et_2O$ and dried at 45° C. for 1 h. Then the residue was stirred in a mixture of dichloromethane (10 mL) and a half saturated aqueous solution of sodium carbonate (10 mL). The heterogenous mixture was stirred for 1 h and then partitioned. The aqueous layer was extracted twice with dichloromethane (10 mL). The combined organic layers were washed once with a saturated aqueous solution of sodium bicarbonate and once with a saturated aqueous solution of sodium chloride, dried using a phase separator, and concentrated under reduced pressure. The residue was suspended in $Et_2O$ (3 mL), then a solution of 2 M HCl in $Et_2O$ (1.3 mL, 2.60 mmol) was added. The suspension was stirred for 3 h, filtered and dried at 45° C. for 18 h to afford the hydrochloride salt of the title compound as an off-white powder (68.4 mg, 94.63% purity, 61% yield, $t_r$=5.24 min). LCMS (Method F): m/z found 396 $[M+H]^+$; $^1$H-NMR (500 MHz, DMSO-$d_6$) δ ppm 1.30 (t, J=6.24 Hz, 6H) 2.13 (dt, J=13.20, 9.78 Hz, 1H) 2.88 (dt, J=13.45, 3.79 Hz, 1H) 3.32-3.44 (m, 3H) 4.12 (br dd, J=11.98, 6.11 Hz, 1H) 5.23 (spt, J=6.19 Hz, 1H) 6.56 (d, J=8.31 Hz, 1H) 7.06-7.12 (m, 4H) 7.56 (dd, J=8.80, 2.45 Hz, 1H) 7.86 (d, J=2.20 Hz, 1H) 8.70 (s, 1H) 9.44-9.65 (m, 2H).

Example 45: N-(3-(4-chlorophenyl)-1-(3-methylbutanoyl)pyrrolidin-3-yl)-4-(trifluoromethoxy)benzenesulfonamide (81)

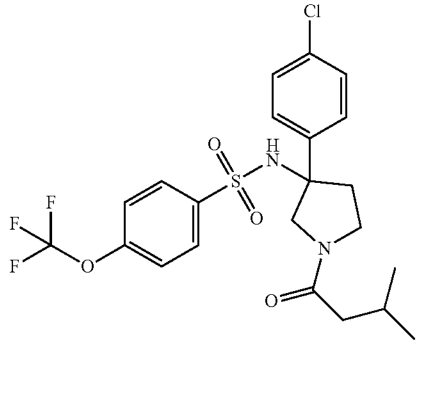 [SMILES: CC(C)CC(=O)N1CCC(NS(=O)(=O)c2ccc(OC(F)(F)F)cc2)(c2ccc(Cl)cc2)C1]

To a stirred solution of N-[3-(4-chlorophenyl)pyrrolidin-3-yl]-4-(trifluoromethoxy)benzenesulfonamide (150 mg, 0.356 mmol) and DIPEA (249 μL, 1.43 mmol) in DCM (3.2 mL) was added 3-methylbutanoyl chloride (48 μL, 0.392 mmol) dropwise at 0° C. The reaction mixture was stirred at room temperature for 18 h. The reaction mixture was quenched with a saturated aqueous solution of ammonium chloride (10 mL), then water (5 mL) and dichloromethane (10 mL) were added. The layers were separated and the aqueous layer was extracted with DCM (2×10 mL). The combined organic layers were washed once with a saturated aqueous solution of sodium bicarbonate and once with a saturated aqueous solution of sodium chloride, dried using a phase separator and concentrated under reduced pressure. The crude was purified by flash chromatography on silica gel using a gradient of methanol in dichloromethane from 0% to 10%. The residue was dissolved in 2 mL of dichloromethane, then diethyl ether (4 mL) and pentane (4 mL). The resulting suspension was filtered, washed with pentane and dried under vacuum at 45° C. for 18 h to afford the title compound as a white powder (147.9 mg, 98.77% purity, 82% yield, $t_r$=2.62 min). LCMS (Method H): m/z found 505 $[M+H]^+$; $^1$H-NMR (500 MHz, DMSO-$d_6$) δ ppm 0.87-0.93 (m, 6H) 1.95-2.04 (m, 1H) 2.04-2.28 (m, 3H) 2.61-2.81 (m, 1H) 3.48 (s, 3H) 4.13-4.23 (m, 1H) 7.04-7.11 (m, 4H) 7.25 (ddd, J=8.86, 4.10, 0.73 Hz, 2H) 7.40-7.45 (m, 2H) 8.59 (s, 1H).

Example 46: N-(4-(3,4-difluorophenyl)piperidin-4-yl)-4-(trifluoromethoxy)benzenesulfonamide (82)

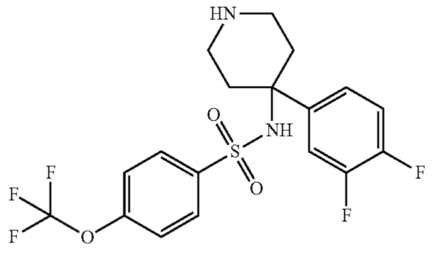 [SMILES: O=S(=O)(NC1(c2ccc(F)c(F)c2)CCNCC1)c1ccc(OC(F)(F)F)cc1]

Step 1: Synthesis of 1-tert-butoxycarbonyl-4-(3,4-difluorophenyl)piperidine-4-carboxylic acid

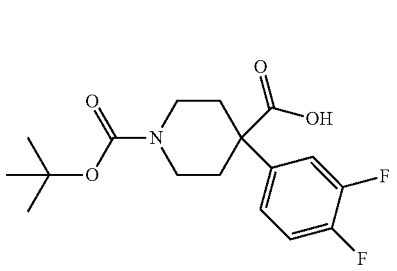 [SMILES: CC(C)(C)OC(=O)N1CCC(C(=O)O)(c2ccc(F)c(F)c2)CC1]

In a sealed tube, to a stirred suspension of tert-butyl 4-cyano-4-(3,4-difluorophenyl)piperidine-1-carboxylate (95%, 200 mg, 0.589 mmol) in ethanol (4.3 mL) at room temperature was added NaOH (1.2 mL, 11.8 mmol). The reaction mixture was stirred at 80° C. overnight. The mixture was poured on an ice water solution, and acidified with a saturated aqueous solution of potassium hydrogen sulfate to reach pH=3. The precipitate formed was filtered, washed with water and dried under reduced pressure at 50° C. for 4 h to afford the title compound as a brown solid (191.6 mg, 94% purity, 90% yield, $t_r$=0.92 min). LCMS (Method E): m/z found 242.3 $[M+H-Boc]^+$; $^1$H-NMR (DMSO, 400 MHz): δ (ppm) 12.89 (s, 1H), 7.54-7.35 (m, 2H), 7.30-7.17 (m, 1H), 3.77 (dt, J=4.0, 13.9 Hz, 2H), 2.98 (s, 2H), 2.40-2.25 (m, 2H), 1.72 (ddd, J=4.2, 11.0, 13.4 Hz, 2H), 1.39 (s, 9H).

Step 2: Synthesis of tert-butyl 4-[[1-tert-butoxycarbonyl-4-(3,4-difluorophenyl)-4-piperidyl]carbamoylamino]-4-(3,4-difluorophenyl)piperidine-1-carboxylate

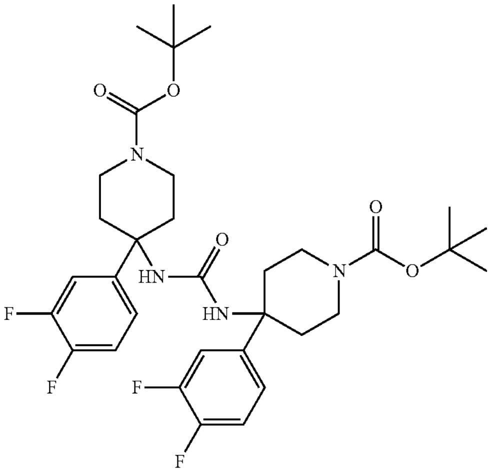 [SMILES: CC(C)(C)OC(=O)N1CCC(NC(=O)NC2(c3ccc(F)c(F)c3)CCN(C(=O)OC(C)(C)C)CC2)(c2ccc(F)c(F)c2)CC1]

In a sealed tube, to a stirred solution of 1-tert-butoxycarbonyl-4-(3,4-difluorophenyl)piperidine-4-carboxylic acid (94%, 130 mg, 0.358 mmol) in tert-butanol (3.6 mL) at room temperature under nitrogen were added successively diphenyl phosphorazidate (100 μL, 0.465 mmol) and triethylamine (100 μL, 0.716 mmol). The reaction mixture was stirred at 90° C. overnight. The reaction mixture was allowed to cool to room temperature and was quenched with water, then DCM was added. The aqueous layer was extracted twice with DCM. The combined organic layers were washed with brine, dried over sodium sulfate, filtered and concentrated under reduced pressure. The crude was purified by flash chromatography on silica gel using a gradient of MeOH in DCM from 1% to 8%. The desired fractions were combined and concentrated under reduced pressure to afford the title compound as a yellow oil (90 mg, 94% purity, 54% yield, $t_r$=1.09 min). LCMS (Method E): m/z found 651.4 $[M+H]^+$; $^1$H-NMR (DMSO, 400 MHz): δ (ppm) 7.39-7.24 (m, 4H), 7.17 (dt, J=10.6, 3.4 Hz, 2H), 6.50 (s, 2H), 3.84 (d, J=13.2 Hz, 4H), 3.01 (s, 5H), 2.08 (d, J=13.1 Hz, 4H), 1.72 (td, J=13.0, 4.5 Hz, 4H), 1.42 (s, 18H).

Step 3: Synthesis of tert-butyl 4-amino-4-(3,4-difluorophenyl)piperidine-1-carboxylate

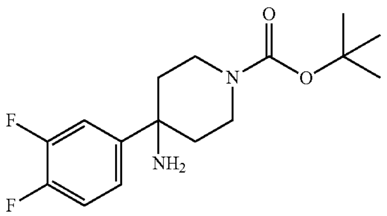 [SMILES: CC(C)(C)OC(=O)N1CCC(N)(c2ccc(F)c(F)c2)CC1]

A sealed vial was charged with tert-butyl 4-[[1-tert-butoxycarbonyl-4-(3,4-difluorophenyl)-4-piperidyl]carbamoylamino]-4-(3,4-difluorophenyl)piperidine-1-carboxylate (94%, 90 mg, 0.130 mmol) and N-(2-aminoethyl) ethane-1,2-diamine (0.42 mL, 3.90 mmol). The reaction mixture was warmed up to 130° C. and stirred at this temperature overnight. Then, the reaction mixture was warmed up to 140° C. for 4 h and stirred at room temperature for 2 days. Additional N-(2-aminoethyl)ethane-1,2-diamine (0.49 mL, 4.55 mmol) was added at room temperature and the reaction mixture was stirred at 140° C. for 3 h. The reaction mixture was cooled to room temperature, then dichloromethane and a saturated aqueous solution of ammonium chloride were added. The layers were separated. The aqueous layer was extracted twice with dichloromethane. The combined organic layers were washed once with a saturated aqueous solution of ammonium chloride, once with a saturated aqueous solution of sodium bicarbonate and once with a saturated aqueous solution of sodium chloride, dried using a phase separator and concentrated under vacuum to afford the title compound as a pale yellow oil (30.6 mg, 70% purity, 27% yield, $t_r$=0.61 min). LCMS (Method D): m/z found 313.2 $[M+H]^+$; (DMSO, 400 MHz): δ (ppm) 7.64-7.54 (m, 1H), 7.38-7.29 (m, 2H), 3.73 (d, J=13.0 Hz, 2H), 1.94 (d, J=23.8 Hz, 2H), 1.76 (ddd, J=13.2, 12.0, 4.7 Hz, 2H), 1.51 (dq, J=13.6, 2.8 Hz, 2H), 1.41 (s, 9H).

Step 4: Synthesis of tert-butyl 4-(3,4-difluorophenyl)-4-((4-(trifluoromethoxy)phenyl)sulfonamido) piperidine-1-carboxylate

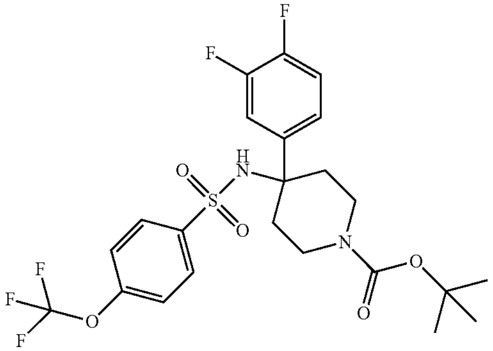 [SMILES: CC(C)(C)OC(=O)N1CCC(NS(=O)(=O)c2ccc(OC(F)(F)F)cc2)(c2ccc(F)c(F)c2)CC1]

A sealed vial was charged with tert-butyl 4-amino-4-(3,4-difluorophenyl)piperidine-1-carboxylate (90%, 35 mg, 0.101 mmol), triethylamine (70 μL, 0.504 mmol) and 4-dimethylaminopyridine (2.5 mg, 0.0202 mmol) in DCM (0.9328 mL). Then 4-(trifluoromethoxy)benzenesulfonyl chloride (98%, 21 μL, 0.121 mmol) was added and the reaction mixture was stirred at 40° C. for 2 days. The reaction mixture was cooled to room temperature and quenched with a saturated aqueous solution of ammonium chloride (10 mL). Then dichloromethane was added (10 mL) and the layers were separated. The aqueous layer was extracted once with dichloromethane (10 mL). The combined organic layers were washed once with a saturated aqueous solution of sodium bicarbonate (10 mL) and once with a saturated aqueous solution of sodium chloride (10 mL), dried using a phase separator and concentrated under reduced pressure. The crude was purified by flash chromatography on silica gel using a gradient of methanol in dichloromethane from 0% to 10%. The desired fractions were combined and concentrated under reduced pressure to afford the expected compound as a white solid (17.5 mg, 97% purity, 31% yield, $t_r$=1.05 min). LCMS (Method E); $^1$H-NMR (400 MHz, DMSO) δ 8.21 (s, 1H), 7.47-7.41 (m, 2H), 7.31-7.25 (m, 2H), 7.08-6.93 (m, 3H), 3.72 (d, J=13.3 Hz, 2H), 3.28-3.14 (m, 3H), 2.39-2.30 (m, 2H), 1.71 (t, J=11.9 Hz, 2H), 1.40 (s, 9H).

Step 5: Synthesis of N-(4-(3,4-difluorophenyl)piperidin-4-yl)-4-(trifluoromethoxy)benzenesulfonamide (82)

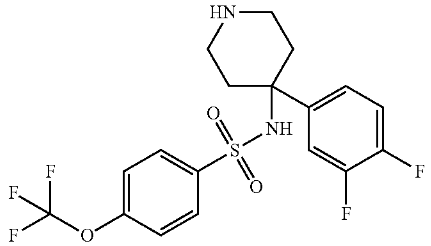 [SMILES: O=S(=O)(NC1(c2ccc(F)c(F)c2)CCNCC1)c1ccc(OC(F)(F)F)cc1]

In a round-bottomed flask, to a stirred suspension of tert-butyl 4-(3,4-difluorophenyl)-4-[[4-(trifluoromethoxy) phenyl]sulfonylamino]piperidine-1-carboxylate (30 mg, 0.0565 mmol) in diethyl ether (0.14 mL) at room temperature under nitrogen was added a solution of 4 M HCl in 1,4-dioxane (0.14 mL, 0.560 mmol). The reaction mixture was stirred at this temperature overnight. The resulting suspension was filtered, washed three times with diethyl ether (3×3 mL) and dried at 45° c. for 24 h to afford the hydrochloride salt of the title compound as a white powder (21 mg, 98.25% purity, 77% yield, $t_r$=1.31 min). LCMS (Method H): m/z found 437 $[M+H]^+$; $^1$H-NMR (DMSO-$d_6$, 600 MHz) δ 8.71 (br s, 2H), 8.48 (s, 1H), 7.4-7.5 (m, 2H), 7.27 (d, 2H, J=8.2 Hz), 6.8-7.1 (m, 3H), 3.23 (br s, 4H), 2.56 (br d, 2H, J=13.6 Hz), 1.8-2.2 (m, 2H).

Example 47: N-(4-(2,4-difluorophenyl)piperidin-4-yl)-4-(trifluoromethoxy)benzenesulfonamide (83)

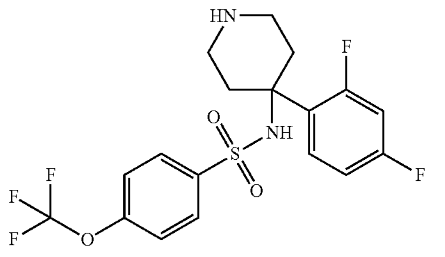

Step 1: Synthesis of 4-(2,4-difluorophenyl)piperidine-4-carbonitrile

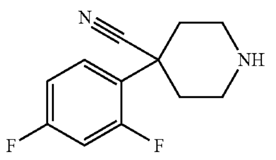 [SMILES: N#CC1(c2ccc(F)cc2F)CCNCC1]

In a round-bottomed flask, to a stirred solution of tert-butyl 4-cyano-4-(2,4-difluorophenyl)piperidine-1-carboxylate (95%, 250 mg, 0.737 mmol) in diethyl ether (1.8501 mL) was added 4 M hydrogen chloride in dioxane (1.8 mL, 7.37 mmol). The mixture was stirred at room temperature for 2 days, then filtered, washed twice with diethyl ether and dried under vacuum at 45° C. for 18 h to afford the hydrochloride salt of the title compound as a white powder (186 mg, 98% purity, 96% yield, $t_r$=0.48 min). LCMS (Method D): m/z found 223.1 $[M+H]^+$; $^1$H-NMR (400 MHz, DMSO) δ 9.12 (s, 2H), 7.57 (td, J=9.0, 6.2 Hz, 1H), 7.47 (ddd, J=12.1, 9.0, 2.7 Hz, 1H), 7.28-7.19 (m, 1H), 3.51 (dt, J=13.9, 3.4 Hz, 2H), 3.13 (td, J=13.2, 2.7 Hz, 2H), 2.48 (m, 2H), 2.31 (td, J=13.7, 4.0 Hz, 2H).

Step 2: Synthesis of 1-benzyl-4-(2,4-difluorophenyl)piperidine-4-carbonitrile

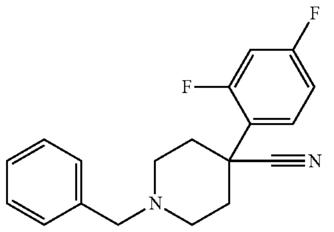 [SMILES: N#CC1(c2ccc(F)cc2F)CCN(Cc2ccccc2)CC1]

In a sealed tube, to a stirred suspension of 4-(2,4-difluorophenyl)piperidine-4-carbonitrile hydrochloride (98%, 186 mg, 0.705 mmol) in ACN (1.6248 mL) at room temperature was added bromomethylbenzene (0.10 mL, 0.846 mmol) and $K_2CO_3$ (0.24 g, 1.76 mmol). The reaction mixture was stirred at 65° C. overnight. The reaction mixture was poured into water. The layers were separated. The aqueous layer was extracted twice with EtOAc. The combined organic layers were washed with a saturated aqueous solution of sodium chloride, dried over sodium sulfate, filtered and concentrated under reduced pressure. The crude was purified by flash chromatography on silica gel using a gradient of EtOAc in Heptane from 5% to 80%. The desired fractions were combined and concentrated to afford the title compound as a colorless oil (140.2 mg, 98% purity, 62.4% yield, $t_r$=0.58 min). LCMS (Method D): m/z found 313.2 $[M+H]^+$; $^1$H-NMR (DMSO, 400 MHz): δ (ppm) 7.55 (td, J=9.1, 6.3 Hz, 1H), 7.46-7.31 (m, 5H), 7.27 (ddd, J=8.7, 5.2, 3.5 Hz, 1H), 7.17 (td, J=8.2, 2.5 Hz, 1H), 3.57 (s, 2H), 2.95 (dt, J=12.7, 3.3 Hz, 2H), 2.35 (td, J=12.2, 2.1 Hz, 2H), 2.23 (dd, J=13.3, 2.5 Hz, 2H), 2.09-1.96 (m, 2H).

Step 3: Synthesis of 1-benzyl-4-(2,4-difluorophenyl)piperidine-4-carboxamide

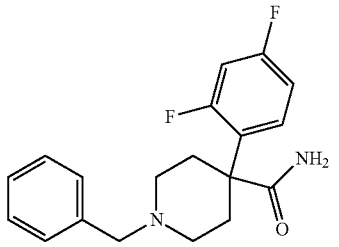 [SMILES: NC(=O)C1(c2ccc(F)cc2F)CCN(Cc2ccccc2)CC1]

In a round-bottom flask, a mixture of 1-benzyl-4-(2,4-difluorophenyl)piperidine-4-carbonitrile (98%, 138 mg, 0.433 mmol) in $H_2SO_4$ (1.7343 mL) and water (0.4336 mL) was stirred at 65° C. for 1 h. The mixture was poured in iced water and basified with aqueous 30% NaOH to reach pH=10-11. Water and DCM were added to obtain two homogeneous layers and the aqueous layer was extracted twice with DCM. The combined organic layers were dried over sodium sulfate, filtered and concentrated under reduced pressure to afford the title compound as a colorless oil (150.6 mg, 87% purity, 91.6% yield, $t_r$=0.51 min). The crude was directly used in next step without any purification. LCMS (Method E): m/z found 331.4 $[M+H]^+$; $^1$H-NMR (DMSO, 400 MHz): δ (ppm) 7.46 (td, J=9.1, 6.5 Hz, 1H), 7.36-7.20 (m, 5H), 7.15 (ddd, J=12.2, 9.2, 2.8 Hz, 1H), 7.11-7.02 (m, 1H), 6.95 (d, J=18.8 Hz, 2H), 5.77 (s, OH), 3.41 (s, 2H), 2.45 (s, 2H), 2.41-2.28 (m, 4H), 2.02-1.89 (m, 2H).

Step 4: Synthesis of 1-benzyl-4-(2,4-difluorophenyl)piperidin-4-amine

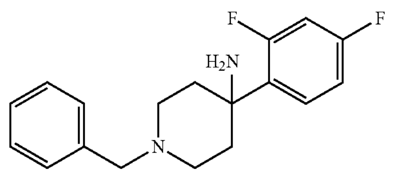 [SMILES: NC1(c2ccc(F)cc2F)CCN(Cc2ccccc2)CC1]

In sealed tube, 1-benzyl-4-(2,4-difluorophenyl)piperidine-4-carboxamide (87%, 147 mg, 0.388 mmol) was charged and dissolved in ACN (1.0997 mL) and water (1.0997 mL). Bis(trifluoroacetoxy)iodobenzene (96%, 177 mg, 0.396 mmol) was then charged, and the reaction was stirred at rt for 3 h. The reaction mixture was concentrated under reduced pressure and dried under vacuum overnight.

The residue was dissolved in $Et_2O$ and 2 M hydrogen chloride in $Et_2O$ (1.9 mL, 3.88 mmol) was added. The suspension was stirred at rt overnight, filtered and washed with $Et_2O$. The resulting gum was dissolved in MeOH and concentrated under reduced pressure. The residue was poured in a saturated aqueous solution of $Na_2CO_3$ to reach pH=10 and the aqueous layer was extracted twice with DCM. The combined organic layers were washed with brine, dried over sodium sulfate, filtered and concentrated under reduced pressure to afford the title compound as a pale pink oil (103.1 mg, 83% purity, 72.9% yield, $t_r$=0.42 min). LCMS (Method D): m/z found 303.2 $[M+H]^+$; $^1$H-NMR (DMSO, 400 MHz): δ (ppm) 7.62 (td, J=9.3, 6.9 Hz, 1H), 7.38-7.20 (m, 5H), 7.13 (ddd, J=12.9, 9.2, 2.7 Hz, 1H), 7.02 (td, J=8.5, 2.7 Hz, 1H), 3.49 (s, 2H), 2.53 (d, J=2.9 Hz, 2H), 2.10 (dt, J=13.1, 8.0 Hz, 2H), 1.81 (s, 2H), 1.56 (d, J=12.9 Hz, 2H).

Step 5: Synthesis of N-(1-benzyl-4-(2,4-difluorophenyl)piperidin-4-yl)-4-(trifluoromethoxy)benzenesulfonamide

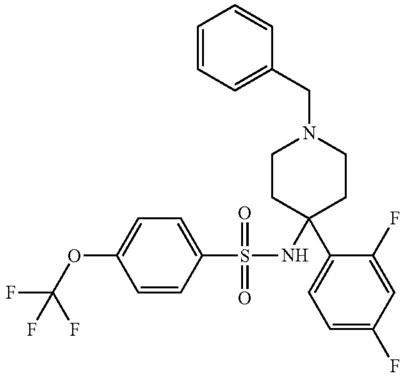 [SMILES: O=S(=O)(NC1(c2ccc(F)cc2F)CCN(Cc2ccccc2)CC1)c1ccc(OC(F)(F)F)cc1]

A round bottom flask was charged with 1-benzyl-4-(2,4-difluorophenyl)piperidin-4-amine (83%, 103 mg, 0.283 mmol) and triethylamine (0.16 mL, 1.12 mmol) in DCM (2.6 mL). 4-(trifluoromethoxy)benzenesulfonyl chloride (57 μL, 0.334 mmol) and N,N-dimethylpyridin-4-amine (6.9 mg, 0.0565 mmol) were then added and the reaction mixture was stirred at 40° C. overnight. The reaction mixture was diluted with DCM and a saturated aqueous solution of $NH_4Cl$ was added. The layers were separated. The aqueous layer was extracted twice with DCM. The combined organic layers were washed with a saturated aqueous solution of $NaHCO_3$, then with brine, dried using a phase separator and concentrated under reduced pressure. The crude (150 mg) was purified by flash chromatography on silica gel using a gradient of MeOH in DCM from 0% to 5%. The desired fractions were combined and concentrated under reduced pressure to afford the title compound as an off-white solid (120.4 mg, 99% purity, 80.1% yield, $t_r$=0.71 min). LCMS (Method D): m/z found 527.2 $[M+H]^+$; $^1$H-NMR ($CDCl_3$, 400 MHz): δ (ppm) 7.48-7.17 (m, 8H), 7.01 (d, J=8.4 Hz, 2H), 6.78-6.69 (m, 1H), 6.14 (ddd, J=12.9, 8.5, 2.7 Hz, 1H), 4.90 (s, 1H), 3.53 (d, J=20.2 Hz, 2H), 2.88-2.39 (m, 6H), 2.05 (s, 2H).

Step 6: N-(4-(2,4-difluorophenyl)piperidin-4-yl)-4-(trifluoromethoxy)benzenesulfonamide (83)

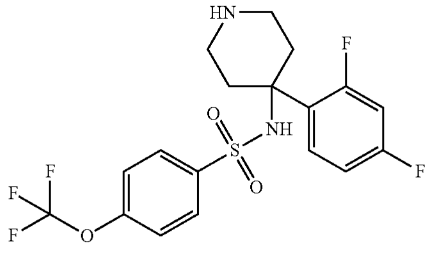 [SMILES: O=S(=O)(NC1(c2ccc(F)cc2F)CCNCC1)c1ccc(OC(F)(F)F)cc1]

To a stirred solution of N-[1-benzyl-4-(2,4-difluorophenyl)-4-piperidyl]-4-(trifluoromethoxy)benzenesulfonamide (99%, 116 mg, 0.218 mmol) in DCE (0.3635 mL) under nitrogen were added 1-chloroethyl carbonochloridate (62 mg, 0.436 mmol). The reaction mixture was stirred at room temperature overnight. Then, the suspension was concentrated under reduced pressure. The residue was dissolved in methanol (0.3635 mL) and the reaction mixture was stirred at 65° C. for 5 h. The reaction mixture was cooled to room temperature and concentrated under reduced pressure. The resulting off-white solid was triturated in a mixture of dichloromethane and methanol (95:5, 7 mL) overnight and the resulting white powder was filtered, washed twice with DCM and once with a mixture of dichloromethane and methanol (95:5). The resulting white powder was once again triturated in a mixture of dichloromethane and methanol (95:5, 5 mL) for 2 h and the resulting powder was filtered, washed twice with a mixture of dichloromethane and methanol (95:5) and dried under vacuum at 45° C. for 1 h. The withe powder was triturated in diethyl ether (1 mL) and 2 M hydrogen chloride in diethyl ether (0.55 mL, 1.09 mmol) was added. The mixture was stirred at rt overnight, filtered and dried under vacuum at 45° C. overnight to afford the hydrochloride salt of the title compound as a white powder (40.5 mg, 95.65% purity, 37.6% yield, $t_r$=1.36 min). LCMS (Method H): m/z found 437 $[M+H]^+$; $^1$H-NMR (500 MHz, DMSO-$d_6$) δ 8.79 (br s, 2H), 8.58 (s, 1H), 7.41-7.37 (m, 3H), 7.36-7.31 (m, 1H), 7.28 (d, J=8.1 Hz, 2H), 6.93 (td, J=8.4, 2.7 Hz, 1H), 6.49-6.33 (m, 1H), 3.25 (br d, J=6.1 Hz, 5H), 2.15-1.96 (m, 2H).

Example 48: N-(3-(4-fluorophenyl)pyrrolidin-3-yl)-4-(trifluoromethoxy)benzenesulfonimidamide (84)

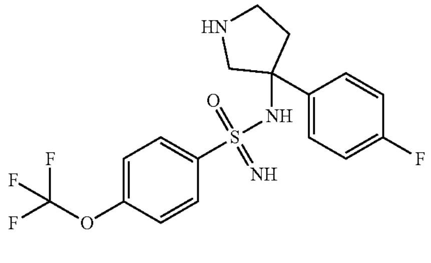

Step 1: Synthesis of benzyl 3-((N'-(3,4-dimethoxybenzyl)-4-(trifluoromethoxy)phenyl)sulfonoamidimidamido)-3-(4-fluorophenyl)pyrrolidine-1-carboxylate

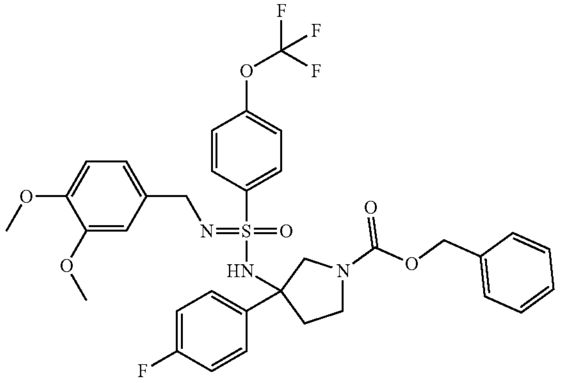 [SMILES: COc1ccc(CN=S(=O)(NC2(c3ccc(F)cc3)CCN(C(=O)OCc3ccccc3)C2)c2ccc(OC(F)(F)F)cc2)cc1OC]

In a round-bottomed flask, to a stirred solution of N-[(3,4-dimethoxyphenyl)methyl]-4-(trifluoromethoxy)benzenesulfinamide (250 mg, 0.666 mmol) in tetrachloromethane (2.5 mL, 26.0 mmol) at 0° C. under nitrogen was added tert-butyl hypochlorite (0.11 mL, 0.932 mmol). The reaction mixture was stirred at 0° C. for 1 h in the dark. The reaction mixture was concentrated under reduced pressure at 2° C. The residue was dissolved in anhydrous THF (2.0833 mL), benzyl 3-amino-3-(4-fluorophenyl)pyrrolidine-1-carboxylate (230 mg, 0.733 mmol), DIPEA (349 μL, 2.00 mmol) and N,N-dimethylpyridin-4-amine (99%, 8.2 mg, 0.0666 mmol) were added successively, and the reaction mixture was stirred at 40° C. for 4 h and at rt for 40 h. The reaction mixture was cooled to rt, quenched with water (20 mL) and ethyl acetate (20 mL) was added. The aqueous layer was extracted with ethyl acetate (20 mL). The combined organic layers were washed with a saturated aqueous solution of sodium chloride, dried over sodium sulfate, filtered and concentrated under reduced pressure. The crude was purified by flash chromatography on silica gel using a gradient of MeOH (0.7 N $NH_3$) in DCM from 0% to 8% to afford the expected compound as a yellow oil (230 mg, 81% purity, 41% yield, $t_r$=1.07 min). LCMS (Method D): m/z found 688.4 $[M+H]^+$.

Step 2: Synthesis of benzyl 3-(4-chlorophenyl)-3-((4-(trifluoromethoxy)phenyl)sulfonoamidimidamido)pyrrolidine-1-carboxylate

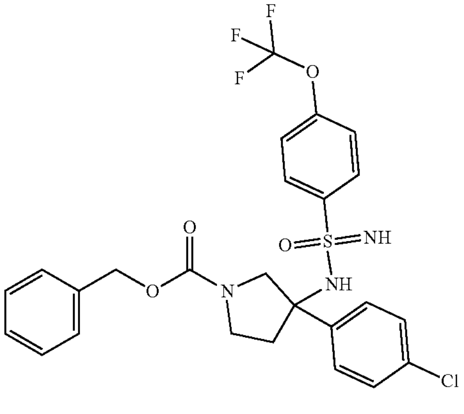 [SMILES: N=S(=O)(NC1(c2ccc(Cl)cc2)CCN(C(=O)OCc2ccccc2)C1)c1ccc(OC(F)(F)F)cc1]

In a round-bottomed flask, to a stirred solution of benzyl 3-[[N-[(3,4-dimethoxyphenyl)methyl]-S-[4-(trifluoromethoxy)phenyl]sulfonimidoyl]amino]-3-(4-fluorophenyl)pyrrolidine-1-carboxylate (81%, 230 mg, 0.271 mmol) in a mixture of ACN (3.612 mL) and water (1.806 mL) at 0° C. under nitrogen was added ammonium cerium (IV) nitrate (371 mg, 0.677 mmol). The reaction mixture was stirred at 0° C. for 2.5 h. The reaction mixture was diluted with water. The aqueous layer was extracted three times with ethyl acetate. The combined organic layers were washed with a saturated aqueous solution of NaCl, dried over $Na_2SO_4$, filtered, concentrated under reduced pressure and purified by flash chromatography on silica gel using a gradient of MeOH in DCM from 2% to 10%. The desired fractions were combined and concentrated to afford the title compound as an off-white solid (109 mg, 90% purity, 65% yield, $t_r$=0.92 min). LCMS (Method D): m/z found 538.2 $[M+H]^+$; $^1$H-NMR (DMSO, 400 MHz): δ (ppm) 8.20-6.50 (m, 14H), 5.16-4.98 (m, 2H), 4.66 (s, 1H), 4.36-3.82 (m, 1H), 3.80-3.37 (m, 3H), 3.05-2.58 (m, 1H), 2.31-1.95 (m, 1H).

Step 3: Synthesis of N-(3-(4-fluorophenyl)pyrrolidin-3-yl)-4-(trifluoromethoxy)benzenesulfonimidamide (84)

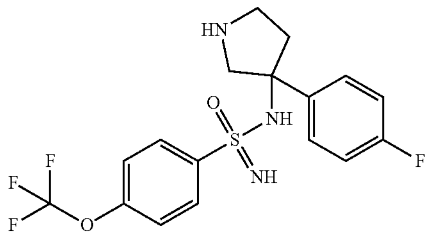 [SMILES: N=S(=O)(NC1(c2ccc(F)cc2)CCNC1)c1ccc(OC(F)(F)F)cc1]

In a sealed vial under nitrogen, a solution of benzyl 3-(4-fluorophenyl)-3-[[[4-(trifluoromethoxy)phenyl]sulfonimidoyl]amino]pyrrolidine-1-carboxylate (90%, 110 mg, 0.184 mmol) in ACN (1.8418 mL) was stirred at rt, then iodo(trimethyl)silane (0.079 mL, 0.553 mmol) was added to the pale yellow suspension, and the resulting orange solution was stirred at rt for 2 h. Additional iodo(trimethyl)silane (0.039 mL, 0.276 mmol) was added and the mixture was stirred for 1 h. Methanol (0.13 mL, 3.32 mmol) was added at 0° C., the mixture was stirred at rt for 1 h, concentrated in vacuo and purified by flash chromatography on silica gel using a gradient of MeOH (0.7 N $NH_3$) in DCM from 0% to 8%. The desired fractions were gathered, washed with a saturated $Na_2CO_3$ solution, filtered through phase separator and concentrated in vacuo. The residue was triturated in $Et_2O$ and filtered to afford the expected product as a white powder (48 mg, 99.25% purity, 64% yield, $t_r$=1.41 min). LCMS (Method H): m/z found 434 $[M+H]^+$; $^1$H-NMR (DMSO-$d_6$, 500 MHz) δ 9.1-9.7 (m, 2H), 7.8-8.0 (m, 2H), 7.2-7.6 (m, 6H), 6.6-7.2 (m, 1H), 3.7-4.3 (m, 1H), 3.4-3.7 (m, 2H), 3.1-3.3 (m, 1H), 2.7-2.8 (m, 1H), 2.0-2.3 (m, 4H).

Example 49: N-(3-(4-chlorophenyl)pyrrolidin-3-yl)-N-methyl-4-(trifluoromethoxy)benzenesulfonamide (85)

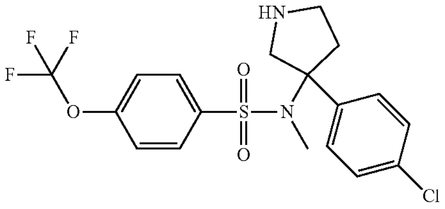 [SMILES: CN(C1(c2ccc(Cl)cc2)CCNC1)S(=O)(=O)c1ccc(OC(F)(F)F)cc1]

Step 1: Synthesis of tert-butyl 3-(4-chlorophenyl)-3-[[4-(trifluoromethoxy)phenyl]sulfonylamino]pyrrolidine-1-carboxylate

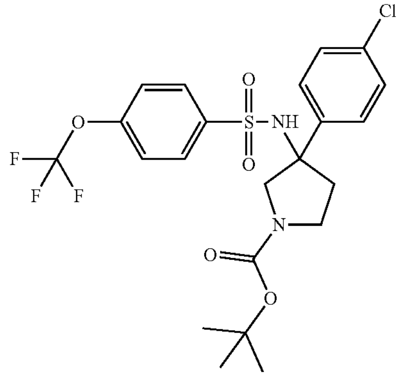 [SMILES: CC(C)(C)OC(=O)N1CCC(NS(=O)(=O)c2ccc(OC(F)(F)F)cc2)(c2ccc(Cl)cc2)C1]

In a sealed vial, to a stirred solution of N-[3-(4-chlorophenyl)pyrrolidin-3-yl]-4-(trifluoromethoxy)benzenesulfonamide (100 mg, 0.238 mmol) and triethylamine (0.13 mL, 0.951 mmol) in DCM (1 mL) was added di-tert-butyl dicarbonate (54 mg, 0.250 mmol). The reaction mixture was stirred at rt overnight. Water and dichloromethane were added and the layers were separated. The aqueous layer was extracted twice with dichloromethane, then the combined organic layers were washed with a saturated solution of $NaHCO_3$, once with a saturated aqueous solution of NaCl, filtered through phase separator, then concentrated under vacuum pressure to afford the title compound as a colorless oil (129.1 mg, 95% purity, 99% yield, $t_r$=1.03 min). LCMS (Method E): m/z found 543.2 $[M+Na]^+$; $^1$H-NMR (400 MHz, DMSO-$d_6$) δ 8.60 (d, J=9.0 Hz, 1H), 7.43 (d, J=8.8 Hz, 2H), 7.25 (d, J=7.8 Hz, 2H), 7.07-7.03 (m, 4H), 4.02 (dd, J=11.0, 6.0 Hz, 1H), 3.52-3.35 (m, 2H), 3.31-3.24 (m, 1H), 2.76-2.61 (m, 1H), 2.23-2.07 (m, 1H), 1.41 (d, J=3.9 Hz, 9H).

Step 2: Synthesis of tert-butyl 3-(4-chlorophenyl)-3-((N-methyl-4-(trifluoromethoxy)phenyl)sulfonamido)pyrrolidine-1-carboxylate

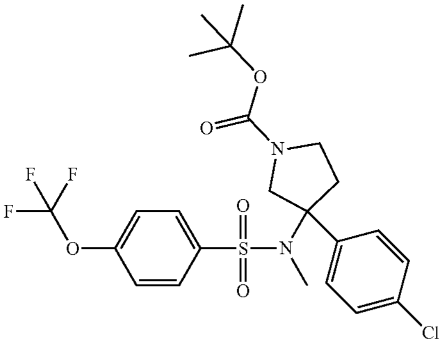 [SMILES: CN(C1(c2ccc(Cl)cc2)CCN(C(=O)OC(C)(C)C)C1)S(=O)(=O)c1ccc(OC(F)(F)F)cc1]

In a sealed tube under nitrogen, a solution of tert-butyl 3-(4-chlorophenyl)-3-[[4-(trifluoromethoxy)phenyl]sulfonylamino]pyrrolidine-1-carboxylate (123 mg, 0.237 mmol) in dry THF (2.2 mL) was stirred at 0° C. Dry methanol (14 μL, 0.355 mmol), triphenylphosphine (93 mg, 0.355 mmol), and diisopropyl azodicarboxylate (70 μL, 0.355 mmol) were added and the mixture was stirred at rt overnight. A half saturated aqueous solution of $NaHCO_3$ was added and the mixture was extracted twice with EtOAc. The combined organic layers were washed with brine, dried over sodium sulfate, filtered and concentrated. The crude was purified by flash chromatography on silica gel using a gradient of ethyl acetate in heptane from 10% to 100%. The desired fractions were concentrated to afford the title compound as a colorless gum (188.9 mg, 63% purity, 94% yield, $t_r$=1.08 min). LCMS (Method E): m/z found 557.2 $[M+Na]^+$; $^1$H-NMR (400 MHz, DMSO-$d_6$) δ 8.87 (s, 2H), 7.55 (dd, J=8.9, 3.4 Hz, 2H), 7.40-7.35 (m, 2H), 7.34-7.25 (m, 4H), 4.26 (t, J=12.8 Hz, 1H), 3.71 (t, J=11.0 Hz, 1H), 3.30-3.21 (m, 1H), 3.05 (s, 3H), 2.88-2.74 (m, 1H), 2.70-2.55 (m, 1H), 2.50-2.42 (m, 1H), 1.38 (d, J=24.4 Hz, 9H).

Step 3: Synthesis of N-[3-(4-chlorophenyl)pyrrolidin-3-yl]-N-methyl-4-(trifluoromethoxy)benzenesulfonamide (85)

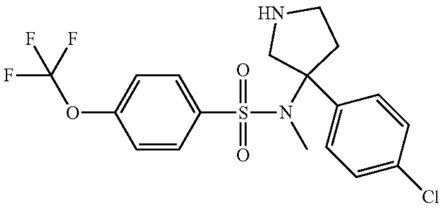 [SMILES: CN(C1(c2ccc(Cl)cc2)CCNC1)S(=O)(=O)c1ccc(OC(F)(F)F)cc1]

In a round-bottomed flask, to a stirred solution of 4 M hydrogen chloride in dioxane (0.60 mL, 2.40 mmol) in diethyl ether (2 mL) was added tert-butyl 3-(4-chlorophenyl)-3-[methyl-[4-(trifluoromethoxy)phenyl]sulfonylamino]pyrrolidine-1-carboxylate (63%, 189 mg, 0.222 mmol). The mixture was stirred overnight at room temperature. Next, the reaction mixture was concentrated, then methanol with 0.7 N ammonia was added. The resulting precipitate was filtered, then the filtrate was concentrated and purified by flash chromatography over silica gel using a gradient of methanol with 0.7 N ammonia in dichloromethane from 2% to 20%. The desired fractions were combined and concentrated. The resulting gum was purified by reverse-phase preparative chromatography (Redisep. C18 AQ 15.5 g) using a gradient of acetonitrile in water from 0% to 100% (0.1% AcOH in both eluants). The desired fractions were combined and organic solvents were removed. The resulting aqueous layers was neutralized with a saturated aqueous solution of $NaHCO_3$, then dichloromethane and a few drops of methanol were added. The layers were separated. The aqueous layer was washed twice with dichloromethane, dried over $Na_2SO_4$, filtered and concentrated under vacuum. The residue was triturated in pentane, filtered, washed with pentane and dried under vacuum at 40° C. for 18 h to afford the expected compound as a white powder (15.1 mg, 99.36% purity, 16% yield, $t_r$=1.91 min). LCMS (Method C): m/z found 435 $[M+H]^+$; $^1$H-NMR (500 MHz, DMSO-$d_6$) δ 7.65 (d, J=9.0 Hz, 2H), 7.45-7.35 (m, 4H), 7.28 (s, 2H), 3.44-3.34 (m, 1H), 3.33-3.31 (m, 1H), 3.25-3.19 (m, 1H), 3.00 (s, 3H), 2.87-2.77 (m, 1H), 2.72-2.61 (m, 1H), 2.43-2.29 (m, 2H).

Example 50: N-(3-phenyl-8-azabicyclo[3.2.1]octan-3-yl)-4-(trifluoromethoxy)benzenesulfonamide (86)

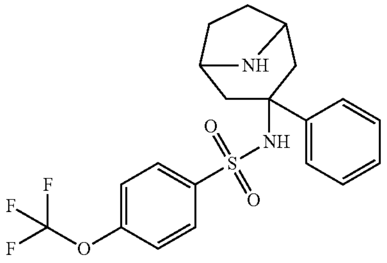 [SMILES: O=S(=O)(NC1(c2ccccc2)CC2CCC(C1)N2)c1ccc(OC(F)(F)F)cc1]

Step 1: Synthesis of 8-benzyl-8-azabicyclo[3.2.1]octan-3-one

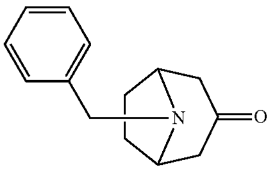 [SMILES: O=C1CC2CCC(C1)N2Cc1ccccc1]

In a sealed round bottom-flask, to a stirred suspension of 8-azabicyclo[3.2.1]octan-3-one hydrochloride (1:1) (98%, 2.00 g, 12.1 mmol) in acetonitrile (30 mL) at room temperature was added $K_2CO_3$ (4.19 g, 30.3 mmol) and bromomethylbenzene (1.8 mL, 15.2 mmol). The reaction mixture was stirred at 60° C. overnight. The reaction mixture was poured into water. The layers were separated. The aqueous layer was extracted twice with DCM. The combined organic layers were washed with a saturated aqueous solution of sodium chloride, dried over sodium sulfate, filtered and concentrated under reduced pressure. The resulting oil was triturated in $Et_2O$. The resulting suspension was filtered and the filtrate was concentrated. The crude was purified by flash chromatography on silica gel using a gradient of EtOAc in Heptane from 10% to 50%. The desired fractions were combined and concentrated to afford the title compound as a light yellow liquid (2.362 g, 98% purity, 88.664% yield, $t_r$=0.41 min). LCMS (Method D): m/z found 216.2 $[M+H]^+$; $^1$H-NMR (400 MHz, DMSO) δ 7.43 (ddt, J=7.5, 1.3, 0.7 Hz, 2H), 7.39-7.32 (m, 2H), 7.28-7.23 (m, 1H), 3.77 (s, 2H), 3.48-3.37 (m, 2H), 2.67 (dd, J=15.8, 4.4 Hz, 2H), 2.10-1.96 (m, 4H), 1.58-1.42 (m, 2H).

Step 2: Synthesis of 8-benzyl-8-azabicyclo[3.2.1]octane-3-carbonitrile

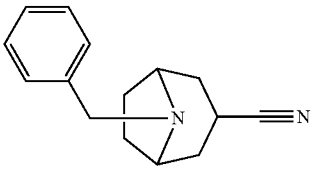 [SMILES: N#CC1CC2CCC(C1)N2Cc1ccccc1]

In a sealed round bottom flask, to a stirred solution of 8-benzyl-8-azabicyclo[3.2.1]octan-3-one (98%, 1.30 g, 5.92 mmol) and 1-(isocyanomethylsulfonyl)-4-methyl-benzene (98%, 1.18 g, 5.92 mmol) in DME (35 mL) at 0° C. was added dropwise a solution of potassium tert-butoxide (1328 mg, 11.8 mmol) dissolved in a 1:1 mixture of tert-butanol (9 mL) and DME (9 mL). The reaction mixture was stirred at 0° C. for 1 h. The reaction mixture was allowed to warm up to room temperature and stirred at this temperature overnight. Water was added and the mixture was extracted three times with EtOAc. The combined organic layers were washed with brine, dried over sodium sulfate, filtered and concentrated under reduced pressure. The crude was purified by flash chromatography using a gradient of MeOH (0.7 N $NH_3$) in DCM from 0.5% to 2%. The desired fractions were combined and concentrated under reduced pressure to afford the title compound as a yellow oil (698 mg, 84% purity, 44% yield, $t_r$=0.43 min). LCMS (Method D): m/z found 227.4 $[M+H]^+$; $^1$H-NMR (DMSO, 400 MHz): δ (ppm) 7.38-7.32 (m, 3H), 7.32-7.28 (m, 1H), 7.26-7.20 (m, 1H), 3.48 (s, 2H), 3.12 (p, J=2.9 Hz, 2H), 3.01 (tt, J=11.9, 6.3 Hz, 1H), 1.98-1.87 (m, 2H), 1.85-1.69 (m, 4H), 1.62-1.57 (m, 2H).

Step 3: Synthesis of 8-benzyl-3-phenyl-8-azabicyclo[3.2.1]octane-3-carbonitrile

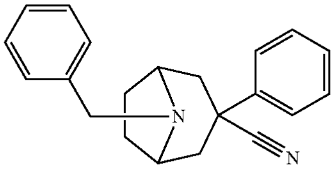 [SMILES: N#CC1(c2ccccc2)CC2CCC(C1)N2Cc1ccccc1]

In a sealed vial, to a stirred solution of 8-benzyl-8-azabicyclo[3.2.1]octane-3-carbonitrile (250 mg, 1.10 mmol) and fluorobenzene (99%, 2.6 mL, 27.6 mmol) at rt under $N_2$ was added 1 M [bis(trimethylsilyl)amino]potassium in THF (2.2 mL, 2.21 mmol). The reaction mixture was stirred at rt for 10 min. The reaction mixture was then irradiated at 100° C. for 18 min. The reaction mixture was poured into a saturated $NH_4Cl$ solution (50 mL), and extracted twice using EtOAc. The organic layer was dried over sodium sulfate, concentrated in vacuo and purified by flash chromatography on silica gel using a gradient of EtOAc in Heptane from 10% to 50% to afford the title compound as a white solid (220 mg, 100% purity, 66% yield, $t_r$=0.58 min). LCMS (Method D): m/z found 303.2 $[M+H]^+$; $^1$H-NMR (DMSO, 400 MHz): δ (ppm) 7.69-7.08 (m, 10H), 3.55 (s, 2H), 3.33-3.26 (m, 2H), 2.39-2.27 (m, 2H), 2.27-2.05 (m, 6H).

Step 4: Synthesis of 8-benzyl-3-phenyl-8-azabicyclo[3.2.1]octane-3-carboxamide

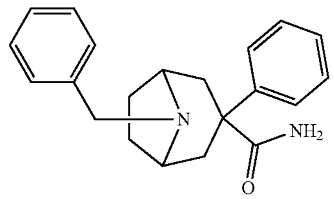 [SMILES: NC(=O)C1(c2ccccc2)CC2CCC(C1)N2Cc1ccccc1]

In a round-bottom flask, a mixture of 8-benzyl-3-phenyl-8-azabicyclo[3.2.1]octane-3-carbonitrile (235 mg, 0.777 mmol) in $H_2SO_4$ (3.0325 mL) and water (0.7581 mL) was stirred at 65° C. for 2 h and at 80° C. for 1 h. The mixture was poured in iced water and basified with aqueous 30% NaOH to reach pH=10-11. Water and DCM were added to obtain two homogeneous layers and the aqueous layer was extracted twice with DCM. The combined organic layers were dried over sodium sulfate, filtered and concentrated under reduced pressure to afford the title compound as a white solid (264 mg, 87% purity, 92% yield, $t_r$=0.51 min). LCMS (Method E): m/z found 321.2 $[M+H]^+$; $^1$H-NMR (DMSO, 400 MHz): δ (ppm) 7.40-7.24 (m, 9H), 7.19 (dt, J=14.2, 7.1 Hz, 2H), 6.88 (s, 1H), 3.46 (s, 2H), 3.13 (s, 2H), 2.93 (d, J=13.4 Hz, 2H), 1.87 (dd, J=9.6, 6.1 Hz, 6H).

Step 5: Synthesis of 8-benzyl-3-phenyl-8-azabicyclo[3.2.1]octan-3-amine

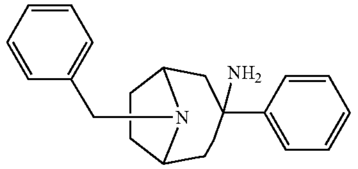 [SMILES: NC1(c2ccccc2)CCCC2CCC(C1)N2Cc1ccccc1]

In sealed tube, 8-benzyl-3-phenyl-8-azabicyclo[3.2.1]octane-3-carboxamide (87%, 264 mg, 0.717 mmol) was charged and dissolved in acetonitrile (2.0307 mL) and water (2.0307 mL). [bis(trifluoroacetoxy)iodo]benzene (96%, 328 mg, 0.731 mmol) was then charged, and the reaction was stirred at rt overnight. The reaction mixture was concentrated under reduced pressure. Saturated $Na_2CO_3$ was added, and the aqueous layer was extracted twice with DCM. The combined organic layers were concentrated under reduced pressure, then $Et_2O$ (4 mL) and 2 M HCl in $Et_2O$ (3.6 mL, 7.17 mmol) were added. The suspension was stirred at rt for 2 h, filtered, and washed with $Et_2O$. The resulting solid was dried at 45° C. under vacuum for 2 hours to afford the dihydrochloride salt of the title compound as an off-white solid (239 mg, 97% purity, 88.528% yield, $t_r$=0.39 min). LCMS (Method E): m/z found 393.4 $[M+H]^+$; $^1$H-NMR (DMSO, 400 MHz): δ (ppm) 10.79 (s, 1H), 8.60 (s, 3H), 7.72 (dd, J=6.6, 3.0 Hz, 2H), 7.67-7.57 (m, 2H), 7.51-7.35 (m, 6H), 4.25 (d, J=6.1 Hz, 2H), 3.95 (d, J=5.4 Hz, 2H), 2.87 (dd, J=16.1, 3.7 Hz, 2H), 2.73 (d, J=15.8 Hz, 2H), 2.56 (s, 2H), 2.35 (d, J=9.8 Hz, 2H).

Step 6: Synthesis of N-(8-benzyl-3-phenyl-8-azabicyclo[3.2.1]octan-3-yl)-4-(trifluoromethoxy)benzenesulfonamide

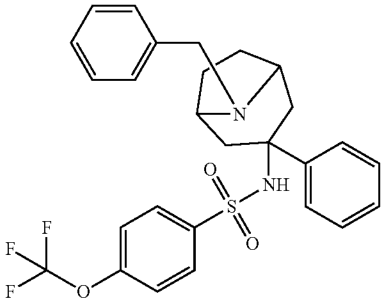 [SMILES: O=S(=O)(NC1(c2ccccc2)CC2CCC(C1)N2Cc1ccccc1)c1ccc(OC(F)(F)F)cc1]

A round bottom flask was charged with 8-benzyl-3-phenyl-8-azabicyclo[3.2.1]octan-3-amine; dihydrochloride (239 mg, 0.654 mmol) and triethylamine (0.46 mL, 3.27 mmol) in DCM (4 mL). 4-(trifluoromethoxy)benzenesulfonyl chloride (0.11 mL, 0.654 mmol) and N,N-dimethylpyridin-4-amine (16 mg, 0.131 mmol) were then added to the reaction mixture and stirred at 40° C. overnight. The reaction mixture was diluted with DCM and an half saturated aqueous solution of $Na_2CO_3$ was added. The layers were separated. The aqueous layer was extracted twice with DCM. The combined organic layers were dried through phase separator and concentrated in vacuo. Anhydrous acetonitrile (4 mL) and pyridine (0.11 mL, 1.31 mmol) were added under nitrogen. was added and the mixture was stirred overnight at rt. The mixture was filtered and the solid was washed with ACN, dissolved in an half saturated solution of $Na_2CO_3$ and DCM. The aqueous layer was extracted once more with DCM, and the combined organic layers were dried using a phase separator and concentrated under reduced pressure to afford the title compound as a yellow solid (169 mg, 100% purity, 50% yield, $t_r$=0.73 min). LCMS (Method E): m/z found 517.4 $[M+H]^+$; $^1$H-NMR (DMSO, 400 MHz): δ (ppm) 7.85 (s, 1H), 7.37-7.16 (m, 7H), 7.14-7.06 (m, 2H), 6.99 (dd, J=6.6, 3.1 Hz, 2H), 6.90-6.79 (m, 3H), 3.50 (s, 2H), 3.21 (s, 2H), 2.75 (d, J=13.8 Hz, 2H), 2.36-2.25 (m, 2H), 2.12-1.90 (m, 4H).

Step 7: Synthesis of N-(3-phenyl-8-azabicyclo[3.2.1]octan-3-yl)-4-(trifluoromethoxy)benzenesulfonamide (86)

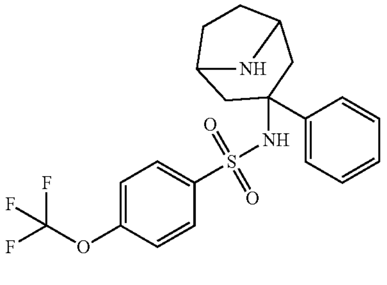 [SMILES: O=S(=O)(NC1(c2ccccc2)CC2CCC(C1)N2)c1ccc(OC(F)(F)F)cc1]

A suspension of N-(8-benzyl-3-phenyl-8-azabicyclo[3.2.1]octan-3-yl)-4-(trifluoromethoxy)benzenesulfonamide (92%, 180 mg, 0.321 mmol) in a mixture of THF (1.6028 mL), ethanol (1.6028 mL), and methanol (20 mL). The resulting homogeneous solution was purged with argon. palladium on carbon (10 wt %, 34 mg, 0.0321 mmol) was added and the reaction mixture was stirred under an hydrogen atmosphere overnight. The solution was filtered through a pad of decalite and the resulting solution was concentrated under reduce pressure. The resulting crude was dissolved in methanol (20 mL) and purged with argon. Palladium on carbon (10 wt %, 34 mg, 0.0321 mmol) was added and the reaction mixture was stirred under an hydrogen atmosphere for 24 h. The solution was filtered through a pad of decalite and the resulting filtrate was concentrated under reduce pressure to provide a solid. To the solid was added diethyl ether (3 mL) to form a suspension, and 2 M HCl (1.6 mL, 3.21 mmol) was added. The resulting suspension was stirred at rt overnight. The residue 30 was filtered and washed with diethyl ether to afford the hydrochloride salt of the title compound as a grey solid (90 mg, 98.06% purity, 61% yield, $t_r$=1.28 min). LCMS (Method H): m/z found 427.3 $[M+H]^+$; $^1$H-NMR (DMSO-$d_6$, 600 MHz): δ (ppm) 8.48-9.19 (m, 2H), 8.30 (s, 1H), 7.26-7.31 (m, 2H), 7.09-7.14 (m, 2H), 6.95-7.00 (m, 2H), 6.86-6.92 (m, 3H), 3.95-4.28 (m, 2H), 2.98 (br d, J=13.8 Hz, 2H), 2.52 (br d, J=8.4 Hz, 2H), 2.21 (br d, J=14.2 Hz, 2H), 1.98-2.10 (m, 2H).

Example 51: N-(4-(5-chloropyridin-2-yl)piperidin-4-yl)-4-(trifluoromethoxy)benzenesulfonamide (87)

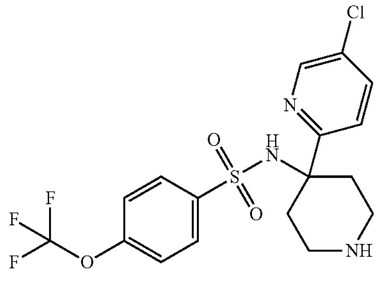 [SMILES: O=S(=O)(NC1(c2ccc(Cl)cn2)CCNCC1)c1ccc(OC(F)(F)F)cc1]

Step 1: Synthesis of 1-benzyl-4-(5-chloro-2-pyridyl)piperidine-4-carbonitrile

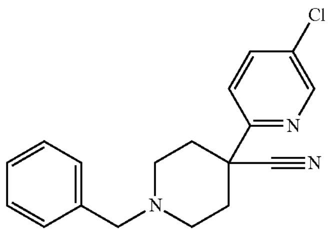 [SMILES: N#CC1(c2ccc(Cl)cn2)CCN(Cc2ccccc2)CC1]

To a stirred solution of 1-benzylpiperidine-4-carbonitrile (91%, 224 mg, 1.02 mmol) in Toluene Anhydrous (10.185 mL) at room temperature under nitrogen was added 2-bromo-5-chloropyridine (98%, 200 mg, 1.02 mmol). The reaction mixture was cooled to 0° C. and 2 M sodium 1,1,1,3,3,3-hexamethyldisilazan-2-ide (1.0 mL, 2.04 mmol) was added dropwise. The reaction mixture was stirred at 0° C. for 1 h then at room temperature for 3 h. The reaction mixture was quenched with a saturated aqueous solution of ammonium chloride to reach pH=7 and EtOAc was added. The aqueous layer was extracted three times with EtOAc. The combined organic layers were washed with brine, dried over sodium sulfate, filtered and concentrated under reduced pressure. The crude material was purified by flash chromatography on silica gel (column) using a gradient of EtOAc in cyclohexane from 10% (EtOAc in cyclohexane) to 30%. The desired fractions was combined and concentrated under reduced pressure to afford the title compound as a colorless solid (270 mg, 100% purity, 85% yield, $t_r$=0.55 min). LCMS (Method E): m/z found 312.4 $[M+H]^+$; $^1$H-NMR (DMSO, 400 MHz): δ (ppm) 8.69 (d, J=2.2 Hz, 1H), 8.04 (dd, J=8.6, 2.6 Hz, 2H), 7.72-7.64 (m, 2H), 7.34 (d, J=4.4 Hz, 6H), 7.32-7.22 (m, 2H), 3.57 (s, 3H), 2.94 (dt, J=12.5, 3.4 Hz, 4H), 2.33 (ddd, J=12.2, 10.8, 3.8 Hz, 4H), 2.20-2.05 (m, 7H).

Step 2: Synthesis of 1-benzyl-4-(5-chloro-2-pyridyl)piperidine-4-carboxamide

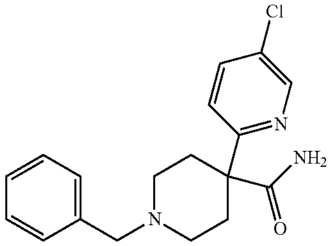 [SMILES: NC(=O)C1(c2ccc(Cl)cn2)CCN(Cc2ccccc2)CC1]

In a sealed tube, a mixture of 1-benzyl-4-(5-chloro-2-pyridyl)piperidine-4-carbonitrile (100%, 270 mg, 0.866 mmol) in $H_2SO_4$ (3.4685 mL) and water (0.8671 mL) was stirred at 65° C. overnight. The mixture was poured in ice water and basified with aqueous 30% NaOH to reach pH=10-11. Water and DCM were added to obtain two homogeneous layers and the 10 aqueous layer was extracted twice with DCM. The combined organic layers were dried over sodium sulfate, filtered, and concentrated under reduced pressure to afford the title compound as a white powder (276.3 mg, 98% purity, 94.81% yield, $t_r$=0.51 min). LCMS (Method E): m/z found 330.4 $[M+H]^+$; $^1$H-NMR (400 MHz, DMSO) δ 8.58 (d, J=2.5 Hz, 1H), 7.89 (dd, J=8.6, 2.6 Hz, 1H), 7.45 (d, J=8.6 Hz, 1H), 7.37-7.19 (m, 5H), 7.09 (s, 1H), 7.02 (s, 1H), 3.39 (s, 2H), 2.43 (s, 2H), 2.30 (dt, J=21.7, 11.7 Hz, 4H), 2.06 (s, 2H). The crude product was used in next step without further purification.

Step 3: Synthesis of 1-benzyl-4-(5-chloro-2-pyridyl)piperidin-4-amine

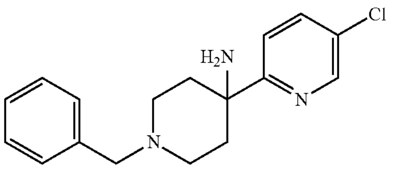 [SMILES: NC1(c2ccc(Cl)cn2)CCN(Cc2ccccc2)CC1]

In sealed tube, 1-benzyl-4-(5-chloro-2-pyridyl)piperidine-4-carboxamide (275 mg, 0.834 mmol) was charged and dissolved in acetonitrile (2.4 mL) and Water (2.4 mL). The flask was charged with [bis(trifluoroacetoxy)iodo]benzene (96%, 381 mg, 0.850 mmol) and the reaction was stirred at room temperature for 16 h, then at 40° C. for 4 h. Additional [bis(trifluoroacetoxy)iodo[benzene (96%, 374 mg, 0.834 mmol) was added at room temperature and the reaction mixture was stirred at room temperature for 18 h. The reaction mixture was concentrated under reduced pressure and dried under vacuum. The residue was dissolved in $Et_2O$ and 2 M HCl in $Et_2O$ (4.2 mL, 8.34 mmol) was added. The suspension was stirred at room temperature for 18 h, filtered and washed with diethyl ether and dried under vacuum at 50° C. for 4 h to afford the hydrochloride salt of the title compound as a beige powder (245 mg, 49% purity, 43% yield, $t_r$=0.42 min). LCMS (Method D): m/z found 302.3 $[M+H]^+$.

Step 4: Synthesis of N-[1-benzyl-4-(5-chloro-2-pyridyl)-4-piperidyl]-4-(trifluoromethoxy)benzenesulfonamide

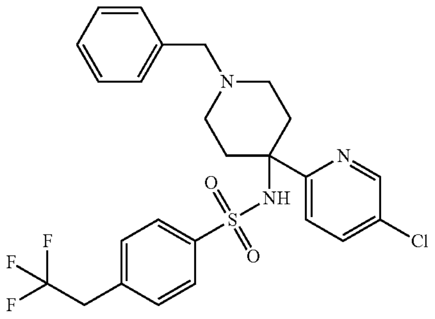 [SMILES: O=S(=O)(NC1(c2ccc(Cl)cn2)CCN(Cc2ccccc2)CC1)c1ccc(CC(F)(F)F)cc1]

A sealed vial was charged with 1-benzyl-4-(5-chloro-2-pyridyl)piperidin-4-amine hydrochloride (50%, 245 mg, 0.362 mmol), triethylamine (153 μL, 1.10 mmol) and DMAP (8.8 mg, 0.0724 mmol) in DCM (2.5 mL). 4-(Trifluoromethoxy)benzenesulfonyl chloride (74 μL, 0.436 mmol) was then added to the reaction mixture and it was stirred at 40° C. for 16 h. The reaction mixture was cooled to room temperature and quenched with a saturated aqueous solution of ammonium chloride (4 mL), then water (10 mL) and dichloromethane (10 mL) were added. The aqueous layer was extracted with dichloromethane (2×10 mL). The combined organic layers were dried over sodium sulfate, filtered and concentrated under reduced pressure. The crude was purified by flash chromatography on silica gel using a gradient of MeOH in DCM from 0% to 5% to afford the title compound as a brown powder (51 mg, 84% purity, 27% yield, $t_r$=0.71 min). LCMS (Method E): m/z found 526.3 $[M+H]^+$; $^1$H-NMR (DMSO, 400 MHz): δ (ppm) 8.20-8.14 (m, 1H), 7.60 (dd, J=8.5, 2.5 Hz, 1H), 7.52-7.43 (m, 2H), 7.36-7.22 (m, 9H), 3.41 (s, 2H), 2.46-2.20 (m, 6H), 2.05 (s, 2H).

Step 5: Synthesis of N-(4-(5-chloropyridin-2-yl)piperidin-4-yl)-4-(trifluoromethoxy)benzenesulfonamide (87)

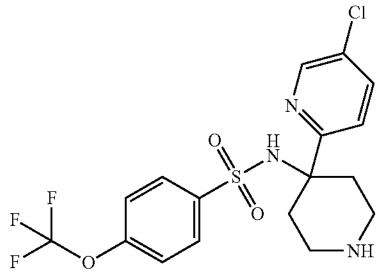 [SMILES: O=S(=O)(NC1(c2ccc(Cl)cn2)CCNCC1)c1ccc(OC(F)(F)F)cc1]

To a stirred solution of 1-chloroethyl carbonochloridate (99%, 17 μL, 0.160 mmol) in DCE (2 mL) under nitrogen were added N-[1-benzyl-4-(5-chloro-2-pyridyl)-4-piperidyl]-4-(trifluoromethoxy)benzenesulfonamide (84%, 50 mg, 0.0799 mmol). The reaction mixture was stirred at room temperature for 16 h. Additional 1-chloroethyl carbonochloridate (99%, 17 μL, 0.160 mmol) was added at room temperature and the reaction mixture was stirred at room temperature for 6 h. Then, the reaction mixture was concentrated under reduced pressure. The residue was dissolved in MeOH (2 mL) and the reaction mixture was stirred at 65° C. for 16 h. The reaction mixture was cooled to room temperature and concentrated under reduced pressure. The resulting solid was triturated in dichloromethane, filtered, washed with dichloromethane, and dried under vacuum. The resulting precipitate was purified by flash chromatography on silica gel using a gradient of ammoniacal methanol in dichloromethane from 2% to 15%. The residue was triturated in 2 M hydrogen chloride in diethyl ether (399 μL, 0.799 mmol) for 4 h, filtered, washed with diethyl ether, and dried under vacuum at 50° C. for 20 h to afford the hydrochloride salt of the title compound as a white powder (8.7 mg, 96.2% purity, 22% yield, $t_r$=1.22 min). LCMS (Method H): m/z found 436 $[M+H]^+$; $^1$H-NMR (600 MHz, DMSO-$d_6$) δ ppm 8.70 (m, 2H), 8.58 (s, 1H), 8.20 (dd, J=2.5, 0.6 Hz, 1H), 7.58 (dd, J=8.5, 2.6 Hz, 1H), 7.43 (d, J=8.9 Hz, 2H), 7.28 (td, J=8.7, 0.7 Hz, 3H), 3.15 (m, 4H), 2.53 (br d, J=1.2 Hz, 2H), 2.19 (m, 2H).

Example 52: N-(4-(2,5-difluorophenyl)piperidin-4-yl)-4-(trifluoromethoxy)benzenesulfonamide (88)

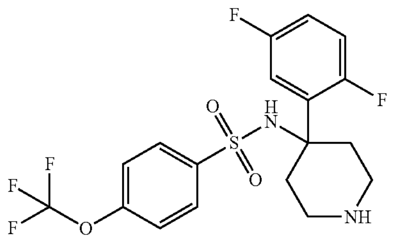 [SMILES: O=S(=O)(NC1(c2cc(F)ccc2F)CCNCC1)c1ccc(OC(F)(F)F)cc1]

Step 1: Synthesis of 4-(2,5-difluorophenyl)piperidine-4-carbonitrile

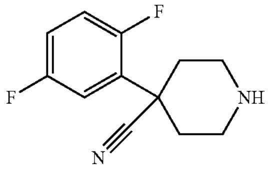 [SMILES: N#CC1(c2cc(F)ccc2F)CCNCC1]

A sealed vial under nitrogen was successively charged with tert-butyl 4-cyano-4-(2,5-difluorophenyl)piperidine-1-carboxylate (95%, 300 mg, 0.884 mmol) and 4 M HCl in 1,4-dioxane (3.3 mL, 13.3 mmol) in diethyl ether (2.28 mL). The reaction mixture was stirred at room temperature for 18 h. The suspension was filtered, washed, with diethyl ether (10 mL) and dried under vacuum at 50° C. for 7 h to afford the hydrochloride salt of the title compound as a beige powder (271 mg, 80% purity, 95% yield, $t_r$=0.46 min). LCMS (Method E): m/z found 223.4 $[M+H]^+$; $^1$H-NMR (DMSO, 400 MHz): δ (ppm) 9.19 (s, 2H), 7.51-7.36 (m, 3H), 3.51 (dt, J=13.6, 3.2 Hz, 2H), 3.13 (td, J=13.4, 2.7 Hz, 2H), 2.55-2.52 (m, 2H), 2.40-2.26 (m, 2H).

Step 2: Synthesis of 1-benzyl-4-(2,5-difluorophenyl)piperidine-4-carbonitrile

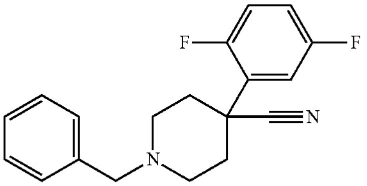 [SMILES: N#CC1(c2cc(F)ccc2F)CCN(Cc2ccccc2)CC1]

In a sealed tube, to a stirred solution of 4-(2,5-difluorophenyl)piperidine-4-carbonitrile hydrochloride (80%, 265 mg, 0.820 mmol) in DMF (2 mL) at room temperature was added bromomethylbenzene (146 μL, 1.23 mmol) and triethylamine (343 μL, 2.46 mmol). The reaction mixture was stirred at room temperature for 18 h. The reaction mixture was quenched with a saturated aqueous solution of ammonium chloride (3 mL), then water (10 mL) and DCM (10 mL) were added. The aqueous layer was extracted with dichloromethane (2×5 mL). The combined organic layers were dried over sodium sulfate, filtered and concentrated under reduced pressure. The crude was purified by flash chromatography on silica gel using a gradient of ethyl acetate in cyclohexane from 0% to 20% to afford the title compound as a colorless oil (278 mg, 100% purity, 93% yield, $t_r$=0.57 min). LCMS (Method E): m/z found 313.4 $[M+H]^+$; $^1$H-NMR (DMSO, 400 MHz): δ (ppm) 7.45-7.21 (m, 8H), 3.57 (s, 2H), 2.95 (dt, J=12.7, 3.2 Hz, 2H), 2.36 (td, J=12.3, 2.2 Hz, 2H), 2.24 (dq, J=13.3, 2.7 Hz, 2H), 2.07-1.99 (m, 2H).

Step 3: Synthesis of 1-benzyl-4-(2,5-difluorophenyl)piperidine-4-carboxamide

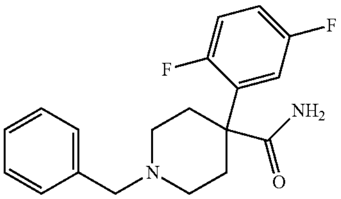 [SMILES: NC(=O)C1(c2cc(F)ccc2F)CCN(Cc2ccccc2)CC1]

In a round-bottom flask, a mixture of 1-benzyl-4-(2,5-difluorophenyl)piperidine-4-carbonitrile (86%, 278 mg, 0.765 mmol) in $H_2SO_4$ (3 mL) and water (0.76 μL) was stirred at 65° C. for 1 h. The mixture was poured in iced water and basified with aqueous 30% NaOH to reach pH=10-11. Water and DCM were added to obtain two homogeneous layers and the aqueous layer was extracted twice with DCM. The combined organic layers were dried over sodium sulfate, filtered and concentrated under reduced pressure to afford the title compound as a white gum (278 mg, 81% purity, 89% yield, $t_r$=0.50 min). LCMS (Method E): m/z found 331.4 $[M+H]^+$; $^1$H-NMR (DMSO, 400 MHz): δ (ppm) 7.36-7.11 (m, 8H), 6.95 (d, J=13.2 Hz, 2H), 3.42 (s, 2H), 2.46 (s, 1H), 2.43-2.29 (m, 5H), 1.95 (ddd, J=13.0, 9.2, 3.6 Hz, 2H). The product was used in the next step without further purification.

Step 4: Synthesis of 1-benzyl-4-(2,5-difluorophenyl)piperidin-4-amine

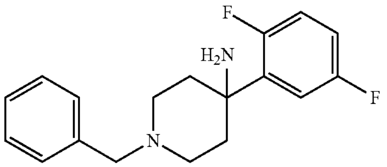 [SMILES: NC1(c2cc(F)ccc2F)CCN(Cc2ccccc2)CC1]

A sealed tube was charged with 1-benzyl-4-(2,5-difluorophenyl)piperidine-4-carboxamide (81%, 278 mg, 0.682 mmol), then in acetonitrile (1.931 mL) and water (1.931 mL). Next, [bis(trifluoroacetoxy)iodo]benzene (96%, 311 mg, 0.695 mmol) was added, and the reaction was stirred at room temperature for 2 h. Acetonitrile was evaporated, then a saturated aqueous solution of sodium bicarbonate (5 mL), water (5 mL), and dichloromethane (10 mL) were added. The aqueous layer was extracted with dichloromethane (2×10 mL). The combined organic layers were dried over sodium sulfate, filtered and concentrated under reduced pressure. The residue was dissolved in diethyl ether (4 mL) and 2 M hydrogen chloride in $Et_2O$ (3.4 mL, 6.82 mmol) were added. The reaction mixture was stirred at room temperature for 2 h, filtered, washed with diethyl ether and dried under vacuum at 50° C. for 3 days to afford the hydrochloride salt of the title compound as an off-white powder (293 mg, 70% purity, 100% yield, $t_r$=0.40 min). LCMS (Method E): m/z found 303.4 $[M+H]^+$.

Step 5: Synthesis of N-[1-benzyl-4-(2,5-difluorophenyl)-4-piperidyl]-4-(trifluoromethoxy)benzenesulfonamide

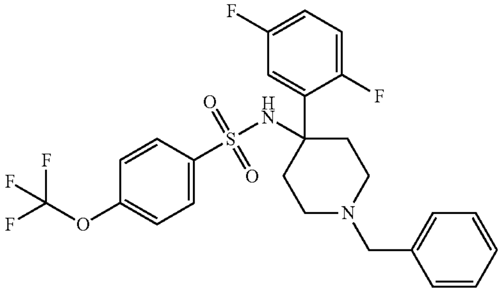 [SMILES: O=S(=O)(NC1(c2cc(F)ccc2F)CCN(Cc2ccccc2)CC1)c1ccc(OC(F)(F)F)cc1]

A sealed vial was successively charged with 1-benzyl-4-(2,5-difluorophenyl)piperidin-4-amine hydrochloride (100%, 290 mg, 0.959 mmol), N,N-dimethylpyridin-4-amine (99%, 24 mg, 0.192 mmol) and triethylamine (0.53 mL, 3.84 mmol) in DCM (9 mL). 4-(trifluoromethoxy) benzenesulfonyl chloride (98%, 0.25 mL, 1.44 mmol) was then added to the reaction mixture and it was stirred at 40° C. for 4 h. The reaction mixture was cooled to room temperature and quenched with a saturated aqueous solution of ammonium chloride. The layers were separated. The aqueous layer was extracted once with dichloromethane. The combined organic layers were dried over sodium sulfate, filtered, and concentrated under reduced pressure. The resulting yellow oil was triturated in a minimal volume of MeOH at 0° C. The precipitate was filtered, washed twice with MeOH, and dried under vacuum at 45° C. for 18 h to afford the title compound as a white powder (106.6 mg). The filtrate was concentrated under reduced pressure and purified by flash chromatography on silica gel using a gradient of methanol in dichloromethane from 0% to 5%. The desired fractions were combined and concentrated. The solid was dried under vacuum at 45° C. for 18 h to afford the title compound as an off-white solid (153 mg, 100% purity, 30.3% yield, $t_r$=0.72 min). LCMS (Method E): m/z found 527.3 $[M+H]^+$; $^1$H-NMR (DMSO, 400 MHz): δ (ppm) 8.20 (s, 1H), 7.50-7.42 (m, 2H), 7.37-7.20 (m, 7H), 7.09 (ddd, J=9.8, 6.3, 3.2 Hz, 1H), 6.90 (ddt, J=10.6, 7.1, 3.2 Hz, 1H), 6.51 (ddd, J=11.6, 9.0, 4.8 Hz, 1H), 3.46 (s, 2H), 2.63-2.51 (m, 2H), 2.51-2.38 (m, 4H), 1.90 (s, 2H).

Step 6: Synthesis of N-(4-(2,5-difluorophenyl)piperidin-4-yl)-4-(trifluoromethoxy)benzenesulfonamide (88)

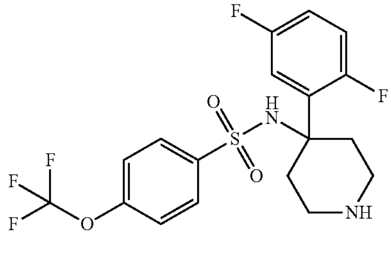 [SMILES: O=S(=O)(NC1(c2cc(F)ccc2F)CCNCC1)c1ccc(OC(F)(F)F)cc1]

To a stirred suspension of N-[1-benzyl-4-(2,5-difluorophenyl)-4-piperidyl]-4-(trifluoromethoxy)benzenesulfonamide (260 mg, 0.494 mmol) in DCE (1.5094 mL) under nitrogen was added 1-chloroethyl carbonochloridate (95%, 112 μL, 0.988 mmol). The reaction mixture was stirred at room temperature overnight. The suspension was concentrated under reduced pressure. The residue was dissolved in MeOH (1.5094 mL) and the mixture was stirred at 65° C. for 2 h. The reaction mixture was cooled to room temperature and concentrated under reduced pressure. The resulting off-white solid was triturated in a mixture of dichloromethane and methanol (95:5, 10 mL) for 1 h, then the resulting white powder was filtered and washed twice with DCM and dried under vacuum at 45° C. for approximately 72 h. The white powder was triturated with diethyl ether (4 mL), then 2 M HCl (2.0 mL, 4.00 mmol) was added. The mixture was stirred at rt overnight, filtered and dried under vacuum at 45° C. overnight to afford the hydrochloride salt of the title compound as a white powder (88 mg, 95.84% purity, 36.6% yield, $t_r$=1.23 min). LCMS (Method C): m/z found 437 $[M+H]^+$; $^1$H-NMR (DMSO-$d_6$, 500 MHz): δ (ppm) 8.86 (br s, 2H), 8.60 (s, 1H), 7.40-7.47 (m, 2H), 7.26-7.32 (m, 2H), 7.13 (ddd, J=9.8, 6.4, 3.2 Hz, 1H), 6.95 (ddt, J=8.9, 7.3, 3.5 Hz, 1H), 6.55 (ddd, J=11.7, 9.0, 4.8 Hz, 1H), 3.23 (br d, J=6.6 Hz, 4H), 2.67 (br d, J=12.7 Hz, 2H), 2.02-2.15 (m, 2H).

Example 53: N-(1-(3,4-dichlorophenyl)cyclopropyl)-4-(trifluoromethoxy)benzenesulfonamide (89)

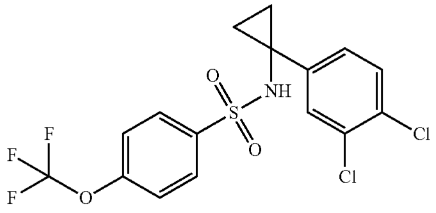 [SMILES: O=S(=O)(NC1(c2ccc(Cl)c(Cl)c2)CC1)c1ccc(OC(F)(F)F)cc1]

Step 1: Synthesis of 1-(3,4-dichlorophenyl)cyclopropan-1-amine

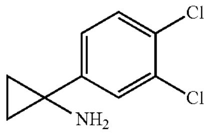 [SMILES: NC1(c2ccc(Cl)c(Cl)c2)CC1]

In a dry three-neck round-bottomed flask, to a stirred solution of 3,4-dichlorobenzonitrile (98%, 200 mg, 1.14 mmol) in Diethyl ether (12 mL) at −70° C. under argon was added $Ti(O\text{-}iPr)_4$ (371 μL, 1.25 mmol) and 3 M ethylmagnesium bromide (0.76 mL, 2.28 mmol). The reaction mixture was stirred at −70° C. for 10 min and then allowed to warm up to rt and stirred at rt for 1 h. $BF_3{\cdot}OEt$ (281 μL, 2.28 mmol) was then added to the mixture, and stirred for 1 h at rt. The reaction mixture was acidified with a 1M aqueous solution of HCl (3.5 mL) and $Et_2O$ (10 mL) was added. A 10% aqueous solution of NaOH (11 mL) was added to the resulting to clear phases, and the aqueous phase was extracted with $Et_2O$. The combined organic layers were dried over sodium sulfate, filtered and concentrated under reduced pressure. The crude was purified by flash chromatography on silica gel using a gradient of MeOH in DCM from 0.2% to 5%. The desired fractions were combined and concentrated to afford the title compound as an orange oil (48.8 mg, 85% purity, 18% yield, $t_r$=0.53 min). LCMS (Method E): m/z found 202.1 $[M+H]^+$; $^1$H-NMR (400 MHz, DMSO-$d_6$) δ (ppm): 7.61 (d, J=2.3 Hz, 1H), 7.49 (d, J=8.5 Hz, 1H), 7.19 (dd, J=8.5, 2.3 Hz, 1H), 2.45 (s, 2H), 1.01 (d, J=8.2 Hz, 2H), 0.95 (d, J=8.2 Hz, 2H).

Step 2: Synthesis of N-(1-(3,4-dichlorophenyl)cyclopropyl)-4-(trifluoromethoxy)benzenesulfonamide (89)

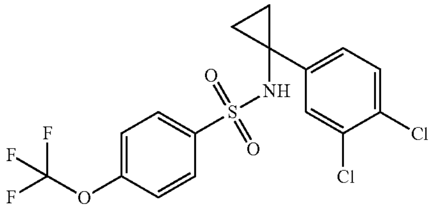 [SMILES: O=S(=O)(NC1(c2ccc(Cl)c(Cl)c2)CC1)c1ccc(OC(F)(F)F)cc1]

In a sealed tube, 4-(trifluoromethoxy)benzenesulfonyl chloride (97%, 38 μL, 0.217 mmol) was added to a stirred solution of 1-(3,4-dichlorophenyl)cyclopropanamine (85%, 47 mg, 0.196 mmol) and $Et_3N$ (82 μL, 0.588 mmol) in DCM (2 mL). The solution was stirred at rt for 18 h. Additional $Et_3N$ (27 μL, 0.196 mmol) and 4-(trifluoromethoxy)benzenesulfonyl chloride (97%, 17 μL, 0.0980 mmol) were added at rt and the reaction mixture was stirred for 18 h. Water (5 mL) was added and the aqueous layer was extracted with DCM (2×10 mL). The combined organic layers were washed with brine, dried over sodium sulfate, filtered and concentrated under reduced pressure. The crude was purified by flash chromatography on silica gel using a gradient of ethyl acetate in heptane from 5% to 40% to afford the title compound as a yellow solid (37.6 mg, 99.31% purity, 45% yield, $t_r$=2.74 min). LCMS (Method H): m/z found 424.1 $[M-H]^-$; $^1$H-NMR (DMSO-$d_6$, 500 MHz): δ (ppm) 8.71-9.29 (m, 1H), 7.60-7.71 (m, 2H), 7.32-7.41 (m, 2H), 7.30 (d, J=8.6 Hz, 1H), 7.26-7.28 (m, 1H), 7.07 (dd, J=8.3, 2.2 Hz, 1H), 1.05-1.23 (m, 4H).

Example 54: N-(3-phenylpiperidin-3-yl)-4-(trifluoromethoxy)benzenesulfonamide (90)

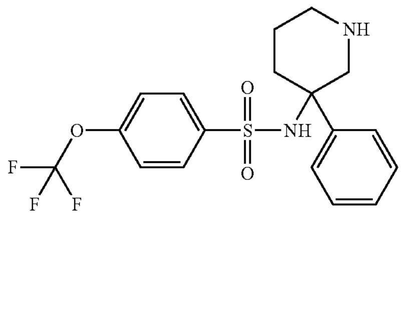 [SMILES: O=S(=O)(NC1(c2ccccc2)CCCNC1)c1ccc(OC(F)(F)F)cc1]

Step 1: Synthesis of benzyl 3-hydroxy-3-phenylpiperidine-1-carboxylate

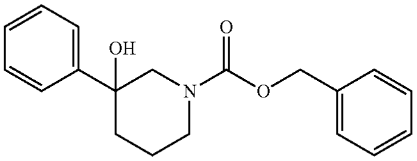 [SMILES: O=C(OCc1ccccc1)N1CCCC(O)(c2ccccc2)C1]

In a three-neck round bottom flask, to a stirred solution of 3 M phenylmagnesium bromide in $Et_2O$ (1.7 mL, 5.10 mmol) in anhydrous THF (8 mL) at 3° C. under nitrogen was added dropwise a solution of benzyl 3-oxopiperidine-1-carboxylate (98%, 0.83 mL, 4.20 mmol) in anhydrous THF (5.5 mL). The reaction mixture was allowed to warm up to room temperature and was stirred at this temperature overnight. To the reaction mixture was poured a saturated aqueous solution of $NH_4Cl$ (10 mL) and EtOAc (10 mL) was added. The layers were separated. The aqueous layer was extracted with EtOAc (2×10 mL). The combined organic layers were washed with a saturated aqueous solution of NaCl (10 mL), dried over sodium sulfate, filtered and concentrated under reduced pressure. The crude (1.38 g) was taken in DCM (0.7 mL, 5 V), and sonicated. The resulting homogenous solution was added portion-wise to 27 mL of pentane (20 V) and the mixture was triturated. The heterogenous mixture was stirred 1 h after observation of precipitation. The solid was then filtered and washed with pentane, dried under vacuum in an oven at 45° C. to afford the expected compound as a yellow solid (961 mg, 90% purity, 66% yield, $t_r$=0.89 min). LCMS (Method D): m/z found 312.2 $[M+H]^+$; $^1$H-NMR (DMSO-$d_6$, 400 MHz): δ (ppm) 7.56-7.49 (m, 2H), 7.39-7.29 (m, 7H), 7.28-7.18 (m, 1H), 5.08 (d, J=12.4 Hz, 3H), 3.96 (d, J=13.2 Hz, 1H), 3.74 (d, J=13.2 Hz, 1H), 3.23 (dd, J=33.2, 15.0 Hz, 1H), 3.11-2.82 (m, 1H), 2.05-1.82 (m, 2H), 1.72 (d, J=12.9 Hz, 1H), 1.46 (d, J=12.3 Hz, 1H).

Step 2: Synthesis of benzyl 3-[(2-chloroacetyl)amino]-3-phenyl-piperidine-1-carboxylate

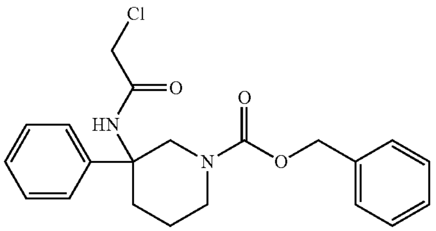 [SMILES: O=C(CCl)NC1(c2ccccc2)CCCN(C(=O)OCc2ccccc2)C1]

A round-bottom flask was charged with benzyl 3-hydroxy-3-phenyl-piperidine-1-carboxylate (90%, 961 mg, 2.78 mmol) in DCM (4.8 mL) and 2-chloroacetonitrile (5.3 mL, 83.3 mmol) at 0° C. Trifluoroacetic acid (5.3 mL, 69.4 mmol) was added dropwise over 1 h and the reaction was stirred at 0° C. for 6 h. The reaction mixture was poured into ice and quenched with a saturated aqueous solution of sodium bicarbonate (pH=9). The aqueous layer was extracted twice with dichloromethane. The combined organic layers were washed with brine, dried using a phase separator and concentrated under reduced pressure to afford the title compound as a yellow oil (1.063 g, 50% purity, 50% yield, $t_r$=0.91 min). LCMS (Method D): m/z found 387.2 min $[M+H]^+$. The crude product was used without further purification Step 3: Synthesis of benzyl 3-amino-3-phenyl-piperidine-1-carboxylate

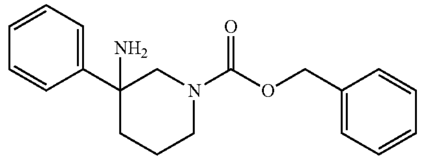

A round-bottom flask was charged with benzyl 3-[(2-chloroacetyl)amino]-3-phenyl-piperidine-1-carboxylate (50%, 1.06 g, 1.37 mmol) in a mixture of EtOH (12.5 mL) and AcOH (2.5 mL) (ratio 5:1), and thiourea (0.14 g, 1.79 mmol) was added. The reaction mixture was stirred at 80° C. for 4 h. The reaction mixture was cooled to room temperature and stirred at rt for 2 days, then heated at 80° C. for 5 h and cooled to rt. The mixture was diluted in DCM and a saturated aqueous solution of $Na_2CO_3$ was added until pH=9 was reached. The aqueous layer was extracted twice with DCM and the combined organic layers were washed with brine, dried using a phase separator and concentrated under reduced pressure. The resulting gum was solubilized in $Et_2O$ and 2 M HCl in $Et_2O$ (6.9 mL, 13.7 mmol) was added. The mixture was stirred at rt overnight. The precipitate formed was filtered, washed with $Et_2O$ and dried under vacuum at 45° C. for 2 h. A minimum amount of Methanol was added to the solid. The resulting homogeneous solution was added to a large volume of $Et_2O$, and the mixture was stirred at rt 4 h. The precipitate formed was filtered, washed with $Et_2O$ and dried under vacuum at 45° C. overnight to afford the hydrochloride salt of the title compound as a beige solid (372 mg, 98% purity, 77% yield, $t_r$=0.60 min). LCMS (Method D): m/z found 311.2 $[M+H]^+$; $^1$H-NMR (DMSO-$d_6$, 400 MHz): δ (ppm) 8.60 (s, 3H), 7.61 (d, J=7.4 Hz, 2H), 7.47-7.30 (m, 8H), 5.12 (s, 2H), 4.05 (s, 1H), 3.85 (d, J=13.7 Hz, 1H), 3.55 (s, 1H), 3.38 (td, J=8.3, 4.0 Hz, 1H), 2.32-2.22 (m, 1H), 2.13 (d, J=9.3 Hz, 1H), 1.81 (s, 1H), 1.47 (s, 1H).

Step 4: Synthesis of benzyl 3-phenyl-3-[[4-(trifluoromethoxy)phenyl]sulfonylamino]piperidine-1-carboxylate

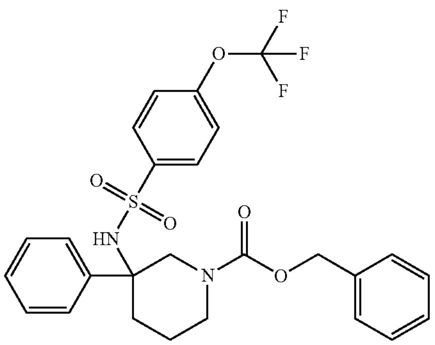 [SMILES: O=C(OCc1ccccc1)N1CCCC(NS(=O)(=O)c2ccc(OC(F)(F)F)cc2)(c2ccccc2)C1]

A sealed vial was charged with benzyl 3-amino-3-phenyl-piperidine-1-carboxylate hydrochloride (98%, 150 mg, 0.424 mmol), N,N-dimethylpyridin-4-amine (10 mg, 0.0848 mmol) and triethylamine (236 μL, 1.70 mmol) in DCM (4 mL). 4-(trifluoromethoxy)benzenesulfonyl chloride (86 μL, 0.509 mmol) was then added to the reaction mixture and it was stirred at 40° C. overnight. The reaction mixture was diluted with DCM and a saturated aqueous solution of $NH_4Cl$. The layers were separated. The aqueous layer was extracted twice with DCM. The combined organic layers were washed with a saturated aqueous solution of NaCl, dried using a phase separator and concentrated under reduced pressure. The crude was purified by flash chromatography on silica gel using a gradient of MeOH in DCM from 0% to 2%. The desired fractions were combined and concentrated. The desired fractions were combined and concentrated to afford the title compound as a white solid (150 mg, 97% purity, 66% yield, $t_r$=1.05 min). LCMS (Method E): m/z found 557.3 $[M+Na]^+$; $^1$H-NMR (DMSO-$d_6$, 400 MHz): δ (ppm) 8.25 (s, 1H), 7.32 (d, J=8.5 Hz, 7H), 7.23-7.13 (m, 2H), 7.10 (s, 2H), 6.98 (t, J=7.2 Hz, 1H), 6.90 (s, 2H), 5.13 (d, J=45.2 Hz, 2H), 4.49 (d, J=13.5 Hz, 1H), 3.58 (d, J=53.0 Hz, 2H), 3.22 (s, 1H), 2.22 (s, 1H), 2.09 (s, 1H), 1.64 (s, 1H), 1.14 (s, 1H).

Step 5: Synthesis of N-(3-phenylpiperidin-3-yl)-4-(trifluoromethoxy)benzenesulfonamide (90)

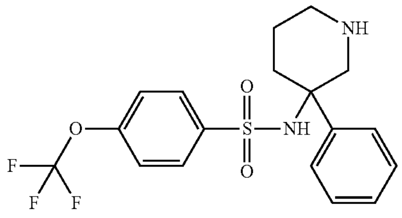 [SMILES: O=S(=O)(NC1(c2ccccc2)CCCNC1)c1ccc(OC(F)(F)F)cc1]

In a four-neck round-bottom flask equipped with a mechanical stirrer, a thermometer and an addition funnel, was stirred a suspension of benzyl 3-phenyl-3-[[4-(trifluoromethoxy)phenyl]sulfonylamino]piperidine-1-carboxylate (97%, 150 mg, 0.272 mmol) in dry ACN (4 mL) at rt under nitrogen. Iodo(trimethyl)silane (119 μL, 0.838 mmol) was added over 3 min, the mixture was stirred at rt for 1.5 h and was concentrated. 2 M HCl in $Et_2O$ (777 μL, 1.55 mmol) then $Et_2O$ (2 mL) were added to the residue, and the suspension was stirred at rt for 2.5 h. MeOH (124 μL) was added and the mixture was stirred at rt for 1 h and filtered. The residue was washed with $Et_2O$ and dried under reduced pressure at 45° C. overnight. The residue was dissolved in MeOH (2 mL), then 7N $NH_3$ in MeOH (124 μL) was added to the stirred solution (turned from clear yellow to colorless solution). The obtained solution was stirred at rt for 2 h and was concentrated. The residue was added to a stirred mixture of water (3 mL), DCM (1.5 mL) and MeOH (51 μL). Next, a saturated aqueous $Na_2CO_3$ was added (4 mL) until pH=8-9 was reached. The mixture was stirred at rt for overnight and the layers were separated. The combined organic layers were washed with a saturated aqueous solution of NaCl, dried using a phase separator and concentrated under vacuum to obtain the title compound as a white powder (78 mg, 100% purity, 72% yield, $t_r$=0.64 min). LCMS (Method E): m/z found 401.4 $[M+H]^+$; $^1$H-NMR (DMSO-$d_6$, 400 MHz): δ (ppm) 7.90 (s, 1H), 7.43-7.34 (m, 2H), 7.21 (dq, J=7.8, 1.1

Hz, 2H), 7.15-7.05 (m, 2H), 7.03-6.91 (m, 3H), 3.18 (dd, J=13.2, 2.3 Hz, 1H), 2.87-2.79 (m, 1H), 2.73 (d, J=13.2 Hz, 1H), 2.47 (d, J=21.4 Hz, 2H), 2.08 (s, 1H), 1.89 (ddd, J=13.5, 11.0, 3.7 Hz, 1H), 1.74-1.60 (m, 1H), 1.35 (dd, J=11.2, 6.7 Hz, 1H).

In a round-bottom flask, to a stirred solution of N-(3-phenyl-3-piperidyl)-4-(trifluoromethoxy)benzenesulfonamide (78 mg, 0.195 mmol) in $Et_2O$ (2 mL) at rt was added 2 M HCl in $Et_2O$ (974 μL, 1.95 mmol). The reaction mixture was stirred at rt overnight. The suspension was filtered, washed with $Et_2O$ and dried under vacuum at 45° C. overnight to afford the hydrochloride salt of the title compound as a white solid (80 mg, 99.29% purity, 94% yield, $t_r$=1.21 min). LCMS (Method H): m/z found 401.3 $[M+H]^+$; $^1$H-NMR (DMSO-$d_6$, 600 MHz): δ (ppm) 9.50 (br s, 1H), 8.54 (s, 1H), 8.29 (br s, 1H), 7.34 (d, J=8.1 Hz, 2H), 7.14 (d, J=8.5 Hz, 2H), 6.97-7.03 (m, 3H), 6.92-6.96 (m, 2H), 4.07 (br d, J=12.5 Hz, 1H), 3.38 (br d, J=12.8 Hz, 1H), 3.24 (br d, J=12.0 Hz, 1H), 2.90-2.96 (m, 1H), 2.44 (br d, J=11.2 Hz, 1H), 2.05-2.13 (m, 1H), 1.71-1.80 (m, 2H).

Example 55: N-(4-(5-chlorothiophen-2-yl)piperidin-4-yl)-4-(trifluoromethoxy)benzenesulfonamide (91)

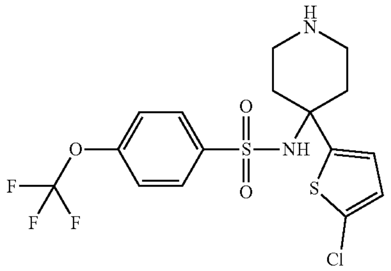 [SMILES: O=S(=O)(NC1(c2ccc(Cl)s2)CCNCC1)c1ccc(OC(F)(F)F)cc1]

Step 1: Synthesis of tert-butyl 4-(5-chloro-2-thienyl)-4-cyano-piperidine-1-carboxylate

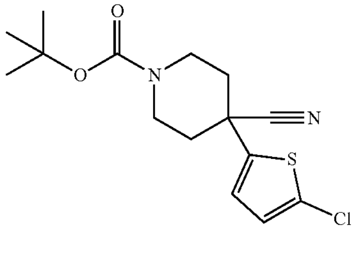 [SMILES: CC(C)(C)OC(=O)N1CCC(C#N)(c2ccc(Cl)s2)CC1]

A sealed vial was charged with tert-butyl 4-cyano-4-(thiophen-2-yl)piperidine-1-carboxylate (370 mg, 1.27 mmol) in anhydrous DMF (7.3 mL) under argon atmosphere. A solution of N-chlorosuccinimide (203 mg, 1.52 mmol) in anhydrous DMF (2.5 mL) was added dropwise at room temperature and the reaction mixture was stirred at room temperature in the dark for 3 days. The reaction mixture was quenched with a saturated aqueous solution of sodium bicarbonate (2 mL), water (2 mL), and dichloromethane (5 mL) were added. The aqueous layer was extracted with dichloromethane (2×5 mL). The combined organic layers were dried over sodium sulfate, filtered and concentrated under reduced pressure. The crude was purified by flash chromatography on silica gel using a gradient of ethyl acetate in cyclohexane from 0% to 20% to afford the title compound as a yellow oil (360 mg, 99% purity, 86% yield, $t_r$=1.03 min). LCMS (Method D); $^1$H-NMR (DMSO-$d_6$, 400 MHz): δ (ppm) 7.18-7.09 (m, 2H), 4.09-3.99 (m, 2H), 3.02 (s, 2H), 2.28 (dq, J=13.5, 2.8 Hz, 2H), 1.90 (ddd, J=13.5, 12.0, 4.3 Hz, 2H), 1.42 (s, 9H).

Step 2: Synthesis of 4-(5-chloro-2-thienyl)piperidine-4-carbonitrile

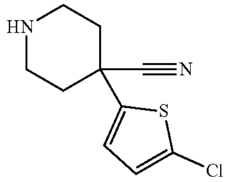 [SMILES: N#CC1(c2ccc(Cl)s2)CCNCC1]

A sealed vial under nitrogen was successively charged with tert-butyl 4-(5-chloro-2-thienyl)-4-cyano-piperidine-1-carboxylate (355 mg, 1.09 mmol) and 2 M HCl in $Et_2O$ (4.3 mL, 8.69 mmol) in $Et_2O$ (3 mL). The reaction mixture was stirred at room temperature for 18 h. Additional 4 M HCl in 1,4-dioxane (4.1 mL, 16.3 mmol) was added at room temperature and the reaction mixture was stirred at room temperature for 6 h. The suspension was filtered, washed with $Et_2O$ (10 mL) and dried under vacuum at 50° C. for 16 h to afford the hydrochloride salt of the title compound as a white powder (254 mg, 100% purity, 89% yield, $t_r$=0.49 min). LCMS (Method E): m/z found 227.2 $[M+H]^+$; $^1$H-NMR (DMSO-$d_6$, 400 MHz): δ (ppm) 9.19 (s, 2H), 7.18 (d, J=4.0 Hz, 1H), 7.16 (d, J=4.0 Hz, 1H), 3.44 (dt, J=13.8, 3.7 Hz, 2H), 3.08 (ddd, J=13.5, 12.2, 2.9 Hz, 2H), 2.60-2.51 (m, 4H), 2.31 (ddd, J=14.2, 12.2, 4.0 Hz, 2H).

Step 3: Synthesis of 1-benzyl-4-(5-chloro-2-thienyl)piperidine-4-carbonitrile

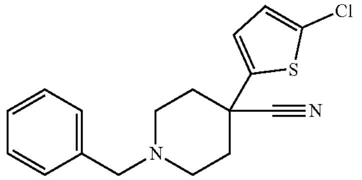 [SMILES: N#CC1(c2ccc(Cl)s2)CCN(Cc2ccccc2)CC1]

In a sealed tube, to a stirred solution of 4-(5-chloro-2-thienyl)piperidine-4-carbonitrile hydrochloride (254 mg, 0.965 mmol) in DMF (2.3 mL) at room temperature was added benzyl bromide (138 μL, 1.16 mmol) and $Et_3N$ (404 μL, 2.90 mmol). The reaction mixture was stirred at room temperature for 20 h. The reaction mixture was quenched with a saturated aqueous solution of ammonium chloride (3 mL), and water (10 mL) and dichloromethane (10 mL) were added. The aqueous layer was extracted with dichloromethane (2×5 mL). The combined organic layers were dried over sodium sulfate, filtered and concentrated under reduced pressure. The crude was purified by flash chromatography on silica gel using a gradient of ethyl acetate in cyclohexane from 0% to 20% to afford the title compound as a colorless oil (285 mg, 100% purity, 93% yield, $t_r$=0.61 min). LCMS (Method E): m/z found 317.3 $[M+H]^+$; $^1$H-NMR (DMSO-$d_6$, 400 MHz): δ (ppm) 7.39-7.22 (m, 5H), 7.12 (d, J=3.9 Hz, 1H), 7.10 (d, J=3.9 Hz, 1H), 3.55 (s, 2H), 2.89 (dt, J=13.1, 3.4 Hz, 2H), 2.35-2.20 (m, 4H), 2.04-1.92 (m, 2H).

Step 4: Synthesis of 1-benzyl-4-(5-chloro-2-thienyl) piperidine-4-carboxamide

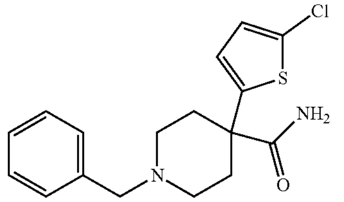 [SMILES: NC(=O)C1(c2ccc(Cl)s2)CCN(Cc2ccccc2)CC1]

In a round bottom flask at 0° C., a mixture of 1-benzyl-4-(5-chloro-2-thienyl)piperidine-4-carbonitrile (270 mg, 0.852 mmol) in $H_2SO_4$ (3.6097 mL) and water (0.9024 mL) was stirred at 60° C. for 16 h. The mixture was cooled to 0° C. and basified with aqueous 30% NaOH to reach pH=11. Water and DCM were added, and the aqueous layer 20 was extracted twice with DCM. The combined organic layers were dried over sodium sulfate, filtered and concentrated under reduced pressure to afford the title compound as a pink gum (152 mg, 75% purity, 40% yield, $t_r$=0.54 min). LCMS (Method E): m/z found 335.3 $[M+H]^+$; $^1$H-NMR (DMSO-$d_6$, 400 MHz): δ (ppm) 7.35-7.20 (m, 5H), 6.97 (d, J=3.9 Hz, 1H), 6.82 (d, J=3.8 Hz, 1H), 3.55 (s, 1H), 3.41 (s, 2H), 2.52 (s, 2H), 2.41-2.14 (m, 4H), 1.87 (d, J=12.2 Hz, 2H). The batch was used in next step without further purification.

Step 5: Synthesis of 1-benzyl-4-(5-chloro-2-thienyl)piperidin-4-amine

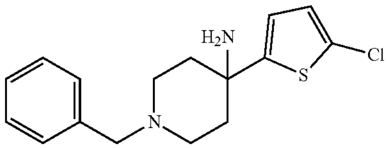 [SMILES: NC1(c2ccc(Cl)s2)CCN(Cc2ccccc2)CC1]

In sealed tube, 1-benzyl-4-(5-chloro-2-thienyl)piperidine-4-carboxamide (75%, 150 mg, 0.336 mmol) was charged and dissolved in ACN (1 mL) and water (1 mL). [Bis(trifluoroacetoxy)iodo]benzene (96%, 154 mg, 0.343 mmol) was then charged to the reaction vessel, and the reaction was stirred at room temperature for 18 h. The reaction mixture was concentrated under reduced pressure. Aqueous saturated solution of sodium bicarbonate (5 mL) was added, and the aqueous layer was extracted twice with dichloromethane (2×10 mL). The combined organic layers were concentrated under reduced pressure, then $Et_2O$ (4 mL) and 2 M HCl in $Et_2O$ (0.93 mL, 1.86 mmol) were added. The suspension was stirred at room temperature for 2 hours, filtered and washed with $Et_2O$ and dried under vacuum at 50° C. for 20 h to afford the hydrochloride salt of the title compound as a beige powder (145 mg, 30% purity, 38% yield, $t_r$=0.44 min). LCMS (Method E): m/z 307.3 $[M+H]^+$.

Step 6: Synthesis of N-[1-benzyl-4-(5-chloro-2-thienyl)-4-piperidyl]-4-(trifluoromethoxy)benzenesulfonamide

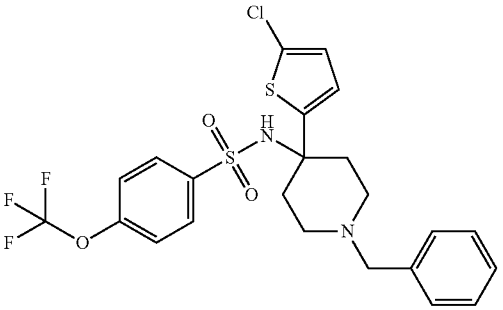 [SMILES: O=S(=O)(NC1(c2ccc(Cl)s2)CCN(Cc2ccccc2)CC1)c1ccc(OC(F)(F)F)cc1]

A sealed vial was charged with 1-benzyl-4-(5-chloro-2-thienyl)piperidin-4-amine hydrochloride (30%, 137 mg, 0.120 mmol), triethylamine (100 μL, 0.718 mmol) and DMAP (7.3 mg, 0.0599 mmol) in DCM (2 mL). 4-(trifluoromethoxy)benzenesulfonyl chloride (61 μL, 0.359 mmol) was then added to the reaction mixture and it was stirred at 40° C. for 16 h. The reaction mixture was cooled to room temperature and quenched with a saturated aqueous solution of ammonium chloride (4 mL). Water (10 mL) and dichloromethane (10 mL) were added. The aqueous layer was extracted with dichloromethane (2×10 mL). The combined organic layers were washed with a saturated aqueous solution of sodium bicarbonate (5 mL), dried over sodium sulfate, filtered and concentrated under reduced pressure. The crude was purified by flash chromatography on silica gel using a gradient of methanol in dichloromethane from 0% to 5% to afford the title compound as a beige powder (38 mg, 100% purity, 60% yield, $t_r$=0.74 min). LCMS (Method E): m/z found 531.3 $[M+H]^+$; $^1$H-NMR (DMSO-$d_6$, 400 MHz): δ (ppm) 8.17 (s, 1H), 7.62-7.54 (m, 2H), 7.39-7.20 (m, 7H), 6.65 (d, J=3.9 Hz, 1H), 6.60 (d, J=3.9 Hz, 1H), 3.42 (s, 2H), 2.42 (s, 5H), 2.27 (d, J=13.6 Hz, 2H), 1.98 (s, 2H).

Step 7: Synthesis of N-(4-(5-chlorothiophen-2-yl) piperidin-4-yl)-4-(trifluoromethoxy)benzenesulfonamide (91)

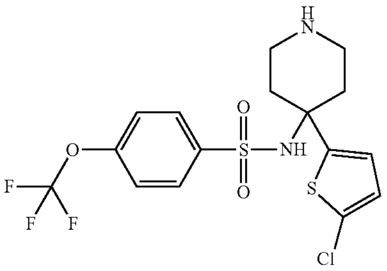 [SMILES: O=S(=O)(NC1(c2ccc(Cl)s2)CCNCC1)c1ccc(OC(F)(F)F)cc1]

To a stirred solution of 1-chloroethyl carbonochloridate (99%, 23 μL, 0.215 mmol) in DCE (1.8 mL) under nitrogen was added N-[1-benzyl-4-(5-chloro-2-thienyl)-4-piperidyl]-4-(trifluoromethoxy)benzenesulfonamide (38 mg, 0.0716 mmol). The reaction mixture was stirred at room temperature for 16 h. Then, the reaction mixture was concentrated under reduced pressure. The residue was dissolved in MeOH (1.8 mL) and the reaction mixture was stirred at 65° C. for 16 h. The reaction mixture was cooled to room temperature and concentrated under reduced pressure. The resulting solid was triturated in dichloromethane, filtered washed with dichloromethane and dried under vacuum. The resulting precipitate was purified by flash chromatography on silica gel using a gradient of ammoniacal methanol in dichloromethane from 2% to 15%. The residue was triturated in 2 M HCl in $Et_2O$ (358 μL, 0.716 mmol) for 16 h, filtered and washed with $Et_2O$ and dried under vacuum at 50° C. for 3 days to afford the hydrochloride salt of the title compound as a white powder (15.7 mg, 99.2% purity, 46% yield, $t_r$=1.4 min). LCMS (Method H): m/z found 441.1 $[M+H]^+$; $^1$H-NMR (500 MHz, DMSO-$d_6$) δ ppm 2.14 (ddd, J=14.37, 10.33, 4.16 Hz, 2H) 2.50-2.53 (m, 2H) 3.12-3.23 (m, 4H) 6.61 (d, J=3.91 Hz, 1H) 6.70 (d, J=3.91 Hz, 1H) 7.35 (d, J=8.01 Hz, 2H) 7.57 (d, J=7.88 Hz, 2H) 8.55 (br s, 1H) 8.83 (br s, 2H).

Example 56: 3-amino-N-(3-(4-fluorophenyl)pyrrolidin-3-yl)-4-(trifluoromethoxy)benzenesulfonamide (92)

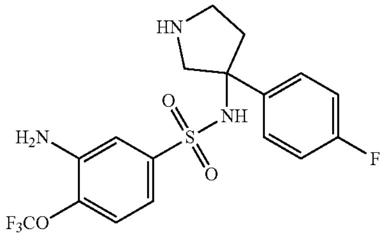 [SMILES: Nc1cc(S(=O)(=O)NC2(c3ccc(F)cc3)CCNC2)ccc1OC(F)(F)F]

Step 1: Synthesis of benzyl 3-[[3-amino-4-(trifluoromethoxy)phenyl]sulfonylamino]-3-(4-fluorophenyl)pyrrolidine-1-carboxylate

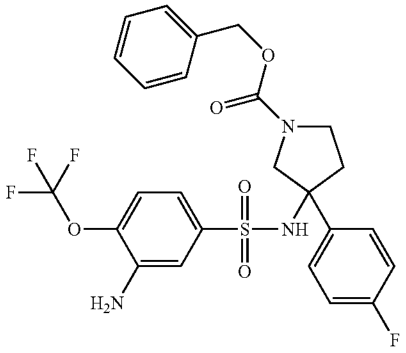 [SMILES: Nc1cc(S(=O)(=O)NC2(c3ccc(F)cc3)CCN(C(=O)OCc3ccccc3)C2)ccc1OC(F)(F)F]

In a sealed tube, a suspension of iron (50 mg, 0.895 mmol) and $NH_4Cl$ (12 mg, 0.228 mmol) in EtOH (1.1 mL) and water (360 μL) was stirred at 70° C. for 1 h. benzyl 3-(4-fluorophenyl)-3-[[3-nitro-4-(trifluoromethoxy)phenyl]sulfonylamino]pyrrolidine-1-carboxylate (95 mg, 0.163 mmol) was added and the mixture was stirred at 80° C. for 1 h. The mixture was allowed to cool to rt and was filtered through a pad of dicalite. The pad was washed with DCM and the filtrate was diluted with water and DCM. The aqueous layer was extracted with DCM and the combined organic layers were washed with brine, dried over sodium sulfate, filtered and concentrated to afford the title compound as a yellow solid (83 mg, 99% purity, 91% yield, $t_r$=0.95 min). LCMS (Method E): m/z found 554.3 $[M+H]^+$; $^1$H-NMR (DMSO, 400 MHz): δ (ppm) 8.40 (s, 1H), 7.45-7.24 (m, 5H), 7.18-7.03 (m, 2H), 6.95 (ddd, J=8.5, 3.2, 1.6 Hz, 1H), 6.89-6.69 (m, 3H), 6.51 (ddd, J=8.5, 3.5, 2.3 Hz, 1H), 5.65 (d, J=2.9 Hz, 2H), 5.17-4.98 (m, 2H), 4.11 (dd, J=16.9, 11.2 Hz, 1H), 3.65-3.34 (m, 3H), 2.78-2.59 (m, 1H), 2.17 (ddt, J=17.6, 12.5, 8.4 Hz, 1H).

Step 2: Synthesis of 3-amino-N-(3-(4-fluorophenyl)pyrrolidin-3-yl)-4-(trifluoromethoxy)benzenesulfonamide (92)

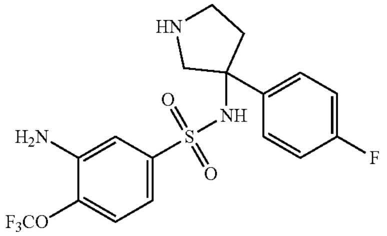 [SMILES: Nc1cc(S(=O)(=O)NC2(c3ccc(F)cc3)CCNC2)ccc1OC(F)(F)F]

In a sealed tube under nitrogen, iodo(trimethyl)silane (63 μL, 0.445 mmol) was added to a stirred mixture of benzyl 3-[[3-amino-4-(trifluoromethoxy)phenyl]sulfonylamino]-3-(4-fluorophenyl)pyrrolidine-1-carboxylate (99%, 83 mg, 0.148 mmol) in dry acetonitrile (2 mL). The mixture was stirred at rt for 1.5 h then was stirred at 0° C. MeOH (72 μL, 1.78 mmol) was added and the suspension was stirred at 0° C. for 1 h and was concentrated. The crude was purified by flash chromatography on silica gel using a gradient of (MeOH+2% $NH_4OH$) in DCM from 1% to 16%. The desired fractions were concentrated and dissolved in MeOH. HCl 2N in $Et_2O$ was added dropwise and the mixture was stirred at rt for 1 h. The suspension was filtered, the residue was washed with $Et_2O$ and dried under reduced pressure at 45° C. for 16 h to afford the hydrochloride salt of the title compound as a white powder (16.8 mg, 99.4% purity, 24% yield, $t_r$=1.03 min). LCMS (Method H): m/z found 420.2 $[M+H]^+$; $^1$H-NMR (600 MHz, DMSO-$d_6$) δ 9.59-9.18 (m, 2H), 8.46 (s, 1H), 7.10 (dd, J=8.5, 5.3 Hz, 2H), 6.92 (d, J=7.9 Hz, 1H), 6.79 (t, J=8.7 Hz, 2H), 6.67 (d, J=2.3 Hz, 1H), 6.48 (dd, J=8.5, 2.3 Hz, 1H), 5.97-5.13 (m, 2H), 4.08 (br dd, J=11.8, 5.9 Hz, 1H), 3.36-3.31 (m, 3H), 2.88-2.75 (m, 1H), 2.13 (dt, J=13.2, 9.8 Hz, 1H).

Example 57: 3-amino-N-(3-(4-fluoro-3-methylphenyl)pyrrolidin-3-yl)-4-(trifluoromethoxy)benzenesulfonamide (93)

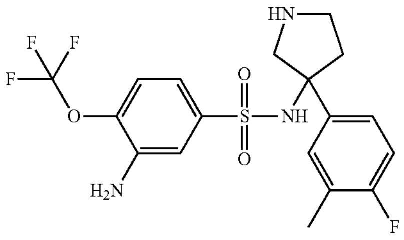 [SMILES: Cc1cc(C2(NS(=O)(=O)c3ccc(OC(F)(F)F)c(N)c3)CCNC2)ccc1F]

Step 1: Synthesis of benzyl 3-(4-fluoro-3-methyl-phenyl)-3-hydroxy-pyrrolidine-1-carboxylate

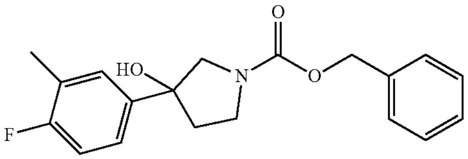 [SMILES: Cc1cc(C2(O)CCN(C(=O)OCc3ccccc3)C2)ccc1F]

In a three-neck round-bottom flask equipped with a thermometer, an addition funnel and a reflux condenser, under nitrogen, a suspension of magnesium (266 mg, 10.9 mmol) and a crystal of 12 in dry THF (8.4 mL) was stirred at rt. The addition funnel was charged with a solution of 4-bromo-1-fluoro-2-methylbenzene (970 μL, 7.63 mmol) in dry THF (3.6 mL) and a few drops were added to the reaction mixture. The orange suspension was stirred at 65° C. until discoloration, and the remainder of the solution was added dropwise. The mixture was stirred at 65° C. for 1 h and was cooled to 0° C. At 0° C., a solution of benzyl 3-oxopyrrolidine-1-carboxylate (1200 mg, 5.47 mmol) in dry THF (3.6 mL) was added dropwise and the mixture was stirred at 0° C. for 1 h. Saturated aqueous $NH_4Cl$ was added dropwise followed by EtOAc. The mixture was stirred at rt for 16 h to dissolve the remaining Mg and the aqueous layer was extracted with EtOAc. The combined organic layers were washed with brine, dried over sodium sulfate, filtered and concentrated. The crude was purified by flash chromatography on silica gel using a gradient of MeOH in DCM from 2% to 5% to afford the title compound as a colorless oil (1322 mg, 65% purity, 48% yield, $t_r$=0.91 min). LCMS (Method D): m/z found 330.3 $[M+H]^+$; $^1$H-NMR (DMSO-$d_6$, 400 MHz): δ (ppm) 7.46-7.27 (m, 7H), 7.09 (ddd, J=9.8, 8.6, 3.8 Hz, 1H), 5.45 (d, J=1.8 Hz, 1H), 5.16-5.04 (m, 2H), 3.65-3.41 (m, 4H), 2.24 (t, J=2.5 Hz, 4H), 2.03 (dt, J=12.9, 6.7 Hz, 1H).

Step 2: Synthesis of benzyl 3-[(2-chloroacetyl) amino]-3-(4-fluoro-3-methyl-phenyl)pyrrolidine-1-carboxylate

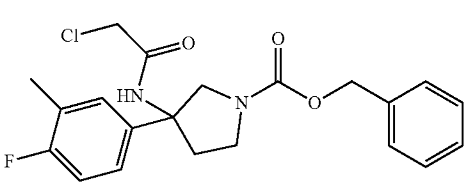 [SMILES: Cc1cc(C2(NC(=O)CCl)CCN(C(=O)OCc3ccccc3)C2)ccc1F]

In a round-bottom flask, at 0° C., 2,2,2-trifluoroacetic acid (7.8 mL, 0.102 mol) was added dropwise to a stirred solution of benzyl 3-(4-fluoro-3-methyl-phenyl)-3-hydroxy-pyrrolidine-1-carboxylate (1343 mg, 4.08 mmol) and 2-chloroacetonitrile (7.7 mL, 0.122 mol) in DCM (7.2016 mL). The mixture was stirred at 0° C. for 6 h and was poured into ice. Saturated aqueous $Na_2CO_3$ was added until pH=9 and the mixture was extracted twice with DCM. The combined organic layers were washed with water, brine, dried over sodium sulfate, filtered and concentrated to afford a mixture of the title compound as an oil (1.4 g, 50% purity, 43% yield, $t_r$=0.91 min). LCMS (Method D): m/z found 405.2 $[M+H]^+$; $^1$H-NMR (DMSO-$d_6$, 400 MHz): δ (ppm) 8.76 (d, J=3.7 Hz, 1H), 7.50-7.23 (m, 1OH), 7.23-7.00 (m, 2H), 5.23-4.98 (m, 4H), 4.50 (d, J=20.7 Hz, 1H), 4.30 (d, J=23.7 Hz, 1H), 4.12-3.92 (m, 2H), 3.65 (dd, J=25.9, 11.3 Hz, 1H), 3.45 (ddd, J=17.2, 8.9, 5.6 Hz, 2H), 2.70-2.52 (m, 1H), 2.39-2.13 (m, 4H).

Step 3: Synthesis of benzyl 3-amino-3-(4-fluoro-3-methyl-phenyl)pyrrolidine-1-carboxylate

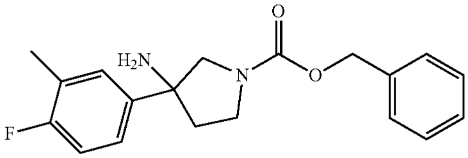 [SMILES: Cc1cc(C2(N)CCN(C(=O)OCc3ccccc3)C2)ccc1F]

In a sealed tube, thiourea (171 mg, 2.25 mmol) was added to a stirred solution of benzyl 3-[(2-chloroacetyl)amino]-3-(4-fluoro-3-methyl-phenyl)pyrrolidine-1-carboxylate (50%, 1.40 g, 1.73 mmol) in EtOH (12.5 mL) and AcOH (2.5 mL). The mixture was stirred at 80° C. for 16 h and poured into water. Saturated aqueous $Na_2CO_3$ was added until pH=9 and the mixture was extracted three times with DCM. The combined organic layers were washed with water, brine, dried over sodium sulfate, filtered and concentrated. The residue was dissolved in $Et_{20}$+MeOH and 2 M HCl in $Et_2O$ (8.6 mL, 17.3 mmol) was added. The mixture was stirred at rt for 16 h and was filtered and dried in vacuo to afford the hydrochloride salt of the title compound as a beige solid (478 mg, 95% purity, 76% yield, $t_r$=0.62 min). LCMS (Method E): m/z found 329.2 $[M+H]^+$; $^1$H-NMR (DMSO-$d_6$, 400 MHz): δ (ppm) 8.71 (s, 3H), 7.52 (d, J=5.9 Hz, 1H), 7.45-7.29 (m, 6H), 7.24 (td, J=9.1, 5.9 Hz, 1H), 5.13 (d, J=2.3 Hz, 2H), 4.09 (dd, J=11.9, 6.8 Hz, 1H), 3.82-3.49 (m, 3H), 2.59 (t, J=10.2 Hz, 1H), 2.49-2.39 (m, 1H), 2.27 (t, J=2.5 Hz, 3H).

Step 4: Synthesis of benzyl 3-(4-fluoro-3-methyl-phenyl)-3-[[3-nitro-4-(trifluoromethoxy)phenyl] sulfonylamino]pyrrolidine-1-carboxylate

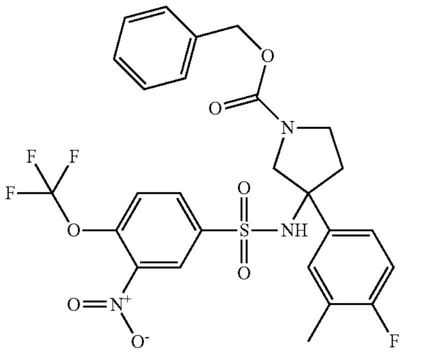 [SMILES: Cc1cc(C2(NS(=O)(=O)c3ccc(OC(F)(F)F)c([N+](=O)[O-])c3)CCN(C(=O)OCc3ccccc3)C2)ccc1F]

In a sealed tube under nitrogen, a solution of benzyl 3-amino-3-(4-fluoro-3-methyl-phenyl)pyrrolidine-1-carboxylate hydrochloride (478 mg, 1.31 mmol), triethylamine (913 μL, 6.55 mmol) and 4-dimethylaminopyridine (32 mg, 0.262 mmol) in dry DCM (11 mL) was stirred at rt. Next, 3-nitro-4-(trifluoromethoxy)benzene-1-sulfonyl chloride (400 mg, 1.31 mmol) was added dropwise and the mixture was stirred at 40° C. for 16 h. The mixture was diluted with DCM and half saturated aqueous solution of $NaHCO_3$. The aqueous layer was extracted with DCM and the combined organic layers were washed with brine, dried over sodium sulfate, filtered and concentrated. The crude was purified by flash chromatography on silica gel using a gradient of EtOAc in heptane from 20% to 70% to afford the title compound as a yellow solid. (170 mg, >90% purity, 21% yield, $t_r$=1.04 min). LCMS (Method D): m/z found 598.2 $[M+H]^+$; $^1$H-NMR (DMSO-$d_6$, 400 MHz): δ (ppm) 8.84 (s, 1H), 7.90 (dd, J=8.8, 2.2 Hz, 1H), 7.82-7.62 (m, 2H), 7.47-7.25 (m, 5H), 7.04-6.82 (m, 2H), 6.71 (q, J=8.4 Hz, 1H), 5.11 (d, J=2.3 Hz, 2H), 4.22 (dd, J=17.4, 11.2 Hz, 1H), 3.51 (ddd, J=36.2, 19.1, 10.2 Hz, 3H), 2.78 (s, 1H), 2.29-2.08 (m, 1H), 1.99 (dd, J=4.5, 1.8 Hz, 3H).

Step 5: Synthesis of N-[3-(4-fluoro-3-methyl-phenyl)pyrrolidin-3-yl]-3-nitro-4-(trifluoromethoxy)benzenesulfonamide

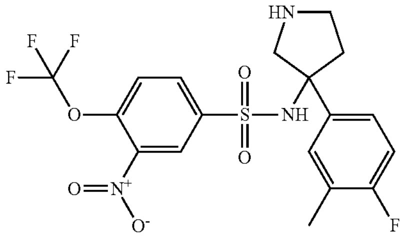 [SMILES: Cc1cc(C2(NS(=O)(=O)c3ccc(OC(F)(F)F)c([N+](=O)[O-])c3)CCNC2)ccc1F]

In a sealed tube under nitrogen, iodo(trimethyl)silane (121 μL, 0.853 mmol) was added to a stirred mixture of benzyl 3-(4-fluoro-3-methyl-phenyl)-3-[[3-nitro-4-(trifluoromethoxy)phenyl]sulfonylamino]pyrrolidine-1-carboxylate (170 mg, 0.284 mmol) in dry acetonitrile (3.4 mL). The mixture was stirred at rt for 1 h and was concentrated. The crude was purified by flash chromatography on silica gel using a gradient of (MeOH+2% $NH_4OH$) in DCM from 1% to 10% to afford the title compound as a yellow solid (24 mg, 76% purity, 13% yield, $t_r$=0.67 min). LCMS (Method E): m/z found 464.3 $[M+H]^+$; $^1$H-NMR (DMSO-$d_6$, 400 MHz): δ (ppm) 7.95-7.62 (m, 2H), 7.48-7.17 (m, 1H), 7.12-6.82 (m, 2H), 6.80-6.60 (m, 1H), 3.72-3.41 (m, 1H), 3.11 (dt, J=10.5, 7.9 Hz, 1H), 2.98-2.78 (m, 2H), 2.60 (ddd, J=11.8, 7.8, 3.6 Hz, 1H), 2.08-1.87 (m, 3H).

Step 6: Synthesis of 3-amino-N-[3-(4-fluoro-3-methyl-phenyl)pyrrolidin-3-yl]-4-(trifluoromethoxy)benzenesulfonamide (93)

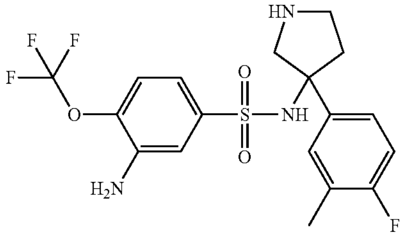 [SMILES: Cc1cc(C2(NS(=O)(=O)c3ccc(OC(F)(F)F)c(N)c3)CCNC2)ccc1F]

In a sealed tube, a suspension of iron (16 mg, 0.285 mmol) and $NH_4Cl$ (3.9 mg, 0.0725 mmol) in EtOH (350 μL) and water (115 μL) was stirred at 70° C. for 1 h. A solution of N-[3-(4-fluoro-3-methyl-phenyl)pyrrolidin-3-yl]-3-nitro-4-(trifluoromethoxy)benzenesulfonamide (24 mg, 0.0518 mmol) in EtOH (350 μL) was added and the mixture was stirred at 80° C. for 45 min. The mixture was allowed to cool to rt and was filtered through a pad of dicalite. The pad was washed with EtOH and DCM the filtrate was concentrated. The residue was dissolved in DCM and water and the aqueous layer was extracted with DCM. The combined organic layers were washed with brine, dried over sodium sulfate, filtered and concentrated. The residue was purified by flash chromatography on silica gel using a gradient of MeOH in DCM from 2% to 20%. The desired fractions were concentrated and $Et_2O$ was added to the residue. 2 N HCl in $Et_2O$ was added to the residue and the suspension was stirred at rt for 16 h and filtered. The residue was washed with $Et_{2O}$ and dried under reduced pressure at 45° C. for 16 h to afford the title compound as a white powder (5 mg, 95.5% purity, 19% yield, $t_r$=1.22 min). LCMS (Method H): m/z found 434.2 $[M+H]^+$; $^1$H-NMR (DMSO-$d_6$, 500 MHz): δ (ppm) 8.87-9.25 (m, 2H), 7.59-7.84 (m, 2H), 7.36 (br d, J=8.3 Hz, 2H), 7.00-7.27 (m, 4H), 3.12-3.55 (m, 4H), 2.51-2.80 (m, 2H), 1.72-2.25 (m, 2H).

Example 58: N-(4-(4-chloro-2-fluorophenyl)piperidin-4-yl)-4-(trifluoromethoxy)benzenesulfonamide (94)

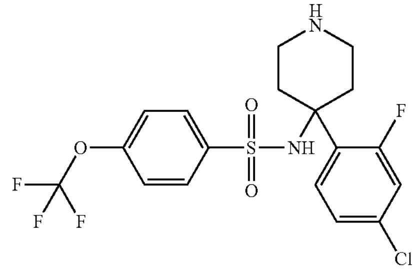

Step 1: Synthesis of benzyl 4-(4-chloro-2-fluorophenyl)-4-hydroxy-piperidine-1-carboxylate

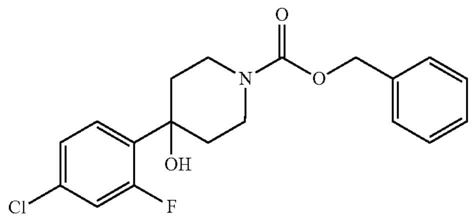 [SMILES: O=C(OCc1ccccc1)N1CCC(O)(c2ccc(Cl)cc2F)CC1]

In a round-bottom flask under nitrogen, a solution of 4-(4-chloro-2-fluorophenyl)piperidin-4-ol hydrochloride (500 mg, 1.88 mmol) and triethylamine (1.0 mL, 7.51 mmol) in MeOH (5 mL) was stirred at 0° C. Benzyl chloroformate (265 μL, 1.88 mmol) was added dropwise and the mixture was stirred at rt for 16 h. The mixture was diluted with half saturated $NaHCO_3$ and DCM. The aqueous layer was extracted with DCM and the combined organic layer were washed with brine, dried over sodium sulfate, filtered and concentrated. The crude was purified by flash chromatography on silica gel using a gradient of MeOH in DCM from 0.4% to 5% to afford the title compound as a colorless oil (150 mg, 98% purity, 21% yield, $t_r$=1.7 min). LCMS (Method E): m/z found 364.4 $[M+H]^+$; $^1$H-NMR (DMSO-$d_6$, 400 MHz): δ (ppm) 7.65 (t, J=8.7 Hz, 1H), 7.44-7.26 (m, 7H), 5.50 (s, 1H), 5.11 (s, 2H), 4.00-3.86 (m, 2H), 3.26 (d, J=23.4 Hz, 2H), 2.03 (td, J=13.1, 4.8 Hz, 2H), 1.59 (d, J=13.3 Hz, 2H).

Step 2: Synthesis of benzyl 4-[(2-chloroacetyl) amino]-4-(4-chloro-2-fluoro-phenyl)piperidine-1-carboxylate

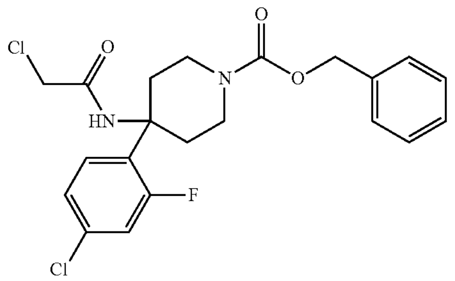 [SMILES: O=C(CCl)NC1(c2ccc(Cl)cc2F)CCN(C(=O)OCc2ccccc2)CC1]

In a sealed tube under nitrogen, at 0° C. was added TFA (789 μL, 10.3 mmol) to a stirred solution of benzyl 4-(4-chloro-2-fluoro-phenyl)-4-hydroxy-piperidine-1-carboxylate (150 mg, 0.412 mmol) and 2-chloroacetonitrile (783 μL, 12.4 mmol) in dry DCM (730 μL). The mixture was stirred at 0° C. for 7 h then at rt for 16 h. The mixture was poured into ice and saturated aqueous $Na_2CO_3$ was added until pH=10. The mixture was extracted twice with DCM and the combined organic layers were washed with brine, dried over sodium sulfate, filtered and concentrated to afford the title compound as a colorless oil (175 mg, 80% purity, 77% yield, $t_r$=0.95 min). LCMS (Method E): m/z found 439.3 $[M+H]^+$; $^1$H-NMR (DMSO-$d_6$, 400 MHz): δ (ppm) 8.58 (s, 1H), 7.46-7.29 (m, 7H), 7.24 (dd, J=8.5, 2.3 Hz, 1H), 5.10 (s, 2H), 4.09 (s, 2H), 3.92 (d, J=13.5 Hz, 2H), 3.16 (s, 2H), 2.45 (d, J=13.3 Hz, 2H), 1.88 (td, J=13.0, 4.4 Hz, 2H).

Step 3: Synthesis of benzyl 4-amino-4-(4-chloro-2-fluoro-phenyl)piperidine-1-carboxylate

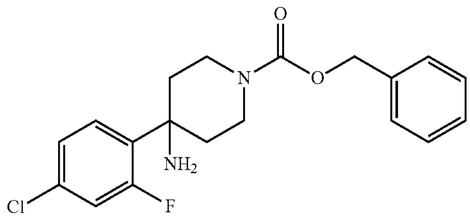

In a sealed tube, a solution of benzyl 4-[(2-chloroacetyl) amino]-4-(4-chloro-2-fluoro-phenyl)piperidine-1-carboxylate (175 mg, 0.398 mmol) in EtOH (2.6 mL) and AcOH (530 μL) was stirred at rt. Thiourea (39 mg, 0.518 mmol) was added, the mixture was stirred at 80° C. for 16 h and poured on ice. Saturated aqueous $Na_2CO_3$ was added until pH=9 and the mixture was extracted twice with DCM. The combined organic layers were washed with brine, dried over sodium sulfate, filtered and concentrated to afford the title compound as an orange oil (120 mg, 90% purity, 83% yield, $t_r$=0.65 min). LCMS (Method E): m/z found 363.2 $[M+H]^+$; $^1$H-NMR (DMSO-$d_6$, 400 MHz): δ (ppm) 7.63 (dd, J=9.3, 8.6 Hz, 1H), 7.44-7.19 (m, 7H), 5.10 (s, 2H), 3.82 (d, J=13.3 Hz, 2H), 3.39 (s, 2H), 2.47-2.06 (m, 2H), 2.06-1.92 (m, 2H), 1.58 (d, J=13.1 Hz, 2H), 1.30-1.13 (m, 1H).

Step 4: Synthesis of benzyl 4-(4-chloro-2-fluoro-phenyl)-4-[[4-(trifluoromethoxy)phenyl]sulfonylamino]piperidine-1-carboxylate

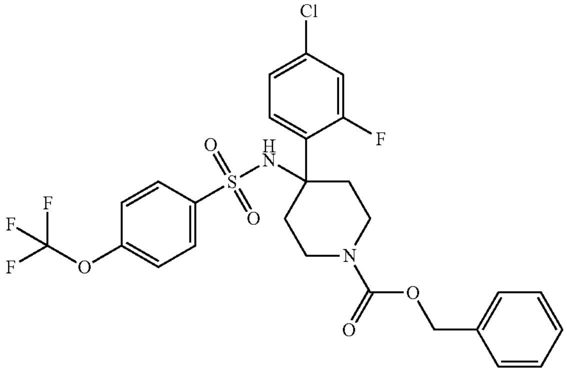 [SMILES: O=C(OCc1ccccc1)N1CCC(NS(=O)(=O)c2ccc(OC(F)(F)F)cc2)(c2ccc(Cl)cc2F)CC1]

In a sealed tube under nitrogen, a solution of benzyl 4-amino-4-(4-chloro-2-fluoro-phenyl)piperidine-1-carboxylate (115 mg, 0.317 mmol), triethylamine (221 μL, 1.58 mmol) and 4-dimethylaminopyridine (7.7 mg, 0.0634 mmol) in dry DCM (2 mL) was stirred at rt. 4-(trifluoromethoxy)benzenesulfonyl chloride (98%, 84 mg, 0.317 mmol) was added dropwise and the mixture was stirred at 40° C. for 16 h. The mixture was diluted with DCM and half saturated $NaHCO_3$. The aqueous layer was extracted with DCM and the combined organic layers were washed with brine, dried over sodium sulfate, filtered and concentrated. The crude was purified by flash chromatography on silica gel using a gradient of EtOAc in heptane from 20% to 70% to afford the title compound as a white solid (60 mg, 99% purity, 31% yield, $t_r$=1.08 min). LCMS (Method E): m/z found 609.3 $[M+Na]^+$; $^1$H-NMR (DMSO-$d_6$, 400 MHz): δ (ppm) 8.84 (s, 1H), 7.90 (dd, J=8.8, 2.2 Hz, 1H), 7.82-7.62 (m, 2H), 7.47-7.25 (m, 5H), 7.04-6.82 (m, 2H), 6.71 (q, J=8.4 Hz, 1H), 5.11 (d, J=2.3 Hz, 2H), 4.22 (dd, 20 J=17.4, 11.2 Hz, 1H), 3.51 (ddd, J=36.2, 19.1, 10.2 Hz, 3H), 2.78 (s, 1H), 2.29-2.08 (m, 1H), 1.99 (dd, J=4.5, 1.8 Hz, 3H).

Step 5: Synthesis of N-(4-(4-chloro-2-fluorophenyl) piperidin-4-yl)-4-(trifluoromethoxy)benzenesulfonamide (94)

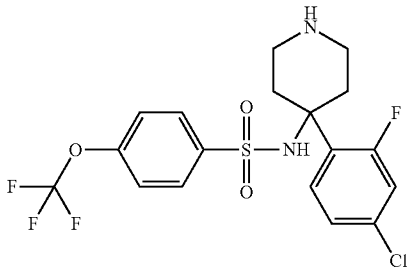 [SMILES: O=S(=O)(NC1(c2ccc(Cl)cc2F)CCNCC1)c1ccc(OC(F)(F)F)cc1]

Iodo(trimethyl)silane (44 µL, 0.307 mmol) was added to a stirred solution of benzyl 4-(4-chloro-2-fluoro-phenyl)-4-[[4-(trifluoromethoxy)phenyl]sulfonylamino]piperidine-1-carboxylate (60 mg, 0.102 mmol) under nitrogen. The mixture was stirred at rt for 1 h and was concentrated under reduced pressure. The residue was dissolved in ACN and concentrated. The residue was dissolved in DCM/MeOH 9/1 and half saturated aqueous $Na_2CO_3$. The organic layer was washed twice with half saturated aqueous $NaHCO_3$, with brine, dried over sodium sulfate, filtered and concentrated. $Et_2O$ was added to the residue, followed by 2 N HCl in $Et_2O$. The suspension was stirred at rt for 16 h and was filtered. The residue was washed with $Et_2O$ and dried under reduced pressure at 45° C. for 16 h to afford the hydrochloride salt of the title compound as a white powder (31 mg, 96.5% purity, 59% yield, $t_r$=1.45 min). LCMS (Method H): m/z found 453.1 $[M+H]^+$; $^1H$-NMR (600 MHz, DMSO-$d_6$) δ 8.75 (br s, 2H), 8.61 (s, 1H), 7.43-7.36 (m, 2H), 7.35-7.29 (m, 1H), 7.27 (d, J=8.1 Hz, 2H), 7.15 (dd, J=8.4, 2.1 Hz, 1H), 6.61 (dd, J=12.0, 2.2 Hz, 1H), 3.28-3.16 (m, 4H), 2.74-2.62 (m, 2H), 2.15-1.96 (m, 2H).

Example 59: N-(4-(5-chloro-3-fluoropyridin-2-yl)piperidin-4-yl)-4-(trifluoromethoxy)benzenesulfonamide (95)

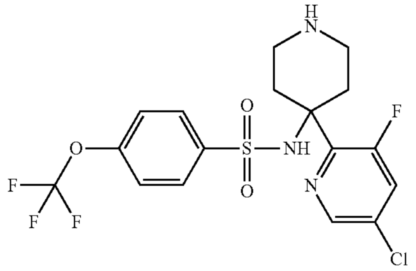 [SMILES: O=S(=O)(NC1(c2ncc(Cl)cc2F)CCNCC1)c1ccc(OC(F)(F)F)cc1]

Step 1: Synthesis of 1-benzyl-4-(5-chloro-3-fluoro-2-pyridyl)piperidine-4-carbonitrile

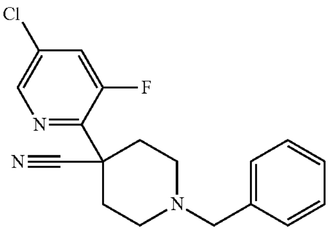 [SMILES: N#CC1(c2ncc(Cl)cc2F)CCN(Cc2ccccc2)CC1]

In a sealed tube, to a stirred solution of 1-benzylpiperidine-4-carbonitrile (300 mg, 1.50 mmol) in anhydrous toluene (14.979 mL) at rt under nitrogen was added 2-bromo-5-chloro-3-fluoropyridine (98%, 322 mg, 1.50 mmol). The reaction mixture was cooled to 0° C. and 1 M sodium 1,1,1,3,3,3-hexamethyldisilazan-2-ide (NaHMDS) (3.0 mL, 3.00 mmol) was added dropwise. The solution was stirred at 0° C. for one hour, then quenched with a saturated aqueous solution of $NH_4Cl$ to reach pH=7 and DCM was added. The aqueous layer was extracted with DCM. The combined organic layers were filtered through phase separator and concentrated under reduced pressure. The crude was purified by flash chromatography on silica gel using a gradient of MeOH in DCM from 2% to 6%. The desired fractions were combined and concentrated under reduced pressure to afford the title compound as a pale yellow solid (222 mg, 96% purity, 43% yield, $t_r$=0.57 min). LCMS (Method E): m/z found 330.3 $[M+H]^+$; $^1H$-NMR (DMSO-$d_6$, 500 MHz): δ (ppm) 8.58 (dd, J=2.1, 0.9 Hz, 1H), 8.24 (dd, J=11.2, 2.0 Hz, 1H), 7.33 (d, J=4.9 Hz, 4H), 7.30-7.22 (m, 1H), 3.56 (s, 2H), 2.98-2.89 (m, 2H), 2.36 (td, J=11.9, 2.9 Hz, 2H), 2.25-2.10 (m, 4H).

Step 2: Synthesis of 1-benzyl-4-(5-chloro-3-fluoro-2-pyridyl)piperidine-4-carboxamide

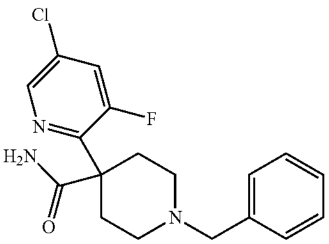 [SMILES: NC(=O)C1(c2ncc(Cl)cc2F)CCN(Cc2ccccc2)CC1]

In a round-bottom flask, a mixture of 1-benzyl-4-(5-chloro-3-fluoro-2-pyridyl)piperidine-4-carbonitrile (282 mg, 0.855 mmol) in $H_2SO_4$ (3.425 mL) and Water (0.8563 mL) was stirred at 65° C. for 3.5 h. The mixture was poured in ice-water and basified with aqueous 30% NaOH (around 10 mL) to reach pH=10 (precipitation). Water and DCM were added and the aqueous layer was extracted twice with DCM. The combined organic layers were washed with brine, filtered through phase separator and concentrated under reduced pressure to afford the title compound as a white powder (247 mg, 95% purity, 79% yield, $t_r$=0.50). LCMS (Method E): m/z found 348.4 $[M+H]^+$; $^1H$-NMR (DMSO-$d_6$, 500 MHz): δ (ppm) 8.51 (dd, J=2.1, 1.0 Hz, 1H), 7.99 (dd, J=11.2, 2.1 Hz, 1H), 7.34-7.20 (m, 5H), 6.98 (d, J=12.5 Hz, 2H), 3.37 (s, 2H), 2.52 (d, J=4.0 Hz, 1H), 2.48 (s, 1H), 2.29 (dd, J=11.3, 5.7 Hz, 2H), 2.20 (t, J=5.5 Hz, 4H).

Step 3: Synthesis of 1-benzyl-4-(5-chloro-3-fluoro-2-pyridyl)piperidin-4-amine

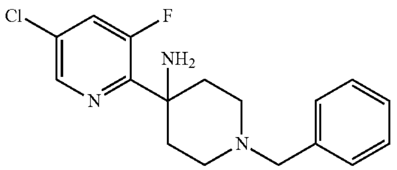 [SMILES: NC1(c2ncc(Cl)cc2F)CCN(Cc2ccccc2)CC1]

In a round-bottom flask, a solution of 1-benzyl-4-(5-chloro-3-fluoro-2-pyridyl)piperidine-4-carboxamide (247 mg, 0.710 mmol) in acetonitrile (1.6423 mL) and water (1.6423 mL) was stirred at rt. [Bis(trifluoroacetoxy)iodo]benzene (96%, 324 mg, 0.724 mmol) was added and the mixture was stirred at rt overnight, then the ACN was evaporated. Aqueous 1 N HCl was added and the mixture was washed twice with DCM. Saturated aqueous $Na_2CO_3$ was added to the aqueous layer until pH=10. The aqueous layer was extracted three times with DCM, the combined organic layers were washed with brine, filtered through phase separator and concentrated under reduced pressure to afford the title compound as a pale yellow oil (205 mg, 91% purity, 82% yield, $t_r$=0.42 min). LCMS (Method D): m/z found 320.3 $[M+H]^+$; $^1$H-NMR (DMSO-$d_6$, 500 MHz): δ (ppm) 8.47-8.42 (m, 1H), 7.98 (dd, J=11.9, 2.1 Hz, 1H), 7.33-7.28 (m, 4H), 7.23 (ddd, J=8.6, 5.6, 2.5 Hz, 1H), 3.46 (s, 2H), 2.56 (td, J=10.8, 2.9 Hz, 2H), 2.49-2.39 (m, 2H), 2.16 (ddd, J=13.8, 10.3, 3.9 Hz, 2H), 1.99 (d, J=34.5 Hz, 2H), 1.67 (dt, J=13.1, 3.2 Hz, 2H).

Step 4: Synthesis of N-[1-benzyl-4-(5-chloro-3-fluoro-2-pyridyl)-4-piperidyl]-4-(trifluoromethoxy)benzenesulfonamide

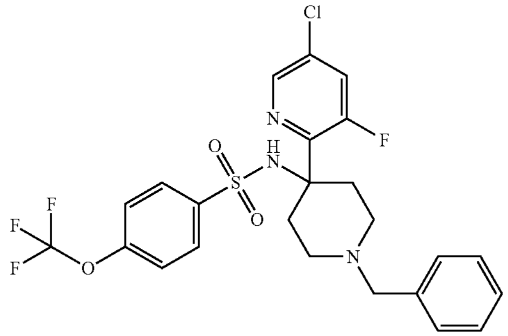 [SMILES: O=S(=O)(NC1(c2ncc(Cl)cc2F)CCN(Cc2ccccc2)CC1)c1ccc(OC(F)(F)F)cc1]

In a sealed vial, to a stirred solution of 1-benzyl-4-(5-chloro-3-fluoro-2-pyridyl)piperidin-4-amine (200 mg, 0.625 mmol) in DCM (4.1693 mL) were added successively triethylamine (0.26 mL, 1.88 mmol) and DMAP (7.6 mg, 0.0625 mmol). 4-(trifluoromethoxy)benzenesulfonyl chloride (0.13 mL, 0.754 mmol) was then added to the reaction mixture and it was stirred at 40° C. overnight. The reaction mixture was cooled to room temperature and quenched with a half saturated aqueous solution of $Na_2CO_3$. The layers were separated. The aqueous layer was extracted once with DCM. The combined organic layers were filtered through phase separator and concentrated under reduced pressure. The crude material was purified by Flash chromatography on silica gel using a gradient of MeOH in DCM from 2% to 10% to afford the expected compound as an off-white powder (250 mg, 98% purity, 72% yield, $t_r$=0.71 min). LCMS (Method E): m/z found 544.3 $[M+H]^+$; $^1$H-NMR (DMSO, 500 MHz): δ (ppm) 8.37 (s, 1H), 8.34-8.28 (m, 1H), 7.53-7.48 (m, 2H), 7.46 (dd, J=11.4, 2.1 Hz, 1H), 7.37-7.28 (m, 4H), 7.27-7.20 (m, 3H), 3.40 (s, 2H), 2.36 (d, J=46.7 Hz, 6H), 2.10 (s, 2H).

Step 5: Synthesis of N-(4-(5-chloro-3-fluoropyridin-2-yl)piperidin-4-yl)-4-(trifluoromethoxy)benzenesulfonamide (95)

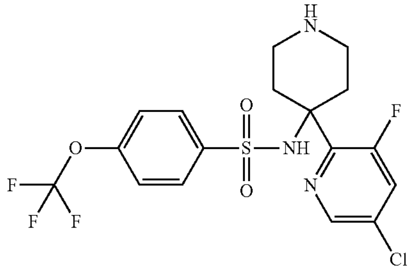 [SMILES: O=S(=O)(NC1(c2ncc(Cl)cc2F)CCNCC1)c1ccc(OC(F)(F)F)cc1]

To a stirred solution of N-[1-benzyl-4-(5-chloro-3-fluoro-2-pyridyl)-4-piperidyl]-4-(trifluoromethoxy)benzenesulfonamide (250 mg, 0.460 mmol) in DCE (5.7449 mL) under nitrogen was added 1-chloroethyl carbonochloridate (99%, 100 μL, 0.919 mmol). The reaction mixture was stirred at room temperature for 16 h. Then, the reaction mixture was concentrated under reduced pressure. The residue was dissolved in MeOH (5.7449 mL) and the reaction mixture was stirred at 65° C. for 16 h. The reaction mixture was cooled to room temperature and filtered. The solid was washed twice with a minimum amount of MeOH. The filtrate and the solid were combined, concentrated under vacuum and purified by flash chromatography on silica gel using a gradient of MeOH (0.7 N $NH_3$) in dichloromethane from 2% to 15%. The residue was triturated in 2 M HCl in $Et_2O$ (2.3 mL, 4.60 mmol) for 4 h, filtered and washed with diethyl ether and dried under vacuum at 40° C. for 20 h to afford the hydrochloride salt of the title compound as a white powder (135 mg, 98.77% purity, 60% yield, $t_r$=1.3 min). LCMS (Method H): m/z found 454.1 $[M+H]^+$; $^1$H-NMR (DMSO-$d_6$, 500 MHz): δ (ppm) 8.80 (br s, 2H), 8.76 (s, 1H), 8.35 (s, 1H), 7.42-7.52 (m, 3H), 7.34 (d, J=8.6 Hz, 2H), 3.16 (br s, 4H), 2.52-2.58 (m, 2H), 2.17-2.33 (m, 2H).

Example 60: N'-(4-(4-chlorophenyl)piperidin-4-yl)-4-(trifluoromethoxy)benzenesulfonimidamide (96)

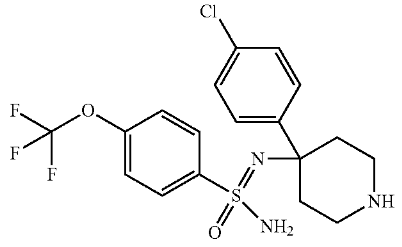 [SMILES: NS(=O)(=NC1(c2ccc(Cl)cc2)CCNCC1)c1ccc(OC(F)(F)F)cc1]

Step 1: Synthesis of tert-butyl 4-(4-chlorophenyl)-4-[[N-[(3,4-dimethoxyphenyl)methyl]-S-[4-(trifluoromethoxy)phenyl]sulfonimidoyl]amino]piperidine-1-carboxylate

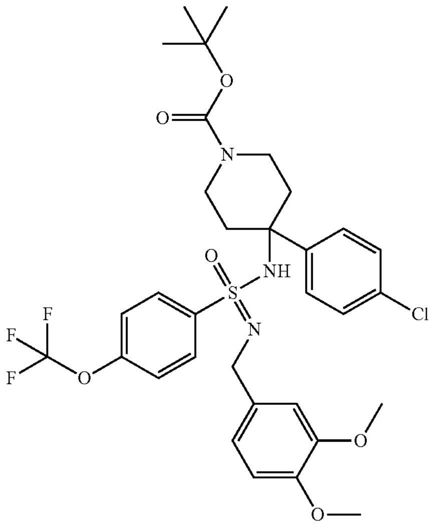 [SMILES: COc1ccc(CN=S(=O)(NC2(c3ccc(Cl)cc3)CCN(C(=O)OC(C)(C)C)CC2)c2ccc(OC(F)(F)F)cc2)cc1OC]

In a round-bottom flask, to a stirred solution of N-[(3,4-dimethoxyphenyl)methyl]-4-(trifluoromethoxy)benzenesulfinamide (250 mg, 0.666 mmol) in tetrachloromethane (2.5 mL, 26.0 mmol) at 0° C. under nitrogen was added tert-butyl hypochlorite (0.11 mL, 0.932 mmol). The reaction mixture was stirred at 0° C. for 2 h in the dark. The solution was concentrated under reduced pressure at 20° C. The residue was dissolved in anhydrous THF (2.0833 mL) under nitrogen, and tert-butyl 4-amino-4-(4-chlorophenyl)piperidine-1-carboxylate (228 mg, 0.733 mmol), DIPEA (349 μL, 2.00 mmol) and N,N-dimethylpyridin-4-amine (99%, 8.2 mg, 0.0666 mmol) were added successively. The reaction mixture was stirred at 40° C. overnight. The reaction mixture was cooled to rt, quenched with water (20 mL), and EtOAc (20 mL) was added. The aqueous layer was extracted with EtOAc (20 mL). The combined organic layers were washed with a saturated aqueous solution of sodium chloride, dried over sodium sulfate, filtered and concentrated under reduced pressure. The crude was purified by flash chromatography on silica gel using a gradient of MeOH (0.7 N $NH_3$) in DCM from 0.4% to 5% to afford the title compound as a white foam (235 mg, 89% purity, 46% yield, $t_r$=1.12 min). LCMS (Method D): m/z found 684.5 $[M+H]^+$; $^1$H-NMR (DMSO, 400 MHz): δ (ppm) 7.81 (d, J=9.0 Hz, 2H), 7.60-7.32 (m, 5H), 7.26-7.22 (m, 2H), 7.02-6.96 (m, 1H), 6.75 (d, J=8.3 Hz, 1H), 6.61 (d, J=2.2 Hz, 1H), 6.47 (d, J=8.0 Hz, 1H), 3.74-3.68 (m, 6H), 3.64 (s, 3H), 3.40 (s, 2H), 2.22 (d, J=13.0 Hz, 2H), 1.80-1.65 (m, 2H), 1.39 (s, 9H).

Step 2: Synthesis of benzyl 3-(4-chlorophenyl)-3-[[[4-(trifluoromethoxy)phenyl]sulfonimidoyl]amino]pyrrolidine-1-carboxylate

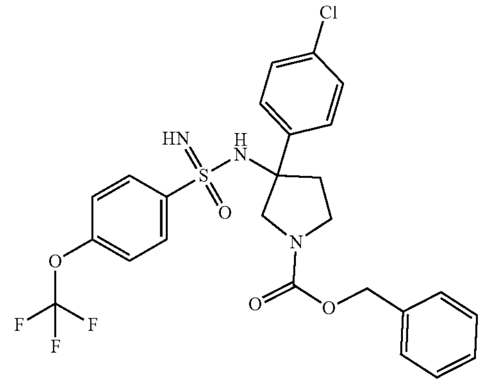 [SMILES: N=S(=O)(NC1(c2ccc(Cl)cc2)CCN(C(=O)OCc2ccccc2)C1)c1ccc(OC(F)(F)F)cc1]

In a round-bottom flask, to a stirred solution of tert-butyl 4-(4-chlorophenyl)-4-[[N-[(3,4-dimethoxyphenyl)methyl]-S-[4-(trifluoromethoxy)phenyl]sulfonimidoyl]amino]piperidine-1-carboxylate (278 mg, 0.407 mmol) in a mixture of acetonitrile (5.2899 mL) and water (2.645 mL) at 0° C. under nitrogen was added $(NH_4)_2Ce(NO_3)_6$ (542 mg, 0.988 mmol). The reaction mixture was stirred at 0° C. for 3 h. The reaction mixture was diluted with water. The aqueous layer was extracted three times with EtOAc. The combined organic layers were washed with a saturated aqueous solution of NaCl, dried over $Na_2SO_4$, filtered, concentrated under reduced pressure and purified by flash chromatography on silica gel using a gradient of MeOH (0.7 N $NH_3$) in DCM from 0% to 6%. The desired fractions were combined and concentrated. The resulting yellow sticky solid was sonicated in diethyl ether and filtered to afford the title compound as a white solid (124 mg, 99% purity, 40% yield, $t_r$=0.96 min). LCMS (Method E): m/z found 534.2 $[M+H]^+$; $^1$H-NMR (DMSO-$d_6$, 400 MHz): δ (ppm) 8.09-6.35 (m, 9H), 4.59 (s, 1H), 3.70 (d, J=39.0 Hz, 2H), 3.31 (s, 2H), 2.64 (d, J=24.5 Hz, 1H), 2.21 (s, 1H), 1.60 (d, J=93.6 Hz, 2H), 1.40 (s, 9H).

Step 3: Synthesis of 4-(4-chlorophenyl)-N-[[4-(trifluoromethoxy)phenyl]sulfonimidoyl]piperidin-4-amine (96)

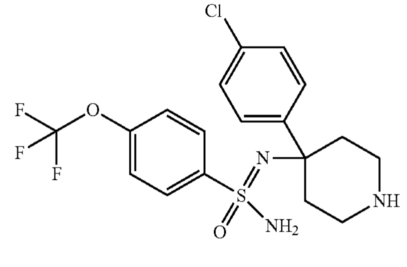 [SMILES: NS(=O)(=NC1(c2ccc(Cl)cc2)CCNCC1)c1ccc(OC(F)(F)F)cc1]

To a stirred suspension of tert-butyl 4-(4-chlorophenyl)-4-[[[4-(trifluoromethoxy)phenyl]sulfonimidoyl]amino]piperidine-1-carboxylate (99%, 88 mg, 0.163 mmol) in $Et_2O$ (1.6315 mL) at rt under nitrogen was added 4 M HCl in 1,4-dioxane (0.41 mL, 1.63 mmol). The obtained solution was stirred at rt for 3 hours, then additional 4 M HCl in 1,4-dioxane (0.41 mL, 1.63 mmol) was added and the colorless solution obtained was stirred overnight at rt. The obtained white suspension was filtered, washed with diethyl ether and dried at 40° C. under vacuum for 2 days, and 1 day at 55° C. to afford the hydrochloride salt of the title compound as a white powder (50.6 mg, 100% purity, 70% yield, $t_r$=1.32 min). LCMS (Method H): m/z found 434 $[M+H]^+$; $^1$H-NMR (DMSO-$d_6$, 500 MHz): δ (ppm) 8.87-9.25 (m, 2H), 7.59-7.84 (m, 2H), 7.36 (br d, J=8.3 Hz, 2H), 7.00-7.27 (m, 4H), 3.12-3.55 (m, 4H), 2.51-2.80 (m, 2H), 1.72-2.25 (m, 2H).

Example 61: N-(4-(4-chlorophenyl)piperidin-4-yl)-4-(trifluoromethyl)benzenesulfonamide (97)

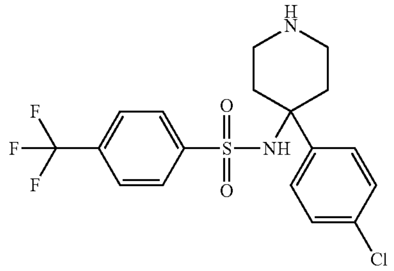 [SMILES: O=S(=O)(NC1(c2ccc(Cl)cc2)CCNCC1)c1ccc(C(F)(F)F)cc1]

Step 1: Synthesis of tert-butyl 4-(4-chlorophenyl)-4-[[4-(trifluoromethyl)phenyl]sulfonylamino]piperidine-1-carboxylate

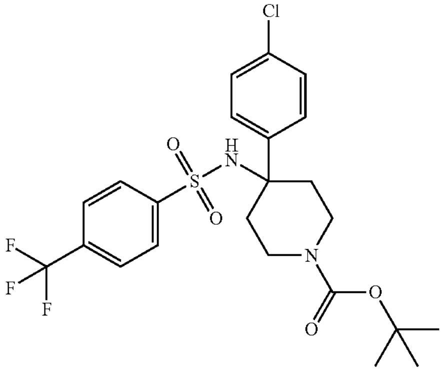 [SMILES: CC(C)(C)OC(=O)N1CCC(NS(=O)(=O)c2ccc(C(F)(F)F)cc2)(c2ccc(Cl)cc2)CC1]

A sealed vial was charged with tert-butyl 4-amino-4-(4-chlorophenyl)piperidine-1-carboxylate (200 mg, 0.643 mmol), DMAP (16 mg, 0.129 mmol) and triethylamine (359 µL, 2.57 mmol) in DCM (10 mL). 4-(trifluoromethyl)benzenesulfonyl chloride (98%, 177 mg, 0.708 mmol) was added and the reaction mixture was stirred at 40° C. for 18 h. The reaction mixture was quenched with a saturated aqueous solution of ammonium chloride (6 mL) and water (3 mL) and dichloromethane (2 mL) were added. The organic layer was dried overusing phase separator and evaporated to dryness. The crude was precipitated in DCM (1 mL) to afford the title compound as a white powder (160 mg, 100% purity, 47.9% yield, $t_r$=2.01 min). LCMS (Method G): m/z found 419.3 $[M\text{-}tBu\text{-}CO_2+H]^+$; $^1$H-NMR (DMSO-$d_6$, 400 MHz): δ (ppm) 8.32 (s, 1H), 7.59 (d, J=8.4 Hz, 2H), 7.45 (d, J=8.2 Hz, 2H), 7.05 (d, J=8.7 Hz, 2H), 6.92 (d, J=8.7 Hz, 2H), 3.70 (d, J=13.4 Hz, 2H), 3.25 (s, 2H), 2.37 (d, J=13.5 Hz, 2H), 1.73 (t, J=10.5 Hz, 2H).

Step 2: Synthesis of N-(4-(4-chlorophenyl)piperidin-4-yl)-4-(trifluoromethyl)benzenesulfonamide (97)

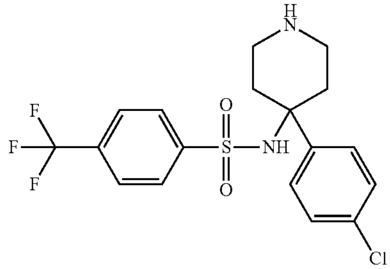 [SMILES: O=S(=O)(NC1(c2ccc(Cl)cc2)CCNCC1)c1ccc(C(F)(F)F)cc1]

In sealed tube, to a white heterogenous stirred suspension of tert-butyl 4-(4-chlorophenyl)-4-[[4-(trifluoromethyl)phenyl]sulfonylamino]piperidine-1-carboxylate (100%, 160 mg, 0.308 mmol) in $Et_2O$ (1.5 mL) was added 2 M HCl in $Et_2O$ (4.6 mL, 9.25 mmol). The mixture was stirred for 18 h at room temperature. 4 M HCl in 1,4-dioxane (1.2 mL, 4.62 mmol) was added. The mixture was stirred for 18 h at room temperature. 4 M HCl in 1,4-dioxane (0.39 mL, 1.54 mmol) was added at rt. The mixture was stirred at rt for 5 days and then filtered and washed with $Et_2O$ (1 mL) to afford the hydrochloride salt of the title compound as a white powder (109 mg, 100% purity, 77.6% yield, $t_r$=1.74 min). LCMS (Method H): m/z found 419 $[M+H]^+$; $^1$H-NMR (600 MHz, DMSO-$d_6$) δ ppm 8.85 (br s, 2H) 8.63 (br s, 1H) 7.58 (d, J=8.36 Hz, 2H) 7.44 (d, J=8.22 Hz, 2H) 7.05 (d, J=8.66 Hz, 2H) 6.94 (d, J=8.80 Hz, 2H) 3.15-3.28 (m, 4H) 2.58 (br d, J=13.50 Hz, 2H) 1.93-2.15 (m, 2H).

Example 62: N-(4-(4-chlorophenyl)piperidin-4-yl)-3-(trifluoromethyl)bicyclo[1.1.1]pentane-1-sulfonamide (98)

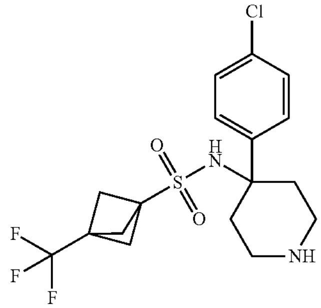 [SMILES: O=S(=O)(NC1(c2ccc(Cl)cc2)CCNCC1)C12CC(C(F)(F)F)(C1)C2]

Step 1: Synthesis of tert-butyl 4-(4-chlorophenyl)-4-[[3-(trifluoromethyl)-1-bicyclo[1.1.1]pentanyl]sulfonylamino]piperidine-1-carboxylate

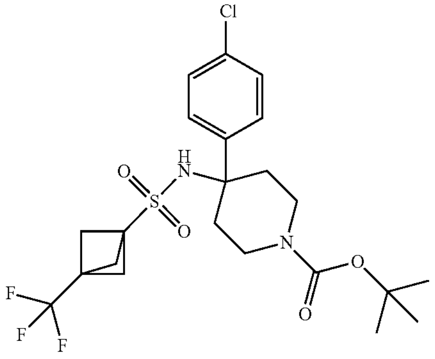 [SMILES: CC(C)(C)OC(=O)N1CCC(NS(=O)(=O)C23CC(C(F)(F)F)(C2)C3)(c2ccc(Cl)cc2)CC1]

A sealed vial was charged with tert-butyl 4-amino-4-(4-chlorophenyl)piperidine-1-carboxylate (200 mg, 0.643 mmol), DMAP (16 mg, 0.129 mmol) and triethylamine (359 μL, 2.57 mmol) in DCM (10 mL). 3-(trifluoromethyl)bicyclo[1.1.1]pentane-1-sulfonyl chloride (95%, 175 mg, 0.708 mmol) was added and the reaction mixture was stirred at 40° C. for 18 h. The reaction mixture was quenched with a saturated aqueous solution of ammonium chloride (6 mL) and water (3 mL) and dichloromethane (2 mL) were added. The organic layer was dried using phase separator and evaporated to dryness. The crude was purified by flash chromatography on silica gel using a gradient of EtOAc in heptane from 0% to 100% to afford the title compound as a white powder (36 mg, 100% purity, 11% yield, $t_r$=1.95 min). LCMS (Method G): m/z found 409.2 $[M-CO_2tBu+H]^+$; $^1$H-NMR (500 MHz, DMSO-$d_6$) δ ppm 1.39 (s, 9H) 1.77-1.90 (m, 2H) 1.96 (s, 6H) 2.24-2.40 (m, 2H) 3.20-3.30 (m, 2H) 3.58 (dt, J=13.51, 4.00 Hz, 2H) 7.44-7.48 (m, 2H) 7.50-7.55 (m, 2H) 7.77 (s, 1H).

Step 2: Synthesis of N-(4-(4-chlorophenyl)piperidin-4-yl)-3-(trifluoromethyl)bicyclo[1.1.1]pentane-1-sulfonamide (98)

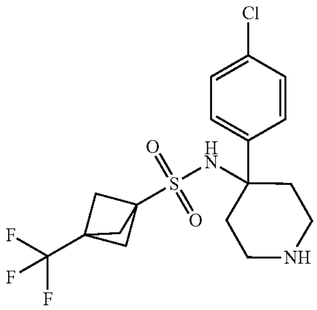 [SMILES: O=S(=O)(NC1(c2ccc(Cl)cc2)CCNCC1)C12CC(C(F)(F)F)(C1)C2]

In sealed tube, to a white homogeneous stirred solution of tert-butyl 4-(4-chlorophenyl)-4-[[3-(trifluoromethyl)-1-bicyclo[1.1.1]pentanyl]sulfonylamino]piperidine-1-carboxylate (36 mg, 0.0707 mmol) in $Et_2O$ (1 mL) was added 4 M HCl in 1,4-dioxane (0.35 mL, 1.41 mmol). The mixture was stirred for 5 days at room temperature. 4 M HCl in 1,4-dioxane (0.35 mL, 1.41 mmol) was added. The mixture was stirred for 18 h at room temperature. 4 M HCl in 1,4-dioxane (0.21 mL, 0.849 mmol) was added at rt. The mixture was stirred for 18 h at room temperature, then 4 M HCl in 1,4-dioxane (0.21 mL, 0.849 mmol) was added. The mixture was stirred for 18 h at room temperature. The reaction mixture was filtered and washed with $Et_2O$ (1 mL) to afford the hydrochloride salt of the compound as a white powder (15.5 mg, 99.2% purity, 48.8% yield, $t_r$=1.28 min). LCMS (Method H): m/z found 409.1 $[M+H]^+$; $^1$H-NMR (DMSO-$d_6$, 500 MHz) δ 8.75 (br s, 2H), 8.05 (s, 1H), 7.53 (d, 4H, J=2.7 Hz), 3.1-3.3 (m, 4H), 2.5-2.6 (m, 2H), 2.1-2.2 (m, 2H), 1.96 (s, 6H).

Example 63: 3-amino-N-(4-(4-chlorophenyl)piperidin-4-yl)-4-(trifluoromethoxy)benzenesulfonamide (99)

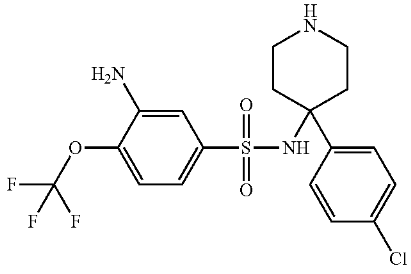 [SMILES: Nc1cc(S(=O)(=O)NC2(c3ccc(Cl)cc3)CCNCC2)ccc1OC(F)(F)F]

Step 1: Synthesis of tert-butyl 4-(4-chlorophenyl)-4-[[3-nitro-4-(trifluoromethoxy)phenyl]sulfonylamino]piperidine-1-carboxylate

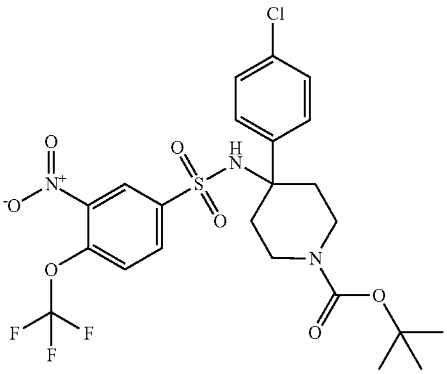

In a sealed tube under nitrogen, 3-nitro-4-(trifluoromethoxy)benzene-1-sulfonyl chloride (98 mg, 0.322 mmol) was added to a stirred solution of tert-butyl 4-amino-4-(4-chlorophenyl)piperidine-1-carboxylate (100 mg, 0.322 mmol), triethylamine (224 μL, 1.61 mmol) and 4-dimethylaminopyridine (7.9 mg, 0.0643 mmol) in dry DCM (2 mL) and was stirred at 40° C. for 16 h. The mixture was diluted with DCM and half saturated $NaHCO_3$. The aqueous layer was extracted with DCM and the combined organic layers were washed with brine, dried over sodium sulfate, filtered and concentrated. The crude was purified by flash chromatography on silica gel using a gradient of (MeOH+2% $NH_4OH$) in DCM from 0.4% to 5% to afford the title compound as a yellow solid (88 mg, 93% purity, 43% yield, $t_r$=1.06 min). LCMS (Method E): m/z found 480.3 $[M-CO_2tBu+H]^+$; $^1$H-NMR (DMSO-$d_6$, 500 MHz): δ (ppm) 8.53 (s, 1H), 7.88 (d, J=2.3 Hz, 1H), 7.72 (dd, J=8.7, 2.3 Hz, 1H), 7.65 (dq, J=8.7, 1.5 Hz, 1H), 7.17-7.06 (m, 2H), 7.04-6.95 (m, 2H), 3.69 (d, J=13.5 Hz, 2H), 3.43-3.15 (m, 4H), 2.39 (d, J=13.7 Hz, 2H), 1.76 (t, J=11.7 Hz, 2H), 1.40 (s, 1OH).

Step 2: Synthesis of tert-butyl 4-[[3-amino-4-(trifluoromethoxy)phenyl]sulfonylamino]-4-(4-chlorophenyl)piperidine-1-carboxylate

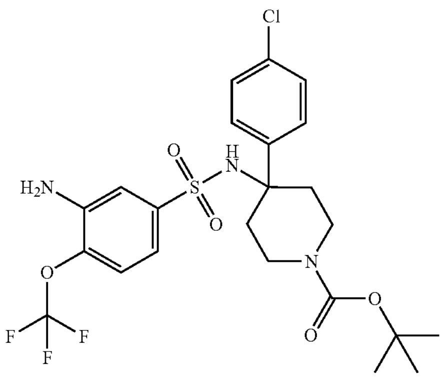 [SMILES: CC(C)(C)OC(=O)N1CCC(NS(=O)(=O)c2ccc(OC(F)(F)F)c(N)c2)(c2ccc(Cl)cc2)CC1]

In a sealed tube, a suspension of iron (43 mg, 0.776 mmol) and ammonium chloride (11 mg, 0.198 mmol) in EtOH (1 mL) and water (500 μL) was stirred at 70° C. for 1 h. A solution of tert-butyl 4-(4-chlorophenyl)-4-[[3-nitro-4-(trifluoromethoxy)phenyl]sulfonylamino]piperidine-1-carboxylate (93%, 88 mg, 0.141 mmol) in EtOH (1 mL) was added and the mixture was stirred at 80° C. for 2 h. The mixture was allowed to cool to rt and was filtered through a pad of dicalite. The pad was washed with EtOH and DCM and the filtrate was concentrated. The residue was dissolved in DCM and half saturated aqueous $NaHCO_3$ and the aqueous layer was extracted with DCM. The combined organic layers were washed with brine, dried over sodium sulfate, filtered and concentrated. The residue was purified by flash chromatography on silica gel using a gradient of (MeOH+2% $NH_4OH$) in DCM from 0.4% to 6% to afford the expected product as a white solid (65 mg, 98% purity, 82% yield, $t_r$=1.01 min). LCMS (Method E): m/z found 572.3 $[M+Na]^+$; $^1$H-NMR (DMSO-$d_6$, 500 MHz): δ (ppm) 8.03 (s, 1H), 7.19-7.14 (m, 2H), 7.08-7.03 (m, 2H), 6.96 (dd, J=8.5, 1.6 Hz, 1H), 6.78 (d, J=2.3 Hz, 1H), 6.52 (dd, J=8.5, 2.3 Hz, 1H), 5.63 (s, 2H), 3.66 (d, J=13.2 Hz, 2H), 3.14 (s, 2H), 2.29 (d, J=13.4 Hz, 2H), 1.69 (t, J=12.7 Hz, 2H), 1.38 (s, 9H).

Step 3: Synthesis of 3-amino-N-(4-(4-chlorophenyl)piperidin-4-yl)-4-(trifluoromethoxy)benzenesulfonamide (99)

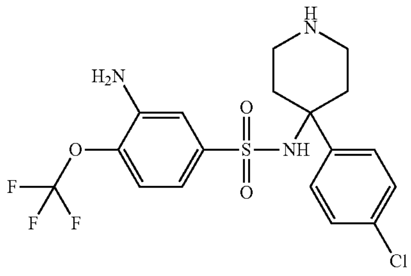 [SMILES: Nc1cc(S(=O)(=O)NC2(c3ccc(Cl)cc3)CCNCC2)ccc1OC(F)(F)F]

In a sealed tube under nitrogen, 4 M HCl in 1,4-dioxane (591 μL, 2.36 mmol) was added to a stirred solution of tert-butyl 4-[[3-amino-4-(trifluoromethoxy)phenyl]sulfonylamino]-4-(4-chlorophenyl)piperidine-1-carboxylate (65 mg, 0.118 mmol) in dry 1,4-dioxane (1 mL). The mixture was stirred at rt for 16 h and concentrated. The residue was dissolved in hot MeOH and added dropwise to gently stirred $Et_2O$. The obtained suspension was stirred at rt for 1 h and was filtered, the residue was washed with $Et_2O$ and dried under reduced pressure at 45° C. for 16 h to afford the hydrochloride salt of the title compound as a white powder (35 mg, 98.4% purity, 59% yield, $t_r$=1.25 min). LCMS (Method H): m/z found 450.1 $[M+H]^+$; $^1$H-NMR (600 MHz, DMSO-$d_6$) δ ppm 8.54-8.73 (m, 2H) 8.24 (s, 1H) 7.11-7.15 (m, 2H) 7.05-7.09 (m, 2H) 6.93 (dd, J=8.58, 1.39 Hz, 1H) 6.73 (d, J=2.35 Hz, 1H) 6.47 (dd, J=8.51, 2.35 Hz, 1H) 5.64 (s, 2H) 3.14-3.25 (m, 4H) 2.52 (br d, J=1.61 Hz, 1H) 1.95-2.04 (m, 2H).

Example 64: N-(4-(4-(difluoromethyl)phenyl)piperidin-4-yl)-4-(trifluoromethoxy)benzenesulfonamide (100)

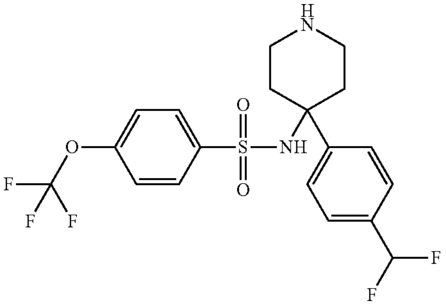 [SMILES: O=S(=O)(NC1(c2ccc(C(F)F)cc2)CCNCC1)c1ccc(OC(F)(F)F)cc1]

Step 1: Synthesis of benzyl 4-[4-(difluoromethyl) phenyl]-4-hydroxy-piperidine-1-carboxylate

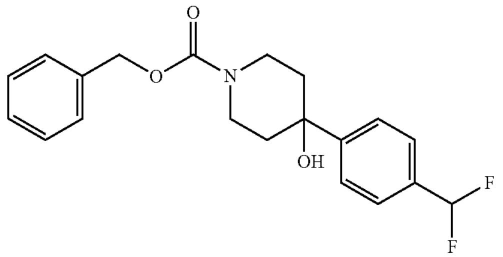 [SMILES: O=C(OCc1ccccc1)N1CCC(O)(c2ccc(C(F)F)cc2)CC1]

In a three necked round bottomed flask equipped with a thermometer, under nitrogen, a solution of 1-bromo-4-(difluoromethyl)benzene (1.00 g, 4.83 mmol) in dry THF (10 mL) was stirred at −78° C. 1.6 M butyllithium (3.3 mL, 5.31 mmol) was added dropwise and the mixture was stirred at −78° C. for 1 h. A solution of benzyl 4-oxopiperidine-1-carboxylate (1.13 g, 4.83 mmol) in dry THF (5 mL) was added dropwise and the mixture was stirred at −78° C. for 1 h and at rt for 1 h. The mixture was quenched with saturated aqueous $NH_4Cl$ and extracted three times with EtOAc. The combined organic layers were dried over sodium sulfate, filtered and concentrated. The crude was purified by flash chromatography on silica gel using a gradient of EtOAc in heptane from 5% to 50% to afford the title compound as a yellow oil. (1.44 g, 80% purity, 66% yield, $t_r$=0.89 min). LCMS (Method E): m/z found 362.4 $[M+H]^+$; $^1$H-NMR (DMSO-$d_6$, 500 MHz): δ (ppm) 7.62 (d, J=8.0 Hz, 2H), 7.52 (d, J=8.1 Hz, 2H), 7.42-7.28 (m, 6H), 7.00 (t, J=56.0 Hz, 1H), 5.25 (s, 1H), 5.11 (d, J=12.2 Hz, 3H), 3.95 (dd, J=12.4, 4.0 Hz, 2H), 3.23 (s, 2H), 1.86 (td, J=13.1, 4.7 Hz, 2H), 1.60 (d, J=13.2 Hz, 2H).

Step 2: Synthesis of benzyl 4-[(2-chloroacetyl) amino]-4-[4-(difluoromethyl)phenyl]piperidine-1-carboxylate

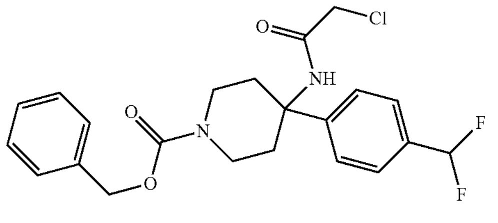 [SMILES: O=C(CCl)NC1(c2ccc(C(F)F)cc2)CCN(C(=O)OCc2ccccc2)CC1]

In a round bottomed flask under nitrogen, a solution of benzyl 4-[4-(difluoromethyl)phenyl]-4-hydroxy-piperidine-1-carboxylate (80%, 1.44 g, 3.19 mmol) and 2-chloroacetonitrile (6.1 mL, 95.6 mmol) in dry DCM (8 mL) was stirred at 0° C. 2,2,2-trifluoroacetic acid (6.1 mL, 79.7 mmol) was added and the green mixture was stirred at 0° C. for 6 h and at rt for 16 h. The mixture was poured into iced water and a saturated aqueous solution of $Na_2CO_3$ was added until pH=9. The aqueous layer was extracted twice with DCM. The combined organic layers were washed with brine, dried over sodium sulfate, filtered and concentrated to afford the title compound as a yellow oil (1.67 g, 60% purity, 71% yield, $t_r$=0.89 min). LCMS (Method E): m/z found 437.3 $[M+H]^+$; $^1$H-NMR (DMSO-$d_6$, 500 MHz): δ (ppm) 8.49 (s, 1H), 7.50 (d, J=2.2 Hz, 4H), 7.41-7.29 (m, 7H), 7.00 (t, J=56.0 Hz, 1H), 5.10 (s, 2H), 4.13 (s, 2H), 3.94 (d, J=13.2 Hz, 2H), 3.12 (s, 2H), 2.33 (d, J=13.4 Hz, 2H), 1.84 (td, J=13.1, 4.5 Hz, 2H).

Step 3: Synthesis of benzyl 4-amino-4-[4-(difluoromethyl)phenyl]piperidine-1-carboxylate

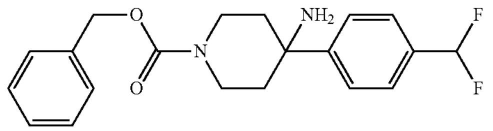 [SMILES: NC1(c2ccc(C(F)F)cc2)CCN(C(=O)OCc2ccccc2)CC1]

In a sealed tube, a solution of benzyl 4-[(2-chloroacetyl) amino]-4-[4-(difluoromethyl)phenyl]piperidine-1-carboxylate (1.67 g, 3.82 mmol) in EtOH (25 mL) and AcOH (5 mL) was stirred at rt. thiourea (378 mg, 4.97 mmol) was added, the mixture was stirred at 80° C. for 16 h and poured into iced water. Saturated aqueous $Na_2CO_3$ was added until pH=9 and the mixture was extracted three times with DCM. The combined organic layers were washed with brine, dried over sodium sulfate, filtered and concentrated. The crude was stirred in $Et_{20}$/MeOH 95/5 (15 mL) and 2 M HCl/$Et_2O$ (3.8 mL, 7.65 mmol) was added dropwise. The obtained suspension was stirred at rt for 64 h and was filtered. The residue was washed with $Et_2O$ and dried under reduced pressure at 45° C. for 4 h to afford the hydrochloride salt of the title compound as a yellow powder (790 mg, 100% purity, 52% yield, $t_r$=0.63 min). LCMS (Method D): m/z found 361.2 $[M+H]^+$; $^1$H-NMR (DMSO-$d_6$, 400 MHz): δ (ppm) 8.62 (s, 3H), 7.79 (d, J=8.2 Hz, 2H), 7.69 (d, J=8.2 Hz, 2H), 7.43-7.27 (m, 5H), 7.09 (t, J=55.7 Hz, 1H), 5.09 (s, 2H), 3.81 (d, J=13.7 Hz, 2H), 3.19 (s, 2H), 2.46 (d, J=14.9 Hz, 2H), 2.07 (t, J=10.8 Hz, 2H).

Step 4: Synthesis of benzyl 4-[4-(difluoromethyl) phenyl]-4-[[4-(trifluoromethoxy)phenyl]sulfonylamino]piperidine-1-carboxylate

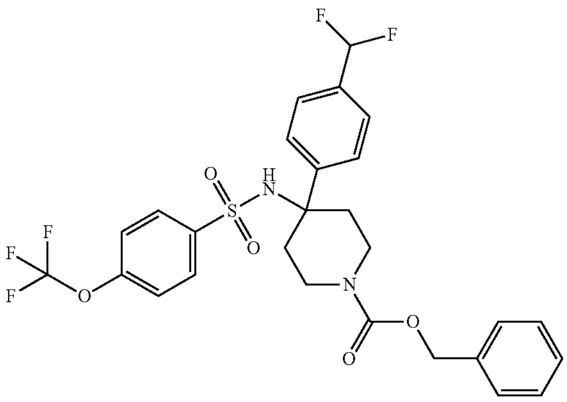 [SMILES: O=C(OCc1ccccc1)N1CCC(NS(=O)(=O)c2ccc(OC(F)(F)F)cc2)(c2ccc(C(F)F)cc2)CC1]

In a sealed tube under nitrogen, a solution of benzyl 4-amino-4-[4-(difluoromethyl)phenyl]piperidine-1-carboxylate hydrochloride (200 mg, 0.504 mmol) triethylamine (281 μL, 2.02 mmol) and 4-dimethylaminopyridine (12 mg, 0.101 mmol) in dry DCM (4 mL) was stirred at rt. Next, 4-(trifluoromethoxy)benzenesulfonyl chloride (86 μL, 0.504 mmol) was added and the mixture was stirred at 40° C. for 16 h. The mixture was diluted with DCM and half saturated aqueous solution of $NaHCO_3$. The aqueous layer was extracted with DCM. The combined organic layers were washed with brine, dried over sodium sulfate, filtered and concentrated. The crude was purified by flash chromatography on silica gel using a gradient of EtOAc in heptane from 5% to 50% to afford the title compound as a white solid (210 mg, 100% purity, 710% yield, $t_r$=1.01 min). LCMS (Method E): m/z found 607.3 $[M+Na]^+$; $^1$H-NMR (DMSO-$d_6$, 400 MHz): δ (ppm) 8.29 (s, 1H), 7.43-7.27 (m, 7H), 7.27-7.11 (m, 6H), 6.84 (t, J=55.9 Hz, 1H), 5.08 (s, 2H), 3.89-3.71 (m, 2H), 3.31 (s, 3H), 2.41 (d, J=13.6 Hz, 2H), 1.92-1.71 (m, 2H).

Step 5: Synthesis of N-(4-(4-(difluoromethyl)phenyl)piperidin-4-yl)-4-(trifluoromethoxy)benzenesulfonamide (100)

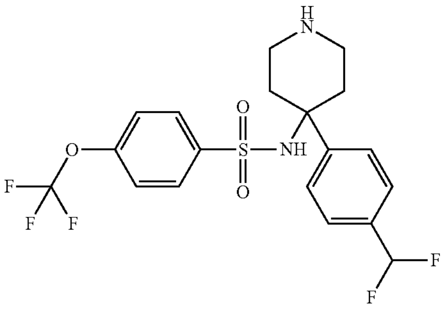 [SMILES: O=S(=O)(NC1(c2ccc(C(F)F)cc2)CCNCC1)c1ccc(OC(F)(F)F)cc1]

In a round bottomed flask under nitrogen, iodo(trimethyl) silane (51 μL, 0.359 mmol) was added to a stirred solution of benzyl 4-[4-(difluoromethyl)phenyl]-4-[[4-(trifluoromethoxy)phenyl]sulfonylamino]piperidine-1-carboxylate (210 mg, 0.359 mmol) in dry ACN (2 mL) and the solution was stirred at rt for 1 h. The mixture was concentrated and the residue was triturated in DCM/MeOH 9/1 (3 mL). The suspension was stirred at rt for 10 min and was filtered. The residue was washed with DCM and dried under reduced pressure at 45° C. for 2 h. A half saturated aqueous solution of $Na_2CO_3$ (10 mL) was added and the suspension was stirred at rt for 16 h and filtered. The residue was washed with water and dried under reduced pressure at 45° C. for 4 h. $Et_2O$/MeOH 95/5 (2 mL) and 2 M HCl/$Et_2O$ (198 μL, 0.395 mmol) were added and the suspension was stirred at rt for 16 h. The suspension was diluted with $Et_2O$ (2 mL), filtered, the residue was washed with $Et_2O$ and dried under reduced pressure at 45° C. for 64 h to afford the hydrochloride salt of the title compound as a white powder (87 mg, 99.5% purity, 49% yield, $t_r$=1.37 min). LCMS (Method H): m/z found 451.2 $[M+H]^+$; $^1$H-NMR (500 MHz, DMSO-$d_6$) δ ppm 2.02-2.13 (m, 2H) 2.61 (br d, J=13.45 Hz, 2H) 3.18-3.29 (m, 4H) 6.84 (t, J=55.75 Hz, 1H) 7.12-7.16 (m, 2H) 7.16-7.20 (m, 2H) 7.20-7.24 (m, 2H) 7.33 (d, J=7.80 Hz, 2H) 8.56 (s, 1H) 8.89 (br s, 2H).

Example 65: Cell Viability Assays

LNCaP Cell Line

LNCaP cell line was used for the cell viability assay. LNCaP cells were plated in 96-well plates at a density of 5000 cells per well. After 24 hours of plating, the cells were treated with increasing doses of compound 1-100 ranging from 1 μM to 80 μM. Relative cell numbers were analyzed after 48 hours using 3-(4,5-dimethylthiazol-2-yl)-5-(3-carboxymethoxyphenyl)-2-(4-sulfophenyl)-2H-tetrazolium (MTS) assay (Promega) according to the manufacturer's instructions.

HCC1937 cell line

HCC1937 cells are plated in a 96 well plate format at a density of 10,000 cells per well. After incubation overnight, cells are treated with compounds 1-100 at following concentrations: 80, 40, 20, 10, 5, 2.5, 1.25 μM. Compound concentrations are prepared in RPMI via serial dilutions from a starting stock of 80 mM. 48 hours after compound treatment, cell viability is assessed using the Promega CellTiter 96 aqueous one proliferation assay (Promega G3582, MTS assay) according to manufacturer's protocol.

The cell viability data was analyzed with GraphPad Prism software. The values were log transformed and analyzed with non-linear regression (curve-fit) using log(inhibitor) vs. response—variable slope (four parameters) and constraining the bottom to equal zero. The results are provided in Table 35. Unless otherwise indicated, the $GI_{50}$ values provided in Table 35 correspond to the LNCaP cell viability assays.

TABLE 35

Cell viability assay data for compounds 1-100

| No. | Structure | Nomenclature | $GI_{50}$ (μM) |
|---|---|---|---|
| 1 | 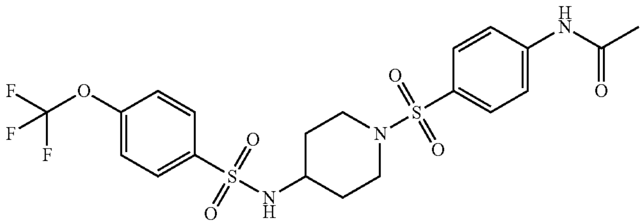 [SMILES: CC(=O)Nc1ccc(S(=O)(=O)N2CCC(NS(=O)(=O)c3ccc(OC(F)(F)F)cc3)CC2)cc1] | N-(4-((4-((4-(trifluoromethoxy)phenyl) sulfonamido)piperidin-1-yl)sulfonyl)phenyl)acetamide | 38.05 |

TABLE 35-continued

| Cell viability assay data for compounds 1-100 | | | |
|---|---|---|---|
| No. | Structure | Nomenclature | $GI_{50}$ (μM) |
| 2 | 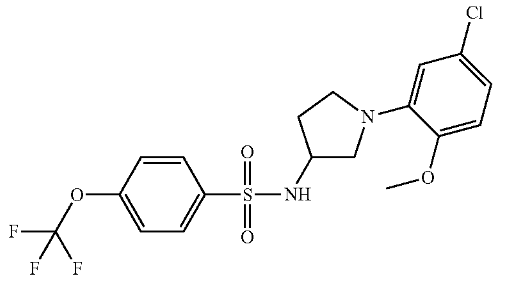 [SMILES: COc1ccc(Cl)cc1N1CCC(NS(=O)(=O)c2ccc(OC(F)(F)F)cc2)C1] | N-(1-(5-chloro-2-methoxyphenyl)pyrrolidin-3-yl)-4-(trifluoromethoxy) benzenesulfonamide | 67.43 |
| 3 | 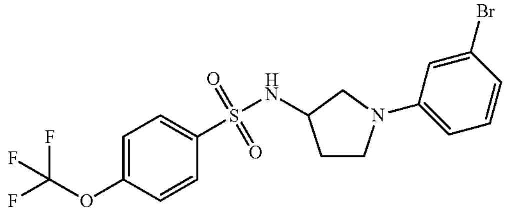 [SMILES: O=S(=O)(NC1CCN(c2cccc(Br)c2)C1)c1ccc(OC(F)(F)F)cc1] | N-(1-(3-bromophenyl)pyrrolidin-3-yl)-4-(trifluoromethoxy) benzenesulfonamide | 77.11 |
| 4 | 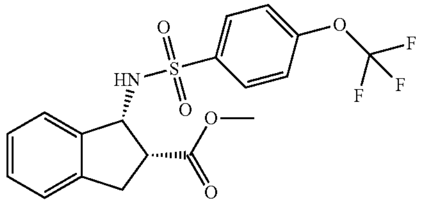 [SMILES: COC(=O)[C@@H]1Cc2ccccc2[C@@H]1NS(=O)(=O)c1ccc(OC(F)(F)F)cc1] | rac (methyl(1R,2R)-1-((4-(trifluoromethoxy)phenyl) sulfonamido)-2,3-dihydro-1H-indene-2-carboxylate) racemic (cis) | 40.37 |
| 5 | 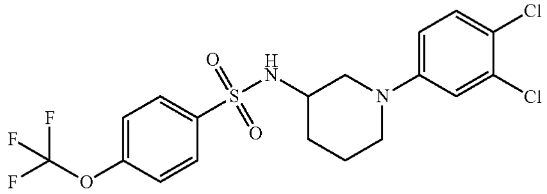 [SMILES: O=S(=O)(NC1CCCN(c2ccc(Cl)c(Cl)c2)C1)c1ccc(OC(F)(F)F)cc1] | N-(1-(3,4-dichlorophenyl)piperidin-3-yl)-4-(trifluoromethoxy) benzenesulfonamide | 52.75 |
| 6 | 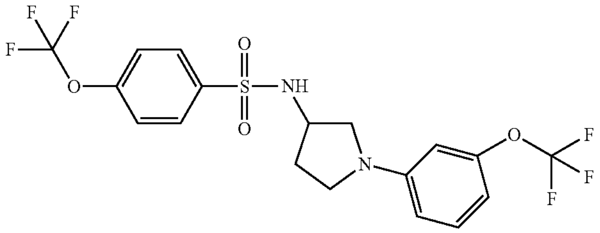 [SMILES: O=S(=O)(NC1CCN(c2cccc(OC(F)(F)F)c2)C1)c1ccc(OC(F)(F)F)cc1] | 4-(trifluoromethoxy)-N-(1-(3-(trifluoromethoxy)phenyl) pyrrolidin-3-yl) benzenesulfonamide | 59.3 |
| 7 | 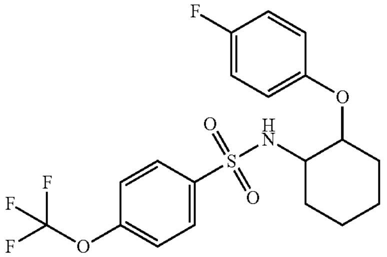 [SMILES: O=S(=O)(NC1CCCCC1Oc1ccc(F)cc1)c1ccc(OC(F)(F)F)cc1] | N-(2-(4-fluorophenoxy)cyclohexyl)-4-(trifluoromethoxy) benzenesulfonamide | 65.94 |

TABLE 35-continued

| No. | Structure | Nomenclature | $GI_{50}$ (μM) |
|---|---|---|---|
| Cell viability assay data for compounds 1-100 | | | |
| 8 | 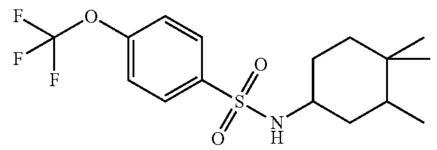 [SMILES: CC1CC(NS(=O)(=O)c2ccc(OC(F)(F)F)cc2)CCC1(C)C] | 4-(trifluoromethoxy)-N-(3,4,4-trimethylcyclohexyl) benzenesulfonamide | 73.29 |
| 9 | 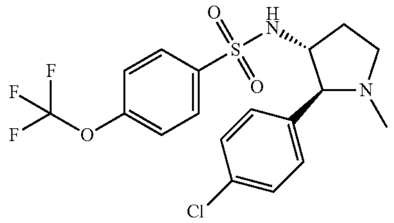 [SMILES: CN1CC[C@@H](NS(=O)(=O)c2ccc(OC(F)(F)F)cc2)[C@@H]1c1ccc(Cl)cc1] | rac N-((2S,3R)-2-(4-chlorophenyl)-1-methylpyrrolidin-3-yl)-4-(trifluoromethoxy) benzenesulfonamide racemic (trans) | 51.51 |
| 10 | 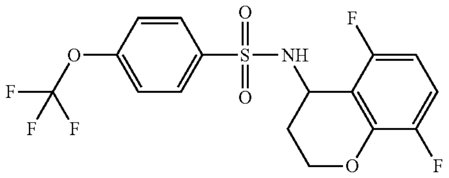 [SMILES: O=S(=O)(NC1CCOc2c(F)ccc(F)c21)c1ccc(OC(F)(F)F)cc1] | N-(5,8-difluorochroman-4-yl)-4-(trifluoromethoxy) benzenesulfonamide | 67.53 |
| 11 | 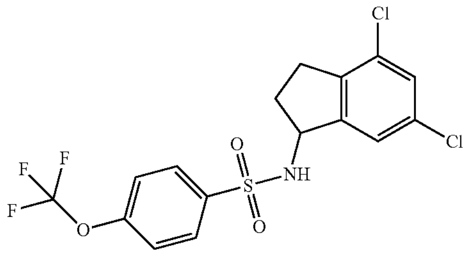 [SMILES: O=S(=O)(NC1CCc2c(Cl)cc(Cl)cc21)c1ccc(OC(F)(F)F)cc1] | N-(4,6-dichloro-2,3-dihydro-1H-inden-1-yl)-4-(trifluoromethoxy) benzenesulfonamide | 44.25 |
| 12 | 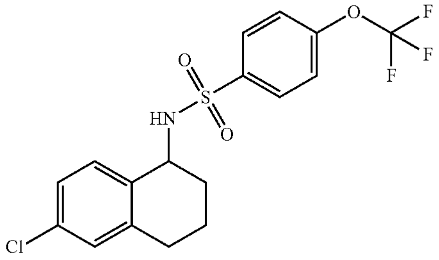 [SMILES: O=S(=O)(NC1CCCc2cc(Cl)ccc21)c1ccc(OC(F)(F)F)cc1] | N-(6-chloro-1,2,3,4-tetrahydronaphthalen-1-yl)-4-(trifluoromethoxy) benzenesulfonamide | 49.01 |
| 13 | 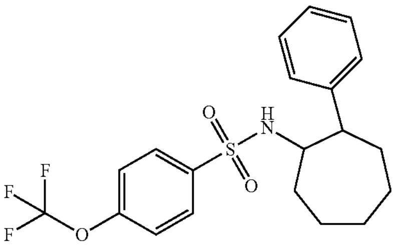 [SMILES: O=S(=O)(NC1CCCCCC1c1ccccc1)c1ccc(OC(F)(F)F)cc1] | N-(2-phenylcycloheptyl)-4-(trifluoromethoxy) benzenesulfonamide | 55.62 |

TABLE 35-continued

Cell viability assay data for compounds 1-100

| No. | Structure | Nomenclature | $GI_{50}$ (μM) |
|---|---|---|---|
| 14 | 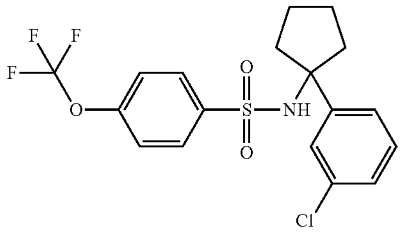 [SMILES: O=S(=O)(NC1(c2cccc(Cl)c2)CCCC1)c1ccc(OC(F)(F)F)cc1] | N-(1-(3-chlorophenyl)cyclopentyl)-4-(trifluoromethoxy) benzenesulfonamide | 42.78 |
| 15 | 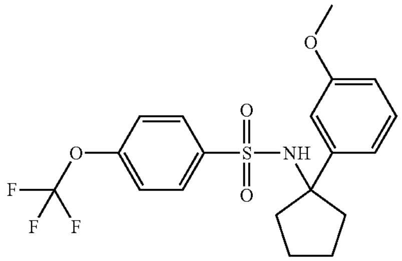 [SMILES: COc1cccc(C2(NS(=O)(=O)c3ccc(OC(F)(F)F)cc3)CCCC2)c1] | N-(1-(3-methoxyphenyl)cyclopentyl)-4-(trifluoromethoxy) benzenesulfonamide | 49.17 |
| 16 | 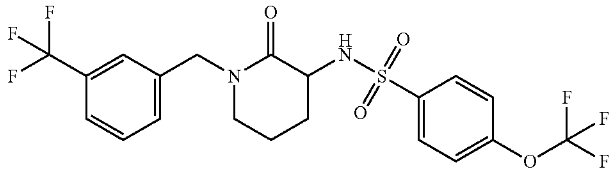 [SMILES: O=C1C(NS(=O)(=O)c2ccc(OC(F)(F)F)cc2)CCCN1Cc1cccc(C(F)(F)F)c1] | N-(2-oxo-1-(3-(trifluoromethyl)benzyl) piperidin-3-yl)-4-(trifluoromethoxy) benzenesulfonamide | 34.43 |
| 17 | 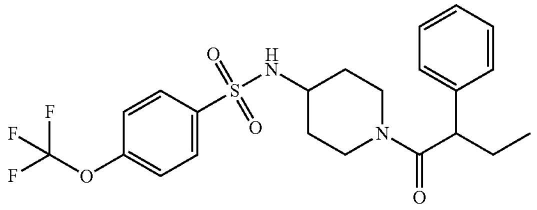 [SMILES: CCC(C(=O)N1CCC(NS(=O)(=O)c2ccc(OC(F)(F)F)cc2)CC1)c1ccccc1] | N-(1-(2-phenylbutanoyl)piperidin-4-yl)-4-(trifluoromethoxy) benzenesulfonamide | 57.96 |
| 18 | 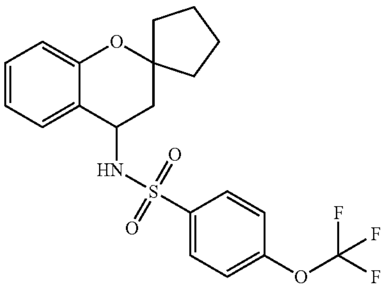 [SMILES: O=S(=O)(NC1CC2(CCCC2)Oc2ccccc21)c1ccc(OC(F)(F)F)cc1] | N-(spiro[chromane-2,1'-cyclopentan]-4-yl)-4-(trifluoromethoxy) benzenesulfonamide | 37.4 |
| 19 | 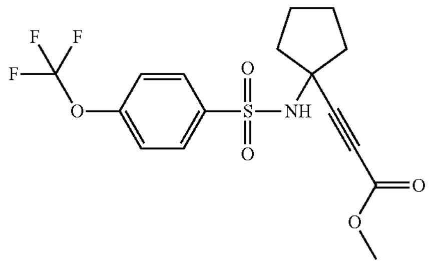 [SMILES: COC(=O)C#CC1(NS(=O)(=O)c2ccc(OC(F)(F)F)cc2)CCCC1] | methyl 3-(1-((4-(trifluoromethoxy)phenyl) sulfonamido)cyclopentyl) propiolate | 43.0 |

TABLE 35-continued

Cell viability assay data for compounds 1-100

| No. | Structure | Nomenclature | $GI_{50}$ (μM) |
|---|---|---|---|
| 20 | 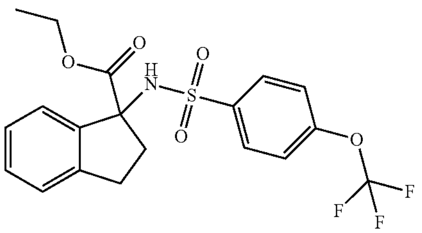 [SMILES: CCOC(=O)C1(NS(=O)(=O)c2ccc(OC(F)(F)F)cc2)CCc2ccccc21] | ethyl 1-((4-(trifluoromethoxy)phenyl) sulfonamido)-2,3-dihydro-1H-indene-1-carboxylate | 60.0 |
| 21 | 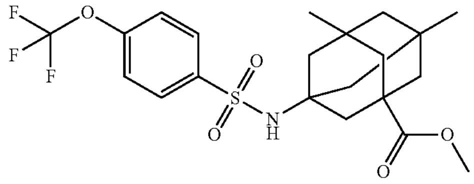 [SMILES: COC(=O)C12CC3(C)CC(C)(CC(NS(=O)(=O)c4ccc(OC(F)(F)F)cc4)(C3)C1)C2] | methyl 3,5-dimethyl-7-((4-(trifluoromethoxy)phenyl) sulfonamido)adamantane-1-carboxylate | 30.0 |
| 22 | 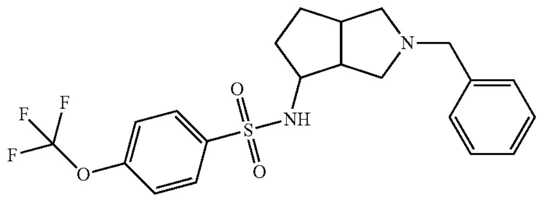 [SMILES: O=S(=O)(NC1CCC2CN(Cc3ccccc3)CC21)c1ccc(OC(F)(F)F)cc1] | N-(2-benzyloctahydrocyclopenta[c] pyrrol-4-yl)-4-(trifluoromethoxy) benzenesulfonamide | 70.0 |
| 23 | 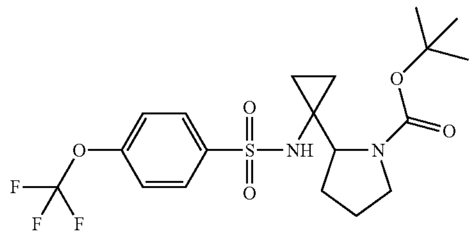 [SMILES: CC(C)(C)OC(=O)N1CCCC1C1(NS(=O)(=O)c2ccc(OC(F)(F)F)cc2)CC1] | tert-butyl 2-(1-((4-(trifluoromethoxy)phenyl) sulfonamido)cyclopropyl) pyrrolidine-1-carboxylate | 26 |
| 24 | 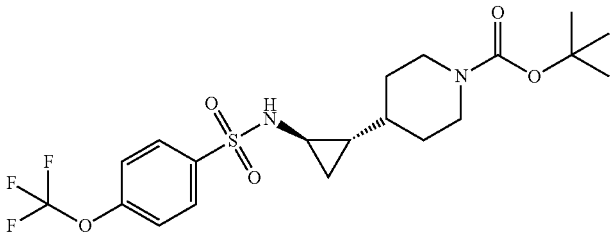 [SMILES: CC(C)(C)OC(=O)N1CCC([C@@H]2C[C@H]2NS(=O)(=O)c2ccc(OC(F)(F)F)cc2)CC1] | rac (tert-butyl 4-((1S,2R)-2-((4-(trifluoromethoxy)phenyl) sulfonamido)cyclopropyl) piperidine-1-carboxylate) racemic (trans) | 16.0 |
| 25 | 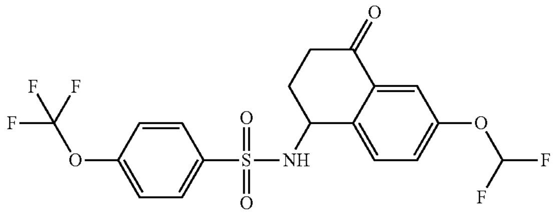 [SMILES: O=C1CCC(NS(=O)(=O)c2ccc(OC(F)(F)F)cc2)c2ccc(OC(F)F)cc21] | N-(6-(difluoromethoxy)-4-oxo-1,2,3,4-tetrahydronaphthalen-1-yl)-4-(trifluoromethoxy) benzenesulfonamide | 30.0 |

TABLE 35-continued

| Cell viability assay data for compounds 1-100 | | | |
|---|---|---|---|
| No. | Structure | Nomenclature | $GI_{50}$ (μM) |
| 26 | 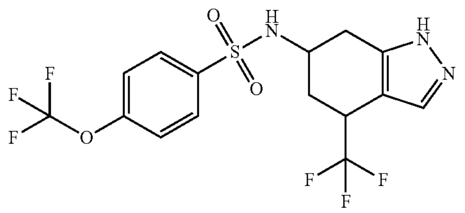 [SMILES: O=S(=O)(NC1Cc2[nH]ncc2C(C(F)(F)F)C1)c1ccc(OC(F)(F)F)cc1] | 4-(trifluoromethoxy)-N-(4-(trifluoromethyl)-4,5,6,7-tetrahydro-1H-indazol-6-yl)benzenesulfonamide | 53.0 |
| 27 | 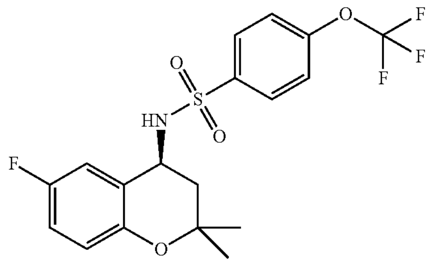 [SMILES: CC1(C)C[C@H](NS(=O)(=O)c2ccc(OC(F)(F)F)cc2)c2cc(F)ccc2O1] | (S)-N-(6-fluoro-2,2-dimethylchroman-4-yl)-4-(trifluoromethoxy) benzenesulfonamide | 12.0 |
| 28 | 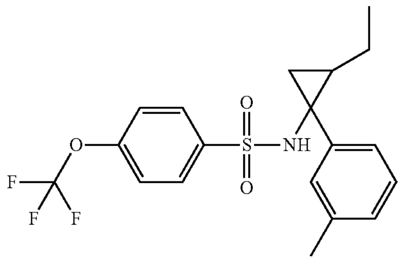 [SMILES: CCC1CC1(NS(=O)(=O)c1ccc(OC(F)(F)F)cc1)c1cccc(C)c1] | N-(2-ethyl-1-(m-tolyl)cyclopropyl)-4-(trifluoromethoxy) benzenesulfonamide | 62.0 |
| 29 | 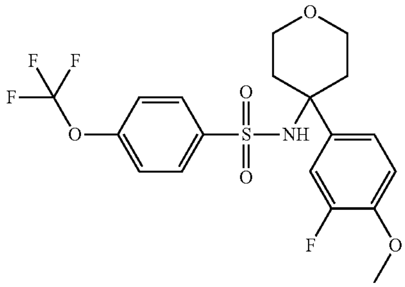 [SMILES: COc1ccc(C2(NS(=O)(=O)c3ccc(OC(F)(F)F)cc3)CCOCC2)cc1F] | N-(4-(3-fluoro-4-methoxyphenyl)tetrahydro-2H-pyran-4-yl)-4-(trifluoromethoxy) benzenesulfonamide | 39.0 |
| 30 | 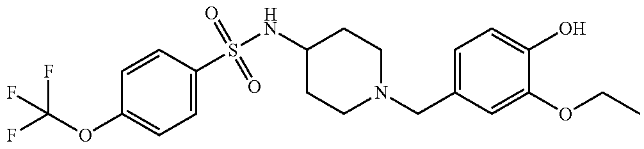 [SMILES: CCOc1cc(CN2CCC(NS(=O)(=O)c3ccc(OC(F)(F)F)cc3)CC2)ccc1O] | N-(1-(3-ethoxy-4-hydroxybenzyl)piperidin-4-yl)-4-(trifluoromethoxy) benzenesulfonamide | 30.0 |
| 31 | 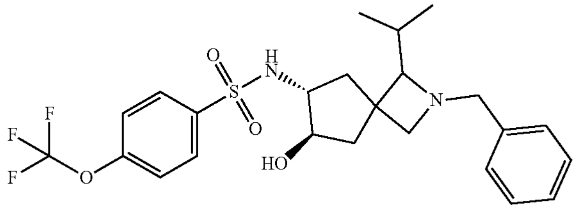 [SMILES: CC(C)C1N(Cc2ccccc2)CC12C[C@@H](O)[C@H](NS(=O)(=O)c1ccc(OC(F)(F)F)cc1)C2] | rac N-((6R,7R)-2-benzyl-7-hydroxy-1-isopropyl-2-azaspiro[3.4]octan-6-yl)-4-(trifluoromethoxy) benzenesulfonamide racemic (trans) | 45 |

TABLE 35-continued

| Cell viability assay data for compounds 1-100 | | | |
|---|---|---|---|
| No. | Structure | Nomenclature | $GI_{50}$ (μM) |
| 32 | 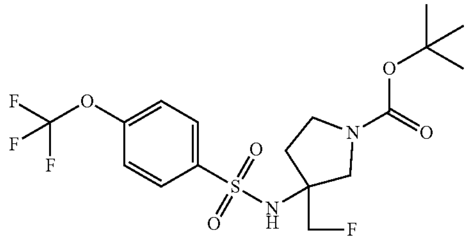 [SMILES: CC(C)(C)OC(=O)N1CCC(CF)(NS(=O)(=O)c2ccc(OC(F)(F)F)cc2)C1] | tert-butyl 3-(fluoromethyl)-3-((4-(trifluoromethoxy)phenyl) sulfonamido)pyrrolidine-1-carboxylate | 30.0 |
| 33 | 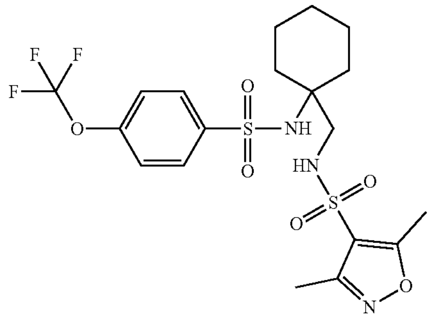 [SMILES: Cc1noc(C)c1S(=O)(=O)NCC1(NS(=O)(=O)c2ccc(OC(F)(F)F)cc2)CCCCC1] | 3,5-dimethyl-N-((1-((4-(trifluoromethoxy)phenyl) sulfonamido)cyclohexyl)methyl) isoxazole-4-sulfonamide | 53.0 |
| 34 | 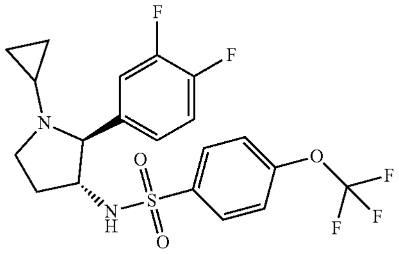 [SMILES: O=S(=O)(N[C@@H]1CCN(C2CC2)[C@H]1c1ccc(F)c(F)c1)c1ccc(OC(F)(F)F)cc1] | rac N-((2S,3R)-1-cyclopropyl-2-(3,4-difluorophenyl)pyrrolidin-3-yl)-4-(trifluoromethoxy) benzenesulfonamide racemic (trans) | 33.0 |
| 35 | 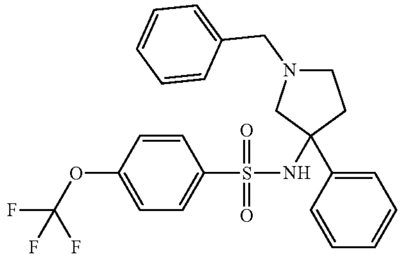 [SMILES: O=S(=O)(NC1(c2ccccc2)CCN(Cc2ccccc2)C1)c1ccc(OC(F)(F)F)cc1] | N-(1-benzyl-3-phenylpyrrolidin-3-yl)-4-(trifluoromethoxy) benzenesulfonamide | 38.73 |
| 36 | 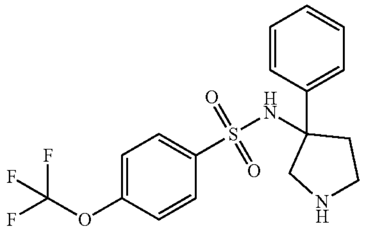 [SMILES: O=S(=O)(NC1(c2ccccc2)CCNC1)c1ccc(OC(F)(F)F)cc1] | N-(3-phenylpyrrolidin-3-yl)-4-(trifluoromethoxy) benzenesulfonamide | 41.93 |

TABLE 35-continued

| Cell viability assay data for compounds 1-100 | | | |
|---|---|---|---|
| No. | Structure | Nomenclature | $GI_{50}$ (μM) |
| 37 | 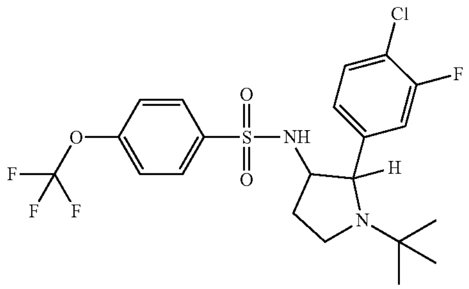 [SMILES: CC(C)(C)N1CCC(NS(=O)(=O)c2ccc(OC(F)(F)F)cc2)C1c1ccc(Cl)c(F)c1] | trans N-(1-(tert-butyl)-2-(4-chloro-3-fluorophenyl)pyrrolidin-3-yl)-4-(trifluoromethoxy) benzenesulfonamide enantiomer 1 | 15.97 |
| 38 | 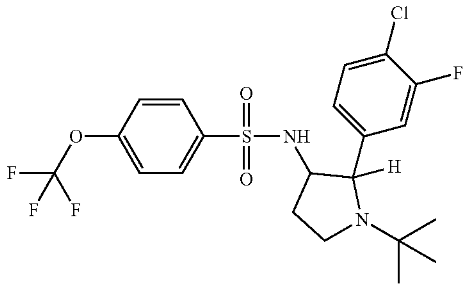 [SMILES: CC(C)(C)N1CCC(NS(=O)(=O)c2ccc(OC(F)(F)F)cc2)C1c1ccc(Cl)c(F)c1] | trans N-(1-(tert-butyl)-2-(4-chloro-3-fluorophenyl)pyrrolidin-3-yl)-4-(trifluoromethoxy) benzenesulfonamide enantiomer II | 19.0 |
| 39 | 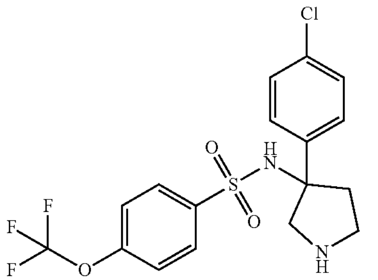 [SMILES: O=S(=O)(NC1(c2ccc(Cl)cc2)CCNC1)c1ccc(OC(F)(F)F)cc1] | N-(3-(4-chlorophenyl)pyrrolidin-3-yl)-4-(trifluoromethoxy) benzenesulfonamide | 14.04 |
| 40 | 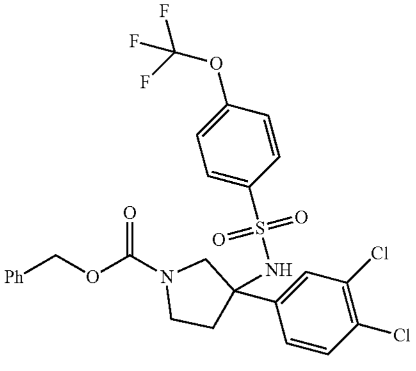 [SMILES: O=C(OCc1ccccc1)N1CCC(NS(=O)(=O)c2ccc(OC(F)(F)F)cc2)(c2ccc(Cl)c(Cl)c2)C1] | benzyl 3-(3,4-dichlorophenyl)-3-((4-(trifluoromethoxy)phenyl) sulfonamido)pyrrolidine-1-carboxylate | 25.54 |
| 41 | 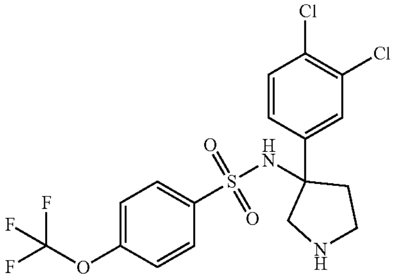 [SMILES: O=S(=O)(NC1(c2ccc(Cl)c(Cl)c2)CCNC1)c1ccc(OC(F)(F)F)cc1] | N-(3-(3,4-dichlorophenyl)pyrrolidin-3-yl)-4-(trifluoromethoxy) benzenesulfonamide | 10.39 |

TABLE 35-continued

Cell viability assay data for compounds 1-100

| No. | Structure | Nomenclature | $GI_{50}$ (μM) |
|---|---|---|---|
| 42 | 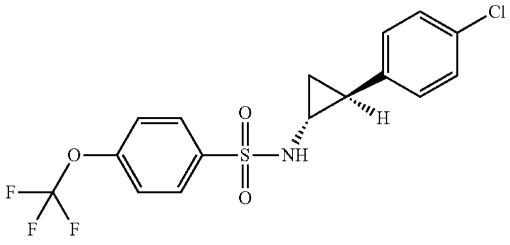 [SMILES: O=S(=O)(N[C@@H]1C[C@H]1c1ccc(Cl)cc1)c1ccc(OC(F)(F)F)cc1] | rac N-((1R,2S)-2-(4-chlorophenyl)cyclopropyl)-4-(trifluoromethoxy) benzenesulfonamide racemic (trans) | 67.16 |
| 43 | 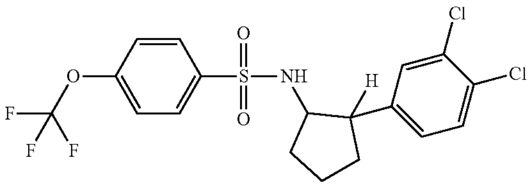 [SMILES: O=S(=O)(NC1CCCC1c1ccc(Cl)c(Cl)c1)c1ccc(OC(F)(F)F)cc1] | N-(2-(3,4-dichlorophenyl)cyclopentyl)-4-(trifluoromethoxy) benzenesulfonamide diastereomer I (racemic) | 37.53 |
| 44 | 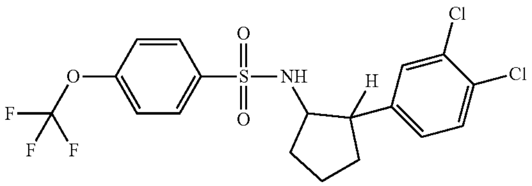 [SMILES: O=S(=O)(NC1CCCC1c1ccc(Cl)c(Cl)c1)c1ccc(OC(F)(F)F)cc1] | N-(2-(3,4-dichlorophenyl)cyclopentyl)-4-(trifluoromethoxy) benzenesulfonamide diastereomer II (racemic) | 45.36 |
| 45 | 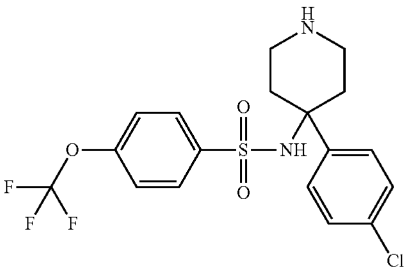 [SMILES: O=S(=O)(NC1(c2ccc(Cl)cc2)CCNCC1)c1ccc(OC(F)(F)F)cc1] | N-(4-(4-chlorophenyl)piperidin-4-yl)-4-(trifluoromethoxy) benzenesulfonamide | 11.0 |
| 46 | 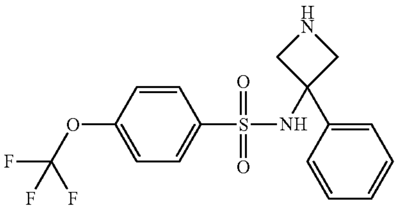 [SMILES: O=S(=O)(NC1(c2ccccc2)CNC1)c1ccc(OC(F)(F)F)cc1] | N-(3-phenylazetidin-3-yl)-4-(trifluoromethoxy) benzenesulfonamide | 80 |
| 47 | 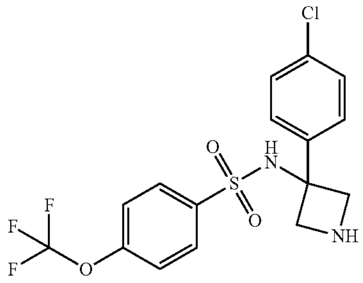 [SMILES: O=S(=O)(NC1(c2ccc(Cl)cc2)CNC1)c1ccc(OC(F)(F)F)cc1] | N-(3-(4-chlorophenyl)azetidin-3-yl)-4-(trifluoromethoxy) benzenesulfonamide | 31.78 |

TABLE 35-continued

| Cell viability assay data for compounds 1-100 | | | |
|---|---|---|---|
| No. | Structure | Nomenclature | $GI_{50}$ (μM) |
| 48 | 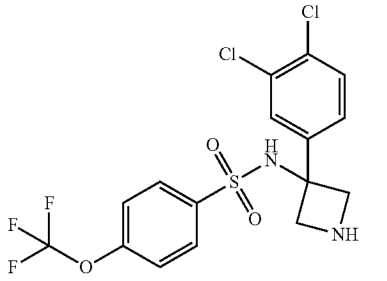 [SMILES: O=S(=O)(NC1(c2ccc(Cl)c(Cl)c2)CNC1)c1ccc(OC(F)(F)F)cc1] | N-(3-(3,4-dichlorophenyl)azetidin-3-yl)-4-(trifluoromethoxy) benzenesulfonamide | 18.18 |
| 49 | 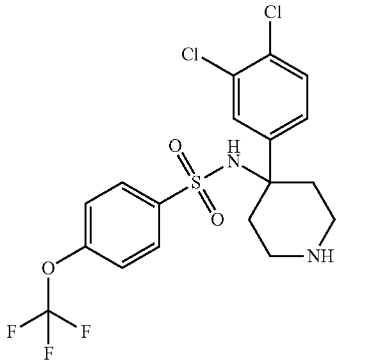 [SMILES: O=S(=O)(NC1(c2ccc(Cl)c(Cl)c2)CCNCC1)c1ccc(OC(F)(F)F)cc1] | N-(4-(3,4-dichlorophenyl)piperidin-4-yl)-4-(trifluoromethoxy) benzenesulfonamide | 6.75 |
| 50 | 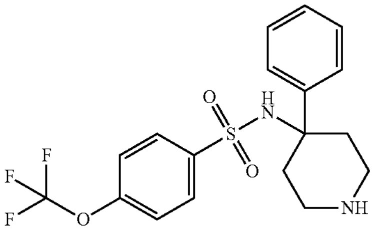 [SMILES: O=S(=O)(NC1(c2ccccc2)CCNCC1)c1ccc(OC(F)(F)F)cc1] | N-(4-phenylpiperidin-4-yl)-4-(trifluoromethoxy) benzenesulfonamide | 23.33 |
| 51 | 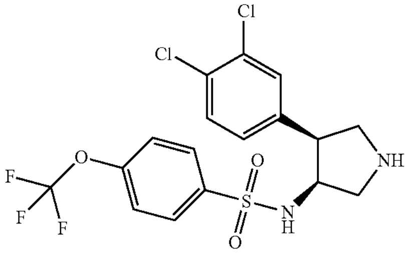 [SMILES: O=S(=O)(N[C@@H]1CNC[C@@H]1c1ccc(Cl)c(Cl)c1)c1ccc(OC(F)(F)F)cc1] | rac N-((3S,4S)-4-(3,4-dichlorophenyl)pyrrolidin-3-yl)-4-(trifluoromethoxy) benzenesulfonamide racemic (cis) | 10.41 |
| 52 | 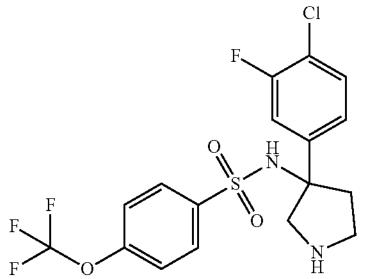 [SMILES: O=S(=O)(NC1(c2ccc(Cl)c(F)c2)CCNC1)c1ccc(OC(F)(F)F)cc1] | N-(3-(4-chloro-3-fluorophenyl)pyrrolidin-3-yl)-4-(trifluoromethoxy) benzenesulfonamide | 23.38 |

TABLE 35-continued

| Cell viability assay data for compounds 1-100 | | | |
|---|---|---|---|
| No. | Structure | Nomenclature | $GI_{50}$ (μM) |
| 53 | 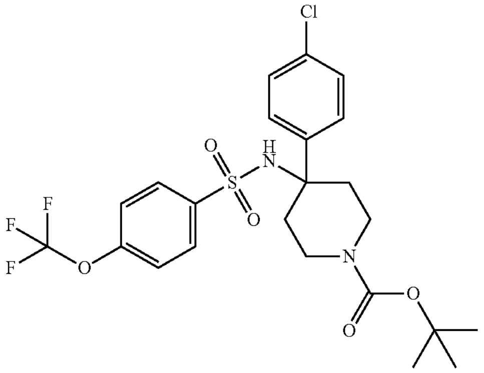 [SMILES: CC(C)(C)OC(=O)N1CCC(NS(=O)(=O)c2ccc(OC(F)(F)F)cc2)(c2ccc(Cl)cc2)CC1] | tert-butyl 4-(4-chlorophenyl)-4-((4-(trifluoromethoxy)phenyl) sulfonamido)piperidine-1-carboxylate | 16.31 |
| 54 | 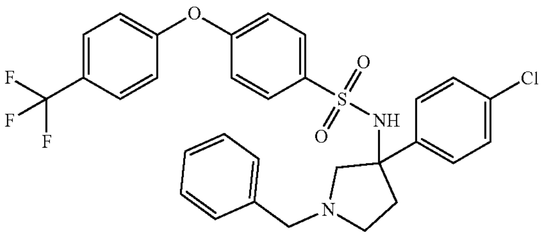 [SMILES: O=S(=O)(NC1(c2ccc(Cl)cc2)CCN(Cc2ccccc2)C1)c1ccc(Oc2ccc(C(F)(F)F)cc2)cc1] | N-(1-benzyl-3-(4-chlorophenyl)pyrrolidin-3-yl)-4-(4-(trifluoromethyl)phenoxy) benzenesulfonamide | 26.82 |
| 55 | 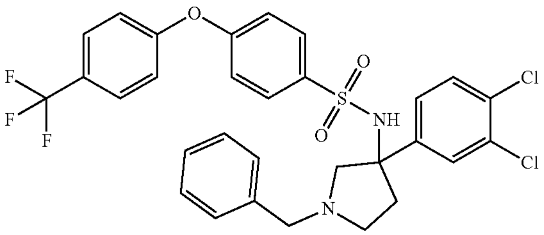 [SMILES: O=S(=O)(NC1(c2ccc(Cl)c(Cl)c2)CCN(Cc2ccccc2)C1)c1ccc(Oc2ccc(C(F)(F)F)cc2)cc1] | N-(1-benzyl-3-(3,4-dichlorophenyl)pyrrolidin-3-yl)-4-(4-(trifluoromethyl)phenoxy) benzenesulfonamide | 37.95 |
| 56 | 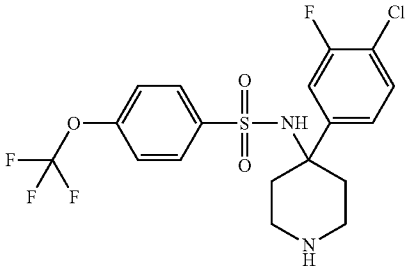 [SMILES: O=S(=O)(NC1(c2ccc(Cl)c(F)c2)CCNCC1)c1ccc(OC(F)(F)F)cc1] | N-(4-(4-chloro-3-fluorophenyl)piperidin-4-yl)-4-(trifluoromethoxy) benzenesulfonamide | 11.01 |
| 57 | 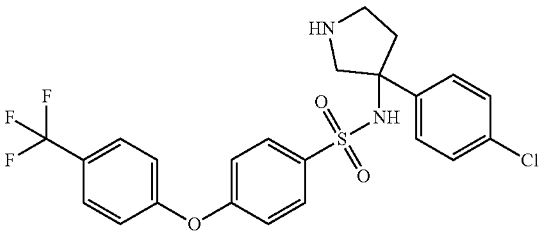 [SMILES: O=S(=O)(NC1(c2ccc(Cl)cc2)CCNC1)c1ccc(Oc2ccc(C(F)(F)F)cc2)cc1] | N-(3-(4-chlorophenyl)pyrrolidin-3-yl)-4-(4-(trifluoromethyl)phenoxy) benzenesulfonamide | 10.64 |

TABLE 35-continued

| Cell viability assay data for compounds 1-100 | | | |
|---|---|---|---|
| No. | Structure | Nomenclature | $GI_{50}$ (μM) |
| 58 | 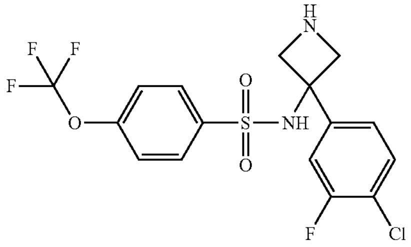 [SMILES: O=S(=O)(NC1(c2ccc(Cl)c(F)c2)CNC1)c1ccc(OC(F)(F)F)cc1] | N-(3-(4-chloro-3-fluorophenyl)azetidin-3-yl)-4-(trifluoromethoxy) benzenesulfonamide | 23.19 |
| 59 | 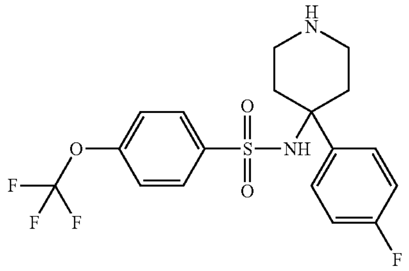 [SMILES: O=S(=O)(NC1(c2ccc(F)cc2)CCNCC1)c1ccc(OC(F)(F)F)cc1] | N-(4-(4-fluorophenyl)piperidin-4-yl)-4-(trifluoromethoxy) benzenesulfonamide | 18.14 |
| 60 | 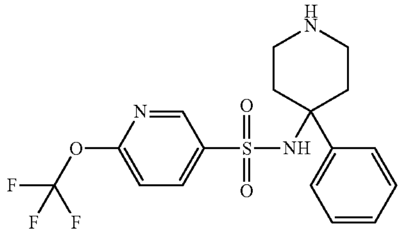 [SMILES: O=S(=O)(NC1(c2ccccc2)CCNCC1)c1ccc(OC(F)(F)F)nc1] | N-(4-phenylpiperidin-4-yl)-6-(trifluoromethoxy)pyridine-3-sulfonamide | 49.56 |
| 61 | 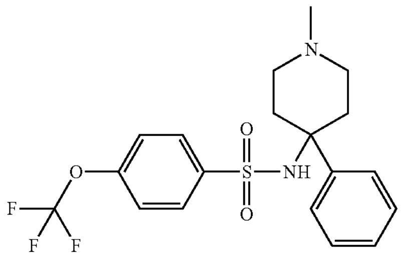 [SMILES: CN1CCC(NS(=O)(=O)c2ccc(OC(F)(F)F)cc2)(c2ccccc2)CC1] | N-(1-methyl-4-phenylpiperidin-4-yl)-4-(trifluoromethoxy) benzenesulfonamide | 44.12 |
| 62 | 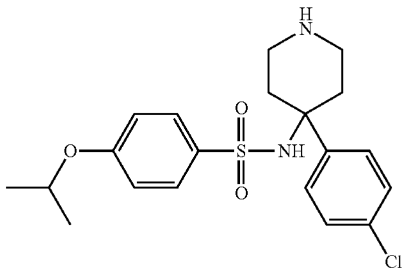 [SMILES: CC(C)Oc1ccc(S(=O)(=O)NC2(c3ccc(Cl)cc3)CCNCC2)cc1] | N-(4-(4-chlorophenyl)piperidin-4-yl)-4-isopropoxybenzenesulfonamide | 11.27 |

TABLE 35-continued

| Cell viability assay data for compounds 1-100 | | | |
|---|---|---|---|
| No. | Structure | Nomenclature | $GI_{50}$ (μM) |
| 63 | 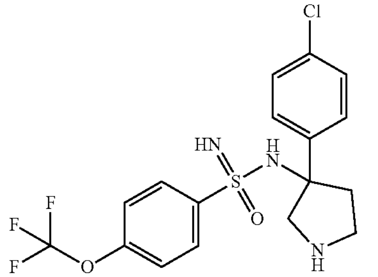 [SMILES: N=S(=O)(NC1(c2ccc(Cl)cc2)CCNC1)c1ccc(OC(F)(F)F)cc1] | N-(3-(4-chlorophenyl)pyrrolidin-3-yl)-4-(trifluoromethoxy) benzenesulfonimidamide | 38.41 |
| 64 | 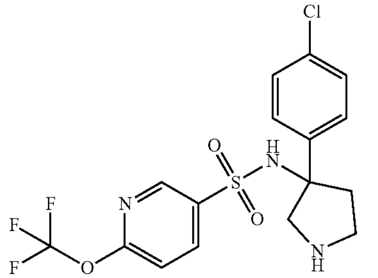 [SMILES: O=S(=O)(NC1(c2ccc(Cl)cc2)CCNC1)c1ccc(OC(F)(F)F)nc1] | N-(3-(4-chlorophenyl)pyrrolidin-3-yl)-6-(trifluoromethoxy)pyridine-3-sulfonamide hydrochloride | 44.86 |
| 65 | 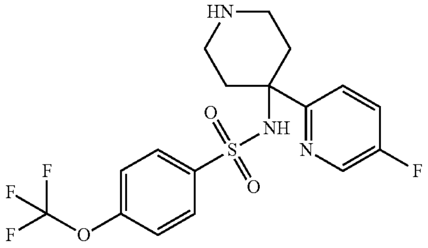 [SMILES: O=S(=O)(NC1(c2ccc(F)cn2)CCNCC1)c1ccc(OC(F)(F)F)cc1] | N-(4-(5-fluoropyridin-2-yl)piperidin-4-yl)-4-(trifluoromethoxy) benzenesulfonamide | 75.09[a] |
| 66 | 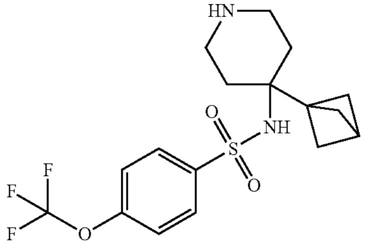 [SMILES: O=S(=O)(NC1(C23CC(C2)C3)CCNCC1)c1ccc(OC(F)(F)F)cc1] | N-(4-(bicyclo[1.1.1]pentan-1-yl)piperidin-4-yl)-4-(trifluoromethoxy) benzenesulfonamide | 68.61 |
| 67 | 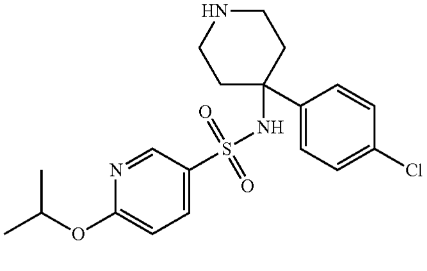 [SMILES: CC(C)Oc1ccc(S(=O)(=O)NC2(c3ccc(Cl)cc3)CCNCC2)cn1] | N-(4-(4-chlorophenyl)piperidin-4-yl)-6-isopropoxypyridine-3-sulfonamide | 18.16 |

TABLE 35-continued

| Cell viability assay data for compounds 1-100 | | | |
|---|---|---|---|
| No. | Structure | Nomenclature | $GI_{50}$ (μM) |
| 68 | 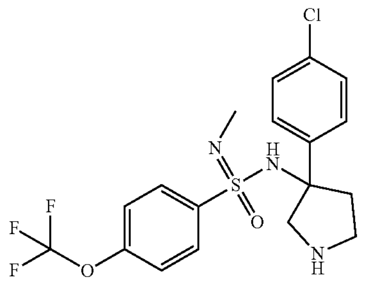 [SMILES: CN=S(=O)(NC1(c2ccc(Cl)cc2)CCNC1)c1ccc(OC(F)(F)F)cc1] | N-(3-(4-chlorophenyl)pyrrolidin-3-yl)-N'-methyl-4-(trifluoromethoxy) benzenesulfonamide | 27.24 |
| 69 | 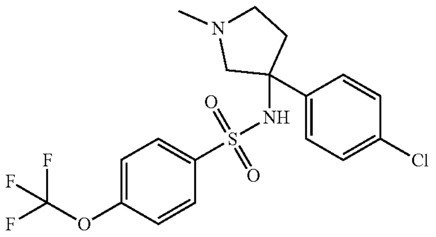 [SMILES: CN1CCC(NS(=O)(=O)c2ccc(OC(F)(F)F)cc2)(c2ccc(Cl)cc2)C1] | N-(3-(4-chlorophenyl)-1-methylpyrrolidin-3-yl)-4-(trifluoromethoxy) benzenesulfonamide | 19.53 |
| 70 | 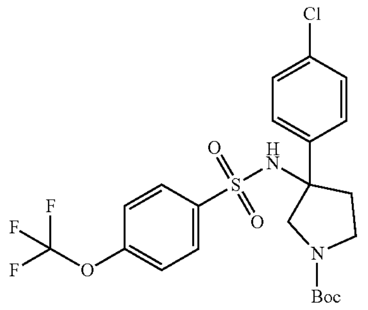 [SMILES: CC(C)(C)OC(=O)N1CCC(NS(=O)(=O)c2ccc(OC(F)(F)F)cc2)(c2ccc(Cl)cc2)C1] | tert-butyl 3-(4-chlorophenyl)-3-((4-(trifluoromethoxy)phenyl) sulfonamido)pyrrolidine-1-carboxylate | 21.66 |
| 71 | 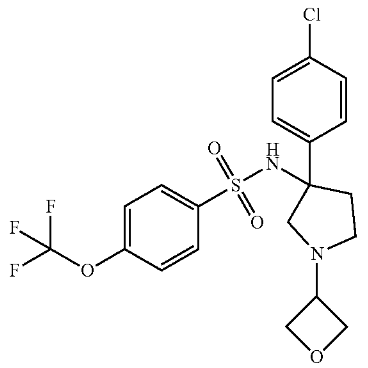 [SMILES: O=S(=O)(NC1(c2ccc(Cl)cc2)CCN(C2COC2)C1)c1ccc(OC(F)(F)F)cc1] | N-(3-(4-chlorophenyl)-1-(oxetan-3-yl)pyrrolidin-3-yl)-4-(trifluoromethoxy) benzenesulfonamide | 59.05 |
| 72 | 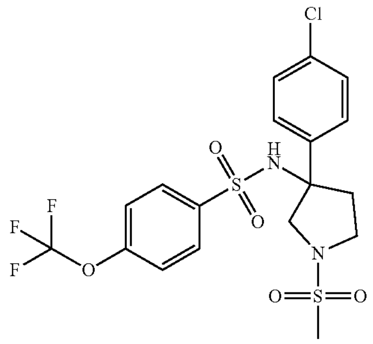 [SMILES: CS(=O)(=O)N1CCC(NS(=O)(=O)c2ccc(OC(F)(F)F)cc2)(c2ccc(Cl)cc2)C1] | N-(3-(4-chlorophenyl)-1-(methylsulfonyl)pyrrolidin-3-yl)-4-(trifluoromethoxy) benzenesulfonamide | 50.35 |

TABLE 35-continued

| Cell viability assay data for compounds 1-100 | | | |
|---|---|---|---|
| No. | Structure | Nomenclature | $GI_{50}$ (μM) |
| 73 | 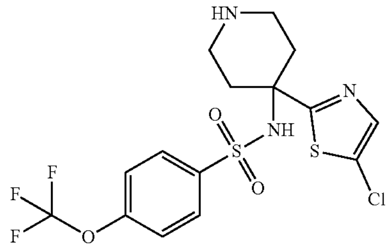 [SMILES: O=S(=O)(NC1(c2ncc(Cl)s2)CCNCC1)c1ccc(OC(F)(F)F)cc1] | N-(4-(5-chlorothiazol-2-yl)piperidin-4-yl)-4-(trifluoromethoxy) benzenesulfonamide | 56.42 |
| 74 | 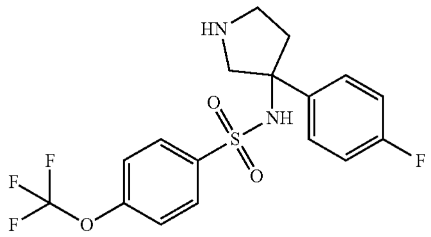 [SMILES: O=S(=O)(NC1(c2ccc(F)cc2)CCNC1)c1ccc(OC(F)(F)F)cc1] | N-(3-(4-fluorophenyl)pyrrolidin-3-yl)-4-(trifluoromethoxy) benzenesulfonamide | 47.89 |
| 75 | 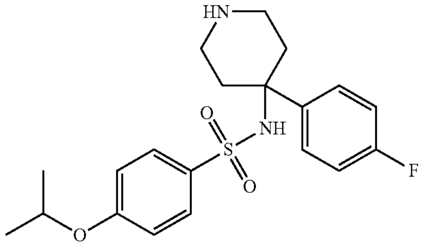 [SMILES: CC(C)Oc1ccc(S(=O)(=O)NC2(c3ccc(F)cc3)CCNCC2)cc1] | N-(4-(4-fluorophenyl)piperidin-4-yl)-4-isopropoxybenzenesulfonamide | 30.65 |
| 76 | 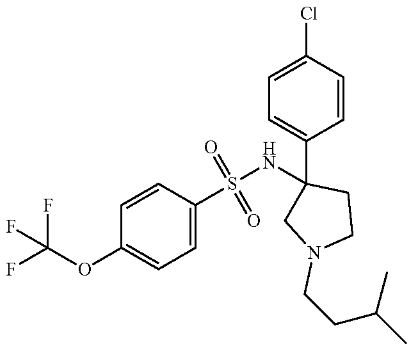 [SMILES: CC(C)CCN1CCC(NS(=O)(=O)c2ccc(OC(F)(F)F)cc2)(c2ccc(Cl)cc2)C1] | N-(3-(4-chlorophenyl)-1-isopentylpyrrolidin-3-yl)-4-(trifluoromethoxy) benzenesulfonamide | 19.86[a] |
| 77 | 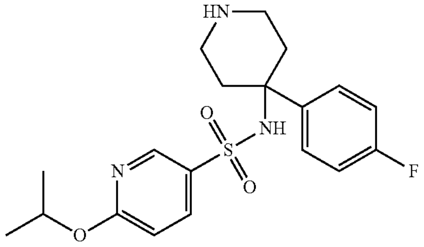 [SMILES: CC(C)Oc1ccc(S(=O)(=O)NC2(c3ccc(F)cc3)CCNCC2)cn1] | N-(4-(4-fluorophenyl)piperidin-4-yl)-6-isopropoxypyridine-3-sulfonamide | 41.67 |

TABLE 35-continued

| Cell viability assay data for compounds 1-100 | | | |
|---|---|---|---|
| No. | Structure | Nomenclature | $GI_{50}$ (μM) |
| 78 | 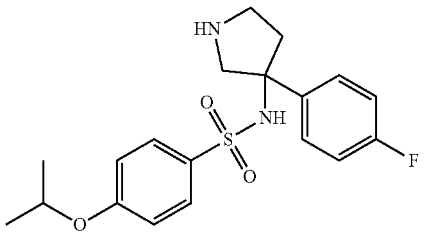 [SMILES: CC(C)Oc1ccc(S(=O)(=O)NC2(c3ccc(F)cc3)CCNC2)cc1] | N-(3-(4-fluorophenyl)pyrrolidin-3-yl)-4-isopropoxybenzenesulfonamide | 70.45 |
| 79 | 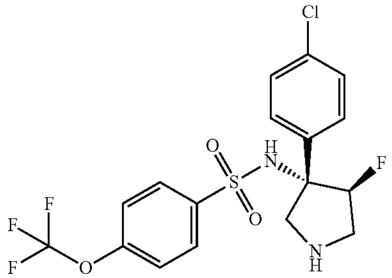 [SMILES: O=S(=O)(N[C@@]1(c2ccc(Cl)cc2)CNC[C@@H]1F)c1ccc(OC(F)(F)F)cc1] | rac N-((3S,4S)-3-(4-chlorophenyl)-4-fluoropyrrolidin-3-yl)-4-(trifluoromethoxy) benzenesulfonamide racemic (trans) | 55.82 |
| 80 | 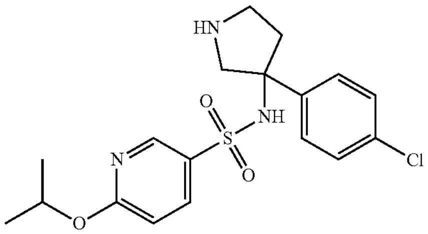 [SMILES: CC(C)Oc1ccc(S(=O)(=O)NC2(c3ccc(Cl)cc3)CCNC2)cn1] | N-(3-(4-chlorophenyl)pyrrolidin-3-yl)-6-isoprpxoypyridine-3-sulfonamide | 50.03 |
| 81 | 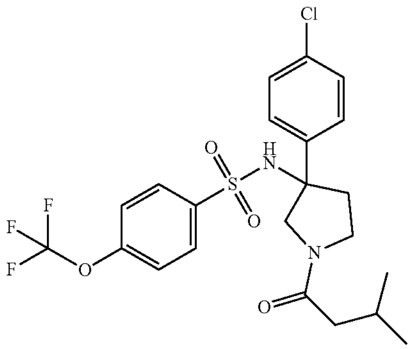 [SMILES: CC(C)CC(=O)N1CCC(NS(=O)(=O)c2ccc(OC(F)(F)F)cc2)(c2ccc(Cl)cc2)C1] | N-(3-(4-chlorophenyl)-1-(3-methylbutanoyl)pyrrolidin-3-yl)-4-(trifluoromethoxy) benzenesulfonamide | 45.75 |
| 82 | 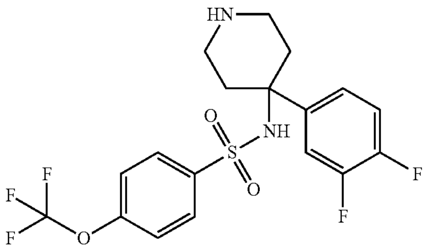 [SMILES: O=S(=O)(NC1(c2ccc(F)c(F)c2)CCNCC1)c1ccc(OC(F)(F)F)cc1] | N-(4-(3,4-difluorophenyl)piperidin-4-yl)-4-(trifluoromethoxy) benzenesulfonamide | 14.44 |

TABLE 35-continued

| No. | Structure | Nomenclature | $GI_{50}$ (μM) |
|---|---|---|---|
| 83 | 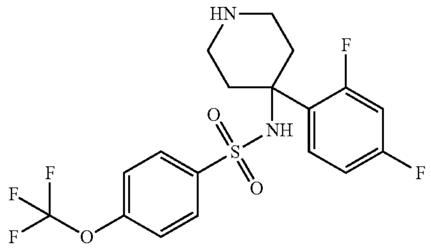 [SMILES: O=S(=O)(NC1(c2ccc(F)cc2F)CCNCC1)c1ccc(OC(F)(F)F)cc1] | N-(4-(2,4-difluorophenyl)piperidin-4-yl)-4-(trifluoromethoxy) benzenesulfonamide | 32.05 |
| 84 | 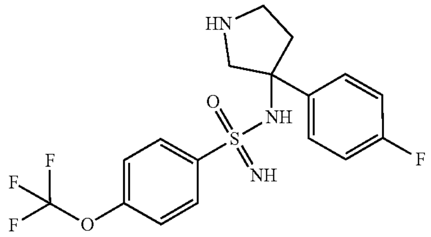 [SMILES: N=S(=O)(NC1(c2ccc(F)cc2)CCNC1)c1ccc(OC(F)(F)F)cc1] | N-(3-(4-fluorophenyl)pyrrolidin-3-yl)-4-(trifluoromethoxy) benzenesulfonamide | 75.09[a] |
| 85 | 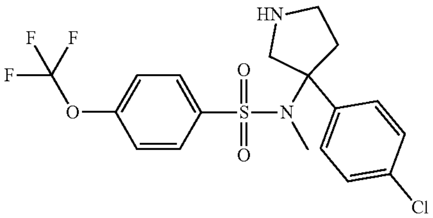 [SMILES: CN(C1(c2ccc(Cl)cc2)CCNC1)S(=O)(=O)c1ccc(OC(F)(F)F)cc1] | N-(3-(4-chlorophenyl)pyrrolidin-3-yl)-N-methyl-4-(trifluoromethoxy) benzenesulfonamide | 33.49 |
| 86 | 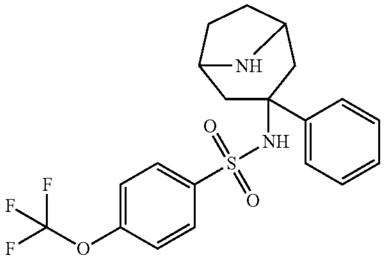 [SMILES: O=S(=O)(NC1(c2ccccc2)CC2CCC(C1)N2)c1ccc(OC(F)(F)F)cc1] | N-(3-phenyl-8-azabicyclo[3.2.1]octan-3-yl)-4 (trifluoromethoxy) benzenesulfonamide | 23.67 |
| 87 | 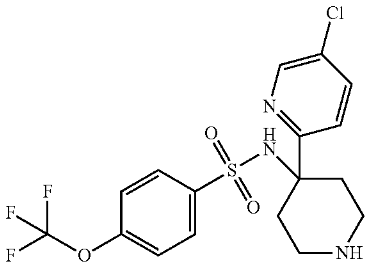 [SMILES: O=S(=O)(NC1(c2ccc(Cl)cn2)CCNCC1)c1ccc(OC(F)(F)F)cc1] | N-(4-(5-chloropyridin-2-yl)piperidin-4-yl)-4-(trifluoromethoxy) benzenesulfonamide | 46.59 |
| 88 | 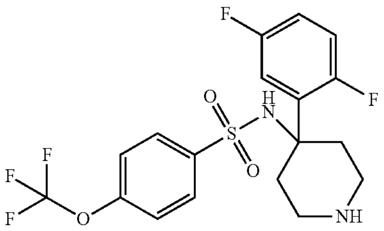 [SMILES: O=S(=O)(NC1(c2cc(F)ccc2F)CCNCC1)c1ccc(OC(F)(F)F)cc1] | N-(4-(2,5-difluorophenyl)piperidin-4-yl)-4-(trifluoromethoxy) benzenesulfonamide | 36.45 |

TABLE 35-continued

Cell viability assay data for compounds 1-100

| No. | Structure | Nomenclature | $GI_{50}$ (μM) |
| --- | --- | --- | --- |
| 89 | 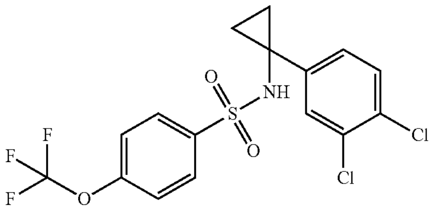 [SMILES: O=S(=O)(NC1(c2ccc(Cl)c(Cl)c2)CC1)c1ccc(OC(F)(F)F)cc1] | N-(2-(3,4-dichlorophenyl)cyclopropyl)-4-(trifluoromethoxy) benzenesulfonamide | 46.65 |
| 90 | 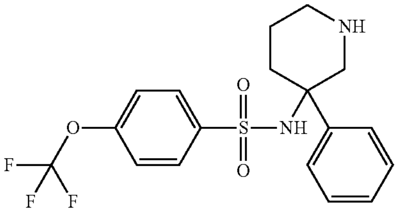 [SMILES: O=S(=O)(NC1(c2ccccc2)CCCNC1)c1ccc(OC(F)(F)F)cc1] | N-(3-phenylpiperidin-3-yl)-4-(trifluoromethoxy) benzenesulfonamide | 48.92 |
| 91 | 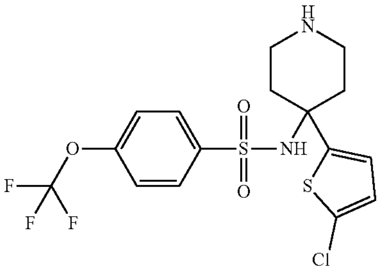 [SMILES: O=S(=O)(NC1(c2ccc(Cl)s2)CCNCC1)c1ccc(OC(F)(F)F)cc1] | N-(4-(5-chlorothiophen-2-yl)piperidin-4-yl)-4-(trifluoromethoxy) benzenesulfonamide | 9.6 |
| 92 | 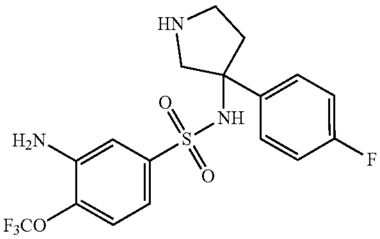 [SMILES: Nc1cc(S(=O)(=O)NC2(c3ccc(F)cc3)CCNC2)ccc1OC(F)(F)F] | 3-amino-N-(3-(4-fluorophenyl)pyrrolidin-3-yl)-4-(trifluoromethoxy) benzenesulfonamide | 50.26[a] |
| 93 | 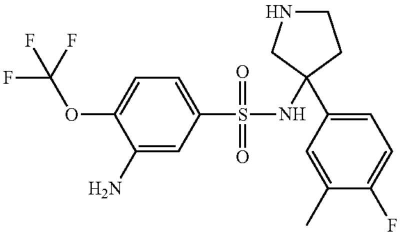 [SMILES: Cc1cc(C2(NS(=O)(=O)c3ccc(OC(F)(F)F)c(N)c3)CCNC2)ccc1F] | 3-amino-N-(3-(4-fluoro-3-methylphenyl)pyrrolidin-3-yl)-4-(trifluoromethoxy) benzenesulfonamide | 65.49 |
| 94 | 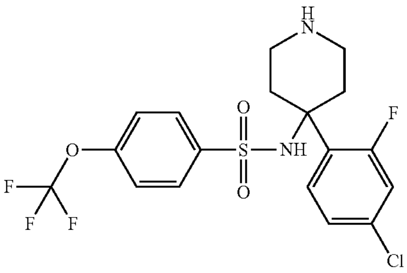 | N-(4-(4-chloro-2-fluorophenyl)piperidin-4-yl)-4-(trifluoromethoxy) benzenesulfonamide | 15.84 |

TABLE 35-continued

| Cell viability assay data for compounds 1-100 | | | |
|---|---|---|---|
| No. | Structure | Nomenclature | $GI_{50}$ (μM) |
| 95 | 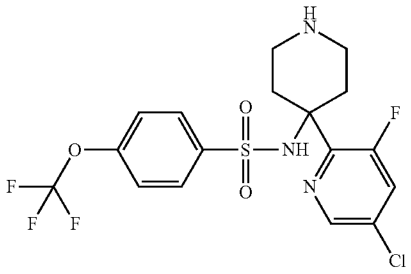 | N-(4-(5-chloro-3-fluoropyridin-2-yl)piperidin-4-yl)-4-(trifluoromethoxy) benzenesulfonamide | 45.82 |
| 96 | 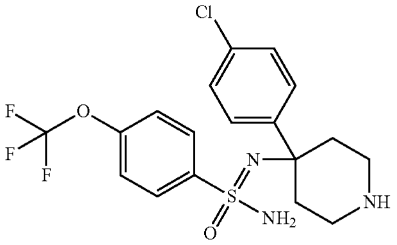 [SMILES: NS(=O)(=NC1(c2ccc(Cl)cc2)CCNCC1)c1ccc(OC(F)(F)F)cc1] | N'-(4-(4-chlorophenyl)piperidin-4-yl)-4-(trifluoromethoxy) benzenesulfonamide | 13.67 |
| 97 | 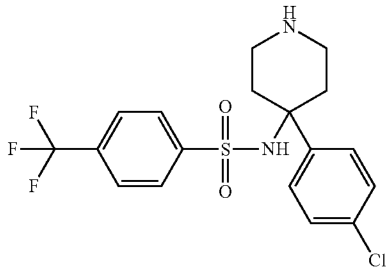 [SMILES: O=S(=O)(NC1(c2ccc(Cl)cc2)CCNCC1)c1ccc(C(F)(F)F)cc1] | N-(4-(4-chlorophenyl)piperidin-4-yl)-4-(trifluoromethyl) benzenesulfonamide | 11.57 |
| 98 | 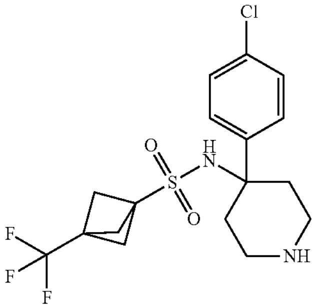 [SMILES: O=S(=O)(NC1(c2ccc(Cl)cc2)CCNCC1)C12CC(C(F)(F)F)(C1)C2] | N-(4-(4-chlorophenyl)piperidin-4-yl)-3-(trifluoromethyl)bicyclo[1.1.1] pentane-1-sulfonamide | 46.59 |
| 99 | 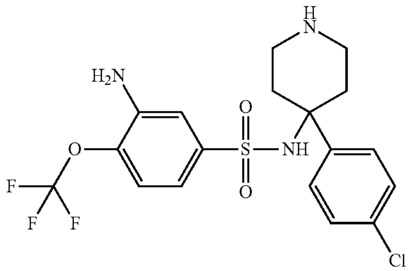 [SMILES: Nc1cc(S(=O)(=O)NC2(c3ccc(Cl)cc3)CCNCC2)ccc1OC(F)(F)F] | 3-amino-N-(4-(4-chlorophenyl)piperidin-4-yl)-4-(trifluoromethoxy) benzenesulfonamide | 46.05 |

TABLE 35-continued

Cell viability assay data for compounds 1-100

| No. | Structure | Nomenclature | $GI_{50}$ (μM) |
|---|---|---|---|
| 100 | 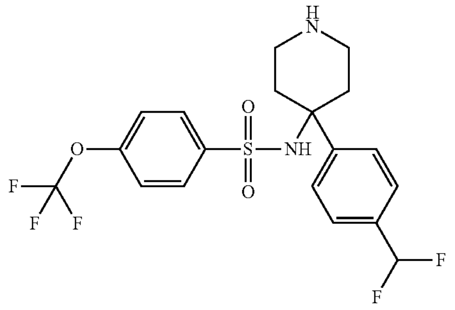 [SMILES: O=S(=O)(NC1(c2ccc(C(F)F)cc2)CCNCC1)c1ccc(OC(F)(F)F)cc1] | N-(4-(4-(difluoromethyl)phenyl)piperidin-4-yl)-4-(trifluoromethoxy) benzenesulfonamide | 22.33 |

[a]$GI_{50}$ value corresponds to HCC1937 cell line assay

The embodiments described hereinbefore may be used in any combination with each other. Several of the embodiments may be combined together to form a further embodiment. A product, a method or a use, to which the invention is related, may comprise at least one of the embodiments described hereinbefore. It will be understood that the benefits and advantages described above may relate to one embodiment or may relate to several embodiments. The embodiments are not limited to those that solve any or all of the stated problems or those that have any or all of the stated benefits and advantages. It will further be understood that reference to 'an' item refers to one or more of those items.

It is obvious to a person skilled in the art that with the advancement of technology, the basic idea of the invention may be implemented in various ways. The invention and its embodiments are thus not limited to the examples described above; instead they may vary within the scope of the claims.

The terms and expressions employed herein are used as terms of description and not of limitation, and there is no intention in the use of such terms and expressions of excluding any equivalents of the features shown and described or portions thereof, but it is recognized that various modifications are possible within the scope of the embodiments of the present application. Thus, it should be understood that although the present application describes specific embodiments and optional features, modification and variation of the compositions, methods, and concepts herein disclosed may be resorted to by those of ordinary skill in the art, and that such modifications and variations are considered to be within the scope of embodiments of the present application.

Enumerated Embodiments

The following exemplary embodiments are provided, the numbering of which is not to be construed as designating levels of importance:

Embodiment 1 provides a compound of formula (I), or a salt, solvate, enantiomer, diastereoisomer, isotopologue, or tautomer thereof, selected from the group consisting of:

(Ia)

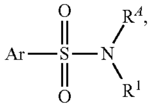

-continued (Ib)

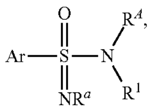

(Ic)

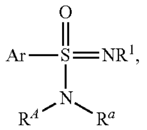

(Id)

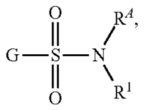

(Ie)

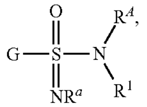

(If)

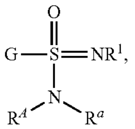

wherein:

Ar is $C_6$-$C_{10}$ aryl or $C_2$-$C_{10}$ heteroaryl, which is optionally substituted with at least one substituent selected from the group consisting of $C_1$-$C_6$ alkyl, $C_1$-$C_6$ haloalkyl, $C_1$-$C_6$ aminoalkyl, $C_1$-$C_6$ hydroxyalkyl, $C_2$-$C_6$ alkenyl, $C_2$-$C_6$ alkynyl, $C_1$-$C_6$ alkoxy, $C_1$-$C_6$ haloalkoxy, $C_2$-$C_{10}$ heteroaryl, $C_6$-$C_{10}$ aryl, $C_6$-$C_{10}$ aryloxy, halogen, OH, $NH_2$, CN, $NO_2$, —C(=O)$R^a$, —C(=O)O$R^a$, and —C(=O)N($R^a$)($R^a$), wherein each $C_6$-$C_{10}$ aryl, $C_2$-$C_{10}$ heteroaryl, or $C_6$-$C_{10}$ aryloxy substituent in Ar is independently optionally substituted with at least one substituent selected from the group consisting of $C_1$-$C_3$ alkyl, $C_1$-$C_3$ haloalkyl, $C_1$-$C_3$ alkoxy, $C_1$-$C_3$ haloalkoxy, F, Cl, Br, I, OH, CN, $NO_2$, —C(=O)O$R^a$, and —C(=O)N($R^a$)($R^a$), and wherein two vicinal substituents of Ar may combine to provide a 5- to 8-membered ring which is fused with Ar;

G is optionally substituted $C_3$-$C_8$ cycloalkyl, which is optionally substituted with at least one substituent selected from the group consisting of $C_1$-$C_6$ alkyl, $C_1$-$C_6$ haloalkyl, $C_1$-$C_6$ alkoxy, $C_1$-$C_6$ haloalkoxy, phenyl, halogen, OH, $NH_2$, CN, $NO_2$, —C(═O)$R^a$, —C(═O)$OR^a$, and —C(═O)N($R^a$)($R^a$), wherein the phenyl in G is optionally substituted with at least one substituent selected from the group consisting of $C_1$-$C_3$ alkyl, $C_1$-$C_3$ haloalkyl, $C_1$-$C_3$ alkoxy, $C_1$-$C_3$ haloalkoxy, F, Cl, Br, I, OH, CN, $NO_2$, —C(═O)$OR^a$, and —C(═O)N($R^a$)($R^a$), and wherein two substituents in G may combine to provide a $C_3$-$C_8$ cycloalkyl which is spiro, fused, or bridged with the $C_3$-$C_8$ cycloalkyl in G;

$R^1$ is selected from the group consisting of

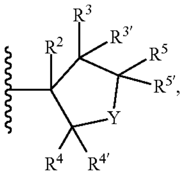, 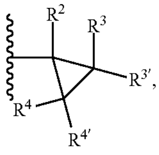, 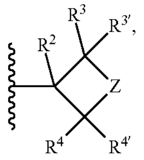, 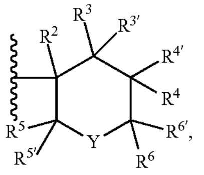, 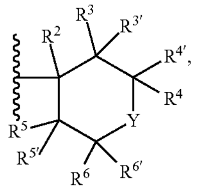, and 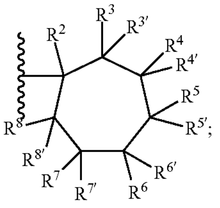;

$R^2$ is selected from the group consisting of H, halogen, optionally substituted $C_1$-$C_6$ alkyl, optionally substituted phenyl, optionally substituted $C_3$-$C_6$ cycloalkyl, optionally substituted $C_2$-$C_{10}$ heterocyclyl, optionally substituted $C_1$-$C_6$ aminoalkyl, optionally substituted $C_1$-$C_6$ alkoxyalkyl. optionally substituted $C_1$-$C_6$ haloalkyl. optionally substituted $C_2$-$C_6$ alkynyl, —C(═O)$OR^a$, and —C(═O)N($R^a$)($R^a$), wherein each optional substituent in $R^2$ is at least one selected from the group consisting of halogen, $C_1$-$C_6$ alkyl, $C_1$-$C_3$ alkoxy, $C_1$-$C_3$ haloalkoxy, $C_1$-$C_3$ haloalkyl, —C(═O)$OR^a$, —S(═O)$_2$—$C_6$-$C_{10}$ aryl, and —S(═O)$_2$—$C_2$-$C_{10}$ heteroaryl;

$R^3$, $R^{3'}$, $R^4$, $R^{4'}$, $R^5$, $R^5$, $R^6$, $R^{6'}$, $R^7$, $R^{7'}$, $R^8$, and $R^{8'}$ are each independently selected from the group consisting of H, $C_1$-$C_6$ alkyl, hydroxyl, $C_1$-$C_4$ haloalkyl, optionally substituted $C_3$-$C_8$ cycloalkyl, optionally substituted $C_2$-$C_6$ heterocyclyl, optionally substituted phenyl, and optionally substituted phenoxy, wherein each optional substituent in the heterocyclyl, phenyl, or phenoxy is at least one selected from the group consisting of $C_1$-$C_3$ alkyl, $C_1$-$C_3$ haloalkyl, $C_1$-$C_3$ alkoxy, $C_1$-$C_3$ haloalkoxy, halogen, OH, C(═O)$OR^a$, and C(═O)N($R^a$)($R^a$), wherein two geminal substituents selected from $R^3$, $R^{3'}$, $R^4$, $R^{4'}$, $R^5$, $R^5$, $R^6$, $R^{6'}$, $R^7$, $R^{7'}$, $R^8$, and $R^{8'}$ may combine with the carbon atom to which they are bound to form a moiety selected from the group consisting of an optionally substituted $C_3$-$C_8$ cycloalkyl and an optionally substituted $C_2$-$C_{10}$ heterocyclyl, wherein two vicinal substituents selected from $R^3$, $R^{3'}$, $R^4$, $R^{4'}$, $R^5$, $R^5$, $R^6$, $R^{6'}$, $R^7$, $R^{7'}$, $R^8$, and $R^{8'}$ may combine with the carbon atoms to which they are bound to form a moiety selected from the group consisting of an optionally substituted $C_3$-$C_8$ cycloalkyl, optionally substituted $C_2$-$C_{10}$ heterocyclyl, and optionally substituted phenyl;

wherein two substituents selected from $R^3$, $R^{3'}$, $R^4$, $R^{4'}$, $R^5$, $R^{5'}$, $R^6$, $R^{6'}$, $R^7$, $R^8$, and $R^{8'}$, which are separated by two to five carbon atoms, may combine with the carbon atoms to which they are bound to form a moiety selected from the group consisting of optionally substituted $C_4$-$C_7$ cycloalkyl and optionally substituted $C_4$-$C_8$ heterocyclyl;

$R^{10}$ is selected from the group consisting of H, $C_1$-$C_6$ alkyl, $C_3$-$C_6$ cycloalkyl, optionally substituted phenyl, optionally substituted benzyl, —C(═O)OR, —C(═O)$R^b$, and —S(═O)$_2$-optionally substituted phenyl, wherein each optional substituent in the phenyl, benzyl, or —S(═O)$_2$-phenyl is independently at least one selected from the group consisting of F, Cl, Br, $C_1$-$C_3$ alkoxy, $C_1$-$C_3$ haloalkoxy, $C_1$-$C_3$ haloalkyl, hydroxyl, and —NH—C(═O)$R^a$;

$R^{10'}$ is selected from the group consisting of phenyl, benzyl, and —C(═O)—$C_1$-$C_6$ alkyl, wherein the benzyl or phenyl in $R^{10'}$ is substituted with at least one substituent selected from the group consisting of halogen, $C_1$-$C_3$ haloalkyl, OH, and N($R^a$)($R^b$), and wherein the alkyl in $R^{10'}$ is substituted with at least one phenyl substituent;

Y is selected from the group consisting of C($R^a$)($R^a$), C═O, $NR^{10}$, $NR^{10'}$, and O, wherein if Y is C($R^a$)($R^a$) and $R^2$ is optionally substituted phenyl, then Ar comprises a $C_6$-$C_{10}$ aryl or $C_2$-$C_{10}$ heteroaryl substituted with at least one trifluoromethoxy substituent;

Z is selected from the group consisting of C═O, $NR^{10}$, $NR^{10'}$, O, and S;

$R^A$ is H or $C_1$-$C_6$ alkyl;

each occurrence of $R^a$ is independently selected from the group consisting of H, $C_1$-$C_6$ alkyl, benzyl, and $C_6$-$C_{10}$ aryl; and each occurrence of $R^b$ is independently selected from the group consisting of H, optionally substituted $C_1$-$C_6$ alkyl, optionally substituted benzyl, optionally substituted phenyl, and optionally substituted naphthyl, wherein the $C_1$-$C_6$ alkyl, benzyl, phenyl, or naphthyl in $R^b$ is independently optionally substituted with at least one selected from the group consisting of $C_1$-$C_3$ alkyl, $C_1$-$C_3$ haloalkyl, $C_1$-$C_3$ alkoxy, $C_1$-$C_3$ haloalkoxy, halogen, OH, CN, $NO_2$, C(═O)$OR^a$, and C(═O)N($R^a$)($R^a$);

wherein in (Ia), (Ib), and (Ic), at least one of the following applies:

a) $R^2$ is phenyl or $C_2$-$C_{10}$ heteroaryl, wherein the phenyl or heteroaryl is optionally substituted with at least one substituent selected from the group consisting of halogen, OH, $C_1$-$C_3$ haloalkoxy, $C_1$-$C_3$ haloalkyl, $C_1$-$C_3$ alkoxy, and $C_1$-$C_6$ alkyl;

b) at least one of $R^3$ and $R^{3'}$ is phenyl or $C_2$-$C_{10}$ heteroaryl, wherein the phenyl or heteroaryl is substituted with at least one substituent selected from the group consisting of halogen, OH, $C_1$-$C_3$ haloalkoxy, $C_1$-$C_3$ haloalkyl, $C_1$-$C_3$ alkoxy, and $C_1$-$C_6$ alkyl;

c) at least one of $R^3$, $R^{3'}$, $R^4$, and $R^{4'}$, is phenyl or $C_2$-$C_{10}$ heteroaryl, wherein the phenyl or heteroaryl is optionally substituted with at least one substituent selected from the group consisting of halogen, OH, $C_1$-$C_3$ haloalkoxy, $C_1$-$C_3$ haloalkyl, $C_1$-$C_3$ alkoxy, and $C_1$-$C_6$ alkyl, wherein one of Y and Z is present, and one of Y and Z is selected from the group consisting of C═O, $NR^{10}$, and O, wherein $R^{10}$ is selected from the group consisting of H, $C_3$-$C_6$ cycloalkyl, phenyl, optionally substituted benzyl, —C(═)OR, —C(═O)$R^b$, —S(═O)$_2$ -optionally substituted phenyl;

d) two geminal substituents selected from $R^3$, $R^{3'}$, $R^4$, $R^{4'}$, $R^5$, $R^{5'}$, $R^6$, $R^{6'}$, $R^7$, $R^{7'}$, $R^8$, and $R^{8'}$ combine with the carbon atom to which they are bound to form a $C_3$-$C_8$ cycloalkyl or $C_2$-$C_6$ heterocyclyl, wherein the cycloalkyl or heterocyclyl is substituted with at least one substituent selected from the group consisting of $C_1$-$C_3$ alkyl, $C_1$-$C_3$ haloalkyl, $C_1$-$C_3$ haloalkoxy, halogen, N($R^a$)($R^a$), O$R^a$, C(═O)$R^a$, C(═O)O$R^a$, and C(═O)N($R^a$)($R^a$), e) two vicinal substituents selected from $R^3$, $R^{3'}$, $R^4$, $R^{4'}$, $R^5$, $R^{5'}$, $R^6$, $R^{6'}$, $R^7$, $R^{7'}$, $R^8$, and $R^{8'}$ combine with the carbon atoms to which they are bound to form a $C_3$-$C_8$ cycloalkyl, $C_2$-$C_{10}$ heterocyclyl, or phenyl, wherein the cycloalkyl, heterocyclyl, or phenyl is substituted with at least one substituent selected from the group consisting of $C_1$-$C_3$ alkyl, $C_1$-$C_3$ haloalkyl, $C_1$-$C_3$ haloalkoxy, halogen, O$R^a$, C(═O)$R^a$, C(═O)O$R^a$, and C(═O)N($R^a$)($R^a$);

f) two geminal substituents selected from $R^3$, $R^{3'}$, $R^4$, $R^{4'}$, $R^5$, $R^{5'}$, $R^6$, $R^{6'}$, $R^7$, $R^{7'}$, $R^8$, and $R^{8'}$ combine with the carbon atom to which they are bound to form a $C_3$-$C_8$ cycloalkyl or $C_2$-$C_6$ heterocyclyl, and two vicinal substituents selected from $R^3$, $R^{3'}$, $R^4$, $R^{4'}$, $R^5$, $R^5$, $R^6$, $R^{6'}$, $R^7$, $R^{7'}$, $R^8$, and $R^{8'}$ combine with the carbon atoms to which they are bound to form a $C_3$-$C_8$ cycloalkyl, $C_2$-$C_{10}$ heterocyclyl, or phenyl, wherein each of the cycloalkyl, heterocyclyl, or phenyl is independently optionally substituted with at least one substituent selected from the group consisting of $C_1$-$C_3$ alkyl, $C_1$-$C_3$ haloalkyl, $C_1$-$C_3$ haloalkoxy, halogen, N($R^a$)($R^a$), O$R^a$, C(═O)$R^a$, C(═O)O$R^a$, and C(═O)N($R^a$)($R^a$);

g) Y is N($R^{10'}$) and each of $R^4$, $R^{4'}$, $R^6$, and $R^{6'}$, if present, are independently selected from the group consisting of H, $C_1$-$C_6$ alkyl, hydroxyl, $C_1$-$C_4$ haloalkyl, phenyl, and phenoxy;

h) at least one of $R^2$, $R^3$, $R^{3'}$, $R^4$, and $R^{4'}$ is optionally substituted $C_3$-$C_8$ cycloalkyl or $C_2$-$C_{10}$ heterocyclyl, wherein each optional substituent in the cycloalkyl or heterocycloalkyl is independently selected from the group consisting of halogen, $C_1$-$C_6$ alkyl, $C_1$-$C_3$ haloalkyl, $C_1$-$C_3$ haloalkoxy, O$R^a$, N($R^a$)($R^b$), C(═O)$R^a$, and C(═O)O$R^a$; and i) $R^2$ is selected from the group consisting of optionally substituted $C_1$-$C_6$ haloalkyl, optionally substituted $C_2$-$C_6$ aminoalkyl and optionally substituted $C_2$-$C_6$ alkynyl, wherein each optional substituent of the haloalkyl, aminoalkyl, and alkynyl in $R^2$ is at least one selected from the group consisting of $C_1$-$C_6$ alkyl, $C_1$-$C_3$ haloalkyl, $C_1$-$C_3$ haloalkoxy, halogen, C(═O)$R^a$, C(═O)O$R^a$, C(═O)N($R^a$)($R^a$), S(═O)$_2$-optionally substituted phenyl and S(═O)$_2$-optionally substituted $C_2$-$C_{10}$ heteroaryl.

Embodiment 2 provides the compound of Embodiment 1, wherein the compound of formula (I) is selected from the group consisting of (Ia-1)

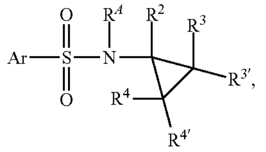

(Ia-2)

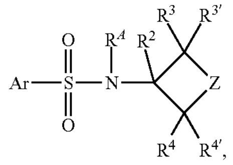

(Ia-3)

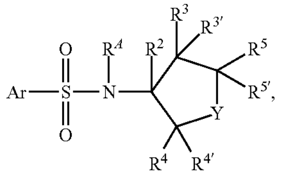

(Ia-4)

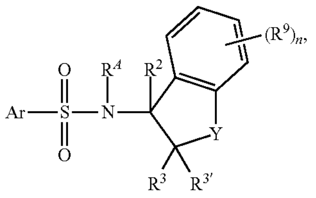

(Ia-5)

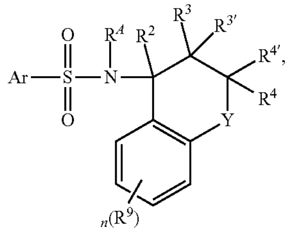

(Ia-6)

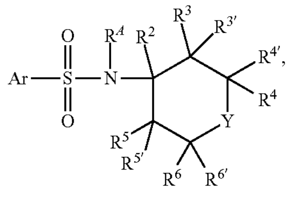

-continued
(Ia-7)
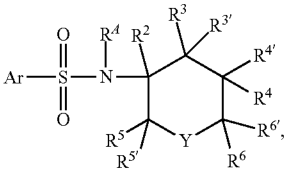
(Ia-8)
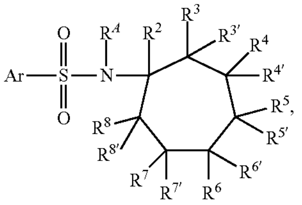
(Ib-1)
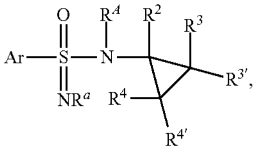
(Ib-2)
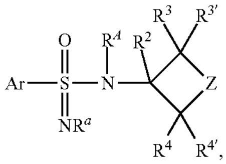
(Ib-3)
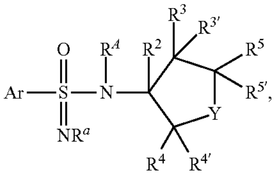
(Ib-4)
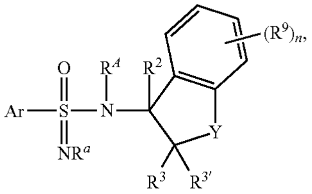
(Ib-5)
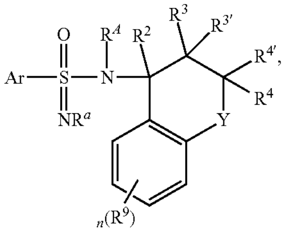
(Ib-6)
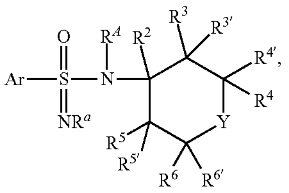
-continued
(Ib-7)
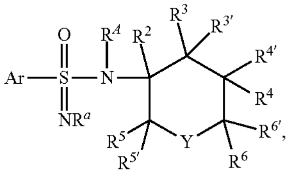
(Ib-8)
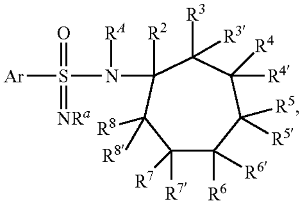
(Ic-1)
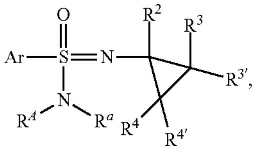
(Ic-2)
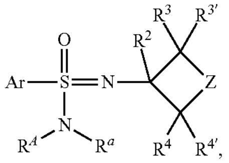
(Ic-3)
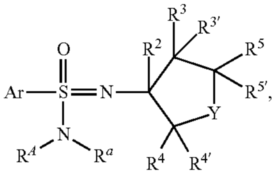
(Ic-4)
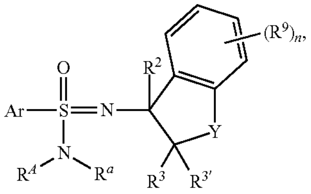
(Ic-5)
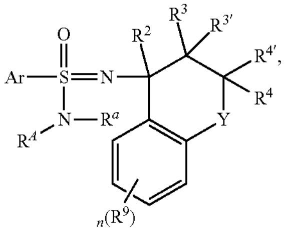
(Ic-6)
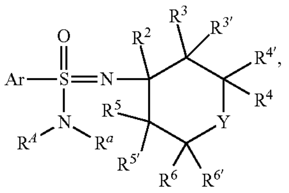

-continued

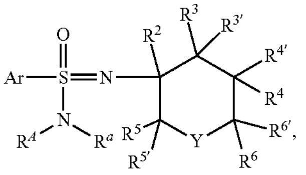

(Ic-7)

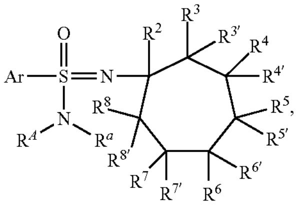

(Ic-8)

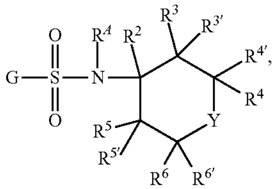

(Id-1)

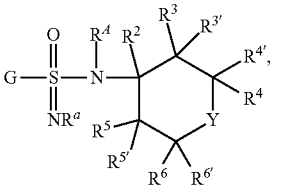

(Ie-1)

and

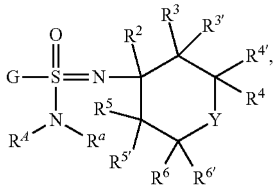

(If-1)

wherein:

each occurrence of $R^9$ is independently selected from the group consisting of F, Cl, Br, $C_1$-$C_3$ alkoxy, and $C_1$-$C_3$ haloalkoxy; and n is an integer selected from the group consisting of 0, 1, and 2.

Embodiment 3 provides the compound of Embodiment 1 or 2, wherein $R^A$ is selected from the group consisting of H and Me.

Embodiment 4 provides the compound of Embodiment 1 or 3, wherein $R^1$ is selected from the group consisting of

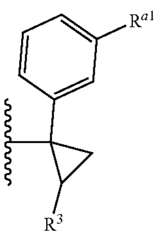

,

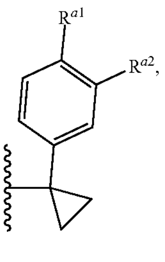

-continued

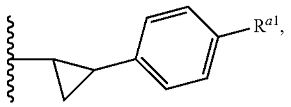

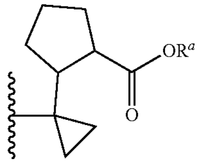

,

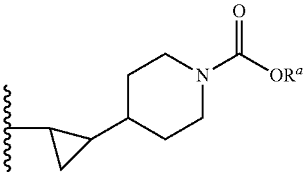

,

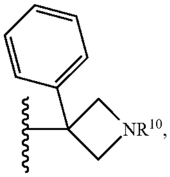

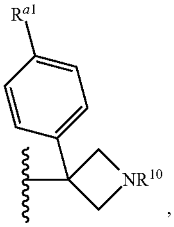

,

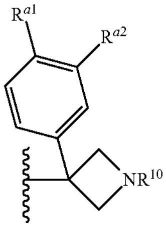

,

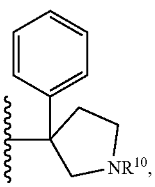

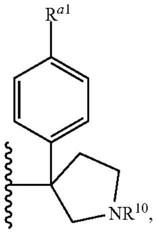

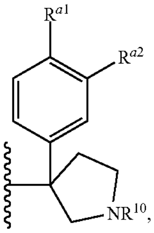

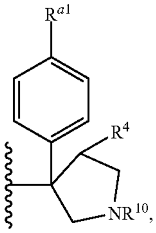

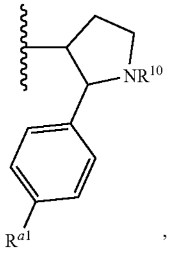

,

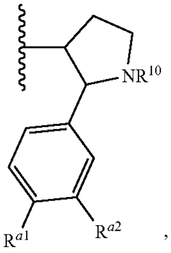

,

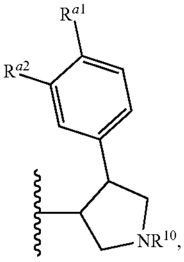

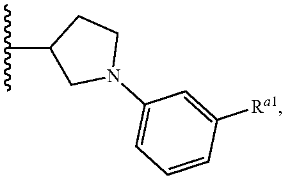

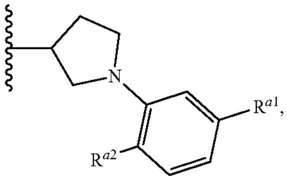

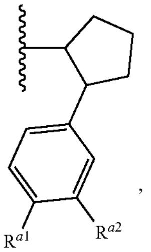

,

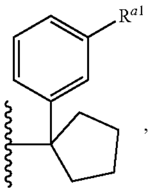

,

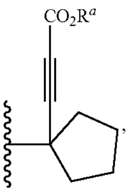

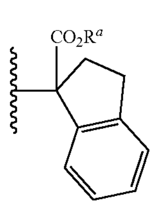

,

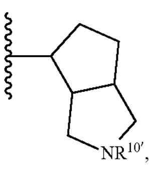

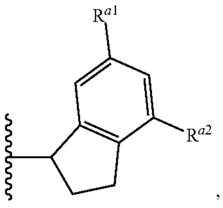

,

-continued

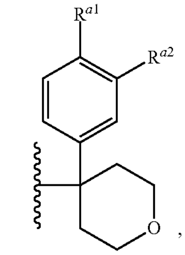
,
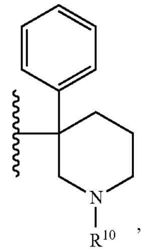
,
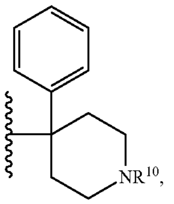
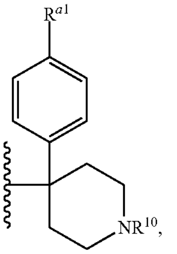
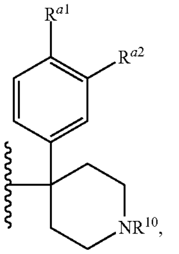
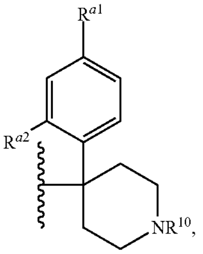
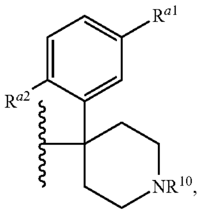
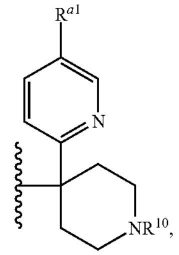
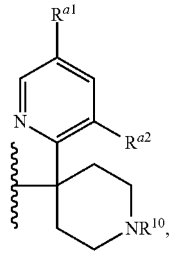
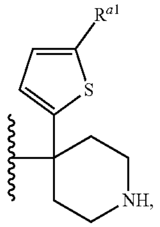
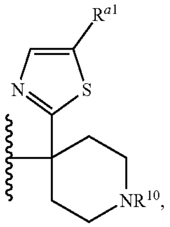
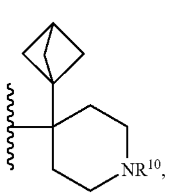
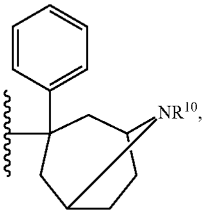
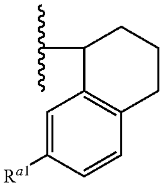
,
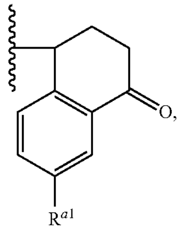
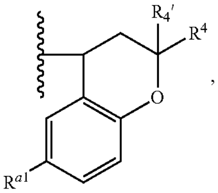
,
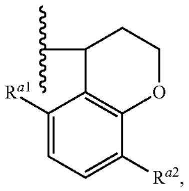
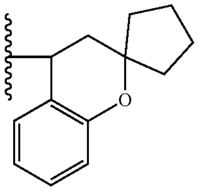
, -continued

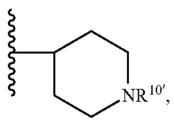
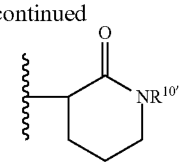
, and
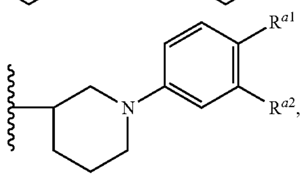

wherein $R^{a1}$ and $R^{a2}$ are each independently selected from the group consisting of F, Cl, Br, $C_1$-$C_3$ alkyl, $C_1$-$C_3$ haloalkyl, $C_1$-$C_3$ alkoxy, and $C_1$-$C_3$ haloalkoxy.

Embodiment 5 provides the compound of any one of Embodiments 1-4, wherein Ar is selected from the group consisting of

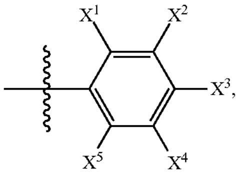
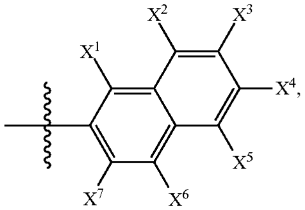
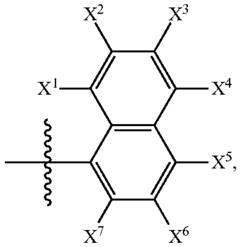
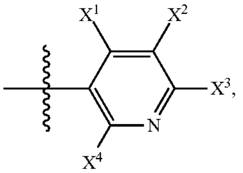
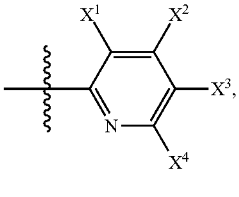
and
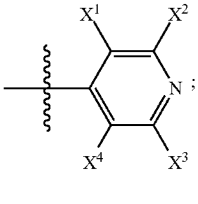

wherein $X^1$, $X^2$, $X^3$, $X^4$, $X^5$, $X^6$, and $X^7$ are each independently selected from the group consisting of $C_1$-$C_6$ alkyl, F, Cl, $N(R^a)(R^b)$, $OR^b$, $—C(=O)OR^a$, $—C(=O)N(R^a)(R^a)$, $NH_2$, OH, $NO_2$, $C_1$-$C_3$ haloalkyl, $C_1$-$C_3$ haloalkoxy, and phenyl.

Embodiment 6 provides the compound of any one of Embodiments 1-3 and 5, wherein at least one of the following applies:

(a) the compound of formula (I) is the compound of formula (Ia-1), wherein at least two of $R^3$, $R^{3'}$, $R^4$, and $R^{4'}$ are H;

(b) the compound of formula (I) is the compound of formula (Ia-2), wherein at least two of $R^3$, $R^{3'}$, $R^4$, and $R^{4'}$ are H;

(c) the compound of formula (I) is the compound of formula (Ia-3), wherein at least four of $R^3$, $R^{3'}$, $R^4$, $R^{4'}$, $R^5$, and $R^5$ are H;

(d) the compound of formula (I) is the compound of formula (Ia-4), wherein at least one of $R^3$ and $R^{3'}$ is H;

(e) the compound of formula (I) is the compound of formula (Ia-5), wherein at least two of $R^3$, $R^{3'}$, $R^4$, and $R^{4'}$ are H;

(f) the compound of formula (I) is the compound of formula (Ia-6), wherein at least six of $R^3$, $R^{3'}$, $R^4$, $R^{4'}$, $R^5$, $R^5$, $R^6$, and $R^{6'}$ are H;

(g) the compound of formula (I) is the compound of formula (Ia-7), wherein at least six of $R^3$, $R^{3'}$, $R^4$, $R^{4'}$, $R^5$, $R^{5'}$, $R^6$, and $R^{6'}$ are H;

(h) the compound of formula (I) is the compound of formula (Ia-8), wherein at least ten of $R^3$, $R^{3'}$, $R^4$, $R^{4'}$, $R^5$, $R^{5'}$, $R^6$, $R^{6'}$, $R^7$, $R^{7'}$, $R^8$, and $R^{8'}$ are H;

(i) the compound of formula (I) is the compound of formula (Ib-1), wherein at least two of $R^3$, $R^{3'}$, $R^4$, and $R^{4'}$ are H;

(j) the compound of formula (I) is the compound of formula (Ib-2), wherein at least two of $R^3$, $R^{3'}$, $R^4$, and $R^{4'}$ are H;

(k) the compound of formula (I) is the compound of formula (Ib-3), wherein at least four of $R^3$, $R^{3'}$, $R^4$, $R^{4'}$, $R^5$, and $R^5$ are H;

(l) the compound of formula (I) is the compound of formula (Ib-4), wherein at least one of $R^3$ and $R^{3'}$ is H;

(m) the compound of formula (I) is the compound of formula (Ib-5), wherein at least two of $R^3$, $R^{3'}$, $R^4$, and $R^{4'}$ are H;

(n) the compound of formula (I) is the compound of formula (Ib-6), wherein at least six of $R^3$, $R^{3'}$, $R^4$, $R^{4'}$, $R^5$, $R^5$, $R^6$, and $R^{6'}$ are H;

(o) the compound of formula (I) is the compound of formula (Ib-7), wherein at least six of $R^3$, $R^3$, $R^4$, $R^{4'}$, $R^5$, $R^{5'}$, $R^6$, and $R^{6'}$ are H;

(p) the compound of formula (I) is the compound of formula (Ib-8), wherein at least ten of $R^3$, $R^{3'}$, $R^4$, $R^{4'}$, $R^5$, $R^{5'}$, $R^6$, $R^{6'}$, $R^7$, $R^{7'}$, $R^8$, and $R^{8'}$ are H;

(q) the compound of formula (I) is the compound of formula (Ic-1), wherein at least two of $R^3$, $R^3$, $R^4$, and $R^{4'}$ are H;

(r) the compound of formula (I) is the compound of formula (Ic-2), wherein at least two of $R^3$, $R^{3'}$, $R^4$, and $R^{4'}$ are H;

(s) the compound of formula (I) is the compound of formula (Ic-3), wherein at least four of $R^3$, $R^{3'}$, $R^4$, $R^{4'}$, $R^5$, and $R^{5'}$ are H;

(t) the compound of formula (I) is the compound of formula (Ic-4), wherein at least one of $R^3$ and $R^{3'}$ is H;

(u) the compound of formula (I) is the compound of formula (Ic-5), wherein at least two of $R^3$, $R^{3'}$, $R^4$, and $R^{4'}$ are H;

(v) the compound of formula (I) is the compound of formula (Ic-6), wherein at least six of $R^3$, $R^{3'}$, $R^4$, $R^{4'}$, $R^5$, $R^5$, $R^6$, and $R^{6'}$ are H;

(w) the compound of formula (I) is the compound of formula (Ic-7), wherein at least six of $R^3$, $R^{3'}$, $R^4$, $R^{4'}$, $R^5$, $R^5$, $R^6$, and $R^{6'}$ are H;

(x) the compound of formula (I) is the compound of formula (Ic-8), wherein at least ten of $R^3$, $R^{3'}$, $R^4$, $R^{4'}$, $R^5$, $R^{5'}$, $R^6$, $R^{6'}$, $R^7$, $R^{7'}$, $R^8$, and $R^{8'}$ are H;

(y) the compound of formula (I) is the compound of formula (Id-1), wherein at least six of $R^3$, $R^{3'}$, $R^4$, $R^{4'}$, $R^5$, $R^5$, $R^6$, and $R^{6'}$ are H;

(z) the compound of formula (I) is the compound of formula (Ie-1), wherein at least six of $R^3$, $R^{3'}$, $R^4$, $R^{4'}$, $R^5$, $R^5$, $R^6$, and $R^{6'}$ are H; and (aa) the compound of formula (I) is the compound of formula (If-1), wherein at least six of $R^3$, $R^{3'}$, $R^4$, $R^{4'}$, $R^5$, $R^5$, $R^6$, and $R^{6'}$ are H.

Embodiment 7 provides the compound of any one of Embodiments 5-6, wherein at least one of $X^1$, $X^2$, $X^3$, $X^4$, $X^5$, $X^6$, and $X^7$, if present, is selected from the group consisting of $CF_3$, $NH_2$, $O(CH(CH_3)_2)$, $OCF_3$, and

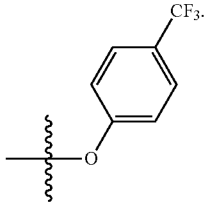 [SMILES: *Oc1ccc(C(F)(F)F)cc1]

Embodiment 8 provides the compound of any one of Embodiments 1-7, wherein Ar is selected from the group consisting of

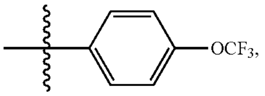

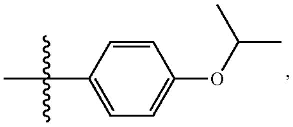

,

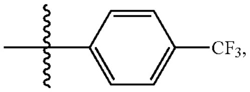

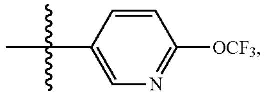

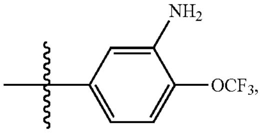

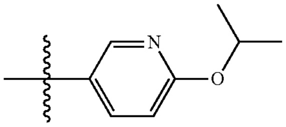

, and

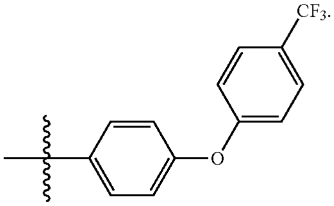

Embodiment 9 provides the compound of Embodiment 1 or 2, wherein G is:

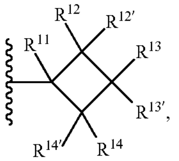

wherein:

$R^{11}$, $R^{12}$, $R^{12'}$, $R^{13}$, $R^{13'}$, $R^{14}$, and $R^{14'}$ are each independently selected from the group consisting of H, $C_1$-$C_6$ alkyl, $C_1$-$C_6$ haloalkyl, and optionally substituted phenyl, wherein each optional substituent in the phenyl is at least one selected from the group consisting of $C_1$-$C_3$ alkyl, $C_1$-$C_3$ haloalkyl, $C_1$-$C_3$ alkoxy, $C_1$-$C_3$ haloalkoxy, halogen, OH, C(=O)OR$^a$, and C(=O)N(R$^a$)(R$^a$), and wherein $R^{11}$ and $R^{13}$ or $R^{11}$ and $R^{13'}$ may optionally combine with the atoms to which they are bound to form a $C_3$-$C_8$ cycloalkyl.

Embodiment 10 provides the compound of Embodiment 9, wherein at least one of the following applies:

(a) at least one of $R^{11}$, $R^{12}$, $R^{12'}$, $R^{13}$, $R^{13'}$, $R^{14}$, and $R^{14'}$ is H;

(b) at least two of $R^{11}$, $R^{12}$, $R^{12'}$, $R^{13}$, $R^{13'}$, $R^{14}$, and $R^{14'}$ are H;

(c) at least three of $R^{11}$, $R^{12}$, $R^{12'}$, $R^{13}$, $R^{13'}$, $R^{14}$, and $R^{14'}$ are H;

(d) at least four of $R^{11}$, $R^{12}$, $R^{12'}$, $R^{13}$, $R^{13'}$, $R^{14}$, and $R^{14'}$ are H;

(e) at least five of $R^{11}$, $R^{12}$, $R^{12'}$, $R^{13}$, $R^{13'}$, $R^{14}$, and $R^{14'}$ are H;

(f) at least six of $R^{11}$, $R^{12}$, $R^{12'}$, $R^{13}$, $R^{13'}$, $R^{14}$, and $R^{14'}$ are H; and (a) each of $R^{11}$, $R^2$, $R^{2'}$, $R^{13}$, $R^{13'}$, $R^{14}$, and $R^{14'}$ are H.

Embodiment 11 provides the compound of Embodiment 9 or 10, wherein at least one of $R^{11}$, $R^{12}$, $R^{12'}$, $R^{13}$, $R^{13'}$, $R^{14}$, and $R^{14'}$ is $CF_3$.

Embodiment 12 provides the compound of any one of Embodiments 1-2 and 10-11, wherein G is

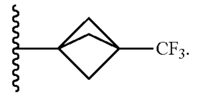 [SMILES: *C12CC(C(F)(F)F)(C1)C2]

Embodiment 13 provides the compound of any one of Embodiments 1-3 and 5-12, wherein $R^2$ is selected from the group consisting of: —$CH_2F$, —C(=O)OEt, Ph,

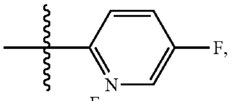 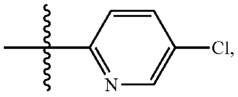

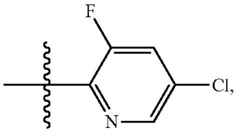 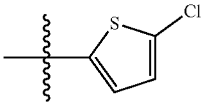 ,

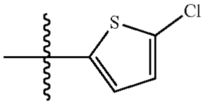 , 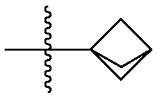 ,

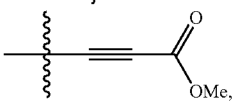 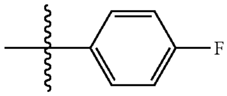 ,

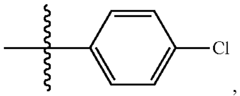 , 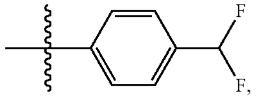

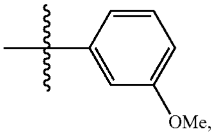 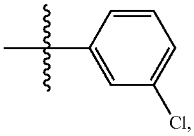

-continued

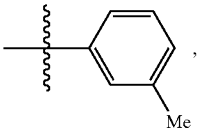 , 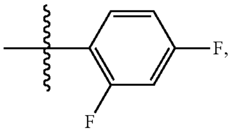

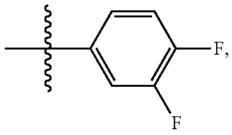 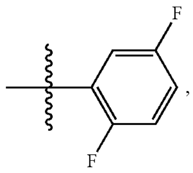 ,

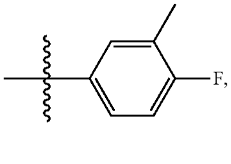 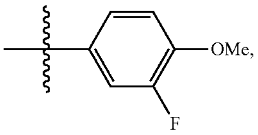

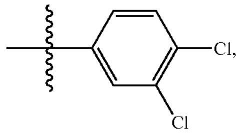 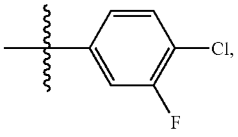

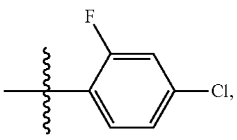 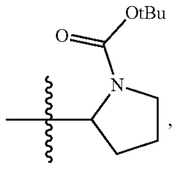 , and

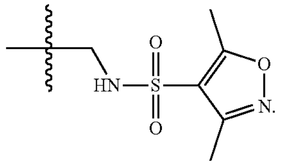

Embodiment 14 provides the compound of any one of Embodiments 1-3 and 5-13, wherein at least one of $R^3$, $R^{3'}$, $R^4$, $R^{4'}$, $R^5$, $R^{5'}$, $R^6$, $R^{6'}$, $R^7$, $R^{7'}$, $R^8$, and $R^{8'}$, if present, is selected from the group consisting of:

methyl, trifluoromethyl, hydroxyl, fluorine, —C(=O)OMe, Ph,

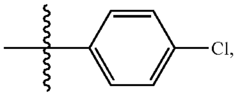 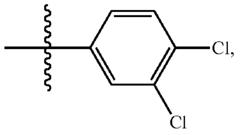

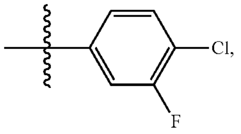 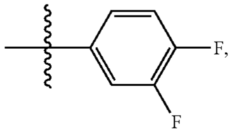 and

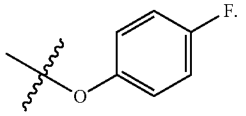

Embodiment 15 provides the compound of any one of Embodiments 1-14, wherein Y is $NR^{10}$.

Embodiment 16 provides the compound of Embodiment 15, wherein $R^{10}$ is selected from the group consisting of H, methyl, 3-methylbutyl, tert-butyl, cyclopropyl, 3-oxetanyl, —C(=O)$CH_2CH(CH_3)_2$, —C(=O)Ot-Bu, S(=O)$_2$Me, benzyl,

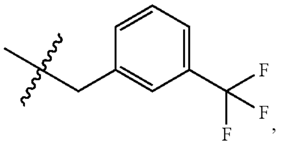

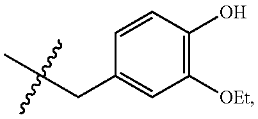

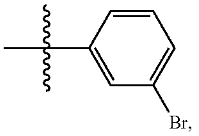

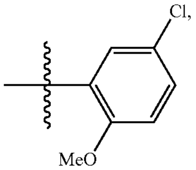

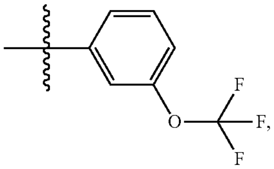

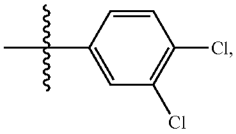

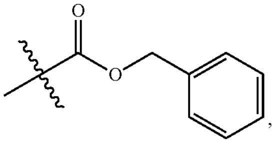

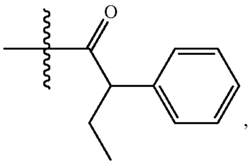

and

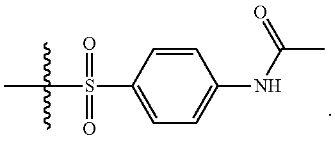

Embodiment 17 provides the compound of any one of Embodiments 1-14, wherein Y is NR$^{10'}$.

Embodiment 18 provides the compound of Embodiment 17, wherein R$^{10'}$ is selected from the group consisting of

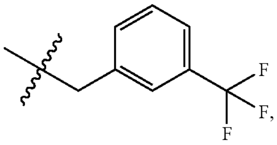

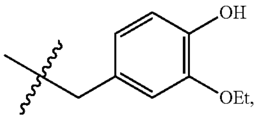

-continued

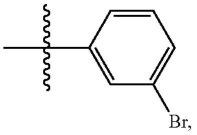

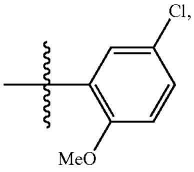

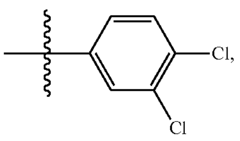

and

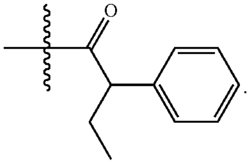

Embodiment 19 provides the compound of any one of Embodiments 1, 3, and 9-12 wherein R$^1$ is selected from the group consisting of

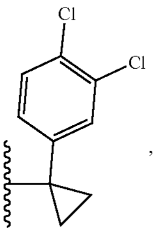

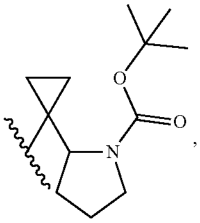

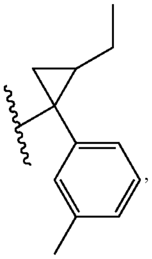

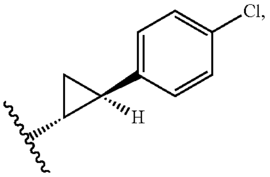

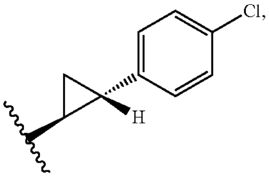

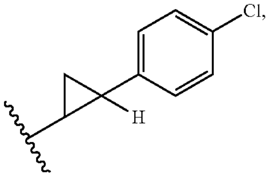

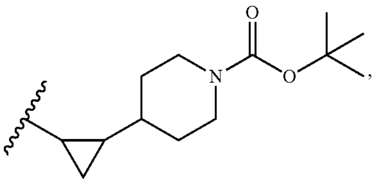

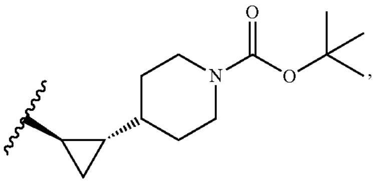

-continued
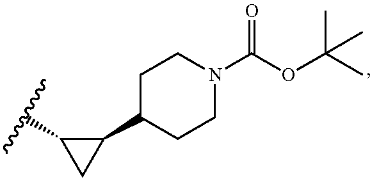,
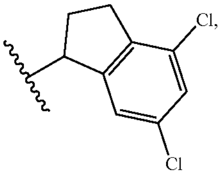,
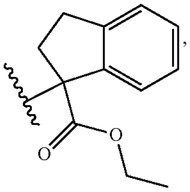,
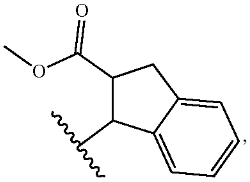,
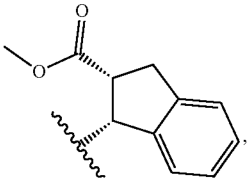,
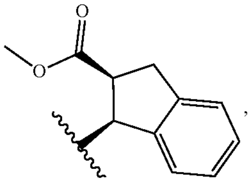,
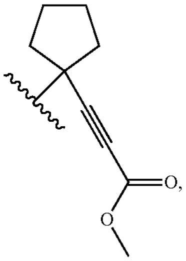,
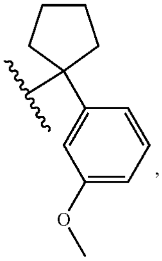,
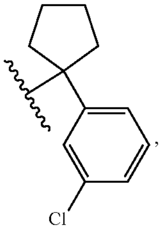,
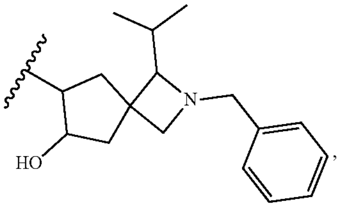,
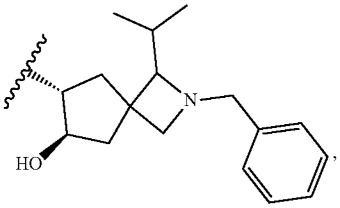,
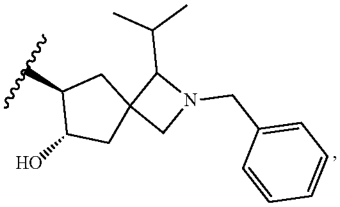,
-continued
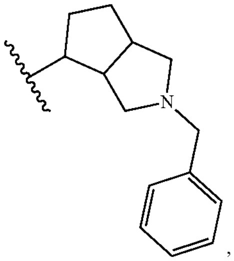,
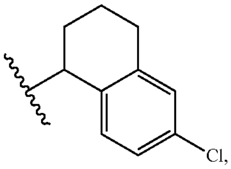,
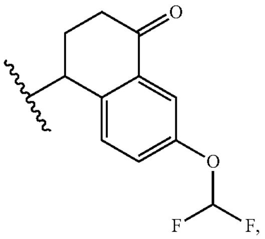,
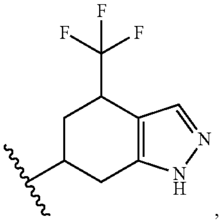,
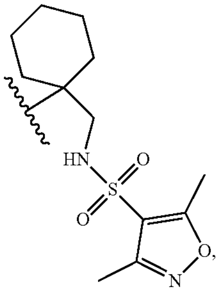,
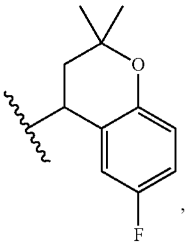,
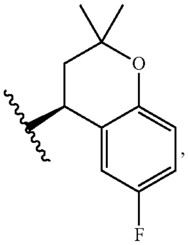,
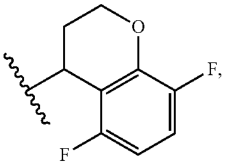,
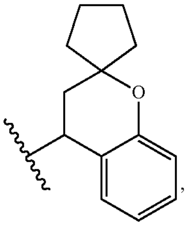,
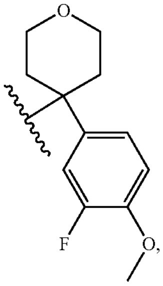,
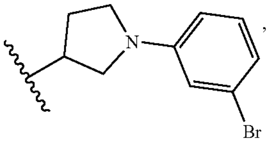,
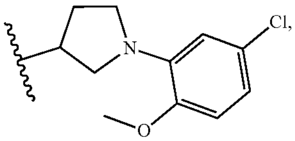,
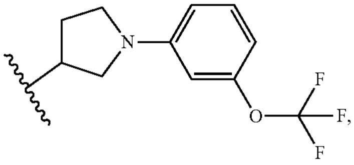, -continued
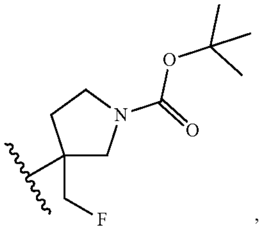
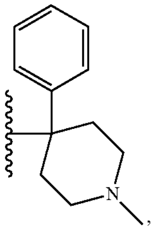
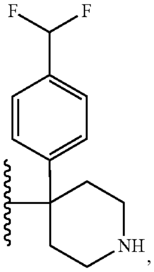
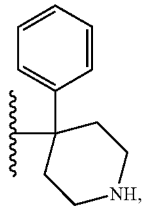
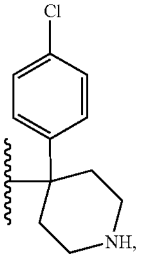
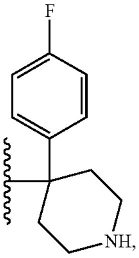
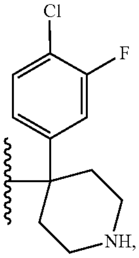
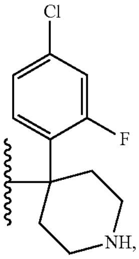
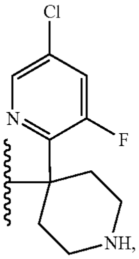
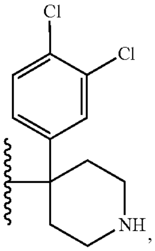
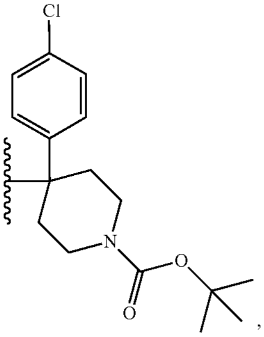
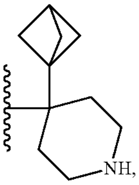
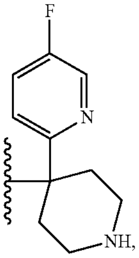
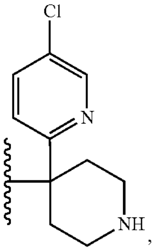
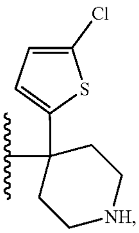
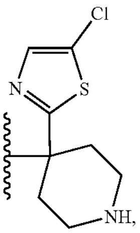
-continued
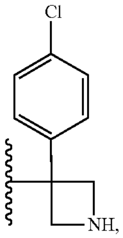
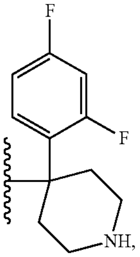
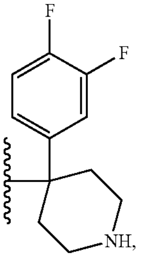
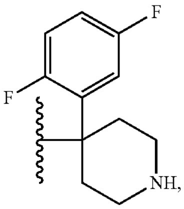
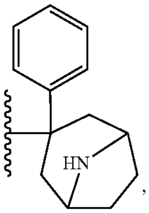
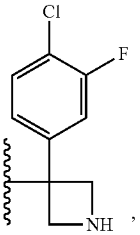
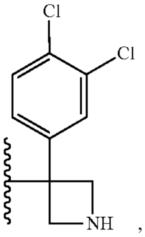
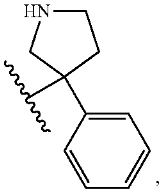
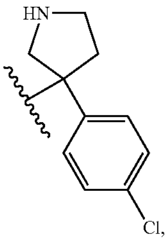
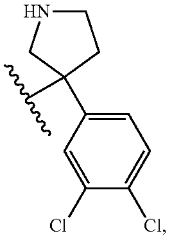
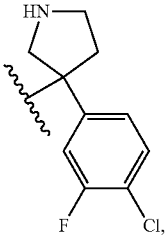
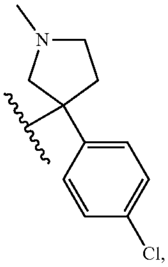
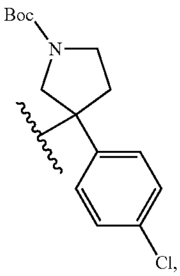
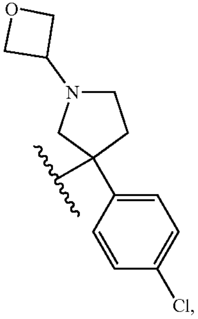
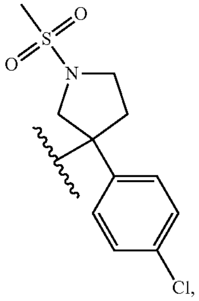
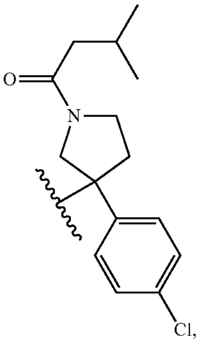

-continued
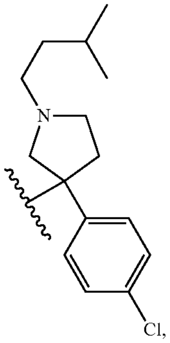,
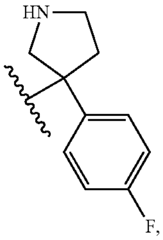,
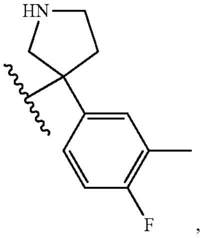,
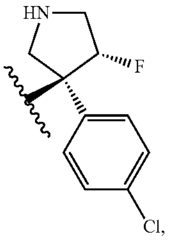,
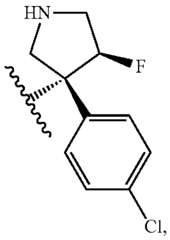,
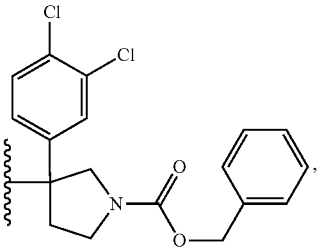,
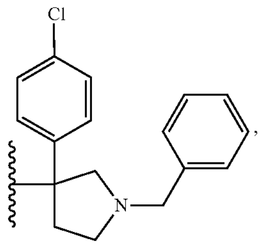,
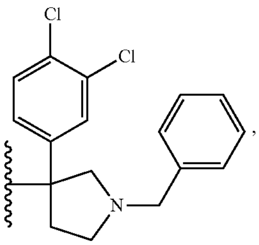,
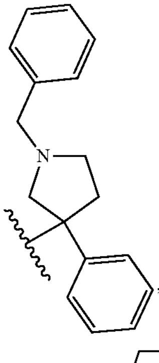,
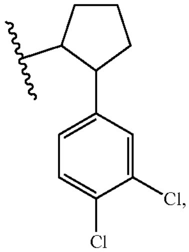,
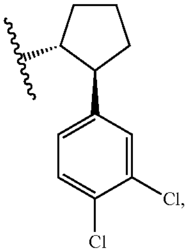,
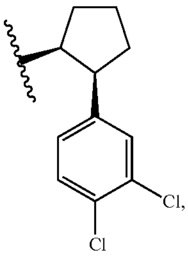,
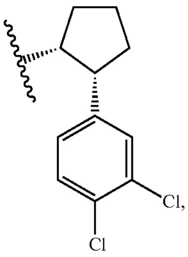,
-continued
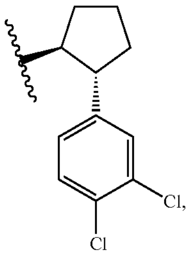,
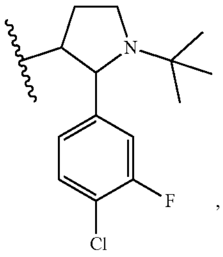,
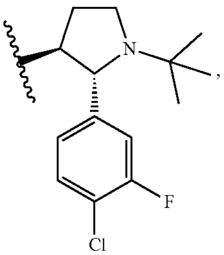,
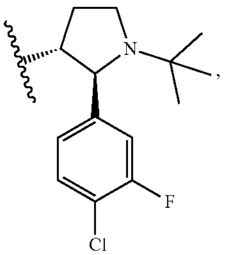,
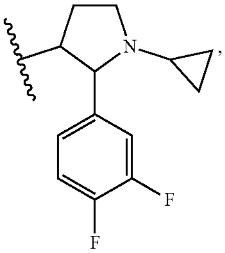,
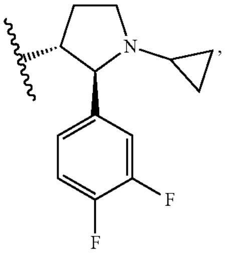,
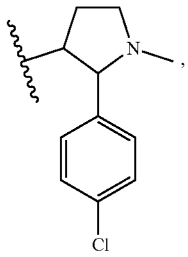,
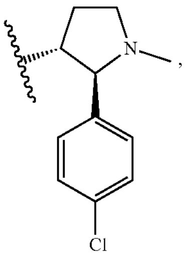,
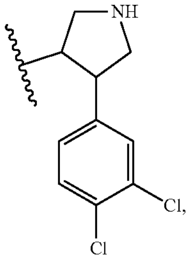,
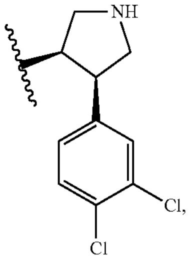,
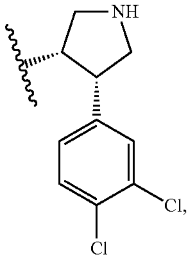,
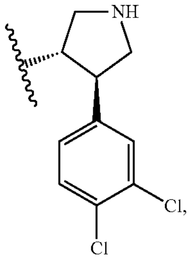,
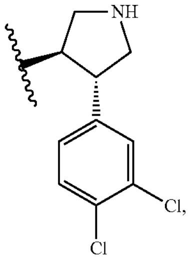, -continued

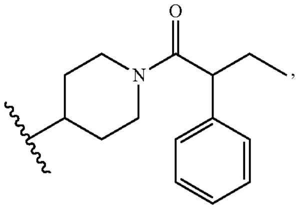

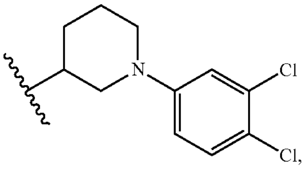

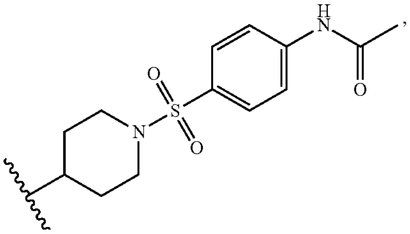

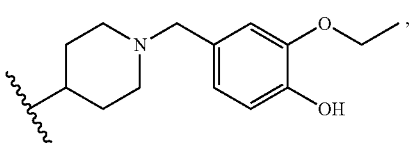

and

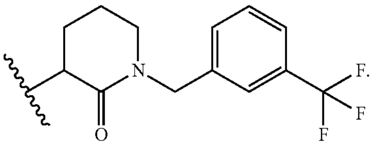

Embodiment 20 provides a compound of formula (II), or a salt, solvate, enantiomer, diastereoisomer, isotopologue, or tautomer thereof, selected from the group consisting of:

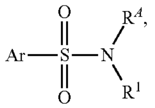

(IIa)

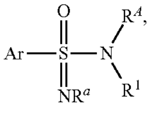

and (IIb)

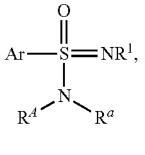

(IIc)

wherein:

Ar is $C_6$-$C_{10}$ aryl or $C_2$-$C_{10}$ heteroaryl, which is optionally substituted with at least one substituent selected from the group consisting of $C_1$-$C_6$ alkyl, $C_1$-$C_6$ haloalkyl, $C_1$-$C_6$ aminoalkyl, $C_1$-$C_6$ hydroxyalkyl, $C_2$-$C_6$ alkenyl, $C_2$-$C_6$ alkynyl, $C_1$-$C_6$ alkoxy, $C_1$-$C_6$ haloalkoxy, $C_2$-$C_{10}$ heteroaryl, $C_6$-$C_{10}$ aryl, $C_6$-$C_{10}$ aryloxy, halogen, OH, $NH_2$, CN, $NO_2$, —C(═O)OR$^a$, and —C(═O)N(R$^a$)(R$^a$), wherein each $C_6$-$C_{10}$ aryl, $C_2$-$C_{10}$ heteroaryl, or $C_6$-$C_{10}$ aryloxy substituent in Ar is independently optionally substituted with at least one substituent selected from the group consisting of $C_1$-$C_3$ alkyl, $C_1$-$C_3$ haloalkyl, $C_1$-$C_3$ alkoxy, $C_1$-$C_3$ haloalkoxy, F, Cl, Br, I, OH, CN, $NO_2$, —C(═O)OR$^a$, and —C(═O)N(R$^a$)(R$^a$), and wherein two vicinal substituents of Ar may combine to provide a 5- to 8-membered ring which is fused with Ar;

R$^A$ is H or $C_1$-$C_6$ alkyl; and $R^1$ is selected from the group consisting of

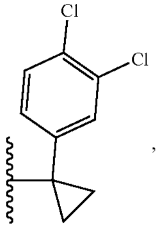

,

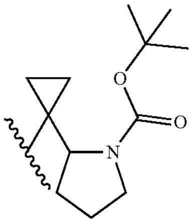

,

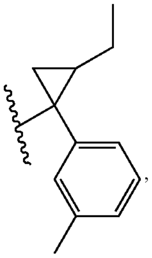

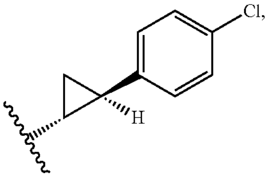

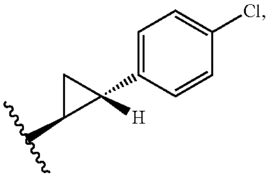

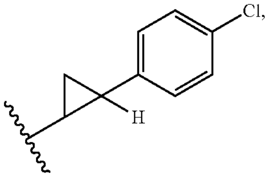

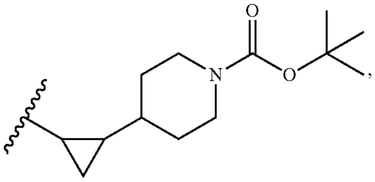

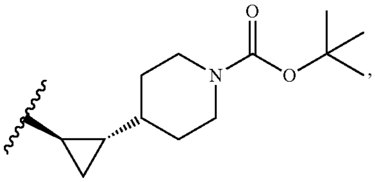

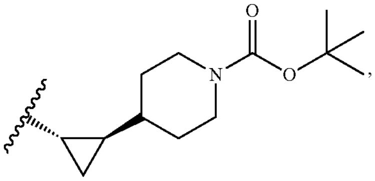

-continued
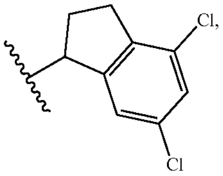
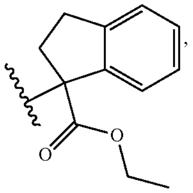
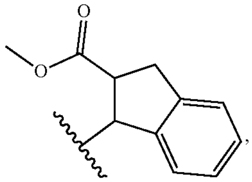
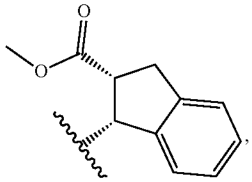
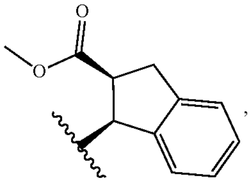
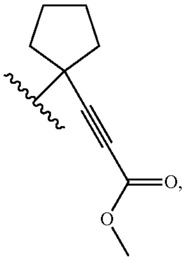
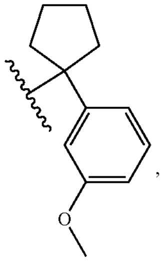
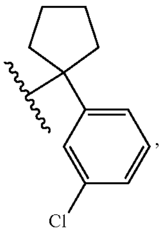
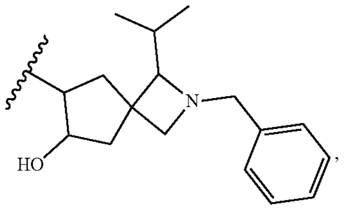
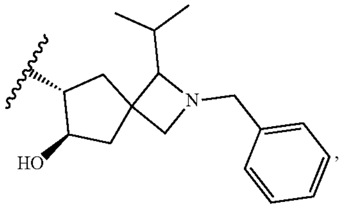
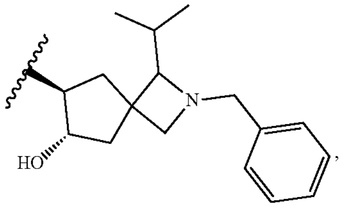
-continued
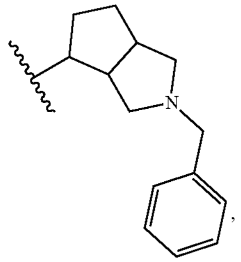
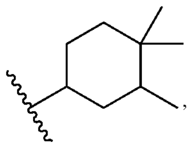
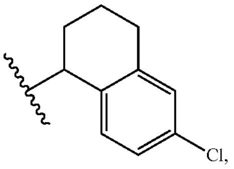
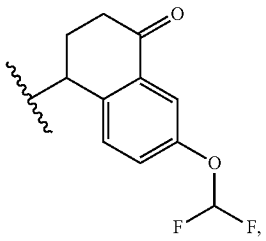
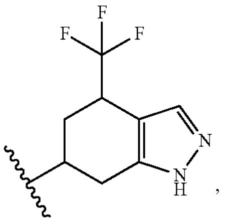
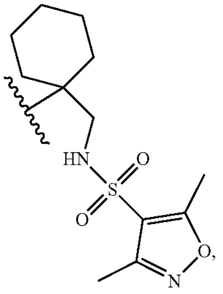
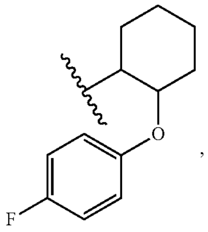
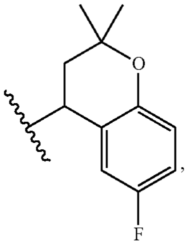
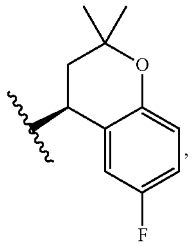
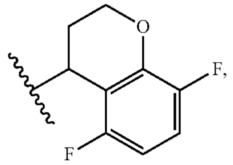
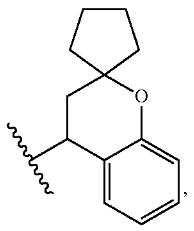
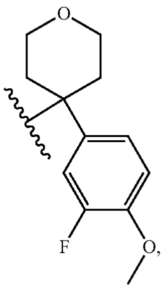
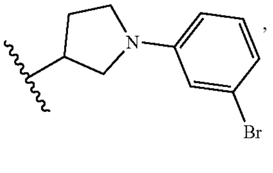
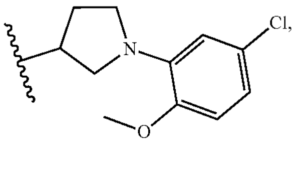

-continued
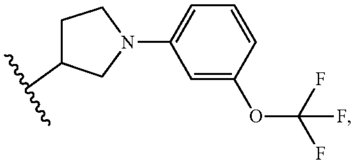
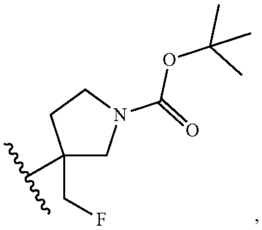
,
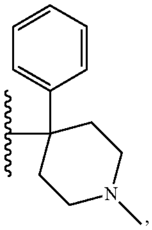
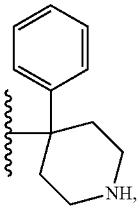
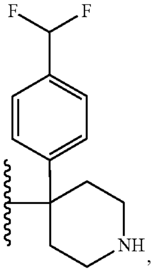
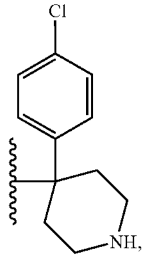
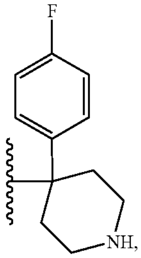
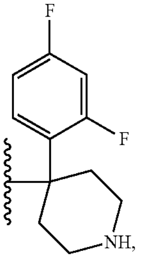
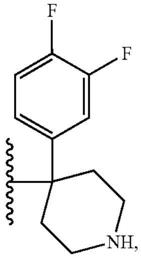
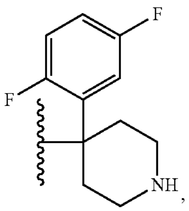
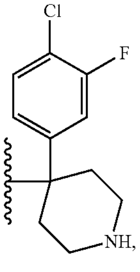
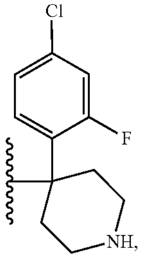
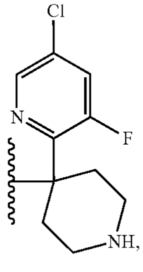
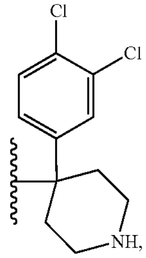
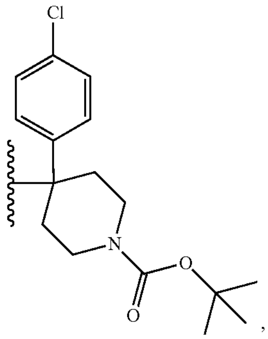
,
-continued
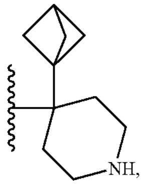
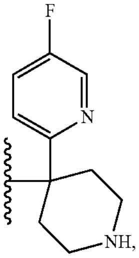
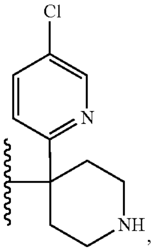
,
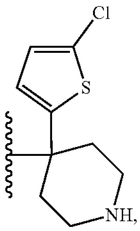
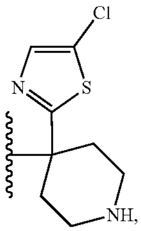
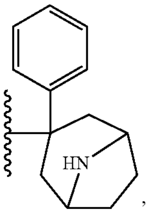
,
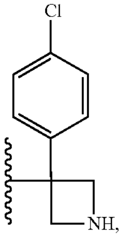
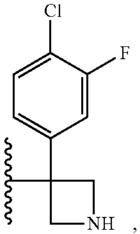
,
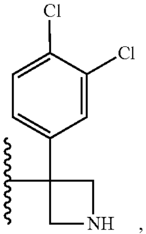
,
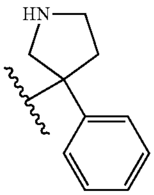
,
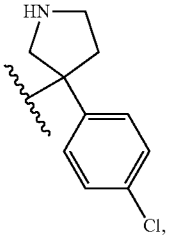
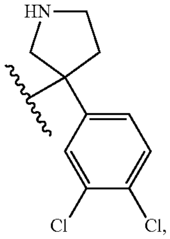
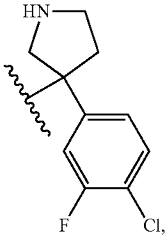
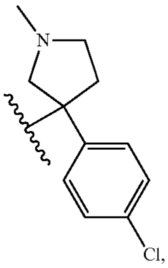
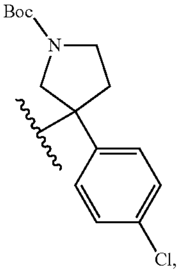
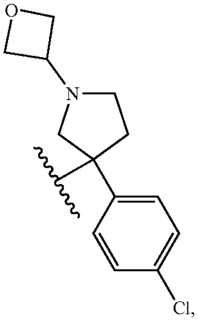
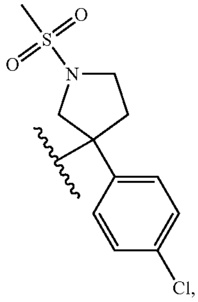

-continued
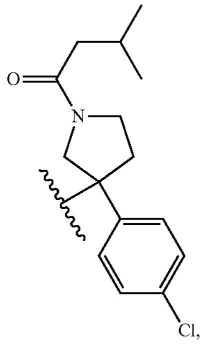,
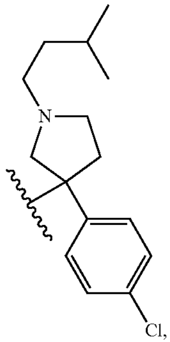,
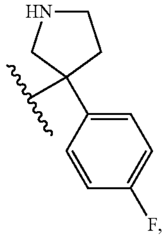,
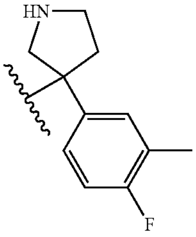,
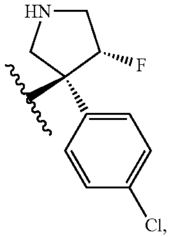,
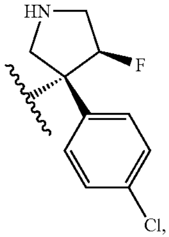,
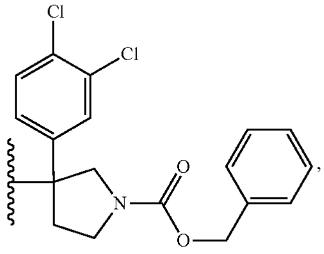,
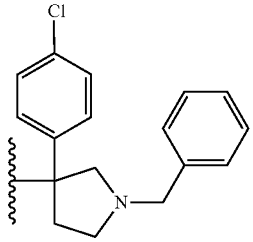,
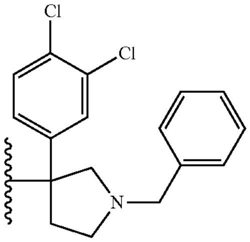,
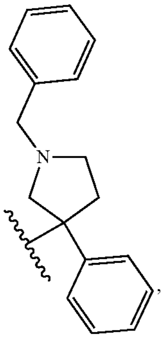,
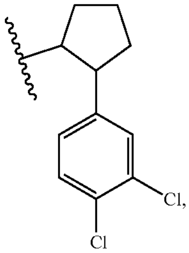,
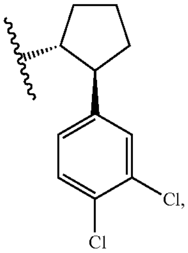,
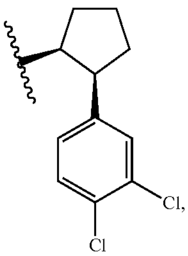,
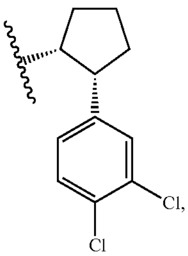,
-continued
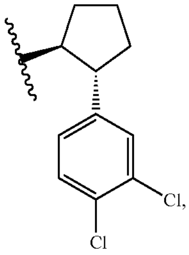,
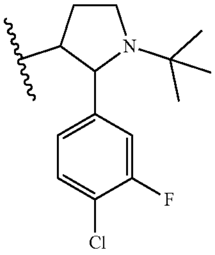,
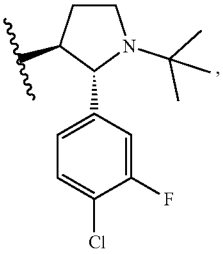,
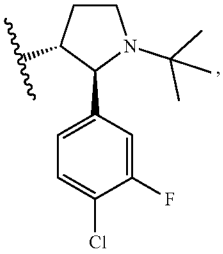,
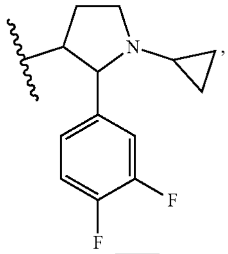,
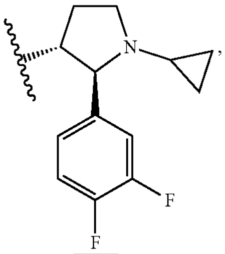,
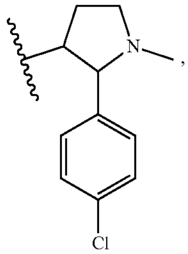,
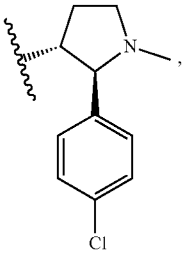,
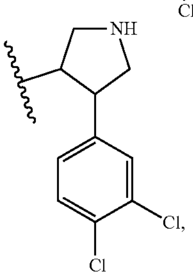,
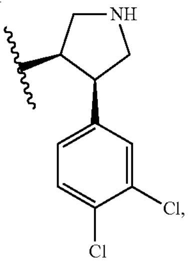,
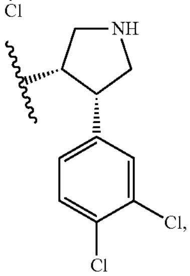,
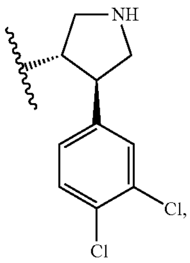,
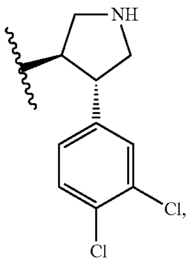,
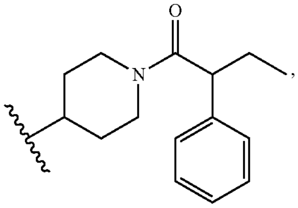, -continued

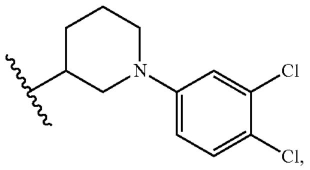

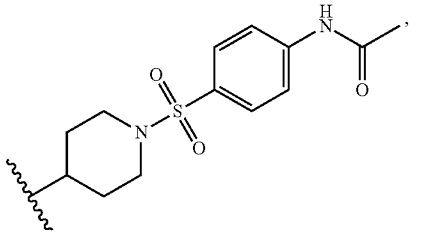

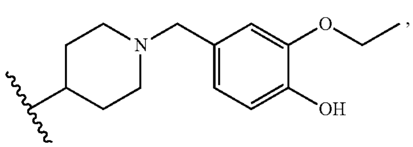

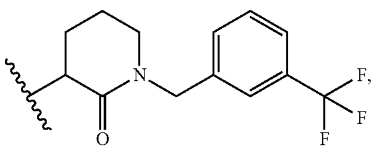

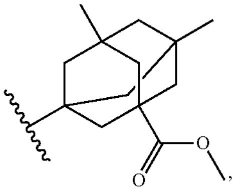

and

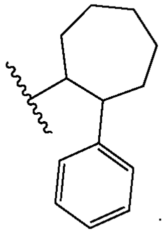

Embodiment 21 provides the compound of Embodiment 20, wherein $R^A$ is H or Me.

Embodiment 22 provides the compound of Embodiment 20 or 21, wherein Ar is selected from the group consisting of

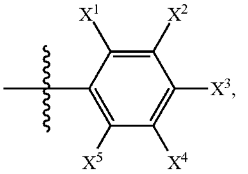

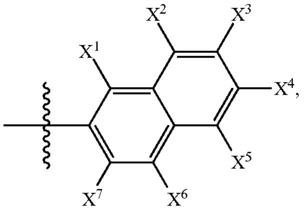

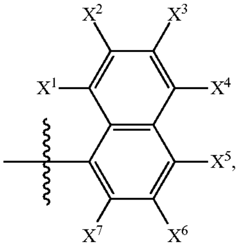

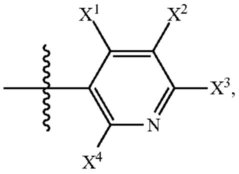

-continued

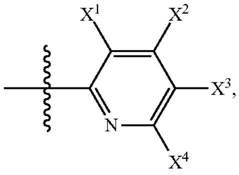

and

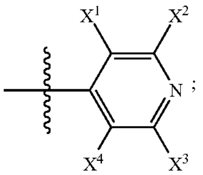

and wherein $X^1$, $X^2$, $X^3$, $X^4$, $X^5$, $X^6$, and $X^7$ are each independently selected from the group consisting of $C_1$-$C_6$ alkyl, F, Cl, $N(R^a)(R^b)$, $OR^b$, —C(═O)$OR^a$, —C(═O)$N(R^a)(R^a)$, $NH_2$, OH, $NO_2$, $C_1$-$C_3$ haloalkyl, $C_1$-$C_3$ haloalkoxy, and phenyl.

Embodiment 23 provides the compound of any one of Embodiments 20-22, wherein at least one of $X^1$, $X^2$, $X^3$, $X^4$, $X^5$, $X^6$, and $X^7$, if present, is selected from the group consisting of $CF_3$, $NH_2$, $O(CH(CH_3)_2)$, $OCF_3$, and

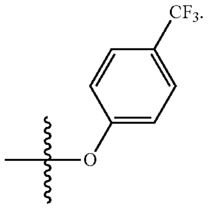 [SMILES: *Oc1ccc(C(F)(F)F)cc1]

Embodiment 24 provides the compound of any one of Embodiments 20-23, wherein Ar is selected from the group consisting of

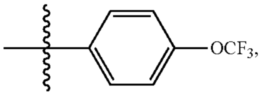

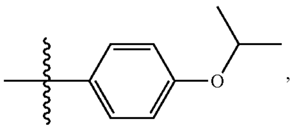

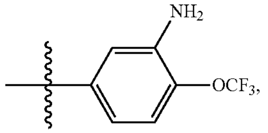

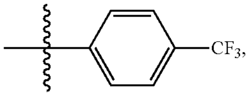

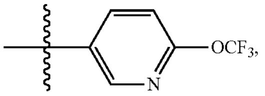

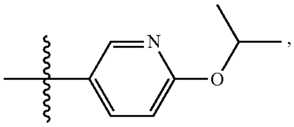

, and

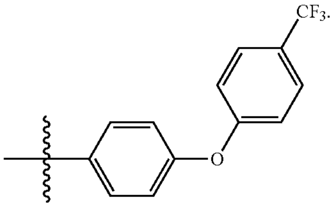

Embodiment 25 provides the compound of Embodiment 1, which is selected from the group consisting of:

N-(6-fluoro-2,2-dimethylchroman-4-yl)-4-(trifluoromethoxy)benzenesulfonamide;

N-(1-(tert-butyl)-2-(4-chloro-3-fluorophenyl)pyrrolidin-3-yl)-4-(trifluoromethoxy)benzenesulfonamide;
tert-butyl 4-(2-((4-(trifluoromethoxy)phenyl)sulfonamido)cyclopropyl)piperidine-1-carboxylate;
tert-butyl 2-(1-((4-(trifluoromethoxy)phenyl)sulfonamido)cyclopropyl)pyrrolidine-1-carboxylate;
N-(6-(difluoromethoxy)-4-oxo-1,2,3,4-tetrahydronaphthalen-1-yl)-4-(trifluoromethoxy)benzenesulfonamide;
N-(1-(3-ethoxy-4-hydroxybenzyl)piperidin-4-yl)-4-(trifluoromethoxy)benzenesulfonamide;
tert-butyl 3-(fluoromethyl)-3-((4-(trifluoromethoxy)phenyl)sulfonamido)pyrrolidine-1-carboxylate;
N-(1-cyclopropyl-2-(3,4-difluorophenyl)pyrrolidin-3-yl)-4-(trifluoromethoxy)benzenesulfonamide;
N-(2-oxo-1-(3-(trifluoromethyl)benzyl)piperidin-3-yl)-4-(trifluoromethoxy)benzenesulfonamide;
N-(spiro[chromane-2,1'-cyclopentan]-4-yl)-4-(trifluoromethoxy)benzenesulfonamide;
N-(1-benzyl-3-phenylpyrrolidin-3-yl)-4-(trifluoromethoxy)benzenesulfonamide;
N-(4-(3-fluoro-4-methoxyphenyl)tetrahydro-2H-pyran-4-yl)-4-(trifluoromethoxy)benzenesulfonamide;
N-(3-phenylpyrrolidin-3-yl)-4-(trifluoromethoxy)benzenesulfonamide;
N-(1-(3-chlorophenyl)cyclopentyl)-4-(trifluoromethoxy)benzenesulfonamide;
methyl 3-(1-((4-(trifluoromethoxy)phenyl)sulfonamido)cyclopentyl)propiolate;
N-(4,6-dichloro-2,3-dihydro-1H-inden-1-yl)-4-(trifluoromethoxy)benzenesulfonamide;
N-2-benzyl-7-hydroxy-1-isopropyl-2-azaspiro[3.4]octan-6-yl)-4-(trifluoromethoxy)benzenesulfonamide;
N-(6-chloro-1,2,3,4-tetrahydronaphthalen-1-yl)-4-(trifluoromethoxy)benzenesulfonamide;
N-(1-(3-methoxyphenyl)cyclopentyl)-4-(trifluoromethoxy)benzenesulfonamide;
N-(2-(4-chlorophenyl)-1-methylpyrrolidin-3-yl)-4-(trifluoromethoxy)benzenesulfonamide;
N-(1-(3,4-dichlorophenyl)piperidin-3-yl)-4-(trifluoromethoxy)benzenesulfonamide;
3,5-dimethyl-N-((1-((4-(trifluoromethoxy)phenyl)sulfonamido)cyclohexyl)methyl)isoxazole-4-sulfonamide;
N-(1-(2-phenylbutanoyl)piperidin-4-yl)-4-(trifluoromethoxy)benzenesulfonamide;
4-(trifluoromethoxy)-N-(1-(3-(trifluoromethoxy)phenyl)pyrrolidin-3-yl)benzenesulfonamide;
N-(2-ethyl-1-(m-tolyl)cyclopropyl)-4-(trifluoromethoxy)benzenesulfonamide;
N-(1-(5-chloro-2-methoxyphenyl)pyrrolidin-3-yl)-4-(trifluoromethoxy)benzenesulfonamide;
N-(5,8-difluorochroman-4-yl)-4-(trifluoromethoxy)benzenesulfonamide;
N-(2-(4-chlorophenyl)cyclopropyl)-4-(trifluoromethoxy)benzenesulfonamide;
N-(2-(3,4-dichlorophenyl)cyclopentyl)-4-(trifluoromethoxy)benzenesulfonamide;
N-(3-(4-chlorophenyl)pyrrolidin-3-yl)-4-(trifluoromethoxy)benzenesulfonamide;
N-(3-(3,4-dichlorophenyl)pyrrolidin-3-yl)-4-(trifluoromethoxy)benzenesulfonamide;
N-(4-(4-chlorophenyl)piperidin-4-yl)-4-(trifluoromethoxy)benzenesulfonamide;
N-(1-(3-bromophenyl)pyrrolidin-3-yl)-4-(trifluoromethoxy)benzenesulfonamide;
N-(3-(4-chlorophenyl)azetidin-3-yl)-4-(trifluoromethoxy)benzenesulfonamide;
N-(3-(3,4-dichlorophenyl)azetidin-3-yl)-4-(trifluoromethoxy)benzenesulfonamide;
N-(4-(3,4-dichlorophenyl)piperidin-4-yl)-4-(trifluoromethoxy)benzenesulfonamide;
N-(4-phenylpiperidin-4-yl)-4-(trifluoromethoxy)benzenesulfonamide;
benzyl 3-(3,4-dichlorophenyl)-3-((4-(trifluoromethoxy)phenyl)sulfonamido)pyrrolidine-1-carboxylate;
N-(3-(4-chloro-3-fluorophenyl)pyrrolidin-3-yl)-4-(trifluoromethoxy)benzenesulfonamide;
tert-butyl 4-(4-chlorophenyl)-4-((4-(trifluoromethoxy)phenyl)sulfonamido)piperidine-1-carboxylate;
N-(1-benzyl-3-(4-chlorophenyl)pyrrolidin-3-yl)-4-(4-(trifluoromethyl)phenoxy)benzenesulfonamide;
N-(1-benzyl-3-(3,4-dichlorophenyl)pyrrolidin-3-yl)-4-(4-(trifluoromethyl)phenoxy)benzenesulfonamide;
N-(4-(4-chloro-3-fluorophenyl)piperidin-4-yl)-4-(trifluoromethoxy)benzenesulfonamide;
N-(3-(4-chlorophenyl)pyrrolidin-3-yl)-4-(4-(trifluoromethyl)phenoxy)benzenesulfonamide;
N-(3-(4-chloro-3-fluorophenyl)azetidin-3-yl)-4-(trifluoromethoxy)benzenesulfonamide;
N-(4-(4-fluorophenyl)piperidin-4-yl)-4-(trifluoromethoxy)benzenesulfonamide;
N-(4-phenylpiperidin-4-yl)-6-(trifluoromethoxy)pyridine-3-sulfonamide;
N-(1-methyl-4-phenylpiperidin-4-yl)-4-(trifluoromethoxy)benzenesulfonamide;
N-(4-(4-chlorophenyl)piperidin-4-yl)-4-isopropoxybenzenesulfonamide;
N-(3-(4-chlorophenyl)pyrrolidin-3-yl)-4-(trifluoromethoxy)benzenesulfonimidamide;
N-(3-(4-chlorophenyl)pyrrolidin-3-yl)-6-(trifluoromethoxy)pyridine-3-sulfonamide;
N-(4-(5-fluoropyridin-2-yl)piperidin-4-yl)-4-(trifluoromethoxy)benzenesulfonamide;
N-(4-(bicyclo[1.1.1]pentan-1-yl)piperidin-4-yl)-4-(trifluoromethoxy)benzenesulfonamide;
N-(4-(4-chlorophenyl)piperidin-4-yl)-6-isopropoxypyridine-3-sulfonamide;
N-(3-(4-chlorophenyl)pyrrolidin-3-yl)-N'-methyl-4-(trifluoromethoxy)benzenesulfonimidamide;
N-(3-(4-chlorophenyl)-1-methylpyrrolidin-3-yl)-4-(trifluoromethoxy)benzenesulfonamide;
tert-butyl 3-(4-chlorophenyl)-3-((4-(trifluoromethoxy)phenyl)sulfonamido)pyrrolidine-1-carboxylate;
N-(3-(4-chlorophenyl)-1-(oxetan-3-yl)pyrrolidin-3-yl)-4-(trifluoromethoxy)benzenesulfonamide;
N-(3-(4-chlorophenyl)-1-(methylsulfonyl)pyrrolidin-3-yl)-4-(trifluoromethoxy)benzenesulfonamide;
N-(4-(5-chlorothiazol-2-yl)piperidin-4-yl)-4-(trifluoromethoxy)benzenesulfonamide;
N-(3-(4-fluorophenyl)pyrrolidin-3-yl)-4-(trifluoromethoxy)benzenesulfonamide;
N-(4-(4-fluorophenyl)piperidin-4-yl)-4-isopropoxybenzenesulfonamide;
N-(3-(4-chlorophenyl)-1-isopentylpyrrolidin-3-yl)-4-(trifluoromethoxy)benzenesulfonamide;
N-(4-(4-fluorophenyl)piperidin-4-yl)-6-isopropoxypyridine-3-sulfonamide;
N-(3-(4-fluorophenyl)pyrrolidin-3-yl)-4-isopropoxybenzenesulfonamide;
rac N-((3S,4S)-3-(4-chlorophenyl)-4-fluoropyrrolidin-3-yl)-4-(trifluoromethoxy)benzenesulfonamide;
N-(3-(4-chlorophenyl)pyrrolidin-3-yl)-6-isopropoxypyridine-3-sulfonamide;

N-(3-(4-chlorophenyl)-1-(3-methylbutanoyl)pyrrolidin-3-yl)-4-(trifluoromethoxy)benzenesulfonamide;
N-(4-(3,4-difluorophenyl)piperidin-4-yl)-4-(trifluoromethoxy)benzenesulfonamide;
N-(4-(2,4-difluorophenyl)piperidin-4-yl)-4-(trifluoromethoxy)benzenesulfonamide;
N-(3-(4-fluorophenyl)pyrrolidin-3-yl)-4-(trifluoromethoxy)benzenesulfonimidamide;
N-(3-(4-chlorophenyl)pyrrolidin-3-yl)-N-methyl-4-(trifluoromethoxy)benzenesulfonamide;
N-(3-phenyl-8-azabicyclo[3.2.1]octan-3-yl)-4-(trifluoromethoxy)benzenesulfonamide;
N-(4-(5-chloropyridin-2-yl)piperidin-4-yl)-4-(trifluoromethoxy)benzenesulfonamide;
N-(4-(2,5-difluorophenyl)piperidin-4-yl)-4-(trifluoromethoxy)benzenesulfonamide;
N-(1-(3,4-dichlorophenyl)cyclopropyl)-4-(trifluoromethoxy)benzenesulfonamide;
N-(3-phenylpiperidin-3-yl)-4-(trifluoromethoxy)benzenesulfonamide;
N-(4-(5-chlorothiophen-2-yl)piperidin-4-yl)-4-(trifluoromethoxy)benzenesulfonamide;
3-amino-N-(3-(4-fluorophenyl)pyrrolidin-3-yl)-4-(trifluoromethoxy)benzenesulfonamide;
3-amino-N-(3-(4-fluoro-3-methylphenyl)pyrrolidin-3-yl)-4-(trifluoromethoxy)benzenesulfonamide;
N-(4-(4-chloro-2-fluorophenyl)piperidin-4-yl)-4-(trifluoromethoxy)benzenesulfonamide;
N-(4-(5-chloro-3-fluoropyridin-2-yl)piperidin-4-yl)-4-(trifluoromethoxy)benzenesulfonamide;
N'-(4-(4-chlorophenyl)piperidin-4-yl)-4-(trifluoromethoxy)benzenesulfonimidamide;
N-(4-(4-chlorophenyl)piperidin-4-yl)-4-(trifluoromethyl)benzenesulfonamide;
N-(4-(4-chlorophenyl)piperidin-4-yl)-3-(trifluoromethyl)bicyclo[1.1.1]pentane-1-sulfonamide;
3-amino-N-(4-(4-chlorophenyl)piperidin-4-yl)-4-(trifluoromethoxy)benzenesulfonamide; and
N-(4-(4-(difluoromethyl)phenyl)piperidin-4-yl)-4-(trifluoromethoxy)benzenesulfonamide;
or a salt, solvate, isotopologue, or tautomer thereof.

Embodiment 26 provides the compound of Embodiment 1, which is selected from the group consisting of:
(R)—N-(6-fluoro-2,2-dimethylchroman-4-yl)-4-(trifluoromethoxy)benzenesulfonamide;
N-((2R,3R)-1-(tert-butyl)-2-(4-chloro-3-fluorophenyl)pyrrolidin-3-yl)-4-(trifluoromethoxy)benzenesulfonamide;
N-((2R,3S)-1-(tert-butyl)-2-(4-chloro-3-fluorophenyl)pyrrolidin-3-yl)-4-(trifluoromethoxy)benzenesulfonamide;
tert-butyl 4-((1R,2R)-2-((4-(trifluoromethoxy)phenyl)sulfonamido)cyclopropyl)piperidine-1-carboxylate;
tert-butyl 4-((1R,2S)-2-((4-(trifluoromethoxy)phenyl)sulfonamido)cyclopropyl)piperidine-1-carboxylate;
(R)-tert-butyl 2-(1-((4-(trifluoromethoxy)phenyl)sulfonamido)cyclopropyl)pyrrolidine-1-carboxylate;
(R)—N-(6-(difluoromethoxy)-4-oxo-1,2,3,4-tetrahydronaphthalen-1-yl)-4-(trifluoromethoxy)benzenesulfonamide;
tert-butyl (R)-3-(fluoromethyl)-3-((4-(trifluoromethoxy)phenyl)sulfonamido)pyrrolidine-1-carboxylate;
N-((2R,3R)-1-cyclopropyl-2-(3,4-difluorophenyl)pyrrolidin-3-yl)-4-(trifluoromethoxy)benzenesulfonamide;
N-((2R,3S)-1-cyclopropyl-2-(3,4-difluorophenyl)pyrrolidin-3-yl)-4-(trifluoromethoxy)benzenesulfonamide;
(R)—N-(2-oxo-1-(3-(trifluoromethyl)benzyl)piperidin-3-yl)-4-(trifluoromethoxy)benzenesulfonamide;
(R)—N-(spiro[chromane-2,1'-cyclopentan]-4-yl)-4-(trifluoromethoxy)benzenesulfonamide;
(R)—N-(1-benzyl-3-phenylpyrrolidin-3-yl)-4-(trifluoromethoxy)benzenesulfonamide;
(R)—N-(3-phenylpyrrolidin-3-yl)-4-(trifluoromethoxy)benzenesulfonamide;
(R)—N-(4,6-dichloro-2,3-dihydro-1H-inden-1-yl)-4-(trifluoromethoxy)benzenesulfonamide;
N-((6R,7R)-2-benzyl-7-hydroxy-1-isopropyl-2-azaspiro[3.4]octan-6-yl)-4-(trifluoromethoxy)benzenesulfonamide;
N-((6R,7S)-2-benzyl-7-hydroxy-1-isopropyl-2-azaspiro[3.4]octan-6-yl)-4-(trifluoromethoxy)benzenesulfonamide;
(R)—N-(6-chloro-1,2,3,4-tetrahydronaphthalen-1-yl)-4-(trifluoromethoxy)benzenesulfonamide;
N-((2R,3R)-2-(4-chlorophenyl)-1-methylpyrrolidin-3-yl)-4-(trifluoromethoxy)benzenesulfonamide;
N-((2R,3S)-2-(4-chlorophenyl)-1-methylpyrrolidin-3-yl)-4-(trifluoromethoxy)benzenesulfonamide;
(R)—N-(1-(3,4-dichlorophenyl)piperidin-3-yl)-4-(trifluoromethoxy)benzenesulfonamide;
(R)—N-(1-(2-phenylbutanoyl)piperidin-4-yl)-4-(trifluoromethoxy)benzenesulfonamide;
(R)-4-(trifluoromethoxy)-N-(1-(3-(trifluoromethoxy)phenyl)pyrrolidin-3-yl)benzenesulfonamide;
N-((1R,2R)-2-ethyl-1-(m-tolyl)cyclopropyl)-4-(trifluoromethoxy)benzenesulfonamide;
N-((1R,2S)-2-ethyl-1-(m-tolyl)cyclopropyl)-4-(trifluoromethoxy)benzenesulfonamide;
(R)—N-(1-(5-chloro-2-methoxyphenyl)pyrrolidin-3-yl)-4-(trifluoromethoxy)benzenesulfonamide;
(R)—N-(5,8-difluorochroman-4-yl)-4-(trifluoromethoxy)benzenesulfonamide;
N-((1R,2R)-2-(4-chlorophenyl)cyclopropyl)-4-(trifluoromethoxy)benzenesulfonamide;
N-((1R,2S)-2-(4-chlorophenyl)cyclopropyl)-4-(trifluoromethoxy)benzenesulfonamide;
N-((1R,2R)-2-(3,4-dichlorophenyl)cyclopentyl)-4-(trifluoromethoxy)benzenesulfonamide;
N-((1R,2S)-2-(3,4-dichlorophenyl)cyclopentyl)-4-(trifluoromethoxy)benzenesulfonamide;
(R)—N-(3-(4-chlorophenyl)pyrrolidin-3-yl)-4-(trifluoromethoxy)benzenesulfonamide;
(R)—N-(3-(3,4-dichlorophenyl)pyrrolidin-3-yl)-4-(trifluoromethoxy)benzenesulfonamide;
(R)—N-(1-(3-bromophenyl)pyrrolidin-3-yl)-4-(trifluoromethoxy)benzenesulfonamide;
(R)-benzyl 3-(3,4-dichlorophenyl)-3-((4-(trifluoromethoxy)phenyl)sulfonamido)pyrrolidine-1-carboxylate;
N-((3R,4R)-4-(3,4-dichlorophenyl)pyrrolidin-3-yl)-4-(trifluoromethoxy)benzenesulfonamide;
N-((3R,4S)-4-(3,4-dichlorophenyl)pyrrolidin-3-yl)-4-(trifluoromethoxy)benzenesulfonamide;
(R)—N-(3-(4-chloro-3-fluorophenyl)pyrrolidin-3-yl)-4-(trifluoromethoxy)benzenesulfonamide;
(R)—N-(1-benzyl-3-(4-chlorophenyl)pyrrolidin-3-yl)-4-(4-(trifluoromethyl)phenoxy)benzenesulfonamide;
(R)—N-(1-benzyl-3-(3,4-dichlorophenyl)pyrrolidin-3-yl)-4-(4-(trifluoromethyl)phenoxy)benzenesulfonamide;
(R)—N-(3-(4-chlorophenyl)pyrrolidin-3-yl)-4-(4-(trifluoromethyl)phenoxy)benzenesulfonamide;
(R)—N—((R)-3-(4-chlorophenyl)yrrolidine-3-yl)-4-(trifluoromethoxy)benzenesulfonimidamide;
(R)—N—((S)-3-(4-chlorophenyl)yrrolidine-3-yl)-4-(trifluoromethoxy)benzenesulfonimidamide;

(R)—N-(3-(4-chlorophenyl)yrrolidine-3-yl)-6-(trifluoromethoxy)pyridine-3-sulfonamide;

(R)—N—((R)-3-(4-chlorophenyl)yrrolidine-3-yl)-N'-methyl-4-(trifluoromethoxy)benzenesulfonimidamide;

(R)—N—((S)-3-(4-chlorophenyl)yrrolidine-3-yl)-N'-methyl-4-(trifluoromethoxy)benzenesulfonimidamide;

(R)—N-(3-(4-chlorophenyl)-1-methylpyrrolidin-3-yl)-4-(trifluoromethoxy)benzenesulfonamide;

tert-butyl (R)-3-(4-chlorophenyl)-3-((4-(trifluoromethoxy)phenyl)yrrolidine)pyrrolidine-1-carboxylate;

(R)—N-(3-(4-chlorophenyl)-1-(oxetan-3-yl)yrrolidine-3-yl)-4-(trifluoromethoxy)benzenesulfonamide;

(R)—N-(3-(4-chlorophenyl)-1-(methylsulfonyl)yrrolidine-3-yl)-4-(trifluoromethoxy)benzenesulfonamide;

(R)—N-(3-(4-fluorophenyl)yrrolidine-3-yl)-4-(trifluoromethoxy)benzenesulfonamide;

(R)—N-(3-(4-chlorophenyl)-1-isopentylpyrrolidin-3-yl)-4-(trifluoromethoxy)benzenesulfonamide;

(R)—N-(3-(4-fluorophenyl)yrrolidine-3-yl)-4-isopropoxybenzenesulfonamide;

N-((3R,4R)-3-(4-chlorophenyl)-4-fluoropyrrolidin-3-yl)-4-(trifluoromethoxy)benzenesulfonamide;

N-((3R,4S)-3-(4-chlorophenyl)-4-fluoropyrrolidin-3-yl)-4-(trifluoromethoxy)benzenesulfonamide;

(R)—N-(3-(4-chlorophenyl)yrrolidine-3-yl)-6-isopropoxypyridine-3-sulfonamide;

(R)—N-(3-(4-chlorophenyl)-1-(3-methylbutanoyl)yrrolidine-3-yl)-4-(trifluoromethoxy)benzenesulfonamide;

(R)—N—((R)-3-(4-fluorophenyl)pyrrolidin-3-yl)-4-(trifluoromethoxy)benzenesulfonimidamide;

(R)—N—((S)-3-(4-fluorophenyl)pyrrolidin-3-yl)-4-(trifluoromethoxy)benzenesulfonimidamide;

(R)—N-(3-(4-chlorophenyl)pyrrolidin-3-yl)-N-methyl-4-(trifluoromethoxy)benzenesulfonamide;

(R)—N-(3-phenylpiperidin-3-yl)-4-(trifluoromethoxy)benzenesulfonamide;

(R)-3-amino-N-(3-(4-fluorophenyl)pyrrolidin-3-yl)-4-(trifluoromethoxy)benzenesulfonamide; and (R)-3-amino-N-(3-(4-fluoro-3-methylphenyl)pyrrolidin-3-yl)-4-(trifluoromethoxy)benzenesulfonamide;

or a salt, solvate, isotopologue, or tautomer thereof.

Embodiment 27 provides the compound of Embodiment 1, which is selected from the group consisting of:

(S)—N-(6-fluoro-2,2-dimethylchroman-4-yl)-4-(trifluoromethoxy)benzenesulfonamide;

N-((2S,3S)-1-(tert-butyl)-2-(4-chloro-3-fluorophenyl)pyrrolidin-3-yl)-4-(trifluoromethoxy)benzenesulfonamide;

N-((2S,3R)-1-(tert-butyl)-2-(4-chloro-3-fluorophenyl)pyrrolidin-3-yl)-4-(trifluoromethoxy)benzenesulfonamide;

tert-butyl 4-((1S,2S)-2-((4-(trifluoromethoxy)phenyl)sulfonamido)cyclopropyl)piperidine-1-carboxylate;

tert-butyl 4-((1S,2R)-2-((4-(trifluoromethoxy)phenyl)sulfonamido)cyclopropyl)piperidine-1-carboxylate;

(S)-tert-butyl 2-(1-((4-(trifluoromethoxy)phenyl)sulfonamido)cyclopropyl)pyrrolidine-1-carboxylate;

(S)—N-(6-(difluoromethoxy)-4-oxo-1,2,3,4-tetrahydronaphthalen-1-yl)-4-(trifluoromethoxy)benzenesulfonamide;

tert-butyl (S)-3-(fluoromethyl)-3-((4-(trifluoromethoxy)phenyl)sulfonamido)pyrrolidine-1-carboxylate;

N-((2S,3S)-1-cyclopropyl-2-(3,4-difluorophenyl)pyrrolidin-3-yl)-4-(trifluoromethoxy)benzenesulfonamide;

N-((2S,3R)-1-cyclopropyl-2-(3,4-difluorophenyl)pyrrolidin-3-yl)-4-(trifluoromethoxy)benzenesulfonamide;

(S)—N-(2-oxo-1-(3-(trifluoromethyl)benzyl)piperidin-3-yl)-4-(trifluoromethoxy)benzenesulfonamide;

(S)—N-(spiro[chromane-2,1'-cyclopentan]-4-yl)-4-(trifluoromethoxy)benzenesulfonamide;

(S)—N-(1-benzyl-3-phenylpyrrolidin-3-yl)-4-(trifluoromethoxy)benzenesulfonamide;

(S)—N-(3-phenylpyrrolidin-3-yl)-4-(trifluoromethoxy)benzenesulfonamide;

(S)—N-(4,6-dichloro-2,3-dihydro-1H-inden-1-yl)-4-(trifluoromethoxy)benzenesulfonamide;

N-((6S,7S)-2-benzyl-7-hydroxy-1-isopropyl-2-azaspiro[3.4]octan-6-yl)-4-(trifluoromethoxy)benzenesulfonamide;

N-((6S,7R)-2-benzyl-7-hydroxy-1-isopropyl-2-azaspiro[3.4]octan-6-yl)-4-(trifluoromethoxy)benzenesulfonamide;

(S)—N-(6-chloro-1,2,3,4-tetrahydronaphthalen-1-yl)-4-(trifluoromethoxy)benzenesulfonamide;

N-((2S,3S)-2-(4-chlorophenyl)-1-methylpyrrolidin-3-yl)-4-(trifluoromethoxy)benzenesulfonamide;

N-((2S,3R)-2-(4-chlorophenyl)-1-methylpyrrolidin-3-yl)-4-(trifluoromethoxy)benzenesulfonamide;

(S)—N-(1-(3,4-dichlorophenyl)piperidin-3-yl)-4-(trifluoromethoxy)benzenesulfonamide;

(S)—N-(1-(2-phenylbutanoyl)piperidin-4-yl)-4-(trifluoromethoxy)benzenesulfonamide;

(S)-4-(trifluoromethoxy)-N-(1-(3-(trifluoromethoxy)phenyl)pyrrolidin-3-yl)benzenesulfonamide;

N-((1S,2S)-2-ethyl-1-(m-tolyl)cyclopropyl)-4-(trifluoromethoxy)benzenesulfonamide;

N-((1S,2R)-2-ethyl-1-(m-tolyl)cyclopropyl)-4-(trifluoromethoxy)benzenesulfonamide;

(S)—N-(1-(5-chloro-2-methoxyphenyl)pyrrolidin-3-yl)-4-(trifluoromethoxy)benzenesulfonamide;

(S)—N-(5,8-difluorochroman-4-yl)-4-(trifluoromethoxy)benzenesulfonamide;

N-((1S,2S)-2-(4-chlorophenyl)cyclopropyl)-4-(trifluoromethoxy)benzenesulfonamide;

N-((1S,2R)-2-(4-chlorophenyl)cyclopropyl)-4-(trifluoromethoxy)benzenesulfonamide;

N-((1S,2S)-2-(3,4-dichlorophenyl)cyclopentyl)-4-(trifluoromethoxy)benzenesulfonamide;

N-((1R,2S)-2-(3,4-dichlorophenyl)cyclopentyl)-4-(trifluoromethoxy)benzenesulfonamide;

(S)—N-(3-(4-chlorophenyl)pyrrolidin-3-yl)-4-(trifluoromethoxy)benzenesulfonamide;

(S)—N-(3-(3,4-dichlorophenyl)pyrrolidin-3-yl)-4-(trifluoromethoxy)benzenesulfonamide;

(S)—N-(1-(3-bromophenyl)pyrrolidin-3-yl)-4-(trifluoromethoxy)benzenesulfonamide;

(S)-benzyl 3-(3,4-dichlorophenyl)-3-((4-(trifluoromethoxy)phenyl)sulfonamido)pyrrolidine-1-carboxylate;

N-((3S,4S)-4-(3,4-dichlorophenyl)pyrrolidin-3-yl)-4-(trifluoromethoxy)benzenesulfonamide;

N-((3S,4R)-4-(3,4-dichlorophenyl)pyrrolidin-3-yl)-4-(trifluoromethoxy)benzenesulfonamide;

(S)—N-(3-(4-chloro-3-fluorophenyl)pyrrolidin-3-yl)-4-(trifluoromethoxy)benzenesulfonamide;

(S)—N-(1-benzyl-3-(4-chlorophenyl)pyrrolidin-3-yl)-4-(4-(trifluoromethyl)phenoxy)benzenesulfonamide;

(S)—N-(1-benzyl-3-(3,4-dichlorophenyl)pyrrolidin-3-yl)-4-(4-(trifluoromethyl)phenoxy)benzenesulfonamide;

(S)—N-(3-(4-chlorophenyl)pyrrolidin-3-yl)-4-(4-(trifluoromethyl)phenoxy)benzenesulfonamide;

(S)—N—((S)-3-(4-chlorophenyl)pyrrolidin-3-yl)-4-(trifluoromethoxy)benzenesulfonimidamide;

(S)—N—((R)-3-(4-chlorophenyl)pyrrolidin-3-yl)-4-(trifluoromethoxy)benzenesulfonimidamide;

(S)—N-(3-(4-chlorophenyl)pyrrolidin-3-yl)-6-(trifluoromethoxy)pyridine-3-sulfonamide;

(S)—N—((S)-3-(4-chlorophenyl)pyrrolidin-3-yl)-N'-methyl-4-(trifluoromethoxy)benzenesulfonimidamide;

(S)—N—((R)-3-(4-chlorophenyl)pyrrolidin-3-yl)-N'-methyl-4-(trifluoromethoxy)benzenesulfonimidamide;

(S)—N-(3-(4-chlorophenyl)-1-methylpyrrolidin-3-yl)-4-(trifluoromethoxy)benzenesulfonamide;

tert-butyl (S)-3-(4-chlorophenyl)-3-((4-(trifluoromethoxy)phenyl)sulfonamido)pyrrolidine-1-carboxylate;

(S)—N-(3-(4-chlorophenyl)-1-(oxetan-3-yl)pyrrolidin-3-yl)-4-(trifluoromethoxy)benzenesulfonamide;

(S)—N-(3-(4-chlorophenyl)-1-(methylsulfonyl)pyrrolidin-3-yl)-4-(trifluoromethoxy)benzenesulfonamide;

(S)—N-(3-(4-fluorophenyl)pyrrolidin-3-yl)-4-(trifluoromethoxy)benzenesulfonamide;

(S)—N-(3-(4-chlorophenyl)-1-isopentylpyrrolidin-3-yl)-4-(trifluoromethoxy)benzenesulfonamide;

(S)—N-(3-(4-fluorophenyl)pyrrolidin-3-yl)-4-isopropoxybenzenesulfonamide;

N-((3S,4S)-3-(4-chlorophenyl)-4-fluoropyrrolidin-3-yl)-4-(trifluoromethoxy)benzenesulfonamide;

N-((3S,4R)-3-(4-chlorophenyl)-4-fluoropyrrolidin-3-yl)-4-(trifluoromethoxy)benzenesulfonamide;

(S)—N-(3-(4-chlorophenyl)pyrrolidin-3-yl)-6-isopropoxypyridine-3-sulfonamide;

(S)—N-(3-(4-chlorophenyl)-1-(3-methylbutanoyl)pyrrolidin-3-yl)-4-(trifluoromethoxy)benzenesulfonamide;

(S)—N—((S)-3-(4-fluorophenyl)pyrrolidin-3-yl)-4-(trifluoromethoxy)benzenesulfonimidamide;

(S)—N—((R)-3-(4-fluorophenyl)pyrrolidin-3-yl)-4-(trifluoromethoxy)benzenesulfonimidamide;

(S)—N-(3-(4-chlorophenyl)pyrrolidin-3-yl)-N-methyl-4-(trifluoromethoxy)benzenesulfonamide;

(S)—N-(3-phenylpiperidin-3-yl)-4-(trifluoromethoxy)benzenesulfonamide;

(S)-3-amino-N-(3-(4-fluorophenyl)pyrrolidin-3-yl)-4-(trifluoromethoxy)benzenesulfonamide;

and (S)-3-amino-N-(3-(4-fluoro-3-methylphenyl)pyrrolidin-3-yl)-4-(trifluoromethoxy)benzenesulfonamide;

or a salt, solvate, isotopologue, or tautomer thereof.

Embodiment 28 provides a compound selected from the group consisting of N-(4-((4-((4-(trifluoromethoxy)phenyl)sulfonamido)piperidin-1-yl)sulfonyl)phenyl)acetamide;

methyl 1-((4-(trifluoromethoxy)phenyl)sulfonamido)-2,3-dihydro-1H-indene-2-carboxylate;

methyl (1R,2R)-1-((4-(trifluoromethoxy)phenyl)sulfonamido)-2,3-dihydro-1H-indene-2-carboxylate;

methyl (1R,2S)-1-((4-(trifluoromethoxy)phenyl)sulfonamido)-2,3-dihydro-1H-indene-2-carboxylate;

methyl (1S,2S)-1-((4-(trifluoromethoxy)phenyl)sulfonamido)-2,3-dihydro-1H-indene-2-carboxylate;

methyl (1S,2R)-1-((4-(trifluoromethoxy)phenyl)sulfonamido)-2,3-dihydro-1H-indene-2-carboxylate;

N-(2-(4-fluorophenoxy)cyclohexyl)-4-(trifluoromethoxy)benzenesulfonamide;

N-((1R,2R)-2-(4-fluorophenoxy)cyclohexyl)-4-(trifluoromethoxy)benzenesulfonamide;

N-((1R,2S)-2-(4-fluorophenoxy)cyclohexyl)-4-(trifluoromethoxy)benzenesulfonamide;

N-((1S,2S)-2-(4-fluorophenoxy)cyclohexyl)-4-(trifluoromethoxy)benzenesulfonamide;

N-((1S,2R)-2-(4-fluorophenoxy)cyclohexyl)-4-(trifluoromethoxy)benzenesulfonamide;

4-(trifluoromethoxy)-N-(3,4,4-trimethylcyclohexyl)benzenesulfonamide;

(R)-4-(trifluoromethoxy)-N-(3,4,4-trimethylcyclohexyl)benzenesulfonamide;

(S)-4-(trifluoromethoxy)-N-(3,4,4-trimethylcyclohexyl)benzenesulfonamide;

4-(trifluoromethoxy)-N-((1R,3R)-3,4,4-trimethylcyclohexyl)benzenesulfonamide;

4-(trifluoromethoxy)-N-((1R,3S)-3,4,4-trimethylcyclohexyl)benzenesulfonamide;

4-(trifluoromethoxy)-N-((1S,3S)-3,4,4-trimethylcyclohexyl)benzenesulfonamide;

4-(trifluoromethoxy)-N-((1S,3R)-3,4,4-trimethylcyclohexyl)benzenesulfonamide;

N-(2-phenylcycloheptyl)-4-(trifluoromethoxy)benzenesulfonamide;

N-((1R,2R)-2-phenylcycloheptyl)-4-(trifluoromethoxy)benzenesulfonamide;

N-((1R,2S)-2-phenylcycloheptyl)-4-(trifluoromethoxy)benzenesulfonamide;

N-((1S,2S)-2-phenylcycloheptyl)-4-(trifluoromethoxy)benzenesulfonamide;

N-((1S,2R)-2-phenylcycloheptyl)-4-(trifluoromethoxy)benzenesulfonamide;

ethyl 1-((4-(trifluoromethoxy)phenyl)sulfonamido)-2,3-dihydro-1H-indene-1-carboxylate;

ethyl (R)-1-((4-(trifluoromethoxy)phenyl)sulfonamido)-2,3-dihydro-TH-indene-1-carboxylate;

ethyl (S)-1-((4-(trifluoromethoxy)phenyl)sulfonamido)-2,3-dihydro-TH-indene-1-carboxylate;

methyl 3,5-dimethyl-7-((4-(trifluoromethoxy)phenyl)sulfonamido)adamantane-1-carboxylate;

N-(2-benzyloctahydrocyclopenta[c]pyrrol-4-yl)-4-(trifluoromethoxy)benzenesulfonamide;

(R)—N-(2-benzyloctahydrocyclopenta[c]pyrrol-4-yl)-4-(trifluoromethoxy)benzenesulfonamide;

(S)—N-(2-benzyloctahydrocyclopenta[c]pyrrol-4-yl)-4-(trifluoromethoxy)benzenesulfonamide;

4-(trifluoromethoxy)-N-(4-(trifluoromethyl)-4,5,6,7-tetrahydro-1H-indazol-6-yl)benzenesulfonamide;

4-(trifluoromethoxy)-N-((4R,6R)-4-(trifluoromethyl)-4,5,6,7-tetrahydro-TH-indazol-6-yl)benzenesulfonamide;

4-(trifluoromethoxy)-N-((4R,6S)-4-(trifluoromethyl)-4,5,6,7-tetrahydro-1H-indazol-6-yl)benzenesulfonamide;

4-(trifluoromethoxy)-N-((4S,6S)-4-(trifluoromethyl)-4,5,6,7-tetrahydro-TH-indazol-6-yl)benzenesulfonamide; and 4-(trifluoromethoxy)-N-((4S,6R)-4-(trifluoromethyl)-4,5,6,7-tetrahydro-1H-indazol-6-yl)benzenesulfonamide; or a salt, solvate, isotopologue, or tautomer thereof.

Embodiment 29 provides a pharmaceutical composition comprising at least one compound of any one of Embodiments 1-28 and at least one pharmaceutically acceptable carrier.

Embodiment 30 provides a method of treating, preventing, and/or ameliorating a PP2A-related disease in a subject, the method comprising administering to a subject in need thereof a therapeutically effective amount of the compound of any one of Embodiments 1-28 or the pharmaceutical composition of Embodiment 29.

Embodiment 31 provides the method of Embodiment 30, wherein the PP2A-related disease is at least one selected from the group consisting of cancer, diabetes, autoimmune disease, solid organ transplant rejection, graft vs host disease, chronic obstructive pulmonary disease (COPD), non-alcoholic fatty liver disease, abdominal aortic aneurysm, chronic liver disease, heart failure, neurodegenerative disease, and cardiac hypertrophy.

Embodiment 32 provides the method of Embodiment 30 or 31, wherein the subject is a mammal.

Embodiment 33 provides the method of Embodiment 32, wherein the mammal is a human.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A compound of formula (Ia), (Ib), (Ic), (Id), (Ie), or (If), or a salt, solvate, enantiomer, diastereoisomer, isotopologue, or tautomer thereof:

(Ia)

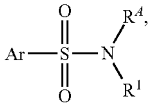

(Ib)

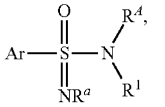

(Ic)

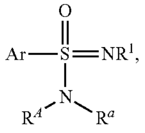

(Id)

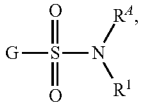

(Ie)

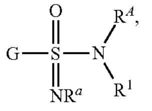

and (If)

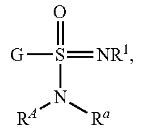

wherein:

Ar is $C_6$-$C_{10}$ aryl or $C_2$-$C_{10}$ heteroaryl, which is optionally substituted with at least one substituent selected from the group consisting of $C_1$-$C_6$ alkyl, $C_1$-$C_6$ haloalkyl, $C_1$-$C_6$ aminoalkyl, $C_1$-$C_6$ hydroxyalkyl, $C_2$-$C_6$ alkenyl, $C_2$-$C_6$ alkynyl, $C_1$-$C_6$ alkoxy, $C_1$-$C_6$ haloalkoxy, $C_2$-$C_{10}$ heteroaryl, $C_6$-$C_{10}$ aryl, $C_6$-$C_{10}$ aryloxy, halogen, OH, $NH_2$, CN, $NO_2$, —C(═O)$R^a$, —C(═O)O$R^a$, and —C(═O)N($R^a$) ($R^a$), wherein each $C_6$-$C_{10}$ aryl, $C_2$-$C_{10}$ heteroaryl, or $C_6$-$C_{10}$ aryloxy substituent in Ar is independently optionally substituted with at least one substituent selected from the group consisting of $C_1$-$C_3$ alkyl, $C_1$-$C_3$ haloalkyl, $C_1$-$C_3$ alkoxy, $C_1$-$C_3$ haloalkoxy, F, Cl, Br, I, OH, CN, $NO_2$, —C(═O)O$R^a$, and —C(═O)N($R^a$) ($R^a$), and wherein two vicinal substituents of Ar may combine to provide a 5- to 8-membered ring which is fused with Ar;

G is optionally substituted $C_3$-$C_8$ cycloalkyl, which is optionally substituted with at least one substituent selected from the group consisting of $C_1$-$C_6$ alkyl, $C_1$-$C_6$ haloalkyl, $C_1$-$C_6$ alkoxy, $C_1$-$C_6$ haloalkoxy, phenyl, halogen, OH, $NH_2$, CN, $NO_2$, —C(═O)$R^a$, —C(═O)O$R^a$, and —C(═O)N($R^a$) ($R^a$), wherein the phenyl in G is optionally substituted with at least one substituent selected from the group consisting of $C_1$-$C_3$ alkyl, $C_1$-$C_3$ haloalkyl, $C_1$-$C_3$ alkoxy, $C_1$-$C_3$ haloalkoxy, F, Cl, Br, I, OH, CN, $NO_2$, —C(═O)O$R^a$, and —C(═O)N($R^a$) ($R^a$), and wherein two substituents in G may combine to provide a $C_3$-$C_8$ cycloalkyl which is spiro, fused, or bridged with the $C_3$-$C_8$ cycloalkyl in G;

$R^1$ is selected from the group consisting of

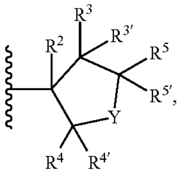

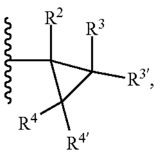

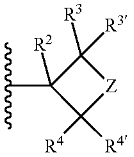

,

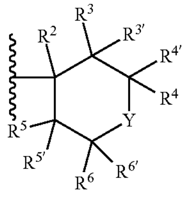

,

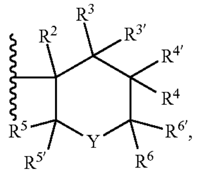

and

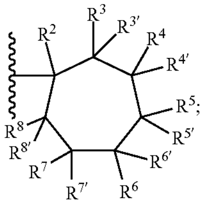

$R^2$ is selected from the group consisting of H, halogen, optionally substituted $C_1$-$C_6$ alkyl, optionally substituted phenyl, optionally substituted $C_3$-$C_6$ cycloalkyl, optionally substituted $C_2$-$C_{10}$ heterocyclyl, optionally substituted $C_1$-$C_6$ aminoalkyl, optionally substituted $C_1$-$C_6$ alkoxyalkyl, optionally substituted $C_1$-$C_6$ haloalkyl, optionally substituted $C_2$-$C_6$ alkynyl, —C(═O)O$R^a$, and—C(═O)N($R^a$) ($R^a$), wherein each optional substituent in $R^2$ is at least one selected from the group consisting of halogen, $C_1$-$C_6$ alkyl, $C_1$-$C_3$ alkoxy, $C_1$-$C_3$ haloalkoxy, $C_1$-$C_3$ haloalkyl, —C(═O)O$R^a$, —S(═O)$_2$—$C_6$-$C_{10}$ aryl, and —S(—O)$_2$—$C_2$-$C_{10}$ heteroaryl;

$R^3$, $R^{3'}$, $R^4$, $R^{4'}$, $R^5$, $R^{5'}$, $R^6$, $R^{6'}$, $R^7$, $R^{7'}$, $R^8$, and $R^{8'}$ are each independently selected from the group consisting of H, $C_1$-$C_6$ alkyl, hydroxyl, $C_1$-$C_4$ haloalkyl, optionally substituted $C_3$-$C_8$ cycloalkyl, optionally substituted $C_2$-$C_6$ heterocyclyl, optionally substituted phenyl, and optionally substituted phenoxy, wherein each optional substituent in the heterocyclyl, phenyl, or phenoxy is at least one selected from the group consisting of $C_1$-$C_3$ alkyl, $C_1$-$C_3$ haloalkyl, $C_1$-$C_3$ alkoxy, $C_1$-$C_3$ haloalkoxy, halogen, OH, C(═O)O$R^a$, and C(═O)N($R^a$) ($R^a$), wherein two geminal substituents selected from $R^3$, $R^{3'}$, $R^4$, $R^{4'}$, $R^5$, $R^{5'}$, $R^6$, $R^6$, $R^7$, $R^{7'}$, $R^8$, and $R^{8'}$ may combine with the carbon atom to which they are bound to form a moiety selected from the group consisting of an optionally substituted $C_3$-$C_8$ cycloalkyl and an optionally substituted $C_2$-$C_{10}$ heterocyclyl, wherein two vicinal substituents selected from $R^3$, $R^{3'}$, $R^4$, $R^{4'}$, $R^5$, $R^{5'}$, $R^6$, $R^6$, $R^7$, $R^{7'}$, $R^8$, and $R^{8'}$ may combine with the carbon atoms to which they are bound to form a moiety selected from the group consisting of an optionally substituted $C_3$-$C_8$ cycloalkyl, optionally substituted $C_2$-$C_{10}$ heterocyclyl, and optionally substituted phenyl;

wherein two substituents selected from $R^3$, $R^{3'}$, $R^4$, $R^{4'}$, $R^5$, $R^{5'}$, $R^6$, $R^{6'}$, $R^7$, $R^8$, and $R^{8'}$, which are separated by two to five carbon atoms, may combine with the carbon atoms to which they are bound to form a moiety selected from the group consisting of optionally substituted $C_4$-$C_7$ cycloalkyl and optionally substituted $C_4$-$C_8$ heterocyclyl;

$R^{10}$ is selected from the group consisting of H, $C_1$-$C_6$ alkyl, $C_3$-$C_6$ cycloalkyl, optionally substituted phenyl, optionally substituted benzyl, —C(═O)OR$^b$, —C(═O)R$^b$, and —S(═O)$_2$-optionally substituted phenyl, wherein each optional substituent in the phenyl, benzyl, or —S(═O)$_2$-phenyl is independently at least one selected from the group consisting of F, Cl, Br, $C_1$-$C_3$ alkoxy, $C_1$-$C_3$ haloalkoxy, $C_1$-$C_3$ haloalkyl, hydroxyl, and—NH—C(═O)R$^a$;

$R^{10'}$ is selected from the group consisting of phenyl, benzyl, and —C(═O)—$C_1$-$C_6$ alkyl, wherein the benzyl or phenyl in $R^{10'}$ is substituted with at least one substituent selected from the group consisting of halogen, $C_1$-$C_3$ haloalkyl, OH, and N($R^a$)($R^b$), and wherein the alkyl in $R^{10'}$ is substituted with at least one phenyl substituent;

Y is selected from the group consisting of C($R^a$) ($R^a$), C═O, NR$^{10}$, NR$^{10'}$, and O, wherein if Y is C($R^a$) ($R^a$) and $R^2$ is optionally substituted phenyl, then Ar comprises a $C_6$-$C_{10}$ aryl or $C_2$-$C_{10}$ heteroaryl substituted with at least one trifluoromethoxy substituent;

Z is selected from the group consisting of C═O, NR$^{10}$, NR$^{10'}$, O, and S;

$R^A$ is H or $C_1$-$C_6$ alkyl;

each occurrence of $R^a$ is independently selected from the group consisting of H, $C_1$-$C_6$ alkyl, benzyl, and $C_6$-$C_{10}$ aryl; and each occurrence of $R^b$ is independently selected from the group consisting of H, optionally substituted $C_1$-$C_6$ alkyl, optionally substituted benzyl, optionally substituted phenyl, and optionally substituted naphthyl, wherein the $C_1$-$C_6$ alkyl, benzyl, phenyl, or naphthyl in $R^b$ is independently optionally substituted with at least one selected from the group consisting of $C_1$-$C_3$ alkyl, $C_1$-$C_3$ haloalkyl, $C_1$-$C_3$ alkoxy, $C_1$-$C_3$ haloalkoxy, halogen, OH, CN, $NO_2$, C(═O)OR$^a$, and C(═O)N($R^a$) ($R^a$);

wherein in (Ia), (Ib), and (Ic), at least one of the following applies:

a) $R^2$ is phenyl or $C_2$-$C_{10}$ heteroaryl, wherein the phenyl or heteroaryl is optionally substituted with at least one substituent selected from the group consisting of halogen, OH, $C_1$-$C_3$ haloalkoxy, $C_1$-$C_3$ haloalkyl, $C_1$-$C_3$ alkoxy, and $C_1$-$C_6$ alkyl;

b) at least one of $R^3$ and $R^{3'}$ is phenyl or $C_2$-$C_{10}$ heteroaryl, wherein the phenyl or heteroaryl is substituted with at least one substituent selected from the group consisting of halogen, OH, $C_1$-$C_3$ haloalkoxy, $C_1$-$C_3$ haloalkyl, $C_1$-$C_3$ alkoxy, and $C_1$-$C_6$ alkyl;

c) at least one of $R^3$, $R^{3'}$, $R^4$, and $R^{4'}$, is phenyl or $C_2$-$C_{10}$ heteroaryl, wherein the phenyl or heteroaryl is optionally substituted with at least one substituent selected from the group consisting of halogen, OH, $C_1$-$C_3$ haloalkoxy, $C_1$-$C_3$ haloalkyl, $C_1$-$C_3$ alkoxy, and $C_1$-$C_6$ alkyl, wherein one of Y and Z is present, and one of Y and Z is selected from the group consisting of C—O, NR$^{10}$, and O, wherein $R^{10}$ is selected from the group consisting of H, $C_3$-$C_6$ cycloalkyl, phenyl, optionally substituted benzyl, —C(═O)OR$^b$, —C(═O)R$^b$, —S(═O)$_2$-optionally substituted phenyl;

d) two geminal substituents selected from $R^3$, $R^{3'}$, $R^4$, $R^{4'}$, $R^5$, $R^{5'}$, $R^6$, $R^{6'}$, $R^7$, $R^{7'}$, $R^8$, and $R^{8'}$ combine with the carbon atom to which they are bound to form a $C_3$-$C_8$ cycloalkyl or $C_2$-$C_6$ heterocyclyl, wherein the cycloalkyl or heterocyclyl is substituted with at least one substituent selected from the group consisting of $C_1$-$C_3$ alkyl, $C_1$-$C_3$ haloalkyl, $C_1$-$C_3$ haloalkoxy, halogen, N($R^a$) ($R^a$), OR$^a$, C(═O)R$^a$, C(═O)OR$^a$, and C(═O)N($R^a$) ($R^a$), e) two vicinal substituents selected from $R^3$, $R^{3'}$, $R^4$, $R^{4'}$, $R^5$, $R^{5'}$, $R^6$, $R^6$, $R^7$, $R^{7'}$, $R^8$, and $R^{8'}$ combine with the carbon atoms to which they are bound to form a $C_3$-$C_8$ cycloalkyl, $C_2$-$C_{10}$ heterocyclyl, or phenyl, wherein the cycloalkyl, heterocyclyl, or phenyl is substituted with at least one substituent selected from the group consisting of $C_1$-$C_3$ alkyl, $C_1$-$C_3$ haloalkyl, $C_1$-$C_3$ haloalkoxy, halogen, OR$^a$, C(═O)R$^a$, C(═O)OR$^a$, and C(═O)N($R^a$) ($R^a$);

f) two geminal substituents selected from $R^3$, $R^{3'}$, $R^4$, $R^{4'}$, $R^5$, $R^{5'}$, $R^6$, $R^{6'}$, $R^7$, $R^{7'}$, $R^8$, and $R^{8'}$ combine with the carbon atom to which they are bound to form a $C_3$-$C_8$ cycloalkyl or $C_2$-$C_6$ heterocyclyl, and two vicinal substituents selected from $R^3$, $R^{3'}$, $R^4$, $R^{4'}$, $R^5$, $R^{5'}$, $R^6$, $R^6$, $R^7$, $R^{7'}$, $R^8$, and $R^{8'}$ combine with the carbon atoms to which they are bound to form a $C_3$-$C_8$ cycloalkyl, $C_2$-$C_{10}$ heterocyclyl, or phenyl, wherein each of the cycloalkyl, heterocyclyl, or phenyl is independently optionally substituted with at least one substituent selected from the group consisting of $C_1$-$C_3$ alkyl, $C_1$-$C_3$ haloalkyl, $C_1$-$C_3$ haloalkoxy, halogen, N($R^a$) ($R^a$), OR$^a$, C(═O)R$^a$, C(═O)OR$^a$, and C(═O)N($R^a$) ($R^a$);

g) Y is N($R^{10'}$) and each of $R^4$, $R^{4'}$, $R^6$, and $R^{6'}$, if present, are independently selected from the group consisting of H, $C_1$-$C_6$ alkyl, hydroxyl, $C_1$-$C_4$ haloalkyl, phenyl, and phenoxy;

h) at least one of $R^2$, $R^3$, $R^{3'}$, $R^4$, and $R^{4'}$ is optionally substituted $C_3$-$C_8$ cycloalkyl or $C_2$-$C_{10}$ heterocyclyl, wherein each optional substituent in the cycloalkyl or heterocycloalkyl is independently selected from the group consisting of halogen, $C_1$-$C_6$ alkyl, $C_1$-$C_3$ haloalkyl, $C_1$-$C_3$ haloalkoxy, OR$^a$, N($R^a$)($R^b$), C(═O)R$^a$, and C(═O)OR$^a$; and i) $R^2$ is selected from the group consisting of optionally substituted $C_1$-$C_6$ haloalkyl, optionally substituted $C_2$-$C_6$ aminoalkyl and optionally substituted $C_2$-$C_6$ alkynyl, wherein each optional substituent of the haloalkyl, aminoalkyl, and alkynyl in $R^2$ is at least one selected from the group consisting of $C_1$-$C_6$ alkyl, $C_1$-$C_3$ haloalkyl, $C_1$-$C_3$ haloalkoxy, halogen, C(=O)$R^a$, C(=O)O$R^a$, C(=O)N($R^a$) ($R^a$), S(=O)$_2$ -optionally substituted phenyl and S(=O)$_2$ -optionally substituted $C_2$-$C_{10}$ heteroaryl.
2. The compound of claim 1, which is selected from the group consisting of:
(Ia-1)
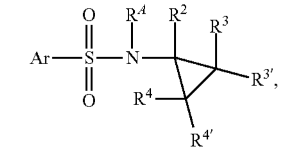
(Ia-2)
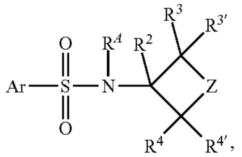
(Ia-3)
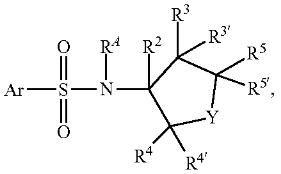
(Ia-4)
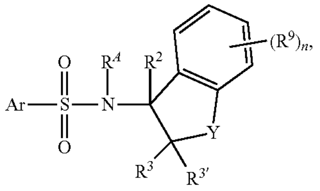
(Ia-5)
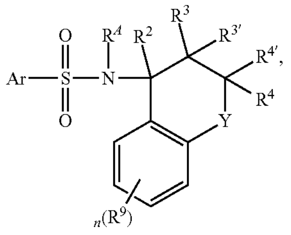
(Ia-6)
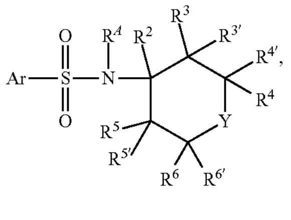
(Ia-7)
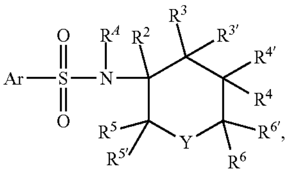
-continued
(Ia-8)
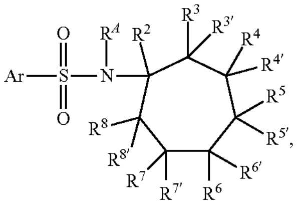
(Ib-1)
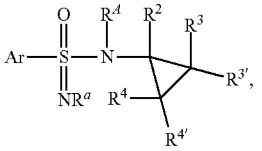
(Ib-2)
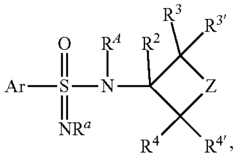
(Ib-3)
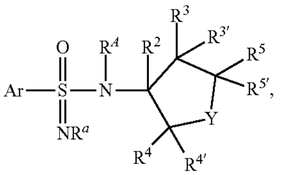
(Ib-4)
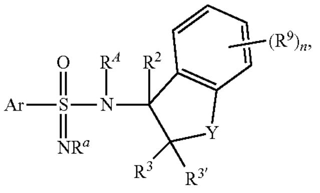
(Ib-5)
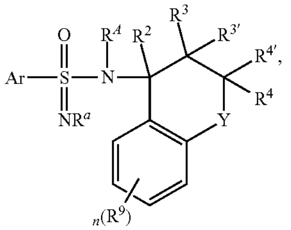
(Ib-6)
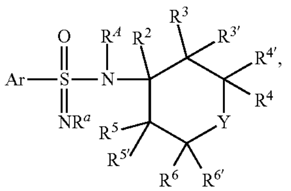
(Ib-7)
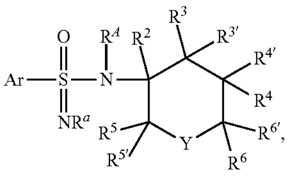

-continued (Ib-8)

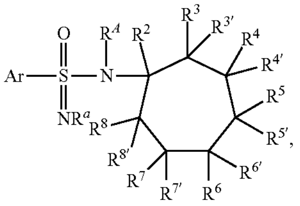

(Ic-1)

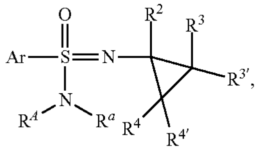

(Ic-2)

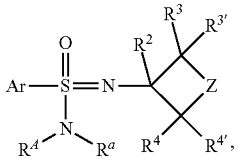

(Ic-3)

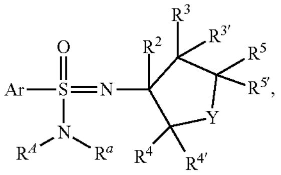

(Ic-4)

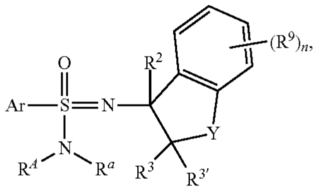

(Ic-5)

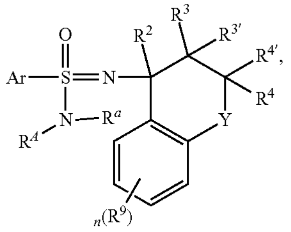

(Ic-6)

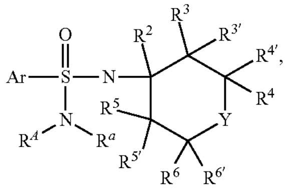

(Ic-7)

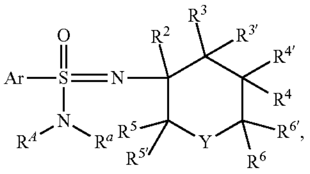

-continued (Ic-8)

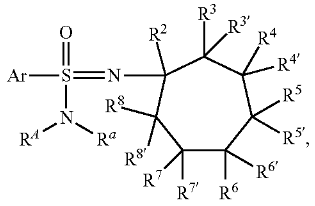

(Id-1)

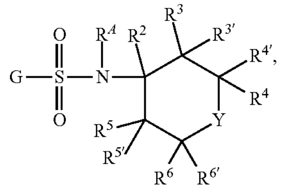

(Ie-1)

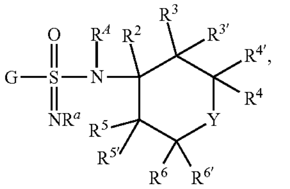

and (If-1)

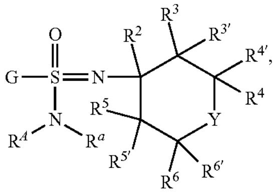

wherein:

each occurrence of $R^9$ is independently selected from the group consisting of F, Cl, Br, $C_1$-$C_3$ alkoxy, and $C_1$-$C_3$ haloalkoxy; and n is an integer selected from the group consisting of 0, 1, and 2.

3. The compound of claim 1, wherein $R^A$ is selected from the group consisting of H and Me.

4. The compound of claim 1, wherein $R^1$ is selected from the group consisting of

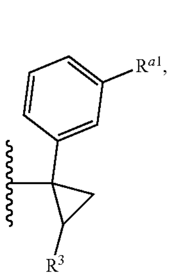

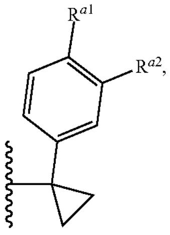

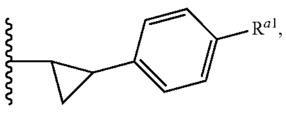

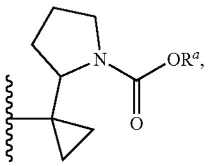

-continued
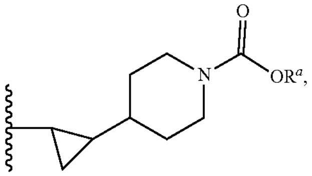
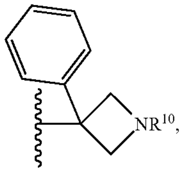
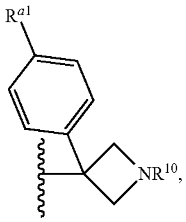
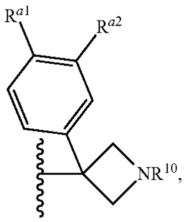
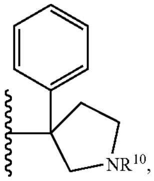
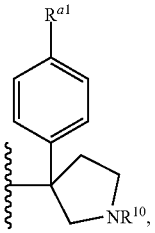
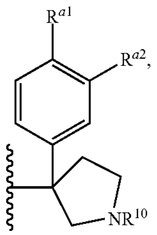
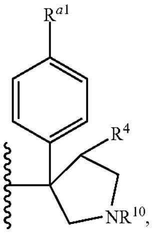
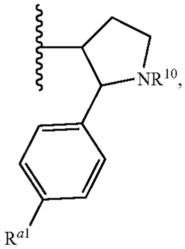
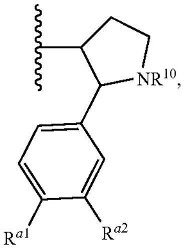
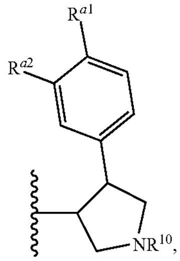
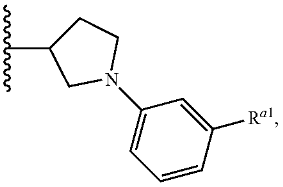
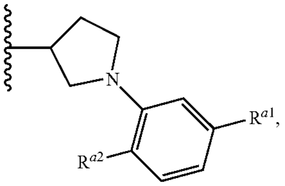
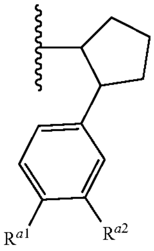
,
-continued
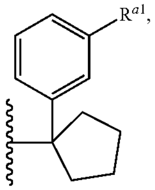
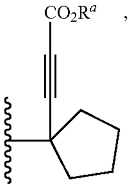
,
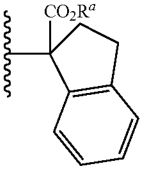
,
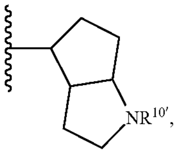
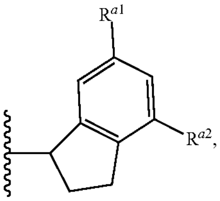
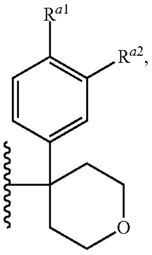
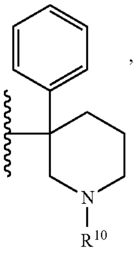
,
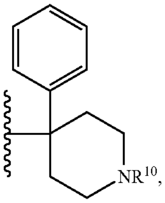
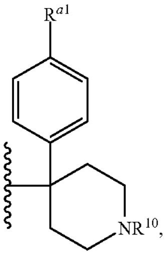
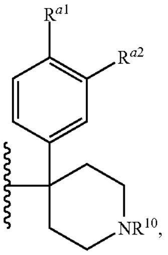
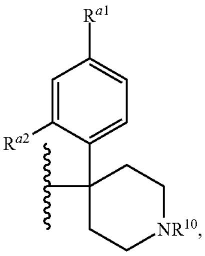
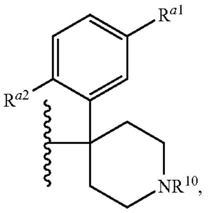
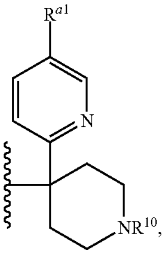
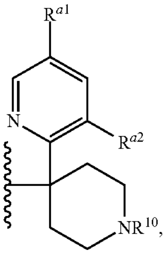
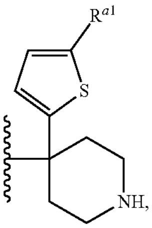

-continued

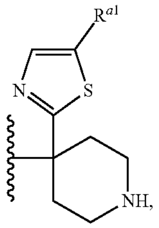

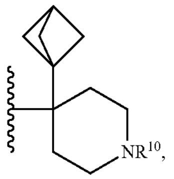

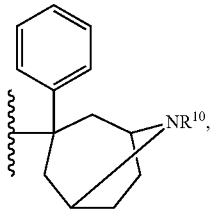

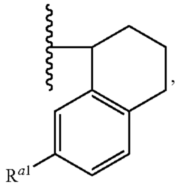

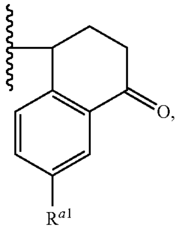

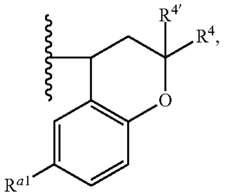

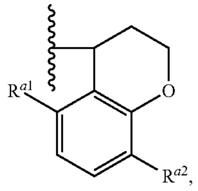

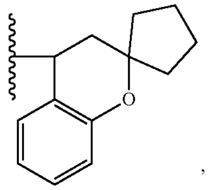

,

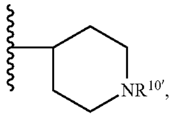

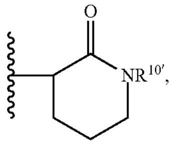

and

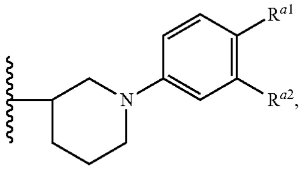

wherein $R^{a1}$ and $R^{a2}$ are each independently selected from the group consisting of F, Cl, Br, $C_1$-$C_3$ alkyl, $C_1$-$C_3$ haloalkyl, $C_1$-$C_3$ alkoxy, and $C_1$-$C_3$ haloalkoxy.

5. The compound of claim 1, wherein Ar is selected from the group consisting of

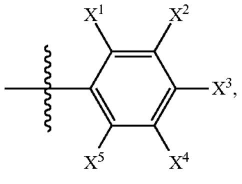

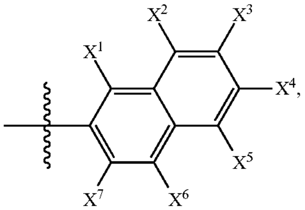

-continued

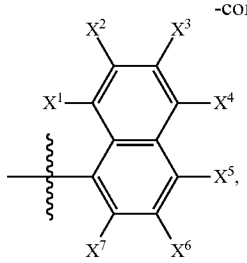

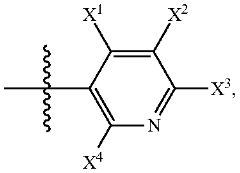

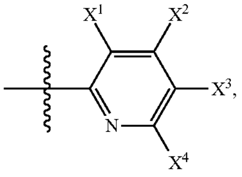

and

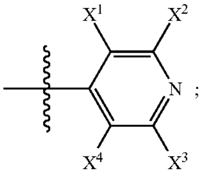

wherein $X^1$, $X^2$, $X^3$, $X^4$, $X^5$, $X^6$, and $X^7$ are each independently selected from the group consisting of $C_1$-$C_6$ alkyl, F, Cl, $N(R^a)(R^b)$, $OR^b$, —C(═O)$OR^a$, —C(═O)$N(R^a)$ $(R^a)$, $NH_2$, OH, $NO_2$, $C_1$-$C_3$ haloalkyl, $C_1$-$C_3$ haloalkoxy, and phenyl.

6. The compound of claim 1, wherein one of the following applies:

(a) the compound is the compound of formula (Ia-1), wherein at least two of $R^3$, $R^{3'}$, $R^4$, and $R^{4'}$ are H;

(b) the compound is the compound of formula (Ia-2), wherein at least two of $R^3$, $R^{3'}$, $R^4$, and $R^{4'}$ are H;

(c) the compound is the compound of formula (Ia-3), wherein at least four of $R^3$, $R^{3'}$, $R^4$, $R^{4'}$, $R^5$, and $R^{5'}$ are H;

(d) the compound is the compound of formula (Ia-4), wherein at least one of $R^3$ and $R^{3'}$ is H;

(e) the compound is the compound of formula (Ia-5), wherein at least two of $R^3$, $R^{3'}$, $R^4$, and $R^{4'}$ are H;

(f) the compound is the compound of formula (Ia-6), wherein at least six of $R^3$, $R^{3'}$, $R^4$, $R^{4'}$, $R^5$, $R^{5'}$, $R^6$, and $R^{6'}$ are H;

(g) the compound is the compound of formula (Ia-7), wherein at least six of $R^3$, $R^{3'}$, $R^4$, $R^{4'}$, $R^5$, $R^{5'}$, $R^6$, and $R^{6'}$ are H;

(h) the compound is the compound of formula (Ia-8), wherein at least ten of $R^3$, $R^{3'}$, $R^4$, $R^{4'}$, $R^5$, $R^{5'}$, $R^6$, $R^{6'}$, $R^7$, $R^{7'}$, $R^8$, and $R^{8'}$ are H;

(i) the compound is the compound of formula (Ib-1), wherein at least two of $R^3$, $R^{3'}$, $R^4$, and $R^{4'}$ are H;

(j) the compound is the compound of formula (Ib-2), wherein at least two of $R^3$, $R^{3'}$, $R^4$, and $R^{4'}$ are H;

(k) the compound is the compound of formula (Ib-3), wherein at least four of $R^3$, $R^{3'}$, $R^4$, $R^{4'}$, $R^5$, and $R^{5'}$ are H;

(l) the compound is the compound of formula (Ib-4), wherein at least one of $R^3$ and $R^{3'}$ is H;

(m) the compound is the compound of formula (Ib-5), wherein at least two of $R^3$, $R^{3'}$, $R^4$, and $R^{4'}$ are H;

(n) the compound is the compound of formula (Ib-6), wherein at least six of $R^3$, $R^{3'}$, $R^4$, $R^{4'}$, $R^5$, $R^{5'}$, $R^6$, and $R^{6'}$ are H;

(o) the compound is the compound of formula (Ib-7), wherein at least six of $R^3$, $R^{3'}$, $R^4$, $R^{4'}$, $R^5$, $R^{5'}$, $R^6$, and $R^{6'}$ are H;

(p) the compound is the compound of formula (Ib-8), wherein at least ten of $R^3$, $R^{3'}$, $R^4$, $R^{4'}$, $R^5$, $R^{5'}$, $R^6$, $R^{6'}$, $R^7$, $R^{7'}$, $R^8$, and $R^{8'}$ are H;

(q) the compound is the compound of formula (Ic-1), wherein at least two of $R^3$, $R^{3'}$, $R^4$, and $R^{4'}$ are H;

(r) the compound is the compound of formula (Ic-2), wherein at least two of $R^3$, $R^{3'}$, $R^4$, and $R^{4'}$ are H;

(s) the compound is the compound of formula (Ic-3), wherein at least four of $R^3$, $R^{3'}$, $R^4$, $R^{4'}$, $R^5$, and $R^{5'}$ are H;

(t) the compound is the compound of formula (Ic-4), wherein at least one of $R^3$ and $R^{3'}$ is H;

(u) the compound is the compound of formula (Ic-5), wherein at least two of $R^3$, $R^{3'}$, $R^4$, and $R^{4'}$ are H;

(v) the compound is the compound of formula (Ic-6), wherein at least six of $R^3$, $R^{3'}$, $R^4$, $R^{4'}$, $R^5$, $R^{5'}$, $R^6$, and $R^{6'}$ are H;

(w) the compound is the compound of formula (Ic-7), wherein at least six of $R^3$, $R^{3'}$, $R^4$, $R^{4'}$, $R^5$, $R^{5'}$, $R^6$, and $R^{6'}$ are H;

(x) the compound is the compound of formula (Ic-8), wherein at least ten of $R^3$, $R^{3'}$, $R^4$, $R^{4'}$, $R^5$, $R^{5'}$, $R^6$, $R''$, $R^7$, $R^{7'}$, $R^8$, and $R^{8'}$ are H;

(y) the compound is the compound of formula (Id-1), wherein at least six of $R^3$, $R^{3'}$, $R^4$, $R^{4'}$, $R^5$, $R^{5'}$, $R^6$, and $R^{6'}$ are H;

(z) the compound is the compound of formula (Ie-1), wherein at least six of $R^3$, $R^{3'}$, $R^4$, $R^{4'}$, $R^5$, $R^{5'}$, $R^6$, and $R^{6'}$ are H; and (aa) the compound is the compound of formula (If-1), wherein at least six of $R^3$, $R^{3'}$, $R^4$, $R^{4'}$, $R^5$, $R^{5'}$, $R^6$, and $R^{6'}$ are H.

7. The compound of claim 5, wherein at least one of $X^1$, $X^2$, $X^3$, $X^4$, $X^5$, $X^6$, and $X^7$ is selected from the group consisting of $CF_3$, $NH_2$, $O(CH(CH_3)_2)$, $OCF_3$, and

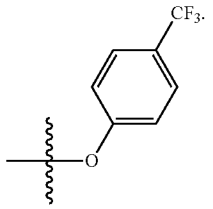 [SMILES: *Oc1ccc(C(F)(F)F)cc1]

8. The compound of claim 1, wherein Ar is selected from the group consisting of

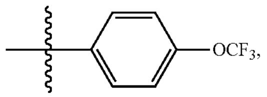

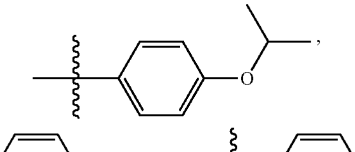

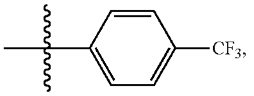

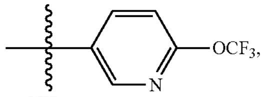

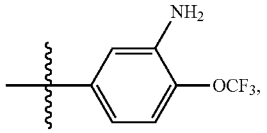

-continued

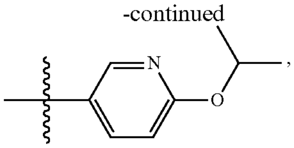

and

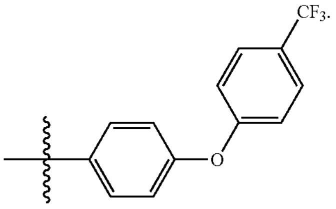

9. The compound of claim 1, wherein G is:

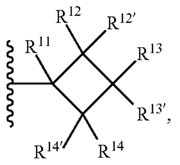

wherein:

$R^{11}$, $R^{12}$, $R^{12'}$, $R^{13}$, $R^{13'}$, $R^{14}$, and $R^{14'}$ are each independently selected from the group consisting of H, $C_1$-$C_6$ alkyl, $C_1$-$C_6$ haloalkyl, and optionally substituted phenyl, wherein each optional substituent in the phenyl is at least one selected from the group consisting of $C_1$-$C_3$ alkyl, $C_1$-$C_3$ haloalkyl, $C_1$-$C_3$ alkoxy, $C_1$-$C_3$ haloalkoxy, halogen, OH, $C(=O)OR^a$, and $C(=O)N(R^a)(R^a)$, and wherein $R^{11}$ and $R^{13}$ or $R^{11}$ and $R^{13'}$ may optionally combine with the atoms to which they are bound to form a $C_3$-$C_8$ cycloalkyl.

10. The compound of claim 9, wherein at least one of the following applies:

(a) at least one of $R^{11}$, $R^{12}$, $R^{12'}$, $R^{13}$, $R^{13'}$, $R^{14}$, and $R^{14'}$ is H;

(b) at least two of $R^{11}$, $R^{12}$, $R^{12'}$, $R^{13}$, $R^{13'}$, $R^{14}$, and $R^{14'}$ are H;

(c) at least three of $R^{11}$, $R^{12}$, $R^{12'}$, $R^{13}$, $R^{13'}$, $R^{14}$, and $R^{14'}$ are H;

(d) at least four of $R^{11}$, $R^{12}$, $R^{12'}$, $R^{13}$, $R^{13'}$, $R^{14}$, and $R^{14'}$ are H;

(e) at least five of $R^{11}$, $R^{12}$, $R^{12'}$, $R^{13}$, $R^{13'}$, $R^{14}$, and $R^{14'}$ are H;

(f) at least six of $R^{11}$, $R^{12}$, $R^{12'}$, $R^{13}$, $R^{13'}$, $R^{14}$, and $R^{14'}$ are H; and (a) each of $R^{11}$, $R^{12}$, $R^{12'}$, $R^{13}$, $R^{13'}$, $R^{14}$, and $R^{14'}$ are H.

11. The compound of claim 9, wherein at least one of $R^{11}$, $R^{12}$, $R^{12'}$, $R^{13}$, $R^{13'}$, $R^{14}$, and $R^{14'}$ is $CF_3$.

12. The compound of claim 1, wherein G is

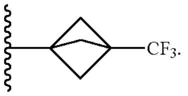 [SMILES: *C12CC(C(F)(F)F)(C1)C2]

13. The compound of claim 1, wherein $R^2$ is selected from the group consisting of: $-CH_2F$, $-C(=O)OEt$, Ph,

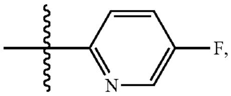,
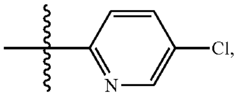,
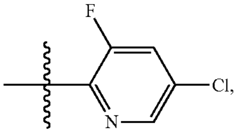,
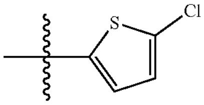,
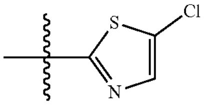,
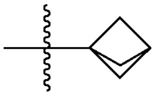,
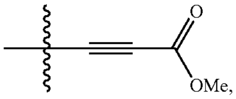,
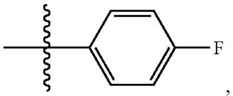,
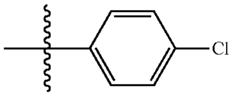,
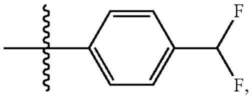,
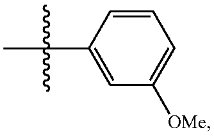,
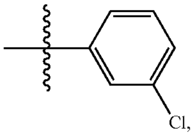,
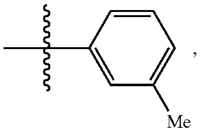,
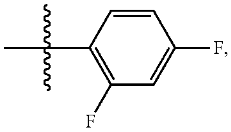,
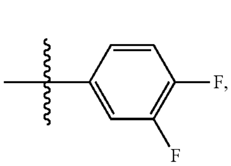,
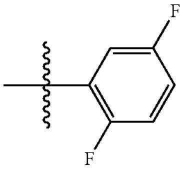,
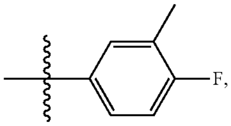,
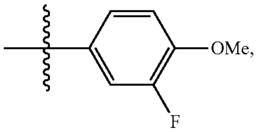,
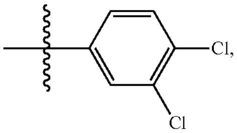,
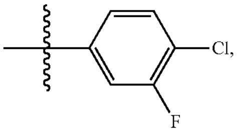,
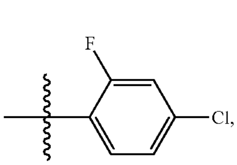,
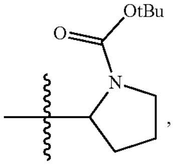, and
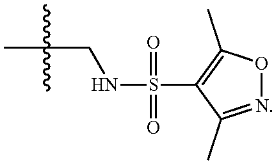.

14. The compound of claim 1, wherein at least one of $R^3$, $R^{3'}$, $R^4$, $R^{4'}$, $R^5$, $R^{5'}$, $R^6$, $R^{6'}$, $R^7$, $R^{7'}$, $R^8$, and $R^{8'}$ is selected from the group consisting of:

methyl, trifluoromethyl, hydroxyl, fluorine, —C(═O)OMe, Ph,

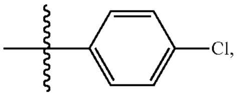,
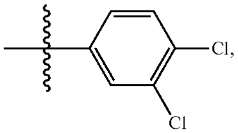,
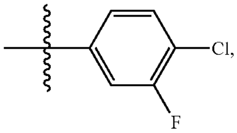,
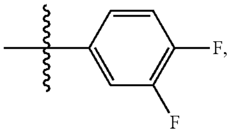, and
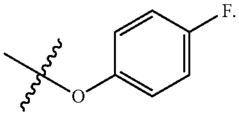.

15. The compound of claim 1, wherein Y is $NR^{10}$ or $NR^{10'}$.

16. The compound of claim 15, wherein one of the following applies:

(a) $R^{10}$ is selected from the group consisting of H, methyl, 3-methylbutyl, tert-butyl, cyclopropyl, 3-oxetanyl, —C(═O) $CH_2CH(CH_3)_2$, —C(═O)Ot-Bu, $S(═O)_2$ Me, benzyl,

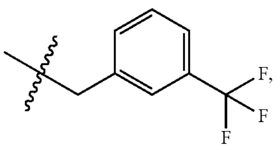,
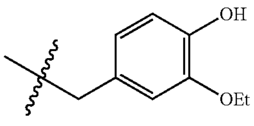,
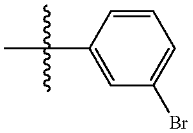,
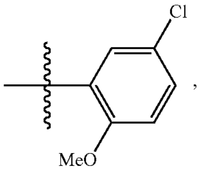,
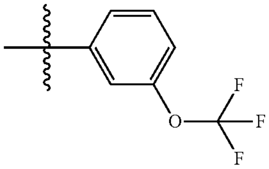,
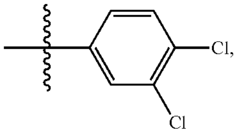,
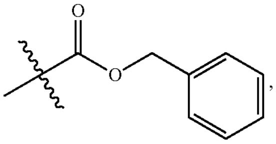,
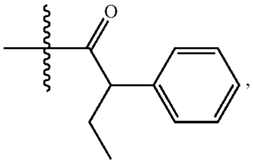, and
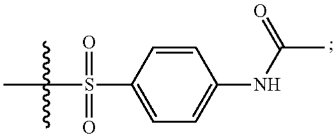;

or
(b) $R^{10'}$ is selected from the group consisting of
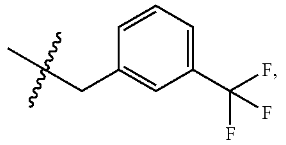
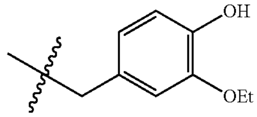,
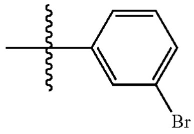,
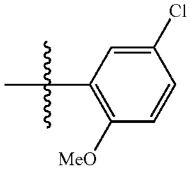,
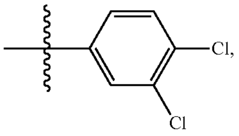
and
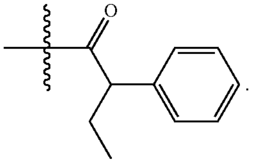.
17. The compound of claim 1, wherein $R^1$ is selected from the group consisting of
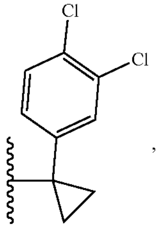,
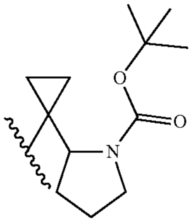,
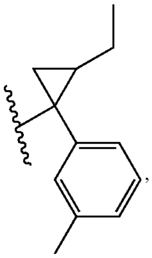,
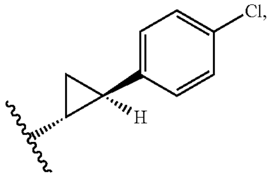
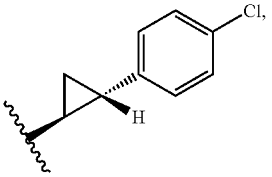
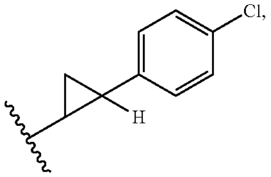
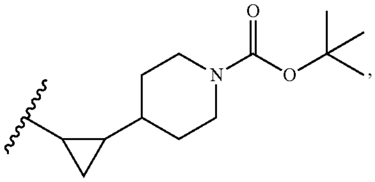,
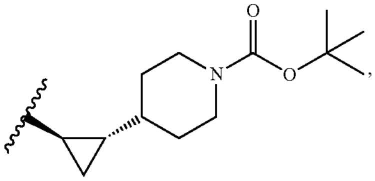,
-continued
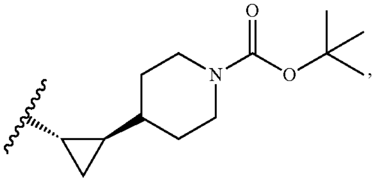,
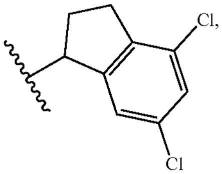
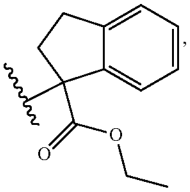,
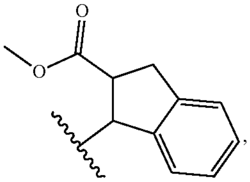,
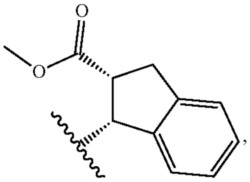,
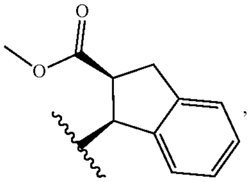,
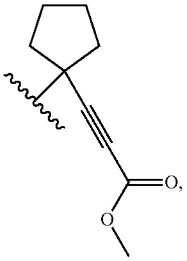
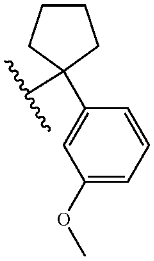,
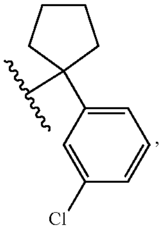,
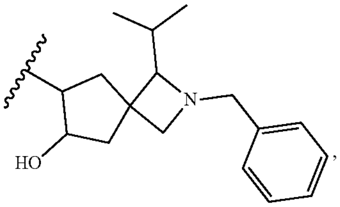,
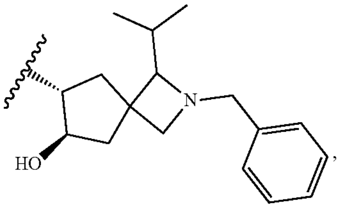,
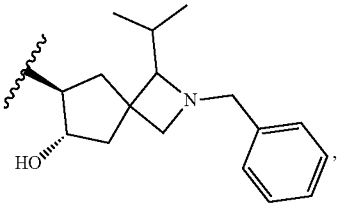, -continued
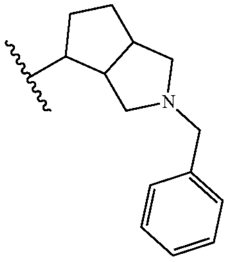
,
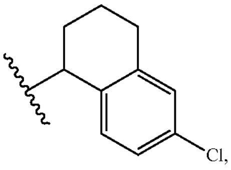
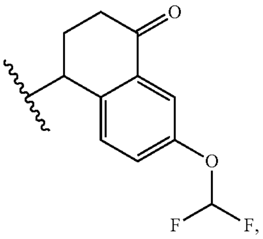
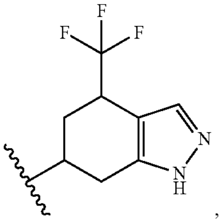
,
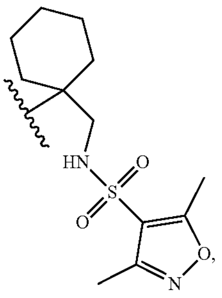
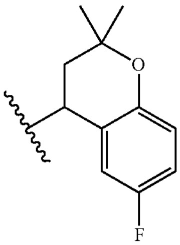
,
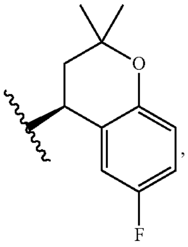
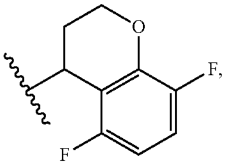
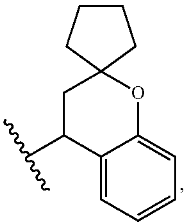
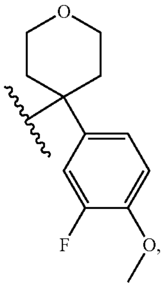
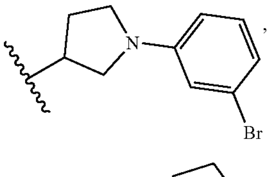
,
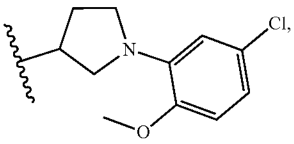
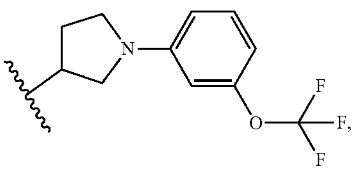
-continued
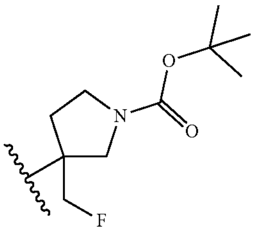
,
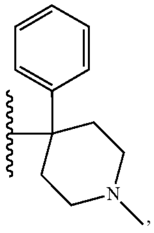
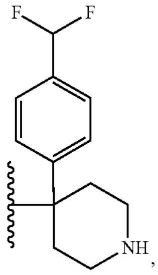
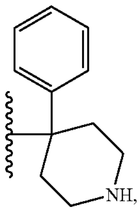
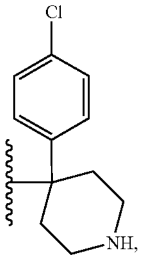
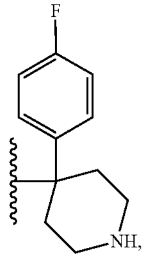
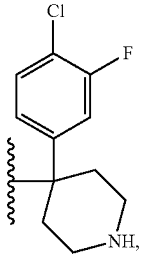
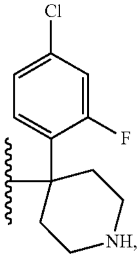
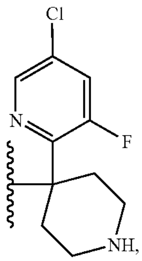
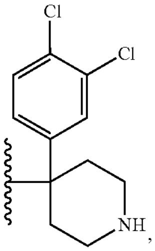
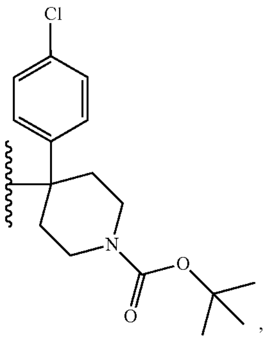
,
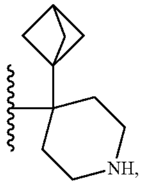
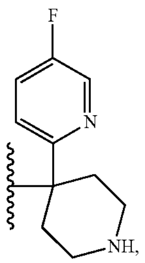
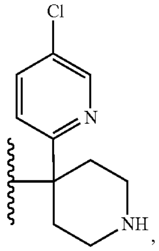
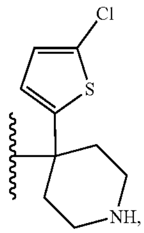
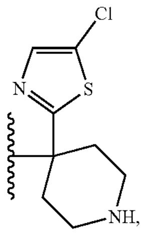

-continued
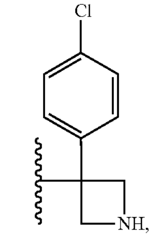
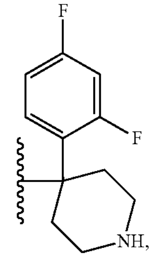
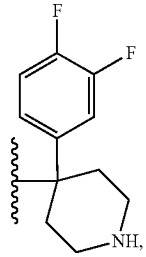
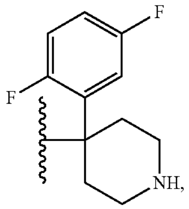
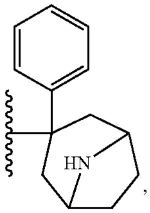
,
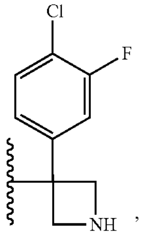
,
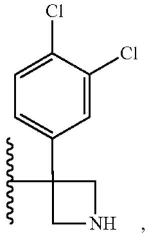
,
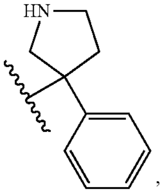
,
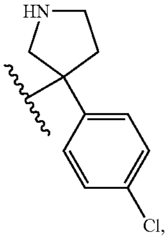
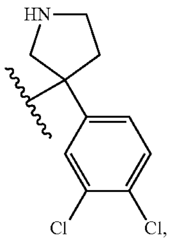
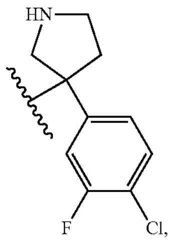
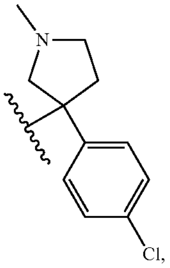
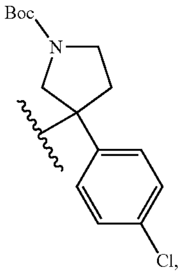
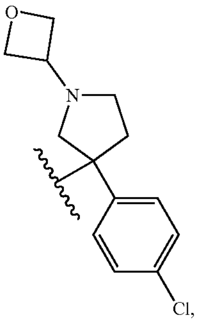
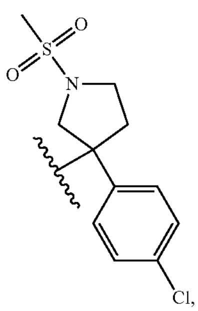
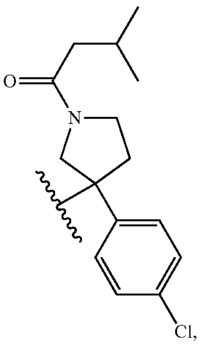
-continued
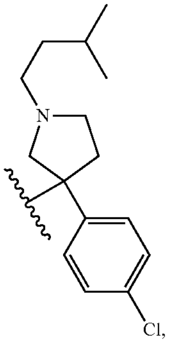
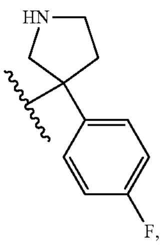
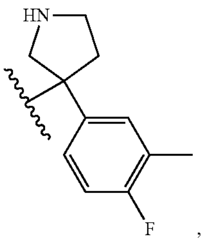
,
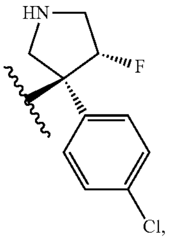
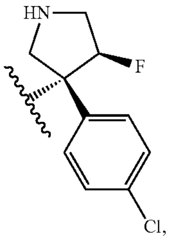
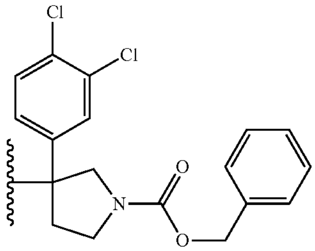
,
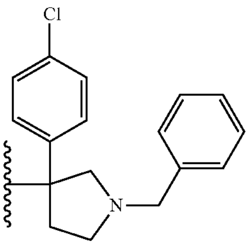
,
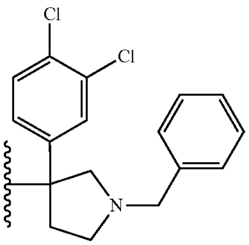
,
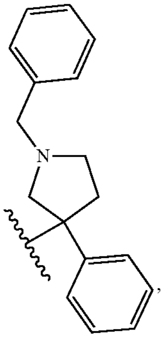
,
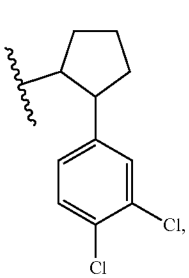
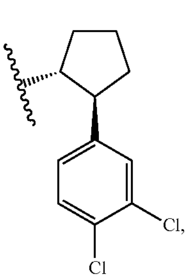
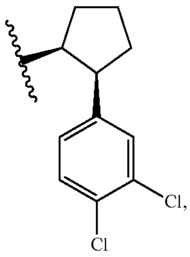
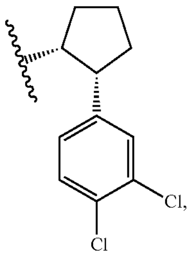

-continued

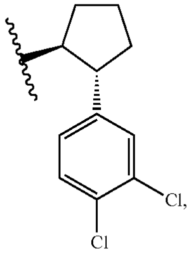

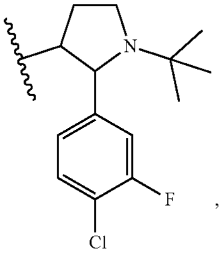

,

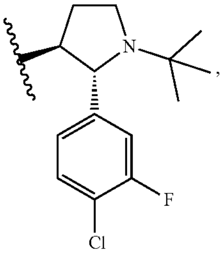

,

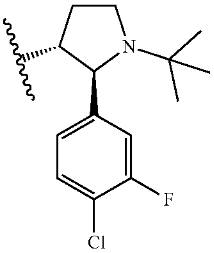

,

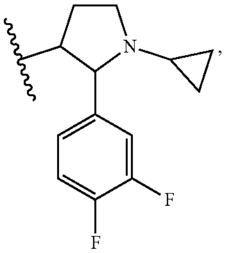

,

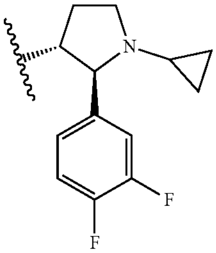

,

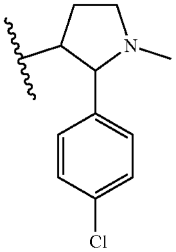

,

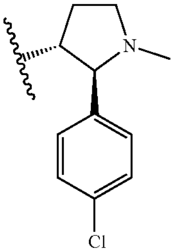

,

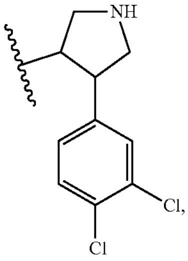

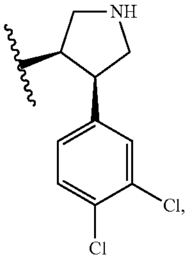

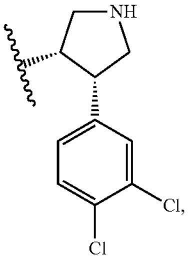

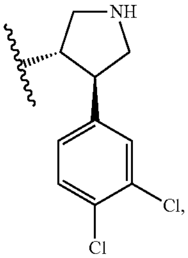

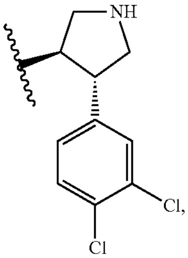

-continued

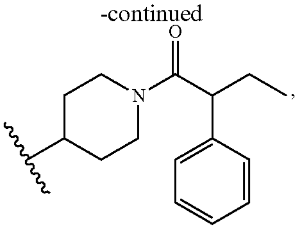

,

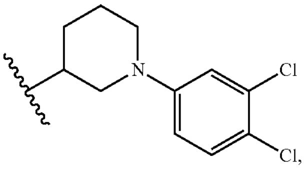

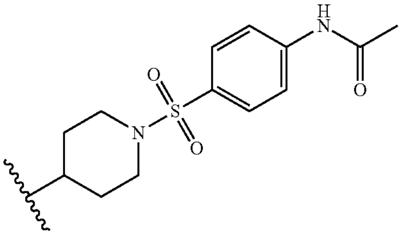

,

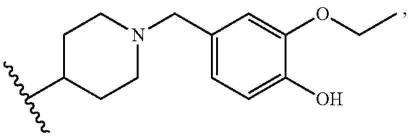

, and

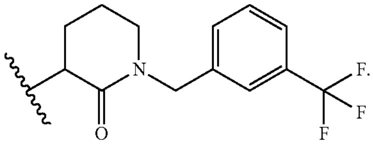

18. The compound of claim 1, which is selected from the group consisting of:

N-(6-fluoro-2,2-dimethylchroman-4-yl)-4-(trifluoromethoxy)benzenesulfonamide;

N-(1-(tert-butyl)-2-(4-chloro-3-fluorophenyl) pyrrolidin-3-yl)-4-(trifluoromethoxy)benzenesulfonamide;

tert-butyl 4-(2-((4-(trifluoromethoxy)phenyl) sulfonamido)cyclopropyl) piperidine-1-carboxylate;

tert-butyl 2-(1-((4-(trifluoromethoxy)phenyl) sulfonamido)cyclopropyl) pyrrolidine-1-carboxylate;

N-(6-(difluoromethoxy)-4-oxo-1,2,3,4-tetrahydronaphthalen-1-yl)-4-(trifluoromethoxy)benzenesulfonamide;

N-(1-(3-ethoxy-4-hydroxybenzyl) piperidin-4-yl)-4-(trifluoromethoxy)benzenesulfonamide;

tert-butyl 3-(fluoromethyl)-3-((4-(trifluoromethoxy)phenyl) sulfonamido) pyrrolidine-1-carboxylate;

N-(1-cyclopropyl-2-(3,4-difluorophenyl) pyrrolidin-3-yl)-4-(trifluoromethoxy)benzenesulfonamide;

N-(2-oxo-1-(3-(trifluoromethyl)benzyl) piperidin-3-yl)-4-(trifluoromethoxy)benzenesulfonamide;

N-(spiro[chromane-2,1'-cyclopentan]-4-yl)-4-(trifluoromethoxy)benzenesulfonamide;

N-(1-benzyl-3-phenylpyrrolidin-3-yl)-4-(trifluoromethoxy)benzenesulfonamide;

N-(4-(3-fluoro-4-methoxyphenyl)tetrahydro-2H-pyran-4-yl)-4-(trifluoromethoxy)benzenesulfonamide;

N-(3-phenylpyrrolidin-3-yl)-4-(trifluoromethoxy)benzenesulfonamide;

N-(1-(3-chlorophenyl)cyclopentyl)-4-(trifluoromethoxy) benzenesulfonamide;

methyl 3-(1-((4-(trifluoromethoxy)phenyl) sulfonamido) cyclopentyl) propiolate;
N-(4,6-dichloro-2,3-dihydro-1H-inden-1-yl)-4-(trifluoromethoxy)benzenesulfonamide;
N-2-benzyl-7-hydroxy-1-isopropyl-2-azaspiro[3.4]octan-6-yl)-4-(trifluoromethoxy)benzenesulfonamide;
N-(6-chloro-1,2,3,4-tetrahydronaphthalen-1-yl)-4-(trifluoromethoxy)benzenesulfonamide;
N-(1-(3-methoxyphenyl)cyclopentyl)-4-(trifluoromethoxy)benzenesulfonamide;
N-(2-(4-chlorophenyl)-1-methylpyrrolidin-3-yl)-4-(trifluoromethoxy)benzenesulfonamide;
N-(1-(3,4-dichlorophenyl) piperidin-3-yl)-4-(trifluoromethoxy)benzenesulfonamide;
3,5-dimethyl-N-((1-((4-(trifluoromethoxy)phenyl) sulfonamido)cyclohexyl) methyl) isoxazole-4-sulfonamide;
N-(1-(2-phenylbutanoyl) piperidin-4-yl)-4-(trifluoromethoxy)benzenesulfonamide;
4-(trifluoromethoxy)-N-(1-(3-(trifluoromethoxy)phenyl) pyrrolidin-3-yl)benzenesulfonamide;
N-(2-ethyl-1-(m-tolyl)cyclopropyl)-4-(trifluoromethoxy) benzenesulfonamide;
N-(1-(5-chloro-2-methoxyphenyl) pyrrolidin-3-yl)-4-(trifluoromethoxy)benzenesulfonamide;
N-(5,8-difluorochroman-4-yl)-4-(trifluoromethoxy)benzenesulfonamide;
N-(2-(4-chlorophenyl)cyclopropyl)-4-(trifluoromethoxy) benzenesulfonamide;
N-(2-(3,4-dichlorophenyl)cyclopentyl)-4-(trifluoromethoxy)benzenesulfonamide;
N-(3-(4-chlorophenyl) pyrrolidin-3-yl)-4-(trifluoromethoxy)benzenesulfonamide;
N-(3-(3,4-dichlorophenyl) pyrrolidin-3-yl)-4-(trifluoromethoxy)benzenesulfonamide;
N-(4-(4-chlorophenyl) piperidin-4-yl)-4-(trifluoromethoxy)benzenesulfonamide;
N-(1-(3-bromophenyl) pyrrolidin-3-yl)-4-(trifluoromethoxy)benzenesulfonamide;
N-(3-(4-chlorophenyl) azetidin-3-yl)-4-(trifluoromethoxy)benzenesulfonamide;
N-(3-(3,4-dichlorophenyl) azetidin-3-yl)-4-(trifluoromethoxy)benzenesulfonamide;
N-(4-(3,4-dichlorophenyl) piperidin-4-yl)-4-(trifluoromethoxy)benzenesulfonamide;
N-(4-phenylpiperidin-4-yl)-4-(trifluoromethoxy)benzenesulfonamide;
benzyl 3-(3,4-dichlorophenyl)-3-((4-(trifluoromethoxy) phenyl) sulfonamido) pyrrolidine-1-carboxylate;
N-(3-(4-chloro-3-fluorophenyl) pyrrolidin-3-yl)-4-(trifluoromethoxy)benzenesulfonamide;
tert-butyl 4-(4-chlorophenyl)-4-((4-(trifluoromethoxy) phenyl) sulfonamido) piperidine-1-carboxylate;
N-(1-benzyl-3-(4-chlorophenyl) pyrrolidin-3-yl)-4-(4-(trifluoromethyl) phenoxy)benzenesulfonamide;
N-(1-benzyl-3-(3,4-dichlorophenyl) pyrrolidin-3-yl)-4-(4-(trifluoromethyl) phenoxy)benzenesulfonamide;
N-(4-(4-chloro-3-fluorophenyl) piperidin-4-yl)-4-(trifluoromethoxy)benzenesulfonamide;
N-(3-(4-chlorophenyl) pyrrolidin-3-yl)-4-(4-(trifluoromethyl) phenoxy)benzenesulfonamide;
N-(3-(4-chloro-3-fluorophenyl) azetidin-3-yl)-4-(trifluoromethoxy)benzenesulfonamide;
N-(4-(4-fluorophenyl) piperidin-4-yl)-4-(trifluoromethoxy)benzenesulfonamide;
N-(4-phenylpiperidin-4-yl)-6-(trifluoromethoxy)pyridine-3-sulfonamide;
N-(1-methyl-4-phenylpiperidin-4-yl)-4-(trifluoromethoxy)benzenesulfonamide;
N-(4-(4-chlorophenyl) piperidin-4-yl)-4-isopropoxybenzenesulfonamide;
N-(3-(4-chlorophenyl) pyrrolidin-3-yl)-4-(trifluoromethoxy)benzenesulfonimidamide;
N-(3-(4-chlorophenyl) pyrrolidin-3-yl)-6-(trifluoromethoxy)pyridine-3-sulfonamide;
N-(4-(5-fluoropyridin-2-yl) piperidin-4-yl)-4-(trifluoromethoxy)benzenesulfonamide;
N-(4-(bicyclo[1.1.1]pentan-1-yl) piperidin-4-yl)-4-(trifluoromethoxy)benzenesulfonamide;
N-(4-(4-chlorophenyl) piperidin-4-yl)-6-isopropoxypyridine-3-sulfonamide;
N-(3-(4-chlorophenyl) pyrrolidin-3-yl)-N'-methyl-4-(trifluoromethoxy)benzenesulfonimidamide;
N-(3-(4-chlorophenyl)-1-methylpyrrolidin-3-yl)-4-(trifluoromethoxy)benzenesulfonamide;
tert-butyl 3-(4-chlorophenyl)-3-((4-(trifluoromethoxy) phenyl) sulfonamido) pyrrolidine-1-carboxylate;
N-(3-(4-chlorophenyl)-1-(oxetan-3-yl) pyrrolidin-3-yl)-4-(trifluoromethoxy)benzenesulfonamide;
N-(3-(4-chlorophenyl)-1-(methylsulfonyl) pyrrolidin-3-yl)-4-(trifluoromethoxy)benzenesulfonamide;
N-(4-(5-chlorothiazol-2-yl) piperidin-4-yl)-4-(trifluoromethoxy)benzenesulfonamide;
N-(3-(4-fluorophenyl) pyrrolidin-3-yl)-4-(trifluoromethoxy)benzenesulfonamide;
N-(4-(4-fluorophenyl) piperidin-4-yl)-4-isopropoxybenzenesulfonamide;
N-(3-(4-chlorophenyl)-1-isopentylpyrrolidin-3-yl)-4-(trifluoromethoxy)benzenesulfonamide;
N-(4-(4-fluorophenyl) piperidin-4-yl)-6-isopropoxypyridine-3-sulfonamide;
N-(3-(4-fluorophenyl) pyrrolidin-3-yl)-4-isopropoxybenzenesulfonamide;
rac N-((3S,4S)-3-(4-chlorophenyl)-4-fluoropyrrolidin-3-yl)-4-(trifluoromethoxy)benzenesulfonamide;
N-(3-(4-chlorophenyl) pyrrolidin-3-yl)-6-isopropoxypyridine-3-sulfonamide;
N-(3-(4-chlorophenyl)-1-(3-methylbutanoyl) pyrrolidin-3-yl)-4-(trifluoromethoxy)benzenesulfonamide;
N-(4-(3,4-difluorophenyl) piperidin-4-yl)-4-(trifluoromethoxy)benzenesulfonamide;
N-(4-(2,4-difluorophenyl) piperidin-4-yl)-4-(trifluoromethoxy)benzenesulfonamide;
N-(3-(4-fluorophenyl) pyrrolidin-3-yl)-4-(trifluoromethoxy)benzenesulfonimidamide;
N-(3-(4-chlorophenyl) pyrrolidin-3-yl)-N-methyl-4-(trifluoromethoxy)benzenesulfonamide;
N-(3-phenyl-8-azabicyclo[3.2.1]octan-3-yl)-4-(trifluoromethoxy)benzenesulfonamide;
N-(4-(5-chloropyridin-2-yl) piperidin-4-yl)-4-(trifluoromethoxy)benzenesulfonamide;
N-(4-(2,5-difluorophenyl) piperidin-4-yl)-4-(trifluoromethoxy)benzenesulfonamide;
N-(1-(3,4-dichlorophenyl)cyclopropyl)-4-(trifluoromethoxy)benzenesulfonamide;
N-(3-phenylpiperidin-3-yl)-4-(trifluoromethoxy)benzenesulfonamide;
N-(4-(5-chlorothiophen-2-yl) piperidin-4-yl)-4-(trifluoromethoxy)benzenesulfonamide;
3-amino-N-(3-(4-fluorophenyl) pyrrolidin-3-yl)-4-(trifluoromethoxy)benzenesulfonamide;
3-amino-N-(3-(4-fluoro-3-methylphenyl) pyrrolidin-3-yl)-4-(trifluoromethoxy)benzenesulfonamide;

N-(4-(4-chloro-2-fluorophenyl) piperidin-4-yl)-4-(trifluoromethoxy)benzenesulfonamide;

N-(4-(5-chloro-3-fluoropyridin-2-yl) piperidin-4-yl)-4-(trifluoromethoxy)benzenesulfonamide;

N'-(4-(4-chlorophenyl) piperidin-4-yl)-4-(trifluoromethoxy)benzenesulfonimidamide;

N-(4-(4-chlorophenyl) piperidin-4-yl)-4-(trifluoromethyl)benzenesulfonamide;

N-(4-(4-chlorophenyl) piperidin-4-yl)-3-(trifluoromethyl) bicyclo[1.1.1]pentane-1-sulfonamide;

3-amino-N-(4-(4-chlorophenyl) piperidin-4-yl)-4-(trifluoromethoxy)benzenesulfonamide; and N-(4-(4-(difluoromethyl)phenyl) piperidin-4-yl)-4-(trifluoromethoxy)benzenesulfonamide;

or a salt, solvate, isotopologue, or tautomer thereof.

19. The compound of claim 1, which is selected from the group consisting of:

(R)—N-(6-fluoro-2,2-dimethylchroman-4-yl)-4-(trifluoromethoxy)benzenesulfonamide;

N-((2R,3R)-1-(tert-butyl)-2-(4-chloro-3-fluorophenyl) pyrrolidin-3-yl)-4-(trifluoromethoxy)benzenesulfonamide;

N-((2R,3S)-1-(tert-butyl)-2-(4-chloro-3-fluorophenyl) pyrrolidin-3-yl)-4-(trifluoromethoxy)benzenesulfonamide;

tert-butyl 4-((1R,2R)-2-((4-(trifluoromethoxy)phenyl) sulfonamido)cyclopropyl) piperidine-1-carboxylate;

tert-butyl 4-((1R,2S)-2-((4-(trifluoromethoxy)phenyl) sulfonamido)cyclopropyl) piperidine-1-carboxylate;

(R)-tert-butyl 2-(1-((4-(trifluoromethoxy)phenyl) sulfonamido)cyclopropyl) pyrrolidine-1-carboxylate;

(R)—N-(6-(difluoromethoxy)-4-oxo-1,2,3,4-tetrahydronaphthalen-1-yl)-4-(trifluoromethoxy)benzenesulfonamide;

tert-butyl (R)-3-(fluoromethyl)-3-((4-(trifluoromethoxy) phenyl) sulfonamido) pyrrolidine-1-carboxylate;

N-((2R,3R)-1-cyclopropyl-2-(3,4-difluorophenyl) pyrrolidin-3-yl)-4-(trifluoromethoxy)benzenesulfonamide;

N-((2R,3S)-1-cyclopropyl-2-(3,4-difluorophenyl) pyrrolidin-3-yl)-4-(trifluoromethoxy)benzenesulfonamide;

(R)—N-(2-oxo-1-(3-(trifluoromethyl)benzyl) piperidin-3-yl)-4-(trifluoromethoxy)benzenesulfonamide;

(R)—N-(spiro[chromane-2,1'-cyclopentan]-4-yl)-4-(trifluoromethoxy)benzenesulfonamide;

(R)—N-(1-benzyl-3-phenylpyrrolidin-3-yl)-4-(trifluoromethoxy)benzenesulfonamide;

(R)—N-(3-phenylpyrrolidin-3-yl)-4-(trifluoromethoxy) benzenesulfonamide;

(R)—N-(4,6-dichloro-2,3-dihydro-1H-inden-1-yl)-4-(trifluoromethoxy)benzenesulfonamide;

N-((6R, 7R)-2-benzyl-7-hydroxy-1-isopropyl-2-azaspiro [3.4]octan-6-yl)-4-(trifluoromethoxy)benzenesulfonamide;

N-((6R, 7S)-2-benzyl-7-hydroxy-1-isopropyl-2-azaspiro [3.4]octan-6-yl)-4-(trifluoromethoxy)benzenesulfonamide;

(R)—N-(6-chloro-1,2,3,4-tetrahydronaphthalen-1-yl)-4-(trifluoromethoxy)benzenesulfonamide;

N-((2R,3R)-2-(4-chlorophenyl)-1-methylpyrrolidin-3-yl)-4-(trifluoromethoxy)benzenesulfonamide;

N-((2R,3S)-2-(4-chlorophenyl)-1-methylpyrrolidin-3-yl)-4-(trifluoromethoxy)benzenesulfonamide;

(R)—N-(1-(3,4-dichlorophenyl) piperidin-3-yl)-4-(trifluoromethoxy)benzenesulfonamide;

(R)—N-(1-(2-phenylbutanoyl) piperidin-4-yl)-4-(trifluoromethoxy)benzenesulfonamide;

(R)-4-(trifluoromethoxy)-N-(1-(3-(trifluoromethoxy)phenyl) pyrrolidin-3-yl)benzenesulfonamide;

N-((1R,2R)-2-ethyl-1-(m-tolyl)cyclopropyl)-4-(trifluoromethoxy)benzenesulfonamide;

N-((1R,2S)-2-ethyl-1-(m-tolyl)cyclopropyl)-4-(trifluoromethoxy)benzenesulfonamide;

(R)—N-(1-(5-chloro-2-methoxyphenyl) pyrrolidin-3-yl)-4-(trifluoromethoxy)benzenesulfonamide;

(R)—N-(5,8-difluorochroman-4-yl)-4-(trifluoromethoxy) benzenesulfonamide;

N-((1R,2R)-2-(4-chlorophenyl)cyclopropyl)-4-(trifluoromethoxy)benzenesulfonamide;

N-((1R,2S)-2-(4-chlorophenyl)cyclopropyl)-4-(trifluoromethoxy)benzenesulfonamide;

N-((1R,2R)-2-(3,4-dichlorophenyl)cyclopentyl)-4-(trifluoromethoxy)benzenesulfonamide;

N-((1R,2S)-2-(3,4-dichlorophenyl)cyclopentyl)-4-(trifluoromethoxy)benzenesulfonamide;

(R)—N-(3-(4-chlorophenyl) pyrrolidin-3-yl)-4-(trifluoromethoxy)benzenesulfonamide;

(R)—N-(3-(3,4-dichlorophenyl) pyrrolidin-3-yl)-4-(trifluoromethoxy)benzenesulfonamide;

(R)—N-(1-(3-bromophenyl) pyrrolidin-3-yl)-4-(trifluoromethoxy)benzenesulfonamide;

(R)-benzyl 3-(3,4-dichlorophenyl)-3-((4-(trifluoromethoxy)phenyl) sulfonamido) pyrrolidine-1-carboxylate;

N-((3R,4R)-4-(3,4-dichlorophenyl) pyrrolidin-3-yl)-4-(trifluoromethoxy)benzenesulfonamide;

N-((3R,4S)-4-(3,4-dichlorophenyl) pyrrolidin-3-yl)-4-(trifluoromethoxy)benzenesulfonamide;

(R)—N-(3-(4-chloro-3-fluorophenyl) pyrrolidin-3-yl)-4-(trifluoromethoxy)benzenesulfonamide;

(R)—N-(1-benzyl-3-(4-chlorophenyl) pyrrolidin-3-yl)-4-(4-(trifluoromethyl) phenoxy)benzenesulfonamide;

(R)—N-(1-benzyl-3-(3,4-dichlorophenyl) pyrrolidin-3-yl)-4-(4-(trifluoromethyl) phenoxy)benzenesulfonamide;

(R)—N-(3-(4-chlorophenyl) pyrrolidin-3-yl)-4-(4-(trifluoromethyl) phenoxy)benzenesulfonamide;

(R)—N—((R)-3-(4-chlorophenyl)yrrolidine-3-yl)-4-(trifluoromethoxy)benzenesulfonimidamide;

(R)—N—((S)-3-(4-chlorophenyl)yrrolidine-3-yl)-4-(trifluoromethoxy)benzenesulfonimidamide;

(R)—N-(3-(4-chlorophenyl)yrrolidine-3-yl)-6-(trifluoromethoxy)pyridine-3-sulfonamide;

(R)—N—((R)-3-(4-chlorophenyl)yrrolidine-3-yl)-N'-methyl-4-(trifluoromethoxy)benzenesulfonimidamide;

(R)—N—((S)-3-(4-chlorophenyl)yrrolidine-3-yl)-N'-methyl-4-(trifluoromethoxy)benzenesulfonimidamide;

(R)—N-(3-(4-chlorophenyl)-1-methylpyrrolidin-3-yl)-4-(trifluoromethoxy)benzenesulfonamide;

tert-butyl (R)-3-(4-chlorophenyl)-3-((4-(trifluoromethoxy)phenyl)yrrolidine) pyrrolidine-1-carboxylate;

(R)—N-(3-(4-chlorophenyl)-1-(oxetan-3-yl)yrrolidine-3-yl)-4-(trifluoromethoxy)benzenesulfonamide;

(R)—N-(3-(4-chlorophenyl)-1-(methylsulfonyl)yrrolidine-3-yl)-4-(trifluoromethoxy)benzenesulfonamide;

(R)—N-(3-(4-fluorophenyl)yrrolidine-3-yl)-4-(trifluoromethoxy)benzenesulfonamide;

(R)—N-(3-(4-chlorophenyl)-1-isopentylpyrrolidin-3-yl)-4-(trifluoromethoxy)benzenesulfonamide;

(R)—N-(3-(4-fluorophenyl)yrrolidine-3-yl)-4-isopropoxybenzenesulfonamide;

N-((3R,4R)-3-(4-chlorophenyl)-4-fluoropyrrolidin-3-yl)-4-(trifluoromethoxy)benzenesulfonamide;

N-((3R,4S)-3-(4-chlorophenyl)-4-fluoropyrrolidin-3-yl)-4-(trifluoromethoxy)benzenesulfonamide;
(R)—N-(3-(4-chlorophenyl)yrrolidine-3-yl)-6-isopropoxypyridine-3-sulfonamide;
(R)—N-(3-(4-chlorophenyl)-1-(3-methylbutanoyl)yrrolidine-3-yl)-4-(trifluoromethoxy)benzenesulfonamide;
(R)—N—((R)-3-(4-fluorophenyl) pyrrolidin-3-yl)-4-(trifluoromethoxy)benzenesulfonimidamide;
(R)—N—((S)-3-(4-fluorophenyl) pyrrolidin-3-yl)-4-(trifluoromethoxy)benzenesulfonimidamide;
(R)—N-(3-(4-chlorophenyl) pyrrolidin-3-yl)-N-methyl-4-(trifluoromethoxy)benzenesulfonamide;
(R)—N-(3-phenylpiperidin-3-yl)-4-(trifluoromethoxy) benzenesulfonamide;
(R)-3-amino-N-(3-(4-fluorophenyl) pyrrolidin-3-yl)-4-(trifluoromethoxy)benzenesulfonamide;
(R)-3-amino-N-(3-(4-fluoro-3-methylphenyl) pyrrolidin-3-yl)-4-(trifluoromethoxy)benzenesulfonamide;
(S)—N-(6-fluoro-2,2-dimethylchroman-4-yl)-4-(trifluoromethoxy)benzenesulfonamide;
N-((2S,3S)-1-(tert-butyl)-2-(4-chloro-3-fluorophenyl) pyrrolidin-3-yl)-4-(trifluoromethoxy)benzenesulfonamide;
N-((2S,3R)-1-(tert-butyl)-2-(4-chloro-3-fluorophenyl) pyrrolidin-3-yl)-4-(trifluoromethoxy)benzenesulfonamide;
tert-butyl 4-((1S,2S)-2-((4-(trifluoromethoxy)phenyl) sulfonamido)cyclopropyl) piperidine-1-carboxylate;
tert-butyl 4-((1S,2R)-2-((4-(trifluoromethoxy)phenyl) sulfonamido)cyclopropyl) piperidine-1-carboxylate;
(S)-tert-butyl 2-(1-((4-(trifluoromethoxy)phenyl) sulfonamido)cyclopropyl) pyrrolidine-1-carboxylate;
(S)—N-(6-(difluoromethoxy)-4-oxo-1,2,3,4-tetrahydronaphthalen-1-yl)-4-(trifluoromethoxy)benzenesulfonamide;
tert-butyl(S)-3-(fluoromethyl)-3-((4-(trifluoromethoxy) phenyl) sulfonamido) pyrrolidine-1-carboxylate;
N-((2S,3S)-1-cyclopropyl-2-(3,4-difluorophenyl) pyrrolidin-3-yl)-4-(trifluoromethoxy)benzenesulfonamide;
N-((2S,3R)-1-cyclopropyl-2-(3,4-difluorophenyl) pyrrolidin-3-yl)-4-(trifluoromethoxy)benzenesulfonamide;
(S)—N-(2-oxo-1-(3-(trifluoromethyl)benzyl) piperidin-3-yl)-4-(trifluoromethoxy)benzenesulfonamide;
(S)—N-(spiro[chromane-2,1'-cyclopentan]-4-yl)-4-(trifluoromethoxy)benzenesulfonamide;
(S)—N-(1-benzyl-3-phenylpyrrolidin-3-yl)-4-(trifluoromethoxy)benzenesulfonamide;
(S)—N-(3-phenylpyrrolidin-3-yl)-4-(trifluoromethoxy) benzenesulfonamide;
(S)—N-(4,6-dichloro-2,3-dihydro-1H-inden-1-yl)-4-(trifluoromethoxy)benzenesulfonamide;
N-((6S,7S)-2-benzyl-7-hydroxy-1-isopropyl-2-azaspiro [3.4]octan-6-yl)-4-(trifluoromethoxy)benzenesulfonamide;
N-((6S,7R)-2-benzyl-7-hydroxy-1-isopropyl-2-azaspiro [3.4]octan-6-yl)-4-(trifluoromethoxy)benzenesulfonamide;
(S)—N-(6-chloro-1,2,3,4-tetrahydronaphthalen-1-yl)-4-(trifluoromethoxy)benzenesulfonamide;
N-((2S,3S)-2-(4-chlorophenyl)-1-methylpyrrolidin-3-yl)-4-(trifluoromethoxy)benzenesulfonamide;
N-((2S,3R)-2-(4-chlorophenyl)-1-methylpyrrolidin-3-yl)-4-(trifluoromethoxy)benzenesulfonamide;
(S)—N-(1-(3,4-dichlorophenyl) piperidin-3-yl)-4-(trifluoromethoxy)benzenesulfonamide;
(S)—N-(1-(2-phenylbutanoyl) piperidin-4-yl)-4-(trifluoromethoxy)benzenesulfonamide;
(S)-4-(trifluoromethoxy)-N-(1-(3-(trifluoromethoxy)phenyl) pyrrolidin-3-yl)benzenesulfonamide;
N-((1S,2S)-2-ethyl-1-(m-tolyl)cyclopropyl)-4-(trifluoromethoxy)benzenesulfonamide;
N-((1S,2R)-2-ethyl-1-(m-tolyl)cyclopropyl)-4-(trifluoromethoxy)benzenesulfonamide;
(S)—N-(1-(5-chloro-2-methoxyphenyl) pyrrolidin-3-yl)-4-(trifluoromethoxy)benzenesulfonamide;
(S)—N-(5,8-difluorochroman-4-yl)-4-(trifluoromethoxy) benzenesulfonamide;
N-((1S,2S)-2-(4-chlorophenyl)cyclopropyl)-4-(trifluoromethoxy)benzenesulfonamide;
N-((1S,2R)-2-(4-chlorophenyl)cyclopropyl)-4-(trifluoromethoxy)benzenesulfonamide;
N-((1S,2S)-2-(3,4-dichlorophenyl)cyclopentyl)-4-(trifluoromethoxy)benzenesulfonamide;
N-((1R,2S)-2-(3,4-dichlorophenyl)cyclopentyl)-4-(trifluoromethoxy)benzenesulfonamide;
(S)—N-(3-(4-chlorophenyl) pyrrolidin-3-yl)-4-(trifluoromethoxy)benzenesulfonamide;
(S)—N-(3-(3,4-dichlorophenyl) pyrrolidin-3-yl)-4-(trifluoromethoxy)benzenesulfonamide;
(S)—N-(1-(3-bromophenyl) pyrrolidin-3-yl)-4-(trifluoromethoxy)benzenesulfonamide;
(S)-benzyl 3-(3,4-dichlorophenyl)-3-((4-(trifluoromethoxy)phenyl) sulfonamido) pyrrolidine-1-carboxylate;
N-((3S,4S)-4-(3,4-dichlorophenyl) pyrrolidin-3-yl)-4-(trifluoromethoxy)benzenesulfonamide;
N-((3S,4R)-4-(3,4-dichlorophenyl) pyrrolidin-3-yl)-4-(trifluoromethoxy)benzenesulfonamide;
(S)—N-(3-(4-chloro-3-fluorophenyl) pyrrolidin-3-yl)-4-(trifluoromethoxy)benzenesulfonamide;
(S)—N-(1-benzyl-3-(4-chlorophenyl) pyrrolidin-3-yl)-4-(4-(trifluoromethyl) phenoxy)benzenesulfonamide;
(S)—N-(1-benzyl-3-(3,4-dichlorophenyl) pyrrolidin-3-yl)-4-(4-(trifluoromethyl) phenoxy)benzenesulfonamide;
(S)—N-(3-(4-chlorophenyl) pyrrolidin-3-yl)-4-(4-(trifluoromethyl) phenoxy)benzenesulfonamide;
(S)—N—((S)-3-(4-chlorophenyl) pyrrolidin-3-yl)-4-(trifluoromethoxy)benzenesulfonimidamide;
(S)—N—((R)-3-(4-chlorophenyl) pyrrolidin-3-yl)-4-(trifluoromethoxy)benzenesulfonimidamide;
(S)—N-(3-(4-chlorophenyl) pyrrolidin-3-yl)-6-(trifluoromethoxy)pyridine-3-sulfonamide;
(S)—N—((S)-3-(4-chlorophenyl) pyrrolidin-3-yl)-N'-methyl-4-(trifluoromethoxy)benzenesulfonimidamide;
(S)—N—((R)-3-(4-chlorophenyl) pyrrolidin-3-yl)-N'-methyl-4-(trifluoromethoxy)benzenesulfonimidamide;
(S)—N-(3-(4-chlorophenyl)-1-methylpyrrolidin-3-yl)-4-(trifluoromethoxy)benzenesulfonamide;
tert-butyl(S)-3-(4-chlorophenyl)-3-((4-(trifluoromethoxy)phenyl) sulfonamido) pyrrolidine-1-carboxylate;
(S)—N-(3-(4-chlorophenyl)-1-(oxetan-3-yl) pyrrolidin-3-yl)-4-(trifluoromethoxy)benzenesulfonamide;
(S)—N-(3-(4-chlorophenyl)-1-(methylsulfonyl) pyrrolidin-3-yl)-4-(trifluoromethoxy)benzenesulfonamide;
(S)—N-(3-(4-fluorophenyl) pyrrolidin-3-yl)-4-(trifluoromethoxy)benzenesulfonamide;
(S)—N-(3-(4-chlorophenyl)-1-isopentylpyrrolidin-3-yl)-4-(trifluoromethoxy)benzenesulfonamide;
(S)—N-(3-(4-fluorophenyl) pyrrolidin-3-yl)-4-isopropoxybenzenesulfonamide;
N-((3S,4S)-3-(4-chlorophenyl)-4-fluoropyrrolidin-3-yl)-4-(trifluoromethoxy)benzenesulfonamide;

N-((3S,4R)-3-(4-chlorophenyl)-4-fluoropyrrolidin-3-yl)-4-(trifluoromethoxy)benzenesulfonamide;

(S)—N-(3-(4-chlorophenyl) pyrrolidin-3-yl)-6-isopropoxypyridine-3-sulfonamide;

(S)—N-(3-(4-chlorophenyl)-1-(3-methylbutanoyl) pyrrolidin-3-yl)-4-(trifluoromethoxy)benzenesulfonamide;

(S)—N—((S)-3-(4-fluorophenyl) pyrrolidin-3-yl)-4-(trifluoromethoxy)benzenesulfonimidamide;

(S)—N—((R)-3-(4-fluorophenyl) pyrrolidin-3-yl)-4-(trifluoromethoxy)benzenesulfonimidamide;

(S)—N-(3-(4-chlorophenyl) pyrrolidin-3-yl)-N-methyl-4-(trifluoromethoxy)benzenesulfonamide;

(S)—N-(3-phenylpiperidin-3-yl)-4-(trifluoromethoxy) benzenesulfonamide;

(S)-3-amino-N-(3-(4-fluorophenyl) pyrrolidin-3-yl)-4-(trifluoromethoxy)benzenesulfonamide; and (S)-3-amino-N-(3-(4-fluoro-3-methylphenyl) pyrrolidin-3-yl)-4-(trifluoromethoxy)benzenesulfonamide;

or a salt, solvate, isotopologue, or tautomer thereof.

20. A pharmaceutical composition comprising at least one compound of claim 1 and at least one pharmaceutically acceptable carrier.

21. A method of treating prostate cancer in a subject, the method comprising administering to a subject in need thereof a therapeutically effective amount of the compound of claim 1 or a pharmaceutical composition thereof comprising at least one pharmaceutically acceptable carrier.

22. The method of claim 21, wherein the subject is a human.

23. N-(3-phenylpyrrolidin-3-yl)-4-(trifluoromethoxy) benzenesulfonamide or a pharmaceutically acceptable salt thereof.

24. (R)—N-(3-phenylpyrrolidin-3-yl)-4-(trifluoromethoxy)benzenesulfonamide or a pharmaceutically acceptable salt thereof.

25. (S)—N-(3-phenylpyrrolidin-3-yl)-4-(trifluoromethoxy)benzenesulfonamide or a pharmaceutically acceptable salt thereof.

26. A method of treating prostate cancer in a subject, the method comprising administering to a subject in need thereof a therapeutically effective amount of the compound of claim 24 or a pharmaceutical composition thereof comprising at least one pharmaceutically acceptable carrier.

27. The method of claim 26, wherein the subject is a human.

28. A pharmaceutical composition comprising the compound of claim 24 and at least one pharmaceutically acceptable carrier.

* * * * *